US011193925B2

(12) United States Patent
Dennis et al.

(10) Patent No.: US 11,193,925 B2
(45) Date of Patent: Dec. 7, 2021

(54) MEDICATION ADHERENCE MONITORING DEVICE

(71) Applicants: UNIVERSITY OF FLORIDA RESEARCH FOUNDATION, INC., Gainesville, FL (US); XHALE, INC., Gainesville, FL (US)

(72) Inventors: Donn Dennis, Gainesville, FL (US); Matthew Booth, Gainesville, FL (US); Scott Wasdo, Gainesville, FL (US); Chris Batich, Gainesville, FL (US); Hank Wohltjen, Gainesville, FL (US); Douglas Crumb, Gainesville, FL (US); Mark Tanner, Gainesville, FL (US); Susan Baumgartner, Gainesville, FL (US); Poonam Kaul, Gainesville, FL (US)

(73) Assignees: University of Florida Research Foundation, Inc., Gainesville, FL (US); Xhale, Inc., Gainesville, FL (US)

(*) Notice: Subject to any disclaimer, the term of this patent is extended or adjusted under 35 U.S.C. 154(b) by 0 days.

(21) Appl. No.: 16/384,122

(22) Filed: Apr. 15, 2019

(65) Prior Publication Data

US 2020/0103394 A1    Apr. 2, 2020

Related U.S. Application Data

(63) Continuation of application No. 15/123,424, filed as application No. PCT/US2015/018317 on Mar. 2, 2015, now abandoned.

(Continued)

(51) Int. Cl.
*G01N 33/497* (2006.01)
*G01N 30/74* (2006.01)
(Continued)

(52) U.S. Cl.
CPC ........... *G01N 33/497* (2013.01); *A61B 5/082* (2013.01); *A61B 5/0836* (2013.01); *A61B 5/097* (2013.01);
(Continued)

(58) Field of Classification Search
USPC ..................................................... 422/83, 84
See application file for complete search history.

(56) References Cited

U.S. PATENT DOCUMENTS 4,849,155 A    7/1989  Penzhorn et al.
5,962,335 A *  10/1999 Katzman ............ A61K 51/1206
                                                    436/181

(Continued)

FOREIGN PATENT DOCUMENTS

WO    2013040494 A1    3/2013
WO    2013115933 A1    8/2013

OTHER PUBLICATIONS

International Search Report for PCT/US2015/18317 dated Mar. 2, 2015.

(Continued)

*Primary Examiner* — Brian R Gordon
(74) *Attorney, Agent, or Firm* — Thomas | Horstemeyer, LLP

(57) ABSTRACT

A Self Monitoring And Reporting Therapeutics, SMART® composition, method apparatus and system are provided which flexibly provide options, by combining different embodiments of the device with different embodiments of the composition, the ability to conduct definitive medication adherence monitoring over the short term (Acute Medication Adherence Monitoring, immediately up to an hour or so after taking a medication), intermediate term (Intermediate Medication Adherence Monitoring, IMAM, an hour or so to a day or so after taking a medication), and longer term (Continued)

(Chronic Medication Adherence Monitoring, CMAM, a day to several days after taking a medication).

17 Claims, 88 Drawing Sheets

Related U.S. Application Data

(60) Provisional application No. 61/947,669, filed on Mar. 4, 2014.

(51) Int. Cl.
<table>
<tr><td>A61B 5/00</td><td>(2006.01)</td></tr>
<tr><td>A61B 5/083</td><td>(2006.01)</td></tr>
<tr><td>A61B 5/097</td><td>(2006.01)</td></tr>
<tr><td>A61B 5/08</td><td>(2006.01)</td></tr>
<tr><td>A61B 5/087</td><td>(2006.01)</td></tr>
<tr><td>A61B 10/00</td><td>(2006.01)</td></tr>
<tr><td>G01N 30/02</td><td>(2006.01)</td></tr>
</table>

(52) U.S. Cl.
CPC .......... *A61B 5/4833* (2013.01); *A61B 5/4848* (2013.01); *G01N 30/74* (2013.01); *A61B 5/087* (2013.01); *A61B 2010/0087* (2013.01); *G01N 2030/025* (2013.01); *G01N 2030/743* (2013.01); *G01N 2033/4975* (2013.01)

(56) References Cited

U.S. PATENT DOCUMENTS

| | | | |
|---|---|---|---|
| 6,180,414 B1 | 1/2001 | Katzman | |
| 6,238,078 B1 | 5/2001 | Hed | |
| 6,636,811 B1 | 10/2003 | Walte et al. | |
| 8,026,103 B2* | 9/2011 | Van Herpen | A61B 5/097 422/50 |
| 2005/0233459 A1* | 10/2005 | Melker | A61B 5/411 436/56 |
| 2007/0224128 A1 | 9/2007 | Dennis et al. | |
| 2008/0101434 A1 | 5/2008 | Horovitz et al. | |
| 2009/0042309 A1* | 2/2009 | Van Herpen | A61B 5/097 436/133 |
| 2010/0255598 A1* | 10/2010 | Melker | A61K 49/00 436/144 |
| 2012/0252129 A1 | 10/2012 | Fu et al. | |
| 2013/0040494 A1 | 2/2013 | Mische | |
| 2014/0311215 A1* | 10/2014 | Keays | G01N 33/4972 73/23.3 |

OTHER PUBLICATIONS

Extended European Search Report corresponding to European Patent Application No. 15758856.7 (7 pages) (dated Jul. 2, 2018).

International Search Report and the Written Opinion of the International Searching Authority corresponding to International Patent Application No. PCT/US2015/018317 (12 pages) (dated Jul. 9, 2015).

Van Der Vaart, D. R., et al., "Thermal and Catalytic Incinerators for the Controlof VOCs", Journal of the Air & Waste Management Association, 41(1)92-98 (1991).

Peled, Nir, et al., "Absract A36: Breath Biomarkers in the Post NLST-era for the Discrimination between Malignant from Benign Pulmonary Nodules," https://clincancerres.aacrjournals.org/content/18/3_Supplement/A36, accessed on Aug. 6, 2021.

* cited by examiner

A.

B.

Ethnicity – 50 subjects
- White: 37 (74%)
  - White (non-Hispanic): 31 (62%)
  - White (Hispanic): 4 (8%)
  - White (non-Hispanic) + African-American + Native Indian: 1 (2%)
  - White (non-Hispanic) + Native American: 1 (2%)
- African-American: 8 (16%)
  - African-American: 5 (10%)
  - African-American + White (non-Hispanic): 2 (4%)
  - African-American + Eastern Asian: 1 (2%)
- Other: 5 (10%)
  - Eastern Asian: 4 (8%)
  - Native American 1 (2%)

BMI (kg/m$^2$) – 50 subjects
Mean (SD): 26.2 (7.9)
Median: 24.1
Min, Max: 17.7, 51.7

| *Last Meal Statistic | AEM Formulation Type (four crossover limbs) | | | | Overall (includes all formulations) |
|---|---|---|---|---|---|
| | 20 mg 2-butanol | 20 mg 2-butanol combo | 40 mg 2-butanol | 40 mg 2-butanol combo | |
| N | 50 subjects | 50 subjects | 50 subjects | 50 subjects | 200 subject visits |
| Mean (SD) | 6.7 (7.9) hrs | 5.2 (6.1) hrs | 6.0 (6.4) hrs | 6.7 (7.5) hrs | 6.1 (7.0) hrs |
| Median | 2.5 hrs | 2.1 hrs | 2.8 hrs | 2.8 hrs | 2.6 hrs |
| Min, Max | 0.3, 24 hrs | 0.1, 24 hrs | 0.3, 23.9 hrs | 0.3, 24 hrs | 0.1, 24 hrs |

*, if time since last meal was > 24 hrs, a value of 24 hrs was used in the analysis
Data shown is mean (standard deviation)

Figure 16e

| Change from Baseline in 2-Butanone Concentration | Time Point Post-Dosing | 20 mg 2-Butanol (N=50) Number of Subjects Above Threshold [cumulative %] | 20 mg 2-Butanol Combo (N=50) *Number of Subjects Above Threshold [cumulative %] | 40 mg 2-Butanol (N=50) Number of Subjects Above Threshold [cumulative %] | 40 mg 2-Butanol Combo (N=50) §Number of Subjects Above Threshold [cumulative %] |
|---|---|---|---|---|---|
| ≥5 ppb | 10 Minutes | 41/50 [82%] | 35/50 [70%] | 41/50 [82%] | 40/50 [80%] |
| | 20 Minutes | 49/50 [98%] | 45/50 [90%] | 49/50 [98%] | 48/50 [96%] |
| | 30 Minutes | 50/50 [100%] | 47/50 [94%] | 50/50 [100%] | 48/50 [96%] |
| | 45 Minutes | 50/50 [100%] | 47/50 [94%] | 50/50 [100%] | 49/50 [98%] |
| | 60 Minutes | 50/50 [100%] | 47/49 [96%] | 50/50 [100%] | 49/50 [98%] |
| ≥7.5 ppb | 10 Minutes | 40/50 [80%] | 35/50 [70%] | 38/50 [76%] | 38/50 [76%] |
| | 20 Minutes | 49/50 [98%] | 44/50 [88%] | 49/50 [98%] | 47/50 [94%] |
| | 30 Minutes | 50/50 [100%] | 46/50 [92%] | 50/50 [100%] | 48/50 [96%] |
| | 45 Minutes | 50/50 [100%] | 47/50 [94%] | 50/50 [100%] | 49/50 [98%] |
| | 60 Minutes | 50/50 [100%] | 46/49 [94%] | 50/50 [100%] | 49/50 [98%] |
| ≥10 ppb | 10 Minutes | 39/50 [78%] | 33/50 [66%] | 37/50 [74%] | 37/50 [74%] |
| | 20 Minutes | 49/50 [98%] | 43/50 [86%] | 49/50 [98%] | 47/50 [94%] |
| | 30 Minutes | 49/50 [98%] | 44/50 [88%] | 50/50 [100%] | 48/50 [96%] |
| | 45 Minutes | 50/50 [100%] | 45/50 [90%] | 50/50 [100%] | 48/50 [96%] |
| | 60 Minutes | *48/50 [96%] | 45/49 [92%] | 50/50 [100%] | 48/50 [96%] |

\*, 2 subjects (26 and 33) did not have 2-butanone appear in their breath during the 60 min study period
§, 1 subject (18) did not have 2-butanone appear in their breath during the 60 min study period

Figure 17g

| Factor | Δ2-Butanone Breath Concentration-Time Relationships: Main Effect Model with Covariates – P Values |
|---|---|
| Visit | 0.11 |
| Formulation; Rank Order | <0.0001<br>40 mg 2-butanol > 40 mg 2-butanol combo > 20 mg 2-butanol > 20 mg 2-butanol combo |
| Time | <0.0001 |
| Tobacco Use | 0.85 |
| Alcohol Use | 0.56 |

Stability of 2 Butanol within the Softgel Capsules

Ethanol: $CH_3-CH_2-OH$

ASPARTAME
(L-ASPARTYL-L-PHENYLALANINE METHYL ESTER)

CLOFIBRATE
CHEMICAL NAMES
CLOFIBRATE, ETHYL 2-(2-{[(4-CHLOROPHENYL)SULFONYL]METHYL}PHENOXY)ACETATE

MEDICATION ADHERENCE MONITORING DEVICE

0.0 CROSS-REFERENCE TO RELATED APPLICATIONS

This application is a continuation of U.S. Non-Provisional application entitled "Medication Adherence Monitoring Device," having Ser. No. 15/123,424 and filed Sep. 2, 2016, now abandoned, which claims priority to U.S.C. § 371 national stage application of PCT Application No. PCT/US2015/018317, filed Mar. 2, 2015, which claims priority to U.S. Provisional Application Ser. No. 61/947,669, filed Mar. 4, 2014, which are hereby incorporated by reference herein in their entireties.

1.0 FIELD OF THE INVENTION

An improved Medication Adherence Monitoring System (MAMS) referred to as SMART®, an acronym for Self Monitoring and Reporting Therapeutics, is provided comprising an optimized device, medication composition, and method of making and using the system and its components.

2.0 BACKGROUND OF THE INVENTION

As recently as 2012, it has been acknowledged in the literature (see, for example, Oberguggenberger et al., BMC Cancer, 2012, 12:474, "Adherence evaluation of endocrine treatment in breast cancer: methodological aspects"), that the assessment of long-term adherent behavior with respect to medication regimens "is methodologically challenging. Studies have yielded inconclusive results indicating adherence rates between 20% and 100% across different phases of antineoplastic treatment. This variability of non-adherence rates found in the literature has been suggested to be attributed to heterogeneous study designs as well as inconsistencies in methodological approaches.

Among the latter the indirect methods of self-report, prescription refill and pharmacy records have been predominately used in studies on adherence to endocrine agents. Direct methods which are supposed to reveal more objective results due to the assessment of medication consumption in an unmediated way have not been employed in respective studies. There is currently no Gold Standard of adherence measurement available [8]." Reference [8] to which Oberguggenberger et al., point in support of these assertions is a 2003 WHO report entitled "ADHERENCE TO LONG-TERM THERAPIES—Evidence for action". At page XIII of the report, the WHO articulated "Take Home Messages" which, in sum, stand for the proposition that there remains a long-felt need in the field of medication adherence monitoring that is currently not being adequately met by any available system.

Xhale, Inc., is a medical device development company which, for the last several years, has been developing, improving and perfecting a state of the art Medication Adherence Monitoring System (MAMS). The improved (MAMS) according to this invention, referred to as SMART®, an acronym for Self Monitoring and Reporting Therapeutics, is provided comprising an optimized device, medication composition, and method of making and using the system. The improved SMART® system according to this invention provides an integrated series of solutions to meet the long-felt need for a reliable, gold-standard system to enable automated confirmation of subject adherence to a wide range of medication dosage regimens and contexts.

Whereas various specific and general solutions have been reported in the art aimed at meeting this need, some of which are discussed below, the present patent disclosure for the provides an integrated system capable of providing definitive medication adherence assessments and monitoring, both on an acute (dose-to-dose) basis, and on the basis of longer time frames, in the case of certain specific embodiments disclosed herein, up to and including over several doses of a given medication, over several days, or both. This is enabled by providing: a highly sophisticated device which includes heretofore unknown features and combinations of features for integrated use in combination with novel medication compositions, thus defining novel methods of utilizing the system to achieve medication adherence monitoring. Each of these elements of the integrated system is taken up in turn in this patent disclosure, with extensive but non-limiting exemplary support, to enable and fully describe the various embodiments and equivalents thereof encompassed by the present system.

Those skilled in the art will appreciate that the field of MAMS, including that of the SMART® system mentioned in art discussed herein below, is typically an incremental process, as reflected in different publications and patent filings over an extended period of time. At a certain point of development, enough incremental advances on several fronts coalesce, with a plurality of inter-related improvements having been discovered in technical competence, enhancements in the apparatuses utilized to ask diverse questions which enable new methods to be applied and tested. The present patent disclosure aspires to provide a detailed written description of what the current state of this technology now enables.

To provide an adequate context for the plethora of advances found in the detailed disclosure of the invention herein below, there is now provided a brief review of some key developments previously reported in this field, in related or competing fields, and, in some instances, in unrelated fields.

In 1999, a patent filing was conducted which ultimately led to issuance of U.S. Pat. No. 7,820,108, for a "Marker detection method and apparatus to monitor drug compliance", which generically disclosed and claimed a method to determine whether a patient has taken a medication by: providing to a patient a medication comprising a combination of at least one active therapeutic agent and a marker which was not chemically part of the active therapeutic agent itself, but which was detectable in gaseous exhaled breath; obtaining a sample of the patient's gaseous exhaled breath; analyzing the sample of the patient's breath utilizing an electronic nose to detect the marker in gaseous exhaled breath to ascertain the presence or absence of the marker in the patient's breath. The presence of the marker being taken as an indication that the patient took the medication at a prescribed time and in a prescribed dosage and the absence of the marker being taken as an indication that the patient did not take the medication at all or at a prescribed time or in a prescribed dosage.

In 2007, another generic application was filed for a Medication Adherence Monitoring System, published as US 2010-0255598 which is still pending. That filing is directed generically to inclusion of a non-ordinary isotope (e.g., deuterium) in the marker used in the method essentially as disclosed and claimed in U.S. Pat. No. 7,820,108.

Further, in 2011, a new patent filing, published in 2013 as WO2013/040494, generically disclosed solid oral dosage forms (SODFs) for use in combination with the SMART® system.

As will be apparent from a review of this entire disclosure, the present disclosure provides a plethora of select improvements, either in specific components of the SMART® system, as in the device, the compositions of matter for use in combination with the device in particular contexts, in methods of making the device or composition of matter, or, in combination, to the system as a whole.

By contrast, for example, Proteus Biomedical, Inc., (now known as Proteus Digital Health) has taken the approach to medication adherence monitoring, as disclosed, for example, in U.S. Pat. No. 8,258,962, a "Multi-mode communication ingestible event markers (IEMs) and systems, and methods of using the same", in which an integrated circuit comprising a conductive communication module is ingested to confirm medication adherence by sending out a signal (e.g., an RFID signal) once the circuitry has been ingested by a subject with a medication bearing that circuitry.

AiCure, by contrast, is an artificial intelligence company which utilizes facial recognition and motion-sensing technology to monitor medication ingestion using a smartphone camera.

These approaches are, of course, distinguishable from metabolic studies designed to determine the functional (phenotypic) efficiency of specific enzyme systems (e.g., CYP 1A2, CYP 3A4) in which metabolism of a compound is determined by including in the compound (a substrate for a specific enzyme) to be studied a radioactive or non-radioactive but non-ordinary isotope, as in Katzman, U.S. Pat. No. 5,962,335, since in that instance, there is no doubt about whether a medication has been taken, and, in addition, an isotopic label in the active therapeutic agent is required as opposed to a label in a marker included with an active therapeutic agent.

Likewise, the medication adherence monitoring technology described herein is distinguishable from, for example, the implantation of a drug delivery device, such as, for example the osmotic delivery device disclosed in Ayer, U.S. Pat. No. 6,283,953, comprising an implantable reservoir having at least one opening for delivering a beneficial agent contained within an interior of the reservoir to an organ of an animal, an osmotic engine adapted to cause the release of the beneficial agent contained within the reservoir to the animal, and means for noninvasively measuring the release of the beneficial agent from the reservoir from outside or tissue in which the delivery device is implanted. The Ayer system requires the invasive implantation of a mechanical medication delivery device. Noninvasive monitoring is conducted to ensure correct operation of the implanted device, but, once implanted, there is no question of medication adherence—if the device is implanted and is operating as it should, the subject receives medication. In addition, the Ayer system is not scalable—for a large scale clinical trial, thousands of implantation surgeries would be required to implant the drug delivery device. By contrast, the system according to the present invention does not require the implantation of a drug delivery device.

Notwithstanding the significant and incremental developments that have occurred in this field, some of which are discussed above, none of the known systems, devices and methods fully meet the need in the art for an integrated system capable of providing both acute and chronic medication adherence monitoring options. The present invention meets this need by providing improved MAMS components, including an optimized SMART® device, improved compositions of matter and methods of making and use thereof, and, in particular, an integrated system in which these components operate together to accommodate a wide range of medication adherence monitoring requirements in varying contexts. The present disclosure, therefore, represents a quantum leap forward in that an integrated system is provided herein wherein commercial embodiments of a SMART® device are disclosed in combination with selected embodiments of SMART® compositions of matter and methods of using such embodiments in optimized combinations with each other to provide a gold-standard in the field of acute and chronic medication adherence monitoring.

3.0 SUMMARY OF THE INVENTION

The present invention accommodates a number of aspects of MAMS not heretofore adequately addressed by any known medication adherence monitoring system. Included in these aspects are improved embodiments of the SMART® device, improved embodiments of SMART® composition of matter for use in combination with the improved SMART® device, and improved embodiments of methods of making and using the SMART® device and composition of matter as an integrated system to address different contexts in which medication adherence monitoring is desired. These advances in each of the related elements of the system may be summarized as follows:

---

THE SMART ® SYSTEM ACCORDING TO THIS INVENTION COMPRISES COMBINATIONS/PERMUTATIONS OF THE:

---

SMART ® DEVICE: See section 6 + 8; examples 1-4; figures 1-18

(a) biometric capture concurrent with breath collection;
(b) portable GC with 5ppb sensitivity for select VOCs;
(c) catalytic incineration + IR detection;
(d) EBM measurement without separation
(e) small footprint device;
(f) combinations of (a)-(e);
SMART ® COMPOSITION OF MATTER: See Section 7 + 8; examples 5-26; FIGS. 19-69

(a) optimized gelatin capsules containing optimized adherence enabling marker (AEM) formulations with appropriate release kinetics and retention characteristics/barriers to loss/admixture with API;
(b) i-AEMs - AEMs containing non-ordinary isotopes which appear as i-EBMs in exhaled breath with appropriate release kinetics and retention characteristics;
(c) optimized compositions and methods for surface coating of APIs with the AEM;
SMART ® METHOD OF MAKING: See Sections 6-9; examples 1-26

---

The SMART ® device;
The SMART ® compositions of matter;
SMART ® METHOD OF USING AND SMART SYSTEM: See Section 8 + 9, FIGS. 1-69; examples 1-28

---

Embodiments of the device in combination with embodiments of the compositions of matter to achieve definitive medication adherence monitoring system to enable a method for:
(a) Acute Medication Adherence Monitoring (AMAM) = immediately to about an hour or two after a medication is taken;
(b) Intermediate Medication Adherence Monitoring (IMAM) = immediately to 12-24 hours after a medication is taken;
(c) Chronic Medication Adherence Monitoring (CMAM) = immediately to about 3 hours to greater than 2-3 days after a medication is taken and insight into adherence across multiple doses.

Accordingly, it is a first object of this invention to provide an improved SMART® medication adherence monitoring system.

A further object of the invention is to provide an improved SMART® device.

A further object of the invention is to provide an improved SMART® composition of matter.

A yet further object of the invention is to provide an improved method of making and using the SMART® system, device, and composition of matter.

A further object of the invention is to provide a system for medication adherence monitoring which enables acute medication adherence monitoring (AMAM), intermediate medication adherence monitoring (IMAM), and chronic medication adherence monitoring (CMAM).

Those skilled in the art will further appreciate that the inverse of medication adherence monitoring is the detection of drug diversion and/or drug counterfeiting. That is, if a subject is definitively confirmed to be taking their prescribed medication, there cannot be drug diversion or counterfeiting. Conversely, if a subject is thought to be non-adherent, the system and method according to this invention provides a basis for exploration of whether the subject has been prescribed a counterfeit medication or if the subject is diverting their medication to another person or persons. Therefore, it is a further aspect of this invention to provide an improved method, system, and device for detection of drug diversion or counterfeiting.

In light of the general disclosure provided herein, including the detailed exemplary support, and the claims which follow, those skilled in the art will appreciate from a review of this entire disclosure, that the invention disclosed herein encompasses a system for medication adherence monitoring comprising at least the following elements:

A state of the art device or apparatus configured to identify and/or quantitate volatile compounds in a gas sample. The device includes at least one sensor adapted for identification and/or quantitation of a volatile compound of interest present in the gas sample and at least one capture device which captures volatile compounds in the gas sample. The sensor is selected from any of an array of known sensors, including but not limited to metal oxide sensors (MOS sensors), infrared sensors (IR), Surface Acoustic Wave sensors (SAW sensors) or the like.

Combinations of such sensors may be included in the device such that the gas or components of the gas introduced into the device is/are contacted with each such sensor before being released from the device into the atmosphere. The capture device is selective in that, while it is efficient at capture of volatile compounds, especially volatile organic compounds, it either does not capture at all or is inefficient in the capture of moisture, hydrogen, nitrogen, or carbon dioxide, present in the gas sample. These latter components in the gas sample, therefore, merely flow through the capture device and are vented to the atmosphere. The capture device is selected and adapted to further exhibit the property of releasing captured volatile compounds for sensing by the at least one sensor at a time coordinated in the device to coincide with readiness of the at least one sensor to be contacted with released volatile compounds that had been captured.

A device which includes these elements, to come within the scope of the present invention, further must include at least one or a combination of:

a. a catalytic incinerator between the at least one capture device and the at least one sensor which converts volatile compounds to carbon dioxide and water prior to contact with the at least one sensor;

b. at least one volatile compound separator between the at least one capture device and the at least one sensor which separates volatile compounds released by the capture device prior to contact with the at least one sensor;

c. at least one wireless data transceiver;

d. an air scrubber for removal of moisture and volatile organic compounds present in ambient air to provide a scrubbed air stream for driving volatile compounds through said apparatus; and e. a battery.

In a first preferred embodiment of this device, the apparatus is adapted for identifying and/or quantitating volatile compounds present in the exhaled breath of a subject. The adaptations for this purpose include, but are not limited to at least one or a combination of:

f. at least one biometric capture device for concurrent capture of a biometric specific to a subject when the gas sample is provided by the subject to the apparatus;

g. a mouthpiece for delivery of an exhaled breath sample by a subject to the apparatus, where the mouthpiece is operatively coupled with an exhaled breath detection sensor; and h. an actuator, such as a push button or touch sensitive screen element or the like, on the apparatus, for a subject to actuate to report adherence in taking or administering a dose of a medication.

In a further preferred embodiment of this device, the apparatus includes at least two sensors with differential sensitivity to a volatile compound of interest in the exhaled breath of a subject. When appropriately selected and configured, as described herein above, the differential sensitivity or selectivity of the at least two sensors allows information to be derived by manipulation, including by comparison of signals from each such sensor (e.g., addition of one signal to the other, subtraction of one signal from the other and the like) about the presence and optionally the amount of a particular analyte of interest in the exhaled breath sample.

In another embodiment of this aspect of the invention, the device includes at least one or a combination of:

(i) a catalytic incinerator and an infrared sensor adapted to detect water or carbon dioxide containing non-ordinary but stable isotopes of carbon, oxygen or hydrogen;

(ii) a compound separator such as, in a preferred embodiment, a gas chromatograph that is operatively coupled with an air scrubber that provides a scrubbed air stream which is driven through the gas chromatograph by a pump;

(iii) a thermally desorbable concentrator column operating as a volatile organic compound capture device in intimate association with a heating element such that, upon heating of the heating element, captured volatile compounds are released from the capture device;

(iv) a wireless data transceiver comprising at least one or a combination of: a WiFi transceiver; a mobile cellular data transceiver; a Bluetooth® transceiver; or the like;

(v) a camera operating as a biometric capture device which captures at least one still image of the subject at the time that the subject exhales into a mouthpiece incorporated into and in operative coupling with the device;

(vi) the battery is a rechargeable battery;

(vii) a microcontroller in operative electrical coupling with other components of the apparatus;

(viii) a limit of detection for a volatile compound of interest of 5-100 parts per billion to as low as several parts per trillion. Preferably 10 ppt-5 ppb.

In another aspect of this invention, the device described above is used in a method for medication adherence monitoring, which comprises contacting the device (e.g., breathing into the device; separately capturing a breath or breaths in a capture device, (e.g., a breath capture bag, a breath capture column which efficiently captures organic compounds in the exhaled breath but which does not efficiently capture moisture, hydrogen, nitrogen or carbon dioxide), and then releasing captured breath or breath components into the device), with an exhaled breath sample of a subject. In a preferred embodiment of this method, the device is used by a subject in combination with a medication adapted for provision of a marker which the device is configured to detect in exhaled breath. Thus, in this embodiment of the method, an Active Pharmaceutical Ingredient (API) is provided with or without a separate Adherence Enabling Marker (AEM). The API, the AEM, or both when taken or administered to a subject generates a sufficient quantity of an Exhaled Breath Marker (EBM) in the exhaled breath of the subject to be detected by the at least one sensor. In a preferred embodiment, the device is used to detect the EBM within a specified time period after a subject takes or is administered or applies a single dose of the medication. In a preferred embodiment according to this aspect of the invention, the device and the medication are selected and configured such that the EBM is detectable in the exhaled breath of the subject after the subject takes or is administered or applies multiple doses of the medication, and/or in relatively wide windows of time, or even random times, after a subject has or should have taken one or multiple doses of a medication. As described herein above and as further supported by specific examples provided herein below, the medication formulation options and device feature options are sufficiently malleable that the method can be practiced in any or each of these modes to reliably achieve AMAM, IMAM, CMAM, as needed for a given medication, subject, or set of clinical trial requirements.

The method described herein may, in one preferred embodiment, be practiced with an API, an AEM, or both, which includes a non-ordinary isotope. As described herein, the non-ordinary isotope is preferably selected to exist in the API, AEM or both such that the non-ordinary isotope is included in a resulting EBM, when it appears in the exhaled breath of a subject that takes or applies or is administered such a medication. Preferably, the non-ordinary isotope appears in the exhaled breath of a subject at a known and/or predictable concentration in the exhaled breath of such a subject at a time after taking such a medication which is convenient, or randomly selected, for the subject to provide an exhaled breath sample to the device. Accordingly, the method according to this aspect of the invention includes embodiments in which:

(a) A SMART® (Self Monitoring And Reporting Therapeutic) medication is provided to a subject which enables monitoring of the subject's adherence in taking or administration of at least one Active Pharmaceutical Ingredient (API) included in the medication in which the medication includes: (i) an i-API fraction, that is a known percentage of the total amount of the API delivered, which includes at least one non-ordinary but stable isotope; or (ii) an i-AEM, an Adherence Enabling Marker, which includes at least one non-ordinary but stable isotope; or (iii) both an i-API fraction and an i-AEM; such that, on taking or administration of the medication by or to the subject, an i-EBM, (an Exhaled Breath Marker comprising at least one non-ordinary but stable isotope), is produced in the exhaled breath of the subject; and/or (b) An i-EBM is detected and/or quantitated in the exhaled breath of a subject utilizing a device which comprises a component element that strips the exhaled breath sample of moisture and carbon dioxide, without impacting (e.g., removing, depleting) the i-EBM. The device used according to this method may further include a catalyst for converting the i-EBM to carbon dioxide and water, such that: (a) the isotope from the i-EBM is included in the water fraction, such that, following catalysis, isotopically labeled water is quantitated in the exhaled breath sample; and/or (b) the isotope from the i-EBM is included in the carbon dioxide fraction, such that, following catalysis, isotopically labeled carbon dioxide is quantitated in the exhaled breath sample.

The system according to this invention includes a medication comprising an API and an AEM, wherein the AEM is contained in a chemical form or within a barrier adequate to contain loss of the AEM and/or to prevent the AEM from contacting the API prior to being taken or administered by a subject. In a preferred embodiment, the chemical form or barrier facilitates rapid release of the AEM and/or API in a subject to permit medication adherence monitoring by measurement of an EBM in the exhaled breath of a subject within a specified time period, either immediately or a short period (up to about an hour), or a longer period, (from about one hour up to and including several days) after a medication is ingested by, taken by, is administered to or applied onto the subject. In a medication for use according to the method or in the system according to this invention, the barrier in a preferred embodiment comprises a softgel capsule shell which is optionally coated by a barrier, surface coating, or materials which prevent loss of the AEM from the capsule. Alternatively, or in addition, the AEM is provided in a chemical form that is stable until exposed to the biological environment of the subject, whereupon it quickly forms the AEM in situ and is then expired in the exhaled breath as the EBM. In a further preferred embodiment of such a medication, the AEM comprises either or both (a) a non-ordinary isotope; (b) butanol, isopropanol, or both, either or both of which may include a non-ordinary isotope, or other selected secondary alcohols, or other AEMs. In a further embodiment, the medication includes a surface coating comprising an i-AEM. Given the sensitivity of a $D_2O$ detector described herein, a low quantity (e.g., 1-10 mg) of a deuterated AEM placed on the surface (partial surface or total surface) of SODFs (solid tablets, capsules) is adequate to permit medication adherence monitoring. Surface coating and containment, for example, in a blister pack or equivalent preserves the AEM or i-AEM on the surface of the SODF. Likewise, in some embodiments, the AEM is incorporated into the surface coating of the SODF so that it does not require storage in a blister pack, but rather can be stored in a standard pill bottle.

In a further aspect of this invention, the Adherence Enabling Marker (AEM) composition comprises at least one of:

(a) at least one secondary alcohol which when ingested produces an Exhaled Breath Marker (EBM) detectable in the exhaled breath;

(b) at least one flavorant to mask taste reactions associated with the AEM following ingestion of the AEM composition; and (c) at least one bulking agent or other functional excipient to permit reliable filling of softgel capsules and stable storage of the AEM composition within a softgel capsule.

In iterations of this embodiment of the AEM formulation for medication adherence monitoring, the AEM formulation includes permutations or combinations of the following: the AEM is preferably a secondary alcohol, e.g., 2-butanol, isopropyl alcohol, or both, or other combinations and equivalents of other AEMs as disclosed herein; the bulking agent comprises PEG-400, or any of a wide array of other bulking agents known in the art (fractionated coconut oil; Acconon® surfactant/dispersing agents, e.g., MC-8-2; Phosal® lipids; oleic acid (refined); various grades of PEG; HPC, e.g., Klucel®; povidone; Capmul® emulsifiers; potassium acesulfame); the flavorant, if present, comprises e.g., vanillin, DL-menthol, or both, or other flavorants known in the art. In specific AEM compositions according to this invention, the formulation consists of: (a) 20 mg 2-butanol+ 0.7 mg DL-menthol+5 mg vanillin+9.3 mg PEG-400; or (b) 40 mg 2-butanol+1.4 mg DL-menthol+10 mg vanillin+18.6 mg PEG-400; (c) 20 mg of 2-butanol alone; (d) 40 mg of 2-butanol alone; (e) combinations of 2-butanol and isopropyl alcohol, alone or in combination with other excipients. Of course, those skilled in the art will appreciate that the amount of AEM used may be varied, depending on the concentration of EBM required to be detected in the exhaled breath. This may require as little as 1 µg and as much as 200 mg. It is generally sufficient to utilize between about 1 mg and 50 mg of, e.g. 2 butanol to measure butanone increases in the ppb range in the exhaled breath. The advantage of combinations of AEMs is that the SMART® device according to this invention can detect either or both AEMs in the exhaled breath, and either or both EBMs generated from the AEMs (e.g., butanone and acetone), and any interferents can thereby be identified if the ratio of AEMs/EBMs is inconsistent with a detected compound which could not have been generated from the AEM in the relative amount detected in exhaled breath.

In light of the many optional configurations described herein for the device, medication, and method according to this invention, the system for medication adherence monitoring according to this invention comprises the use of an apparatus as described herein in combination with a medication comprising an API, an AEM, or an API and AEM, wherein the API, the AEM, or both are present in a chemical form or contained within barriers adequate to contain the API, the AEM, or both from loss or contact between the AEM (if present) and the API. In such a system, it is preferred for the barrier to facilitate rapid release of the AEM, the API or both, in a subject to permit medication adherence monitoring by measurement of an EBM in the exhaled breath of such a subject generated from the AEM, from the API, or both, within a specified time period after the medication is ingested or otherwise administered or applied to or by the subject.

In further embodiments according to this aspect of the invention, the system includes:

(a) a SMART® drug comprising an API, an AEM, or both which generate a marker or markers, Exhaled Drug Ingestion Marker(s) (EDIMs) that appear(s) in the exhaled breath of humans or other vertebrates, to confirm definitive medication adherence, and (b) a SMART® device, which accurately measures the EDIMs and optionally provides medication reminder functions, and orchestrates critical adherence information flow between the relevant stakeholders; wherein the SMART® drug comprises an Adherence Enabling Marker (AEM) composition comprising: (i) at least one secondary alcohol which when ingested or otherwise taken or administered to a subject produces an Exhaled Drug Ingestion Marker (EDIM) detectable in the exhaled breath of the subject; (ii) an adequate quantity of flavorant such that greater than 90% of recipients of the AEM composition report little or no adverse taste following ingestion of the AEM composition; and (iii) an adequate quantity of bulking agent to permit reliable filling of soft-gel capsules and stable storage of the AEM composition within a soft-gel capsule. Preferably, the SMART® device accurately measures the EDIMs, optionally provides medication reminder functions, and orchestrates critical adherence information flow between the relevant stakeholders. This is achieved at least in part by selecting a sensor from the group consisting of miniaturized Gas Chromatography linked to any or a combination of a Metal Oxide Sensor (mGC-MOS), a surface acoustic wave (SAW) sensor, an infrared (IR) sensor, and an ion mobility spectroscopy (IMS) sensor.

Those skilled in the art reading this disclosure will further appreciate that the present invention provides a method for using an Adherence Enabling Marker, $AEM_x$, (which may include use of an API acting as its own marker), or measuring an Exhaled Drug Ingestion Marker X, $EDIM_x$ produced on ingestion of an $AEM_x$ comprising characterizing the pharmacokinetics, including concentration-time relationships of appearance and clearance of $EDIM_x$ in the exhaled breath of a subject.

In a further refinement of this method, $AEM_x$ comprises a non-ordinary isotope of an atom which constitutes $AEM_x$ such that the non-ordinary isotope is included in $EDIM_x$ in the exhaled breath upon dosing of a subject with a medication comprising $AEM_x$. In a particularly preferred embodiment, the non-ordinary isotope is deuterium. Where a non-ordinary isotope is included in the EBM, because the background level of deuterated molecules in the exhaled breath is essentially zero, the Limit of Detection, LOD, of the method is only constrained by the lowest concentration of $EDIM_x$ that the sensor used in the method is able to reliably measure, thereby providing a lookback period limited only by the LOD of the sensor, and the relationship of steady state concentration $EDIM_x$ (related to its half life) and the mass of the AEM delivered to the subject. This method may also be practiced with a combination of AEMs and EDIMs concurrently, (that is $AEM_x$, $EDIM_x$; $AEM_A$, $EDIM_A$; $AEM_B$, $EDIM_B$; $AEM_C$, $EDIM_C$; . . . . $AEM_N$, $EDIM_N$).

See Example 28 herein below for detailed description of this aspect of the invention.

An optimized device or system according to this invention is optimized by including in the device:

A. a sensor selected for accurate detection in the exhaled breath of at least one subject of at least one Exhaled Drug Ingestion Marker X, $EDIM_x$ produced on ingestion of at least one Adherence Enabling Marker, $AEM_x$;

B. data storage (as in hard drive, flash drive, EEPROM, in a form now known or which is developed in the future) operatively coupled to the sensor, for retention of data generated by the sensor in the course of characterizing the pharmacokinetics of the $EDIM_x$ in the exhaled breath of a subject, Y, or in a population of subjects, Z; and C. computing means, (including, for example, a programmed central processing unit) which compares each such measurement for each subject or population of subjects with stored data, as described herein below, for said subject or population of subjects, preferably in real time or near real time. For each measurement of the concentration of $EDIM_x$, a measure of adherence A is generated by the computing means for each subject.

The characterizing data for storage preferably includes measurement data, to within defined confidence limits, of:

a. the Limit of Detection (LoD) of a sensor included in said device for said marker;

b. the background level of said marker or interferents in said subject or population of subjects;

c. the half life of appearance ($t_{1/2a}$) and elimination ($t_{1/2e}$) of said marker from the exhaled breath of said subject or population of subjects;

d. the steady state ("SS") concentration of said marker in the exhaled breath at various time points during Adherence Enabling Marker (AEM) dosing, selected from the group consisting of trough ($C_{Trough,SS}$), maximum ($C_{MAX,SS}$), and other time point post dosing of the AEM concentrations of said subject or population of subjects; and e. the time required to attain the maximum concentration ($T_{MAX}$) of said marker from the exhaled breath of said subject or population of subjects.

Such a device according to this invention is preferably configured to integrate the pharmacokinetic parameters defined above to provide an adherence lookback window, $T_{AdhWindow}$, defined as the period of time required for the marker (EDIM) concentration in breath of the subject to decay from an initial value ($C_{EDIMo}$) to a lower concentration ($C_{EDIM,Limit}$)

$$T_{AdhWindow} = \frac{t_{1/2e}}{0.693} * \ln\left(\frac{C_{EDIMo}}{C_{EDIMLimit}}\right)$$

wherein:

$C_{EDIMo}$=original or starting concentration of marker (EDIM) in breath at times equal to or greater than $T_{MAX}$ (i.e., $C_{EDIMo} \leq C_{MAX}$) of said patient;

$C_{EDIMLimit}$=the final concentration of EDIM in breath of said patient, provided that, if $C_{EDIMLimit}$ denotes the limit of EDIM detection due to the device LoD or background interference, it would define the maximum $T_{AdhWindow}$; and $t_{1/2e}$=the elimination half life for said EDIM.

Such a device preferably exhibits a $T_{AdhWindow}$ between about 1 hour and about 400 hours, and includes a sensor with a LoD for the marker of between 1 part per trillion and 5 parts per billion or, naturally, higher, as the higher the concentration the easier it is to define a sensor with an adequate LOD. In one preferred embodiment, the sensor is adapted to distinguish between ordinary and non-ordinary isotopes present in EDIMs and volatile compounds which otherwise would interfere with selective measurement of EDIMs in the exhaled breath.

The invention disclosed herein includes an improved system for medication adherence monitoring wherein the system comprises:

(A) an Adherence Enabling Marker (AEM) which is administered to or is taken by a subject concurrently with or substantially concurrently with a medication according to a medication dosage regimen the adherence to which by the subject is to be monitored. When the subject is adherent to the medication regimen, the AEM or a metabolite of the AEM, referred to as an Exhaled Drug Ingestion Marker (EDIM), is detectable in the exhaled breath of the subject over a time period T following each dose of the medication being taken;

(B) a device adapted for (i) sampling, collection, or both sampling and collection of exhaled breath or a portion of exhaled breath of a subject, and (ii) detection, measurement or both detection and measurement of the EDIM, (which can be the AEM or a metabolite of the AEM) if present in the exhaled breath or portion of exhaled breath of the subject; and (iii) a display, data output, or both, reporting the detection, measurement or both of the EDIM.

The improvements in such a system as disclosed herein comprise at least one or a combination of the following elements, with respect to the AEM, the device or both:

(a) the AEM is characterized such that the kinetics of appearance and clearance of the EDIM in the exhaled breath of a subject or a population of subjects is sufficient to provide known confidence limits for such kinetics to be valid for a given subject, such that an optimal time for detecting the EDIM in the exhaled breath of a subject over time period T is not restricted to a time associated with only a single dose of medication;

(b) the AEM is selected for use in combination with a device adapted for medication adherence monitoring of a subject by detection of an EDIM, such that an incremental change in the EDIM is detected in the exhaled breath of the subject each time a medication dose containing the AEM is taken by or is administered to the subject;

(c) the device comprises a means for distinguishing and/or separating volatile compounds present in the exhaled breath of a subject and a detector for detecting, measuring or both detecting and measuring such volatile compounds or derivatives of such compounds (e.g. $D_2O$), wherein the device further includes at least one of the following elements:

i. means for subject biometric capture and reporting for definitive identification of a subject concurrent with the subject providing an exhaled breath sample via a mouthpiece. In this embodiment, the mouthpiece and subject biometric capture device are configured to enable reliable identification of the subject each time a breath sample is provided by the subject;

ii. a breath flow sensor;

iii. a wireless data transceiver;

iv. a breath collection and sampling subsystem operatively coupled with the mouthpiece;

v. an air scrubber;

vi. a rechargeable battery pack subsystem; and vii. a microcontroller subsystem in operative electrical coupling with between one and all electrical components of elements (i)-(v).

To support development and facilitate regulatory filings, a number of complementary in vitro (benchtop) and clinical (human) studies have been carried out to characterize the SMART® Adherence System. In terms of human exposure, the system has been safely used to date in 32 human studies (oral, sublingual, and microbicide administration routes), encompassing 1,293 experiments in 303 subjects and 8,474 breath analyses. Of particular note, three recent prospective, blinded, randomized, cross over clinical validation studies (127 subjects with 472 experiments and 2,464 breath analyses) using the SMART® Adherence System designed for oral medications were executed that focused on identifying an optimal adherence-enabling marker (AEM) formulation and carrying out receiver operating characteristic (ROC) curve analyses to make an optimal cutoff determination and assess diagnostic performance. System performance was favorable across a wide range of subject factors, including age, gender, race, body mass index (BMI), disease conditions, and time of food ingestion, and even in populations enriched with subjects who chronically consumed alcohol and/or used tobacco products. Specifically, after ingestion of the SMART® Adh Caps containing an optimized AEM formulation, the following notable clinical study (study 1, see examples) outcomes were found: 1) greater than 98% of subjects gave an overall positive response (detection of breath marker by the SMART® Device), and 2) adherence accuracies exceeding 95% are achieved when a 20-90 min breath marker detection window is employed. We disclose methods, compositions and devices for extending that window considerably, over many hours to days, and/or over more than one dose of medication. Given the above results, we conclude that the SMART® Adherence System holds significant promise as a novel technology to definitively measure and monitor medication adherence in various clinical settings.

Based on the extensive disclosure provided herein, other objects, advantages, and permutations, variations, combinations or equivalents of this invention will be clear to those skilled in the art from a review of the complete disclosure and appended claims.

4.0 BRIEF DESCRIPTION OF THE DRAWINGS

FIG. 1. Provides an illustrative example of how the system and method according to this invention works. The figure illustrates enzymatic catalysis and resultant exhalation of 2-butanone following oral ingestion of 2-butanol (40 mg) in subjects (n=7). Panel A: metabolism of the AEM, 2-butanol, by aa-alcohol dehydrogenase (ADH) to generate the volatile product, 2-butanone, an Exhaled Drug Ingestion Marker (EDIM)/Exhaled Breath Marker (EBM). Panel B: breath concentration-time relationship for the exhalation of 2-butanone (an EDIM) in breath following consumption of 2-butanol at time 0 min. Data shown are mean±SD. *, $P<0.05$ for a given time point compared to time point 0 min. The arrow denotes time of ingestion of a capsule containing 2-butanol. Concentrations less than the level of 1.0 parts-per-billion (ppb) are noted as "<LOD". As can be seen from this figure, 2-butanol as the AEM and 2-butanone as the EBM provides the ability to measure adherence over a time period of a few minutes to about one hour or so from the time of taking a medication containing the AEM.

FIGS. 2A and 2B. Graphic representations of a Handheld Miniature SMART® Device according to this invention.

FIG. 3. SMART® device block diagram showing breath sampling, separation, biometric capture, data and instruction display, data communication, microcontroller and power subsystems.

FIG. 4A-E. SMART® GC Subsystem Interconnect Block Diagrams.

FIG. 5. Graphic representation of a first embodiment of a Mouthpiece (Straw).

FIG. 6. Technical Drawing of Disposable Mouthpiece.

FIG. 7A-C. Mouthpiece Sensor, Breath Flow Sensor and Vapor Inlet in two different embodiments of the SMART® device according to this invention.

FIGS. 8A and 8B. Flow Diagrams for Breath Collection and component separation in a miniature GC (mGC) embodiment of the SMART® device according to this invention.

FIG. 9. Exemplary representation of a SMART® mGC chromatographic separation of isoprene, acetone, and 2-butanone in human breath.

FIGS. 10A and 10B. Photograph of internal architecture of one exemplary embodiment of internal components of the SMART® device.

FIG. 11. Photograph of internal architecture of obverse view shown in FIG. 10 in one exemplary embodiment of the SMART® device.

FIG. 12. Air flow path for scrubbed carrier air in the SMART® device.

FIG. 13. Exemplary representation of one embodiment of a user interface and SMART® device operational flow diagram.

FIG. 14. SMART® device logic flow diagram.

FIG. 15. SMART® device logic and data flow diagram.

FIG. 16a-g. A Prospective Randomized Cross Over Clinical Study in 50 Subjects to Determine the Optimal Configuration of the SMART® Adherence System: Effect of Four Adherence-Enabling Marker Formulations and Validation of the SMART® device operation; 16a Age; 16b Gender; 16c Ethnicity; 16d Body Mass Index (BMI); 16e Time From Last Meal; 16f Alcohol Use; 16g Tobacco Use; none of these factors appeared to be confounding factors.

FIG. 17a-j. 2-Butanone Breath Concentration-Time Relationship—Effect of Adherence-Enabling Marker (AEM) Formulation, see FIG. 17a; Δ2-Butanone (Change In Concentration From Baseline Values) Breath Concentration-Time Relationship, see FIG. 17b; Effect of Adherence-Enabling Marker (AEM) Formulation on Δ2-Butanone Breath Concentration-Time Relationship: Effect of AEM Formulation; Individual Δ2-Butanone Concentration-Time Curves in 50 Subjects: 20 mg 2-Butanol—see FIG. 17c; Individual Δ2-Butanone Concentration-Time Curves in 50 Subjects: 20 mg 2-Butanol Combo—see FIG. 17d; Individual Δ2-Butanone Concentration-Time Curves in 50 Subjects: 40 mg 2-Butanol—see FIG. 17e; Individual Δ2-Butanone Concentration-Time Curves in 50 Subjects: 40 mg 2-Butanol Combo—see FIGS. 17f and 17g; Distribution of 2-Butanone Concentrations by Time, AEM Formulation, and Concentration Threshold Levels; Percent of Subjects (N=50) with Δ2-Butanone Concentrations ≥5 PPB; see FIG. 17h; Percent of Subjects (N=50) with Δ2-Butanone Concentrations 7.5 PPB—see FIG. 17i; Percent of Subjects (N=50) with Δ2-Butanone Concentrations ≥10 PPB—see FIG. 17j.

FIG. 18a-j. Effect of Meal Timing on Δ2-Butanone Concentrations Across AEM Formulations—see FIG. 18a; Covariates: Tobacco and Alcohol Use—see FIG. 18b; $\Delta T_{Max}$: Effect of AEM Formulation—see FIG. 18c; Cumulative Frequency (%) of Subjects Achieving $\Delta T_{Max}$ by Time and Formulation—see FIG. 18d; $\Delta C_{Max}$: Effect of AEM Formulation—see FIG. 18e; ΔAUC: Effect of AEM Formulation—see FIG. 18f; SMART® Device Performance: Full 2-Butanone Concentration Range—See FIG. 18g, which shows 2-butanone breath concentration-mGC response relationships by device across four AEM formulations; relationship between 2-butanone concentration and mGC response is curvilinear (i.e., square root function), but is highly linear in regions, including lower concentrations (0-100 ppb; see FIG. 18h) and higher (300-3000 ppb) concentrations relevant to the doses of 2-butanol ingested; Sensitivity of mGC SMART® Devices: Low 2-Butanone Concentrations=0-100 ppb; see FIG. 18h; stability of a softgel containing the AEM according to this invention is shown in FIG. 18i.

FIG. 19. Schematic of optional features, permutations and combinations of features for embodiments of the SMART® device (Type II) according to this invention.

FIG. 20. Schematic details of a first optional arrangement of Type II SMART® device components.

FIG. 21. Schematic details of a second optional arrangement of Type II SMART® device components and output example from analysis of i-EBM.

FIG. 22. Schema showing the metabolic fate of selected ordinary isotope and non-ordinary isotope labeled alcohols, aldehydes and carboxylic acids.

FIGS. 23-53. Schemes showing particular biochemical conversions of selected molecules to exemplify fate of particular atoms which may act as non-ordinary isotopes for use as i-AEMs/i-EBMs in combination with an embodiment of the SMART® device (Type II) according to this invention.

FIG. 54. Breath Concentration-Time Profile from a 30 mg bolus of isopropyl alcohol (IPA; isopropanol; 2-propanol) delivered in a size 0 capsule to a fasting subject, showing IPA induced increase above baseline for acetone in the exhaled breath of the subject. See FIG. 55 for mGC analysis after ingestion of 10 mg IPA.

FIGS. 55A and 55B. First derivative of the mGC profile for 0, 5, 10, 15, and 30 minutes post ingestion of 10 mg IPA; 55B shows the ratio of first derivatives for the acetone/isoprene mGC profiles.

FIGS. 56A, 56B, 57A, 57B, and 57C. Real time Analysis of Acetone Breath Kinetics following Ingestion of 3 mg d8-Isopropanol Using the OrbiTrap LC/MS.

FIG. 58. Real time Analysis of Acetone Breath Kinetics following two repeated ingestions of 10 mg d8-Isopropanol and 10 mg Isopropanol Using the OrbiTrap LC/MS.

FIG. 59A. Breath kinetics of exhaled 2-butanol and 2-butanone following the concurrent ingestion of 2-butanol and ethanol. Plotting the peak height of each compound of interest as a function of time yields the breath kinetics for each potential breath marker. Even with a reasonable dose of ethanol present in the stomach, the kinetics of 2-butanone appears unaffected (or at least very similar to a typical response following the ingestion of just 2-butanol) and no significant 2-butanol was detected. FIG. 59B Breath kinetics of 2-butanone and d6-acetone following ingestion of neat 2-butanol (40 mg) and d8-isopropanol after lunch.

FIG. 60A. FTIR Analysis of Acetone and Isopropyl Alcohol along with their perdeuterated isotopologues; a tracing showing the infrared spectrum from a NIST Webbook Gas Phase IR Spectrum of 2-Propanol; In FIG. 60B, there is provided a spectrum obtained by the inventors using a Thermo Nicolet 6700 FTIR Gas Phase IR Spectrum of 2-Propanol.

FIG. 61. Panel A shows a tracing of the FTIR analysis of acetone and d6-acetone showing clear areas where these spectra are distinguishable from each other; Panel A' shows an expanded portion of the tracing from Panel A in which this is very clearly shown; Panel B shows a tracing of the FTIR analysis of IPA and d8-IPA, again showing clear areas where these spectra are distinguishable from each other. FTIR Spectra in Panel A shows the HC=O stretch for acetone at 2985 cm$^{-1}$ versus the DC=O stretch for d6-acetone at 2261 cm$^{-1}$. FTIR Spectra in Panel B shows the H3C—OH stretch for IPA at 2970 cm$^{-1}$ versus the D3C—OH stretch for d3-IPA at 2231 cm$^{-1}$. Both of these spectral shifts are easily distinguishable.

FIG. 62. FTIR Spectra of Acetone and Isopropyl Alcohol with their perdeuterated isotopologues, with a detail of each tracing in the Fingerprint Region (1170 cm$^{-1}$ to 1300 cm$^{-1}$, 8.5470 mm to 7.6923 mm).

FIG. 63. FTIR Analysis of Acetone and Isopropyl Alcohol along with their perdeuterated isotopologues; In A, FTIR Spectra of d6-acetone versus Blank Breath, with details of portions of these spectra being shown in B and C.

FIG. 64. Breath kinetics of exhaled d6-acetone following topical application of d8-isopropanol in a carbomer gel or oral ingestion of d8-isopropanol; left axis=100 mg d8-IPA oral; right axis, 20 mg d8-IPA oral and 240 mg d8-IPA topical.

FIG. 65-69. Breath kinetics of exhaled d6-acetone following the ingestion of 100 mg of d8-isopropanol per diem for 5 days.

FIG. 65 shows that native acetone peak heights remained reasonably constant throughout the study.

FIG. 66 shows that baseline levels for ion 82 (the ion used to monitor d6-acetone) were low and less than 1000 (<1% of typical acetone levels). An increase of exhaled d6-acetone was apparent within 2-4 minutes of ingesting each dose of d8-IPA. Maximum breath levels were achieved after 1-2 h and ranged from 450,000 to 800,000 peak height (~2-5× concentrations of endogenous/native acetone).

Figure 69:
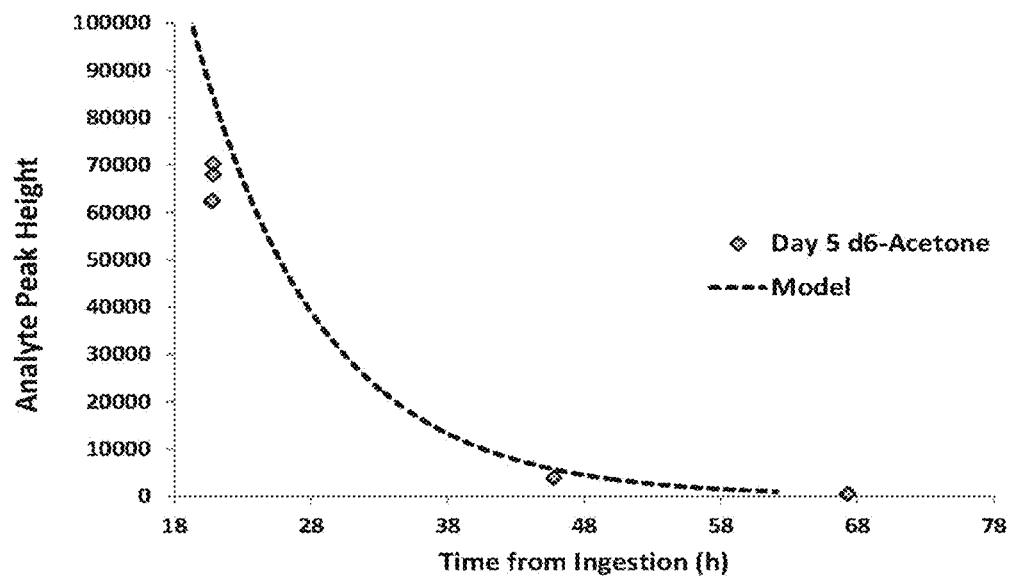
Figure 69:
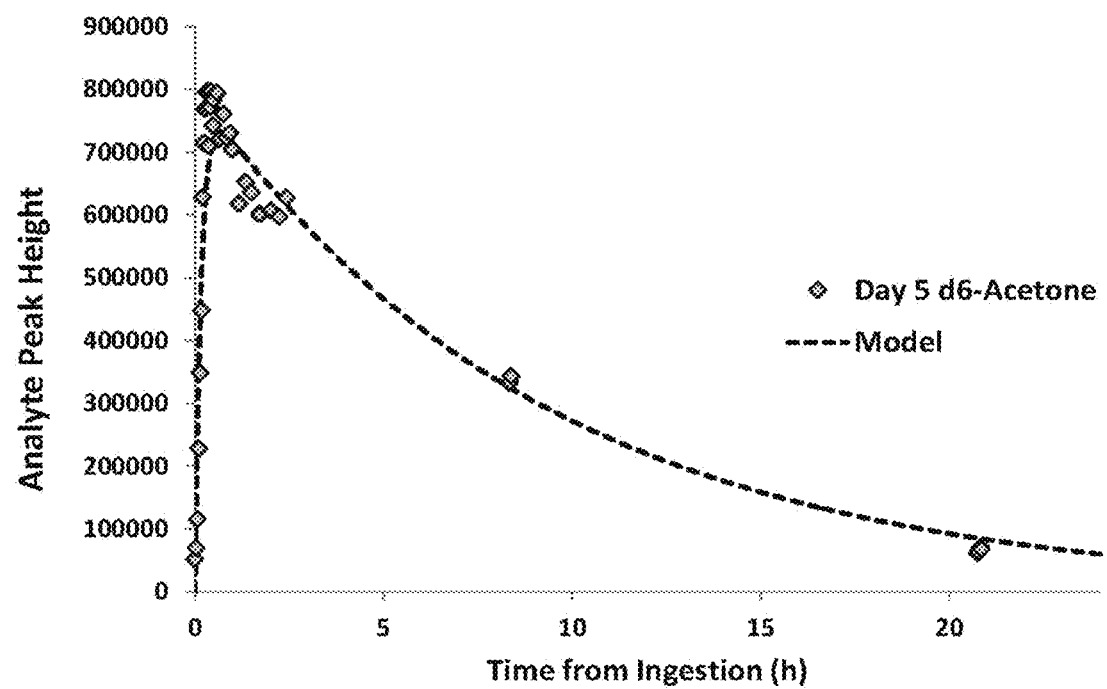

FIG. 69 shows that at this rate of elimination, approximately 6-10% of maximum peak response remains after 24 h. Such kinetics should produce steady-state trough levels that are also ~10% of the maximum peak. This matches the observed trough levels during the study.

Figure 70A:
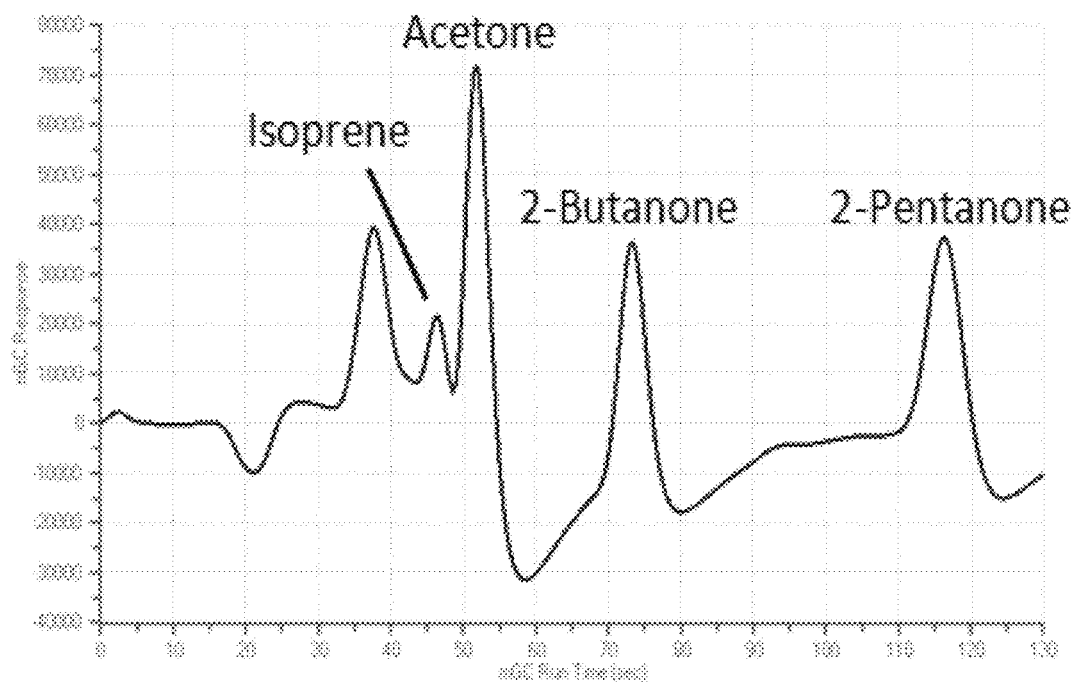
Figure 70B:
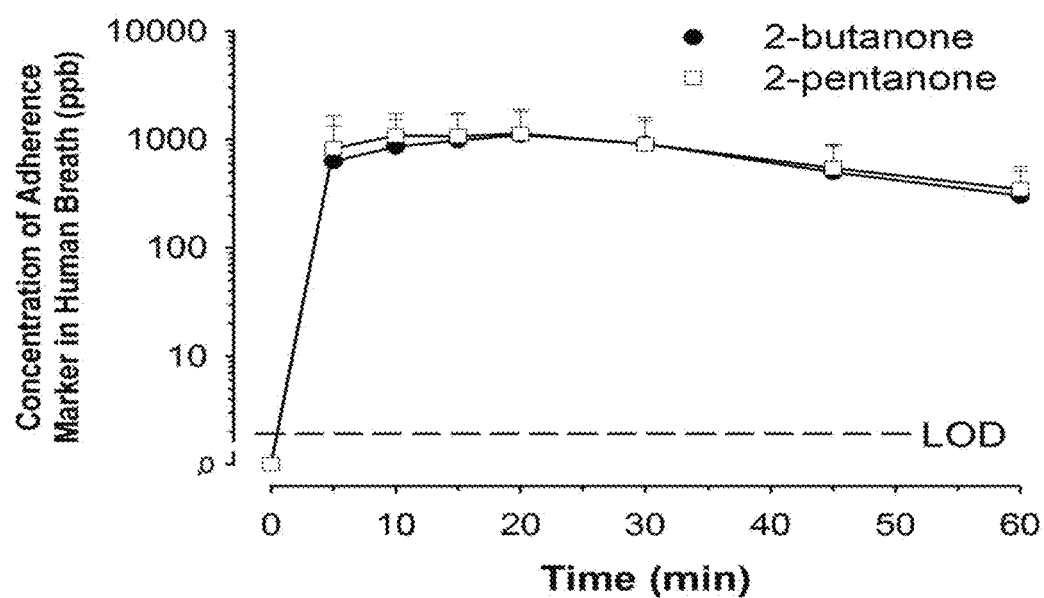
Figure 70C:
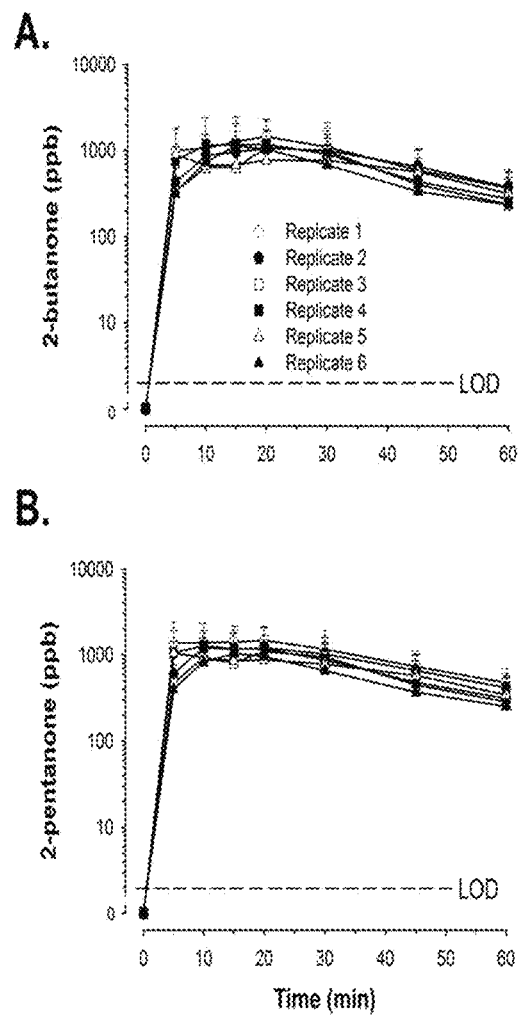
Figure 70D:
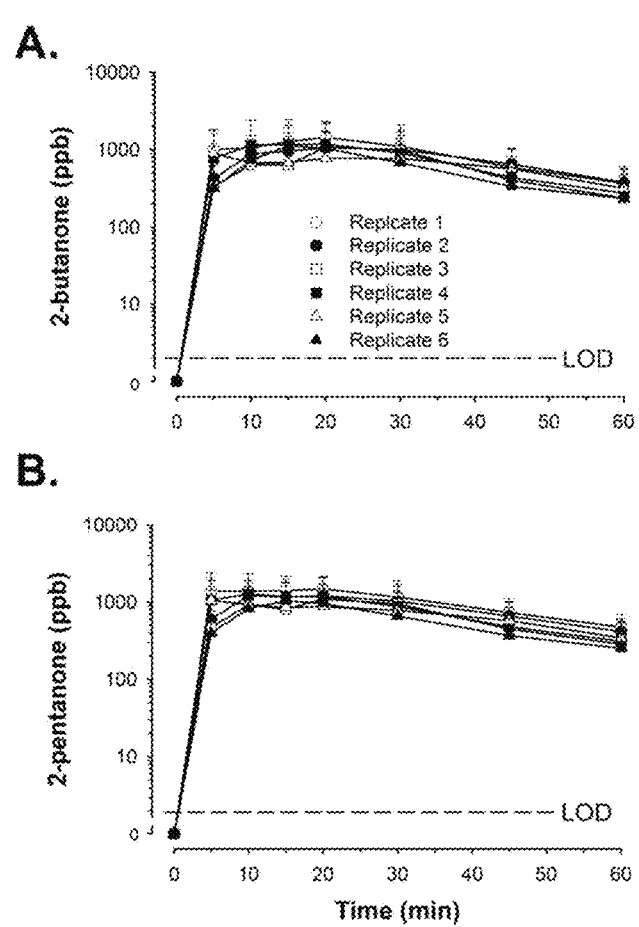
Figure 70E:
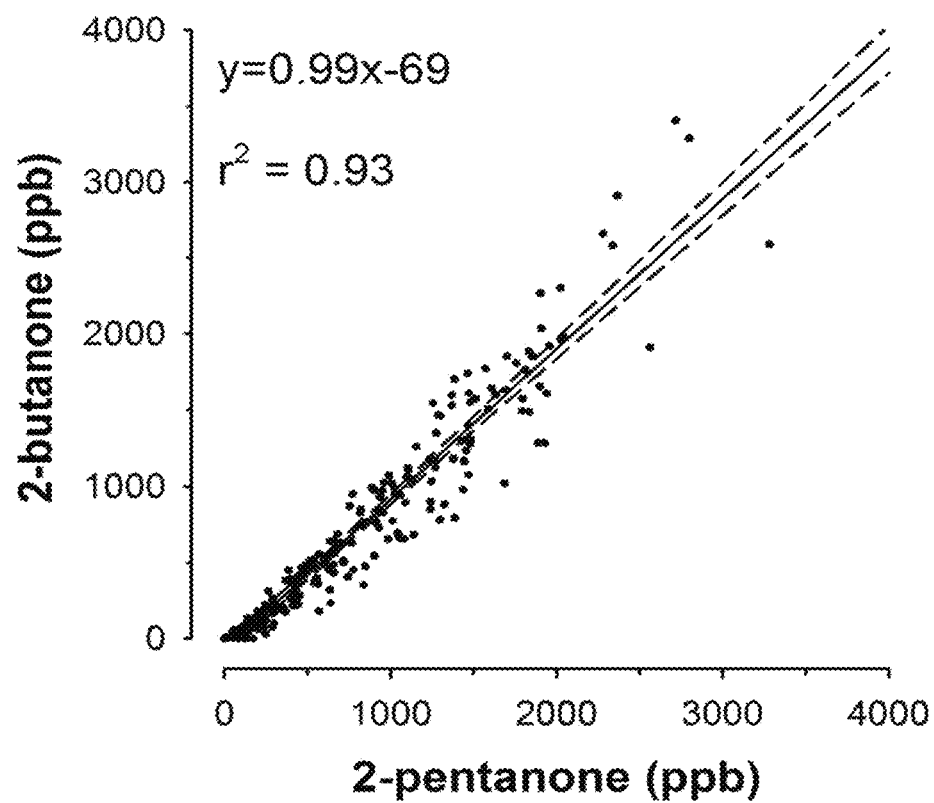

FIGS. 70A-70E. FIG. 70A—A sample mGC chromatogram of a human breath sample following ingestion of the hard gel capsule containing 60 mg 2-butanol and 60 mg 2-pentanone; FIG. 70B—concentration-time relationships for human subjects (n=5) to exhale 2-butanone or 2-pentanone after concurrently orally consuming encapsulated 2-butanol (60 mg) and 2-pentanone (60 mg) immediately after time 0 min; six replicates were conducted for each subject; note the logarithmic scaling of the ordinate axis; the horizontal dashed line designates the lower limit of detection (LOD) for the miniature-gas chromatograph; data shown as mean±standard deviation for parts-per-billion (ppb) based on molar fractions; the overall concentration-time plots for 2-butanone and 2-pentanone shown in FIG. 70B demonstrate the similarity of these relationships for both exhaled markers; FIG. 70C—inter-individual variability of the concentration-time relationships for human subjects (n=5) to exhale 2-butanone (Panel A) or 2-pentanone (Panel B) after orally consuming 2-butanol (60 mg) and 2-pentanone (60 mg) immediately after time 0 min; six replicates were conducted for each subject; note the logarithmic scaling of the ordinate axis; the horizontal dashed line designates the lower limit of detection (LOD) for the miniature-gas chromatograph; data shown as mean±standard deviation for parts-per-billion (ppb) based on molar fractions; the legend applies to both panels; FIG. 70D-intra-individual variability of the concentration-time relationships for human subjects (n=5) to exhale 2-butanone (Panel A) or 2-pentanone (Panel B) after orally consuming 2-butanol (60 mg) and 2-pentanone (60 mg) immediately after time 0 min.; the same five subjects composed each replicate; the horizontal dashed line designates the lower limit of detection (LOD) for the miniature-gas chromatograph; data shown as mean±standard deviation for parts-per-billion (ppb) based on molar fractions; the legend applies to both panels; FIG. 70E—Concentration of 2-butanone compared to that of concurrently collected 2-pentanone for all specimens collected (n=240) from human subjects (n=5) after orally consuming 2-butanol (60 mg) and 2-pentanone (60 mg); note the regressed solid line with dashed 99% confidence limits; data shown as mean±standard deviation for parts-per-billion (ppb) based on molar fractions.

Figure 71:
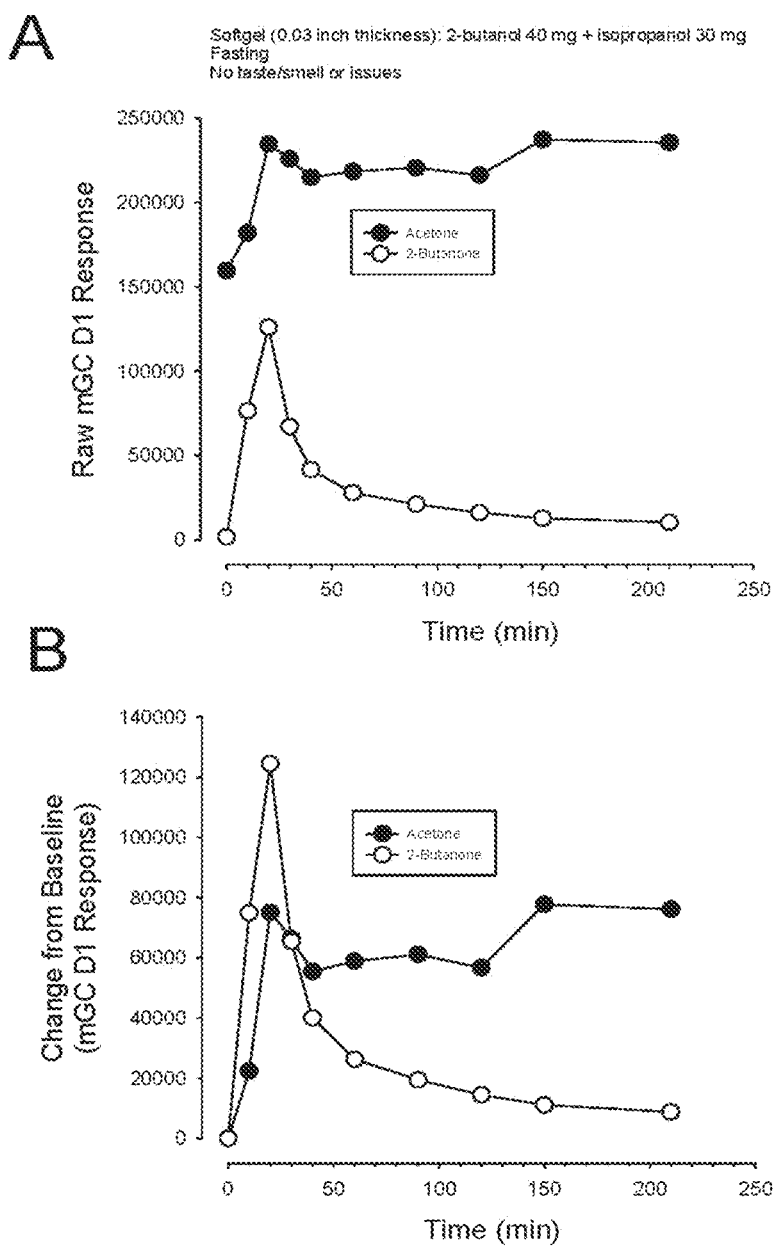

FIG. 71. Shown in Panel A of FIG. 71 is the 1$^{st}$ derivative mGC response (proportional to EDIM breath concentration) in a Type 1 SMART Device for acetone and 2-butanone as a function of breath sampling times post ingestion of the capsule. Shown in Panel B is the same data as a difference from baseline (little change in the appearance of the 2-butanone curve due to little or no background, but shifting of the acetone curve downward after subtraction of background acetone).

Figure 72A:
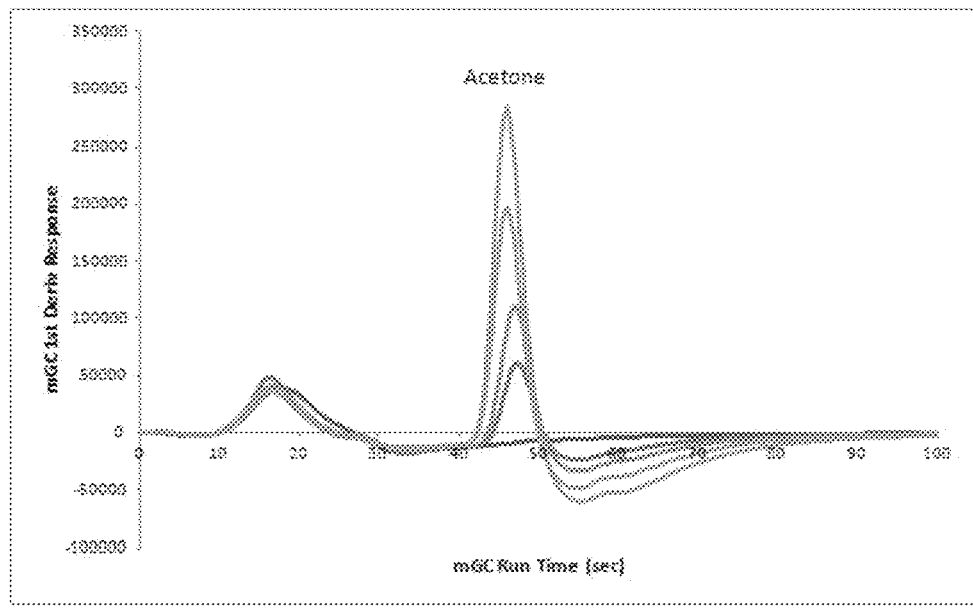
Figure 72B:
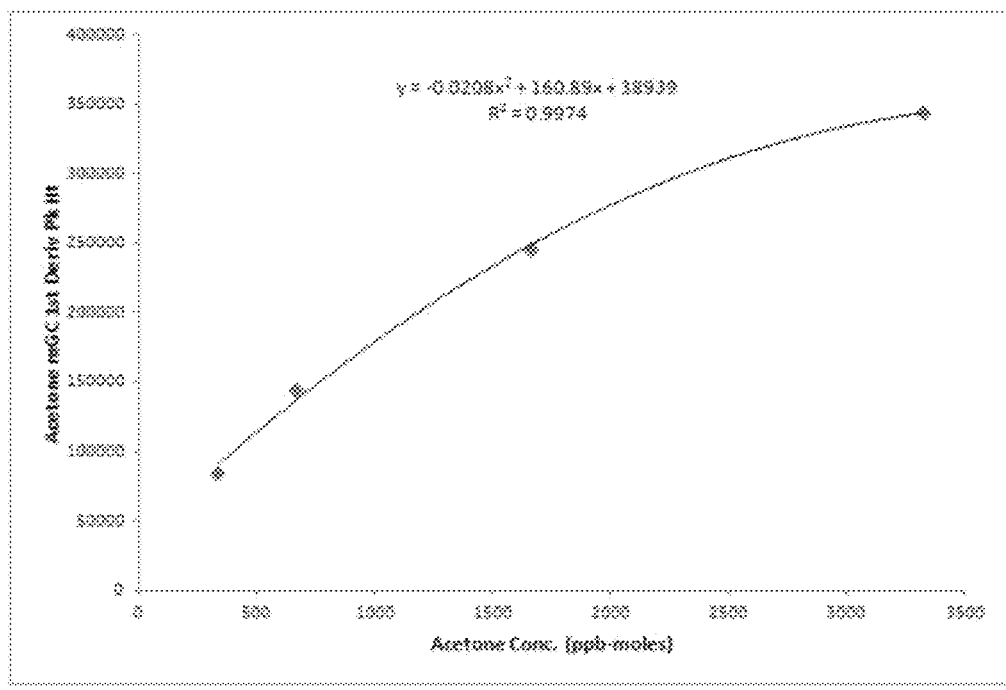
Figure 72C:
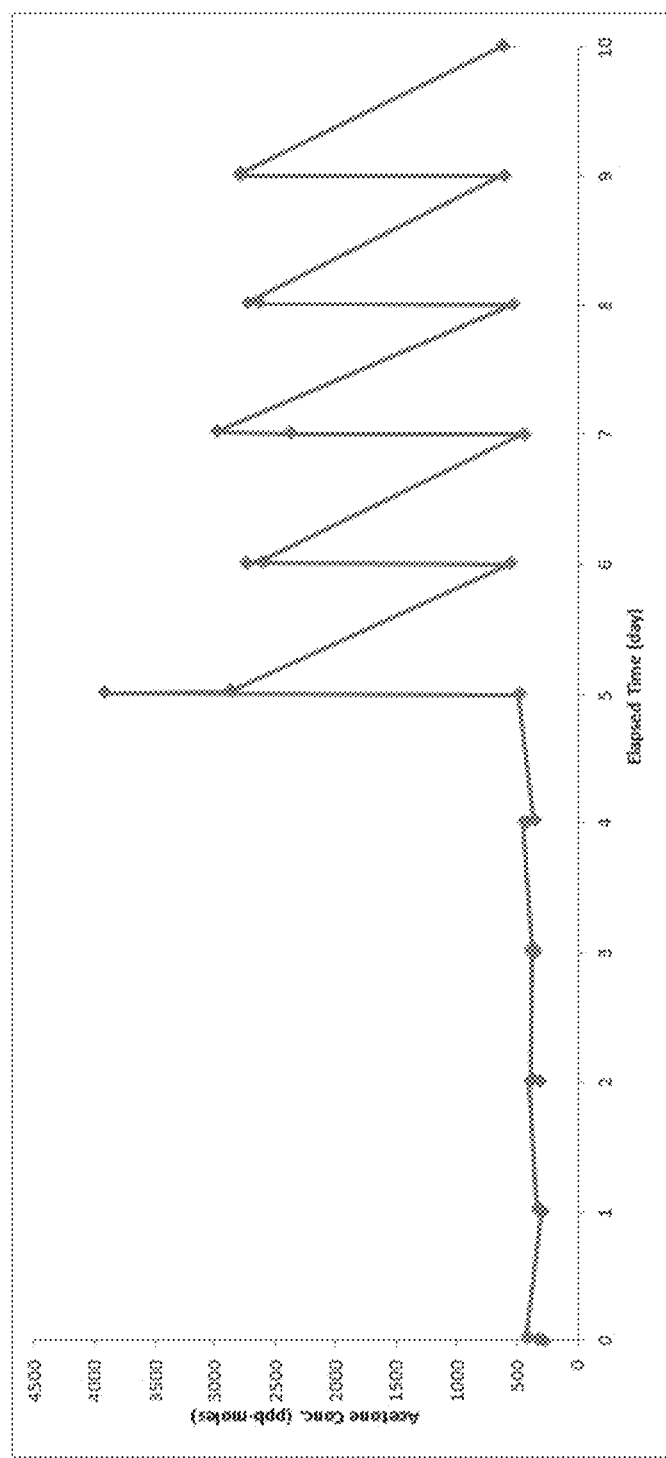

FIGS. 72A-C. IPA as an AEM using a Type I SMART® Device according to this invention. FIG. 72A—mGC-MOS Chromatograms for IPA Calibration Curve; FIG. 72B—IPA Calibration Curve analyzed on the mGC-MOS; FIG. 72C—acetone in exhaled breath (concentration in ppb) vs. time. In this example, Ingestion of 100 mg of isopropyl alcohol (IPA) rapidly increased the acetone concentrations in breath above baseline values. The rise was greater than 6× (baseline: 450 ppb vs maximum: 2800 ppb) that of baseline acetone concentrations.

Figure 73:
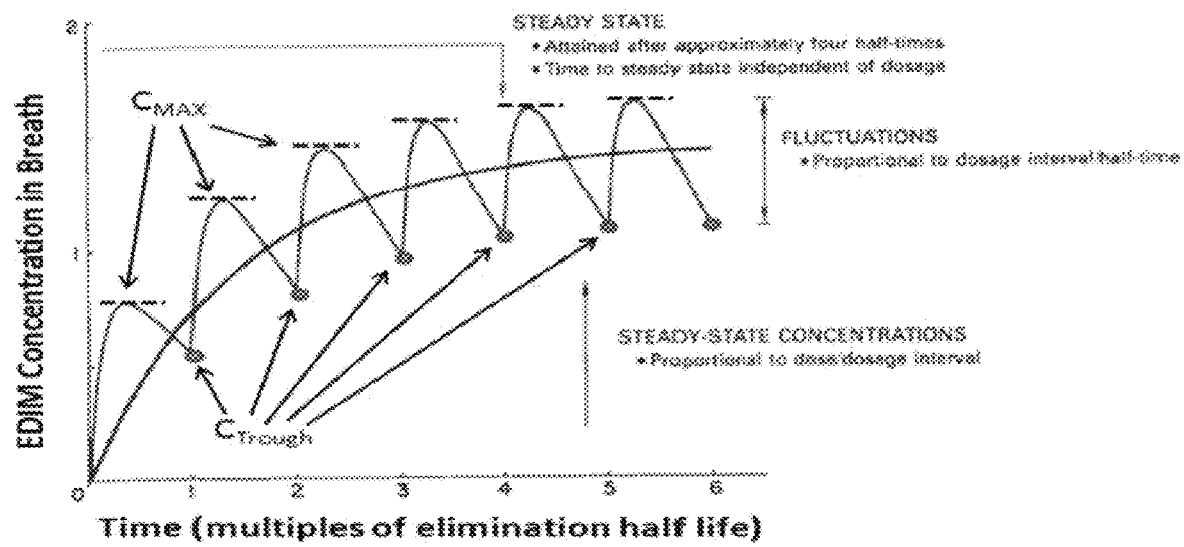

FIG. 73: Fundamental pharmacokinetic relationships for six successive administrations of an oral drug. The light line is the pattern of drug accumulation during repeated administration of a drug at an interval equal to its elimination half life, when drug absorption is very rapid relative to elimination. The concentration maxima approach 2 and the minima approach 1 during the steady state. The heavy line depicts the pattern during administrating of equivalent dosage by continuous intravenous infusion. Curves are based upon a one compartment model. The x axis represents time, as indicated by multiples of elimination half life ($t_{1/2e}$). Reference: modified FIG. 1-6, page 27, Goodman and Gilman, The Pharmacological Basis of Therapeutics, 8$^{th}$ Edition, 1993, Pergamon Press, New York, N.Y. Abbreviation Key: $C_{Trough}$, trough concentration of EDIM (circle symbols); $C_{MAX}$, maximum concentration of EDIM in breath (horizontal dotted lines).

Figure 67:
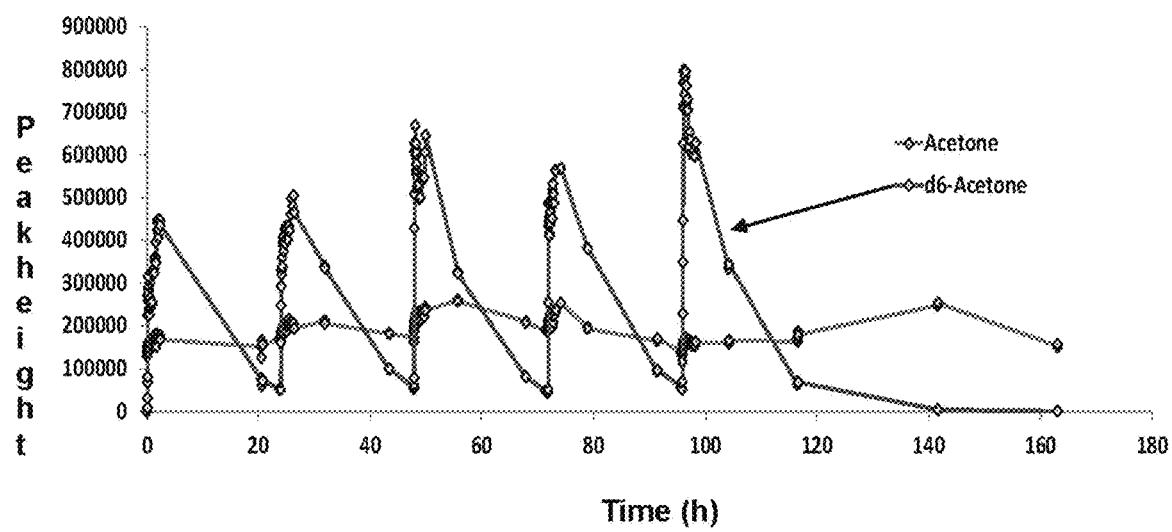
FIG. 67 shows that 24-hour trough levels were relatively unchanged over the course of the study and were ~10% of peak maximum.
Figure 74:
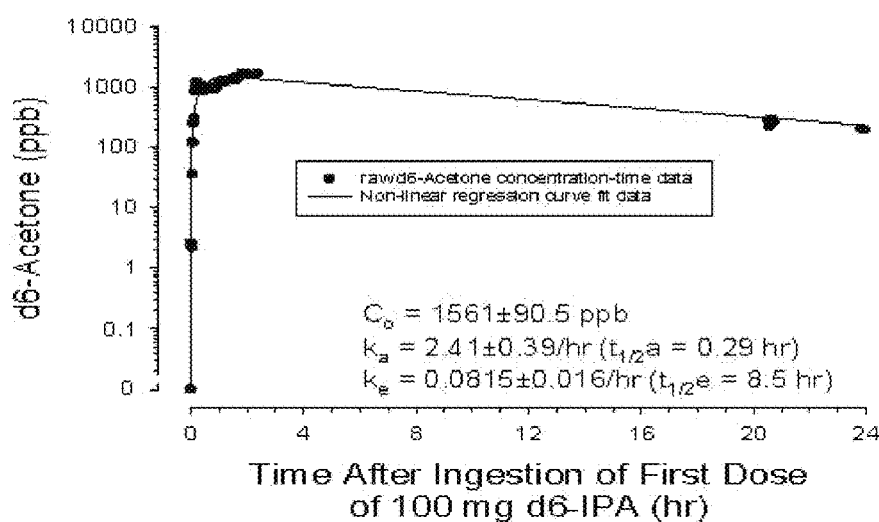

FIG. 74. First Dose PK using d8-Isopropyl Alcohol (IPA) as the AEM. The d6-acetone breath concentration-time data following the 1$^{st}$ oral dose of d8-IPA (100 mg) in a specific subject, as depicted in FIG. 67, is shown. The experimental data was curve fit (parameter estimates±SE) to Equation 1 using a non-linear, least squares (Marquardt-Levenburg) algorithm (SigmaPlot 11, Systat Software, Inc., San Jose, Calif.). According to the curve fit ($R^2$=0.84), during the 1$^{st}$ 24 hr dosing period, the values of $t_{1/2e}$ and $C_{Trough}$ level were 8.50 hr and 229 ppb, respectively. Note how absorption was faster than metabolism. Per Equation 2, $T_{Max}$ was 1.46 hr. Thus, the $F_{Lost}$ of d6-acetone during the 1$^{st}$ dosing interval with a dosing interval of 24 hr, according to Equation 6, is 0.859, and from Equation 5 the accumulation factor (AF) is 1.165. Thus, at steady state QD dosing, the EDIM $C_{Trough}$ (Equation 8) and $C_{MAX}$ (Equation 7) levels of d6-acetone are 267 ppb (=1.165×229 ppb) and 1819 (=1.165×1561) ppb, respectively. Using a limiting EDIM concentration of 100 ppt, the $T_{AdhWindow}$ for $C_{Trough}$ and $C_{MAX}$ levels of d6-acetone according to Equation 9 is 96.8 hrs (4.0 days) and 120.3 hrs (5.0 days), respectively. Note: the logarithmic scale is used on the y axis.

Figure 75:
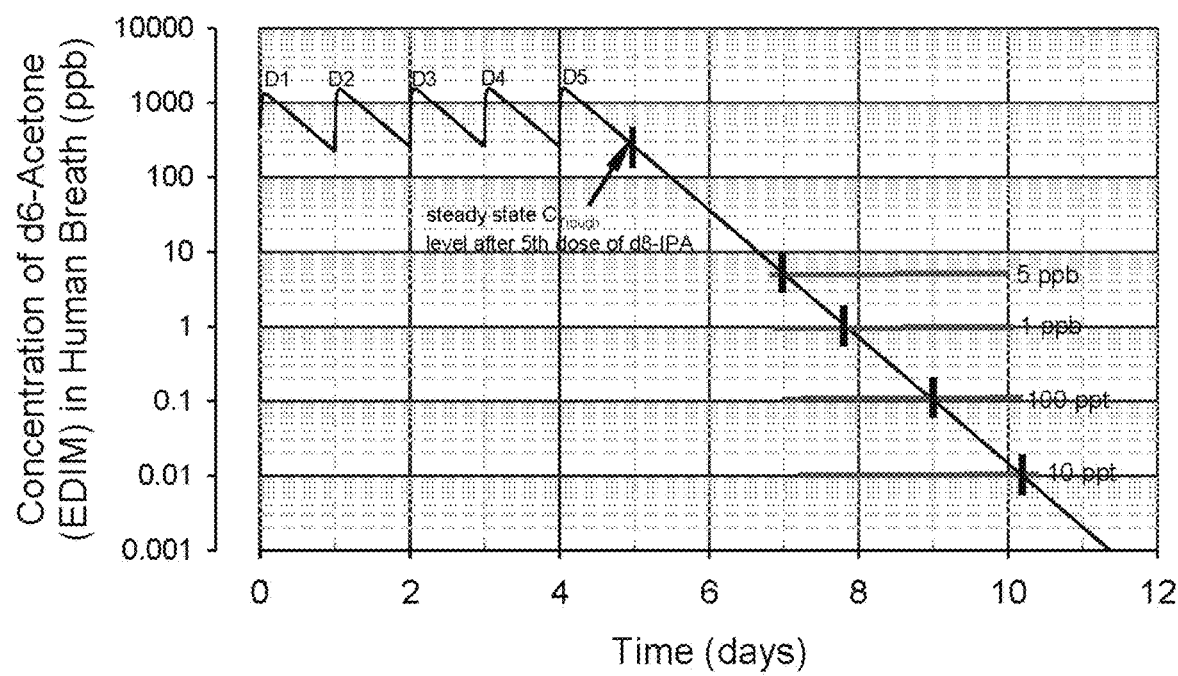

FIG. 75: d6-acetone (EDIM) concentration-time curve in a human after 5 sequential doses (D1 to D5) of d8-IPA (100 mg) with adherence "look back" windows shown at various device LoDs. With a steady state d6-acetone $C_{Trough}$ level of 267 ppb and QD dosing (dosing interval=24 hr), according to Equation 9, if the sensor LoD was 10 ppt, 100 ppt, and 1 ppb we would have adherence "look back" windows of 125.1 hr (5.2 d), 96.6 hr (4.0 d), and 68.6 hr (2.9 d), respectively. These times are indicated by the short vertical lines on the time axis. Note: Because there is no significant background d6-acetone in breath, the limit in this situation will be the device LoD. The y axis is plotted on the log 10 scale.

Figure 76:
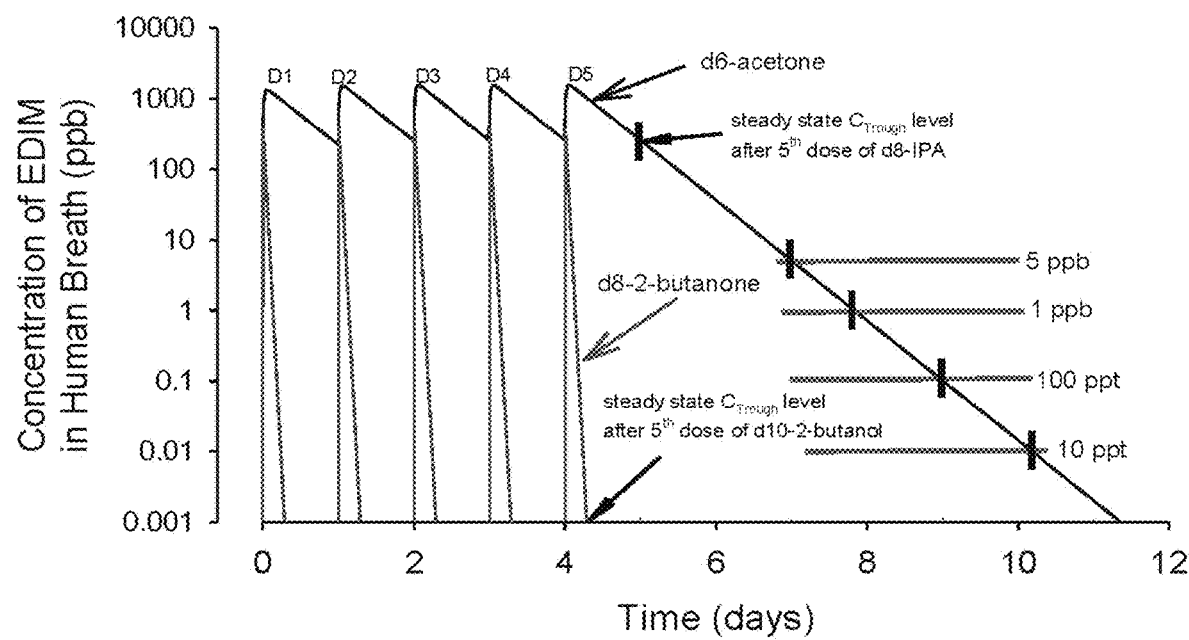

FIG. 76: Simulated EDIM concentration-time relationships generated from Equation 1 following ingestion of d8-IPA (40 mg) and d10-2-butanol (40 mg) using actual (experimental) human PK parameters for IPA and 2-butanol. The rate constant of 2-butanone, which is immediately and completely generated from 2-butanol, for absorption ($k_a$) and elimination ($k_e$) were 0.025/hr and 0.367/hr, respectively. The rate constants of acetone, which is immediately and completely generated from IPA, for absorption ($k_a$) and elimination ($k_e$) were 2.40/hr and 0.0815/hr, respectively. In the case of 2-butanol administration, between dosing (QD), the trough concentrations always return to baseline values. Thus, the presence or absence of d8-2-butanone in breath can be used to effectively detect and prevent deceit by subjects when using d8-IPA for AMAM and/or CMAM. In other words, because the d8-2-butanone generated from d10-2-butanol has a short $t_{1/2e}$, its presence should not be there if a breath is being provided later than 3 hours after ingesting the medication, or if performing a breath sample to measure $C_{Trough}$ for acetone. Hence, it can serve to prevent deception and eliminate potential interferents to the system. For example, in a 2 breath scenario with QD morning (8 AM) dosing of a medication containing the AEMs d8-IPA and d10-2-butanol, unlike d6-acetone, d8-2-butanone should not be present in the baseline breath sample during the 8 AM morning dosing. The lack of 2-butanone in breath ensures that the subject did not simply ingest the medication containing the AEMs immediately before the 8 AM dosing when they were randomly called to provide a breath sample to the SMART® device to ensure compliance. Likewise, if the subjects were randomly called at night to provide breath samples at 8 PM (12 hours after the daily morning dose), again, no d8-2-butanone should be present. The latter approach has the advantage of providing major convenience to the subjects (one breath script at night) without having to provide breath samples during the busy morning time). Note: the logarithmic scale is used on the y axis.

Figure 77:
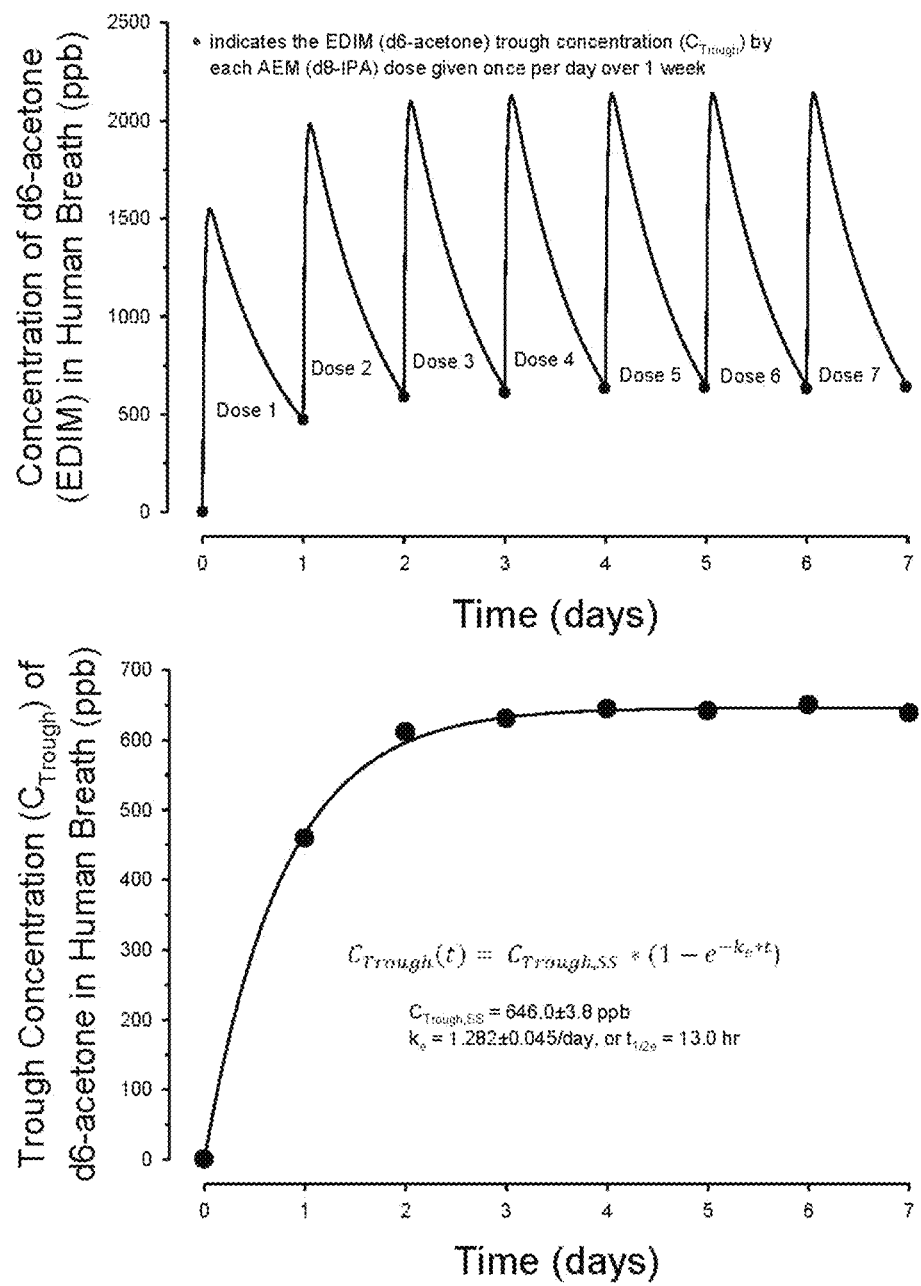

FIG. 77: Procedure to Use d6-Acetone (EDIM) Trough Concentrations ($C_{Trough}$) to Determine EDIM elimination half life ($t_{1/2e}$) and the Adherence Look Back Window ($T_{AdhWindow}$) using $C_{Trough}$ at the Individual Subject Level. Shown in the top panel is hypothetical acetone (EDIM) concentration-time data, modeled after inputting experimental values into Equation 1, for a specific subject receiving an oral medication containing 100 mg d8-IPA at a dosage interval of 1 day (administered once per day, or QD) for an introductory 7 day test period, which serves to acclimate the subject to the SMART® Adherence System and determine steady state trough levels of d6-acetone. The only parameter measured in this subject is $C_{Trough}$ for acetone, as indicated by the circles in the top panel. The $C_{Trough}$ values are measured just prior to administering the new dose of medication containing 100 mg d8-IPA. The bottom panel shows the $C_{Trough}$ versus time over the 7 dosing days at one dose per day. The experimental $CO_{Trough}$-time data was curve fit to the equation shown in the bottom panel using a non-linear, least squares (Marquardt-Levenburg) algorithm (SigmaPlot 11, Systat Software, Inc., San Jose, Calif.) to determine a $C_{Trough}$ at steady state ($C_{Trough,SS}$) and the elimination rate constant ($k_e$) of 646 ppb and 1.282/day, respectively. From Equation 4, this $k_e$ value corresponds to a d6-acetone (EDIM) $t_{1/2e}$=13.0 hr. Per Equation 9, this value of $t_{1/2e}$ using a Type 2 SMART device (IR-based) with a LoD of either 100 or 10 ppt, correspond to values of $T_{AdhWindow}$ of 164.6 hrs (6.9 d) and 207.8 hrs (8.7 d), respectively. Note: In Equation 9, the $C_{Trough,SS}$ is now $C_{EDIM,o}$ and the LoD is $C_{EDIM,Limit}$ because with d6-acetone there is no background interference. If a subject continues to reliably take his/her medication linked to the d6-IPA once per day at approximately the same time each day, the d6-acetone $C_{Trough}$ levels stay constant. In other words, if a subject is randomly called to provide a breath sample to establish a trough level at the usual time in the morning when the medication is ingested, the value of $C_{Trough}$ should be the same (within the range of values) as what was determined from the 7 day introductory period. In contrast, if the $C_{Trough}$ level measured when the subject is randomly called is lower than the $C_{Trough,SS}$, the period of time since he/she did not take their medication can be calculated by using Equation 3. For example, during a random check, the EDIM $C_{Trough}$ was found to be 50 ppb, far below the expected $C_{Trough,SS}$ value of 646 ppb. How long was the subject non-adherent? Using Equation 3, the elapsed time since the last dose was 48 hrs, or 2 days (=13 hrs/ 0.693*ln (646 ppb/50 ppb). This subject will need to be counseled and may require daily adherence assessments versus random calling.

Figure 78A:
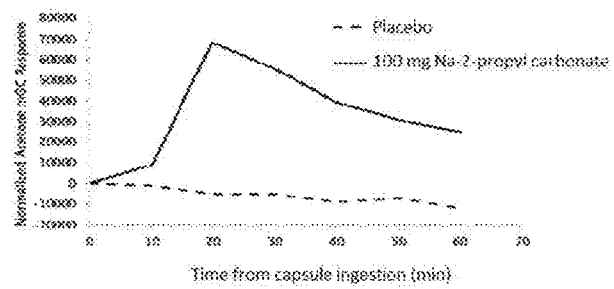
Figure 78B:
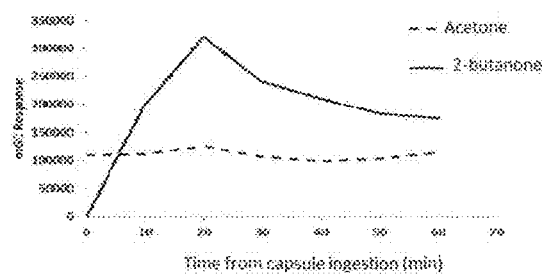

FIGS. 78A-B: FIG. 78A. Breath acetone normalized to baseline as measured by the mGC following the ingestion of a placebo capsule (dashed line) and a capsule containing 100 mg of Na-2-propyl carbonate. FIG. 78B. Breath acetone (dashed line) and 2-butanone (solid line) as measured by the mGC following the ingestion of 100 mg of Na-2-butyl-carbonate.

FIGS. 79A-D show the ability, using different AEM strategies, to achieve different rates of EBM production, from as quick as 10 minutes from ingestion for peak EBM to much longer peak EBM production times.

5.0 DETAILED DISCLOSURE OF THE PREFERRED EMBODIMENTS ACCORDING TO THE INVENTION

It is acknowledged at the outset that this patent disclosure provides a highly detailed, definite and enabling written description of a sophisticated set of technological improvements which in sum and in cooperation with each other provides those skilled in the art with reasonable certainty as to which elements to include and which combinations of elements are needed to produce a commercially viable, highly flexible, and integrated system for medication adherence monitoring. As a result, a new definition of the state of the art is provided by this disclosure. What follows is a road map for negotiating this detailed disclosure.

At least in part because of the significant adaptability of the present system to desired medication adherence monitoring modalities, the following conceptual framework is provided at the outset as a guide, or map, as to how the various cooperating components of the new system interface with each other to provide the operative system exhibiting sufficient in-built flexibility to accommodate definitive medication adherence monitoring in at least the following significantly different contexts: Acute, Intermediate and Chronic Medication Adherence Monitoring (AMAM, IMAM and CMAM, respectively).

In determining how to design, assemble, and optimize a SMART® system to provide "gold standard" performance for acute medication adherence monitoring (AMAM), intermediate medication adherence monitoring (IMAM), and/or chronic medication adherence monitoring (CMAM), four key factors are involved:

1) the half life of the EDIM in humans,
2) the concentration of EDIM or EBM in breath,
3) the sensitivity of the sensor to detect the EDIM or EBM, and
4) the level of background EDIM/EBM interference that may be present in breath.

The triad of circumstances consisting of an EDIM having the longest half life in breath being detected with the most sensitive sensor with no background interference (e.g an EBM already present or other breath markers that could mimic the EBM to the sensor) provides an optimal SMART architecture for a CMAM system.

In contrast, a triad of circumstances consisting of an EDIM having a short half life in breath being detected with a less sensitive sensor with significant background interference (EBM already present or other breath markers that could mimic the EBM to the sensor) provides a SMART architecture most suitable as an AMAM system. In such a system, it may be desirable to utilize a baseline breath, (prior to a subject having an AEM introduced into their system, to determine a profile of markers in the breath). Where it is known that there is little or no interference possible, (e.g. utilizing an i-AEM, as described herein below), a single breath may be all that is required. In addition, a single AEM may be utilized in each such mode (AMAM, IMAM, CMAM), different AEMs may be used for each such mode, or combinations of AEMS may be utilized to achieve definitive medication adherence monitoring and exclusion of interferents.

The ability to use this technology to produce a "look back" on overall medication adherence, (with or without using the system on a daily basis), over a preceding time period as disclosed further herein below, is clinically important, novel and inventive. On the one hand, to carry out ideal pharmacometric modeling, the expert wants dose by dose documentation and timing between dosing (interdosing intervals). On the other hand, the ability to conveniently monitor medication adherence over a wide range of time periods, or even at random times in the course of a medication regimen, substantially and significantly expands the medication adherence options available, beyond those of any known system, for definitive medication adherence monitoring.

5.1 Acute Medication Adherence Monitoring (AMAM)

In this context, medication adherence is monitored typically on a dose-to-dose basis, and usually from immediately or almost immediately (seconds to minutes) after a given dose of a medication is or should have been taken, up to about an hour after a given dose has been or should have been taken. In the art to date, this is the typical context for medication adherence monitoring. That notwithstanding, as will be apparent from a review of the complete disclosure which follows, the present invention disclosure provides novel and inventive advances relevant to the SMART® medication adherence device, compositions of matter, methods of making and using these and an integrated system for SMART® medication adherence monitoring. The time frame for monitoring medication adherence per this aspect of the invention is typically from as immediately as possible after a medication is taken by a subject up to about an hour or two after the medication is taken or administered in which a marker according to this invention is included with the medication for appearance and detection in the exhaled breath. For optimal marker absorption and expression of the Exhaled Breath Marker (EBM) in the shortest amount of time possible, it is desirable for AMAM enabling markers (AEMs) to have significant gastric absorption, while for IMAM and CMAM this is less critical (i.e., the marker may be taken up in the duodenum, or lower in the digestive tract). We have found that isopropyl alcohol (IPA) is an excellent marker for both AMAM, IMAM and even CMAM, as it is gastrically processed but also rapidly generated an EDIM (i.e., acetone) after oral ingestion that has a longer half life in breath—see further discussion herein below—than does butanol.

5.2 Intermediate Medication Adherence Monitoring (IMAM)

In this context, medication adherence is monitored typically on a more than single dose-to-dose basis or, even if just on a dose-to-dose basis, the time-window for monitoring is substantially more flexible than having to confirm adherence within an hour to two hours after a medication is taken. That is, a major advance provided by the present disclosure is that it enables medication adherence monitoring to occur immediately (if significant gastric absorption of the AEM occurs) to a period of several hours (up to a day) after a given dose of a medication is or should have been taken. In this embodiment the system has features of AMAM (pill by pill adherence) and IMAM (adherence look back window up to one day). In contrast, if the AEM is not significantly absorbed in the stomach and generates EDIMs with longer half lives in breath, the system could be used to monitor IMAM but not AMAM. In the art to date, there is no known system which can provide definitive medication adherence monitoring with the flexibility of this much delay from the time of taking a medication to the time when adherence has to be confirmed. The time frame for monitoring medication adherence per this aspect of the invention is typically from about one hour to up to about twelve hours following a given medication dose in which a marker is included with the medication for appearance and detection in the exhaled breath. Thus, monitoring according to this aspect of the invention may be conducted five, six, seven, eight, nine, ten, eleven or even twelve hours after a given medication dose is taken. That is, there is increased flexibility such that adherence may be confirmed any time during a specified window after taking a dose, at pre-specified time points within the relevant window, or at random times within the window.

In addition, as will be apparent from a review of the complete disclosure provided herein, more than one dose of a given medication may be confirmed in such time period, and doses of different medications may likewise be monitored in this time frame.

5.3 Chronic Medication Adherence Monitoring (CMAM)

In this context, medication adherence is monitored typically on a more than single dose-to-dose basis, and the time window for medication adherence monitoring post dose is even further extended. Insight into whether a subject is following a medication regimen as instructed is obtained. That is, a major advance provided by the present disclosure is that it enables medication adherence monitoring to occur at any time, including many hours or even days after a given dose of a medication is or should have been taken. In the art to date, there is no known system which can provide definitive medication adherence monitoring with the flexibility of this much delay from the time of taking a medication to the time when adherence has to be confirmed. The time frame for monitoring medication adherence per this aspect of the invention is typically from about eight hours, and up to about forty eight hours or more following a given medication dose in which a marker is included with the medication for appearance and detection in the exhaled breath. Thus, monitoring according to this aspect of the invention may be conducted eight, nine, ten, eleven, twelve, twenty four, forty eight or even more hours after a given medication dose is taken.

In addition, as will be apparent from a review of the complete disclosure provided herein, more than one dose of a given medication may be confirmed in such time period, and doses of different medications may likewise be monitored in this time frame.

5.4 Layout and Contents of this Patent Disclosure

In the disclosure which follows, we take up, in turn, detailed and enabling written description of:

In Section 6—the SMART® device according to this invention is described in detail, with particular emphasis on improvements made therein over and above the known generic description of such a device, with particular focus on improvements in the device for purposes of enabling AMAM, IMAM, and CMAM;

In Section 7—the SMART® composition of matter and methods of making and use thereof is/are described in detail, with particular emphasis on improvements made therein over and above the known generic description of such a composition of matter, with particular focus on improvements in the composition for purposes of enabling AMAM, IMAM, and CMAM;

In Section 8—with reference to the SMART® device according to this invention and the SMART® composition of matter, we next take up a detailed description of the improved SMART® system and methods of making and use thereof, with particular focus on improvements in the system for purposes of enabling AMAM, IMAM, and CMAM.

In Section 9—specific but non-limiting exemplary support is provided to extend the enabling written description and to provide guidance on specific implementations of the invention in different contexts.

Various permutations and combinations of these aspects of the invention enable the practice of the AMAM, IMAM, and CMAM configurations of the invention mentioned herein above. To practice this invention, an "Adherence Enabling Marker" or "AEM" is included in a medication dosage which results in the production in exhaled breath of an "Exhaled Drug Ingestion Marker" or "EDIM", also referred to herein as an Exhaled Breath Marker or "EBM". The AEM and EDIM may be the same compound, or the EDIM may be a metabolite of the AEM. Table 1 below provides a convenient guide to some of the key permutations and combinations as disclosed and described in detail in the written description which follows:

TABLE 1

SMART ® Composition and Device Combinations
Optimized for AMAM, IMAM, CMAM

| SMART ® Mode | Exemplary SMART ® Composition Embodiment - AEM | EDIM/EBM | SMART ® Device Embodiment; ordinary isotopes | SMART ® Device Embodiment; non-ordinary isotopes |
|---|---|---|---|---|
| AMAM | Short half life - e.g., secondary alcohols (e.g., 2-butanol, 2-pentanol) ± nonordinary isotopes | Ketone, e.g., 2-butanone, 2-pentanone) | GC-MOS | GC-IR ± catalytic incineration |
| IMAM | Longer half life - e.g., isopropyl alcohol ± non-ordinary isotopes | Ketones, e.g., acetone | GC-MOS | GC-IR ± catalytic incineration |
| CMAM | Longer half life - e.g., isopropyl alcohol, more complex alcohols (2-heptanol; cyclohexanol), sulfur containing food additives (e.g., dimethyl disulfoxide, allicin) ± nonordinary isotopes | ketones, e.g., acetone, ketones from larger alcohols; sulfides from sulfur containing food additives | GC-MOS | GC-IR ± catalytic incineration |

According to one embodiment of the SMART® device according to this invention, and methods of using the device and compositions of matter, the use of non-ordinary isotopes in combination with catalytic incineration is described in detail herein below. Those skilled in the art will appreciate from this summary disclosure and the detailed disclosure which follows, that in practicing the present invention, there is the need to consider the interplay of at least the following parameters:

Practice of this invention for IMAM or CMAM involves the use of AEMs with longer half lives in the biological system, including in the exhaled breath, than those used for AMAM. The longer the half life of the AEM, the longer the potential "lookback" period the AEM enables. There are also mass of marker considerations relevant to practicing this aspect of the invention. The greater the mass of marker present, the greater the potential lookback period. Maximizing the "lookback" period, however, also depends on the amount of background and noise present which can confound accurate measurement of the EDIM in exhaled breath. Use of non-ordinary isotopes in the AEM which are retained in the EDIM goes a great distance, as disclosed in detail herein below, to extending the "lookback" period and minimizing signal noise. As will become apparent, all of these considerations require optimization for a given dosage form, medication, and adherence regimen. The guidance provided herein teaches those skilled in the art to utilize appropriate markers with selected half-lives, masses, device/detector embodiments and dosage forms accommodating different marker delivery options in combination with each other in optimized configurations to facilitate definitive medication adherence monitoring in the AMAM, IMAM, and CMAM contexts to which the present system is adapted.

6.0 IMPROVED SMART® DEVICE AND METHODS OF MAKING AND USE THEREOF

From U.S. Pat. No. 7,820,108, for a "Marker detection method and apparatus to monitor drug compliance", a device is generically disclosed to determine whether a patient has taken a medication which operates by providing to a patient a medication comprising a combination of at least one active therapeutic agent and a marker which was not chemically part of the active therapeutic agent itself, but which was detectable in gaseous exhaled breath; obtaining a sample of the patient's gaseous exhaled breath; analyzing the sample of the patient's breath utilizing an electronic nose to detect the marker in gaseous exhaled breath to ascertain the presence or absence of the marker in the patient's breath. The presence of the marker being taken as an indication that the patient took the medication at a prescribed time and in a prescribed dosage and the absence of the marker being taken as an indication that the patient did not take the medication at all or at a prescribed time or in a prescribed dosage. That, in essence, defines the basis of the SMART® device, composition of matter, method and system known in the art.

Per the present disclosure, as will be seen from the detailed description provided herein below, the art is significantly advanced by greatly refining and extending what has been possible to date. This includes the establishment of a SMART® device which has a detection limit as low as 5 parts per billion (ppb) for particular EDIMs (e.g., 2-butanone, using 2-butanol as the AEM).

Detection at these and lower concentrations (see below) are established for this device with confidence limits of at least 90% and higher (see the examples). Where non-ordinary isotopes are utilized as part of the marker, detection limits in the parts per trillion (e.g. 10 PPT-1000 PPT; or 10 PPT-1 PPB; or 100 PPT-10 PPB) are enabled by particular embodiments of the SMART® device described herein. Improved combinations of biometric capture concurrent with sample collection are provided to ensure definitive medication adherence monitoring and elimination or substantially reduced possibility for "gaming the system". Portability, reliability and other enhancements are likewise provided.

In general, the device of the present invention may take any one of the following forms, each of which is described in detail herein below:

| Device Type Designation | Exhaled Breath Compound Concentration | Exhaled Breath Compound Separation | Exhaled Breath Compound Detection | Exhaled Breath Compound Incineration then Detection |
|---|---|---|---|---|
| I | + | + | + | − |
| II | + | + | --------> | + |
| III | + | − | + | − |

Each of these device types and their mode of manufacture and operation is taken up in turn herein below, following which, specific compositions (including AEMs) for use with a given device type are described and then systems integrated for use of a given device type in combination with a given composition are described.

6.1 Detailed Description of a First Embodiment (Type I) of the Improved SMART® Device A SMART® device according to this embodiment of the invention is a device comprising integrated subsystems for reliable and accurate medication adherence monitoring when a SMART® medication is taken by or is administered to a subject. The device at the heart of this invention is, where compound separation occurs, a miniature Gas Chromatograph (mGC) integrated with a sensor, such as a Metal Oxide Sensor (MOS), or an Infrared Sensor, or a Surface Acoustic Wave (SAW) sensor, together referred to herein as the mGC-MOS, mGC-IR, or mGC-SAW, respectively. The device provides integrated exhaled breath collection, analysis, biometric capture for subject identification, alarms, and data communications capabilities.

A Self Monitoring and Reporting Therapeutics (SMART®) apparatus according to this embodiment of the invention facilitates definitive documentation of medication adherence, as described herein below.

In a preferred embodiment, the SMART® system uses FDA-approved food additives, termed adherence-enabling markers (AEMs), which are or which generate volatile compounds, which appear in the exhaled breath, including the AEM itself or metabolites thereof in vivo, referred to herein as the Exhaled Drug Ingestion Marker, or EDIM, or Exhaled Drug Emplacement Marker, or EDEM, to distinguish between ingested medications with a marker (EDIM) and medications that are delivered non-orally, e.g., vaginally, rectally, transdermally, etc. (the EDEM). EDIMs and EDEMs are collectively referred to herein as Exhaled Breath Markers, EBMs. The EDIM or EDEM is exhaled by a subject following ingestion, emplacement or other means of administration of a medication including the AEM. Measurement of these markers and/or metabolites thereof in a breath sample unambiguously documents adherence (ingestion, administration or application of the medication). Where the AEMs are FDA designated Generally Recognized as Safe (GRAS) compounds, they are co-packaged or co-formulated with an active drug, also referred to herein as the Active Pharmaceutical Ingredient (API), into a capsule, tablet, cream, suppository, transdermal patch, or any other appropriate dosage form, in a manner that preferably alters neither the drug's manufacturing processes nor bioavailability. Of course, the AEM may just as well be associated with a placebo, active control or other clinical material, rather than the API, and the same or different AEM's may be used to tag different API's, placebos and/or active controls. Once ingested or otherwise administered, the AEM(s) is/are absorbed by the stomach and small intestine, or is taken up across the skin, vaginal or rectal lining, and which then appears directly in the exhaled breath or is metabolized to a volatile marker(s) which appear(s) in exhaled breath (see FIG. 1) according to kinetics known for that marker. The concentration(s) of the EBM(s) in a breath sample (~20 mL) is automatically measured by a portable, lightweight, miniature gas chromatograph (mGC) or other compound separation technology included in the SMART® device with minimal subject effort. For the first time, to the best of the knowledge of the inventors of this device, as further described herein below, a portable gas chromatographic apparatus is provided which, in combination with a sensor (e.g., a MOS sensor, an Infrared sensor, a SAW sensor, or the like), provides low parts per billion or even parts per trillion sensitivity with precision and accuracy, for particular analytes in exhaled breath. Thus, for example, using 2-butanol as the AEM, the EDIM, 2-butanone, is measured by the device according to this invention in the exhaled breath of subjects with confidence at as low as 5 ppb within fifteen to twenty minutes of ingestion of the AEM. See the examples below for details, which show that the device according to this invention provides highly linear responses at low 2-butanone concentrations (0-100 ppb), which are relevant to yes/no AMAM adherence decisions (rise in concentration=5-10 ppb).

By measuring the metabolite(s) in breath, one can be assured that the subject did, indeed, consume or otherwise receive the medication because native gastric wall and hepatic enzymes (e.g., metabolism of secondary alcohols by aa-alcohol dehydrogenase) are needed to metabolize the AEM(s) to the volatile, exhaled metabolite(s), i.e. the EDIM. Similarly, for the EDEMs, once in the biological system, appropriate uptake is demonstrated by appearance of EDEM(s) in the subject's breath. All data (date/time stamps, breath chromatographs, yes/no adherence assessments, mGC self-diagnostic quality assurance logs) are stored locally in the mGC device on an, e.g., internal USB flash drive or equivalent storage medium for later collection and/or transmitted in near real-time using integrated encrypted Health Insurance Portability and Accountability Act (HIPAA)-compliant wireless or cellular router technology to a central data repository for analysis.

Additional, optional, data streams are available to investigators or other clinical study personnel should the study or medication regimen requirements warrant collection when compared to subject privacy concerns: 1) a camera in the SMART® device is time-gated to concurrent breath collection; this biometric capture (e.g., facial picture; in one embodiment, if the biometric data captured does not match biometric data stored in the device or in a central data collection facility, the breath collection may be terminated, or the data may be flagged, or appropriate personnel may be alerted) allows investigators to definitively confirm that the breath analyzed by the SMART® device originated from a specific subject at a particular time (when the breath sample was collected), and, 2) the concentration of other compounds, e.g., ethanol in a subject's breath sample that may be of particular interest to investigators in a given field (e.g., for investigators studying psychotropic drugs, or drugs with CNS effects, it is relevant to know if observed behavioral effects arise as a result of the study medication or due to confounding effects produced by ingestion of other compounds, such as ethanol). These data can likewise be stored locally on the SMART® device and/or transmitted to a HIPAA-compliant data repository.

Those skilled in the art will appreciate that in place of or in addition to the camera, other biometric or subject identification means may be employed. For example, rather than a camera, a retinal scanner may be used. Alternatively, each subject may be accorded a radio frequency identification (RFID) transmitter or the like, so that actuation of the SMART® device includes confirmation by the device that the RFID of the subject providing a given exhaled breath sample is the appropriate individual being monitored. In yet another alternative, the device is adapted to detect an RFID on a blister pack, medication container or the medication itself to confirm appropriate medication and/or dose is being taken. Of course, unless implanted, intentional "gaming" of the system could potentially still occur by, for example, handoff of an RFID tag by a given subject. Accordingly, biometric confirmation concurrent with exhaled breath sample provision is preferred.

Data acquired by the device are logged into secure, for example internet-based, HIPAA-compliant storage for review by authorized investigators anywhere on the globe with an internet or equivalent distributed data connection. Investigators may choose to actively review the data on a daily basis to understand day-to-day adherence (active management), to maintain data securely in a blinded fashion until assignment unmasking (passive management), or some combination of active/passive review desired by the study team. Considerable flexibility may be built into this aspect of the system. For example, Data may or may not be reviewed as it is acquired. If reviewed, it may be reviewed in a blinded or unblinded context (with respect to subject identity, treatment modality), and action can be taken based on incoming data review or not. In a preferred embodiment according to this invention, biometrics are encrypted. In a further preferred embodiment, the biometric data are automatically checked against a biometric record of a given subject, without the need for any human access to the biometric. In yet a further preferred embodiment according to this invention, photographic images of a subject are obtained via a camera adjusted for focus to a very close focal length, so that essentially only the face of the subject is captured in the image, without much or any background capture, to avoid privacy concerns. As the camera is time gated to breath sample provision, other privacy concerns are likewise eliminated.

These data allow researchers to know if subjects were actually ingesting/administering the assigned research article (e.g., a particular study medication), and following scheduled dosing. This information is important when assessing the safety and efficacy of a drug. As a result, dose-to-dose intervals and pharmacokinetic/pharmacometric/pharmacodynamic drug modeling options are available from this system to inform ongoing treatment modalities. The health outcomes associated with suboptimal adherence to a drug could be assessed, and motivations for adherence in different states (e.g., healthy/ill; home/travelling) could be investigated since adherence data by time/date is made available by this system. In addition, this system enables reliable study of the effects of behavioral interventions to improve adherence. Clinical investigators will likely identify other new uses for this system as it becomes available for full use in a broad swath of studies across multiple populations and locations.

The key to understanding adherence, like any scientific data, is measuring it. The breath-based SMART® technology system provides this tool to scientists and clinical trial investigators.

From a subject's perspective, the adherence measurement system is easily portable and designed to be self-administered by subjects in their own residences, workplaces, or in an appropriate clinical setting. This feature offers significant subject convenience and investigator economic benefits compared to frequent appointments with study staff for directly observed therapy (DOT), the "gold standard" of adherence, (to the extent that up to now any gold standard could be said to exist). Additionally, no study staff is required for daily assessments, the SMART® system provides a cost-effective option for definitive adherence monitoring and data acquisition, as compared with DOT, which is generally available only during business hours and not during weekends or holidays. Overall, the change in subject behavior is simply an approximately 5 or so second breath exhalation into the mGC within an optimal time period after orally consuming or otherwise emplacing a medication comprising a SMART® AEM. A somewhat longer lag time may be required for transdermally delivered medications, but the principles are the same. By altering AEM dose and/or type, the rate of appearance in breath and duration of marker persistence in breath can be adjusted to maximize versatility of the SMART® system. All breath analyses and data logging/transmissions are preferably automatic (i.e. do not require subject action). Alternatively, in one embodiment according to this invention, the device is adapted to receive an active indication by a subject that a dose of medication has been taken, and that data may be included in the acquired data that is logged, transmitted and available for analysis. Usability studies conducted under NIMH 2R44MH081767-02A1 with an early prototype of the SMART® device indicated a high degree of satisfaction with this system by HIV/AIDS patients receiving adherence measurement for highly active antiretroviral therapy (HAART) (Morey 2012 J. Clin. Pharm; Morey AIDS beh. 2012; van der Straten AIDS Beh. 2013).

6.1.1 SMART® Medication Adherence

To date, Xhale, Inc. has focused its development efforts on commercial development of the SMART® adherence devices for use in combination with Solid Oral Dosage Forms, SODFs, particularly tablet- or capsule-based medications, which are swallowed, enter the stomach, and are absorbed in the gastrointestinal tract. In this case, definitive adherence is indicated within minutes or at most hours from the time of ingestion of such a SODF by the detection in the exhaled breath of a metabolite of an AEM, also referred to herein as a taggant (preferably a GRAS flavorant and most preferably a direct food additive) which may also be the EDIM or which is the source for the production of the EDIM. The taggant is packaged together with the API in the final SODF, although means for separation of the taggant from the API is preferably employed, according to the disclosure found in WO2013/040494. In such embodiments, the SMART® system has successfully employed 1) various formulation strategies that incorporate taggants into the final dosage form, preferably without or minimally altering the CMC per se of the CTM (Clinical Trial Material), investigational drug, or marketed drug, and 2) a mGC-MOS as the SMART® device to measure the EDIMs.

Prior to describing elements of the current invention in detail, a brief review of some key aspects of taggant chemistry is provided here.

Consider a scenario where a patient with a specific disease ingests an active drug, A, for treatment, which is metabolized by enzyme(s) to Al plus other irrelevant metabolites. In this example, a safe taggant (e.g., GRAS flavorant) without pharmacological activity called T, which may be metabolized to a major metabolite, Tl plus other irrelevant metabolites, is packaged with A. Thus, the two relevant metabolic reactions are: 1: A→A1+others 2: T→T1+others.

With regard to measuring a marker that appears in breath, the EDIM(s), which can be measured to verify that A was orally ingested by the patient, four chemical candidates are available: 1) A; 2) a major metabolite of A, Al; 3) a taggant, T, which was ingested with the medication containing A; or 4) a metabolite of any taggant (T), Tl, which was generated via enzyme metabolism of a taggant (T). The appearance of Tl about 5-10 minutes later in the breath can be used to document the active drug A (the Active Pharmaceutical Ingredient, or API or CTM) was actually ingested. To optimize performance of the adherence system, we have developed novel compositions of matter (see Section 7 below) wherein a taggant is included in, for example, a soft gel capsule or in another physical or chemical form which is stable, (see exemplary support for e.g. a carbonate which is surface coated onto or surface printed onto an API dosage form, while persevering, where considered necessary, an impermeable physico-chemical barrier between the taggant and the API, and which is rapidly converted into the Exhaled Breath Marker, EBM, on introduction into the biological system), and which is well tolerated by subjects, which generates markers in the exhaled breath which are quickly and reliably detected, and which do not interfere with co-delivered APIs.

Any appropriate AEM composition (and resultant EBMs, including EDIMs, EDEMs), including but not limited to the taggants, markers, dosage forms and the like disclosed in, for example, "Marker detection method and apparatus to monitor drug compliance", U.S. Pat. No. 7,820,108; US 2005/0233459; "System and Method of Monitoring Health Using Exhaled Breath", US2007016785; "Methods and Systems for Preventing Diversion of Prescription Drugs", US20080059226; "Medication Adherence Monitoring System", US 2010/0255598; or in WO2013/040494, published 21 Mar. 2013, entitled "SMART™ SOLID ORAL DOSAGE FORMS", may be used in combination with the SMART® device disclosed herein.

6.1.2 The SMART® Adherence Device According to this Embodiment of the Invention Definitions and Product Name References Components described as being "operatively coupled" are components that are at least in communication with each other and operation of one of the operatively coupled components has an impact on the operation of the other operatively coupled components. This can include one of the operatively coupled components directly or indirectly controlling the operation of the other component, as in a CPU programmed to control peripheral elements of a device or system. This can also mean that operation of the first operatively coupled component results in modification of the operation of the second component, including when the first component does not directly or indirectly control operation of the second component.

Contacting a device with a gas means that a sample of the gas is introduced into the device's operative mechanism for analysis of components of the gas. This may include separation of components of the gas. It may include detection of particular species in the gas. It may include quantitation of species in the gase. It may include contacting of the gas with sensors of different specificity such that by comparing what is sensed by a first sensor with what is sensed by a second sensor, the difference in what the two sensors detect provides affirmative information about the presence, absence and even concentration of a given gas species.

Acronyms

CPU: Central Processing Unit
GC Gas Chromatograph
GUI: Graphical User Interface
lbs: pounds
LPM: Liters per minute
ml: milliliters
mm: millimeters
ppb(v): parts per billion (by volume)
ppm(v): parts per million (by volume)
ppt(v): parts per trillion (by volume)
sccm: standard cubic centimeters per minute
SOP: Standard Operating Procedure
USP: United States Pharmacopoeia
VOC: Volatile Organic Compound
Product Name References Throughout the development of the SMART® mGC system, we have utilized several reference names for the device.
SMART® Model 100 Adherence Monitor
SMART® adherence monitor
SMART® device
Mini GC
Handheld Miniature GC
Handheld GC
mGC
mGC-MOS
We also refer to the disposable patient interface as:
Straw
Mouthpiece
Disposable straw
Disposable Mouthpiece
When used herein, the terms "operative communication" or "operative coupling" or "operative electrical coupling" mean, based on the context of where these terms are used, that the described elements communicate with each other or one element is controlled by another, either electrically or mechanically, based on system design features and/or programming scripts included in a controller device to which other devices are linked.

EDIM—Exhaled Drug Ingestion Marker, an Exhaled Breath Marker (EBM) generated when an AEM is ingested.

EDEM—Exhaled Drug Emplacement Marker, an Exhaled Breath Marker (EBM) generated when an AEM is applied topically or introduced by a means other than ingestion.

AEM—Adherence Enabling Marker, which itself can be the EBM (EDIM or EDEM), or which gives rise to the EDIM or EDEM via metabolism, in vivo, of the AEM; while specific secondary alcohols are provided as examples, such examples should be considered non-limiting for the AEM; preferably, the AEM according to this invention is a GRAS compound, including but not limited to food additives which give rise to volatile metabolites in the body when metabolized.

EBM—Exhaled Breath Marker (e.g., EDIM, EDEM).

To the extent possible, the same numbering is used for like elements shown in various representations of the device according to this invention, with, not necessarily, all elements being shown in every such representation.

Figure 1:
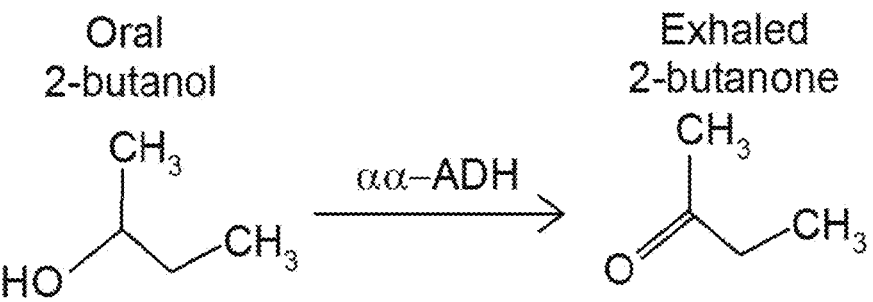
Figure 1:
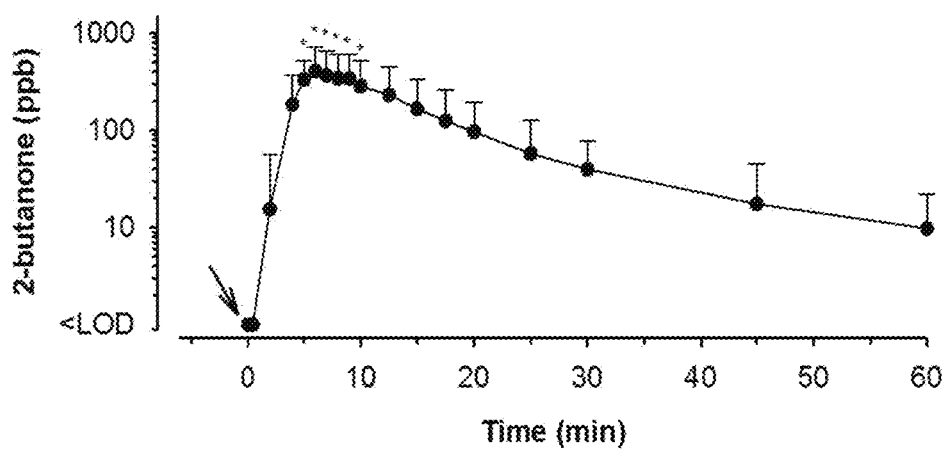
Figure 2A:
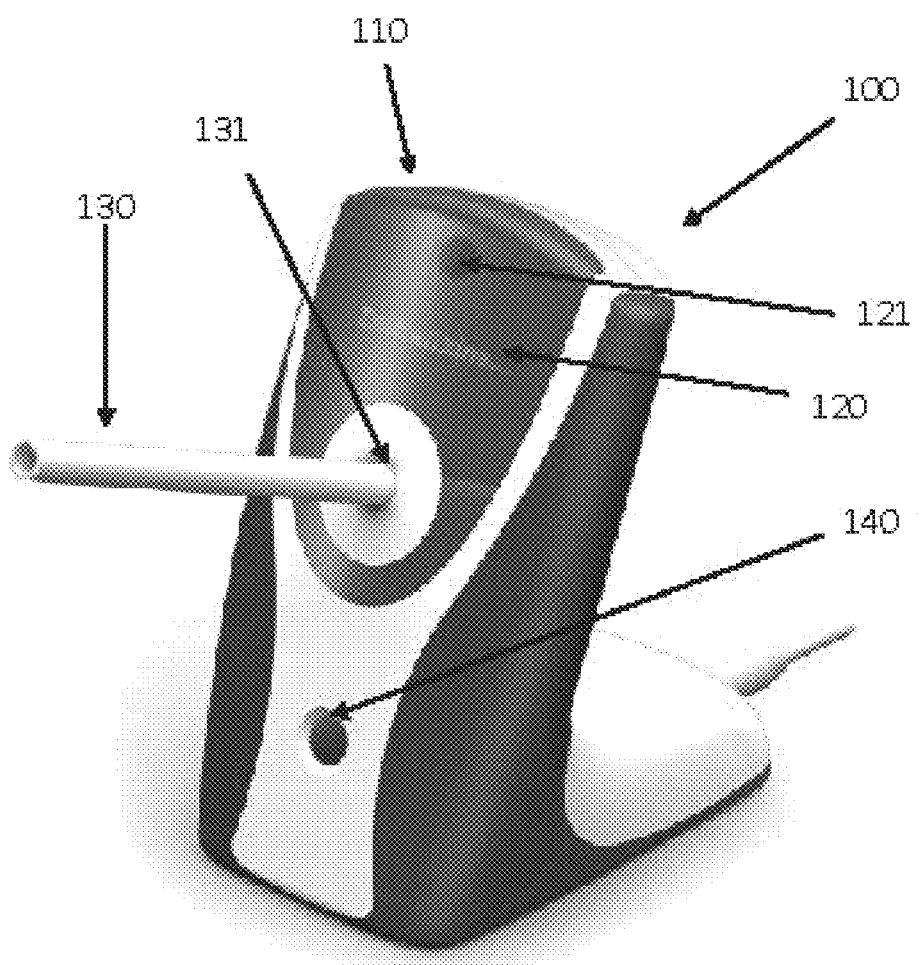

With reference now to FIG. 2A, there is provided a first representation of one embodiment of the SMART® mGC system 100 according to this invention. The SMART® mGC system 100 is an easy-to-use, handheld instrument which is essentially a miniature gas chromatograph ("mGC") comprising a housing 110, a display 120 which may also include, in a preferred embodiment, a photographic image capture device 121 to concurrently document the image of the subject exhaling into the device, an exhaled breath receiving mouthpiece 130, inert to VOCs in the exhaled breath, also referred to herein as a "straw", which is inserted into the mouthpiece receiver port 131, and an activation or "Start" button 140.

Those skilled in the art will appreciate that while this representation provides a first configuration of the physical parameters of one embodiment of the SMART® device according to this invention, alternate configurations come within the scope of this invention, as shown and discussed in the "Alternate Configurations" section of this disclosure.

Figure 2B:
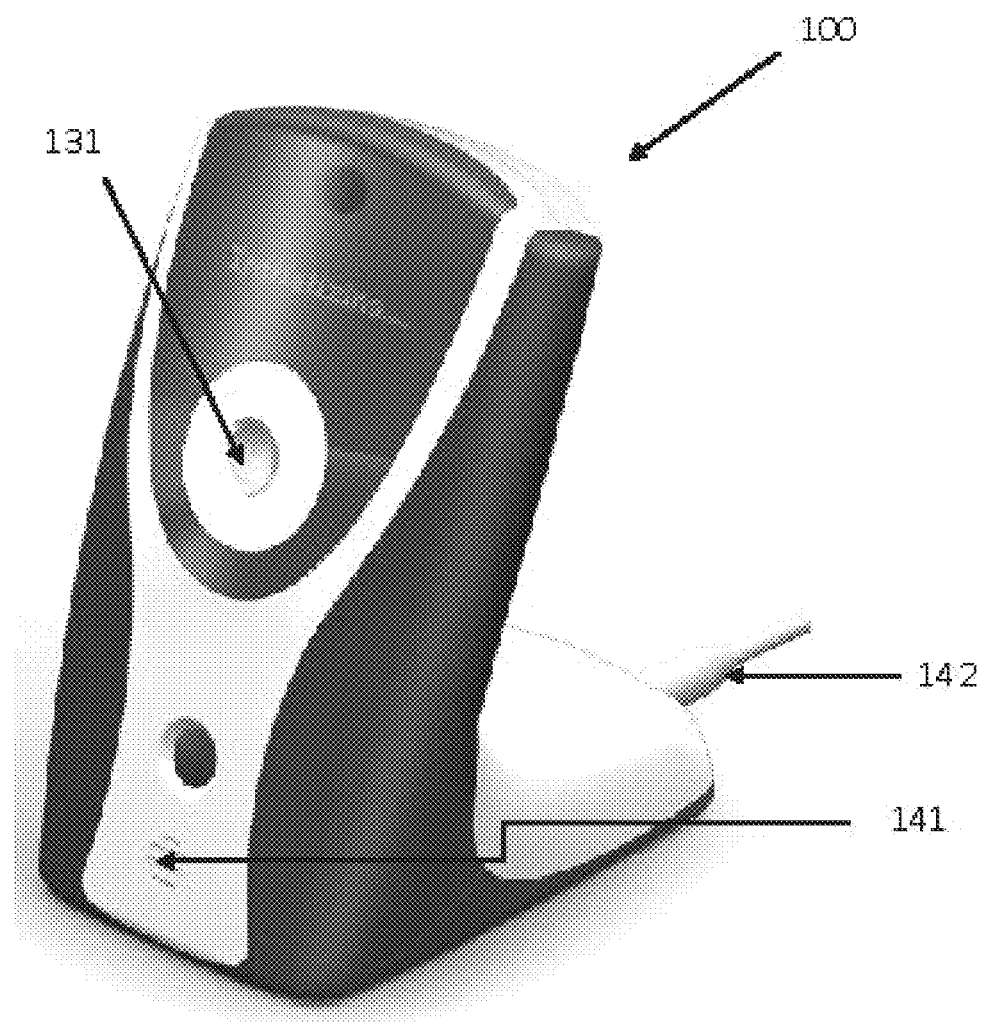

In FIG. 2B, there is shown an embodiment of the SMART® device, 100, identical to that shown in FIG. 2a, (and therefore elements labeled in FIG. 2a are not again labeled in this figure), with an added representation of a loudspeaker 141 which provides audible alerts and user prompts. In this representation, the mouthpiece 130 has been removed to more clearly reveal the mouthpiece receiver port 131. On the rear panel of the housing 110, there is provided, in appropriate embodiments, an input power jack and electrical power connection 142 for powering the device or, in an embodiment which includes an internal or external rechargeable power pack, recharging the battery pack via an external wall transformer. In alternate embodiments, the battery pack itself may be exchanged out of the device or be rechargeable or other forms of replaceable power may be utilized, such as standard disposable batteries.

The SMART® mGC System according to this invention is designed to analyze gaseous samples (e.g., human breath or breath of other vertebrates) for suitable organic molecules of clinical interest, and, particularly, EDIMs and/or EDEMs.

Gas chromatography is an extensively used analytical technology, and the physicochemical basis of its operation is well documented and understood. While the principles of operation for the breath analysis (or gas sample analysis) performed by the SMART® mGC are similar to the principles of operation for a standard gas sample analysis using currently marketed bench-top gas chromatographs, the specifics of the mGC SMART® device according to this invention are unique. Thus, an aspect of the present invention is the provision of a robust, miniaturized, portable, accurate, HIPAA-compliant commercial device and systems and methods for using this device for medication adherence monitoring. Naturally, of course, the mGC according to this invention may be utilized in a wide variety of applications wherever an accurate portable gas chromatograph would be of use. Thus, for in-the-field monitoring of volatiles, e.g., in the industrial workplace, or to monitor emissions, the mGC according to this invention would be an accurate and valuable tool. Naturally, for such applications, features included in the present disclosure need not necessarily be included—such as, for example, the biometrics capture discussed herein above.

6.1.3 Device Subsystem Block Diagram

Figure 3:
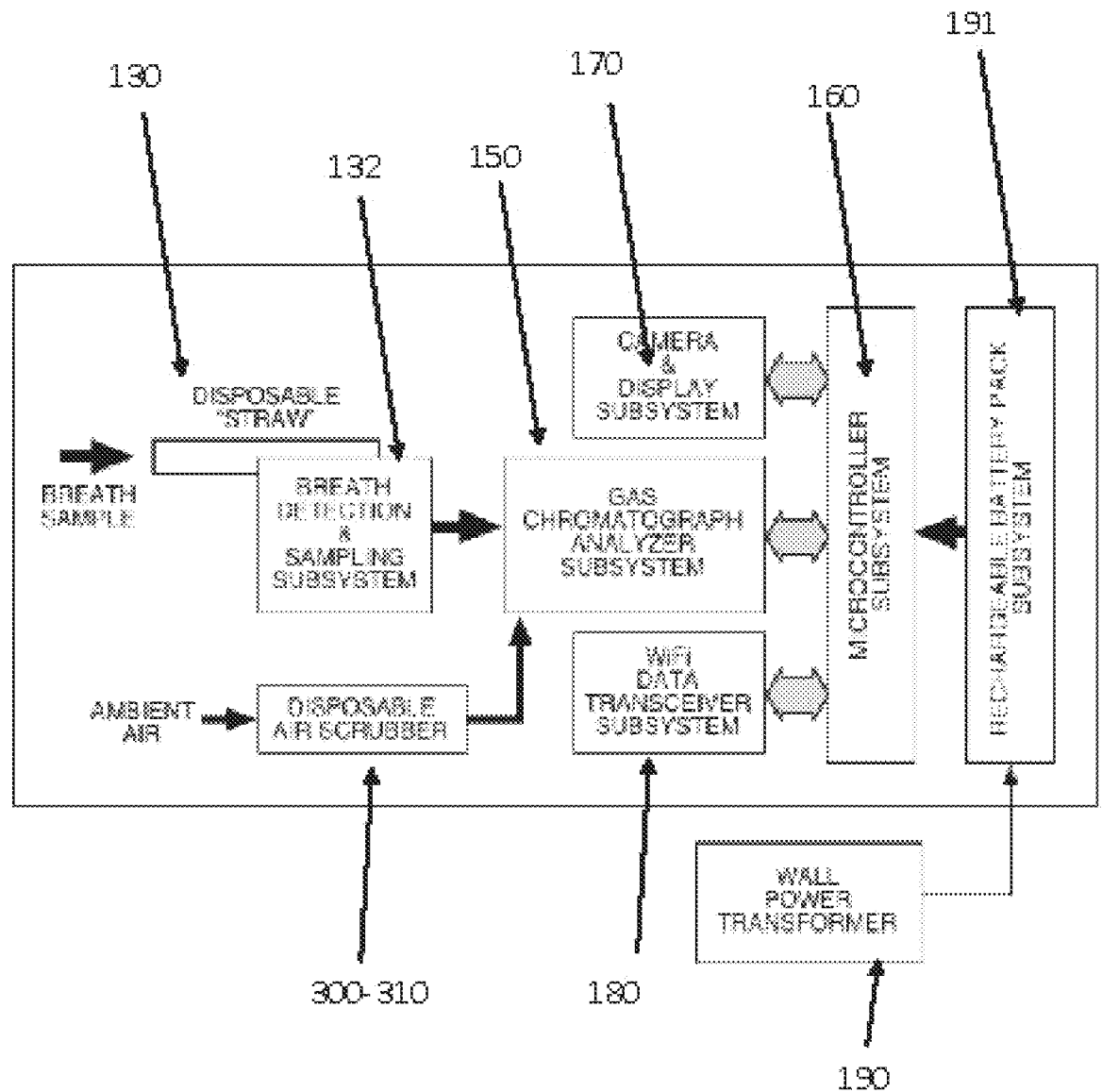

The block diagrams in FIGS. 3 and 4 detail key subsystems and their interconnections within the SMART® mGC apparatus according to this aspect of the invention.

Referring now to FIG. 3, there is shown an embodiment of the mouthpiece that accepts the breath sample, also referred to as a disposable straw, 130, which is configured to supply breath components to a breath detection and sampling subsystem, 132, which is operatively coupled to a gas chromatograph analyzer subsystem 150. On insertion into the device, the mouthpiece 130 is detected by a straw/mouthpiece sensor 133 to confirm proper engagement and readiness to receive an exhaled breath sample. An ambient air stream is routed via a disposable air scrubber (see description below, FIG. 4C, elements 300-310), to provide a carrier air system for the gas chromatograph analyzer subsystem 150. A microcontroller subsystem 160 integrates with the gas chromatograph analyzer subsystem 150, and concurrently controls the operation of a camera and display subsystem 170, and a WiFi, cellular or other communication means including data transceiver or mobile cellular data hotspot subsystem 180. A wall power transformer 190 provides power to the device including, optionally, a rechargeable battery pack subsystem 191.

6.1.4 Device Subsystems

Figure 4A:
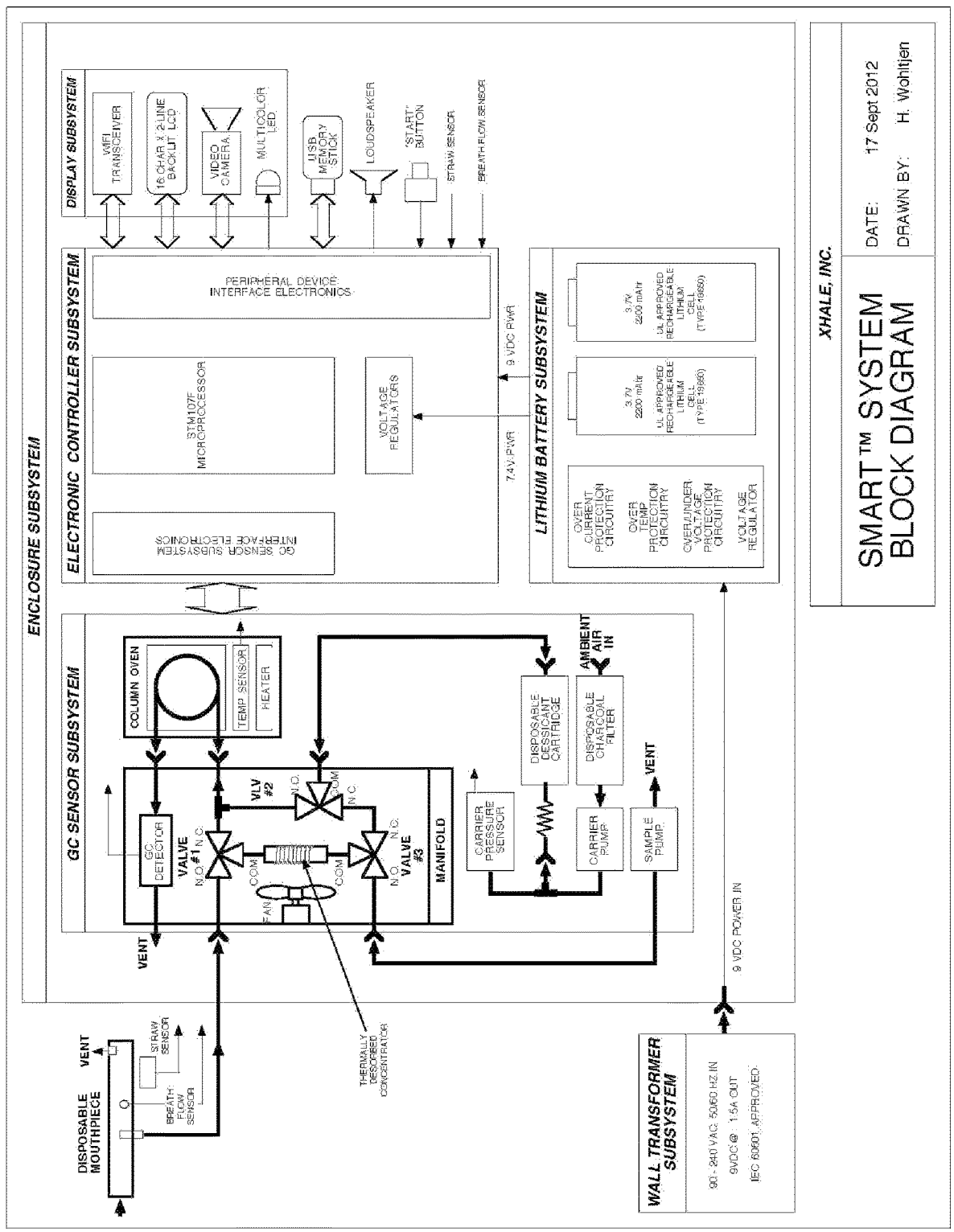

Further detail of each subsystem and the order of operative flow of the SMART® device 100 is shown in FIG. 4A, with detailed description provided for each subsystem being provided in FIGS. 4B-4E.

6.1.5 Mouthpiece Subsystem

Figure 4B:
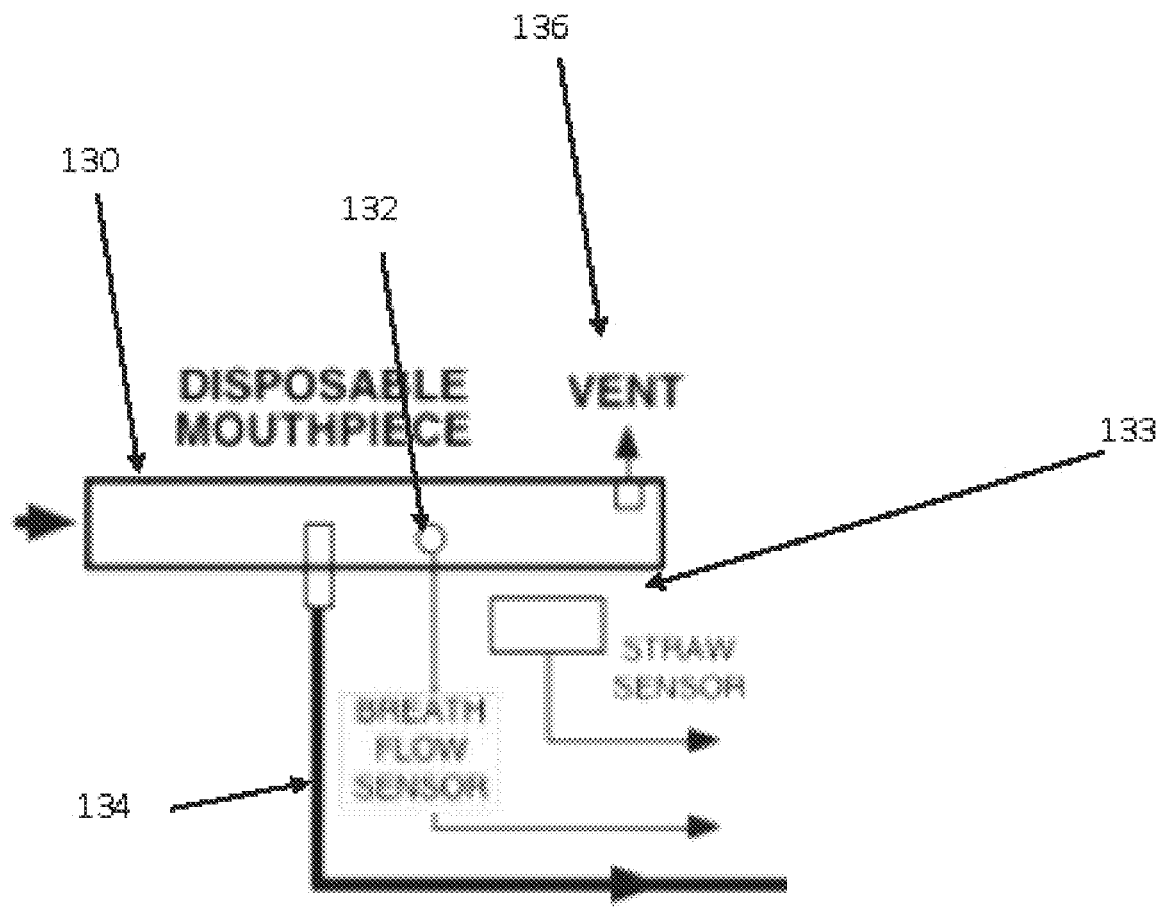

In FIG. 4B, the disposable mouthpiece subsystem 130 is shown. Preferably, included in this subsystem is a vent, 136, such that exhaled air passing through the mouthpiece is vented to the exterior of the device. Also included in this subsystem are a breath flow sensor 132 to indicate to the system that a breath sample is being received by the device 100, and a straw sensor 133, which is activated when a breath collection straw is inserted into the device 100 for breath sample collection. Finally, a conduit 134 provides for a metered quantity of breath to be routed from the disposable mouthpiece 130 into the SMART® device 100 for gas chromatographic analysis. The breath volume collected is controlled by the time that the sample pump is energized. The sample rate is controlled by the vacuum pressure developed by the vacuum pump and the flow resistance presented by the concentrator.

Figure 5:
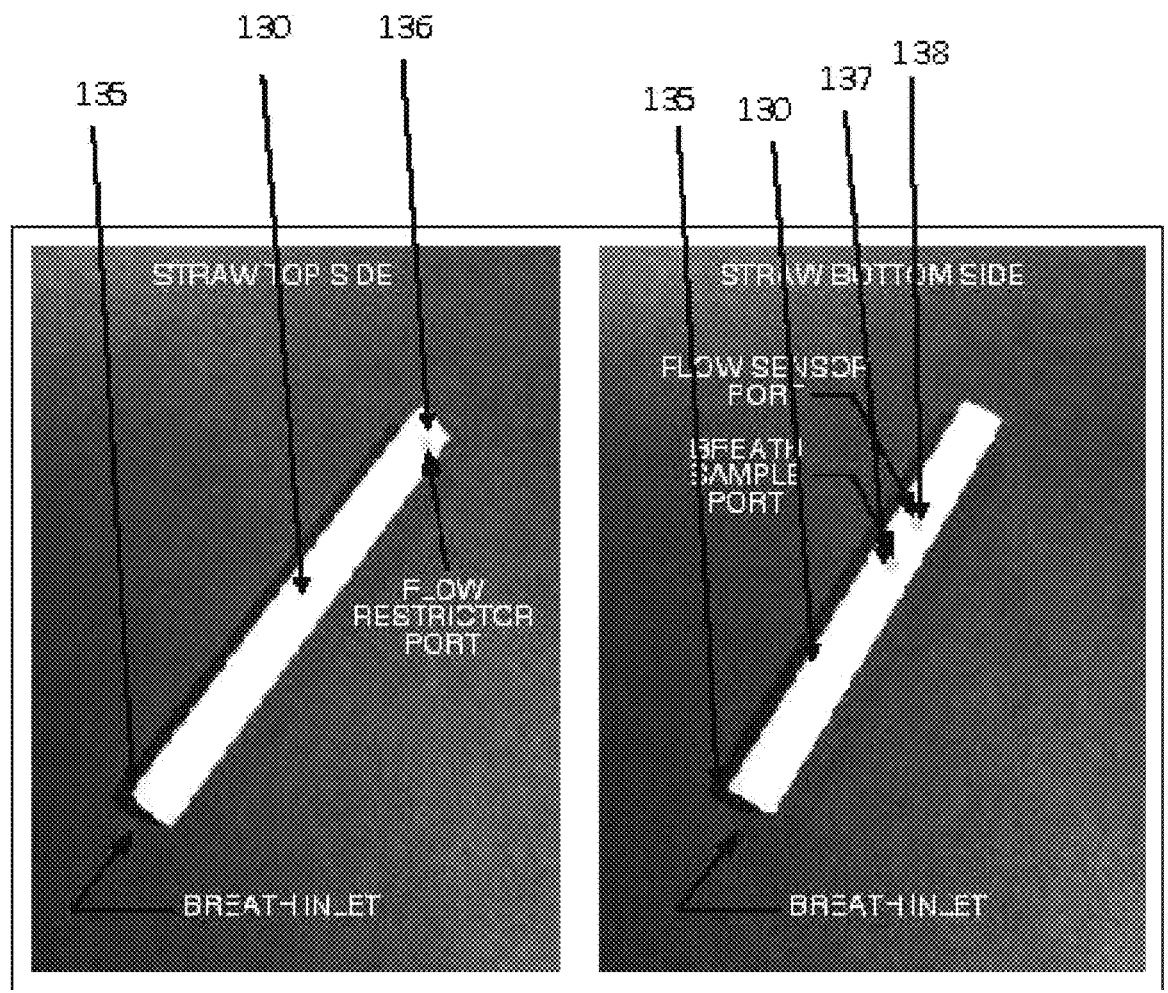

Referring now to FIG. 5, detailed photographs are shown of the disposable, single patient use mouthpiece (straw) 130 provided to facilitate collection of the breath sample.

FIG. 5A shows the mouthpiece/straw from a top view, while FIG. 5B shows the straw bottom view. As can be seen, each straw 130 includes a breath inlet end 135, a flow restrictor/vent port 136, (in this embodiment, the second end of the straw is sealed), a breath sample port 137 which couples with the conduit 134 which provides for a metered quantity of breath to be routed from the disposable mouthpiece 130 into the SMART® device 100 for gas chromatographic analysis. Finally, there is provided a flow sensor port 138 which couples with the breath flow sensor 132. In addition to directly receiving exhaled breath samples from a subject as the subject exhales, the SMART® device may also receive samples via gas-sampling bags or gas-tight syringes by coupling these devices to the breath inlet end 135 of a straw, or directly to the breath sample conduit 134.

Figure 6:
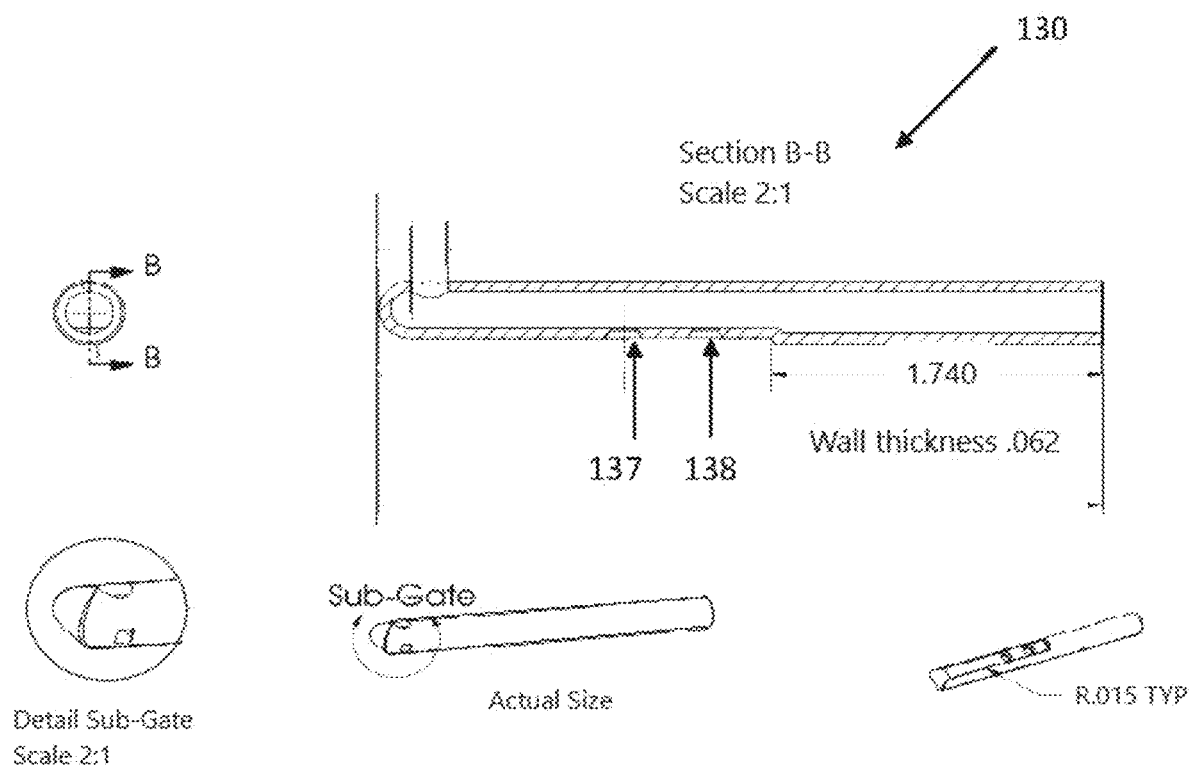

FIG. 6 provides a schematic showing a first embodiment of how the mouthpiece/straw 130 aligns with the device. Failure to align the mouthpiece correctly prevents it from locking into place in the SMART® device straw holder 131, particularly with respect to alignment of the breath sample port 137 and the flow sensor port 138.

Figure 7A:
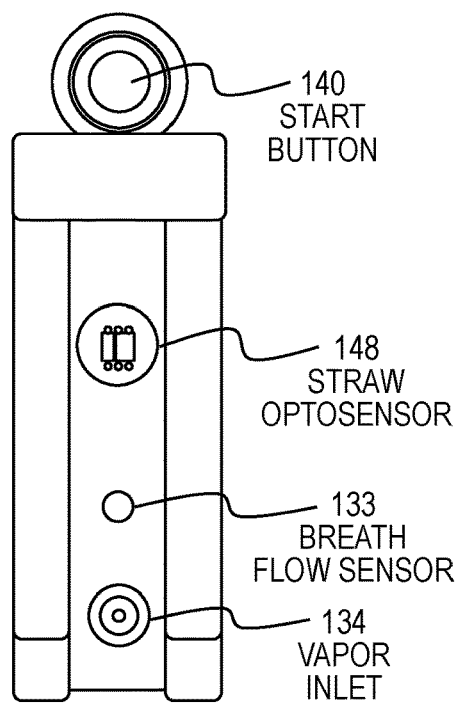

FIG. 7A provides a photographic representation of an embodiment of the mouthpiece receiver 131 of the SMART® device, including the vapor inlet port 134, the breath flow sensor 132, the straw optosensor 133, all of which align with and engage the mouthpiece shown in FIGS. 5 and 6. Also shown is the start button, 176.

In a preferred embodiment according to this invention, the mouthpiece/straw 130 is simplified to use of a simple tube, as shown in FIG. 2A, open at both ends, 135 and 136 for delivering exhaled breath from the subject to the device.

Figure 7B:
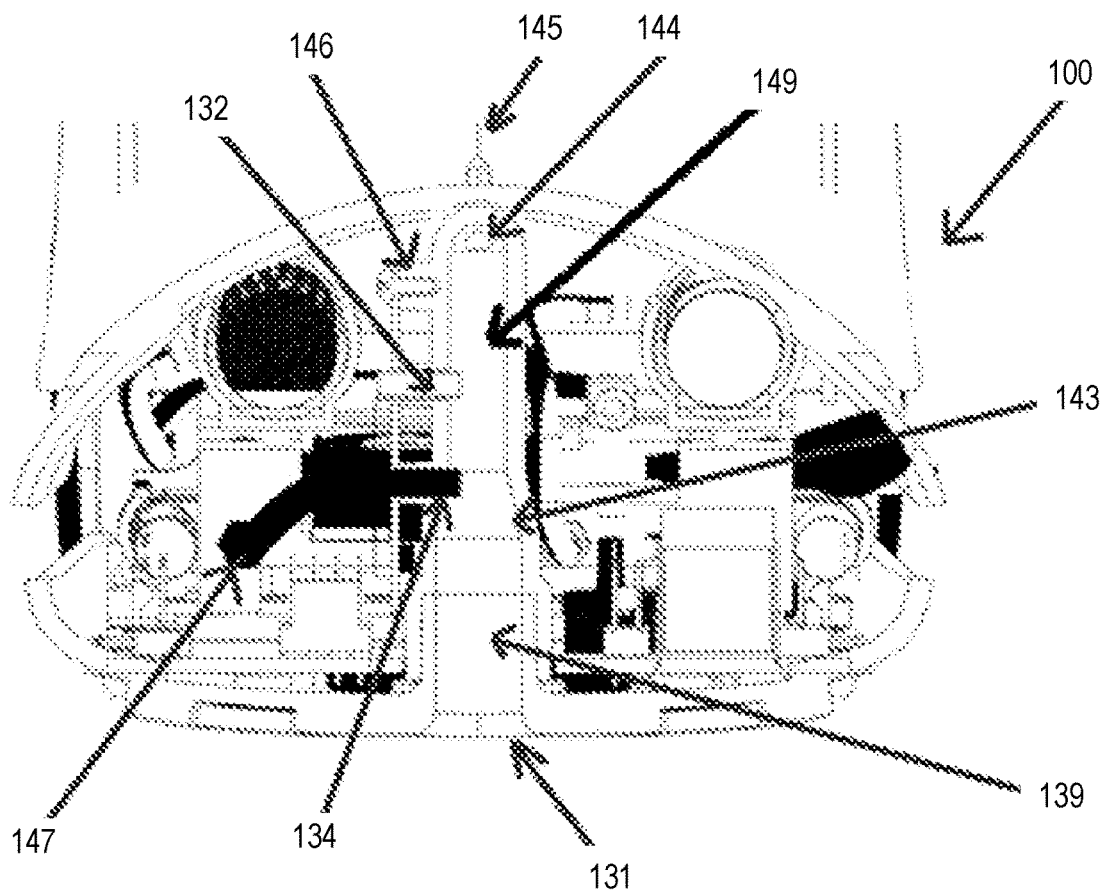
Figure 7C:
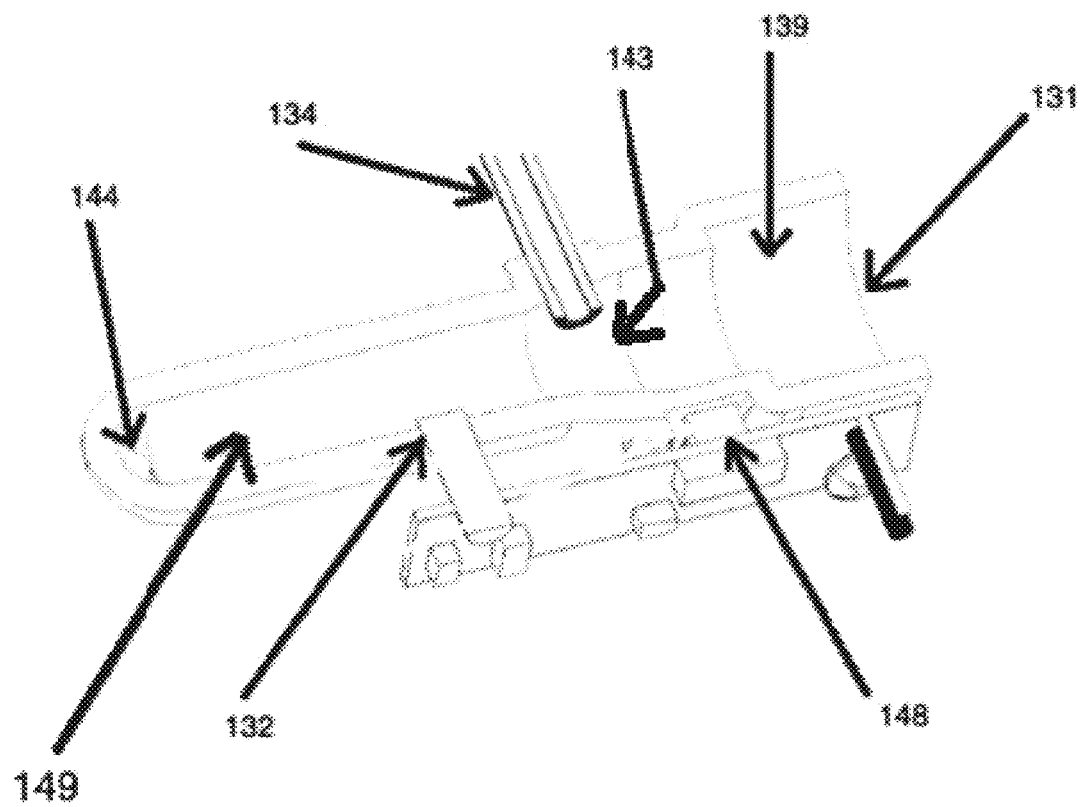

In this embodiment, the ports, sensors and other elements shown in FIGS. 4B, 5, 6, and 7A, are all removed from the mouthpiece straw 130 into the docking port, 131, visible from the exterior of the device only as a port, as can be seen in FIG. 2B. This substantially reduces the complexity and cost of the straw and simplifies the use thereof for the user of the SMART® device. In FIGS. 7B and 7C, the internal structure of the straw/mouthpiece port 131 is shown via a cross section through the top of the device 100 through the port 131, represented in FIGS. 2A and 2B. An isolated view of this cross-section through the port 131 is provided in FIG. 7C. A simple straw with an inlet and an outlet and no other features other than it being inert and of dimensions to tightly fit the port is inserted into the straw/mouthpiece receiver port 131. In one preferred embodiment, the port comprises a first cylindrical chamber area 139 with a diameter sufficient to easily accommodate insertion of the straw 130 therethrough. A second area 143 follows area 139 with a diameter which tapers from that of antechamber 139, which is greater than that of the mouthpiece tube/straw, down to a final diameter of a narrower cylindrical area 149, the diameter of which is less than that of the mouthpiece tube/straw. The ends of the mouthpiece straw and the surface at the start of the cylindrical area 143 are preferably machined to have mating surfaces and taper such that the inserted end of the straw locks in place within area 143 on correct insertion of the end of the mouthpiece straw. The inserted end of the straw 130 thus mates with but cannot enter into area 143 much beyond the very initial section of area 143 as the narrowing taper thereof prevents this. As a result, an air-tight seal is formed between the external surface of straw 130 and the internal walls of the mouthpiece receiver port 131 in area 143. Alternative embodiments include providing threading on the ends of the straw and mating threads in area 143. Further alternative embodiments include press-fit, flanging or other means for the straw end to be retained in the receiver port in an air-tight fashion. In each such embodiment, exhaled air is channeled from the end of the straw into area 143, and from there passes into area 149 and excess exhaled air is vented out of vent port 144. Vent port 144 is in communication with the external aspect of the device 100 housing via external vent 145, which permits excess exhaled breath and any breath condensate to be discharged from the device. Exhaled air sample port 134 (leading to exhaled breath sample conduit 147 and from there into the separation and detection subunits, see below) and flow sensor 132 are both in fluid communication with the exhaled air stream by being open to the conduit defined by areas 143 and 149. Correct placement of the straw in docking port 131 is confirmed by the straw sensor (e.g., an optosensor) 148 shown in FIG. 7C. A retaining screw 146 is provided to retain the docking port 131 in correct placement within device 100. In a preferred embodiment, the inlet port is composed of a material which prevents condensation. Silcosteel, for example, is a preferred embodiment for this element. In a further preferred embodiment, the inlet tube is heated to prevent condensation—particularly important for embodiments of the device intended for use in cold climates.

6.1.6 GC Subsystem and Sensor

Referring back to FIG. 4C, detail is provided for the gas chromatograph subsystem 150. Included in this subsystem are the following components: an exhaled breath sample receiver port 151 coupled to the conduit 134, via conduit 147 (preferably which provides the breath sample from the disposable mouthpiece 130 when a subject exhales into the SMART® device 100, as described in detail above. The exhaled breath sample is directed from the exhaled breath sample receiver port 151 into a thermally desorbable concentrator subsystem 200, comprising a hydrophobic concentrator column 201 around which is wound or otherwise intimately associated a heating coil 202 or equivalent heating element such as a thermoelectric heating element, such as but not limited to a Peltier device which, when activated, heats the thermally desorbable concentrator column 201, to thereby desorb any bound compounds from the concentrator column. A fan 205 is provided to ensure even heat distribution over the column and efficient and rapid dissipation of heat within the enclosure 110. At either end of the thermally desorbable concentrator column 201, valves, 203 and 204, are provided on the proximal and distal ends, respectively. The valve 203 on the end proximal to sample receiver port 151 controls the receipt of the exhaled breath sample from the exhaled breath sample receiver port 151 into the thermally desorbable concentrater column 201 when the breath flow sensor 132 indicates that an exhaled breath is being received. When the appropriate quantity of exhaled breath sample has been received into the thermally desorbable concentrator column 201, the sample pump is de-energized to stop the collection of the breath sample onto the thermally desorbable concentrator column 201, and any excess air is vented via the vent 330. When the SMART® device 100 is ready to analyze the breath sample, the heating element 202 heats the concentrator 201 to release bound compounds, and the valve 203 on the proximate end of the concentrator 201 opens to permit delivery of bound molecules to the gas chromatograph column 152, housed inside a column oven 153 which includes a heater 154 and temperature sensor 155 for precise regulation of the gas chromatograph column 152. The desorbed molecules travel from the concentrator 201 via valve 203 through connector 156 and into the gas chromatograph column 152 via GC inlet port 157. At the distal end of the concentrator 201, valve 204 opens to permit delivery of carrier gas from the carrier pump 304 via carrier pump coupling 305, flow restrictor 307, disposable desiccant cartridge 308, port 309 to port 310, and, via valve 302 to valve 204 to drive the desorbed molecules into and through the GC column 152. Once the desorbed sample has been delivered, valve 302 remains open permitting scrubbed ambient air which has been drawn through a disposable charcoal filter 303 to drive the sample through the GC column 152 then through the GC detector 158 and out of vent 159. As will be appreciated from this disclosure, coordination of valves 203, 204, and 302 is required to ensure that desorbed molecules from the concentrator 201 are driven into the GC column 152 at the appropriate rate, temperature and pressure. This coordination is achieved by the electronic microcontroller subsystem, 160, which, in a preferred embodiment, also coordinates the taking of a biometric record, in a preferred embodiment, a photograph, of the subject at the time of delivery of the exhaled breath sample.

To ensure that appropriate carrier air pressures are not exceeded, there is provided a carrier air pressure sensor 311 which feeds back to the carrier pump 304 via electronic microcontroller 160 to control carrier air pressure. As the desorbed molecules travel from the concentrator 201 into the GC column 152 they are fractionated and then detected by a GC detector 158 and then vented from the SMART® device 100 via vent 159.

Depending on the nature of the molecules to be detected, and the adherence environment in which the device is utilized, the detector, 158, may be a MOS detector, an infrared detector, and, as discussed in some detail below, for certain embodiments according to this invention, the detector includes a catalytic incineration feature. While a preferred embodiment according to this invention utilizes a mGC, coupled to a MOS, those skilled in the art will appreciate that other means of separation and/or detection may be utilized for a particular application. For example, a concentrator and an array of surface acoustic wave (SAW) sensors may be utilized as an "electronic nose" in place of the GC column and MOS sensor.

The chromatographic separation of the various breath components and markers occurs on the column 152 which, in one embodiment, consists of a 5 meter long piece of 0.53 mm ID metal tubing whose walls are coated with a polymeric stationary phase (e.g. Restek MXT BAC-1). The stationary phase adsorbs and desorbs the various chemical vapors injected in the initial plug. The adsorption and desorption rates of each vapor vary, depending on physicochemical characteristics such as boiling point and hydrogen bonding affinity. Since a constant stream (nominally 3 sccm) of clean, dry air carrier gas is flowing through the wall-coated metal column, those compounds that are more volatile are swept through most rapidly and emerge from the GC tube 152 at an earlier time than those molecules that are heavier and less volatile. The detector 158 that produces a signal proportional to the number of organic molecules exiting the tube is used to record when the different molecules emerge. Thus, each compound can be identified by its retention time, and the concentration can be determined by the peak height, when comparing it to analytical standards of known concentration. The GC detector used in the SMART® GC is, in one preferred embodiment, a solid-state, metal oxide semiconductor (MOS) chip sensitive to the presence of oxidizable hydrocarbons.

To provide consistent performance, the SMART® column 152 is operated at a constant temperature, e.g., 40° C. via regulation by the column oven 153, and the associated temperature sensor 155 and heater 154. The temperature is regulated to keep the temperature steady. Those skilled in the art will appreciate that, and will know from their own skills and from the guidance provided herein that, different column packing, temperature, mobile phase and the like are required to optimize separation of different components, as needed, of exhaled breath to optimize detection and non-interference with detection of the EBM.

6.1.7 Stand-Alone Mouthpiece, Camera, Sample Collection Module

In an alternate embodiment according to this invention, the biometric, e.g., time-stamped photograph of the subject, and collection of the exhaled breath sample, are provided as a separate module from the remainder of the apparatus. On provision of the time-stamped breath sample to the remainder of the apparatus, the sample is analyzed as in a fully-integrated embodiment. The advantage of this embodiment is that the breath sample and biometric may be trapped at any location, without the need to carry the entire device. This creates an even more portable option for users of the system. The components of this embodiment would include the breath straw, a camera, a pressure sensor, and a desorbable concentrator column—as discussed above. On combining this module with the remainder of the device, ordinary operation of the device is initiated by desorption of the collected sample and injection of the sample into the GC column. Alternate configurations of this aspect of the invention may include just a mouthpiece/straw, which acts as the sample capture device (e.g., the mouthpiece itself operates as a desorbable concentrator column). Naturally, as technology continues to miniaturize, in due course, the portable components of this aspect and other aspects or embodiments of the invention or the rest of the apparatus components of this invention will include, e.g. a mass spectrometer on a chip, (see, for example, the high pressure mass spectrometer included in the M908 device available from 908 Devices, Inc., 27 Drydock Ave., 7th Floor, Boston, Mass. 02210, and U.S. Pat. Nos. 8,816,272; 8,525,111; and 8,921,774) an IR spectrometer on a chip, or other versions of such technologies which provide enhanced portability, reduced cost, increased precision in analysis, the ability to analyze different isotopologues included in the EBM and the like at the point of use.

6.1.8 Electronic Microcontroller

Figure 4C:
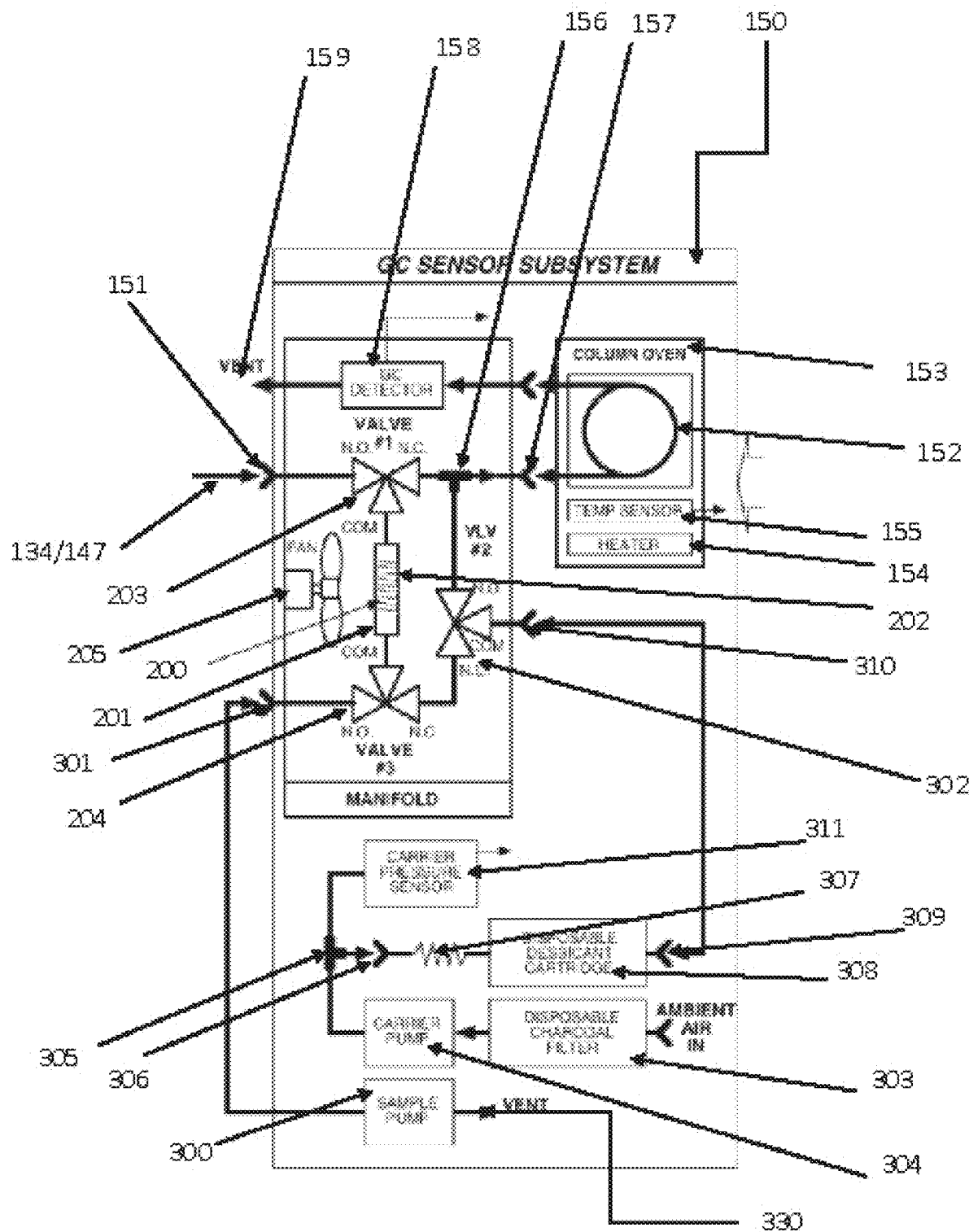
Figure 4D:
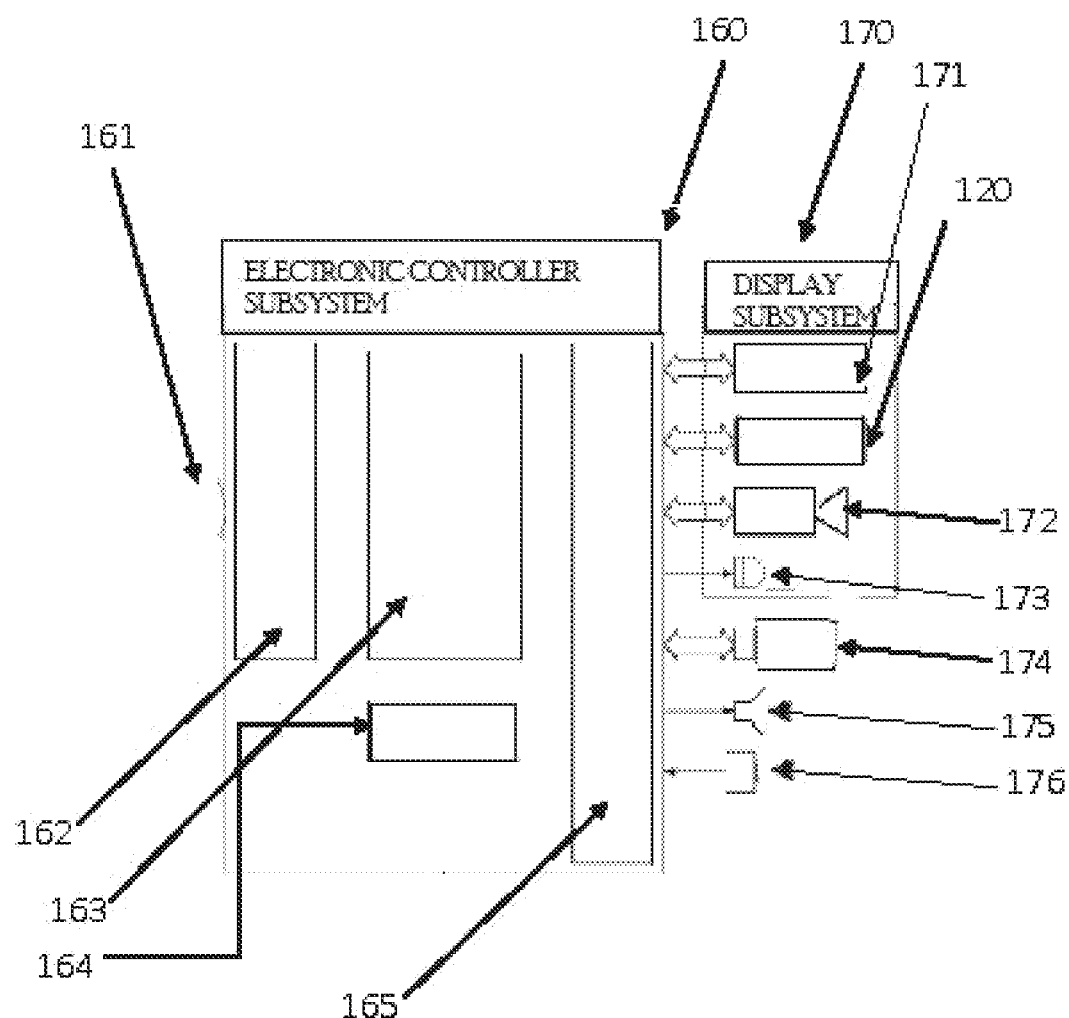

Referring now to FIG. 4D, there is provided a detailed schematic of the electronic microcontroller subsystem 160 and the camera and display subsystem 170. The microcontroller 160 is in operative communication 161 with the above-described disposable mouthpiece subsystem 130 (FIG. 4B), and the GC and sensor subsystem 150 (FIG. 4C), as well as the subsystems described herein below. Preferably, included in the microcontroller subsystem 160 are the following elements: GC sensor subsystem interface electronics 162, microprocessor 163, such as, but not limited to a STM107F microprocessor, or the equivalent, now known or which hereafter comes to be known; voltage regulators 164 for gating power from the power subsystem (see discussion below) and transmission of appropriately regulated power to all other subsystems of the SMART® device; peripheral device interface electronics 165. Each of these elements, based on current state of the art, are available as components, integrated circuits or modules and those skilled in the art will know, based on this disclosure, which particular components, integrated circuits or modules are useable for the functions disclosed and described herein. The peripheral device electronics 165 controls, for example, all elements of the camera and display subsystem 170, including, but not limited to: a WiFi, RFID, or mobile cellular data transceiver 171, or combinations thereof, which permits communication between the SMART® device and external devices for data capture and analysis and for communication of control and updates to the SMART® device; an information display 120 associated with the SMART® device, such as but not limited to a sixteen character, two line, backlit LCD display; a video or still camera 172; an LED 173, such as a multicolor light emitting diode to indicate system status and to provide a flash function as needed when taking an image with the digital camera. Additional peripheral devices controlled by the peripheral device interface electronics 165 may include but are not limited to: memory 174, such as but not limited to a USB memory stick or the like, EEPROM memory, or other electronic memory forms now known or hereafter developed for this purpose; a loudspeaker 175 to provide audible alerts and/or instructions to users of the SMART® device 100; a "Start" button 176 to activate the entire system for operation; the breath flow sensor 132; and the straw sensor 133. Each of these elements is in either two-way or one-way communication with the peripheral device interface electronics 165, as indicated by either two-way or one-way arrows in FIG. 4D between these elements.

6.1.9 Power Subsystem, GPS, Wireless Communication

Figure 4E:
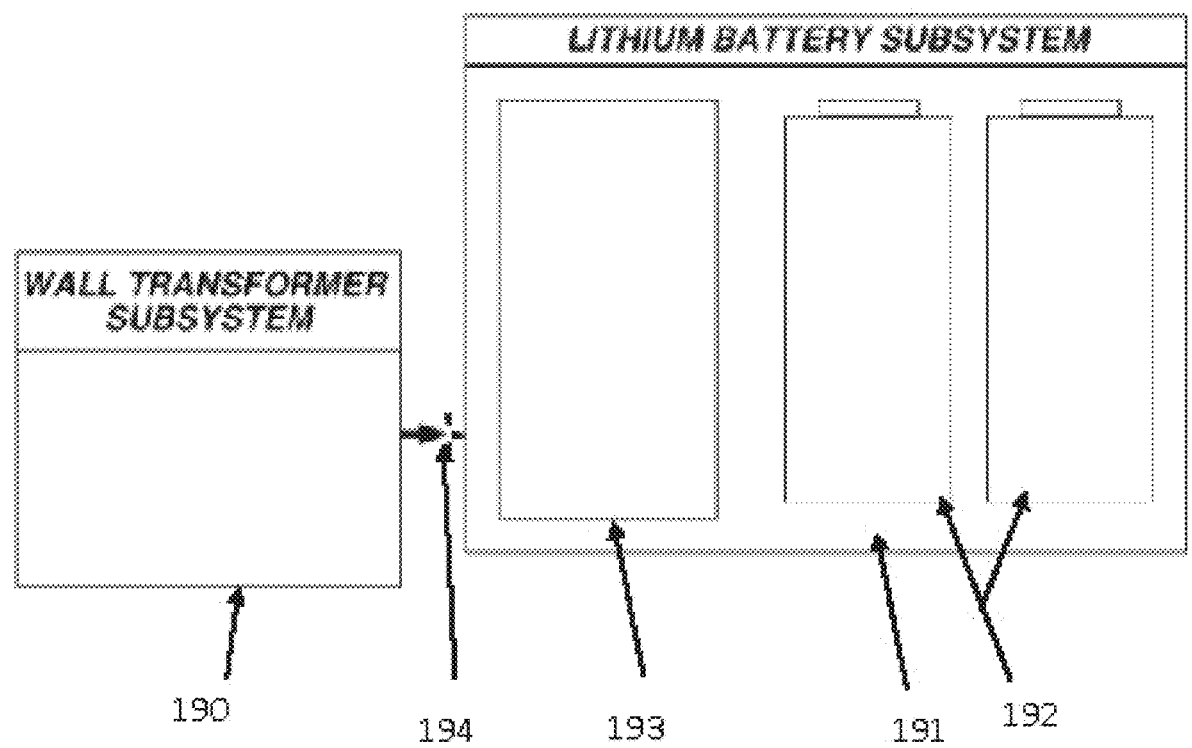

With reference to FIG. 4E, powering the entire device is achieved by in various embodiments by a wall power transformer subsystem 190 alone or in operative communication with an internal rechargeable battery subsystem 191. The wall power transformer subsystem 190 is, for example, a 90-240 volt AC, 50/60 Hz in, 9 volt DC. 1.5 amp output, preferably an IEC 60601 approved device. The internal rechargeable battery subsystem 191 is, for example, composed of a pair 192 of UL approved rechargeable lithium cells (e.g., type 18650), providing 3.7 V, 2200 mAhr per battery. In addition, included in the battery subsystem there is desirably provided over-current protection circuitry 193, over-temperature protection circuitry, over/under voltage protection circuitry, and voltage regulation. Power is supplied from the wall power transformer subsystem 190 to the internal rechargeable battery subsystem 191 via an appropriate jack 194.

Preferably, power supplied from the wall power transformer subsystem 190 is 9 volts DC power. Thus, when start button 176 is activated, the processor 160 "wakes-up" from its "sleep" state and power is provided from the voltage regulator 164 to the peripheral device interface electronics 165 and GC subsystem interface electronics 162 as needed for operation of the system.

The SMART® mGC can operate on rechargeable batteries, 192, which, when fully charged, (e.g., when lithium batteries are used) provides sufficient power for at least 10 complete breath measurement operations without the need to be recharged. In one embodiment, batteries are permanently installed into the battery holder and are not removable, while in other embodiments, the entire battery pack is exchangeable or primary batteries, e.g., lithium ion technology, may be used.

We envision the SMART® device will be utilized in less industrialized countries of the world, as well as all over the globe, where wall A/C power supply is not always available and locating and retrieving the device could potentially become a problem. To overcome these obstacles, in one embodiment according to the invention, miniature recharging solar pack technology is included in the device.

A GPS tracking subsystem is likewise desirably included in an embodiment of the device and is integrated with the microcontroller 160. The internal wireless capability of the SMART® device allows interaction with other wirelessly enabled devices and technologies, including, but not limited to, for example, smart phones (iPhones, Android phones, and the like), tablet computers, other computers and the like. Integrated patient/health monitoring systems and medication containers that manage or track access to medications based on communication with the device according to this invention are likewise optional adjuncts to or may be integrated into the system according to this invention.

6.1.10 Breath Sample and Concurrent Biometric Acquisition

Upon detecting breath flow, a microcontroller activates a small sampling pump that collects a representative breath sample for analysis (nominally 30 cc) over a pre-defined time period—preferably about a five-second time span—at a nominal flow rate of 300-400 sccm. The breath sample is collected on the thermally desorbable concentrator 201. The excess breath flow is vented through the flow restrictor opening on the mouthpiece 136 (FIG. 5). A biometric, e.g., camera image of the subject providing the breath, is obtained and time stamped so that time of biometric and breath sample acquisition can be confirmed as being concurrent.

The concentrator 201 consists of a small stainless steel tube or the like packed with a sorbent polymer (e.g, Tenax™ TA) that is commonly used in gas chromatography to adsorb molecules of interest while allowing molecules that are not of interest (e.g., water vapor and carbon dioxide) to pass through the system. When the temperature of the sorbent is raised, the polymer desorbs the molecules of interest, effectively concentrating them. Once the concentrator has warmed up, valves 203, 204, 302 (FIG. 4C) are energized, causing pressurized clean, dry air from the carrier gas generator to backflush the plug of purged molecules from the concentrator onto the analytical column of the gas chromatograph.

6.1.11 Replaceable Ambient Air

Elements of the ambient air scrubber comprised of elements 300, 303-309 and 311, (see FIG. 4C), are replaced by the manufacturer or user during routine maintenance or service. The carrier gas utilized in the system is preferably generated from ambient air that is passed and cleaned through two different scrubbers. Of course, a portable carrier gas could be utilized, or the device may be linked to a conventional carrier gas, but this involves additional complexity and reduced portability which the present device circumvents by inclusion of the ambient air scrubber described herein. The first 303 contains activated charcoal to remove organic compounds that might be present in the ambient air and which might otherwise interfere with analysis of volatile organic compounds present in samples to be analyzed. The second 308 contains molecular sieve 13× and indicating Drierite™ to remove humidity from the air. Soda lime is useful to remove carbon dioxide. Nafion® tubing (or equivalent perfluorosulfonic acid polymer) is useful to remove water. The small pump 304 compresses the air from the charcoal scrubber 303 and injects it into the desiccant scrubber 308 through a small flow restrictor 307. The pressure generated by the small compressor pump 304 is monitored and controlled by the microcontroller 160 via the carrier pressure sensor 311 to maintain a constant carrier gas flow as necessary to keep the GC column 152 head pressure constant. The system operation is fully automatic once the breath sample has been collected. The analysis process takes about 180-220 seconds. When the analysis is completed, the system purges itself with clean air to eliminate the possibility of breath marker vapor carry-over and to prepare it for the next sample.

6.1.12 Data Handling

All data acquired by the SMART® GC are preferably encrypted and stored on a USB memory stick or equivalent on-board, non-volatile memory. This permits retrieval of data in the event of wireless communication failures. The on-board memory has enough capacity to store all of the data and images associated with more than 100,000 breath measurements.

The microcontroller 160 initiates the breath sample collection process when the breath flow sensor 132 signal exceeds a threshold. The mouthpiece/straw sensor 133 (FIG. 4B) is, in one preferred embodiment, an optoelectronic device that emits a low intensity IR beam and detects the proximity of reflective objects, such as the mouthpiece. This allows the microcontroller to wait until the user has properly inserted the straw 130 before advancing to the breath collection process. The breath flow sensor 132 is, in one preferred embodiment, a heated thermistor that detects resistance changes when cooled by the flow of air passing over the sensor. Breath flow can also be sensed using a pressure sensor.

The GC detector signal 158 is digitized using a voltage-to-frequency converter and frequency counter in the microcontroller 160, which provides excellent dynamic range and noise immunity. Accordingly, all output signal data are reported as "counts". A digital potentiometer, contained in the GC sensor subsystem 162, controlled by the microcontroller 160, is used to attenuate the output voltage from the MOS detector.

During sample elution from the GC analytical column 152, the signal from the MOS detector 158 is logged e.g., twice each second by the microcontroller 160. A peak-detection algorithm resident in the microcontroller 160 locates the retention time and peak height of every compound that elutes during the predetermined chromatographic window. When a peak is found in specific windows specified in the script commands, the computer logs the successful detection of the analyte of interest and reports the presence of the compound that typically appears in that window. Not only can the device detect the analyte, but it is preferably adapted to measure absolute amounts, changes in absolute amounts (referred to herein as the "delta" or $\Delta$ in the given parameter/measurement), and to provide an assessment (e.g., a yes/no readout) for particular compounds.

Key system status information is logged for each measurement. This information includes, but is not limited to, the elapsed run time, time since last service, pump and oven heater duty cycles, and battery voltage. This allows remote assessment of the system functionality.

Figure 14:
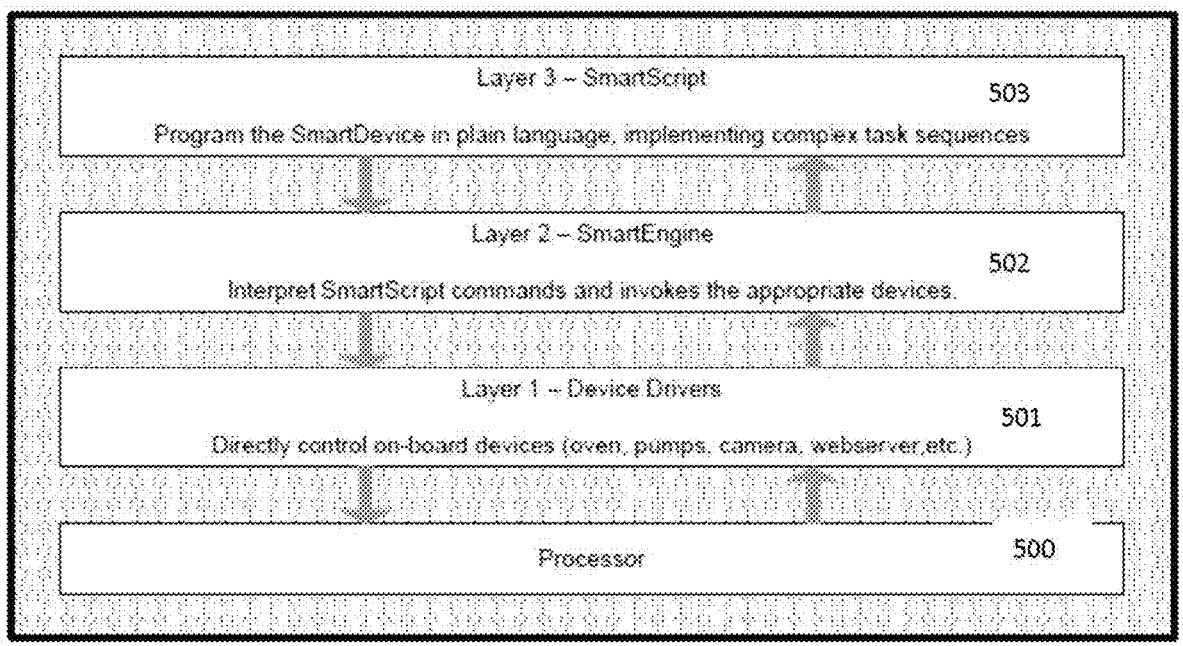

With reference to FIG. 14, there is provided a logic flow diagram for a preferred embodiment according to this invention. Starting from the processor layer 500 which has a two-way communication data flow with layer 1, 501, comprising the various drivers for each of the device's sub-components, including but not limited to the oven, pumps, camera, webserver, solenoids, etc. At the next level of control, there is provided a layer 2, the SmartEngine, 502, which interprets SmartScript commands and invokes appropriate devices, in two-way communication with layer 1 below 501 and layer 3 503 above. Finally, there is provided a third layer, layer 3 503, in two-way communication with layer 2 below. Layer 3 503 implements SmartScripts, permitting users and implementers of the device to program the SMART® device in plain language, implementing complex task sequences and flexibility in altering parameters of device operation.

Figure 15:
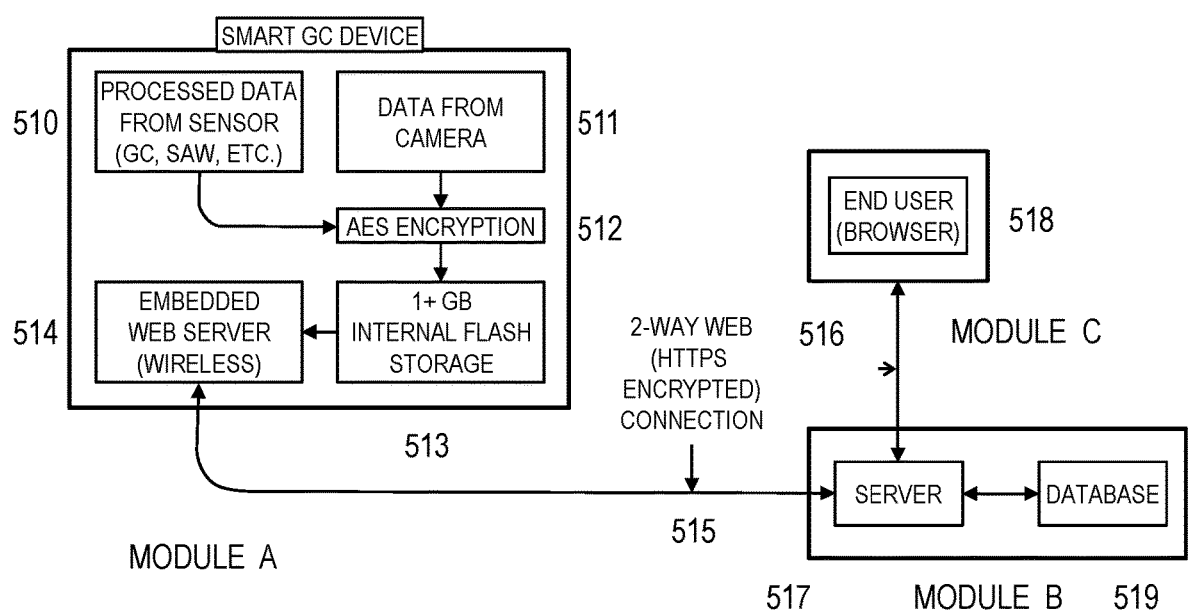
Figure 16A:
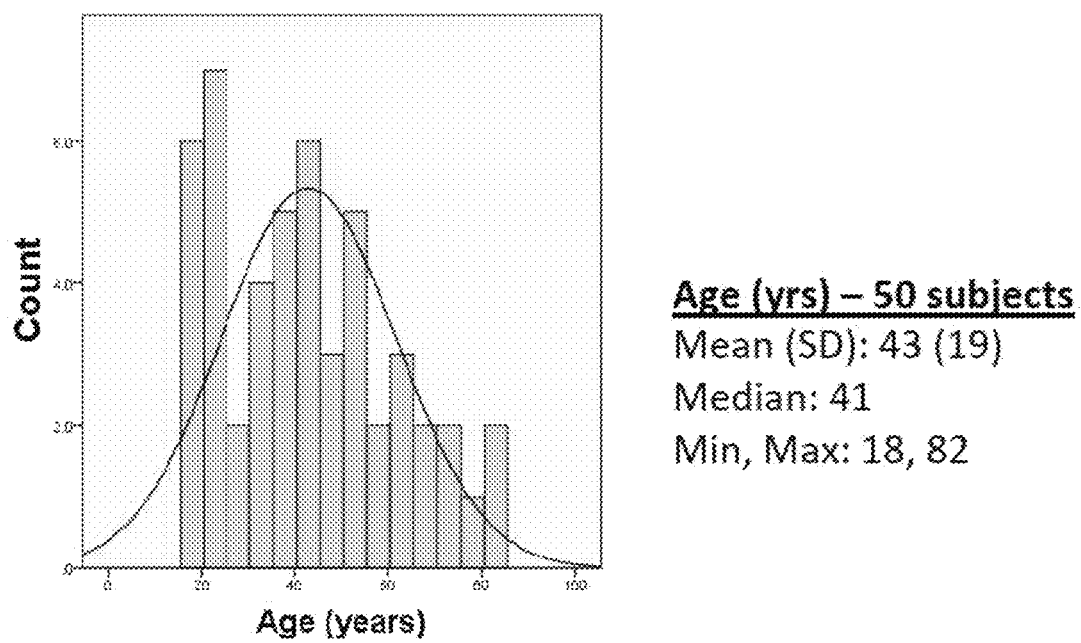
Figure 16B:
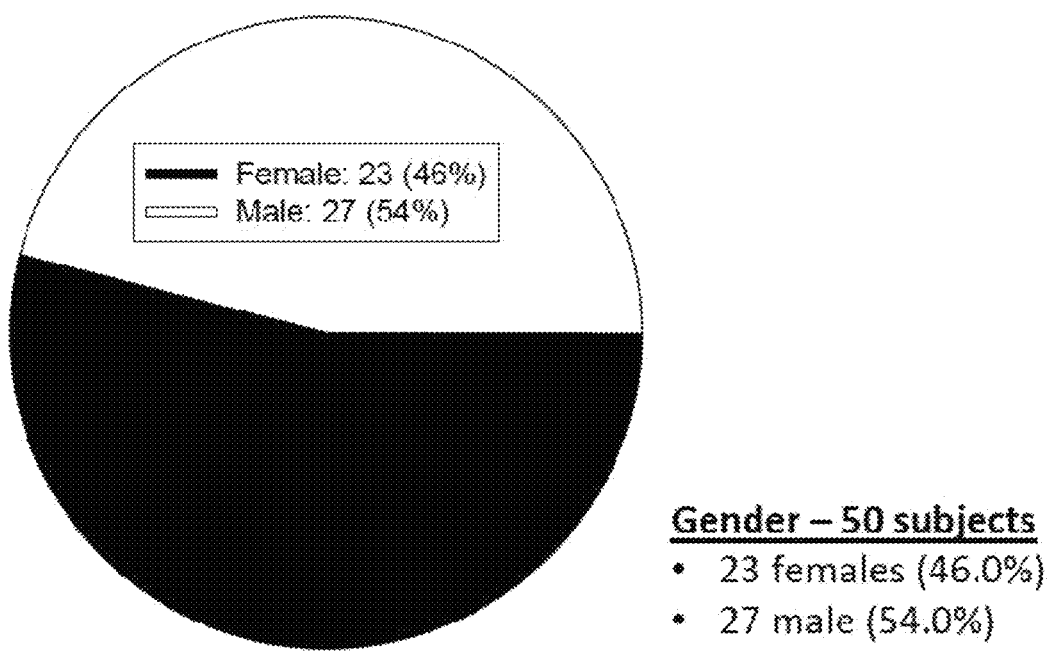
Figure 16C:
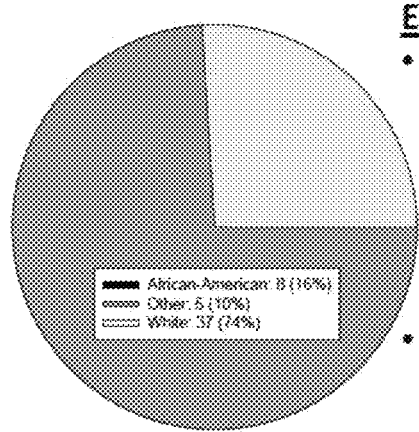
Figure 16D:
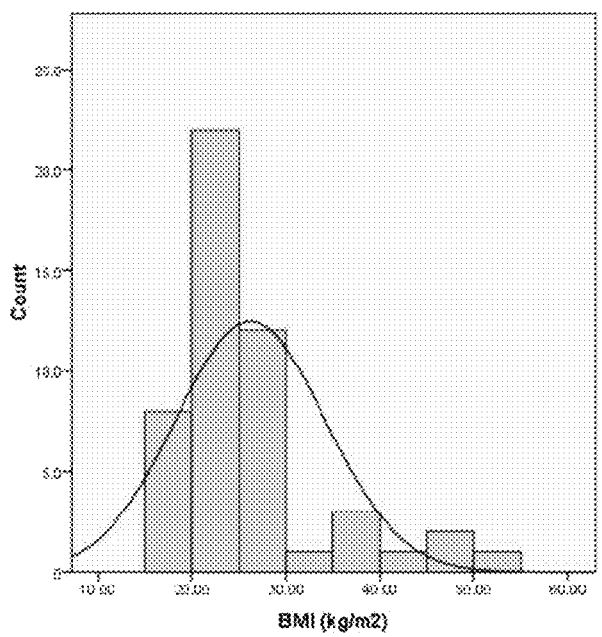
Figure 16F:
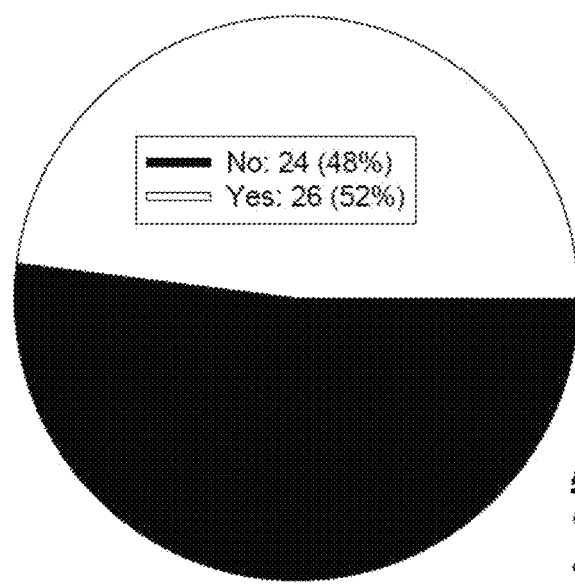
Figure 16G:
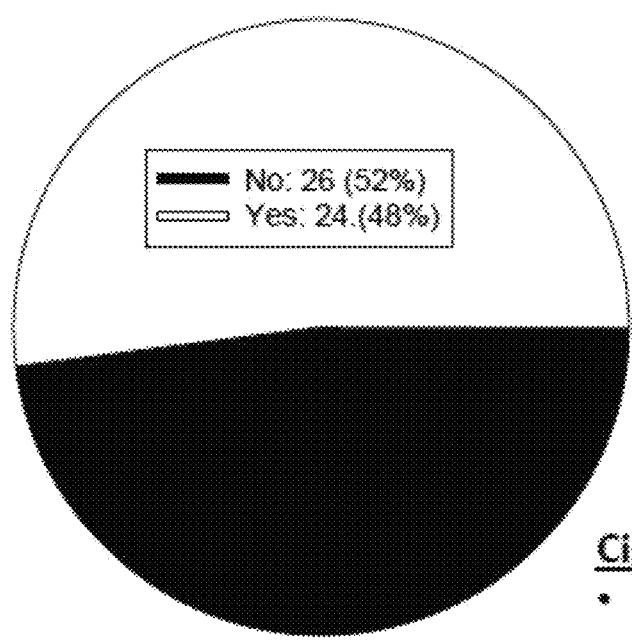

With reference to FIG. 15, there is provided further granularity for comprehending the data flow and operation of one embodiment according to this invention. According to this representation, there are three interconnected modules, Module A, Module B, and Module C. Module A comprises the SMART® gas chromatograph device, including the gas chromatograph and detector which produce data which the device processes, 510, the camera and data from the camera 511, both of which data streams are preferably subject to encryption at 512. The data or encrypted data is then stored on an internal storage, e.g., a 1 gigabyte internal flash storage or equivalent data storage medium, 513. The stored data is uploaded to an embedded, preferably wireless, web server, 514, for transmission to external data storage, analysis and, if appropriate, action. This is accomplished over communication lines 515 and 516, to modules B and C, where data lines 515 and 516 comprise two-way web (HTTPS encrypted) connections, providing data to a data server, 517, and end user(s) (via, e.g., a web browser or equivalent interface), 518. Secure storage and archiving of data is accomplished in an appropriate database and secure storage system 519.

In one preferred embodiment according to this invention, there is provided an RFID communication system whereby, on confirmation of the taking or administration of a medication dose by a subject, a signal is transmitted from the device to a medication dispenser which is locked until the next dose is due to be taken.

6.1.13 Camera and Display

The SMART® mGC incorporates a digital camera 172 and a liquid crystal display 120 for visual prompts. The camera is controlled such that a biometric measurement of the subject providing the exhaled breath sample for analysis is captured and time stamped for each collected breath sample. The camera is selected to permit accurate image capture at a focal length appropriate to the distance from the camera lens to the end of the mouthpiece where each subject interfaces with the device to provide exhaled breath samples for analysis. In a preferred embodiment according to this invention, a camera is utilized which has a wide angle lens (e.g., 120 degree field of view) to ensure acquisition of a reliable image even when the device is held at unusual angles by the user.

In a preferred embodiment according to this invention, a relationship is defined between the length "L" of the mouthpiece 130, and the focal distance "D" of the a photographic image capture device 121 to concurrently document the image of the subject exhaling into the device. In a preferred embodiment L=D$\leq$5 cm. Preferably, L=D<5, 4, 3, 2 or even 1 cm. This permits optimal acuity in capturing the identity of the subject exhaling into the device without at the same time requiring use of long, cumbersome or unsightly straws/ mouthpieces 130. In a preferred embodiment, a camera such as an OmniVision (Sunnyvale, Calif.), OV9655 1.3 megapixel camera-on-a-chip is utilized.

Figure 8A:
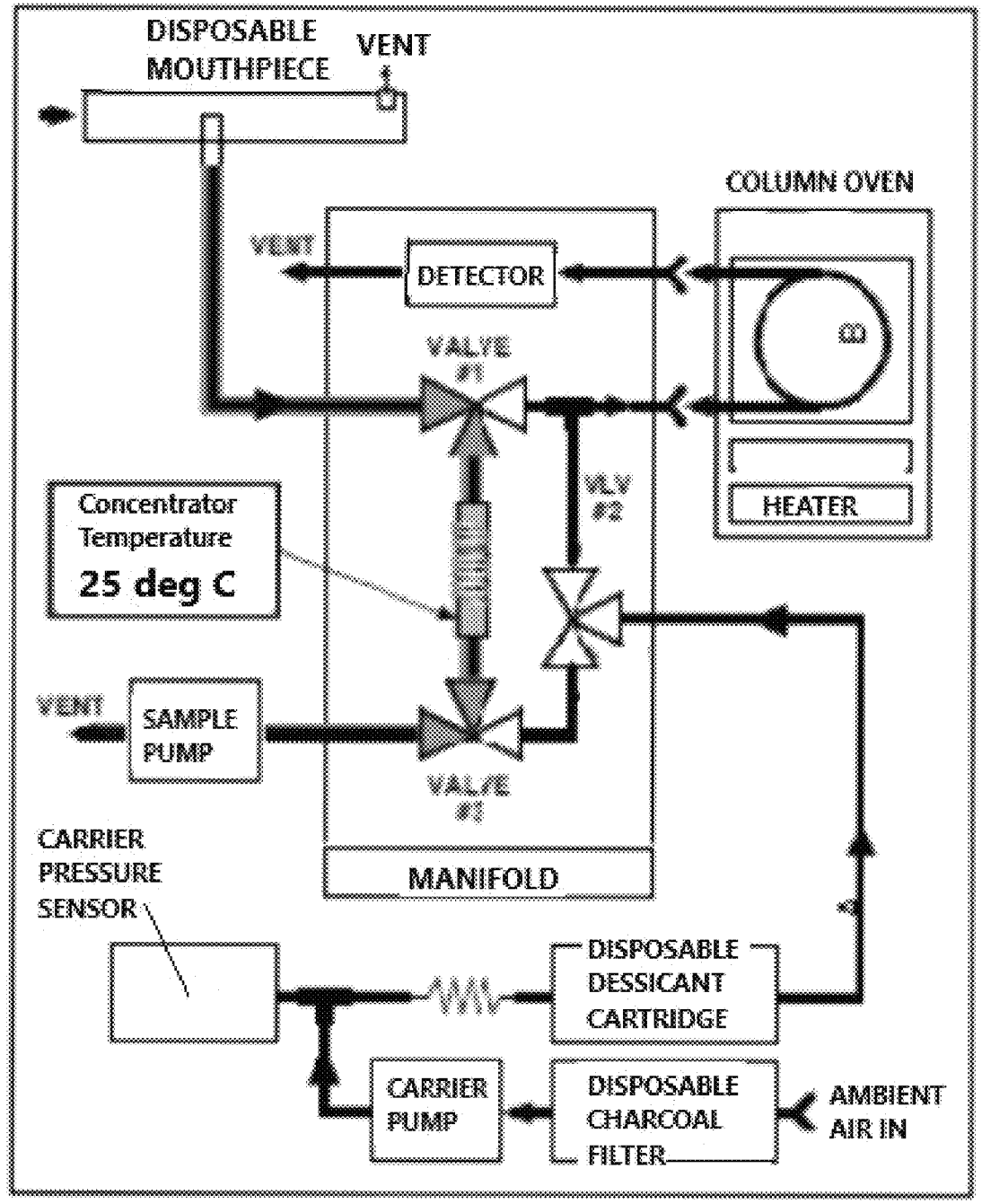
Figure 8B:
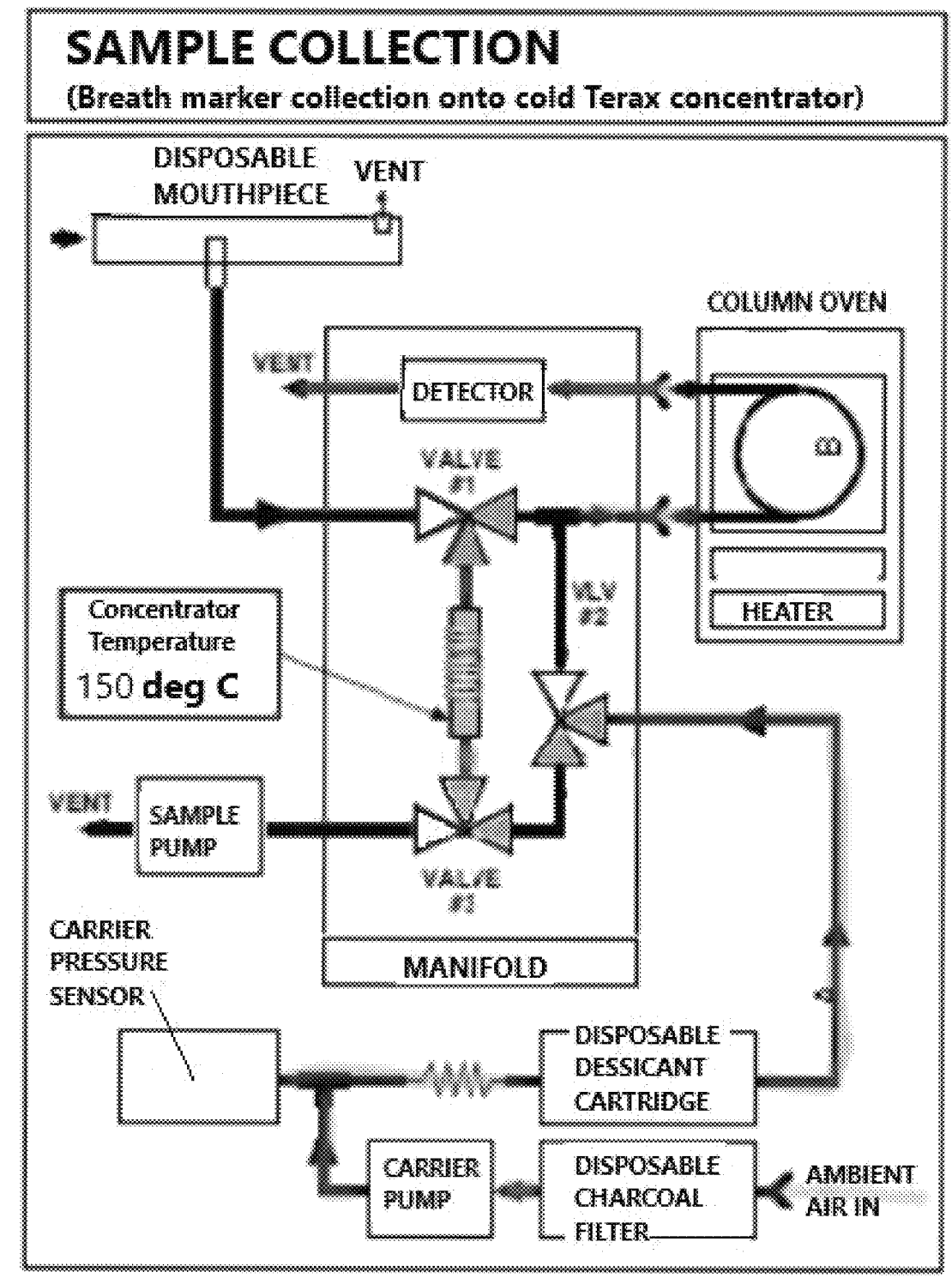

6.1.14 Operational Specifics of the Above Described Device and its Subsystems Referring now to FIG. 8, in FIG. 8A, the valving is shown for sample collection without numbering to keep the figure clear. Reference should be had to FIG. 4C for component numbering. Exhaled air enters the SMART® device via the mouthpiece 130 and is directed to the concentrator column via conduit 134, receiver port 151 and, via valve 203 being adsorbed to concentrator column 201. The sample pump 300 draws the sample into the concentrator 201 and vents air stripped of molecules of interest. The adsorption is conducted at a reduced temperature, such as 25 degrees centigrade. In FIG. 8B, the concentrator 201 is heated to an elevated temperature, such as 150 degrees centigrade, to thermally desorb the breath borne molecules that have been trapped on the concentrator 201. In order to direct desorbed molecules from the concentrator through the GC column 152, valve 203 at the proximal end of the concentrator 201 is closed to the mouthpiece, but opened to the GC column 152. Ambient air is drawn through the scrubber 303 by the carrier pump 304, through the flow restrictor 307 and through the second scrubber 308 and valve 302 for delivery to the distal end of the concentrator column 201 via valve 204, thereby driving the desorbed molecules from the concentrator 201 into the mGC column 152 through the detector 158 and, finally, out the vent 159. See FIG. 9 and Example 2 for a typical chromatogram produced by this system.

Figure 10A:
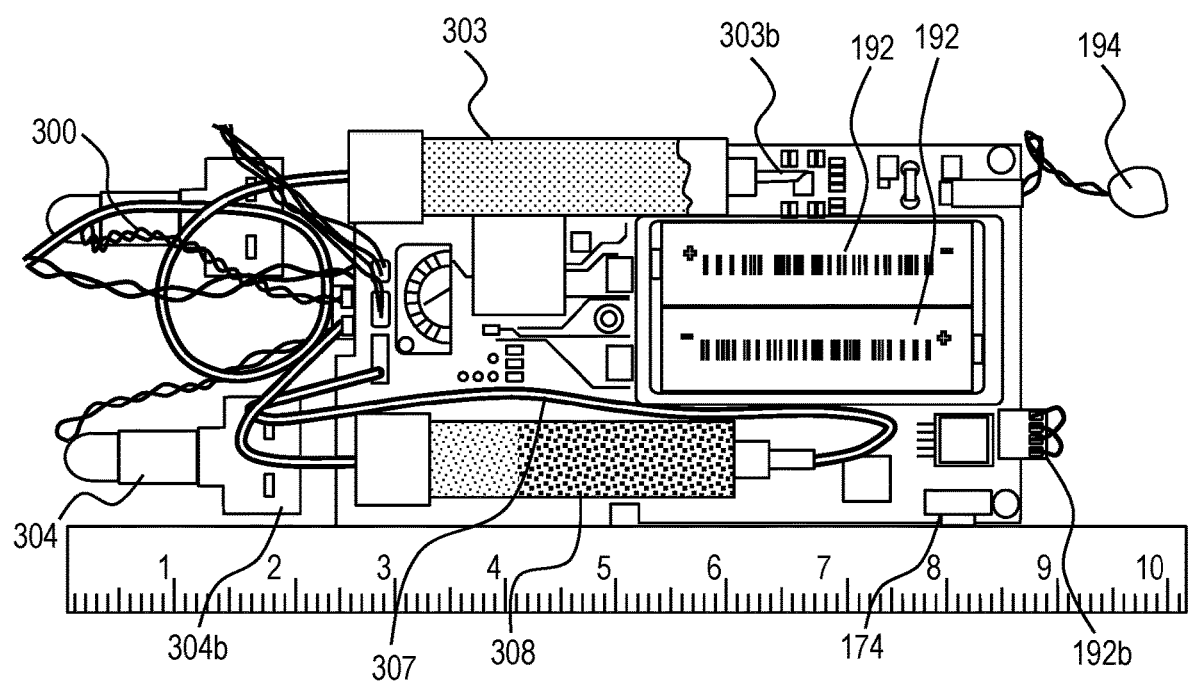
Figure 10B:
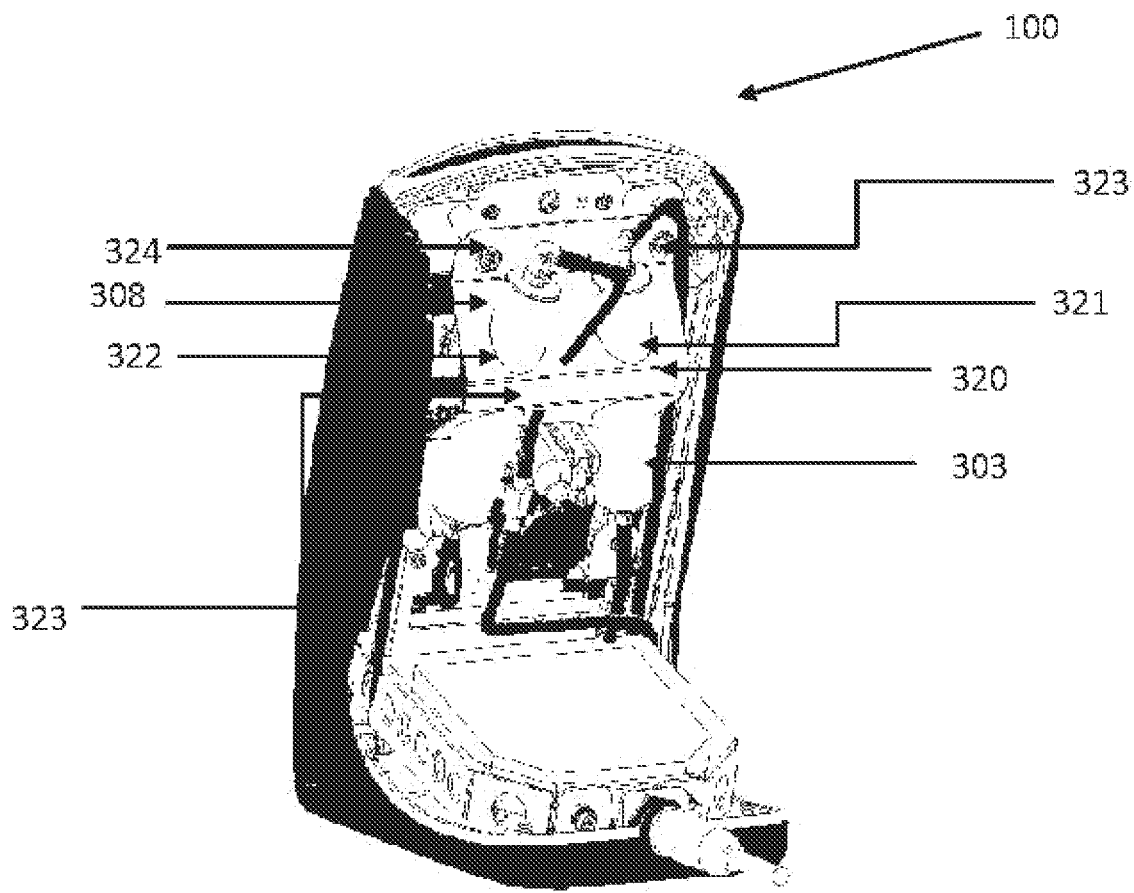

In FIG. 10A, there is shown a photographic representation of the internal components and architecture of a first exemplary embodiment of the SMART® device according to this invention. Visible in this photograph are at least the following components: battery pack 192; external power connector 194; battery pack connector 192b; USB solid state memory 174; replaceable desiccant-sieve cartridge 308; sample pump for breath sample collection 304; scrubber air pump vent 304b; flow restrictor 307; carrier gas pump which pressurizes the scrubber 300; charcoal scrubber 303; and the scrubber air inlet port 303b. In FIG. 10B, there is shown a sling 320 for holding, in one preferred embodiment according to this invention, the desiccant-sieve cartridge 308 and charcoal scrubber 303 in flexible but firm position. The sling 320 comprises a preferably elastomeric material comprising perforations therein 321 and 322 through which the desiccant-sieve cartridge 308 and charcoal scrubber 303

Figure 11:
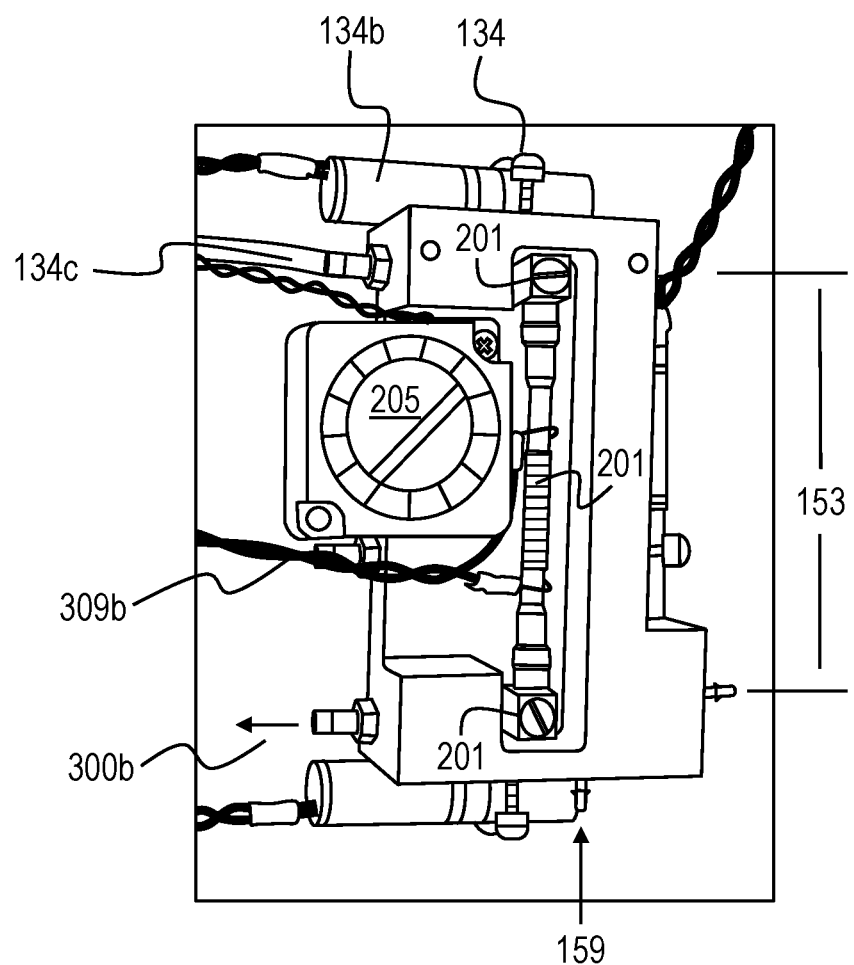

In FIG. 11, the obverse view from that shown in FIG. 10 is provided as a photographic representation of the internal components and architecture of a first exemplary embodiment of the SMART® device according to this invention. Visible in this photograph are at least the following components: attachment; breath inlet port 134c; concentrator column 201; line to sample pump 300b; scrubber air lines 309b; GC column oven 153; fan 205; vent 159 from GC detector 158.

Figure 12:
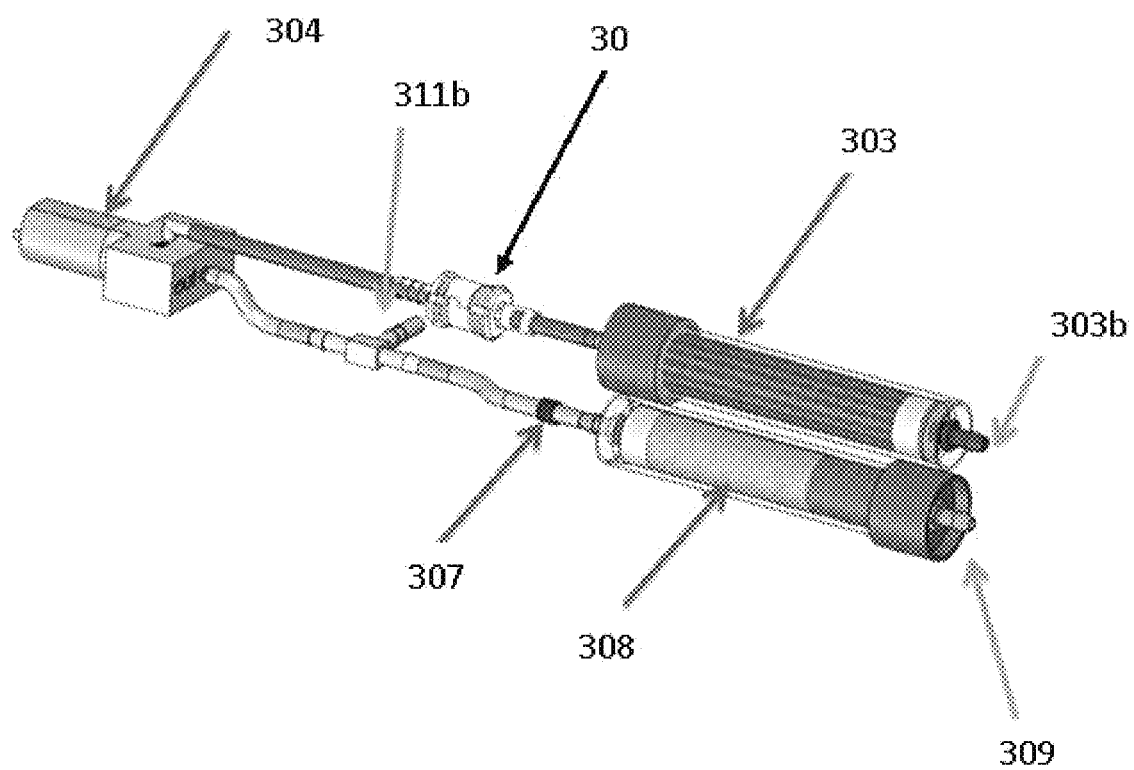

In FIG. 12, there is shown the air filter path in an exemplary embodiment according to the invention. Shown in this figure are: the scrubber air pump 304 which draws ambient air in through port 303b into the charcoal scrubber 303, via carrier pump coupling 305, past the scrubber pump pressure sensor port 311b, through flow restrictor 307, then through the desiccant scrubber 308 and from there out port 309 into the valving leading to the GC column.

Naturally, those skilled in the art will appreciate that these various elements are shown as an exemplary layout in one embodiment according to the invention and different or equivalent layouts and component dimensions are conceivable by those skilled in the art based on the disclosure provided here. In addition, not all components described in the general description are labeled in this figure—such as the PCB on which all the above components are laid and interconnected and the actual GC column which is obscured in these photographs by other components.

Those skilled in the art will further appreciate from the present disclosure that each of the elements shown herein may be further optimized by further miniaturization, such as, for example, through the use of micro-pneumatics.

6.1.15 SMART® Device User Interface and Sequence of Operation

Those skilled in the art will appreciate, based on the present disclosure, that there are wide array of variations to this component of the invention which may be utilized without departing from the core of this invention. Thus, for example, in one embodiment, a single breath collection is all that is required, because essentially no background exists. In other embodiments, an initial breath is obtained prior to medication being taken or administered followed by a second breath thereafter, for each dose of medication.

a. Baseline Breath Sample Acquisition:

It will be appreciated, based on the full disclosure provided herein, that a baseline breath sample may not be required in certain embodiments of this device used in connection with particular combinations of AEMs in various AMAM, IMAM or CMAM applications. Thus, for example, where very low background of a particular EBM is known to occur, a baseline breath may be dispensed with. As a specific example of such a scenario, consider the embodiments of this invention relating to use of i-AEMs where essentially no background exists for particular i-EBMs. Where a baseline breath is considered of value, this is obtained as described here.

Figure 13:
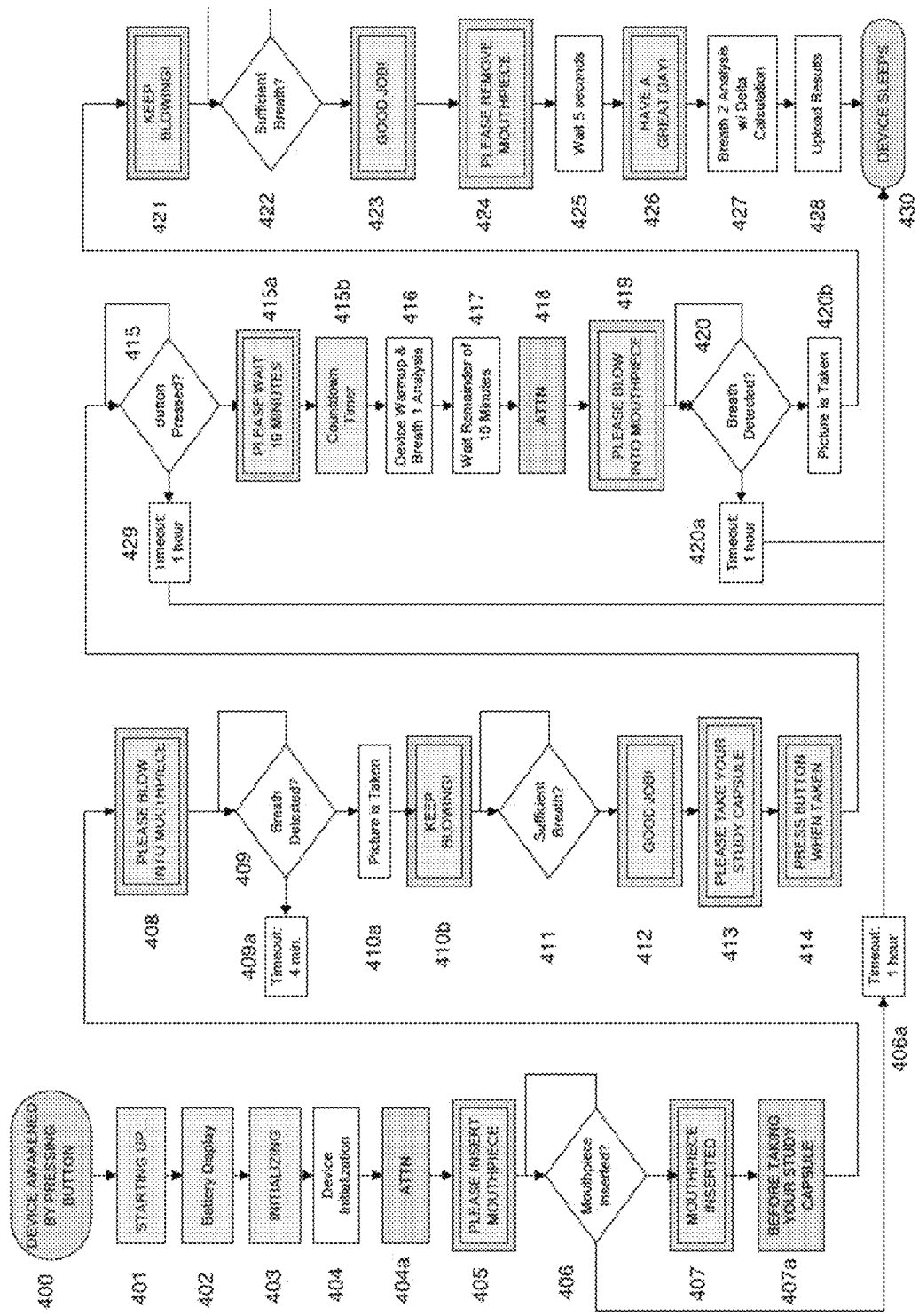

With reference to FIG. 13, in one embodiment according to this invention, at 400, the device is woken by pressing the start button 176, which initiates a startup routine at 401, a battery display to show the user whether the device has sufficient power to operate properly, 402, and if so, the device displays a message that it is initializing 403. The device then initializes all settings to a starting condition ready for exhaled breath sample receipt 404. "ATTN" 404a in the figure refers to an audible signal to alert the user that action is required. The user is then prompted 405 to insert a new, clean mouthpiece "straw". A mouthpiece insertion subroutine is then initiated 406 which, if no mouthpiece is detected, prompts the user to insert the mouthpiece 405, or, the system times out 406a after a pre-set time, optionally about 1 hour, if no mouthpiece is inserted within the preset time period. Once correct mouthpiece insertion has occurred, this is confirmed to the user 407, and the user is advised 407a that, prior to taking a medication or study capsule, to blow/exhale into the mouthpiece, 408. A breath detection subroutine 409 initiates to confirm detection of breath being exhaled into the device (triggered by the flow sensor 132). If no breath is detected, the system times out after a short while, optionally about 4 minutes. If a breath is detected, a biometric measurement of the user is captured, such as a fingerprint, or, preferably, a photograph is taken, 410a, and the user is prompted 410b to continue to blow into the mouthpiece until the device detects that a sufficient amount of breath has been detected 411. When a sufficient amount of breath has been detected, the subject is prompted with a "good job" or similar prompt 412 to indicate that a sufficient breath sample has been collected for analysis.

b. Sample Breath Acquisition to Confirm Medication Adherence

Once the device has confirmed that a sufficient pre-medication baseline sample has been acquired 411, the subject is then prompted to take their medication, study capsule or whatever dosage form it is for which medication adherence monitoring is being conducted 413a and the user is prompted 414 to press the start button 176 when the medication has been taken. The device then enters a subroutine 415 to confirm that the user has pressed the button. If no button press is detected within a preset time, e.g., thirty minutes to an hour, the device times out 429 and goes to sleep 430. However, if the button press is detected at 415, the routine continues, by a prompt 415a advising the user to please wait a pre-set amount of time, (a time optimized for the vast majority of subjects in clinical testing, depending on the medication/AEM combination in use, typically from about five minutes to about an hour, and preferably about ten to about twenty minutes). To ensure that the subject waits the optimal amount of time after taking the medication and to prevent the subject from forgetting to provide a post-medication breath, a countdown timer routine 415b initiates. During that period, the device warms up in readiness for receipt of the breath sample post medication 416 during which time the subject continues to wait for the full optimal time period for post medication breath collection 417. "ATTN" in the FIG. 418 refers to an audible signal to alert the user that action is required. Following this, the user is again prompted to blow into the mouthpiece 419. A breath detection subroutine initiates 420. If no post-medication breath sample is detected, the device is set to time out 420a within a pre-set time period, say about 1 hour. However, if a breath is detected, as before, a biometric is captured, preferably a photograph 420b, and the user is prompted to keep blowing 421 until a sufficient breath sample 422 is detected. When a sufficient amount of breath has been detected, the subject is prompted with a "good job" or similar prompt to indicate that sufficient breath has been collected 423. At this stage, the sample collection procedure has been completed and the user is prompted to remove the used mouthpiece 424. A brief period, e.g., five seconds, is provided 425 for the device to confirm that all operations have been successfully completed, at which point, the user is prompted to advise that the breath samples have been properly collected, by display of a message, e.g., "HAVE A GREAT DAY!" or the like, 426. The second breath sample is analyzed by the device 427, with calculation of changes (delta, Δ) in key analytes (e.g., 2-butanone), and the results are uploaded 428 to a database, locally and/or at a remote site, where medication adherence is optionally checked, confirmed or otherwise evaluated, either automatically or by an appropriate responsible party. At this stage, the device preferably goes into a sleep state, 430.

In light of the forgoing disclosure, those skilled in the art will appreciate that the present invention provides a novel SMART® device for Self Monitoring and Reporting Therapeutics. The Type I Self Monitoring and Reporting Therapeutics (SMART®) device comprises a miniature, portable, gas chromatograph subsystem for separation and analysis of components of a breath sample provided by a subject. The gas chromatograph is, preferably, provided in the device in combination with a separated compound sensor appropriate to detection and/or quantitation of the particular exhaled breath component of interest (VOC, EBM), and at least one or a combination of any one or a combination of:

a. means for subject biometric measurement for definitive identification of a subject concurrent with the subject providing an exhaled breath sample;

b. a breath flow sensor;

c. a wireless data transceiver;

d. a mouthpiece either with ports for breath sampling, venting, correct emplacement confirmation, and excess breath venting, or, a simple tube with a mouthpiece receiver port bearing features as described above for accepting the mouthpiece, breath sampling, venting, and emplacement confirmation;

e. a breath detection and sampling subsystem in operative coupling with the mouthpiece;

f. a disposable air scrubber;

g. a rechargeable battery pack subsystem; and h. a microcontroller subsystem in operative electrical coupling with at least one, several, and preferably all electrical components of elements (a)-(f).

It will further be appreciated that the SMART® device according to this invention may comprise, in various embodiments, any one or combination of the following:

a. the mouthpiece comprises: an exhaled air inlet; a breath flow sensor port; a breath sample conduit receiver port; and a vent; or simply an inlet and an outlet;

b. the breath detection and sampling subsystem in operative coupling with the mouthpiece comprises: a mouthpiece receiver comprising: a breath sample conduit for operative coupling with the breath sample conduit receiver port; a breath flow sensor for operative coupling with the breath flow sensor port; and a mouthpiece sensor for detection of proper insertion of the mouthpiece into the mouthpiece receiver;

c. the disposable air scrubber comprises an activated charcoal filter, a desiccant, or both;

d. the gas chromatograph is included in a subsystem in operative coupling with the breath detection and sampling subsystem and the disposable air scrubber comprises a thermally desorbable concentrator comprising: a thermally desorbable concentrator column; a proximal and a distal three-way valve on either end of the desorbable concentrator column; a heating element in intimate association with the thermally desorbable concentrator column; and a gas chromatograph column with a detector at the distal end thereof;

e. the wireless data transceiver subsystem comprises a WiFi, mobile cellular data transceiver, or both;

f. the biometric measurement means comprises a camera and display subsystem comprising a still or video digital camera which records an image of the subject at the time that the subject exhales into the mouthpiece;

g. the rechargeable battery pack subsystem comprises lithium batteries; and h. the microcontroller subsystem in operative electrical coupling with at least one and preferably all electrical components of elements (a)-(f) comprises a microprocessor, a voltage regulator, peripheral device interface electronics and GC sensor interface electronics.

Exemplary support for use of the Type I device as described herein is provided in the Examples below, (in particular, but not exclusively, in Examples 1-4). It will further be appreciated by those skilled in the art that the SMART® device may include one, different combinations of, or every element (a)-(h) as listed above. In addition, the Type I embodiment of the SMART® device according to this invention may include and incorporate components and elements of other SMART® device embodiments as described herein below.

The Type I embodiment of the device, according to the invention, is excellent for measurement in the exhaled breath of AEMs (which may appear in the exhaled breath) and/or EDIMs (or EDEMs, that is the Exhaled Breath Marker, EBM, which is typically a modified form of or a metabolite of the AEM) which appear shortly after ingestion of or application onto a subject of an AEM. This embodiment of the device is primarily adapted for AMAM, but, depending on the longevity of the EDIM in the exhaled breath, the signal to noise ratio and the total mass of AEM utilized, this device may also provide IMAM and CMAM options. This is described further in section 7, relative to specific AEMs and compositions of matter for delivery of AEMs, and section 8, relating to the SMART® system, in which particular AEM and device embodiments are matched to achieve particular AMAM, IMAM, and CMAM objectives.

Exemplary support is also provided herein below in section 9 of this patent disclosure.

6.2 Detailed Description of a Second Embodiment (Type II) of the Improved SMART® Device For the most part, the description of type I of the device in section 6.1 above, is directly applicable without change or minimal change to a description of a Type II device, unless differences/changes to a particular element or subsystem is specifically described herein below in this section. The key modifications in a Type II device as compared to a Type I device are described in detail in this section. The ways in which such modifications enable use of different AEM compositions of matter, methods of medication adherence, extension of the time for medication adherence monitoring in acute medication adherence monitoring and into intermediate and chronic adherence time frames and options for IMAM and CMAM, as well as alternate SMART® systems, are described here and in sections 7, 8 and 9.

The present invention is directed to the provision of new technology for assessing and improving medication adherence, which remains a critically important health care priority in multiple clinical settings, including pharmaceutical drug trials, management of major diseases (e.g., schizophrenia, diabetes, hypertension), and in the fight against diseases that threaten global health (e.g., TB, HIV/AIDS). In terms of accurately documenting adherence, methodologies, including electronic ones (e.g., pill counters, electronic medication caps and the like), developed to solve this problem, have been inadequate to date, since none detect or document actual drug ingestion/administration/application. Outside of clinical trials and research studies investigating strategies to improve adherence, it is unfortunately measured all too frequently, especially in the clinical setting, by simply questioning patients on their use of medication over the prior several (e.g., 4 or 7) days, or prior weeks or month. To address these shortcomings in assessing adherence, the present inventors provide methods, compositions and devices for achieving breath-based Medication Adherence Monitoring System (MAMS).

The goal of Xhale, Inc's., medication adherence monitoring program is to employ unique chemistry-based technologies to document adherence to oral and other medications. The adherence system, in a preferred embodiment, comprises a smart-phone sized sensor device or smart-phone inter-operable accessory, using breath as the diagnostics matrix to measure metabolites of generally recognized as safe (GRAS) food component-based taggants, that is, the Exhaled Breath Marker (EBM, whether that be an EDIM or EDEM). In other words, GRAS food additive-based taggants are used to document when a dosage form (e.g., a pill) entered the gastrointestinal tract or entered another physiological compartment (e.g., via transdermal, intranasal, vaginal, rectal, or other mode of delivery), was absorbed into the blood, and was metabolized to taggant metabolite(s) detectable in the exhaled breath, a procedure called definitive medication adherence. In contrast, we have also investigated presumptive medication adherence, where we can document that a medication was placed in the mouth of a subject but not actually swallowed. However, certain patients (e.g., schizophrenics, court ordered TB patients on drug therapy, so-called "professional" patients or deceptive patients enrolled in clinical trials) can be deceptive about whether they actually swallowed their medications. The MAMS methodology to which the present invention applies is of the definitive type.

Through human testing, we have identified a number of GRAS food additives, referred to herein as taggants (AEMs) that appear to have the appropriate features (e.g., generation of EDIMs) for an effective breath-based MAMS of the definitive type. One major strategy to achieve this goal is to utilize isotopically-labeled chemicals, preferably GRAS compounds, and particularly deuterated ones, which generate deuterated EDIM(s) (i.e. i-EBMs/i-EDIMs) in breath to document definitive medication adherence.

6.2.1 Key Differences Between Type II and Type I Devices According to this Invention According to this embodiment of the invention, the Type I device described in section 6.1 above is modified to enable use of AEMs comprising non-ordinary (but preferably stable, i.e. non-radioactive) isotopes in the AEM. Such AEMs are referred to herein as i-AEMs, and are manufactured and selected for use with this embodiment of the device such that EDIMs which are produced following ingestion or application of the i-AEMs include the non-ordinary isotope, and are, therefore i-EDIMs. Accordingly, this section of this patent disclosure describes and enables methods of making and using medications, medicinal compositions, devices, and systems and for production and detection of, in exhaled breath of a subject, volatile organic compounds (VOCs) which include non-ordinary, but preferably stable (non-radioactive), atomic isotopes, referred to as i-EBMs, (Exhaled Breath Markers containing at least one non-ordinary, but stable (non-radioactive) isotope), for definitive medication adherence monitoring. A key difference between a Type I device and a Type II device according to this invention is that, while for a Type I device, a simple sensor such as a MOS sensor suffices, for the Type II device, an infrared (IR) sensor is preferred. Another key difference is that in one embodiment of the Type II device, preferably, the device includes a catalytic combustion chamber to convert VOCs into water and carbon dioxide. Inclusion of the catalytic incinerator simplifies detection in this embodiment of the device by allowing the IR detector to be tuned to the particular non-ordinary isotope sought to be detected, whereas, without the catalytic incineration component, a tunable IR sensor may be required to permit the device to be tuned to detect different VOCs of interest. Thus, inclusion of the catalytic incinerator essentially converts a particular IR sensor into a universal IR sensor. For clarity, in the present invention, the catalytic element for IR applications is only required where an IR detector is sought to be used in the same manner as described above for use of a MOS detector in an mGC-MOS embodiment of the device. Further details and description on these aspects of the invention are found herein below.

In this embodiment according to this aspect of the invention, there is provided a device and a method of using the device, for detecting in an exhaled breath sample a VOC comprising a non-ordinary but stable (non-radioactive) atom, e.g., deuterium, wherein, in a preferred embodiment, the device comprises:

(a) means for separating VOCs in the exhaled breath;
(b) means for stripping the exhaled breath sample of moisture, (e.g., using Nafion® tubing or similar perfluorosulfonic acid polymer), carbon dioxide, (e.g., using soda lime) or both;
(c) means for converting VOCs in exhaled breath into carbon dioxide, water, or both, such that said non-ordinary but stable (non-radioactive) atom (e.g., deuterium or other non-ordinary isotope) included in the VOC is included in the water fraction, carbon dioxide fraction, or both, such that, e.g deuterated water, isotopically labelled carbon dioxide (with stable carbon or oxygen isotopes) is produced and available for quantitation in the exhaled breath sample.

6.2.2 Additional Definitions and Abbreviations Relevant to this Aspect of the Invention SMART®—Self Monitoring and Reporting Therapeutics—embodiments of a device, medication, composition, system and method wherein adherence by a subject in taking/receiving a medication is facilitated by detecting a volatile molecule in the exhaled breath of a subject, wherein the volatile molecule only appears in the exhaled breath of a subject a known period of time and at a known concentration after a medication is taken by the correct person, at the correct time, at the correct dose.

i-SMART™, as for SMART®, but including compositions, methods, systems and devices optimized for detection of compounds in the exhaled breath which include a non-ordinary, but preferably stable (non-radioactive) isotope, as further described herein below; those skilled in the art will appreciate that it is the presence of an isotope at an abundance that is completely different than the abundance of the isotope as it occurs in nature (due to that isotope having been selected for inclusion in the i-AEM) that is detected in this mode of practicing this invention, and any detector or sensor now known in the art or which later comes to be know which is sufficiently sensitive to detect the particular isotope of interest and its abundance (concentration) may be used for this purpose.

API—Active Pharmaceutical Ingredient—the medication or medications with the therapeutic effect of which is desired to be delivered to subjects and the administration of which is to be monitored via the SMART® or i-SMART system.

i-API—An API containing at least one non-ordinary, but stable (non-radioactive) isotope of hydrogen (i.e. deuterium), carbon (e.g., $C^{13}$), or the like, and which, on introduction into a living subject, results in the production of at least one i-EBM. This is typically as a result of the metabolism of the i-API to produce a cognate i-EBM specific to that particular i-API. In some cases, the i-API itself may be the i-EBM—e.g., deuterated propofol would appear in the exhaled breath, as does non-deuterated propofol. It will be appreciated that not the entire fraction of the API need contain the non-ordinary isotope, and that fraction that does is referred to herein as the i-API fraction.

EBMs—Exhaled Breath Markers—molecules which appear in the exhaled breath following ingestion or other form of administration of a medication containing a marker which gives rise to the EBM.

i-EBMs—Exhaled Breath Markers (including EDIMs and EDEMs) containing at least one non-ordinary, but stable (non-radioactive) isotope of hydrogen (i.e. deuterium), carbon (e.g., $C^{13}$), or the like.

EDIM—Exhaled Drug Ingestion Marker—a molecule detected in the exhaled breath of a subject who has ingested a medication (drug) which includes, as part of the Active Pharmaceutical Ingredient (API) or as part of a separate molecule packaged for co-delivery with the API.

i-EDIM—an EDIM comprising at least one non-ordinary but non-radioactive (i.e. stable) isotope.

EDEM—Exhaled Drug Emplacement Marker—a molecule detected in the exhaled breath of a subject who receives a medication (drug) which includes, as part of the Active Pharmaceutical Ingredient (API) or as a separate molecule packaged for co-delivery with the API, when received by a route other than ingestion.

i-EDEM—an EDEM comprising at least one non-ordinary but non-radioactive (i.e. stable) isotope.

AEM—Adherence Enabling Marker—a molecule included in a medication which according to this invention gives rise to EBMs in the exhaled breath of subjects who have taken or been administered the medication including the AEM.

i-AEM—An AEM which includes at least one non-ordinary but non-radioactive (i.e. stable) isotope which according to this invention gives rise to i-EBMs in the exhaled breath of subjects who have taken or been administered the medication including the i-AEM.

ADME—Absorption, Distribution, Metabolism, Excretion.

Ordinary and non-ordinary isotopes—non-radioactive isotopologue of a given element that is the dominant form in nature; the dominant non-radioactive isotopologues, termed the "ordinary isotopologues" are bolded, while the non-ordinary isotopes are not bolded: Hydrogen atom: $^1$H (protium), $^2$H or D (deuterium); Carbon atom: $^{12}$C, $^{13}$C; Nitrogen atom: $^{14}$N, $^{15}$N; Oxygen atom: $^{16}$O, $^{17}$O, $^{18}$O; Sulfur atom: $^{32}$S, $^{33}$S, $^{34}$S, $^{36}$S. Sensors are known in the art for measuring and distinguishing these isotopologues with exquisite sensitivity (at levels as low as low parts per trillion).

Where a particular combination or permutation of elements is described in connection with a particular embodiment or element of the present invention, those skilled in the art will appreciate that such combination or permutation of elements may be applicable to any other embodiment of the present invention, unless specifically excluded or, from the given context, this is clearly not appropriate. Thus, for example, in describing herein below formulations, dosage forms, compositions and methods for topical, vaginal or rectal delivery of APIs, i-APIs, and i-AEMs, considerations relevant to quantities of i-AEM delivery, type of i-AEM delivered, separation of the i-AEM from the API, etc. for such mode of delivery are applicable to any other mode of delivery; however, from the context of the description, it is clear that different formulations would be appropriate for each mode of delivery.

6.2.3 Rationale for Use of Isotopic Labeling to Confirm Medication Adherence The isotopic labeling of molecular entities that serve as substrates that, via enzymatic degradation or other processes, liberate isotopically-labeled i-EBMs, is a critically important strategy toward designing and developing an optimal MAMS—particularly for IMAM and CMAM embodiments. In a series of experiments (FIGS. 23-42) using a gas phase Fourier Transform Infrared (FTIR) device (Nicolet 6700 FT-IR, 5 liter Breath Sample, 22 meter path length) using human breath and a nitrogen environment, we confirmed key scientific assumptions, which underlie the advantages listed above for isotopic labeling in MAMS. Specifically, we investigated the effect of non-ordinary isotopic (e.g., deuterium, $^{13}C$; see Table 1) labeling on the FTIR spectrum of key alcohols, aldehydes and ketones, relative to those containing ordinary isotopes at room temperature. Important findings include:

1) FTIR poorly discriminates between deuterated and ordinary alcohols of similar structure; the FTIR absorption spectra for ordinary methanol and ethanol as well as deuterated methanol and ethanol are very similar.

Figure 61:
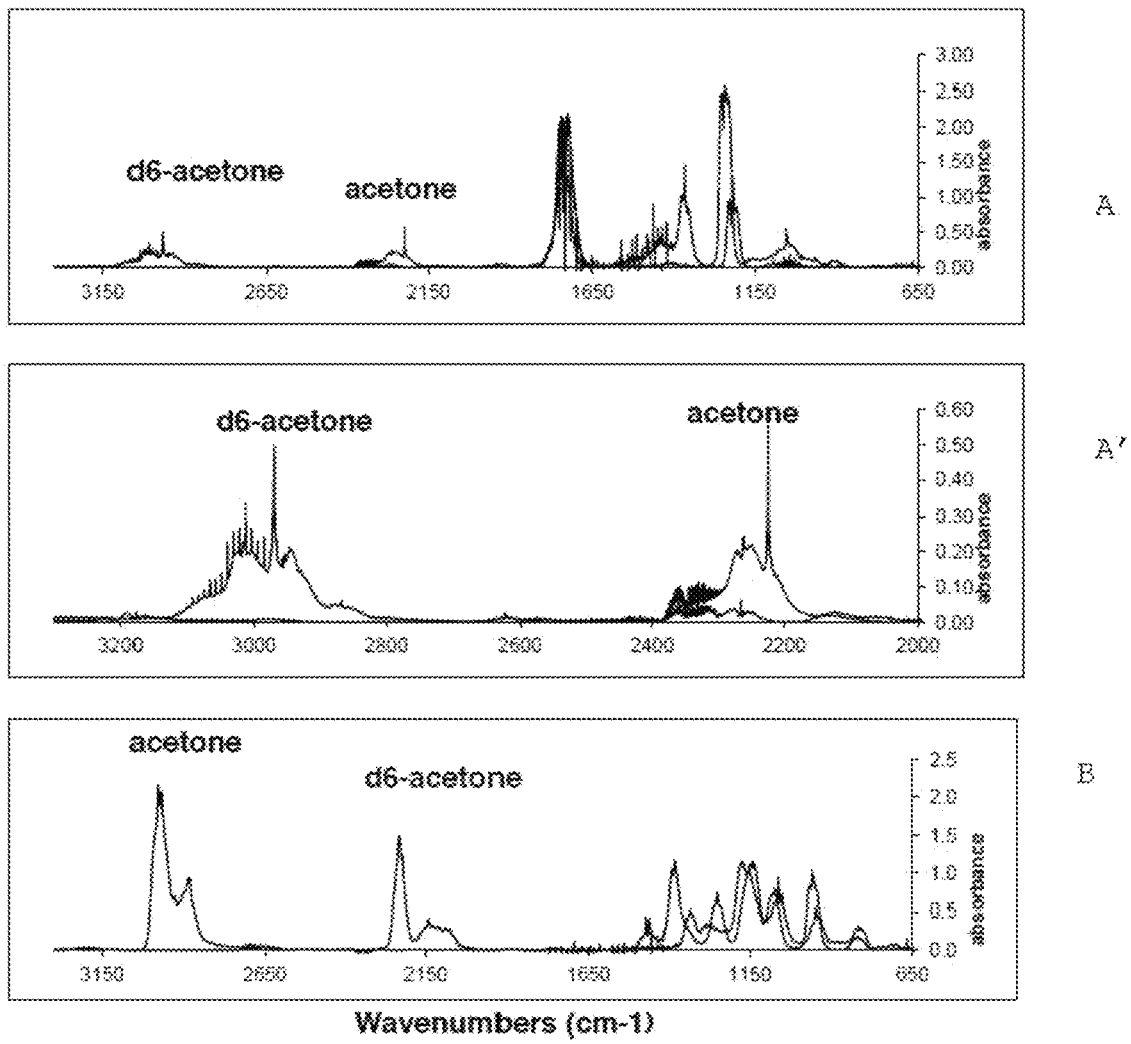

2) FTIR spectra for a given alcohol (ordinary vs deuterated) is highly distinctive and can be used to discriminate among them (i.e., $CD_3$-OH vs $CH_3$—OH or $CD_3D_2$-OH vs $CH_3CH_2$—OH) (see FIG. 61). In contrast, GC-MS can easily distinguish between all these species. The miniature gas chromatograph (mGC) can easily distinguish between specific alcohols of different carbon number but not among deuterated and non-deuterated alcohols with the same number of carbons.

3) FTIR does not provide a high degree of discrimination between deuterated and ordinary aldehydes of similar structure; the FTIR absorption spectra for ordinary formaldehyde and acetaldehyde as well as deuterated formaldehyde and acetaldehyde are similar. 4) FTIR spectra for a given aldehyde (ordinary vs deuterated) is highly distinctive and can be used to discriminate among them (e.g., $CD_3CDO$ vs $CH_3CHO$ or $CD_2O$ vs $CH_2O$). Taken together, the results indicate that isotopic labeling shows great promise in the specific and sensitive detection of i-EBMs in human breath for MAMS.

From the FTIR experiments, it appears that three fundamentally different deuterated i-EBMs could be distinguished by utilizing a tunable midIR laser with a center wavenumber of 2150±10% variability (wavenumber range: 2000 to 2300 $cm^{-1}$). These EBMs include: 1) carbonyl (i.e., acetone with per-deuterations on methyl groups)—wave number=2040 $cm^{-1}$; 2) aliphatic (i.e., hexane with per-deuterations on terminal methyl groups—wavenumber 2240 $cm^{-1}$; and 3) aromatic (e.g., benzaldehyde, cyclopentanone, or cyclohexanone with per-deuterations on the ring—wavenumber 2290 $cm^{-1}$.

Deuterium, depending upon the class of molecules they are placed on, the number of deuterations on a molecule, and their proximity to various bond types (e.g., amine, sulfhydryl, aromatic, etc.) on the molecule, can provide various types of molecular entities with unique analytical "signatures" in various biological media, including but not limited to breath, blood, urine, sweat or saliva. Various analytical techniques such as IR or mass spectroscopy can be used to not only distinguish deuterated parent compounds from their deuterated metabolites (both in the gas and/or liquid states), but can also easily discriminate deuterated molecules from those identical natural compounds containing ordinary hydrogen (e.g., ethanol versus deuterated alcohol; aldehyde versus deuterated aldehyde; methanol versus deuterated methanol). Its use will reduce the need or even eliminate the step of obtaining baseline breath samples, as well as markedly simplify the FDA regulatory process for new drugs allowing for faster time to market with inexpensive and reliable technology. Deuterated compounds are generally regarded as nontoxic and as having the same (or very similar) pharmacodynamic and pharmacokinetic properties as their undeuterated parent compounds. Last, deuterated approaches can be used to potentially monitor the metabolism of many important therapeutic agents.

From these studies, we conclude that the use of primary alcohols as taggants for oral adherence is not ideal. They generate aldehydes, which are very rapidly converted to their corresponding carboxylic acid. It is difficult to measure primary alcohols or their metabolites in the breath of humans following oral ingestion. The use of secondary alcohols as taggants for oral adherence appears very promising. They generate ketones, which persist in the breath of humans, following the oral administration of secondary alcohols. We are currently focusing on several secondary alcohols, including but not limited to 2-butanol, isopropyl alcohol (IPA, isopropanol), and 2-pentanol. These generate 2-butanone, acetone and 2-pentanone, respectively, which, other than acetone, are present in very low concentrations in the baseline breath of humans. Isopropyl alcohol is considered to be an excellent taggant, which will generate the ketone, acetone. In addition to incorporating small quantities of isopropyl alcohol into capsules or tablets, a great variety of GRAS isopropyl-based esters, which would generate isopropyl alcohol via esterases, exist in the food database. From the FTIR experiments, it appears that three fundamentally different deuterated i-EBMs could be distinguished by utilizing a tunable midIR laser (to measure C-D vibrational stretch) with a center wavenumber of 2150±10% range (wavenumber range: 2000 to 2300 $cm^{-1}$). These EBMs include: 1) carbonyl (e.g., acetone with per deuterations on methyl groups)—wave number=2040 $cm^{-1}$; 2) aliphatic (e.g., 2-butanone with deuterations on non-alpha carbons—wavenumber 2240 $cm^{-1}$), and 3) aromatic (e.g., benzaldehyde, with per deuterations on ring—wavenumber 2290 $cm^{-1}$. By combining molecules with molecular attributes including carbonyl, aliphatic and/or aromatic properties, up to 6 different types of molecules could be readily detected using tunable or non-tunable mIR approaches: 1) carbonyl only, 2) aliphatic only, 3) aromatic only, 4) carbonyl+aliphatic, 5) carbonyl+aromatic; 6) aliphatic+aromatic, and 7) carbonyl+aliphatic+aromatic. With the use of other types of optical detection systems, including but not limited to quantum cascade lasers, lead salt lasers, frequency-combed based systems, cavity-enhanced optical frequency comb spectroscopy, mode-locked femtosecond fiber lasers, and virtually imaged phase array (VIPA) detectors, a very large numbers of analytes, particularly in the breath, could be potentially detected.

Metabolic considerations are shown in greater detail in FIGS. 22 and 43-53 to assist in describing, and enabling those skilled in the art, in the practice of designing appropriate i-AEMs to achieve inclusion of non-ordinary isotopes in the i-EBMs. FIGS. 23-42 are provided to show the power of FTIR to distinguish signals obtained from ordinary and non-ordinary isotopes in different candidate i-EBMs, depending on the nature and degree of non-ordinary isotope substitution in select i-AEMS. Further details regarding these figures are provided in the Examples section included herein.

6.2.4 Type II SMART® Device for MAM Using i-EBMs

In light of the foregoing, it will be appreciated by those skilled in the art that, according to this invention, known methods, devices, systems and compositions for medication adherence monitoring, medication tracking and counterfeit medication detection are improved by:

A. provision of medications comprising a SMART® medication comprising an Active Pharmaceutical Ingredient (API or i-API) alone or in combination with at least one non-toxic, preferably Generally Recognized as Safe (GRAS) volatile organic compound (VOC) or incipiently volatile organic compound, the i-EBM (including i-EDIMs and i-EDEMs), preferably a direct food additive, wherein at least one atom of said i-AEM is replaced with a non-ordinary, stable (non-radioactive) isotope, such that, on administration (ingestion, topical application, or other means of delivery) of the medication or a component thereof comprising the labeled VOC, or a metabolite thereof comprising the non-ordinary isotope, the i-EBM, is entrained and is detectable in the exhaled breath or other bodily fluid;

B. provision of a device for detecting in an exhaled breath sample a VOC comprising a non-ordinary isotope, (the i-EBM) wherein, in a preferred embodiment, see further discussion below, the device comprises a means for stripping the exhaled breath sample of moisture, a catalyst for converting the VOC to carbon dioxide and water, such that the non-ordinary isotope from the VOC is included in the water or $CO_2$ fraction, such that, following catalysis, e.g., deuterated water or $CO_2$ containing isotopes of carbon or oxygen are detected and quantitated in the exhaled breath sample; and C. provision of a method for medication adherence monitoring which comprises providing a SMART® medication as described above to a subject and using the device as described above to detect and quantitate i-EBMs within the exhaled breath of the subject.

In a preferred embodiment according to this invention, a VOC, preferably selected from, but not limited to, the group consisting of secondary and tertiary alcohols in which for example hydrogens are replaced with deuterium atoms, or oxygen or carbon atoms are replaced by stable non-ordinary isotopes, is included in a medication for ingestion or delivery by other means (transdermal, vaginal, rectal, etc). The present invention demonstrates that, while kinetics of appearance of e.g., deuterated VOCs in the exhaled breath differs depending on the route of administration, whether delivered orally, transdermally, or via another route of delivery, and depending on the precise nature of the molecule in which deuterium is included, deuterated VOCs are readily detectable in the exhaled breath and are, therefore, excellent markers to definitively confirm medication adherence, to track medications use and to detect and preferably prevent medication diversion or counterfeiting.

In an embodiment of the device according to this invention for detecting i-EBMs produced from e.g., deuterated AEMs or AEMs containing other non-ordinary but stable isotopes, (i.e. i-AEMs) or metabolites thereof in the exhaled breath, there is provided a miniature portable gas chromatograph, similar to but an improvement over a first generation miniature GC device described in Morey et al., "Measurement of Ethanol in Gaseous Breath Using a Miniature Gas Chromatograph", J. Anal. Toxicol., Vol. 35, p. 134-142, (2011). The improvements in the present device include, but are not limited to, inclusion of a forward facing camera which is synchronized with breath sample acquisition to ensure that the breath sample and the identity of the subject providing the breath sample (e.g., by photographic identification) are concurrently time-stamped; and adaptation for maximum efficiency in detecting non-ordinary isotopes.

In a preferred embodiment of the device according to this aspect of the invention, included in the device are the following additional elements:

a. a sample de-humidification means and $CO_2$ stripper through which exhaled breath samples are passed to remove all water (including any background deuterated water which might interfere with subsequent quantitation of deuterated water following catalysis of VOCs to water and carbon dioxide); b. a catalyst for conversion of VOCs in the exhaled breath sample to $H_2O$ or $D_2O$ and Carbon dioxide (see, for example, Eltron Research & Development Inc., and their U.S. Pat. No. 6,458,741 Catalysts for Low-Temperature Destruction of Volatile Organic Compounds in Air; U.S. Pat. No. 6,787,118 Selective Removal of Carbon Monoxide; U.S. Pat. No. 7,329,359 Application of Catalysts for Destruction of Organic Compounds in Liquid Media; U.S. Ser. No. 12/257,811 A Metal Oxide System for Adsorbent Applications; (see http://www.eltronresearch.com/docs/Low_Temp_VOC_Catalyst.pdf); see, also, "Development of Low Temperature ActiveCatalysts for CO and VOC Abatement", Monika Molin, Department of Chemical Engineering, Lund University, Sweden (Jun. 27, 2011, available at http://www.chemeng.lth.se/exjobb/E605.pdf); see, further, "VOC oxidation over $MnOx-CeO_2$ catalysts prepared by a combustion method.". Dimitrios Delimaris and Theophilos Ioannides, Applied Catalysis B: Environmental, Volume 84, Issues 1-2, 25 Oct. 2008, Pages 303-312; see, also, "Low temperature oxidation of volatile organic compounds using gold-based catalysts", Kwenda, E., http://hdl.handle.net/10539/10408;

b. a non-ordinary isotope detector, preferably a $D_2O$ detector.

Figure 19:
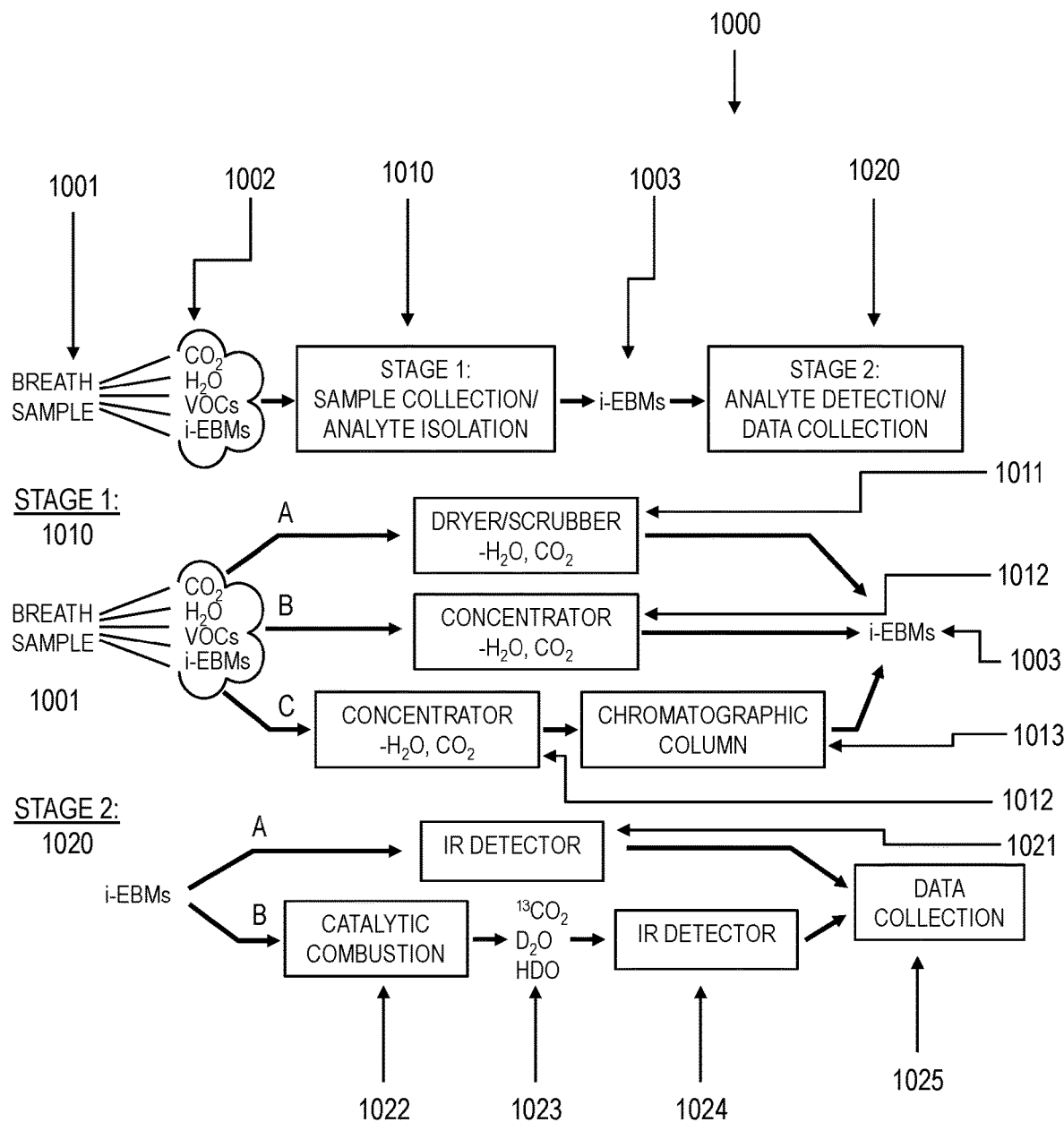

6.2.5 Detailed Description of the Type II Device According to this Aspect of the Invention Referring now to FIG. 19, there is shown a schematic wherein an embodiment 1000 of the device according to this invention is shown. A breath sample, 1001, comprising 1002 $CO_2$, $H_2O$ in the form of water vapor, volatile organic compounds (VOCs), and the included Exhaled Breath Marker (i-EBMs) comprising at least one non-ordinary isotope, is introduced into the Stage 1 of the device, 1010. This stage of the device is for sample collection and analyte isolation, from which only VOCs in the exhaled breath and the i-EBMs comprising the non-ordinary isotope, is released into Stage 2 of the device, 1020, where analyte detection and data collection occurs. According to this figure, further detail is provided with respect to Stage 1, 1010, where, after the breath sample 1001 (comprising $CO_2$, $H_2O$ in the form of water vapor, volatile organic compounds, and the included exhaled breath marker (i-EBMs) comprising at least one non-ordinary isotope, 1002), is introduced into the device, the introduced breath sample receives any of several different treatments, e.g., A, B, C, or modifications, variations, permutations, equivalents and/or combinations thereof.

Thus, referring again to FIG. 19, in treatment A of Stage 1 (1010), the breath sample 1001 (comprising water, carbon dioxide, VOCs and the i-EBM(s)) is passed through a dryer/scrubber 1011, which removes all or substantially all of the water and carbon dioxide endogenous to the exhaled breath sample 1001. An alternative or additional approach is shown in treatment B of Stage 1 (1010), wherein the breath sample 1001 is directed into a concentrator 1012 (e.g., a tenax column or the like) which binds VOCs including the i-EBMs, but not water or carbon dioxide, which merely flow through the concentrator and are vented to the atmosphere, while retained i-EBMs are, for example, thermally desorbed from the column after these contaminants have been removed. In treatment C of Stage 1 (1010), the breath sample 1001 is introduced into a concentrator 1012, as in treatment B, but, in addition, the retained materials are fractionated via a fractionation means, e.g., a chromatographic column. In a preferred embodiment, the chromatographic column is a miniature gas chromatography (GC) column, thus making it possible for the entire device to be portable. The concentrator, 1012, is preferably a material which efficiently retains VOCs, including i-EBMs, while allowing all other breath components to flow through (i.e./ e.g., moisture, carbon dioxide), but is easily desorbed of retained VOCs/i-EBMs, e.g., by application of heat. Of course, both a dryer/scrubber 1011 and concentrator 1012 may be utilized in series to ensure removal of all water and carbon dioxide endogenous to the exhaled breath sample, prior to further treatment (GC column separation and Stage 2 treatment).

Also shown in the figure is further detail of the Stage 2 of the device, 1020, whereby the i-EBMs emergent from Stage 1 can be treated by a treatment such as treatment A or Treatment B in Stage 2 or in equivalents, modifications, permutations or combinations thereof. In Stage 2, treatment A, the i-EBMs 1003 are directly passed through an infra-red (IR) detector and the signals obtained from passage of the sample through the detector is collected and analyzed. In Stage 2, treatment B, the i-EBMs are subjected to catalytic combustion 1022, to produce carbon dioxide and water from the i-EBMs and VOCs. Where non-ordinary isotopes are included in the i-EBMS, these appear in the carbon dioxide or water (deuterium oxide) fraction and are then passed through an IR detector for data collection and analysis 1025. Of course, any VOCs aside from the i-EBMs introduced into Stage 2 will also be converted by this latter treatment into carbon dioxide and water, but, since these produces are not labeled with a non-ordinary isotope, such as deuterium, the IR detector 1021 is easily tuned to provide distinct signals based on e.g., deuterium content.

Naturally, if in Stage 1 1010 there has been a separation of compounds e.g., by chromatographic means (1013) the VOCs including i-EBMs are separated prior to introduction into the IR Detector, whether catalytic combustion is utilized or not. The advantage of including catalytic combustion is that, rather than needing to utilize a tunable IR sensor, which tends to be complex and expensive, a very simple and inexpensive IR sensor, tuned to detect e.g., deuterated carbon dioxide or deuterated water, may be utilized.

Figure 20:
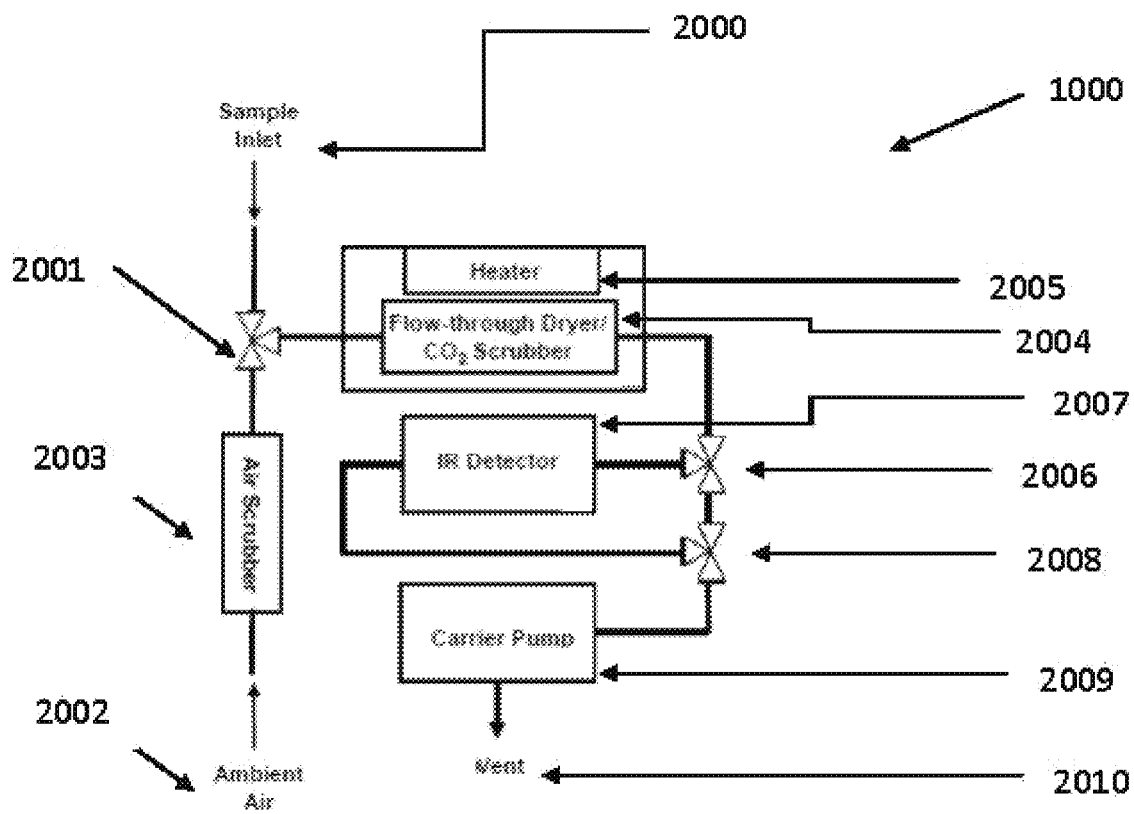

Shown in FIG. 20 is an example of a device according to this invention wherein the treatment B of Stage 1 and the IR detector, treatment A of Stage 2 are arranged in series. According to this embodiment, the device 1000 comprises a sample inlet 2000, which is directed to a three-way valve 2001. The three-way valve 2001 permits ambient air 2002 to pass through an air scrubber 2003 to drive a sample of exhaled breath through a flow-through sample dryer/CO2 scrubber 2004 which removes endogenous water and carbon dioxide from the sample, while allowing VOCs and i-EBMs to pass through. A heater, 2005, is associated with the flow-through dryer/$CO_2$ scrubber to establish controlled temperature conditions, and, in the event that a VOC/i-EBM concentrator is also used, to induce thermal desorption from the concentrator at the desired time point. Where catalytic conversion of VOCs is utilized, a heater is provided to generate elevated temperatures, although systems for conversion of VOCs to $CO_2$ and $H_2O$ at about 50° C. are also available for this purpose. On emerging from the flow-through dryer/CO2 scrubber 2004, the sample is directed through another three-way valve 2006, which directs the sample through an IR detector 2007, and from there, via another three-way valve 2008, via carrier pump 2009, to a vent 2010. In this embodiment, use of a tunable IR sensor may be required to distinguish between i-EBMs and other VOCs which do not contain non-ordinary isotopes.

Figure 21:
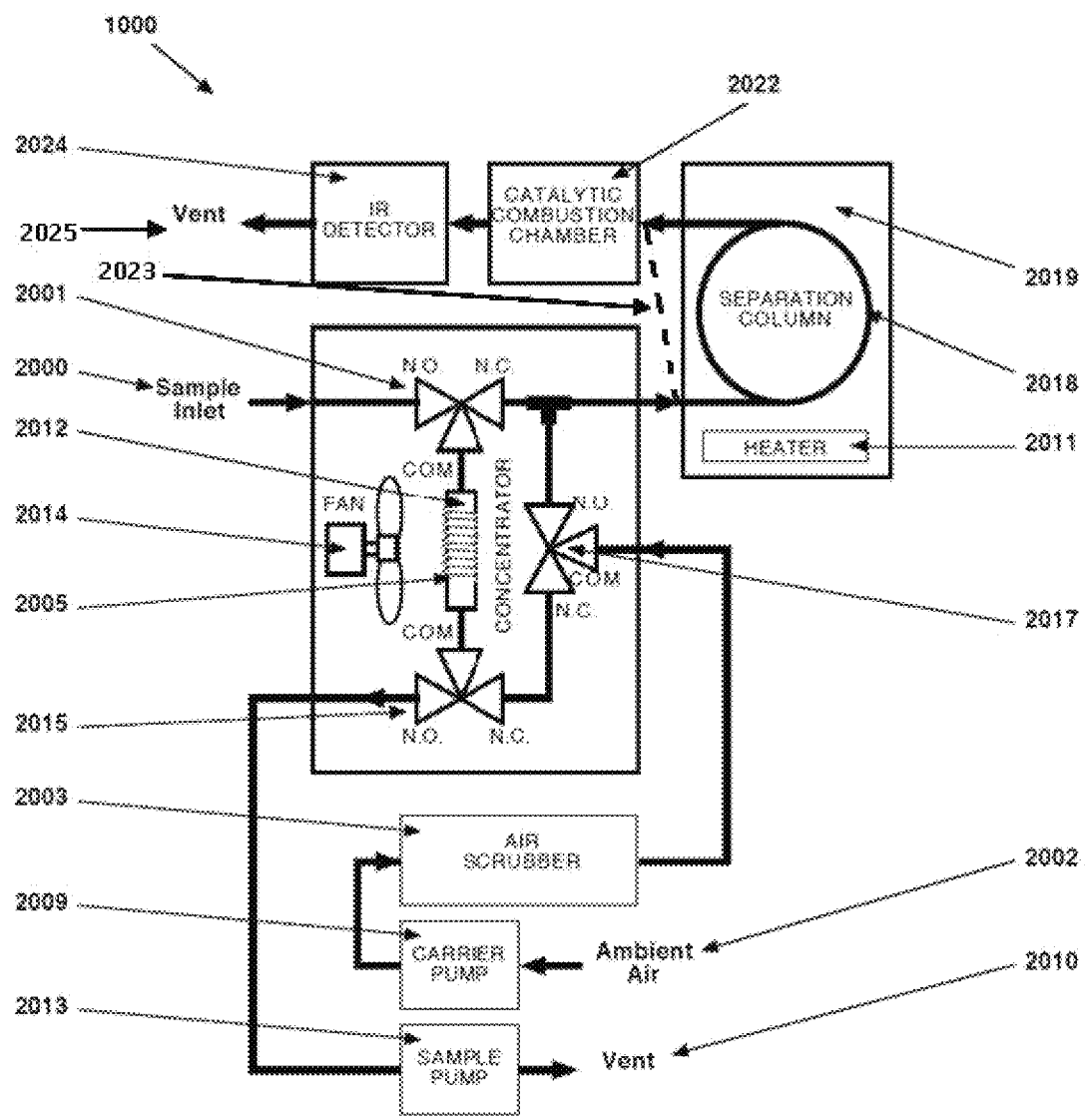

In FIG. 21, there is shown another embodiment of the device 1000 of this aspect of the invention according to which, per FIG. 19, Stage 1, treatment B, and Stage 2, treatment B, are arranged in series. According to this embodiment of the device of the invention, the exhaled breath sample is passed through a separation means, preferably e.g., a separation column such as an appropriate GC column 2018, and then into a catalytic combustion chamber 2022 prior to being passed into a detector 2024. Alternatively, as shown by the dashed line 2023, the separation column 2018 may be bypassed or simply not included in an embodiment according to this aspect of the invention, by directly connecting the outlet from the concentrator 2012 directly to the inlet of the catalytic combustion chamber 2022. Those skilled in the art will be able to configure other alternate embodiments, based on the disclosure and teaching provided herein, to fit particular needs and circumstances. According to this embodiment 1000 (either including or not including a separation means such as the separation column 2018) of the invention as shown in this figure, the device of this invention is utilized by introducing a sample of exhaled air into sample inlet 2000 and from there, the sample is passed via three-way valve 2001 and is trapped/concentrated in a thermally desorbable concentrator 2012—e.g., a hydrophobic column, (e.g., tenax) from which adsorbed molecules are desorbed by activation of heating means 2005, e.g., a peltier device or heating coil wound around the thermally desorbable concentrator 2012. Sample pump 2013 provides pressure as needed to draw sample in via sample inlet 2001 and to vent 2010 as needed. Preferably, a fan 2014 is included to ensure efficient and even heating of the concentrator 2012 and dissipation of heat from the device 1000. Once the sample is adsorbed to the concentrator 2012, a three-way valve 2015 at the distal end of the concentrator 2012 permits ambient air 2002 to pass through an air scrubber 2003 to thereby provide scrubbed ambient air via the three way valve 2015 to the distal end of the concentrator 2012. On actuation of the heating element 2005, the sample is desorbed from the thermally desorbable concentrator 2012, and is driven from the concentrator proximal end of the concentrator 2012 via three-way valve 2001 onto separation column 2018, (if included in the particular embodiment, or directly to the chamber 2022, as noted above), preferably a gas chromatographic column selected to separate molecules according to their partition coefficient (boiling temperature) relative to the mobile and stationary phases in the column 2018. Preferably, the column 2018 is heated to a controlled temperature by heater 2011 to achieve reproducible molecular separation and retention times on the column 2018. Sample molecules emerge from the distal end 2019 of the column 2018 at characteristic retention times. In this embodiment of the device according to this invention, the sample stream is directed to enter a catalytic combustion chamber 2022 where any VOCs and i-EBMs are converted to ordinary carbon dioxide and water, if arising from endogenous VOCs or comprising non-ordinary isotopes, if arising from i-EBMs. Any such molecules are then detected, at characteristic retention times, via IR detector, 2024 which, of course, detects the water or carbon dioxide coming off the column, albeit at the characteristic retention times of the VOCs from which they have been generated. The IR detector, of course, distinguishes any water or carbon dioxide thus generated depending on whether non-ordinary isotopes are present in the water and carbon dioxide, or not. The thus analyzed molecules are then passed from the detector 2024 and then vented 2025. In this embodiment, the IR detector 2024 may be tuned to detect, e.g., water or carbon dioxide containing non-ordinary isotopes (e.g., of hydrogen, carbon or oxygen), while ignoring detection of carbon dioxide or water arising from catalytic combustion of endogenous VOCs which do not contain non-ordinary isotopes. Preferably, the detector 2024 does not require tuning and is set to detect the characteristic signal of a particular non-ordinary isotope of interest (e.g., deuterium, carbon or oxygen).

As discussed above, in Stage 1, i-EBMs are collected from the breath and separated from water, carbon dioxide and, optionally, other volatile organic compounds (VOCs) that may interfere with the subsequent analysis. In its most basic form (Stage 1-A), this may be accomplished by simply passing a portion of the breath through a low pressure scrubber (e.g., Nafion tubing) prior to entering the detector. For lower concentrations of i-EBMs, the scrubber can be replaced with a concentrator (Stage 1-B), and for samples containing multiple i-EBMs, chromatographic separation can be included (Stage 1-C).

In Stage 2, the captured i-EBMs are detected, analyzed, and optionally quantitated by an appropriate sensor, such as an IR-based detector. For i-EBMs with characteristic or intense absorption bands, the parent molecule is measured directly (Stage 2-A). In cases where this is not true, it may be necessary to convert the i-EBM into a more readily detected species. When an organic molecule is combusted, carbon atoms from the molecule are oxidized into $CO_2$ and hydrogen atoms are oxidized to produce water. Isotopically-labeled organic compounds give rise to corresponding isotopically-labeled combustion products. For example, an isotopologue of acetone containing $^{13}C$ in place of $^{12}C$ and deuterium in place of hydrogen would generate $^{13}CO2$ and $D_2O$, respectively. $^{13}CO2$ and $D_2O$ are readily measured IR active species. Since $CO_2$ and water are typical combustion products for all organic molecules, combusting any suitably labeled i-EBM, regardless of its inherent IR absorption, will result in the same IR-active products. By tuning the IR detector to measure these common combustion products (e.g., $^{13}CO_2$ and $D_2O$) instead of the parent i-EBM, the combination of a catalytic combustion chamber and an IR detector functions as a "universal" detector for any i-EBM. In fact, the utility of this embodiment of the device is not limited to medication adherence monitoring applications. Any VOCs may be analyzed in this way, thereby providing significant added flexibility by providing a universal VOC detector.

The various elements depicted in FIG. 19 can be combined to produce several distinct devices. The most basic of these devices is produced by joining the Stage 1-A and Stage 2-A paths in series. Alternatively, the most complex design combines paths 1-C and 2-B, see FIG. 21.

In this embodiment of the device, there is provided a novel detector of compounds comprising non-ordinary but preferably non-radioactive (i.e. stable) isotopes, i.e. i-EBMs. With respect to the key application of interest here, the device is a novel medication adherence device based on measurements of, for example, cold isotopologues of water in human breath. Stable cold isotopologues of water include, but are not limited to: 1) $H_2{}^{18}O$, 2) $H_2{}^{16}O$, 3) $H^{16}OD$, 4) $D_2{}^{16}O$, and 5) $H^{18}OD$, and/or stable cold isotopologues of carbon dioxide. Appropriate routes of drug administration include but are not limited to: oral, intravenous (IV), transdermal, rectal, vaginal. A key point of novelty in this device is that the water and $CO_2$ being used to detect medication adherence are NOT being generated by the body, but rather by mechanisms within the sensor. The system allows a common detection algorithm to be used to detect a great many different drugs, markers, VOCs and the like. For medication adherence monitoring, different types of EDIMs (Exhaled Drug Ingestion Markers) may be used alone or in combination. In a preferred embodiment, the device according to this invention exploits the use of a well-developed cold isotopic monitoring systems for water and/or CO2 for many types of i-EDIMs/i-AEMs/i-EBMs and can function with or without the use of a baseline breath sample. A baseline breath sample can be used to subtract off any background VOCs in the breath, e.g., DHO and $D_2O$, but the baseline levels for these compounds are likely so low that no baseline breath sample may be needed.

The detection can be accomplished with or without a mini-gas chromatograph (mGC). Without using the mGC, there is little delay which is required in an mGC-based process, and results can be obtained in very nearly real time with time otherwise required for separation thereby eliminated. That is, in this embodiment, after the breath is sampled onto the tenax trap, the trap temperature is rapidly increased to about 180° C. to desorb the VOCs from the trap and into the catalytic combustion stage. Depending on the particular VOCs to be analyzed, an optimal contact time with the catalyst to efficiently convert the i-EDIM to $D_2O$ is selected. The $D_2O$ then passes into the IR cell, where it may take a few seconds to be analyzed (typically 16-64 IR scans are run for reliable statistics). This whole process may take between 30 seconds to 1 minute.

This mode of analysis is limited to detecting only an integrated mass of DHO and $D_2O$. With an mGC, the system can separate compounds based on boiling points prior to entering an IR detector or alternate detector element. Where IR is used, this may be used in a manner similar to MOS used in an existing mGC-MOS configuration. It permits robust detection of DHO and $D_2O$ in breath to identify many different types of deuterated or other non-ordinary isotope containing i-EDIMs (i-AEM or metabolites of i-AEMs).

In connection with this aspect of the invention, it is noted that Picarro, Inc., provides a Micro-Combustion Module (A0214) to remove interfering organics from water samples, in-line and efficiently. That module is disclosed as able to: improve data quality for water isotope analysis, treat samples in-line to decompose interfering organics; integrate seamlessly with Picarro's A0211 High-Precision Vaporizer, and to deploy effortlessly in the lab or the field-minimal footprint and energy requirements. Designed to eliminate organic interferences from water isotope analysis using a fully in-line process, and installed between Picarro's High-Precision Vaporizer and the Picarro L2130-i water isotope analyzer, the Micro-Combustion Module (MCM) is described as providing seamless operation by passing a gaseous phase sample from the vaporizer over an enclosed element. The resulting oxidation converts organics into minute quantities of carbon dioxide and nascent water. The MCM includes a self-contained micro-reactor element that can be easily replaced in the field. The MCM effectively removes spectral interference for commonly occurring alcohols and plant products including multicomponent mixtures of alcohols, terpenes and green leaf volatiles. It has optimal efficacy for samples containing total organics in concentrations typical for many plant extracts (<0.5%) due to the production of nascent water. Higher concentrations of alcohols, such as those found in certain beverages, will not be completely broken down in the MCM. However, the process is highly reproducible and can create high-precision fingerprint data. This Picarro module may be incorporated into the Type II device according to this invention.

6.2.6 Detectors and Separators a. CMOS, IR and Mass Spec Detection of Compounds with Included Non-Ordinary Isotopes Such as Deuterium Use of IR sensor technology enables use of deuterated and other non-ordinary isotope containing markers. Depending on the size of the gas sampling cell, detection of deuterated breath markers at levels above 1000 ppbv are readily detected. In the past, gas phase IR technology has typically not been able to go much below 1000 ppbv unless a large, multi-pass gas cell or a molecule that has a huge IR absorption is used. This is rapidly changing, however, and new solutions are constantly being developed in this field. A Nicolet 6700 FTIR, for example, has a detection limit of around 1 ppm for acetone/IPA/deuterated acetone/deuterated IPA using a 5-L gas sampling cell. Inclusion of a concentrator (such as that disclosed herein above in connection with the mGC), 1-L of breath is concentrated down to a volume of about 1-10 cc. This decreases detection limits to enable detection of EDIMs in breath after pill ingestion. A diode laser-based IR instrument is preferred for detection as they emit a much higher intensity light versus continuous light sources (e.g., the ETC Everglo source used in the Nicolet 6700 FTIR). Using such a modification provides detection limits 10-100 times lower than in the unmodified device. Near InfraRed (NIR), Mid Infrared (mIR), diode laser, FTIR, Cavity Ring Down Spectroscopy (CRDS), and related systems are available commercially, for example, from Daylight Solutions, Inc., San Diego, Calif.; Picarro, Inc., Santa Clara, Calif., and the like. Picarro, Inc., for example, affirms its sensors to measure in the low (e.g. 10) parts per trillion range for particular analytes. Organic compounds (both normal and deuterated) can be analyzed by infrared (IR) spectroscopy for both qualitative and quantitative purposes. Either a FTIR (fourier transform infrared) spectrometer can be used to continuously monitor the entire mid-IR wavelength range (4000-400 cm$^{-1}$ or 2.5-25 μm) or a tunable laser diode with an IR detector can be used to monitor selected wavelengths within this range (for example 4.3, 6.8, 8.3, 9.1 and 10.8 μm laser diodes available from Daylight Solutions. A laser diode-based IR spectrometer can also be used in a cavity ringdown mode (CRDS) to monitor the IR absorption of a gas as a time-based measurement instead of an intensity-based absorption measurement used in FTIR spectrometry. The advantages of this configuration is the very high sensitivity and precision of the measurement, resulting in much lower detection limits. See also U.S. Pat. No. 8,410,560, and patent publication no. US 2012/0267532. In a further embodiment, particularly utilizing evolving solutions for "mass spec on a chip", compounds evolved in the exhaled breath are subject to mass spec analysis, either in a central facility or, preferably, built into the SMART® analytical device. Appropriate mass spec technologies appropriate for use in this application include, for example, that reported by Cheung et al., "Chip-Scale Quadrupole Mass Filters for Portable Mass Spectrometry", J. of Microelectromechanical Systems, V.19, Issue 3, pp. 469-483, (2010), and the M908 device available from 908 Devices, Inc., 27 Drydock Ave., 7th Floor, Boston, Mass. 02210, and U.S. Pat. Nos. 8,816,272; 8,525,111; and 8, 921, 774.

b. Miniature Gas Chromatography—mGC

In one embodiment according to this invention, the SMART® device comprises a miniature gas chromatograph, or mGC. According to this embodiment of the invention, volatile organic compounds (VOCs) in the exhaled breath of subjects is introduced into a portable mGC device which separates the VOCs according to partition coefficients for the VOCs as between a mobile phase and a stationary phase inside the mGC column. For purposes of the present invention methods, known in the art can be brought to bear for this purpose. Thus, see, for example, Andrews, A. R. J., Z. Wu, and A. Zlatkis. "The separation of hydrogen and deuterium homologues by inclusion gas chromatography," *Chromatographia* 34.9-10 (1992): 457-460. Such systems may include, but are not limited to, for example, Sigma Aldrich b-Dex 110 Product No. 24302, 60 m×0.25 mm i.d. 0.25 mm film thickness; b-Dex 110 Product No. 24301, 30 m×0.25 mm i.d. 0.25 mm film thickness; CD Type: b (beta) Derivative: Dimethyl Phase: Non-bonded; 10% 2,3-di-O-methyl-6-O-TBDMS-b-cyclodextrin embedded in SPB-35 poly (35% phenyl/65% dimethylsiloxane) (intermediate polarity phase); Sigma Aldrich b-Dex 325, Product No. 24308, 30 m×0.25 mm i.d. 0.25 mm; CD Type: b (beta) Derivative: Dimethyl Phase: Non-bonded; 25% 2,3-di-O-methyl-6-O-TBDMS-b-cyclodextrin embedded in SPB-20 poly(20% phenyl/80% dimethylsiloxane), (intermediate polarity phase), and the like. Results obtained using such systems can be seen, for example, in Gas Chromatographic Determination of Isotopic Molecules by means of Open Tubular Thick Layer Graphitized Carbon Black Columns (J. Chromatog. 34 (1968) 96) (utilizing a custom made column: 9.6 meters, 0.15 mm I.D. open tubular thick layer graphitized carbon black column, 87.5° C. Further information on such products is available, for example, from Restek at restek-.com.

6.3 Detailed Description of a Third Embodiment (Type III) of the Improved SMART® Device The Type III device according to this invention is a much simplified device for medication adherence monitoring. According to this embodiment of the device, components of the Type I device as described above in section 6.1 are included, while others are dispensed with. Thus, preferably, as described above, the Type III device may, but does not necessarily, include exhaled breath capture and concentration. Where this is not included, exhaled breath is directly exposed to sensors. In the Type III device, compound separation is not required as discrimination is achieved at the level of compound detection. According to this aspect of the invention, at least two sensors are utilized: —One specific to the EBM or i-EBM and one sensitive to other VOCs. By difference, the concentration of the EBM of interest is calculated by on-board logic. An example of a device which could be adapted for use for this purpose according to this embodiment has been described in the literature, for a completely different purpose, by Toyooka et al., J. Breath Res. 7 (2013), "A prototype portable breath acetone analyzer for monitoring fat loss". According to that report, acetone contained in exhaled breath is identified as a metabolic product of the breakdown of body fat and is expected to be a good indicator of fat-burning. They note that while, typically, gas chromatography or mass spectrometry are used to measure low-concentration compounds in breath, they state that "such large instruments are not suitable for daily use by diet-conscious people". Naturally, the Type I and Type II embodiments of the SMART® device according to this invention as described herein provides just such a device, and, in addition to MAM applications, those devices may be well applied for the metabolic monitoring purposes of concern to Toyooka at al. Nonetheless, Toyooka et al., describe a prototype portable breath acetone analyzer that has two types of semiconductor-based gas sensors with different sensitivity characteristics, enabling the acetone concentration to be calculated while taking into account the presence of ethanol, hydrogen, and humidity. To investigate the accuracy of their prototype and its use in diet support, they conducted experiments on healthy adult volunteers in which they found that breath acetone concentrations obtained from their prototype and from gas chromatography showed a strong correlation. Moreover, body fat in subjects with a controlled caloric intake and taking exercise decreased significantly, whereas breath acetone concentrations in those subjects increased significantly. They concluded that their prototype is practical and useful for self-monitoring of fat-burning at home or outside to help prevent and alleviate obesity and diabetes. The device described by Toyooka et al., included a pressure sensor to detect exhaled breath and used a first gas sensor with "particularly high sensitivity to acetone", (platinum-doped tungsten oxide, Itami, Japan), and a second sensor which has "almost equal sensitivity to both acetone and interference gases such as hydrogen and ethanol" (tin oxide, SB-30, FIS, Inc.). The sensors were operated at 400 deg. C., and differential calculations of output from the two sensors was used to determine the acetone increases and decreases in exhaled breath on different activities by subjects.

For purposes of a Type III device according to the present invention, a commercial embodiment of a platinum-doped, tungsten oxide sensor is produced and utilized for acetone-specific detection where an AEM or i-AEM which generates breath acetone elevations (e.g., using isopropanol as the AEM) is used. Naturally, the first sensor may be selected for alternate EBM specificity than for acetone. A second sensor, such as the tin-oxide SB-30 sensor, is utilized in combination to measure other compounds in the exhaled breath, to enable acetone (or other EBM) specific calculations to be achieved. Such an embodiment of a Type III device using dual-MOS sensors, of course, affords only 2-dimensions of selectivity (i.e. the "array" coatings and the signal processing used to reject interference signals and deduce the acetone concentrations from the two signals). To achieve enhanced reliability in medication adherence monitoring contexts, a concentrator as described above in the Type I and Type II SMART® device is included ahead of the dual MOS array, thereby providing 4-dimensions of selectivity and sensitivity, (concentrator sorbent, desorption temperature, array coating and signal processing), a significant enhancement over the device described by Toyooka et al. The included concentrator protects the "naked" MOS detectors from environmental contaminants and would therefore also greatly improve longevity. The concentrator would separate humidity, hydrogen, carbon dioxide, carbon monoxide, methane and other contaminants from the e.g., acetone signal. The Type III SMART® device according to this aspect of the invention would preferably be approximately "cigarette-pack" sized.

In an preferred embodiment of the Type III SMART® device according to the invention, all components of the Type I device as described above are included and are incorporated here by reference, except that the separation means, e.g., the mGC, is excluded, and the sensor according to this embodiment of the device are dual sensors with differential sensitivities to analytes to enable detection and measurement of specific analyte(s) of interest.

In light of the forgoing disclosure in this section, it will be appreciated that the device (or a system incorporating the device) according to this invention for medication adherence monitoring comprises;

a. an exhaled breath sampling module which obtains a sample of exhaled breath from a subject;
b. an exhaled breath analysis module operatively coupled to the breath sampling module so as to receive from the breath sampling module a sufficient quantity or fraction of the sample of exhaled breath to permit analysis of the constituent components of the exhaled breath sample or fraction of the exhaled breath sample; and
c. an exhaled breath kinetics module for determining kinetics of appearance and disappearance of a marker identified by analysis of the constituent components of the exhaled breath by the exhaled breath analysis module.

It will be appreciated that the exhaled breath sampling module, exhaled breath analysis module and exhaled breath kinetics module are preferably, but not necessarily all included in a unitary, portable device.

In addition to using experimental approaches as disclosed and enabled herein and in the examples, those skilled in the art will note that sophisticated software, such as WinNonlin, can be used to model and predict intra-individual and inter-individual variability of key PK parameters (Pharsight Corporation, Mountain View, Calif.).

Those skilled in the art will also appreciate that analysis of measured exhaled breath components is optionally conducted on a central data repository after EDIM concentration-time data is uploaded/transmitted from the portable device, or it is conducted locally on the SMART® device itself.

Those skilled in the art will also understand from this disclosure that, although this patent disclosure discloses and enables use of compartmental PK analyses (see Example 28), the invention is also operative using non-compartmental PK approaches, as described, for example, by implementing WinNonlin software (Pharsight Corporation, Mountain View, Calif.).

Accordingly, the invention includes a device or system wherein the exhaled breath kinetics module calculates, for a given marker identified by analysis of the constituent components of an exhaled breath sample of a subject obtained at a time $t_1$, whether the concentration of the marker is consistent with the expected concentration of the marker at the given time $t_1$. This is done with reference to stored pharmacokinetic parameters from the subject for the given marker and the dosage interval (T), if the subject had been adherent to a set regimen for introduction of the marker or a precursor of the marker into the subject over a defined time period prior to obtention of the exhaled breath sample.

Likewise, in an alternate embodiment, the device (or system incorporating the device) according to this invention, the exhaled breath kinetics module calculates, for a given marker identified by analysis of the constituent components of an exhaled breath sample of a subject obtained at a time $t_1$, whether the concentration of the marker is consistent with the expected concentration of the marker at a time $t_1$, with reference to stored pharmacokinetic parameters obtained from a large population of subjects for the marker and the dosage interval (T), if the subject had been adherent to a set regimen for introduction of the marker or a precursor of the marker into the subject over a defined time period prior to obtention of the exhaled breath sample.

An optimized device or system according to this invention is optimized by including in the device:

A. a sensor selected for accurate detection in the exhaled breath of at least one subject of at least one Exhaled Drug Ingestion Marker X, $EDIM_x$ produced on ingestion of at least one Adherence Enabling Marker, $AEM_x$;

B. data storage (as in hard drive, flash drive, EEPROM, in a form now known or which is developed in the future) operatively coupled to the sensor, for retention of data generated by the sensor in the course of characterizing the pharmacokinetics of the $EDIM_x$ in the exhaled breath of a subject, Y, or in a population of subjects, Z; and C. computing means, (including, for example, a programmed central processing unit) which compares each such measurement for each subject or population of subjects with stored data, as described herein below, for said subject or population of subjects, preferably in real time or near real time. For each measurement of the concentration of $EDIM_x$, a measure of adherence A is generated by the computing means for each subject.

The characterizing data for storage preferably includes measurement data, to within defined confidence limits, of:

a. the Limit of Detection (LoD) of a sensor included in said device for said marker;

b. the background level of said marker or interferents in said subject or population of subjects;

c. the half life of appearance ($t_{ea}$) and elimination ($t_{1/2e}$) of said marker from the exhaled breath of said subject or population of subjects;

d. the steady state concentration of said marker in the exhaled breath at various time points during Adherence Enabling Marker (AEM) dosing, selected from the group consisting of trough ($C_{Trough,SS}$), maximum ($C_{MAX,SS}$), and other time point post dosing of the AEM concentrations of said subject or population of subjects; and e. the time required to attain the maximum concentration ($T_{MAX}$) of said marker from the exhaled breath of said subject or population of subjects.

Such a device according to this invention is preferably configured to integrate the pharmacokinetic parameters defined above to provide an adherence lookback window, $T_{AdhWindow}$, defined as the period of time required for the marker (EDIM) concentration in breath of the subject to decay from an initial value ($C_{EDIMo}$) to a lower concentration ($C_{EDIMLimit}$):

$$T_{AdhWindow} = \frac{t_{1/2e}}{0.693} * \ln\left(\frac{C_{EDIMo}}{C_{EDIMLimit}}\right)$$

wherein:

$C_{EDIMo}$=original or starting concentration of marker (EDIM) in breath at times equal to or greater than $T_{MAX}$ (i.e., $C_{EDIMo}$ $C_{MAX}$) of said patient;

$C_{EDIMLimit}$=the final concentration of EDIM in breath of said patient, provided that, if $C_{EDIMLimit}$ denotes the limit of EDIM detection due to the device LoD or background interference, it would define the maximum $T_{AdhWindow}$; and $t_{1/2e}$=the elimination half life for said EDIM.

Such a device preferably exhibits a $T_{AdhWindow}$ between about 1 hour and about 400 hours, and includes a sensor with a LoD for the marker of between 1 part per trillion and 5 parts per billion. In one preferred embodiment, the sensor is adapted to distinguish between ordinary and non-ordinary isotopes present in EDIMs and volatile compounds which otherwise would interfere with selective measurement of EDIMs in the exhaled breath.

7.0 IMPROVED SMART® COMPOSITION OF MATTER AND METHODS OF MAKING AND USE THEREOF

Depending on the mode of SMART® medication adherence monitoring, (e.g., AMAM, IMAMA, CMAM), and the embodiment of SMART® device in use (Type I, II, or III), an appropriately matched SMART® composition is employed. In section 7.1 below, we describe AEMs and compositions of matter comprising AEMs which are adapted for use in a SMART® system which includes the Type I embodiment of the SMART® device according to this invention. In Section 7.2 below, we describe i-AEMs and compositions of matter comprising i-AEMs which are adapted for use in an i-SMART system which includes the Type II embodiment of the SMART® device according to this invention.

7.1 Detailed Description of a First Embodiment of the Improved SMART® Composition of Matter In developing the present invention, commercial imperatives relevant to manufacture of SODFs containing volatile marker molecules (AEMs) have been carefully considered, experimented with and optimized to achieve excellent methods for making and containing the AEM formulation, and deployment with APIs. 2-butanol is utilized herein as a non-limiting exemplary marker (AEM) for SMART® system adherence monitoring. While 2-butanol was disclosed in WO2013/040494 as a marker, the compositions of matter disclosed herein provide advancements in the art by resolving such matters as flashpoint of volatile AEMs during formulation and soft gel encapsulation of the marker, acceptability of the AEM to subjects receiving administered medication, and by disclosing a combination of marker and excipients which optimize handling and/or processing of the marker composition, encapsulation properties, and improving tolerability and acceptability of the marker(s) when included in API dosage forms.

7.1.1 The AEM Composition According to this Embodiment of the Invention

Within this disclosure, considerable disclosure and attention is focused around use of 2-butanol or isopropanol (IPA) as Adherence Enabling Markers (AEM), for generation of Exhaled Drug Ingestion Markers (EDIMs) (which, in the case of 2-butanol as the AEM is the ketone, 2-butanone, as the EDIM and in the case of IPA as the AEM, the EDIM is acetone), which is/are detected in the exhaled breath following ingestion of medication, those skilled in the art will appreciate that other AEMs and EDIMs may be used for this purpose, as disclosed, for example, in WO2013/040494. In addition, while the present disclosure focuses on specific excipients and combinations thereof with the AEMs disclosed herein, those skilled in the art will appreciate that other equivalent excipients and AEMs may be utilized.

In a first AEM composition according to this invention, at least or exclusively the following key components are contained within a "soft" gelatin capsule:

a. An AEM, primarily exemplified herein by 2-butanol;

b. An optional flavorant, primarily exemplified herein by DL-menthol, vanillin, or combinations thereof;

c. An optional bulking agent, primarily exemplified herein by polyethylene glycol. It will be appreciated by those skilled in the art that, in general, pharmaceutical grades of all materials mentioned should be used for utilization in human dosage forms.

In a first AEM composition according to this invention, only the AEM itself (e.g., 2-butanol or IPA or combinations thereof) is included in a gelatin capsule which is then combined with or administered concurrently with an API for medication adherence monitoring. In a second AEM composition according to this invention, the AEM is combined with one or more additional components, including but not limited to flavorants, bulking agents, other excipients, or the like, as described above.

As noted above, those skilled in the art will appreciate that AEMs other than 2-butanol or IPA may be appropriate for a particular application and can, based on the disclosure and guidance provided herein, make appropriate modifications to the formulation to accommodate alternate AEMs, volumes, concentrations and chemical interactions. Flashpoint considerations with respect to the AEM, if it is a volatile compound such as 2-butanol, define parameters for consideration in the safe handling of medication fill formulations in commercial contexts. Working temperatures above 25 degrees centigrade using compounds with a 22 degree centigrade flashpoint, for example, are less than optimal. The flashpoint of neat 2-butanol is about 22 degrees centigrade. However, by careful experimentation with different amounts of 2-butanol, and careful selection of the amount and nature of flavorants, bulking agents, and other excipients optionally included in the AEM formulation, we have been able to increase the flashpoint of the 2-butanol formulation such that the effective flashpoint of the 2-butanol is increased significantly to greater than 26 degrees centigrade. Surprisingly, we have found that certain combinations of vanillin, DL-menthol, or both, as disclosed herein, increase the 2-butanol flashpoint. Likewise, careful selection of bulking agent also can have this desirable effect.

The particular combination of DL-menthol and vanillin has been found in our preliminary testing to be well tolerated by subjects receiving the AEM formulation (see Examples below), but, of course, other combinations of different flavorants (or no flavorant) could likewise be accommodated and adapted for use according to this invention. In addition, as noted above, the combination of flavorants with the volatile AEM has the significant advantage of raising the flashpoint of the volatile AEM.

With respect to the bulking agent, this has several important functions. First, the bulking agent is utilized to bring the total volume of the formulation to a desired total volume. For a consistent volume to be filled in each soft-gel capsule, it is important for the total volume to not be too small for the relevant commercial fill operation, otherwise undue errors are introduced into the total concentration of AEM between different capsules. Those skilled in the art know how to calculate volumes for particular fills which will eliminate or reduce this aspect of variance such that essentially no statistically significant variance in EDIM measurement on the breath can be attributed to differences in AEM fill volumes used in the soft-gel capsules. Second, the bulking agent is preferably one which does not retard release of the AEM upon dissolution of the capsule containing the AEM. Third, preferably, the bulking agent itself is compatible with the containment material for the AEM such that integrity of the soft-gel is not interfered with by any of the constituents included in the AEM formulation. Typically, soft-gel capsules include at least one or a combination of the following components: a shell forming composition, such as but not limited to gelatin; a plasticizer, such as but not limited to glycerin, sorbitan, sorbitol, or similar low molecular weight polyols, and mixtures thereof. The art of soft gel capsule production is mature and those skilled in the art will be aware of at least the following patent documents which disclose various compositions and methods of making this component relevant to the present invention: U.S. Pat. Nos. 5,641,512; 4,164,569; 8,241,665; 8,338,639. There are several well-known and respected commercial producers of soft-gelatin capsules, including, but not limited to, Patheon, 4721 Emperor Blvd., Suite 200, Durham, N.C. 27703-8580, USA; Catalent Pharma Solutions, 14 Schoolhouse Road, Somerset N.J. 08873; LD Industries, 1725 The Fairway, Jenkintown, Pa. 19046-1400; and Soft Gel Technologies, Inc., 6982 Bandini Blvd., Commerce, Calif. 90040, to name but a few.

In a preferred embodiment according to this invention, the AEM composition is contained within a soft-gel composition as follows:

| Ingredient | Use |
|---|---|
| Gelatin Acid Bone (Type 195), NF, EP; clear gelatin with no colorants or opacifiers added | Shell Polymer |
| Sorbitol/Glycerin blend | Plasticizer |

Thus, in one preferred formulation according to this invention, there is included:

20 mg 2-butanol+0.7 mg DL-menthol+5 mg vanillin+9.3 mg PEG-400                                     Formulation A:

40 mg 2-butanol+1.4 mg DL-menthol+10 mg vanillin+18.6 mg PEG-400                                   Formulation B:

It will be appreciated that there are many different grades of polyethylene glycol, PEG, and the selection of PEG-400 in the particular preferred formulations mentioned above comes as a result of optimization of the particular formulation to include the volatile AEM, 2-butanol, and the particular flavorants, DL-menthol and vanillin. The designation PEG-400, indicates an average molecular mass of 400 g/mole. Since the structure for PEG is H—(O—CH$_2$—CH$_2$)$_n$—OH, for PEG-400, n=9. Of course, depending on the viscosity desired, PEG of different average molecular mass may be chosen as the bulking agent, with $3 \leq n \leq 50$. PEG-400 is selected as a preferred component of the AEM formulation according to this invention due to its combination of solubility, viscosity, and other characteristics. It is soluble in water, it acts as a solvent and carrier for the 2-butanol, and flavorants and has a positive effect in increasing the flashpoint of the formulation. We have explored use of other grades of PEG, including, but not limited to PEG-200, PEG-600, and the like. These grades of PEG are functional in the present invention, but we have found that the PEG-400 grade is optimal when the selected AEM is 2-butanol. PEG-400 and PEG-600 are both listed in the US FDA's listing of Inactive Ingredients for approved drugs.

We have also found, via experimentation, that for the purposes of delivering the AEM, the ratios of the AEM (e.g., 2-butanol), to PEG-400, to flavorants, is also important. Thus, as can be seen by comparing the above Formulation A to formulation B, the ratios of these components is retained when twice the amount of AEM is included in the formulation. Naturally, those skilled in the art will appreciate that there can be some variation in these ratios without loss of the ability to successfully deliver the AEM and measure the EDIM on the exhaled breath. However, the ratio disclosed herein has been found to be preferred, providing miscibility of the marker in the formulation, stability in temperature cycling and chilling studies, room temperature stability, and dispersion in 0.01 1N HCl and neutral buffered solution. The formulation, in addition, can be scaled to produce GMP batches for clinical trials and commercial use, it releases rapidly and reliably in the stomach, and is anticipated to exhibit long-term stability (≥1-2 year shelf life at room temperature), while, at the same time, permitting encapsulation in the smallest possible size (i.e. less than 6 mm or less than 5 mm or smaller, if possible) of soft gel capsule (thereby taking up the minimum amount of volume to permit API filling of capsules and other SODF's containing the AEM-soft gel formulation). It is also preferred that the gel capsule thickness containing the AEM be as thin as possible where AMAM is desired to be achieved. A softgel containing the AEM (whether 2-butanol alone or in combination with other excipients) is provided.

For early testing, each formulation is placed directly (i.e. without encapsulation of the AEM in a soft gelatin capsule) in a white size 4 LiCaps® hard gelatin capsule and sealed. The sealed white size 4 LiCaps® capsule will then be placed in a white size 0 LiCaps® capsule which is NOT sealed.

For delivery of an API, the AEM formulation is preferably included in a soft-gel capsule which is then included in a solid dosage form including the API, in a format such as was disclosed in WO2013/040494 but improved as disclosed herein. In a preferred embodiment, the soft-gel capsule comprising the AEM formulation according to this invention is introduced into the apical half of a hard gelatin capsule. The lower portion of the capsule is filled with API composition, and the capsule is closed, thereby containing both the AEM soft-gel capsule and the API in a single dosage form.

7.1.2 the AEM Composition According to this Embodiment of the Invention and its Method of Manufacture The art of encapsulation of solids and liquids is an advanced art area. However, the requirements of the present invention include:
a. the need to prevent loss of the volatile AEM (e.g., 2-butanol, IPA) in the course of encapsulation or storage;
b. the need to prevent migration of the AEM into the API compartment;
c. the need for rapid release of the AEM so that rapid documentation of medication adherence can be achieved by detection of the EBM in the exhaled breath.

These objectives are achieved for this aspect of the invention by producing soft gelatin capsules containing the AEM. Depending on the desired mode of MAM, the capsule containing the AEM is optimized for rapid, intermediate or slow dissolution in the biological system. Thus, for AMAM, extremely thin wall thickness is preferred (see below) so that appearance of the EBM in the exhaled breath is not unduly delayed. Typical hard gel capsules, such as LiCaps® capsule and Conisnaps® capsules are approximately 0.11 mm thick (Capsugel, Morristown, N.J.), whereas softgel capsules typically have a wall thickness of 0.64-0.76 mm (Catalent, Somerset, N.J.). For IMAM and CMAM, these considerations may be less critical, and, in fact, appropriate retardants to dissolution may be utilized to extend the time from which a medication is taken to the time that adherence has to be confirmed using an appropriate embodiment of the SMART® device according to this invention.

For the production of a soft gelatin encapsulated AEM according to this invention, those skilled in the art will appreciate that soft gelatin capsule technology is based on hermetically sealing a liquid in a gelatin shell. It is typically practiced using the rotary die method, although other manufacturing technologies exist.

In the rotary die method, 2 gelatin films are fed between a set of dies containing pockets for forming the capsules. A wedge is used between the dies to inject the fill material between the ribbons such that it forms the capsules in the die cavities as they rotate together. The 2 gelatin ribbons are sealed using a combination of heat and pressure to hermetically encapsulate the fill material.

The gelatin formulation is selected based on the desired properties of the capsule and to be compatible with the fill. Typical gelatin encapsulation formulations include glycerin and/or sorbitol as plasticizers in ratios to gelatin between about 0.5:1 to 0.8:1.

The levels of plasticizer and thickness of the ribbon are adjusted to form capsules that are strong enough to withstand normal handling. The relationship between plasticizer level, shell thickness, and capsule geometry, to capsule strength and VOC permeability is intuitive, but also highly interactive, i.e., changing one will often be additive or subtractive with another.

When choosing a system for encapsulation of a VOC into a soft gelatin capsule, the following considerations come into play regarding VOC loss and capsule breakage.

Plasticizer: Low level=reduced VOC permeation, but increased brittleness (more likely to break)

Capsule Shell: Thick capsule shell=reduced VOC permeation and increased capsule strength (less likely to break), but may impact the rate of release of the VOC. Typical shell thickness levels range from 0.025" to 0.040", with no real constraint provided the tooling is optimized for the thickness. Values outside of these levels are not typical and are optimized for production of the soft gelatin capsules containing the AEM disclosed and claimed herein.

The soft gelatin capsules according to this invention are made by mixing any excipients (including, but not limited to, bulking agents and/or flavorants), preferably under vacuum until all materials are dissolved and then the AEM is added under positive pressure, preferably under a blanket of inert gas, such as, but not limited to, nitrogen. The formulation is stored under an inert atmosphere and is utilized in the encapsulation procedure as described above, followed by drying and packaging.

For purposes of this aspect of the invention, we have successfully produced a soft gelatin capsule containing the AEM (2-butanol) with a wall thickness of as thick as 0.030" and as thin as 0.020". The thinnest wall thickness results in a faster release time.

This testing was conducted on "uncoated" softgels comparing formulation A (40 mg of 2-Butanol, 10 mg of Vanillin, 1.4 mg of Menthol and 18.6 mg of PEG400) with a 0.030" wall thickness to Formulation B softgel where we removed the Menthol and Vanillin, raised the 2-Butanol to 50 mg and the PEG400 to 20 mg with a softgel wall thickness of 0.020". In in vivo testing an overall faster release as shown in FIG. 18j. A baseline breath was obtained, then the softgel formulation A was swallowed and breath samples were collected at 10, 20 & 30 minutes post ingestion. At 60 minutes, a further baseline breath was obtained and formulation B softgel was ingested, and breath samples were again collected at 10, 20 and 30 minutes after this baseline breath.

We have confirmed the stability of 2-butanol within a soft gelatin capsule containing 40 mg 2-butanol; 18.6 mg PEG 400; 10 mg Vanillin; 1.4 mg menthol under accelerated conditions (40° C.; 75% relative humidity) and in real time conditions (25° C.; 60% relative humidity). For both conditions, we observe excellent stability and retention of the AEM in soft gelatin capsules. Three month stability under accelerated conditions are considered to be predictive of twelve month stability under real time conditions. See FIG. 18i.

7.1.3 AEM Capsule Overcoating

As an alternative to increasing shell thickness to contain a VOC such as an AEM according to this invention, we have explored application of a coating to the capsule to reduce the permeation of the AEM from the capsule. Surface coating methods may include, but are not limited to, spray coating, ink jet printing, thermal transfer, laser printing, dip coating and the like.

Thus, where it is desired to rapidly release the AEM, and very thin gelatin wall thicknesses are used to contain the AEM, soft gelatin capsules containing the AEM in a preferred embodiment are over-coated. Coatings for this purpose are known in the art, for example, by the trade names SmartSeal, ProtectSeal, Opadry II, Opadry 200, SmartCoat, BASF Protect, and the like. Thus, Kollicoat Smartseal® 30 D is described by its manufacturer, BASF, as a "unique solution in pellet and particle coating, where other products are too tacky to be applied without individual items sticking together. Kollicoat® Smartseal 30 D features outstanding taste-masking, ensures quick release of the active ingredients in the stomach and offers superior protection with a reduced amount of coating, resulting in lower costs and more efficient production processes". OPADRY® 200, manufactured by Colorcon, Inc., is coated in a 24" fully perforated O'Hara Labcoat II coating pan. Per the manufacturer, 15 kg of biconvex placebo tablets (10 mm diameter) are coated to a 4% weight gain (WG) with the same lot of a blue Opadry 200 formulation.

In our studies with coated and uncoated gelatin capsules containing the AEM, (40 mg of 2-butanol+PEG 400 (18.6 mg)+vanillin (10 mg)+menthol (1.4 mg) and shell thickness of ~0.03") we used 0.1 N HCl as disintegration media and utilized disintegration criteria consistent with The United States Pharmacopeial Convention (2008, available at http://www.usp.org/usp-nf/official-text/accelerated-revision-process/accelerated-revisions-history/disintegration-0) to obtain an average Disintegration Time (DT) for gelatin capsules containing the AEM. We explored several coatings (n=6 capsules for each condition tested). % weight increase is an indication of the average amount of coating applied; Rupture Time (RT) is the average time before AEM odor could be detected; Disintegration Time (DT) is as noted above. Non coated gelatin capsules resulted in disintegration in about 4.7 minutes; Opadry II coating: % weight increase 20, 14.5, 10.4, RT: 7.5-8 minutes; DT: 13.6, 11.5 and 8.1 minutes respectively; Opadry 200: % weight increase 20, 14.6, 9.4, RT between 10 and 8 minutes; DT: 16.2, 13.6, and 9.7 minutes respectively; SmartCoat 30D: % weight increase 20, 14.3, 9.6, RT: 7.0-8.0, 5.5, and 4.5 minutes; DT: 8.2, 7.3, and 5.9 minutes respectively; SmartSeal 30D (20%) coated with ProtectSeal (3%), RT: 7.0-8.0 minutes, DT: 9.3 minutes; BASF Protect: % weight increase 15.5, 9.3, 5.2, RT 9, 6.5, 4.5; DT: 11.9, 7.8, 5.9 minutes respectively. In a separate set of studies, we enclosed three capsules, each containing 40 mg AEM (2-butanol) for 16 hours in a sealed bag, and then sampled the headspace. The coating type and results are shown in the table below, (relative to AEM detected in the headspace of sealed bags containing uncoated capsules, which is set as 100% and all other amounts are normalized relative to the uncoated capsule headspace measurements):

| Coating Type | 2-Butanol release (% Un-coated) | | | | | |
|---|---|---|---|---|---|---|
| | Capsule Set 1 | | Capsule Set 2 | | Capsule Set 3 | |
| | Trial 1 | Trial 2 | Trial 1 | Trial 2 | Trial 1 | Trial 2 |
| Uncoated | 100 | 100 | 100 | 100 | 100 | 100 |
| SmartSeal + ProtectSeal | 69.7 | 99.4 | 56.6 | 67.5 | 57.4 | 66.6 |
| Opadry II | 34.2 | 44.5 | 33.2 | 35.3 | 24.1 | 18.2 |
| Opadry 200 | 0.2 | 0.9 | 0.8 | 0.4 | 0.9 | 0.4 |

As between softgel capsules of 0.02" and 0.03" thickness, we have measured butanol egress overnight and found no significant difference. In addition, with 0.03" thick softgel capsules, as between 15% Opadry®200 and 20%, there was no statistically significant difference in egress. Thus, it appears that a 0.02" thickness softgel capsule coated with 15% Opadry® 200 is a preferred embodiment. Finally, for accelerated 6, month stability data (representing 24 months standard/real-time) conditions, a total egress from 0.03" softgels, a total egress of about 8% (e.g. 3.2 mg/40 mg), but, based on overnight egress data using Opadry® 200, it appears that egress is reduced by a factor of approximately 100 (i.e. for either 0.02" or 0.03" thickness softgels).

From this, we conclude that AEM encapsulated in a thin gelatin softgel capsule overcoated with an appropriate coating, e.g., Opadry 200, exhibits containment and release characteristics desirable for delivery of AEM in combination with an API of interest. The API itself is preferably, and typically is, contained in its own protective coating, including when delivered in a unitary dosage form with the AEM contained as described herein. Utilizing the gelatin capsule contained AEM as disclosed herein, in combination with a wide array of APIs may be conducted according to procedures and structures disclosed in WO2013/040494.

It should further be noted in connection with this aspect of the invention that, (in addition to Medication Adherence Monitoring (MAM), whether for acute, intermediate or chronic applications (AMAM, IMAM, or CMAM)), because this system is exquisitely adept at detection of dissolution of dosage forms in the digestive tract, an additional utility for this invention (device, system) is a method and compositions for measuring residence times and digestive activity. Compositions comprising an AEM and a coating or coatings known to be resistant or susceptible to dissolution in different compartments of the digestive tract are thus considered to come within the scope of this invention. Thus, a composition comprising an AEM encapsulated, for example, in a soft gelatin capsule and coated with a coating resistant to gastric dissolution provides a system for measurement of the rate at which a particular individual or population releases a medication beyond the gastric chamber.

An enteric coating, for example, is a polymer barrier applied on oral medication to protect drugs from the pH (i.e. acidity) of the stomach. Most enteric coatings work by presenting a surface that is stable at the highly acidic pH found in the stomach, but breaks down rapidly at a less acidic (relatively more basic) pH. For example, they will not dissolve in the acidic juices of the stomach (pH 3), but they will in the alkaline (pH 7-9) environment present in the small intestine. Materials used for enteric coatings include fatty acids, waxes, shellac, plastics, and plant fibers.

7.1.4 Additional Containment Methods and Formulations for Retention and Delivery of the AEM Whether the AEM according to this invention is an "ordinary AEM" as compared with an i-AEM, it is desirable to ensure the AEM is not lost in the formulation process, and is stable when co-packaged/formulated with an API of interest. In WO2013/040494, for example, HPC (hydroxypropylcellulose, a well-known excipient in the pharmaceutical arts) was suggested for inclusion with volatile markers in capsules to provide stable compositions for long-term storage in hard gel capsules with minimal hydroscopic forces. It was suggested that HPC "ties up" hydrogen bonding of 2-butanol, which in turn reduces its ability to attract water from the hard gel matrix that would dehydrate the hard gel capsule and reduce its performance. Likewise, in WO/2013/038271, HPC was suggested for inclusion in fill formulations as a polymer such that a fill component (2-butanol, isopropanol, other VOCs) which, in the absence of the at least one polymer will migrate into or through a capsule shell. Such methodologies may likewise be included for the AEM used in the system according to the present invention.

Figure 79A:
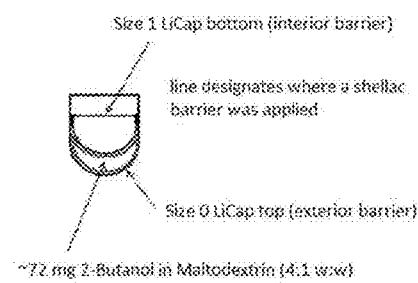
Figure 79A:
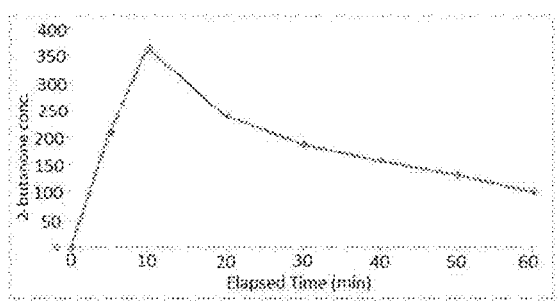
Figure 79B:
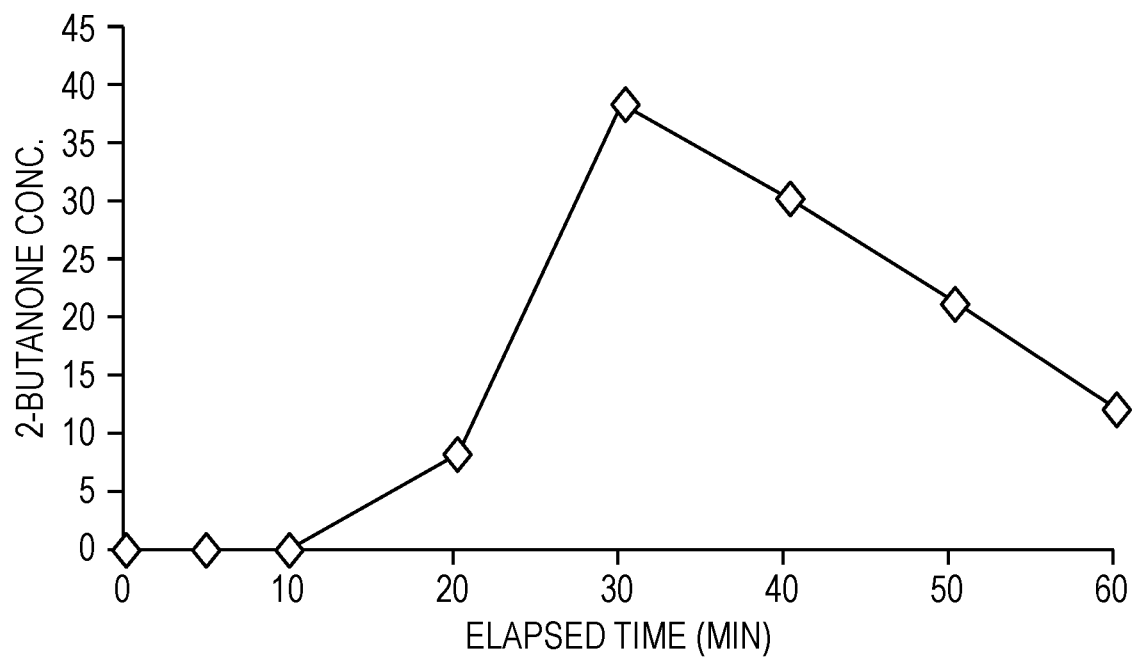
Figure 79B:
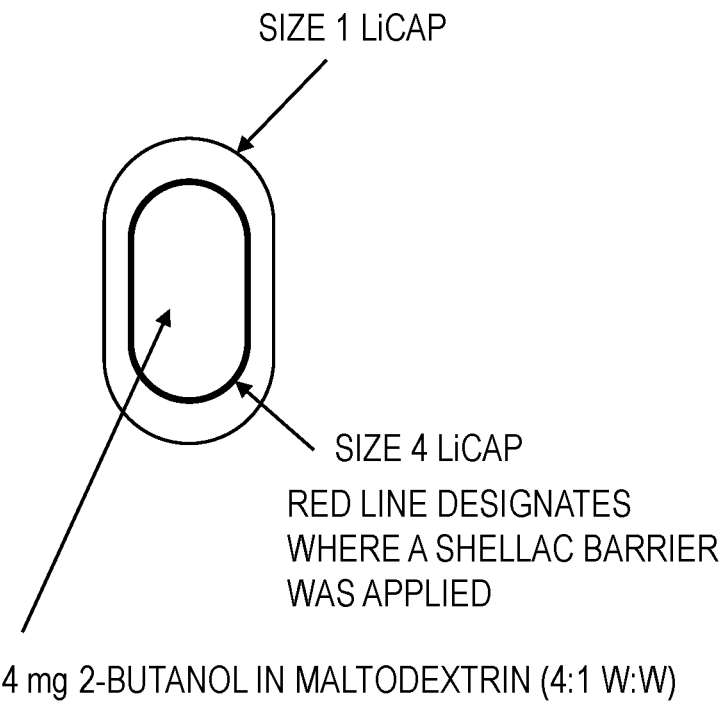
Figure 79C:
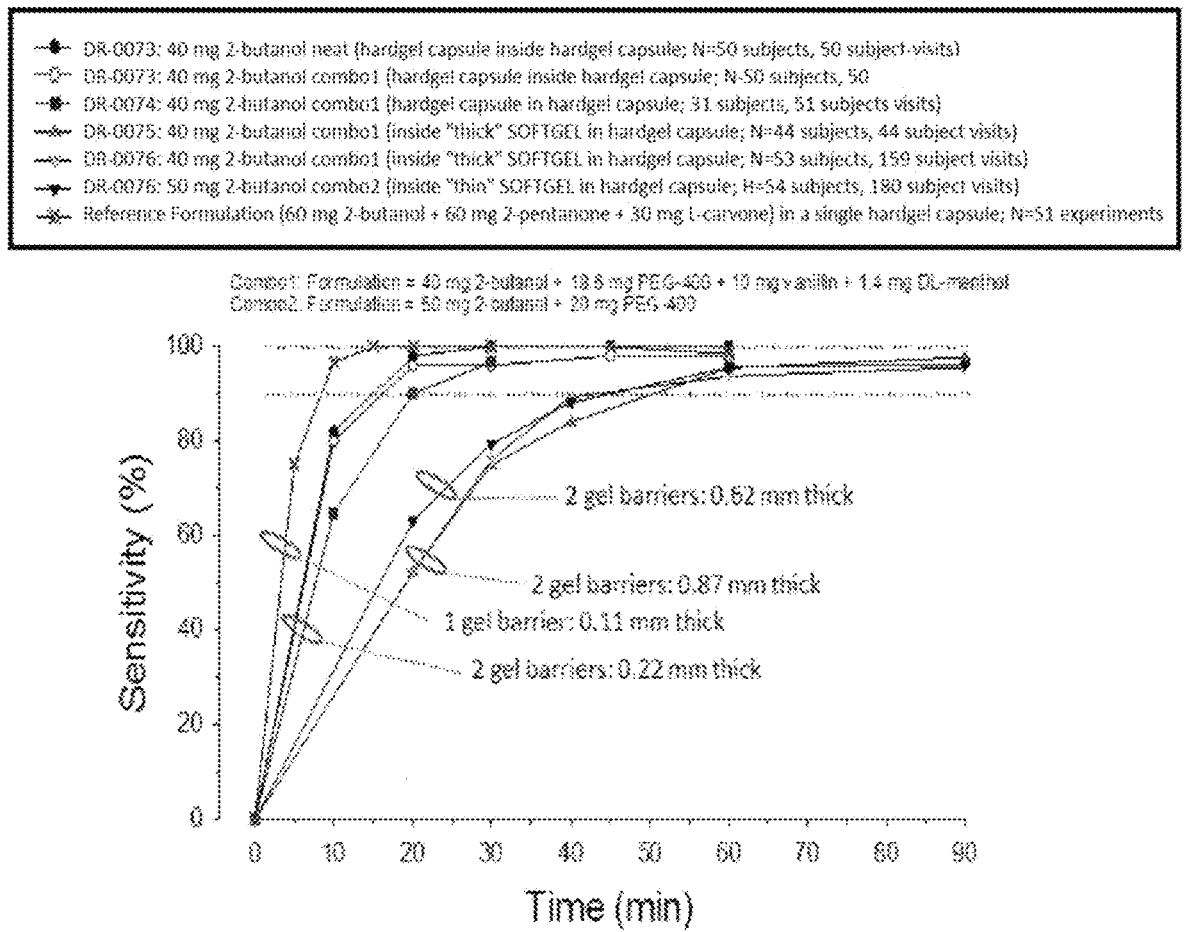
Figure 79D:
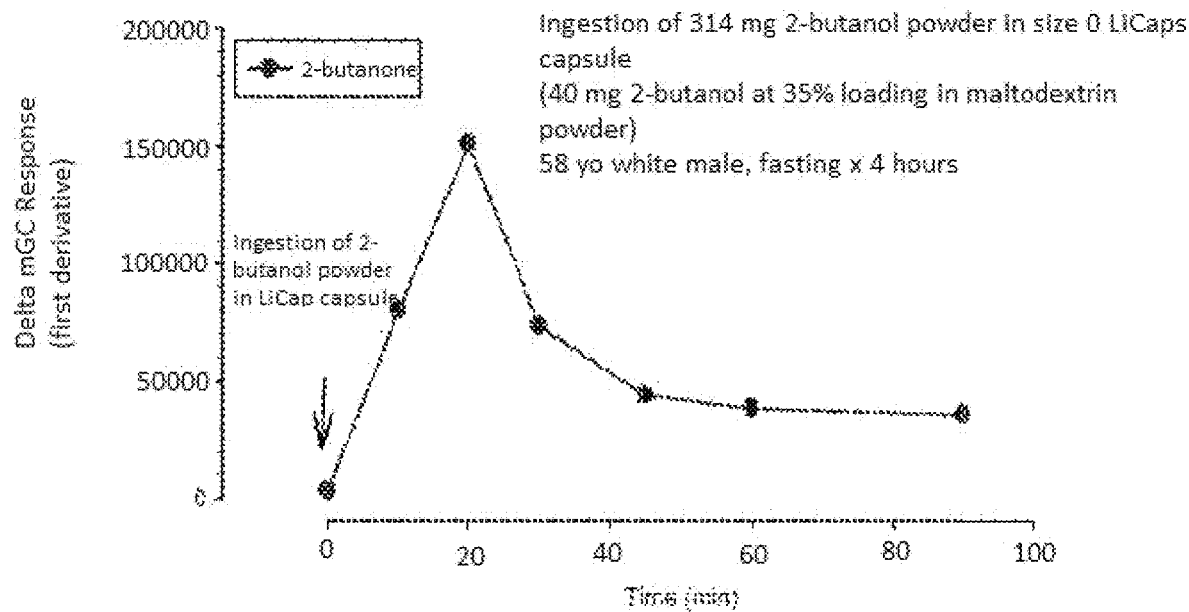

Furthermore, we have found it possible to produce a flowable dextrin powder which contains significant amounts of AEM. Reference for this purpose may be had to a series of patents to General Foods Corporation, including U.S. Pat. Nos. 3,795,747; 3,821,433; 3,956,508; 3,956,509; 3,956,511, each of which describes alcohol (30-60% ethanol) containing dextrin powder and methods to make such powder. Such powders were stable when hermetically packaged. We have explored whether the AEM according to this invention may be formulated in a similar fashion. Using maltodextrin (commercially available, for example, as Maltrin M700 from GPC, Grain Processing Corporation) we successfully achieved binding and retention of 2-butanol as a flowable powder (40.0% 2-butanol, 4.4% water and 55.6% Maltrin M700. Left open to the atmosphere, the AEM-dextrin powder retained from 36% 2-butanol at the time of formulation to about 20% of 2-butanol after 48 hours. The dextrin readily dissolves in water and in the digestive system, rapidly releasing the bound AEM. Accordingly, further aspect of this invention comprises the provision of an AEM-dextrin formulation. In a first embodiment of a medication according to this aspect of the invention, the AEM-dextrin powder is included in a hard gelatin capsule with an AEM. In a second embodiment, the AEM-dextrin powder is encapsulated in a soft gelatin capsule, as described above in sections 7.1.2. In a further embodiment, the AEM-powder is coated, as in and section 7.1.3 above. In yet a further embodiment, the AEM-powder is included in a gelatin capsule which is then coated, as in section 7.1.3. In another embodiment, a polymeric starch based sugar bead is impregnated with liquid 2-butanol or like AEM, and optionally but preferably, coated with a PVA or similar material to trap the 2-butanol or like AEM in the sugar bead. This finished "powder" is utilized in a capsule with the active drug, converted to a slurry for surface coating of a medication, or otherwise associated with an active pharmaceutical ingredient to produce a SMART® formulation for use according to the present disclosure. In a further embodiment, as described in the examples below, a stable metal carbonate of a preferred alcohol marker, e.g. 2-butanol, isopropanol, or the like primary or secondary alcohol, is converted to a carbonate, including carbonates which include non-ordinary but stable isotopes, which can be powderized and applied to the surface of an API by a device and technology known in the industry, such as is available from Nordson Corporation, 28601 Clemens Road, Westlake, Ohio 44145. These procedures, embodiments and formulations are likewise applicable to i-AEMs (section 7.2 below). FIGS. 79A-D show different strategies for associating the AEM with an AEM and the resultant rate of EBM release. FIG. 79A shows a capsule formed with 72 mg 2-Butanol in Maltodextrin (4:1 w:w) in size 0 LiCap top, with size 1 LiCap bottom seal. As can be seen, this results in peak 2-butanol in the exhaled breath within about 10 minutes of ingestion. FIG. 79B shows a capsule formed with 64 mg 2-Butanol in Maltodextrin (4:1 w:w), in size 4 LiCap (interior coated with OPAGLOS) inside size 1 LiCap. As can be seen, this strategy results in a peak 2-butanol in the breath within about 30 minutes of ingestion. FIG. 79C succinctly shows how the sensitivity and rate of EBM release is dependent on the configuration/strategy used to deliver the AEM, e.g. 2-butanol, to the stomach. It is clearly related to the total thickness of the gelatin barriers it has to traverse before being released into the gastric environment. Note the far left curve (designated as reference) is the fastest when only one gel barrier (2-butanol solution placed directly into a hard gel capsule). With a surface coating containing the AEM, e.g. via a powder, only one gel barrier has to be crossed before being releases into the stomach. In any case, it is anticipated that such an approach results in considerably faster release and generation of the EBM than occurs with softgel in a hardgel capsule assembly. FIG. 79D provides another example of maltodextrin powder, "fluffed up" to optimize loading with 2=butanol, to produce a freely flowable powder at 40% loading by weight with 2-butanol. This was ingested (equivalent of 40 mg 2-butanol powder mass) simply placed inside a hard gelatin capsule (Size o LiCap). The breath kinetics: 1st derivative response of the mGC to 2-butanone in breath vs breath sampling time. These examples show how rapidly the powder can release the 2-butanol in the stomach, relative to, e.g. a softgel-based strategy. Each of these strategies permits a balance to be achieved between rapid release in the stomach versus acceptable stability and segregation when the AEM is packaged with an API. Spray drying, microemulsion, and microencapsulation or overencapsulation technologies are advanced and permit an appropriate balance to be struck between these competing requirements.

7.2 Detailed Description of a Second Embodiment of the Improved SMART® Composition of Matter—Compositions and Methods of Making and Use of i-AEMs Much of the enabling description provided in section 7.1 above for provision of AEMs with APIs is applicable here, where delivery and use of i-AEMs is described in detail. However, because the background of i-EBMs is so low, the mass of i-AEM that needs to be delivered according to this aspect of the invention to achieve AMAM, IMAM, and CMAM is generally much lower than when regular AEMs (i.e. AEMs that do not contain non-ordinary isotopes) are utilized. Thus, whereas milligram quantities of 2-butanol may be required to achieve readily measureable quantities of 2-butanone in the exhaled breath shortly after delivery of the medication, microgram quantities of e.g., deuterated 2-butanol or isopropanol are all that is required to achieve detectable quantities of deuterated 2-butanone, or deuterated acetone. Because the quantities of i-AEMs that need to be delivered are much reduced as compared with regular AEMS, the i-AEMs may be much more simply associated with, for example, Solid Oral Dosage Forms ("SODFs"). For example, microdots of i-AEMs which are entirely contained in rapidly dissolvable barriers may be adhered to the exterior of existing SODFs. Alternatively, capsules which are already imprinted with adequate quantities of an i-AEM, either on an external or an internal surface thereof, and adequately contained in a barrier, or included in a capsule shell compartment, are filled with an API. Alternatively, inks comprising an appropriate i-AEM may be used to print on an existing SODF, with an over-coat spray of a rapidly dissolvable barrier being sufficient to contain loss of the i-AEM. In a further preferred embodiment of a medication according to this invention, there is provided an AEM which comprises either or both (a) a non-ordinary isotope; (b) butanol, isopropanol, or both, either or both of which may include a non-ordinary isotope, or other selected secondary alcohols, or other AEMs. In a further embodiment, the medication includes a surface coating comprising an i-AEM. Given the sensitivity of a $D_2O$ detector described herein, a low quantity (1-10 mg) of a deuterated AEM placed on the surface of SODFs (solid tablets, capsules) is adequate to permit medication adherence monitoring. Surface coating and containment, for example, in a blister pack or equivalent preserves the i-AEM on the surface of the SODF.

In addition to simplifying means for delivery of the i-AEM, because of the low background level of i-EBMs in the breath, the period of time following dosage that the i-EBM is unequivocally detectable in the exhaled breath can be extended well beyond the dose-by-dose monitoring shortly after each dose is taken/administered (AMAM), which has been the standard paradigm for medication adherence monitoring to date. Use of i-AEMs enables IMAM and CMAM, often many hours or even days following administration/taking of a given dose or multiple doses.

As shown in Table 1 below, the use of isotopic labeling for this medical application has multiple advantages, including generating distinct molecular entities in the sense of detection, but, in general, these molecules are not so altered as to give rise to regulatory concern; see, for example, "Guidance for Industry, Investigational New Drug Applications (INDs)—Determining Whether Human Research Studies Can Be Conducted Without an IND", U.S. Department of Health and Human Services Food and Drug Administration Center for Drug Evaluation and Research (CDER) Center for Biologics Evaluation and Research (CBER) October 2010 Clinical/Medical, Section V (lines 292-323) for guidance on the use of "cold" (e.g., deuterium) isotopes in clinical trials, which indicates the low level of scrutiny for this type of isotopic marker from a US Regulatory Agency perspective.

Non-radioactive isotopes include a number of elements (e.g., H, C, O, N, S), but for a variety of reasons deuterium is one of the most promising for our adherence application, particularly when mid-IR (mIR) techniques are contemplated to detect the i-EBM (see below Table). Accordingly, reference to deuterium herein, or any other specific isotope, is not intended to be limiting or to exclude the use of other stable (non-radioactive) isotopes.

| Medical Isotope | Stable, Non-radioactive | Radioactive, Unstable |
| --- | --- | --- |
| Hydrogen | $^1H$ (protium) - 99.985%<br>$^2H$ (deuterium) = $^2H$ - 0.015% | $^3H$ (tritium) |
| Carbon | $^{12}C$ - 98.89%<br>$^{13}C$ - 1.11% | $^{14}C$ |
| Oxygen | $^{16}O$ - 99.759%<br>$^{17}O$ - 0.037% [MRI scans]<br>$^{18}O$ - 0.204% [PET scans] | $^{15}O$<br>$^{19}O$ |
| Nitrogen | $^{14}N$ - 99.63%<br>$^{15}N$ - 0.37% [biochemical tracers] | No convenient |
| Sulfur | $^{32}S$ - 95.00%<br>$^{33}S$ - 0.76%<br>$^{34}S$ - 4.22%<br>$^{36}S$ - 0.014% | $^{35}S$ (other S-based radioisotopes very short lived) |

The table shows examples of stable and non-stable isotopes that may have applications in biology (medicine), including application to human breath. For purposes of the present invention, it is the stable, non-radioactive isotopes shown in this table that are of principal interest. Using isotopic labels in breath analysis has many advantages including but not limited to 1) creating a distinctive "fingerprint" in the breath, which can be used to distinguish labeled compounds from endogenous compounds already present in the body from natural metabolism or diet (e.g., ingestion of food, flavoring additives, drugs or excipients of drugs) and 2) can produce changes in the detection characteristics (e.g., shifts in the absorption spectra using FTIR) that make these molecules easily distinguishable from major analytical interferants in biological media. The % data indicate the percent of all atoms of that particular element in this isotopic form. Successful integration of isotopically labeled GRAS taggants into or onto hard gel capsules, pills, tablets, creams, topical compositions, vaginal compositions or rectal compositions for medication adherence will have the following requirements (referencing deuterium as a preferred but non-exclusive isotope for this purpose):

1) an adequate mass of e.g., deuterated taggant be interfaced (e.g., be part of the API itself, or be part of a taggant included with the API, so that upon delivery of the API, there is concurrent delivery of the taggant) to the active pharmaceutical ingredient (API) to generate a deuterated i-EDIM (i-EBM) breath signal, which can be measured with a portable sensor (e.g., midIR) to confirm medication adherence;

2) the deuterated taggant is rapidly released from hard gel capsules, soft gel capsules, tablets, or other dosage form in which the taggant is provided, and, in turn, rapidly generates the deuterated i-EDIM (i-EBM);

3) the deuterated taggant must be interfaced to the commercial capsule, tablet or other dosage form in a manner that does not alter its performance characteristics;

4) the deuterated taggants must be linked to the commercial pill or other dosage form (or clinical trial material) containing the API in a way that does not cause issues with API CMC or pharmacokinetics (PK: ADME) including bioavailability, and/or pharmacodynamics (PD); and 5) the taggant must create a deuterium-labeled i-EDIM (i-EBM) that is easily detected by a portable sensor (i.e., mIR device) in a sensitive and specific manner.

Those skilled in the art will readily determine, in consultation with appropriate regulatory bodies, whether potential additional regulatory assays (e.g., toxicology on GRAS component of hard gel capsule; toxicology of API with hard gel capsule containing deuterated GRAS taggants) may be required.

7.2.1 Chemistry for i-AEMs and i-EBMS

In order to make a $1^{st}$ generation medication adherence device (without use of isotopic labeling strategies), a number of studies were undertaken. Key results include: 1) identification of several classes of GRAS food additives suitable for definitive adherence (i.e., as taggants interfaced to medications that generate appropriate EDIMs in exhaled breath shortly after oral ingestion to document adherence); 2) demonstration that metabolites of taggants (EBMs, including EDIMs or EDEMs) were detectable in human breath using gas chromatography-mass spectroscopy (GC-MS), mGC-MOS, or variations of such techniques, and had kinetics (breath concentration-time relations) that were suitable for definitive MAMS; and 3) production of a portable miniature gas chromatography metal oxide sensor (mGC-MOS) prototype to detect EDIMs. It having now been demonstrated that MAMS is technologically feasible (chemistry+physiology+sensor—all work), the present invention provides a more advanced, refined, and flexible medication adherence system based on isotopic labeling (e.g., deuterium) chemical approaches.

A. Candidate Taggants for Definitive Medication Adherence Using i-AEMs:

A number of regulatory databases exist that provide information about food additives, flavorings and colorings that are legally found in or which can be added to food. GRAS taggants are preferably selected from those provided in the authoritative, proprietary Leffingwell & Associates (Canton, Ga.) "Flavor-Base 2007". This listing is the world's most extensive database on GRAS flavoring materials and food additives (4,085 listings). All compounds in the Flavor-2007 database contain information from the relevant FDA and international regulatory databases. In all 1,603 esters, 926 alcohols, 222 aldehydes and 557 ketones were initially identified as potential taggant candidates. Of these the esters and carbonate esters can be used to easily generate a wide variety of corresponding alcohols and carboxylic acids. In this embodiment, depending upon the ester, the i-EBM could be 1) an isotopically-labeled ester, 2) an isotopically-labeled alcohol derived from the isotopically labeled ester, and/or 3) an isotopically-labeled acid derived from the isotopically-labeled ester. In addition, various combinations of isotopically-labeled esters and their associated labeled acids and/or labeled alcohols could be used to provide unique i-EBM signatures in the breath. The type of substituents may be varied to sterically/electronically alter the susceptibility of the ester to hydrolysis, and will thus regulate the rate of appearance of ester-based labeled i-EBM(s). The physicochemical properties (e.g., physical state, volatility) of the ester will be a function of its substituents (R groups). By incorporating various isotopic labels (preferably deuterium) into various atomic sites of the esters, various i-EBMs (arising from the ester, acid and/or alcohol) containing one or more isotopic labels is/are generated that fulfill the requirements of an effective MAMS.

The following criteria are relevant to selection of appropriate i-AEMs (and, indeed, to AEMs, unless specifically referenced to i-AEM selection criteria): 1) state of matter: solid versus liquid; 2) taste: absent or present (pleasant vs unpleasant); 3) physicochemical properties: boiling point, melting point, Henry's Law constant ($K_H$); 4) PK properties: ADME, including metabolism rates and routes (non-CYP-450 to avoid adverse drug reactions [ADRs]); 5) extensive safety data: stability, toxicological data such as permissible daily exposure (PDE) in humans and $LD_{50}$ values in various species (typically in the gms/kg range for oral administration); 6) minimal-to-no implications from a regulatory perspective (no impact on CMC of API [study drug or FDA approved drug] or PK/PD of API); and 7) metabolism of taggant generates i-EBMs that are easily detected by the mGC-MOS or mGC-mIR (e.g., i-EBM is detected by the sensor and is neither a significant endogenous chemical nor widely generated via ingestion of different foods or medications).

Based on these considerations, a preferred set of fourteen compounds are 2-propanol (isopropyl alcohol), 2-butanol, 2-pentanol, ethyl acetate, ethyl butyrate, ethyl isobutyrate, hexyl acetate, isoamyl (isopentyl) acetate, methyl butyrate, methyl isobutyrate, methyl propionate, propyl acetate, 2-pentyl butyrate, and 2-pentyl acetate.

The list contains three 2° alcohols and eleven esters (nine 1° alcohol-based esters, plus two 2° alcohol-based esters). Secondary esters and their corresponding 2° alcohols offer many advantages in definitive adherence. For example, 133 esters were identified in the food database having boiling points ranging from 30 to 320° C., indicating the wide diversity available for a technology like mGC-MOS, mGC-midIR, which are essentially "boiling point" detectors. Aliphatic esters are rapidly hydrolyzed to their corresponding alcohol and aliphatic carboxylic acids by esterases, which could serve as i-EBMs.

Preferred secondary and tertiary alcohols—those that are GRAS compounds include 2-propanol, 2-butanol, 1-butanol (2-methyl-2-propanol), 2-pentanol, 3-pentanol, 3-pentanol, 3-methyl-2-butanol, 3-hexanol, 2-hexanol, 3-methyl-3-pentanol, 2-methyl-2-pentanol, 3-methyl-2-pentanol, 4-methyl-2-pentanol, 2,4-dimethyl-3-pentanol, 2-methyl-3-hexanol, 2,6-dimethyl-2-heptanol, 2,6-dimethyl-4-heptanol, 2-heptanol, 3-heptanol, 4-heptanol, 5-methyl-3-heptanol, 6-methyl-3-heptanol, cyclobutanol, cyclopentanol, cyclohexanol, and cycloheptanol.

TABLE 3

Illustrative Examples of Select Alcohols
R'—OH
Name of Alcohol

Methanol (Methyl alcohol)
Ethanol (Ethyl alcohol)
1-Propanol (n-propyl alcohol)
2-Propanol (isopropyl alcohol)
1-Butanol (n-Butyl alcohol)
2-Butanol (sec-Butyl alcohol)
2-Methyl-1-propanol (Isobutyl alcohol)
2-methyl-2-propanol (Tert-butyl alcohol)
2-Methyl-1-butanol
1-Pentanol (Pentyl alcohol)
3-Methyl-1-butanol (Isopentyl alcohol)
3-Methyl-3-buten-1-ol
2-Methylbut-3-en-1-ol
1-Hexanol (Hexyl alcohol)

Shown in Table 3 are alcohols that are commonly generated via enzymatic degradation of GRAS food additives/flavorants and/or FDA approved drugs (e.g., esterase mediated degradation of esters to their corresponding acids and alcohols). By incorporating various isotopic labels shown in Table 1 (e.g., and preferably, deuterium), into substrates that create the various alcohols shown but not limited to the above table, or even into alcohols directly, various i-EBMs are generated that fulfill the requirements of an effective MAMS.

TABLE 4

Illustrative Examples of Carboxylic Acids
Name of Carboxylic Acid
R'—COOH

Formic Acid
Acetic Acid
Propionic Acid
DL-Lactic Acid
Butyric Acid
Isobutyric acid
1-Methyl butyric acid
Valeric acid
Isovaleric acid
Crotonic acid
3-Methyl crotonic acid (3-Methyl-2-butenoic acid)
Hexanoic acid Shown in Table 4 are different carboxylic acids that are commonly generated via enzymatic degradation of GRAS food additives/flavorants and/or FDA approved drugs (e.g., esterase mediated degradation of esters to their corresponding acids and alcohols). By incorporating various isotopic labels shown in Table 1 (e.g., and preferably, deuterium), into substrates that create the various acids shown but not limited to the above table, or even into acids directly, various i-EBMs are generated that fulfill the requirements of an effective MAMS.

Compared to carboxylic acids, alcohols are more suitable i-EBMs for a variety of reasons (e.g., carboxylic acids have poor [high] $K_H$ values ($=C_L/C_G$, liquid to gas phase concentration ratio that cause them to partition preferably in blood versus breath)). In the case of 1° alcohol-based aliphatic esters (1° esters) such as ethyl butyrate, esterases rapidly create a 1° alcohol (i.e., ethanol). For 2° alcohol-based aliphatic esters (2° esters) such as 2-pentyl butyrate, they are rapidly hydrolyzed to their corresponding 2° alcohol (i.e., 2-pentanol) by esterases, particularly by carboxylesterases (e.g., β-esterase). The carbon that carries the hydroxyl (—OH) group of primary (1°), secondary (2°) and tertiary (3°) alcohols is attached to 1, 2, and 3 alkyl groups, respectively. The 1° and 2° alcohols are primarily converted (oxidized) via alcohol dehydrogenase (ADH) to their corresponding aldehydes and ketones, respectively. In contrast to 1° and 2° alcohols, 3° alcohols, due to steric hindrance with ADH, are very resistant to metabolism in humans and thus are not ideal for MAMS, unless a 3° alcohol-based ester liberated a 3° alcohol (e.g., tert-butyl butyrate→tert-butanol), which was used as the EDIM. The aldehydes are further metabolized by aldehyde dehydrogenase (ALDH), which oxidizes (dehydrogenates) them to their corresponding carboxylic acid. In contrast, methyl ketones undergo α-hydroxylation (e.g., conversion of 2-butanone [methyl ethyl ketone, MEK] to 3-hydroxy-2-butanone [acetoin] via CYP-2E1 and CYP-2B, or conversion of 2-pentanone [methyl propyl ketone, MPK] to 3-hydroxy-2-pentanone) and subsequent oxidation of the terminal methyl group to eventually yield corresponding ketocarboxylic acids. The ketoacids are intermediary metabolites (e.g., α-ketoacids) that undergo oxidative decarboxylation to yield $CO_2$ and simple aliphatic carboxylic acids. The acids may be completely metabolized in the fatty acid pathway and citric acid cycle.

We have tested and confirmed that 2° alcohols (or even 2° esters that generate 2° alcohols) are excellent taggants for definitive adherence monitoring. The presence (and persistence) of their corresponding ketones (EBMs) in exhaled breath represents definitive proof of ingestion of a medication containing 2° alcohols as taggants. In general, due to increased steric hindrance, 2° alcohols are less good as substrates for ADH relative to 1° alcohols. Likewise, the enzymatic pathways to degrade alcohol-derived ketones appear less efficient than those for alcohol-derived aldehydes. Given the fact that 1) the gastric wall has a high concentration of ADH and alcohols (e.g., ethanol) are known to be significantly absorbed through the stomach, and 2) alcohols undergo extensive first pass metabolism via ADH in the liver after absorption from the GI tract, it should not be surprising that when 2-butanol is ingested, 2-butanone levels appear very rapidly in the breath, and its concentrations significantly exceeds those of 2-butanol (ketone:alcohol ratio: 2-butanone/2-butanol>>1). In contrast, when 2-butanol is administered via non-oral routes (e.g., transdermal, mucous membranes, intravenous, eye) to humans, the ketone: alcohol ratio is reversed (<1), relative to the value for oral administration, since the two above factors would not be operative. In addition, the availability of a wide variety of 2° alcohols provides a large number of taggants available for definitive adherence monitoring. In keeping with our hypothesis that 2° alcohols (vis-à-vis 1° alcohols) would generate ketones that would persist in the body and have significant excretion by the lung, diabetic patients readily excrete ketones during the pathophysiological condition of diabetic ketoacidosis (DKA). Ketones generated from other sources (e.g., orally ingested 2° alcohols) would also be excreted by the lung. Using the mGC-MOS, we have already shown these endogenous DKA-related ketones are easily distinguished from the ketones which would be generated from 2° esters or alcohols, including 2-butanone and 2-pentanone.

Below is a summary of some key advantages and disadvantages of using esters, 1° alcohols and 2° alcohols for definitive MAMS:

B. Advantages and Disadvantages of Using Various Chemical Classes of Compounds as i-AEMs/i-EBMs 1. Esters Advantages Great variety of GRAS food additives Esterases generate corresponding alcohol and carboxylic acid via enzyme systems that are widely present in humans and not easily saturable Many exist in liquid and solid state forms Relative to alcohols, many more choices for selecting solids Great variety of favorable tastes 2° alcohol-based esters such as 2-pentyl butyrate are primarily degraded by carboxylesterase to 2-pentanol and butyric acid:

Disadvantages

Greater mass of taggant required to be interfaced to API in order to generate a fixed mass of EDIM (e.g., 2-butanone)

Some esters not optimal from a stability standpoint

1° alcohol-based esters as GRAS compounds are much more common than 2° alcohol-based esters in food databases; these alcohols generate aldehydes, which are not ideal EDIMs relative to ketones derived from 2° alcohols 2. 1° Alcohols Advantages Much greater variety of GRAS food 1° alcohols relative to 2° alcohols Larger 1° alcohols via ADH generate aldehydes, particularly those that are branched, which are better EDIMs (e.g., low $K_H$ values; distinct from endogenous compounds) than more simple 1° alcohols, but have lower vapor pressures Disadvantages ADH forms aldehydes from 1° alcohols, which are generally not as good EDIMs as ketones, particularly with the more simple 1° alcohols Many have classic alcohol taste; may require CMC architecture approaches or addition of taste "maskers" to avoid Disulfiram, a drug used to treat alcoholism that blocks the action of aldehyde dehydrogenase, may interfere with the degradation of corresponding aldehydes, and cause side effects; this effect is expected to be clinically irrelevant due to the small mass of alcohol (or its corresponding ester) required for definitive MAMS Ethanol consumption (via interaction with ADH) can theoretically reduce the conversion of 1° alcohol taggant to its corresponding aldehyde; this has not been found to be clinically significant for a number of non-ethanol alcohols (excludes methanol)

Note: In addition of 1° alcohols, a number of critically important CYP-450 metabolic reactions for pharmaceutical agents, via dealkylations (FIG. 26), generate various aldehydes (FIG. 27), include formaldehyde via desmethylation, acetaldehyde via desethylation, propionaldehyde via despropylation, and butyraldehyde via desbutylation.

3. 2° Alcohols

Advantages

ADH generates ketones, which generally have more favorable physicochemical and metabolism characteristics as EDIMs than do aldehyde EBMs.

The ADH that generates ketones from 2° alcohols is not affected by genetic polymorphisms, as is the case with the ADH that generates aldehydes from 1° alcohols.

Disulfiram, an inhibitor of aldehyde dehydrogenase, will not interfere with the degradation of ketones formed from 2° alcohols (e.g., methyl ethyl ketone, derived from 2-butanol, is converted to 3-hydroxy-2-butanone via CYP-2E1 and 2B).

Disadvantages

Many have classic alcohol (ethanol) taste; may require CMC architecture approaches or addition of taste "maskers" to avoid the taste of these compounds.

Fewer 2° alcohols, relative to 1° alcohols, are listed in GRAS food databases

Fewer 2° alcohol-based esters are listed in GRAS food databases (e.g., these would generate the 2° alcohol, and later a ketone)

Figure 22:
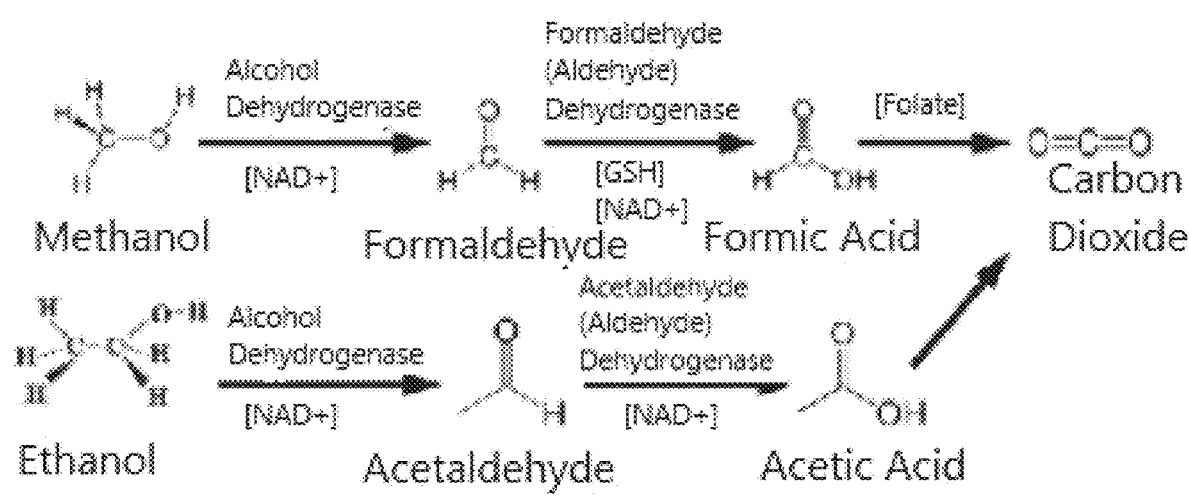
Figure 23:
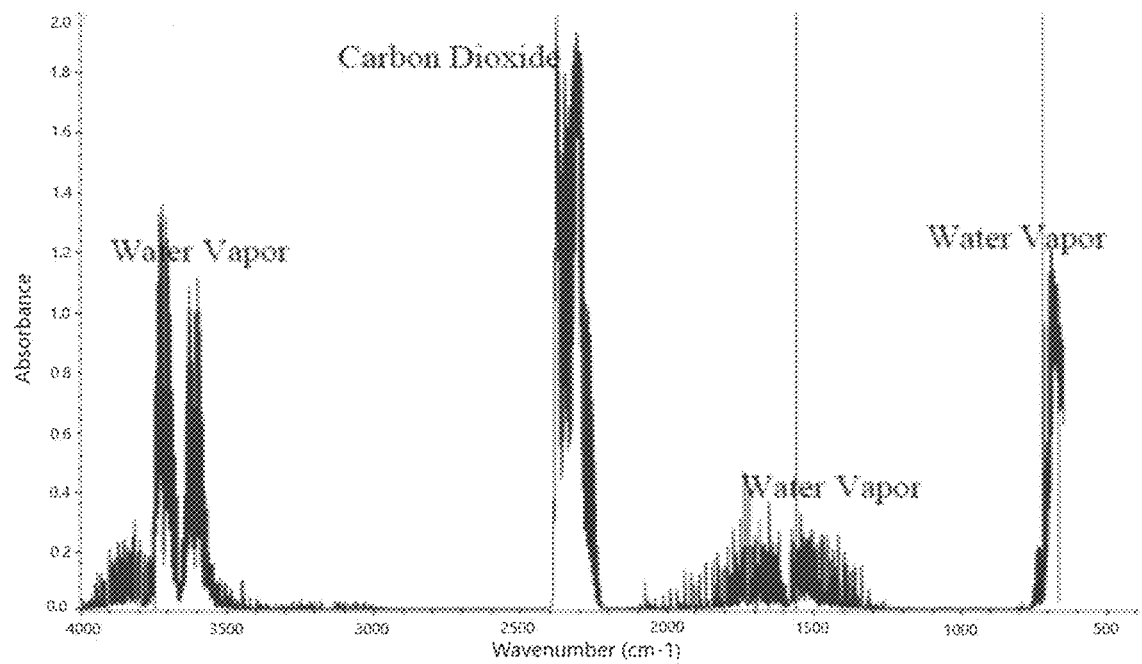
Figure 24:
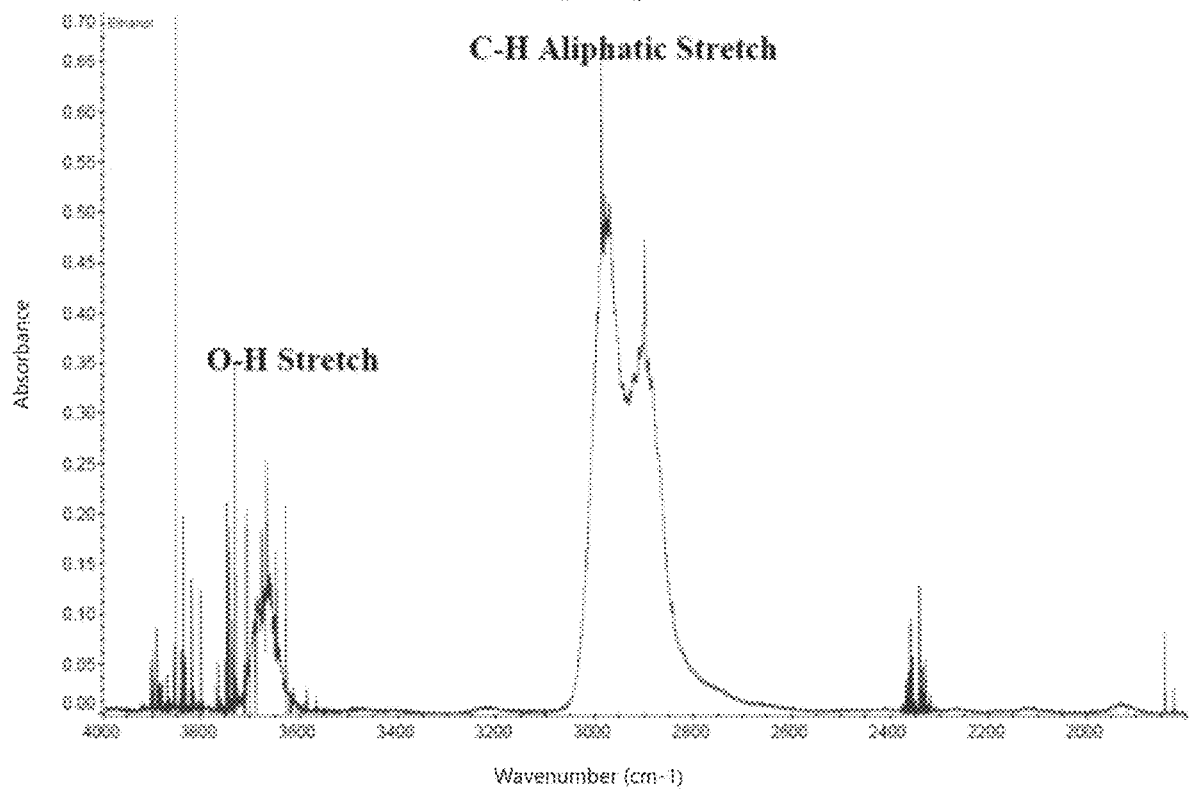
Figure 25:
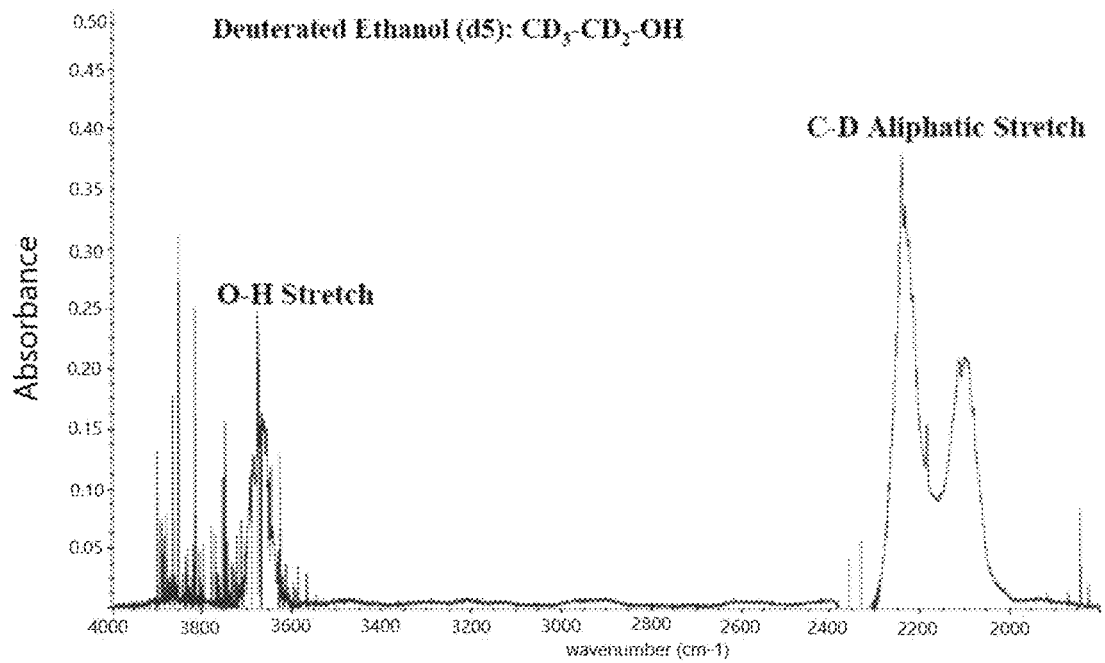
Figure 26:
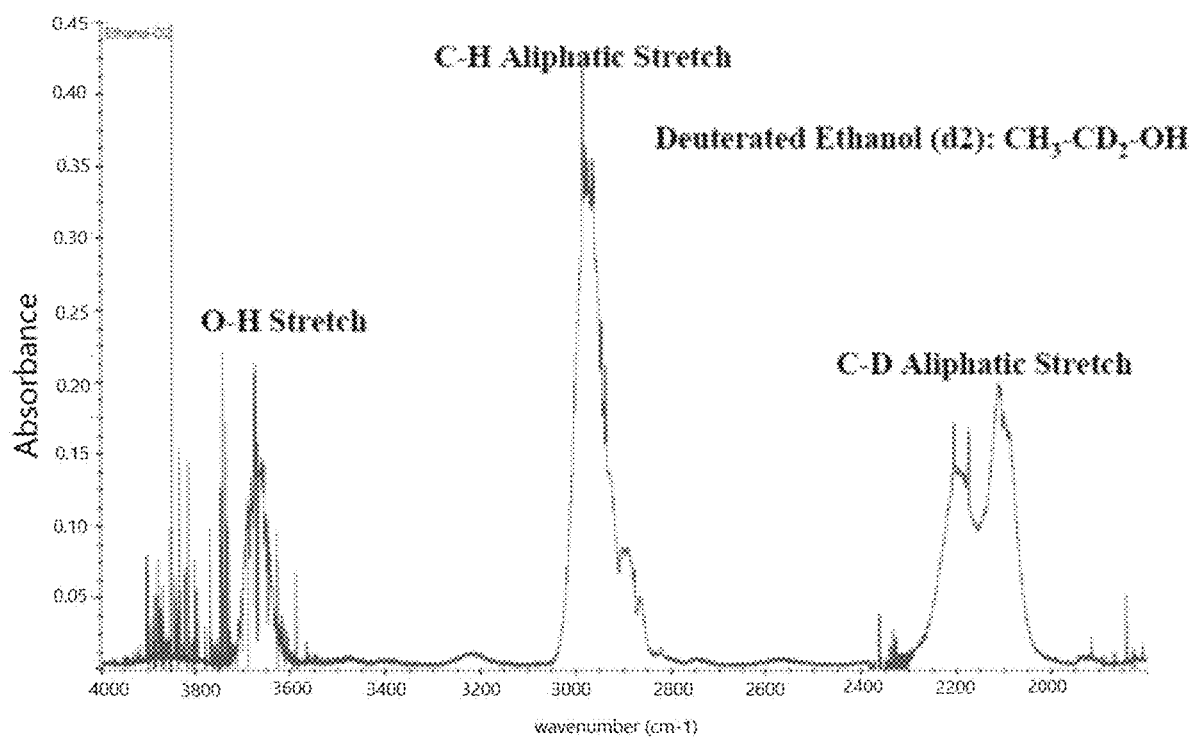
Figure 27:
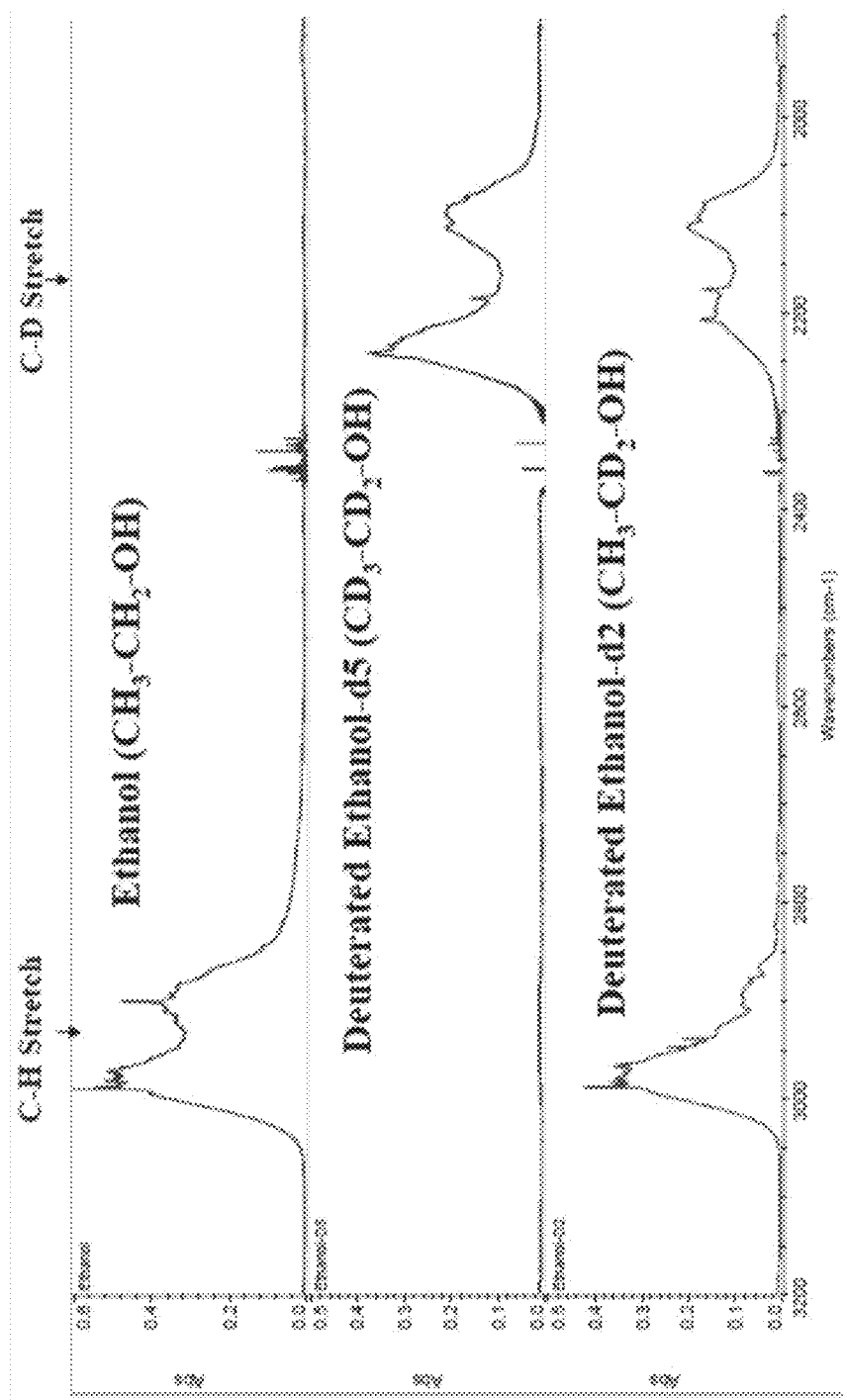
Figure 28:
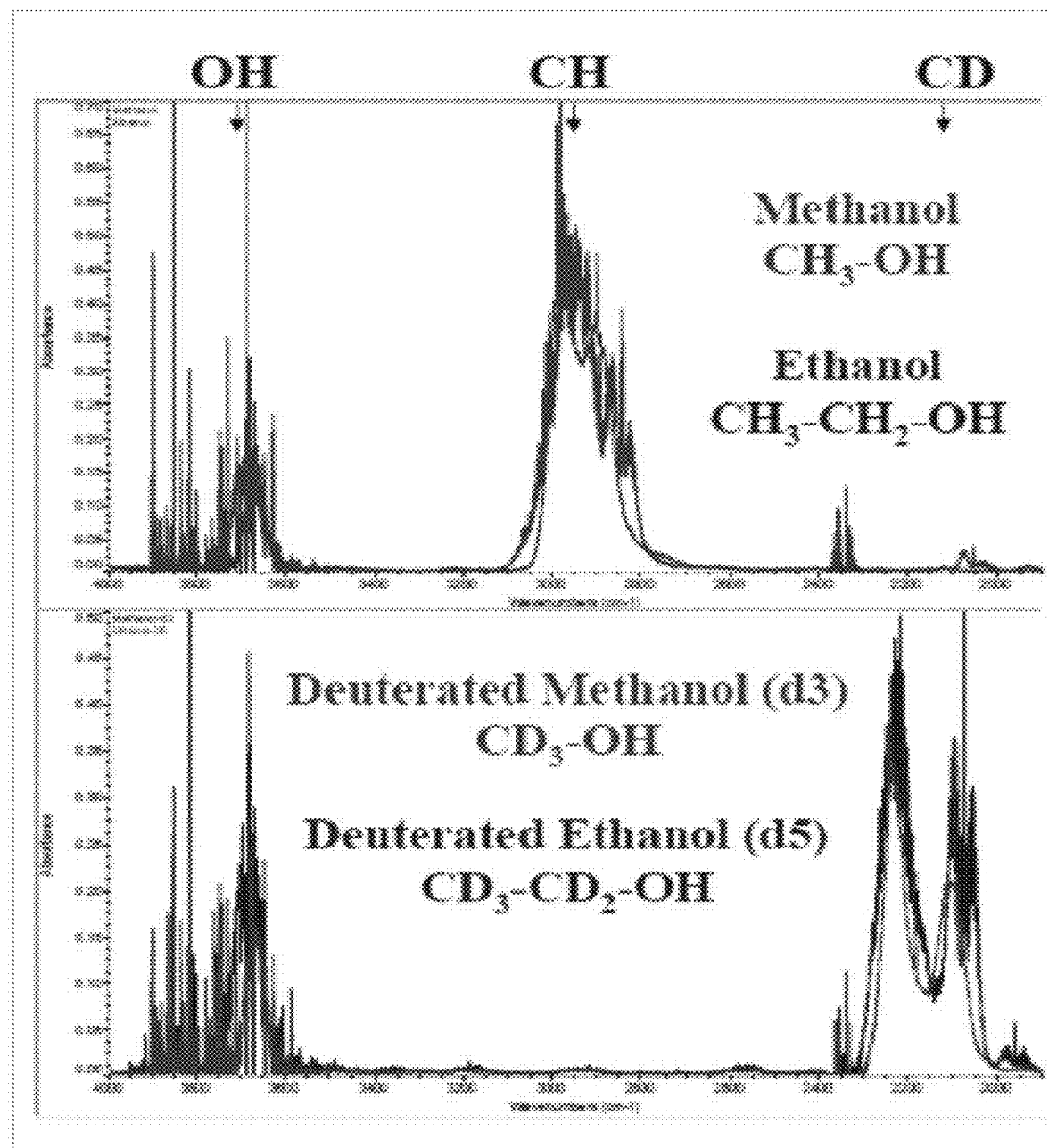
Figure 29:
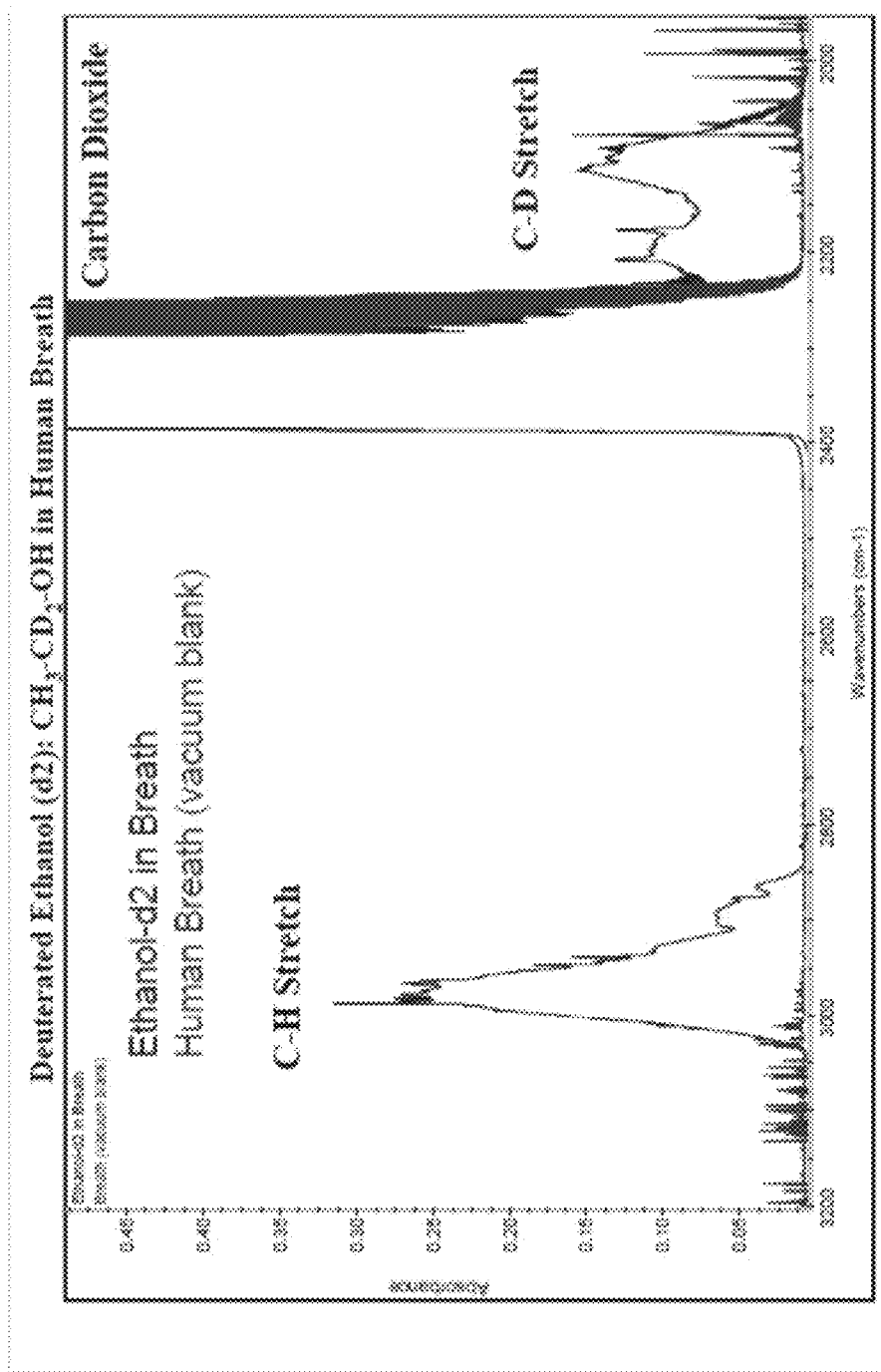
Figure 30:
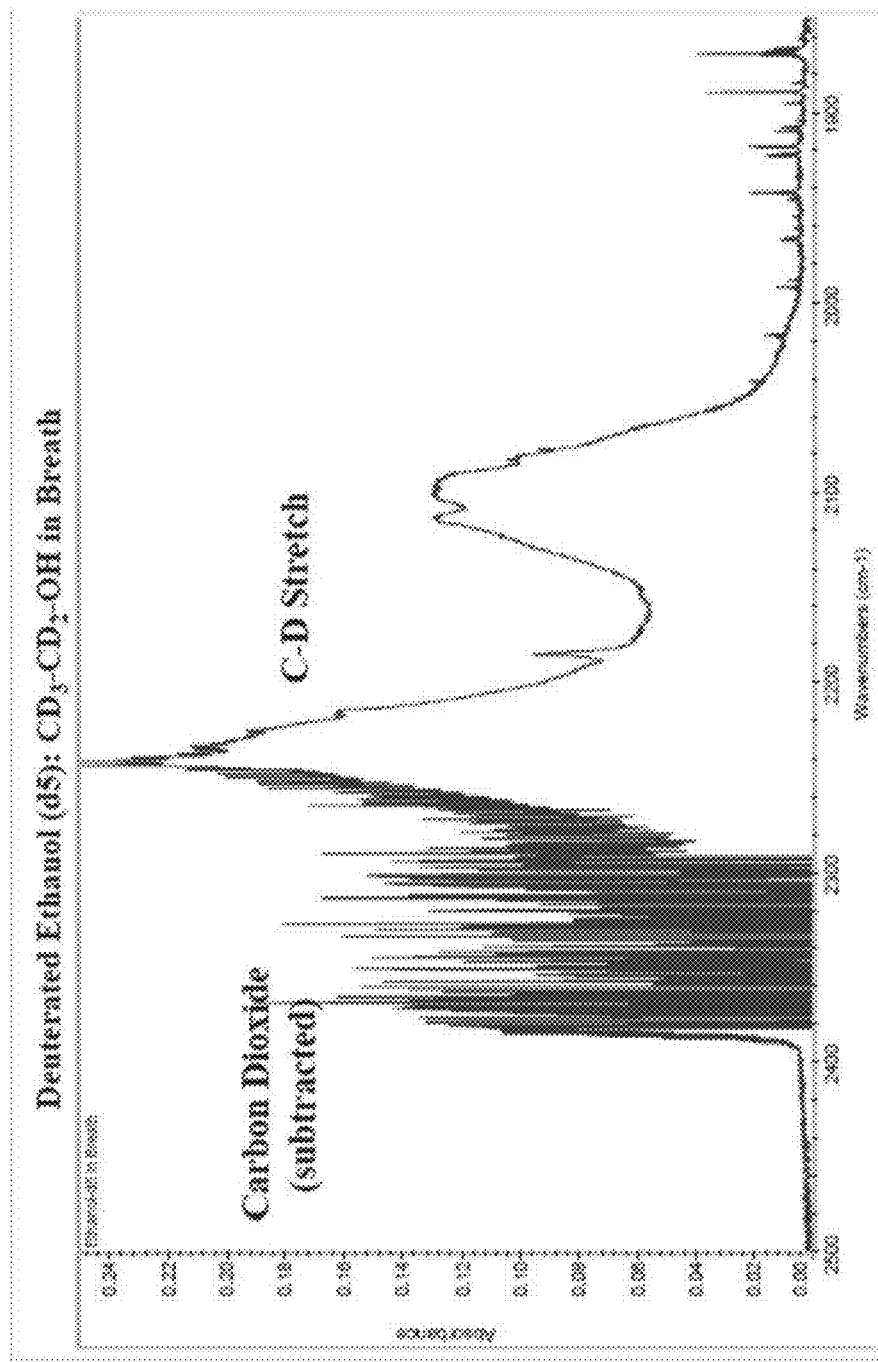
Figure 31:
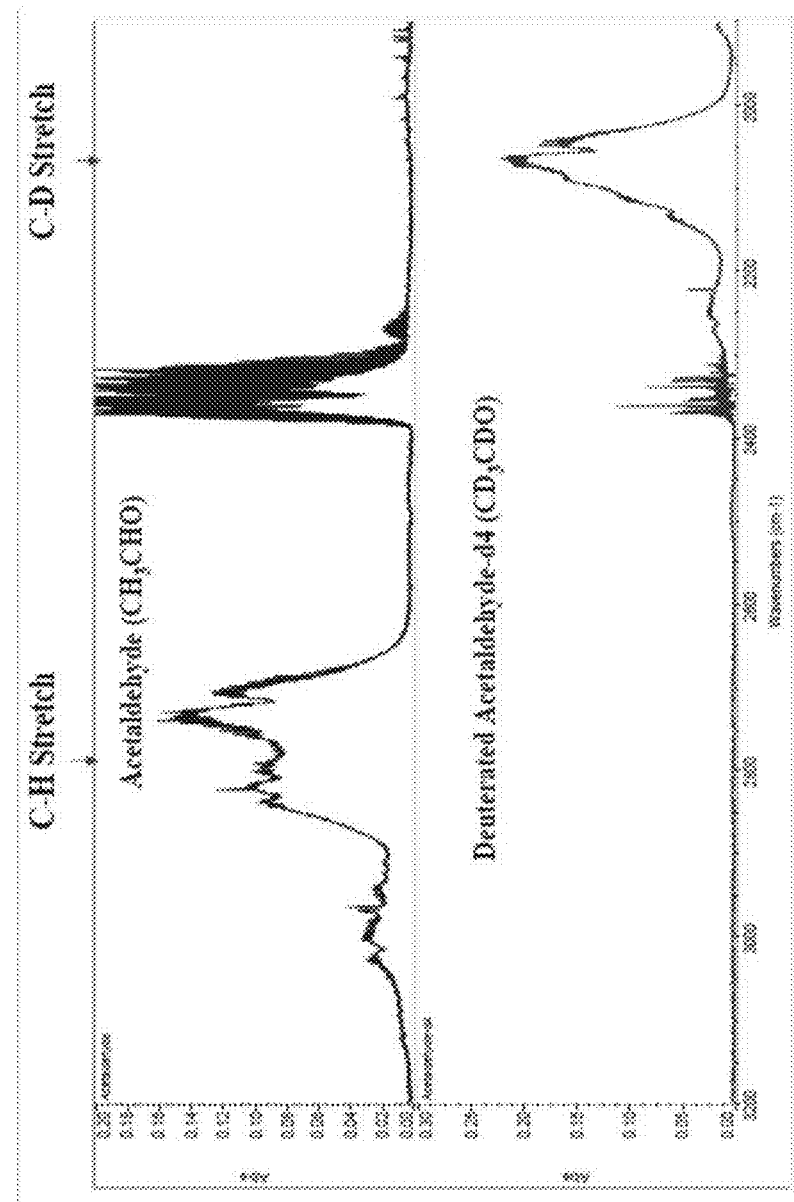
Figure 32:
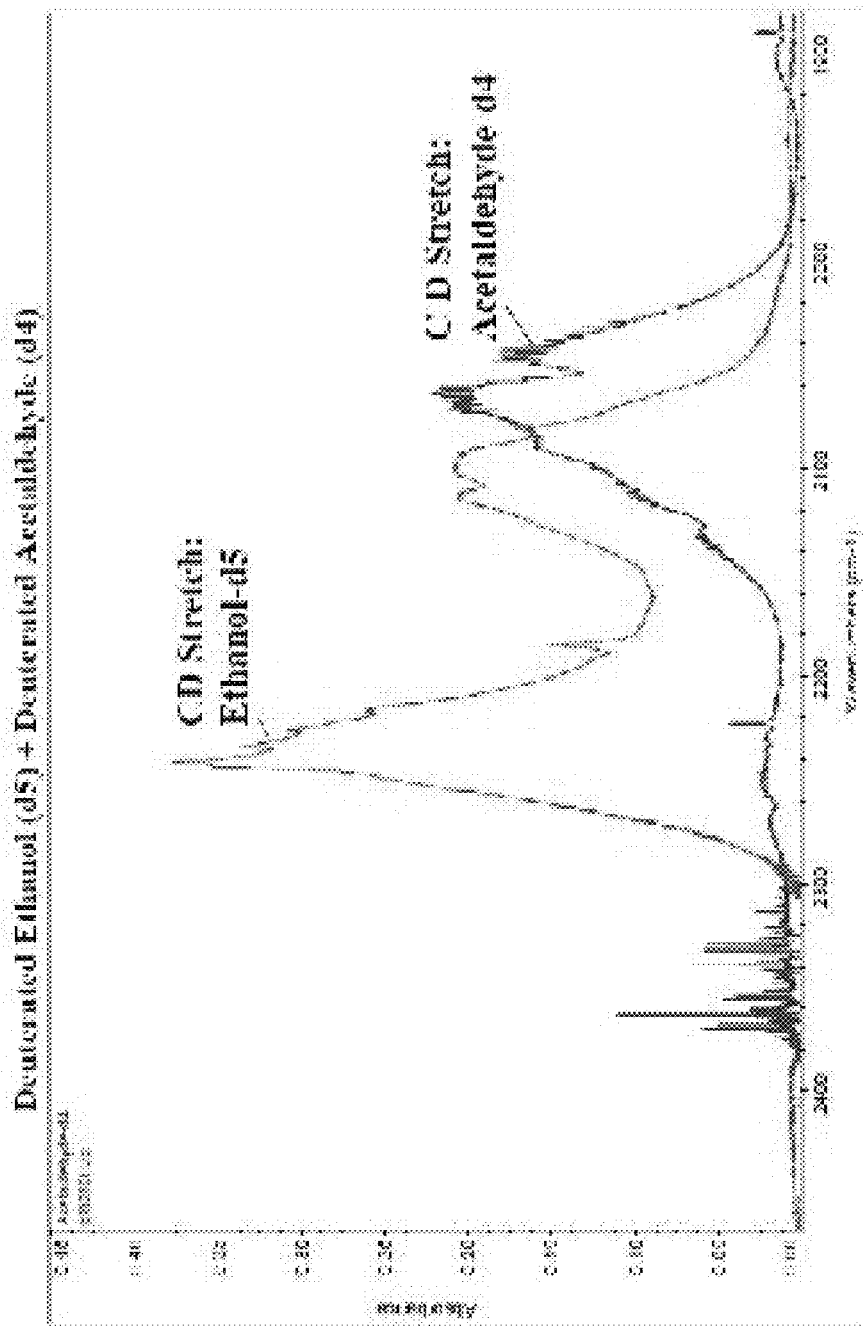
Figure 33:
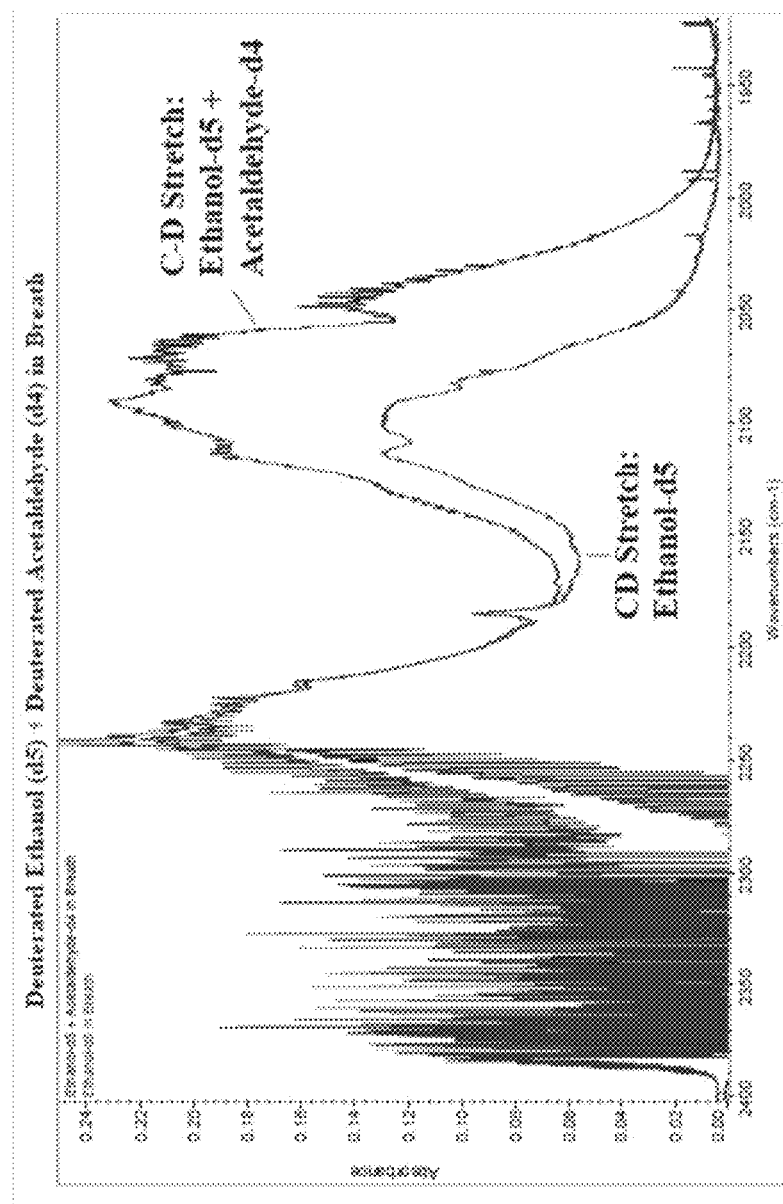
Figure 34:
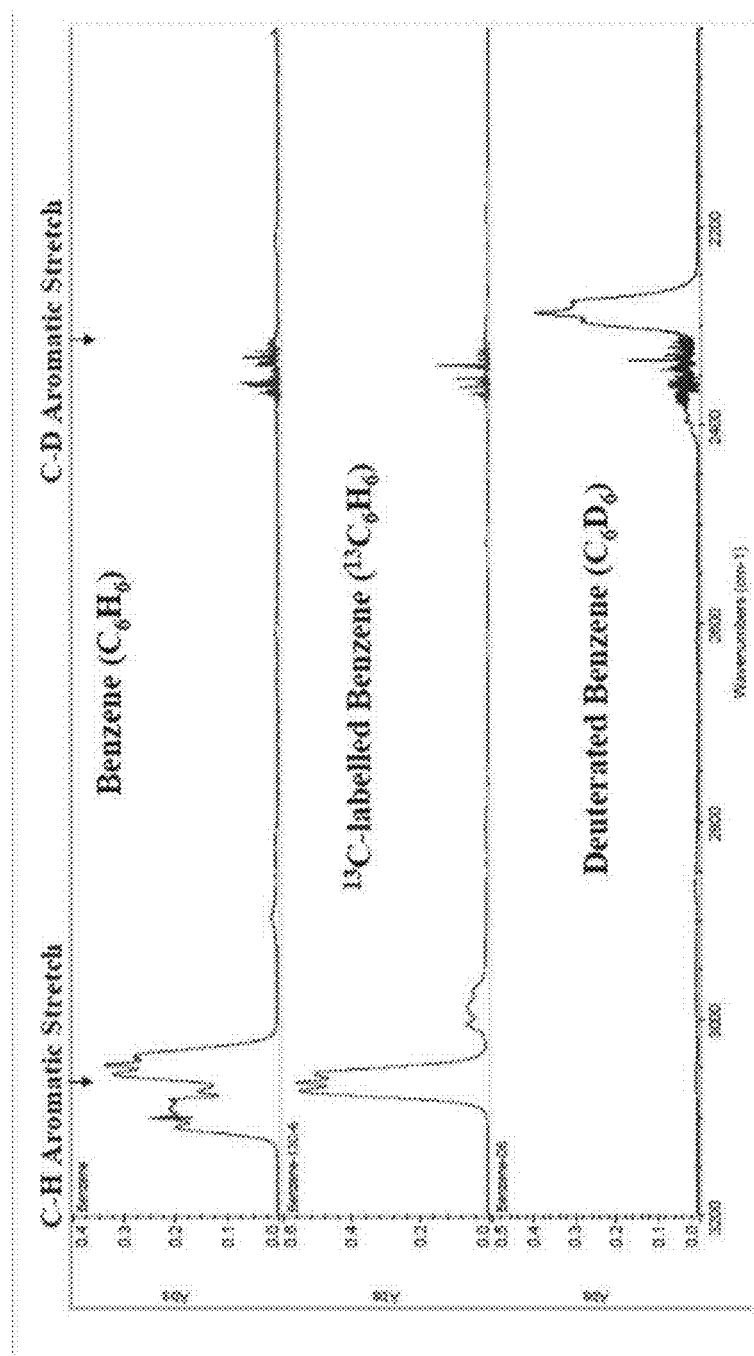
Figure 35:
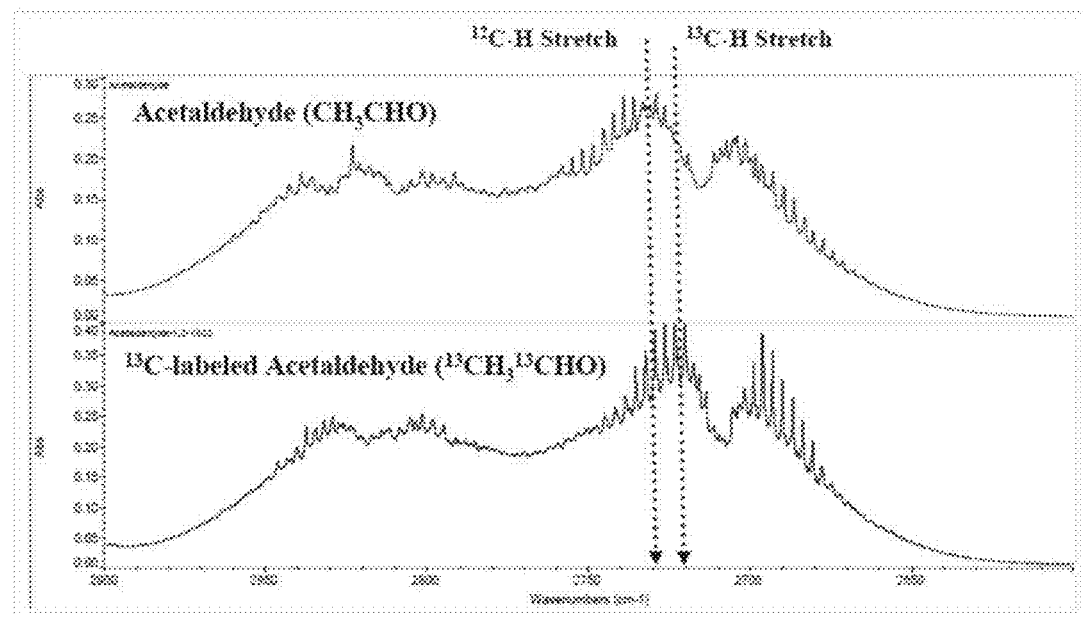
Figure 36:
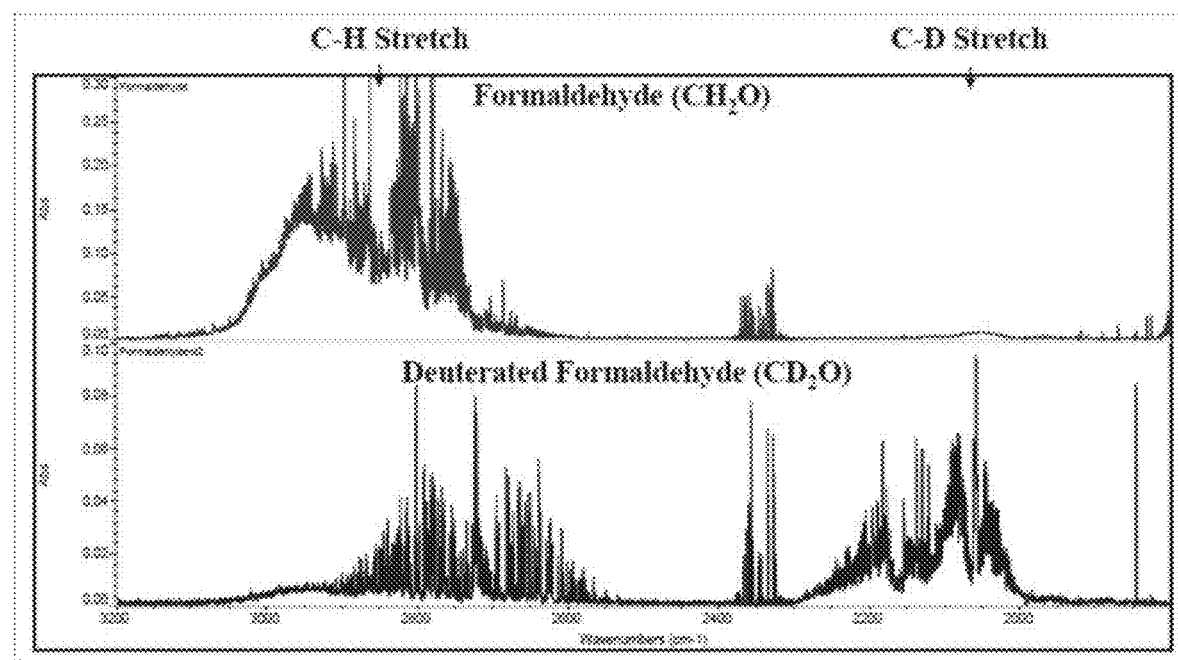
Figure 37:
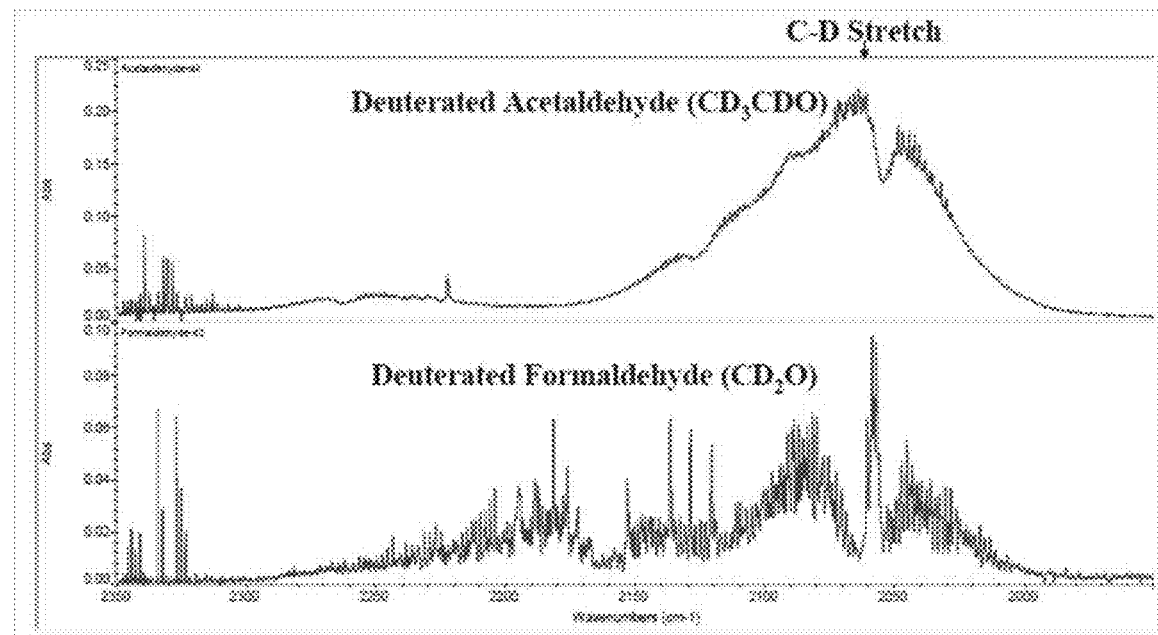
Figure 38:
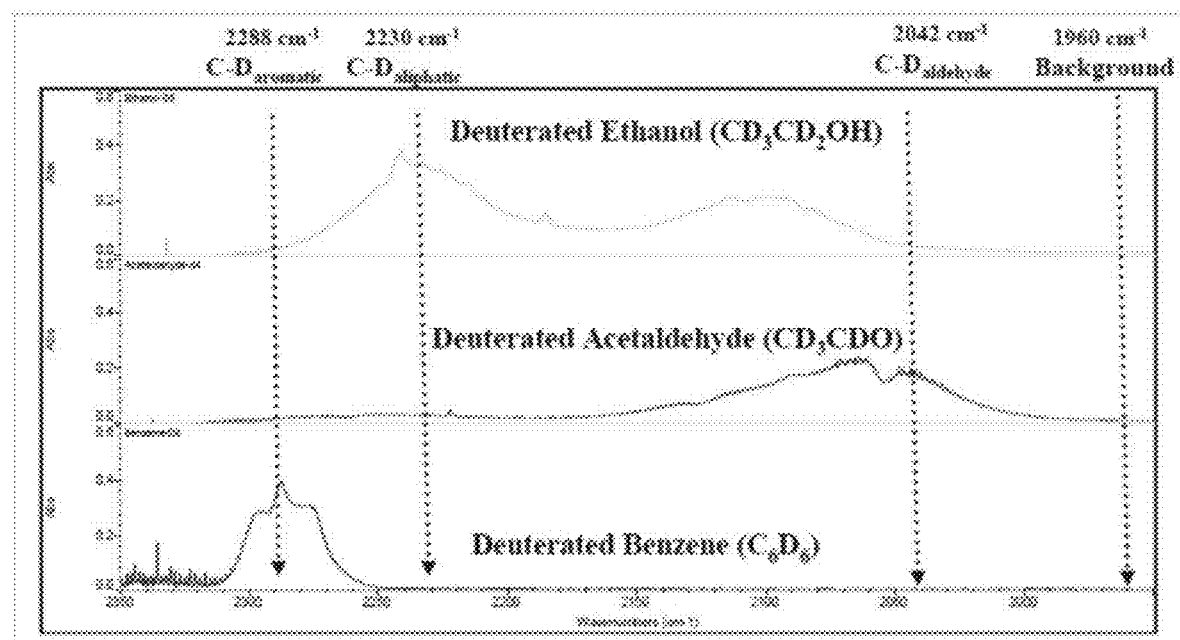
Figure 39:
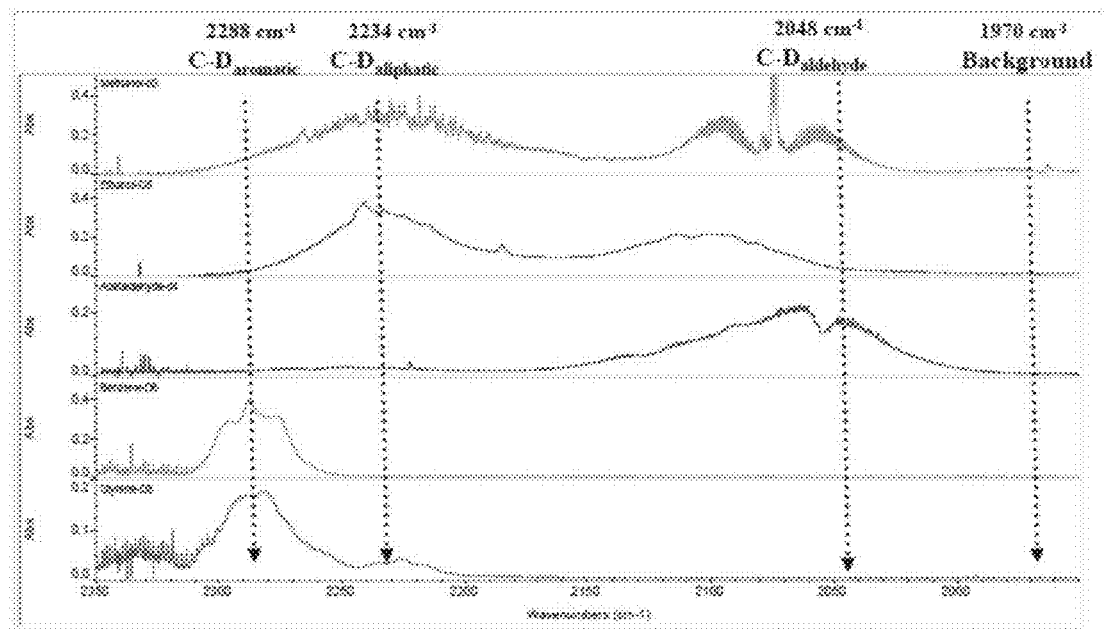
Figure 40:
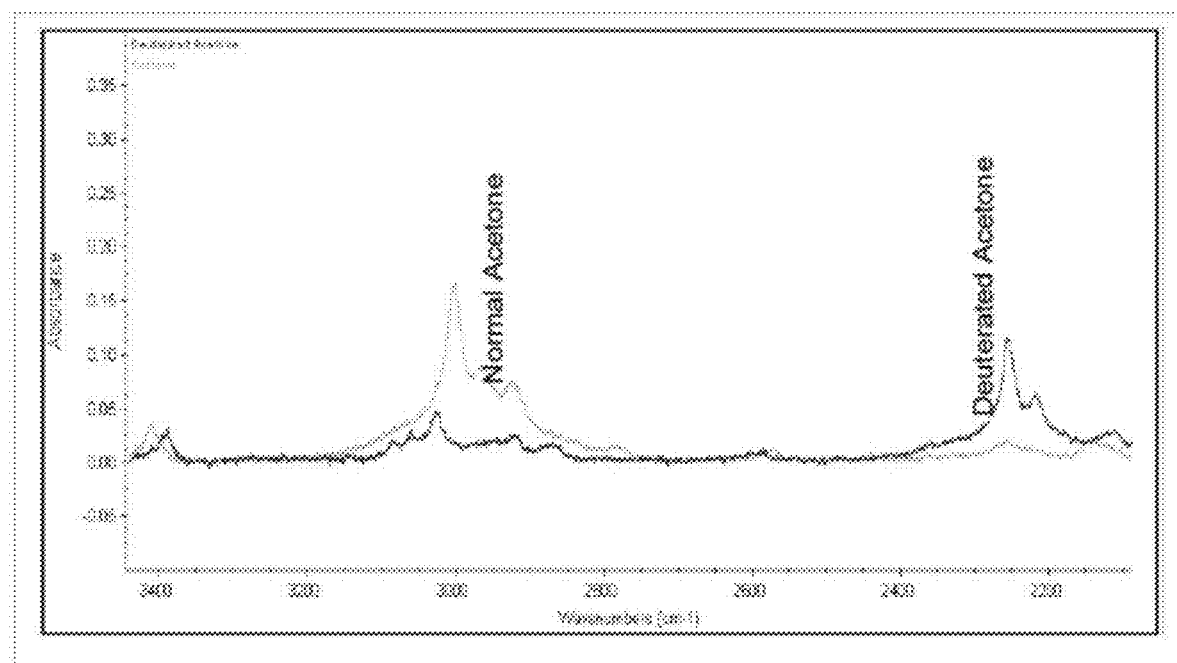
Figure 41:
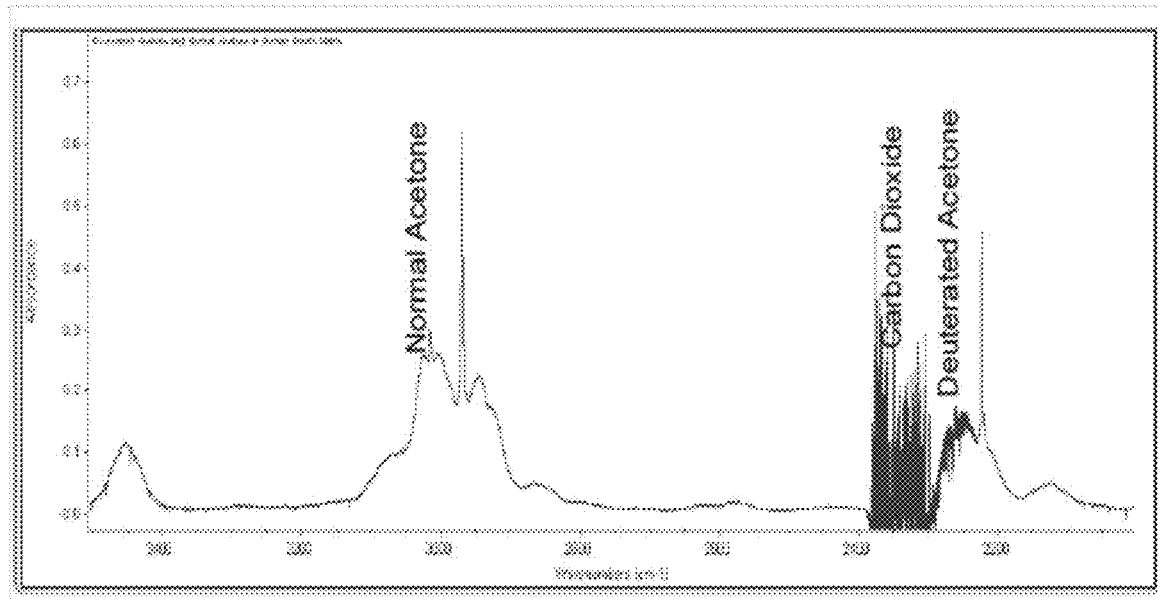
Figure 42:
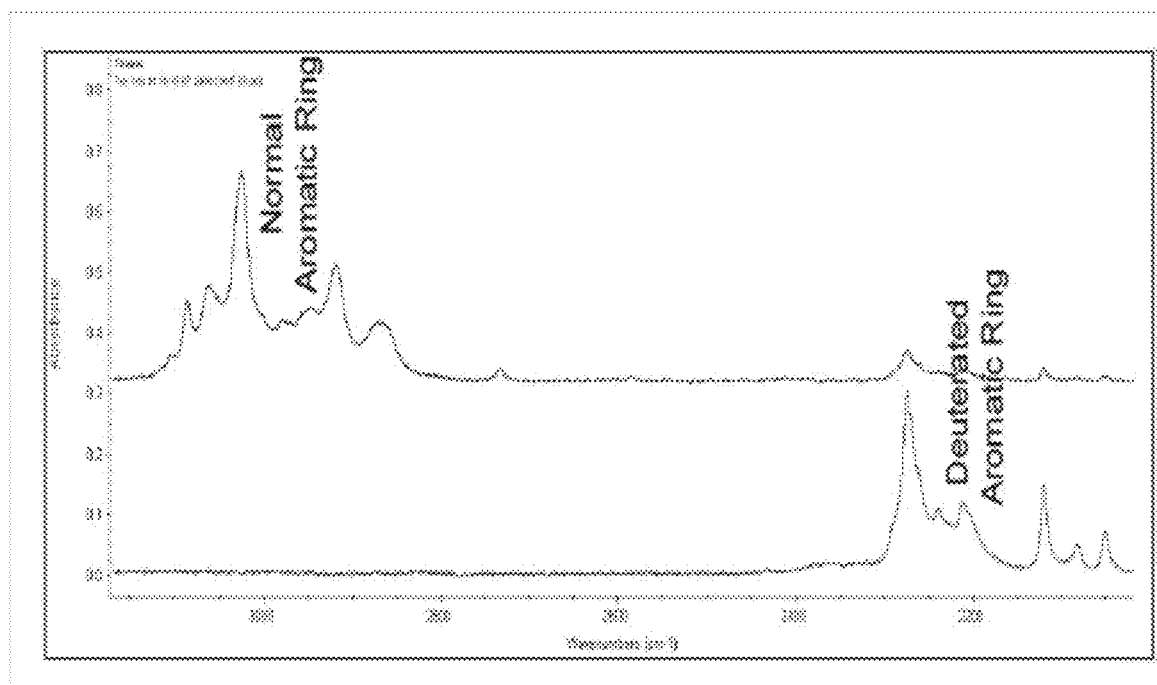
Figure 43:
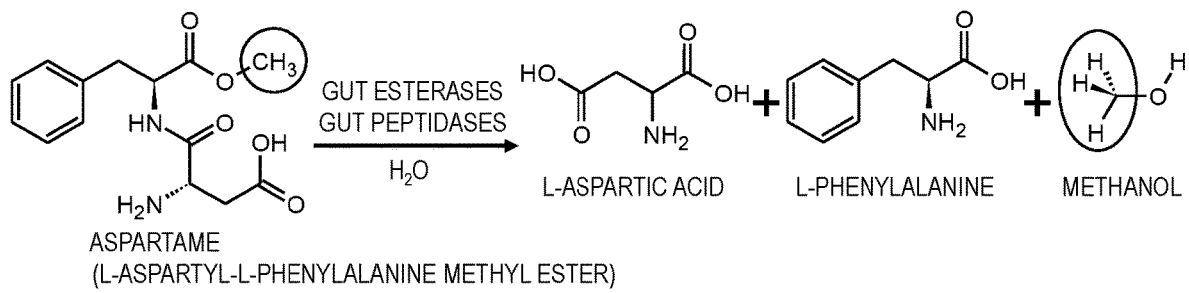
Figure 44:
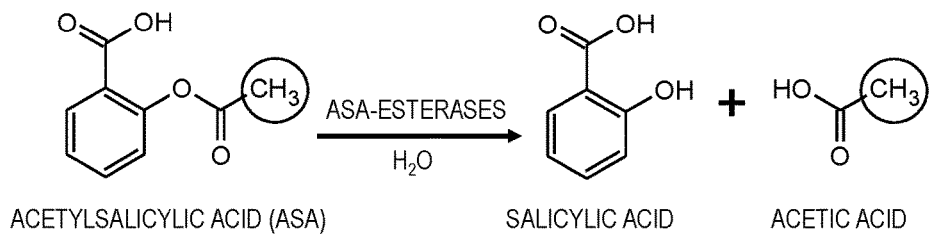
Figure 45:
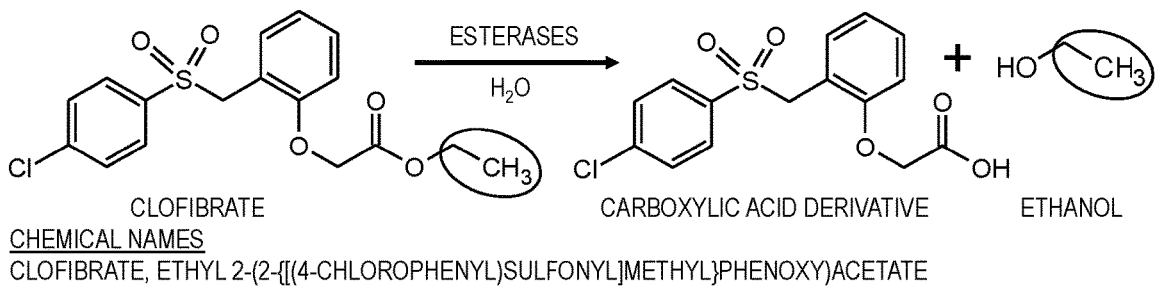
Figure 46:
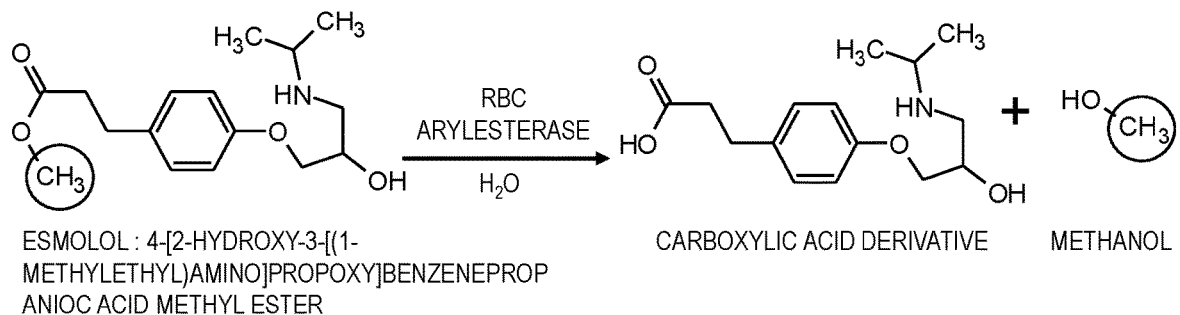
Figure 47:
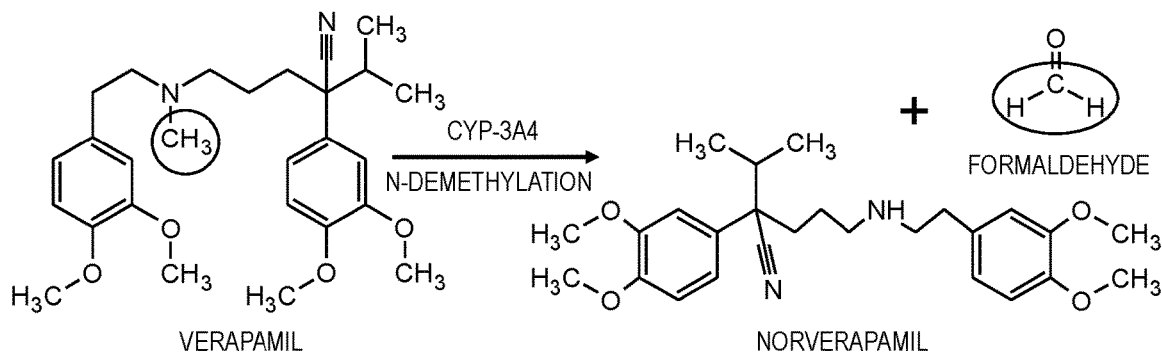
Figure 48:
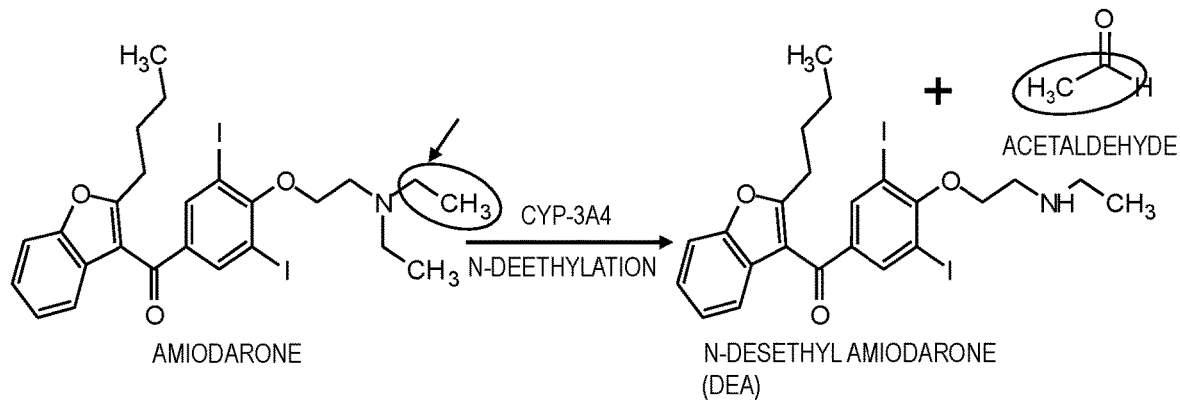
Figure 49:
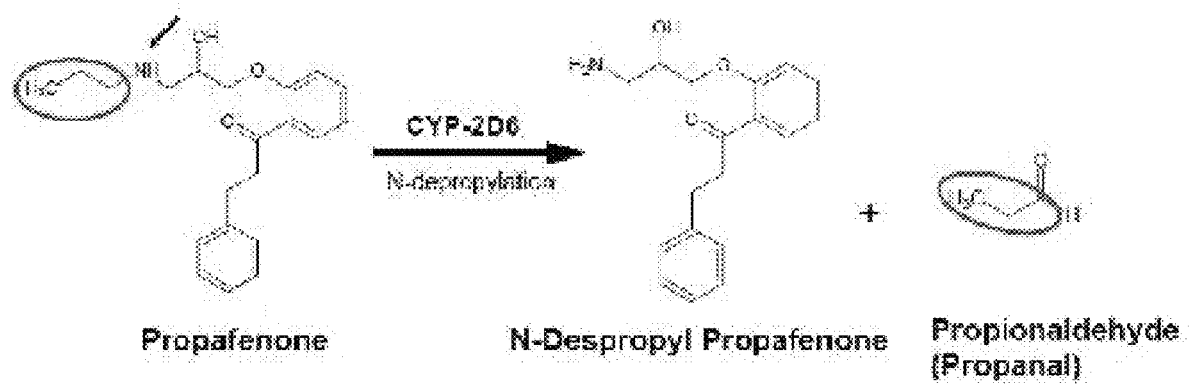
Figure 50:
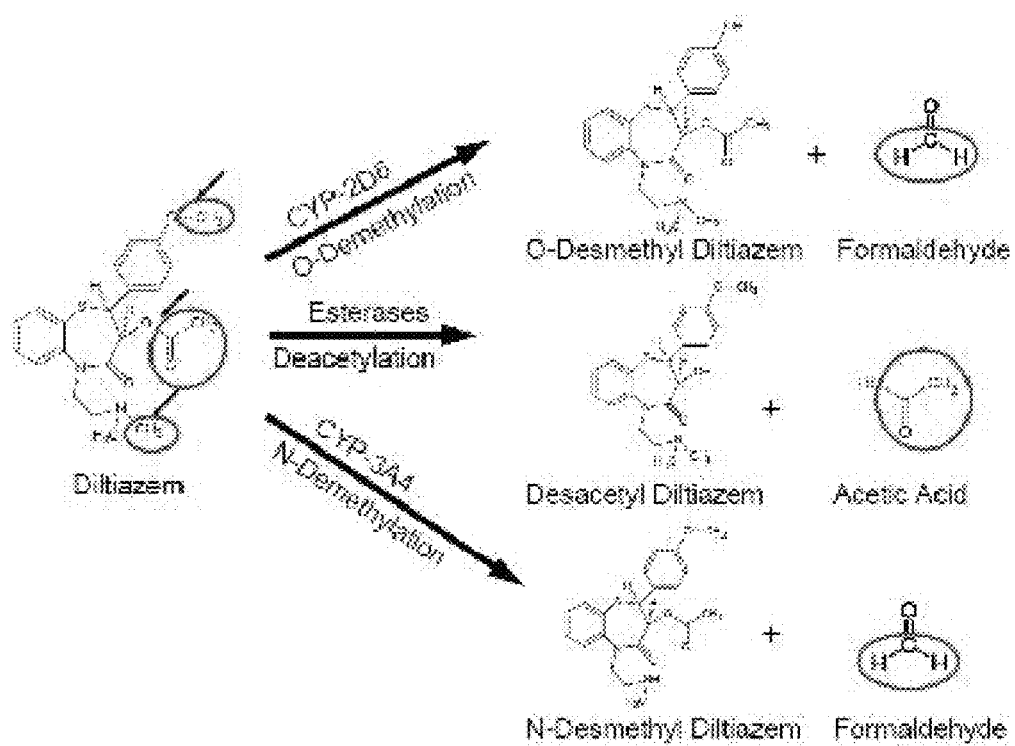
Figure 51:
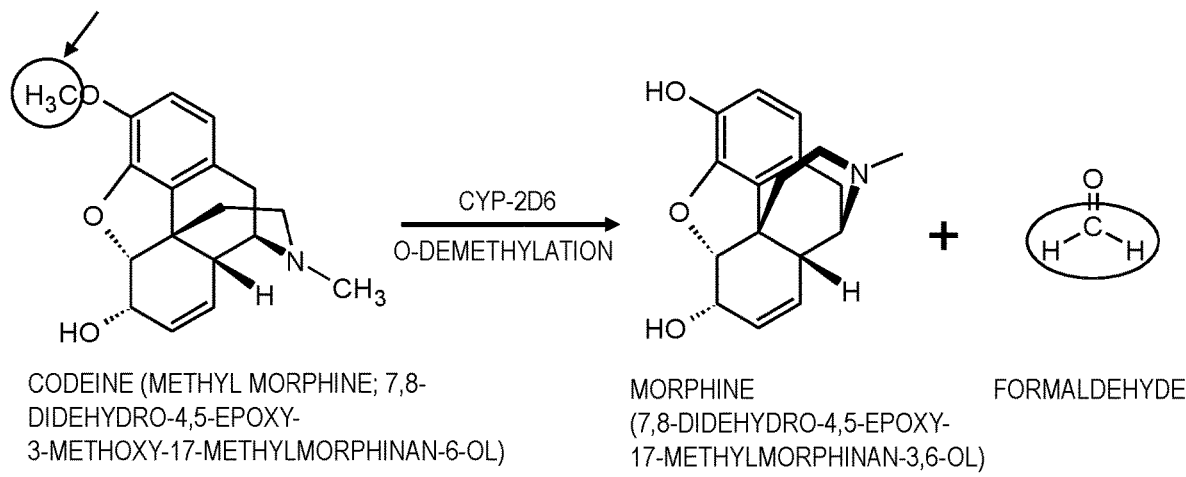
Figure 52:
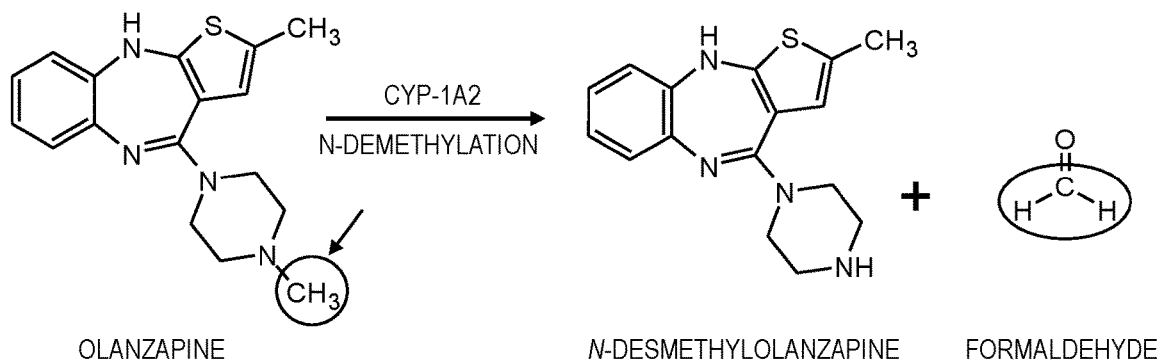

To assist understanding of this invention by those reviewing this patent disclosure, reference is now made to FIG. 22 herein, which shows the metabolic fate of selected ordinary isotope and non-ordinary isotope labeled alcohols, aldehydes and carboxylic acids. In humans alcohol dehydrogenases are a group of dehydrogenase enzymes that catalyze the interconversion between alcohols and aldehydes (or ketones). Their primary function is to degrade alcohols. The enzyme is contained within the gastric lining and in the liver. Aldehyde dehydrogenases are enzymes that catalyze the oxidation (dehydrogenation) of a various aldehydes. Multiple forms exist at various locations in humans, including the cytosol, mitochondria and endoplasmic reticulum. They are classified in the following manner: Class 1 (cytosolic), Class 2 (mitochondrial) and Class 3 (tumor and other isozymes). Panel B shows potential isotopic labeling sites. *, indicates a deuterium (stable isotope) label but could be other types as shown in Table 1. Likewise, multiple deuterated labels could be placed on the molecule or alternately a combination of different isotopic labels (H, C and/or O-based) could be used; t, indicates a carbon isotopic label (see Table 1). Note: In this scheme, where appropriate, other potential isotopic labels (Table 1) could be used including 17O and/or 18O for ordinary oxygen. Direct isotopic labeling of alcohols, aldehydes and acids is possible and adds to chemical diversity for MAMs. For example, during alcohol oxidation, the oxygen atom remains with the alcohol. It may be seen as a dehydrogenation of the alcohol i.e. only one hydrogen atom leaves the alpha carbon, and the molecule converts from alcohol to the carbonyl, which would be an aldehyde for a primary alcohol. Thus, if oxygen of a primary alcohol was labeled, it is possible to efficiently monitor the formation of the corresponding aldehyde after oxidation.

7.2.2 Methods of Making and Use and Compositions for Different Routes of SMART® Medication (Containing, e.g., Deuterated i-AEMs) Administration In a first embodiment according to this aspect of the invention, there is disclosed a SMART® medication, and a method of making the SMART® medication (or a composition comprising the SMART® medication), comprising an Active Pharmaceutical Ingredient (API) in combination with an AEM, that is at least one non-toxic, preferably Generally Recognized as Safe (GRAS) volatile organic compound (VOC), or incipiently volatile organic compound (i.e. on introduction into or onto a subject, the AEM is exhaled or gives rise to a compound which is exhaled), preferably a direct food additive, wherein at least one atom thereof is a non-ordinary isotope, e.g., a hydrogen of said VOC is replaced with a deuterium atom, such that, on administration (ingestion, topical application, or other means of delivery) of the medication comprising the deuterium-labeled AEM (e.g., the VOC or a metabolite thereof comprising) the deuterium atom is entrained and is detectable in the exhaled breath as an i-EBM. In addition, disclosed herein are certain novel APIs or compositions comprising APIs wherein the API itself incudes the non-ordinary isotope and acts as the i-AEM or produces the i-EBM.

The various types of i-AEMs which produce i-EBMs detectable in the breath are discussed above. Depending on the route of administration of the medication, different formulations and physical arrangement of the API and i-AEM are preferred, as discussed below:

7.2.3 Oral i-AEM Medications

A wide variety of oral dosage forms including AEMs are disclosed in WO2013/040494, published 21 Mar. 2013, entitled "SMART™ SOLID ORAL DOSAGE FORMS". A number of physical forms for delivery of active therapeutic agents in combination with markers were disclosed. Wherever in that publication there is mention of AEMs, per the present invention, non-ordinary isotopes may be included in the AEMs to produce i-AEMs, such that, upon introduction into the biological system, there is produced in the exhaled breath i-EBMs which may be monitored according to the present invention. The contents of WO2013/040494 are herein incorporated by reference as if fully set forth herein, to describe and enable those skilled in the art to utilize the various dosage forms that could be used to include i-AEMs according to the present invention.

In a preferred embodiment according to this aspect of the invention, the i-AEM is contained within a barrier, which keeps the i-AEM separate from any API being co-delivered. The barrier may be composed of gelatin or other containment mixture known in the art. Where a very small quantity of neat i-AEM is desired to be used, it may be printed onto or otherwise adhered to an existing dosage form and under and/or overcoated with a quickly dissolving i-AEM impermeable layer. Coatings known in the art for this purpose may be utilized. Thus, microcrystalline cellulose, hydroxypropyl methyl cellulose, other polymeric or non-polymeric barriers, and the like, such as disclosed in, for example, U.S. Pat. No. 6,352,719; US2007/0212411; US2004/0110891 and the like may be utilized for this purpose.

7.2.4 Vaginal/Rectal i-AEM Medications

Generally, non-toxic, and preferably GRAS secondary and tertiary alcohols with between three and up to eight carbon atoms, including at least one non-ordinary isotope of hydrogen (i.e deuterium), carbon, oxygen or nitrogen, are useful for this purpose. Thus, for example, any or each of the following compounds which include at least one non-ordinary but stable (non-radioactive) isotope may be used according to this invention as an i-AEM for non-oral delivery of i-AEMs for use in combination with the i-SMART® system: isopropanol; 2-butanol; 2-methyl-2-butanol; 2-pentanol; 3-pentanol, and the like. Preferred secondary and tertiary alcohols are those that are GRAS compounds.

In addition, while the present disclosure focuses on specific excipients and combinations thereof with the i-AEMs disclosed herein, those skilled in the art will appreciate that other equivalent excipients may be utilized with the disclosed i-AEMs.

An optimized i-AEM composition is disclosed herein which comprises at least or exclusively the following key components, mixed either prior to delivery or at the site of delivery at an appropriate concentration with a vaginal or rectal gel or other appropriate medium known in the art or which hereafter comes to be known in the art:

a. An i-AEM, e.g., deuterated 2-butanol, deuterated IPA, (but which may be any of the i-AEMs discussed herein;

b. A gel medium for delivery of the i-AEM and/or Active Pharmaceutical Ingredient (API);

c. At least one API, unless the i-AEM is being delivered in a placebo.

Those skilled in the art can, based on the disclosure and guidance provided herein, make appropriate modifications to vaginal or rectal delivery formulations to accommodate alternate i-AEMs, volumes, concentrations and chemical interactions. When delivering an i-AEM via a vaginal or rectal route, particularly where an anti-HIV API is being co-delivered with the i-AEM, it is critical to ensure that the amount and concentration of secondary or tertiary alcohol acting as the i-AEM be so low as to avoid inflammatory responses known to be caused when high concentrations and amounts of alcohol, e.g., ethanol, are delivered via these routes. This is because it is known that high concentrations of alcohol when introduced into the vagina or rectum, while able to cross the cellular barrier, induce significant inflammation. Aside from the associated discomfort, this also reduces a critical natural barrier to infection—actually increasing the susceptibility to infection by, for example, HIV.

Surprisingly, successful detection of i-EDEMs in exhaled breath is achieved following inclusion of as little as about 3 to 10 mg of e.g., deuterated 2-butanol. These doses, especially when dissolved in standard volumes of microbicide gel (typically 4 ml), are very unlikely to elicit any inflammatory response at the site of delivery. For example, when a dose range of about 3 to 30 mg of deuterated 2-butanol or IPA is delivered vaginally or rectally in an appropriate carrier medium, e.g., tenofovir placebo gel (i.e. the same medium in which tenofovir is delivered but with or without the active agent tenofovir) even more reliable detection of deuterated 2-butanol, 2-butanone or acetone in the exhaled breath is achieved in a time frame and concentration sufficient to definitively confirm product placement with a high level of confidence, and without induction of inflammation at the delivery site. While greater amounts of i-AEM could be delivered by this route without causing inflammation, it is preferred to deliver no more than 100 mg of i-AEM, and, most preferably, to deliver between about 0.003 to 30 mg, and, most preferably, to deliver between about 0.03 and 3 mg. Because there is so little background when using i-AEMs, it is generally possible to achieve reliable adherence monitoring utilizing amounts of the i-AEM that otherwise would not be easily detectable in exhaled breath.

The physiology of the vaginal lining includes a significant barrier to delivery and diffusion of i-AEMs and APIs, due to the thick, stratified squamous epithelial lining. Nevertheless, the inventors herein are able to successfully deliver i-AEMs via the vaginal route. Thus, rectal delivery, where a single epithelial cell layer forms the surface of the rectum, is assured. Compositions, means and devices for rectal delivery include gels, as for vaginal delivery, and such dosage forms as suppositories, which may include the API in an appropriate suppository vehicle known in the art, with the i-AEM admixed therein or in a separate suppository compartment, coating or the like.

In formulating the i-AEM according to this invention for vaginal or rectal delivery concurrently with an API, it is important to utilize gels, lubricants, vehicles, and the like for i-AEM/API delivery which do not enhance transmission of disease causing agents, such as HIV. For example, see Begay et al., "Identification of Personal Lubricants That Can Cause Rectal Epithelial Cell Damage and Enhance HIV Type 1 Replication in Vitro", AIDS Research and Human Retroviruses, Volume: 27 Issue 9: Aug. 23, 2011, which found that many over-the-counter personal lubricants damage epithelial linings and, in some cases, enhance HIV-1 replication. The same or similar formulation as used for Tenofovir placebo gel may be used with substitution of a small fraction of the glycerol with the preferred alcohol according to this invention. From a chemical standpoint the alcohol substitutes very well for glycerol in these systems, and ensures excellent compatibility and solubility of even higher doses of alcohols.

Different i-AEM's may be included in a single composition in order to permit differential kinetics of appearance in breath to be optimized. Thus, more complex i-AEMs (higher carbon atom content) generally exhibit longer half life in the breath, whereas the smaller, simpler i-AEM's are more quickly cleared from the breath. Understanding these kinetic considerations will permit those skilled in the art, based on the present disclosure, to select different i-AEMs and combinations of i-AEMs, in order to tailor detection kinetics in the breath for monitoring adherence with respect particular APIs and different modes of clinical use. In addition, or alternatively, a mixture of different APIs in a delivery medium or substrate, wherein each API is associated with a different i-AEM, may be utilized, and thereby, delivery of each API may be tracked by detection of distinct markers on the breath, even if/when a mixture is prepared for delivery of several different APIs/i-AEMs.

In one embodiment according to this invention, a gel composition used commercially for vaginal or rectal delivery of tenofovir is utilized. This gel comprises 0 (placebo), 0.2, 1, or 5% tenofovir (Gilead Sciences, Inc., Foster City, Calif.) in a gel containing purified water, edentate disodium, citric acid, glycerin, propylparaben, methylparaben, and hydroxycellulose adjusted to pH 4 to 5. (Published Ahead of Print 10 Oct. 2011. 10.1128/AAC.00597-11. *Antimicrob. Agents Chemother.* 2012, 56(1):103. DOI: Nuttall et al., Pharmacokinetics of Tenofovir following Intravaginal and Intrarectal Administration of Tenofovir Gel to Rhesus Macaques). It will be appreciated by those skilled in the art that different compositions known in the art may be used as the vehicle/substrate for vaginal or rectal delivery of the i-AEM and API. For example, those skilled in the art are referred to U.S. Pat. Nos. 7,192,607; 7,935,710; 8,367,098 for disclosure on such substrates and procedures known in the art.

Those skilled in the art will be aware that a wide range of different APIs may be delivered via the rectum or vagina in a wide range of delivery media and mechanisms. Thus, while the terms "microbicide" or "microbicidally active" are generically applied to APIs for delivery by these routes, and while the intent is to include such compounds as tenofovir, emtricitabine, or combinations thereof (e.g., tenofovir disoproxil fumarate, marketed by Gilead Sciences under the trade name VIREAD®), emtricitabine, and combinations of emtricitabine and tenofovir, e.g., TRUVADA®), the term is also intended to include any known or hereafter discovered reverse transcriptase inhibitors, protease inhibitors, other mode-of-action antiretroviral APIs and, indeed, any other API for which vaginal or rectal delivery is a known or desired route of medication administration (e.g., valium).

In a preferred embodiment according to this aspect of the invention, the microbicidal composition according to this invention includes an i-AEM and the microbicidally active compound is selected from the group consisting of marketed or investigational antiretroviral drugs used either solely or in combination to treat HIV infection, selected from the group consisting of:

A. Nucleoside Reverse Transcriptase Inhibitors (NRTIs) abacavir, abacavir sulfate, azidothymidine, didanosine, dideoxycytidine, dideoxyinosine, emtricitabine, lamivudine, tenofovir disoproxil fumarate, stavudine, zalcitabine, zidovudine;

B. Non-nucleoside Reverse Transcriptase Inhibitors (NNRTIs): delavirdine, efavirenz, etravirine, nevirapine, rilpivirine;

C. Protease Inhibitors (PIs): amprenavir, atazanavir sulfate, darunavir, fosamprenavir calcium, indinavir, lopinavir, nelfinavir mesylate, ritonavir, saquinavir, saquinavir mesylate, tipranavir;

D. Fusion Inhibitors: enfuvirtide;

E. Entry Inhibitors—CCR5 co-receptor antagonist: maraviroc;

F. HIV integrase strand transfer inhibitors: raltegravir; and

G. Combinations thereof.

Where there is any concern about potential negative impact of admixture of an i-AEM according to this invention with an API for delivery via the rectal, vaginal, or indeed, any other route (including oral), because of stability considerations (e.g., shelf-life, interactions between the API and the i-AEM and the like), desire to avoid modification of compositions that have already received regulatory approval in the absence of the i-AEM, or other considerations, the present invention contemplates means for admixture of the i-AEM at the site of delivery. This is achieved, for example, by maintaining the microbicidally active compound and the i-AEM in compartments in the drug delivery means such that they are not in contact with each other until delivered vaginally or rectally. Accordingly, in one embodiment according to this aspect of the invention, the API and i-AEM are maintained, prior to delivery, in separate barrels of a two-barreled syringe. Alternate arrangements and embodiments to achieve a similar result include, for example, by including the i-AEM in (a) a Luer-lock tip which fits over the delivery means, e.g., a syringe, for the API in substrate; (b) in a slip-tip, either coaxially located, eccentrically located, or elongated, as in a catheter tip, which fits over the delivery means, e.g., a syringe, for the API in substrate. Naturally, those skilled in the art will appreciate that in commercial embodiments, such combinations of physical means for keeping the i-AEM and API separate from each other may be refined and may appear less like syringes than as unitary delivery means, but the operative principles inherent in these non-exclusive examples are the same. In another embodiment according to this aspect of the invention, the i-AEM is maintained in a softgel capsule which is broken on delivery, e.g., by impact with a plunger, pin or needle tip, or the like, thereby mixing the i-AEM with vehicle, microbicidally active compound or both, at the site of delivery. Likewise, the intact softgel containing the i-AEM could be delivered from the syringe along with the microbicidally active compound at the time of product use, and the softgel dissolves in the warm environment of the vagina. In yet another embodiment according to this aspect of the invention, the i-AEM is coated on a syringe applicator tip which admixes the i-AEM on delivery of the vehicle and the microbicidally active compound. In yet another embodiment according to this invention, the Chemistry, Manufacturing and Controls (CMC) of a medication is modified to directly accommodate the i-AEM. For example, for this approach, in the vehicle for a vaginally or rectally administered API, where glycerin is generally a major component of the vehicle, a tiny amount of glycerin is replaced with the i-AEM, such as deuterated 2-butanol or IPA. Yet another means of delivery of the API and i-AEM may be via a vaginal ring, or similar device. According to this embodiment of this aspect of the invention, a polymeric drug delivery device provides controlled release of drug and i-AEM for intravaginal delivery over an extended period of time. The drug/i-AEM delivery device is inserted into the vagina and can provide contraceptive protection, microbicidal protection, and delivery of the i-AEM. By inclusion of the i-AEM, and confirming ongoing detection of i-EBM in the exhaled breath, clinicians can be assured that the drug delivery device is working correctly and has not been prematurely removed. For rectal delivery, of course, a gel or suppository device/composition is preferred. With respect to a suppository, the i-AEM may be admixed with the API and suppository vehicle, or the i-AEM may be in a separate compartment which is dissolved upon API/suppository delivery, thereby releasing the i-AEM for detection in the breath or for metabolism to generate the i-EBM.

7.2.5 Transdermal i-AEM Medications

A wide variety of transdermal medications and formulations exist and any of these may be used in combination with the i-AEMs as disclosed herein.

Of particular interest with respect to this invention are "ethosomes", defined by N. A. Pratima and T Shailee, *IJRPS* 2(1) JANUARY-MARCH 2012 "Ethosomes: A Novel Tool for Transdermal Drug Delivery", as follows: "Ethosomes are the slight modification of well established drug carrier liposome. Ethosomes are lipid vesicles containing phospholipids, alcohol (ethanol and isopropyl alcohol) in relatively high concentration and water. Ethosomes are soft vesicles made of phospholipids and ethanol (in higher quantity) and water. The size range of ethosomes may vary from tens of nanometers (nm) to microns (μ) ethosomes permeate through the skin layers more rapidly and possess significantly higher transdermal flux." See also, for example, "ETHOSOMES: A NOVEL TOOL FOR TRANSDERMAL DRUG DELIVERY", Rasheed et al., World Journal of Pharmaceutical Research, Volume 1, Issue 2, 59-71. Review Article ISSN 2277-7105. See also U.S. Pat. Nos. 5,716,638 and 5,540,934. Due to the inclusion of alcoholic or VOC constituents in ethosomes, delivery of APIs with an i-AEM according to this invention, to produce i-EBMs is a preferred embodiment according to this invention for purposes of adherence using transdermally delivered medications. For other modes and compositions for API/i-AEM delivery via the transdermal route, those skilled in the art are directed to consider, e.g., Malakar et al., "Development and Evaluation of Microemulsions for Transdermal Delivery of Insulin", ISRN Pharmaceutics, Volume 2011, Article ID 780150, 7 pages, doi:10.5402/2011/780150; Kalluri and Banga, Transdermal Delivery of Proteins, AAPS PharmSciTech, Vol. 12, No. 1, March 2011 (#2011), DOI: 10.1208/s12249-011-9601-6; Lauren A. Trepanier, "TRANSDERMAL DRUGS: WHAT DO WE KNOW?" See, also, for example, U.S. Pat. Nos. 6,946,144; 5,597,796; 7,537,795; 7,220,427. Clearly, this is a sampling of techniques and compositions for transdermal delivery, and this is a well established field in which those skilled in the art are able to utilize what is disclosed herein to enable transdermal delivery of the i-AEMs as disclosed herein.

7.2.6 Other i-AEM Medications and Modes of Delivery

Those skilled in the art will appreciate, based on the disclosure provided herein, that i-AEMs may be delivered by other modes, including, but not limited to, intravenously, intramuscularly, intraperitoneallly, intranasally, inhalationally, intraoccularly, while still producing i-EBMs detectable in the exhaled breath. Naturally, kinetics of i-EBM production, half-life, and other relevant considerations will come into play and appropriate modifications of compositions and times for breath monitoring will need to be adjusted accordingly. Thus, for example, certain products that are available commercially include compounds which could function as i-AEMs if they were to include a non-ordinary isotope according to this invention. Thus, for example, commercially available eyedrops include chlorobutanol, while certain cosmetics include phenylethanol. Chlorobutanol is an alcohol that acts by increasing lipid solubility, and its antimicrobial activity is based on its ability to cross the bacterial lipid layer. Chlorobutanol is a widely used, very effective preservative in many pharmaceuticals and cosmetic products, for example, injections, ointments, products for eyes, ears and nose, dental preparations, etc. It has antibacterial and antifungal properties. Chlorobutanol is typically used at a concentration of 0.5% where it lends long-term stability to multi-ingredient formulations. Phenylethanol is an antimicrobial, antiseptic, and disinfectant, which is used also as an aromatic essence and preservative in pharmaceutics and perfumery. Accordingly, inclusion of at least a fraction of the total chlorobutanol or phenylethanol which is deuterated in such products which already include non-deuterated forms of these molecules, provides a means for medication adherence monitoring by detecting the appropriate i-EBM produced in the breath.

7.2.7 Preferred Aspects of the i-AEM Medications and Compositions According to this Embodiment of the Invention Based on the foregoing disclosure, it will be appreciated that in one aspect of this invention, a SMART® (Self Monitoring And Reporting Therapeutic) medication is provided for delivery and monitoring of adherence in taking or administration of at least one Active Pharmaceutical Ingredient (API) by a subject. This medication comprises:
 (a) An i-API fraction, wherein at least one atom of at least a fraction of the API is a non-ordinary but stable isotope; or
 (b) An i-AEM, an Adherence Enabling Marker comprising at least one non-ordinary but stable isotope; or
 (c) Both an i-API fraction and an i-AEM;
such that, on taking or administration of the medication by or to the subject, an i-EBM, an Exhaled Breath Marker comprising at least one non-ordinary but stable isotope, is produced in the exhaled breath of the subject. Preferably, the stable but non-ordinary isotope is selected from the group consisting of deuterium, or a stable but non-ordinary isotope of carbon, oxygen, nitrogen, or sulfur. Preferably, where not the API itself, the i-AEM is selected from the group consisting of secondary and tertiary alcohols, and more preferably, the secondary or tertiary alcohol is a compound which is a Generally Recognized as Safe (GRAS) compound, or a direct food additive, or both.

The SMART® medication is preferably delivered in a dosage form selected from the group consisting of: a solid oral dosage form, (SODF), intravenously, transdermally, vaginally, rectally, intranasally, intraocularly, intramuscularly, inhalationally.

For optimal use of the medication as described above, a SMART® device is provided for detecting in a gas sample a molecule which is labeled with a non-ordinary isotope wherein the device comprises a means for stripping the gas sample of moisture and carbon dioxide, optionally a catalytic incinerator for converting the molecule to carbon dioxide and water, such that: (a) the isotope from the i-AEM is included in the water fraction, such that, following catalysis, isotopically labeled water is quantitated in the gas sample; (b) the isotope from the i-AEM is included in the carbon dioxide fraction, such that, following catalysis, isotopically labeled carbon dioxide is quantitated in the gas sample; or (c) both (a) and (b). Preferably, the device includes a means for separating i-EBMs in exhaled breath prior to catalysis and detection. The system and method according to this aspect of the invention includes a method for medication adherence monitoring which comprises providing a SMART® medication to a subject and measuring in the exhaled breath of the subject at least one i-EBM utilizing a Type II SMART® device. The method preferably includes monitoring kinetics of appearance of i-EBMs in the exhaled breath and, depending on the particular i-AEMs used and the route of administration, determining adherence characteristics for the given subject and medication. According to this embodiment of the invention, monitoring is conducted from immediately to one hour, from one hour to several hours, or from several hours to several days after the SMART® medication is taken by the subject.

The system for medication adherence monitoring according to this aspect of the invention comprises: A. Providing to a subject a SMART® (Self Monitoring And Reporting Therapeutic) medication for delivery and monitoring of adherence in taking or administration of at least one Active Pharmaceutical Ingredient (API) by a subject, comprising:
  (a) An i-API fraction, wherein at least one atom of at least a fraction of the API is a non-ordinary but stable isotope; or
  (b) An i-AEM, an Adherence Enabling Marker comprising at least one non-ordinary but stable isotope; or
  (c) Both an i-API fraction and an i-AEM;

such that, on taking or administration of the medication by or to the subject, an i-EBM, an Exhaled Breath Marker comprising at least one non-ordinary but stable isotope, is produced in the exhaled breath of the subject; and B. Measuring in the exhaled breath of the subject an i-EBM utilizing a device which comprises a means for stripping the exhaled breath sample of moisture and carbon dioxide, optionally, a catalyst for converting the i-EBM to carbon dioxide and water, such that: (a) the isotope from the i-EBM is included in the water fraction, such that, following catalysis, isotopically labeled water is quantitated in the exhaled breath sample; (b) the isotope from the i-EBM is included in the carbon dioxide fraction, such that, following catalysis, isotopically labeled carbon dioxide is quantitated in the exhaled breath sample; or (c) both (a) and (b).

8.0 IMPROVED SMART® SYSTEM AND METHODS OF USE THEREOF

This section of the patent disclosure relies on the previous sections (6 and 7) to combine particular embodiments of the SMART® device with particular AEMs and compositions of AEMs in a system which achieves heretofore unachievable results in the areas of AMAM, IMAM and CMAM. The combinations of the improved method, device, and composition, as described herein, provides a system for medication adherence monitoring capable of exquisite sensitivity and flexibility, including in the provision of options for "look-back periods" of short, intermediate and chronic medication adherence.

This patent disclosure enables novel and inventive methods, means and systems for reliably measuring acute, cumulative, chronic, and even randomly timed medication adherence monitoring within particular time windows relative to the time a SMART® medication is taken or should have been taken. This represents a significant step forward in the art in that acute medication adherence monitoring known in the art can be analogized to a single measurement of blood glucose concentration testing in a diabetic, as compared to the HbA1C test for glycosylated hemoglobin, which provides an indication of glycemic control over a preceding time period. It furthermore significantly alleviates the burden on clinicians and subjects whose adherence is being monitored, by substantially expanding the period in which monitoring can reliably be conducted.

The medication adherence monitoring tools disclosed and enabled herein provide progressively greater technological capabilities that facilitate definitive measurement and monitoring of adherence on an acute (dose by dose), semi-chronic (1-2 days) and/or a chronic (preceding 3 to 14 days) basis with maximum patient convenience and system accuracy. The SMART® system can be used to monitor adherence to drugs delivered via virtually any route, including but not limited to oral, i.v., transcutaneous, transdermal, intra-rectal, vaginal, i.p., inhalational, etc. Oral medications represent the biggest market segment and understanding adherence to oral drugs will have the greatest impact on improving clinical trial and disease outcomes in the near future. Thus, the table below is focused on adherence technologies that can be used to effectively monitor ingestion of any medication delivered within a solid oral dosage form (SODF), including capsules, hard tablets, sublingual (SL), and orally disintegrating tablets (ODTs).

To emphasize the variety of contexts in which the present system operates and to outline how this is achieved, the following table provides a useful reference:

| | SMART ® Adherence System | | | | |
|---|---|---|---|---|---|
| Feature of SMART ® | Type 1A: Metal Oxide Sensor (MOS)-based sensor engine | | | Type 1B: Surface Acoustic Wave (SAW)-based sensor engine | Type II: mid-Infrared (mIR)-based sensor engine |
| Sensory Configuration | mGC-MOS | mGC-MOS | Dual MOS | SAW | mGC-mIR |
| Type of adherence | Acute (pill by pill) | Acute and Semi-chronic (preceding 1-2 days) | Acute and Semi-chronic (preceding 1-2 days) | Acute (pill by pill) | Acute (pill by pill), Semi-chronic (preceding 1-2 days), and Chronic (preceding 3-14 days) |
| Preferred Adherence-Enabling Marker (AEM) | One simple (low boiling point) direct food additive (e.g., 2° alcohols: 2-butanol) | Two simple (low boiling point) direct food additives (e.g., 2° alcohols: 2-butanol and 2-propanol) | One simple (low boiling point) direct food additive (e.g., 2° alcohol: 2-propanol) | One higher boiling point food flavorant (e.g., methyl salicylate) | One cold isotopologues of simple (low boiling point) direct food additives (e.g., 2° alcohols: deuterated 2-butanol or 2-propanol) |
| Mass of AEM required | | 20-60 mg | | 10-30 micrograms | 1-10 milligrams |
| Breath marker(s) detected by SMART ® sensor | One AEM metabolite: ketone (e.g., 2-butanone) | Two AEM metabolites: ketones (e.g., 2-butanone and acetone) | One AEM metabolite: ketone (e.g., acetone) | AEM itself (e.g., methyl salicylate) | One AEM metabolite: Ketone (e.g., deuterated 2-butanone) |

SMART® Adherence System

| Feature of SMART® | Type 1A: Metal Oxide Sensor (MOS)-based sensor engine | | Type 1B: Surface Acoustic Wave (SAW)-based sensor engine | | Type II: mid-Infrared (mIR)-based sensor engine |
|---|---|---|---|---|---|
| Preferred location of AEM | Small capsule (e.g., softgel or hardgel) placed inside a DB Cap along with a physically separated active pharmaceutical ingredient (API) | | Standard flavorant co-formulated with API in the formulation matrix of ODT or SL tablets | | Layer (e.g., ink logo) sprayed on a small area of the surface of any SODF containing the API |
| Minimum time to reliably detect breath marker | ≥20 min (soft gel-based AEM inside DB cap with API physically separate); 5-20 min within softgel-based smart drug | | Immediate (<30 sec) | | ≥5 min |
| Persistence of breath marker | Minimum 60-90 min | Minimum 60-90 min to a maximum 1-2 days | Minimum 60-90 min to a maximum 1-2 days | <5-10 min | 60-90 min to several Days |
| Can use with multiple drugs and/or drug doses? | Yes | | | | |
| Potential interferents to function | Minor | None | None-to-Minor | Minor | None |
| Number of breaths required | | Preferably 2 breaths | | | Only 1 breath required |
| Approximate Size | H2 × W4 × L6 inches | H2 × W4 × L6 inches | Cigarette Pack size | Cigarette Pack size | iPhone size |

This aspect of the present invention provides an improved method, system, compositions of matter and apparatus for medication adherence monitoring which extends the window of time from medication ingestion to time for confirmation of medication adherence. This is achieved by (a) characterizing the kinetics of appearance and disappearance of Exhaled Drug Ingestion Markers (EDIMs) in the exhaled breath of subjects receiving medications which include selected Adherence Enabling Markers (AEMs). The AEMs may themselves be the EDIMs or may be converted to the EBM (including EDIMs or EDEMs) in vivo via metabolism of the AEM.

In certain embodiments according to the invention, a first AEM, $AEM_1$, is selected which provides the ability to confirm adherence on an acute, dose by dose basis, by virtue of rapid appearance in and disappearance from the exhaled breath of subjects, in combination with a second AEM, $AEM_2$, selected for its ability to confirm adherence over a longer time frame. For such embodiments, simple alcohols, such as 2-butanol, are selected for $AEM_1$. Such markers are rapidly metabolized in vivo into simple ketones. The half-life for detection of the ketones is typically on the order of minutes to several hours, but generally less than, say, 5 hours. For $AEM_2$, in such embodiments, an AEM with a longer half-life in exhaled breath is selected. Isopropyl alcohol, (IPA), for example, is converted in vivo into acetone. As shown herein, the half-life of acetone derived from IPA is on the order of about 6.5 hours. By appropriately adjusting the frequency of medication adherence monitoring, based on the AEMs in use, subjects' adherence to medication regimens may be checked on a dose by dose basis, or less frequently, with a lookback period defined by the kinetic considerations relating to half life, steady state concentration, and background noise and limits of detection criteria, as defined in further detail herein.

In a further embodiment according to the invention, only $AEM_2$, is included in the medication.

In a further embodiment according to the invention, an AEM is selected which includes an non-radioactive, non-ordinary isotope, such that the lookback period may be significantly extended, due at least in part due to lower or almost non-existent background, and enhanced detection capabilities of the sensor and separation device utilized to confirm adherence.

Accordingly, it is an object of this aspect of the invention to provide a medication adherence monitoring method, system, composition of matter and apparatus, which enables acute (dose by dose) and more extended (over more than a single dose and over the course of more than a single day) medication adherence monitoring.

It is a further object of this aspect of the invention to provide a medication adherence monitoring method, system, composition of matter and apparatus, which alleviates the need for subjects to provide exhaled breath samples for medication adherence monitoring only within tightly defined time limits after the time a medication containing the AEM has been administered or taken by the subject.

8.1 AMAM

For Acute Medication Adherence Monitoring (AMAM), the system according to this invention comprises a SMART® device for use in combination with at least one ordinary AEM or an i-AEM formulated in such a way that on a dose-by-dose basis, it can be definitively determined that the correct person has taken the correct dosage of the correct medication at the correct time. This is achieved by combining a Type I, Type II or Type III device with an AEM delivered for example in a softgel capsule or, for example, printed on an existing dosage form (in the case of an i-AEM) concurrent with delivery of the particular medication dosage being monitored. Within minutes up to about one hour after taking the medication dose, the Type I-III device as described herein in sections 6.1-6.3, delivers definitive AMAM data (identify of the person by biometric capture, identity and concentration of EBM included in the exhaled breath) all within minutes of taking a particular medication dosage. The AEM may, of course, be an AEM as described herein in section 7.1, or it may be an i-AEM, as described herein in section 7.2. In the latter case, the device is preferably a Type II SMART® device, as described herein in section 6.2, and may be used to advantage including where only dose-by-dose AMAM is required.

8.2 IMAM and CMAM Using Ordinary AEMS and i-AEMS

Essentially all of the elements to practice the method and use a SMART® system according to this invention are described herein above for use of ordinary AEMs (i.e. AEMs not containing non-ordinary isotopes). A Type I or III device in combination with an AEM which has a long half-life for appearance of the EBM in the exhaled breath, or persistence of the EBM in the exhaled breath, is all that is required for IMAM and CMAM using ordinary AEMs. Achieving a steady-state of medication delivery with a medication comprising one or more AEMs has predictable effects for purposes of EBM measurement in the exhaled breath. Deviations from the steady state EBM concentration are detected, and the subject may be queried or challenged with respect to adherence.

In moving the field from AMAM to IMAM to CMAM, the ability to measure a marker in breath accurately for progressively longer periods of time is key. This can be accomplished in preliminary studies with a given individual or a population of individuals, and with a given AEM, to determine the half life in breath. Once if population PK has been established for a given AEM, that data may be stored on board, or used in a remote location, to analyze adherence for a given subject, and a preliminary phase for the given subject is not required.

By way of example, 2-butanol is converted to 2-butanone within minutes of release of 2-butanol into the digestive system (i.e. following release of encapsulants or any other barriers implemented for containment of the AEM). 2-Butanone has a relatively short half-life for appearance in the exhaled breath, and definitive medication adherence using 2-butanol alone is thus limited to a relatively short look-back period of a few minutes to, at most, several hours. Medication adherence thus would need to be confirmed in that relatively short time-window, and failure to test adherence in that time window means that such data may be lost altogether, even if the subject was perfectly adherent in taking the medication. Using an AEM such as isopropanol provides a longer window for medication adherence monitoring. Elevations in basal acetone exhalation due to ingestion of IPA as the AEM can be measured over at least one 6.5 hour half-life, or even two such half lives, but this requires measurement of the delta, that is change in acetone in exhaled breath and interference by endogenous acetone exhalation quickly becomes a confounding factor thereafter. Use of more complex AEMs provide options for more extended medication adherence monitoring (IMAM and even CMAM). Further details on the pharmacokinetic/pharmacodynamic considerations (which includes data on the breath concentration-time relationships for EBM development and clearance for any given AEM/EBM) relevant to IMAM and CMAM are provided below in connection with the discussion of use of primarily i-AEMs, but much of that disclosure applies to use of ordinary AEMs.

To extend the ability of the SMART® system into reliable IMAM and CMAM, it is preferred to utilize a medication adherence monitoring system and method which comprises providing an i-SMART® medication or composition of matter, as described above (section 7.2), to a subject and using the device, as described above (section 6.2), to detect and quantitate a non-ordinary isotope in the exhaled breath of the subject. In a preferred embodiment, the method is applied to medication adherence monitoring. However, for the avoidance of doubt, any device or method or system which utilizes a novel device as disclosed herein is included within the scope of this invention, including when in a field or utility unrelated to medication adherence monitoring.

Because of the very low background of non-ordinary isotopes found in VOCs in the exhaled breath, the present invention permits minute amounts of i-AEMs to be used to generate i-EBMs which are readily detectable at the parts per billion and even at the parts per trillion level in exhaled breath. In addition to the advantage this provides by way of reducing the mass/volume of AEM required, the use of i-AEMs and the i-SMART device as described herein facilitates monitoring adherence either immediately, (Acute Medication Adherence Monitoring, AMAM) several hours (Intermediate Medication Adherence Monitoring, IMAM) or even several days (Chronic Medication Adherence Monitoring, CMAM) after a particular medication dose including an i-AEM or i-API is taken or is applied or administered to a subject. Steady-state concentrations of AEMs are readily determined (for example using the SMART device according to this invention and providing careful oversight of medication delivery of medication on a regimen designed to reach steady state levels of AEMs) and related to steady-state EBM concentrations, and, therefore, based on whether a given subject at a given time exhibits appropriate concentrations of i-EBMs, it can be determined whether the subject has taken a particular dose at a particular time, and/or whether over time the subject has been adherent. Intervention can therefore be undertaken if any departure from the known, calculated and/or expected pharmacokinetics and pharmacodynamics is detected.

FIGS. 65-69 are instructive with respect to the power of the SMART® system which incorporates the use of a Type II SMART® device according to this invention in combination with an i-AEM. Whereas changes in unmarked acetone are barely detectable in the exhaled breath, (as shown in example 26 herein below), the breath kinetics of exhaled d6-acetone following the ingestion of 100 mg of d8-isopropanol per diem for 5 days is readily followed, as each dose of d8-IPA is reflected in clearly distinguishable rises in d6-acetone. Deviations from steady state levels of d6-acetone in the exhaled breath are detectable up to 65 hours after any given dose of d8-IPA, providing a significant window for confirming medication adherence, i.e. IMAM and CMAM.

To further enable and extend IMAM and CMAM, the system according to this aspect of the invention includes computational features which are described in detail below. The analytical and computational aspects of the invention are achieved by the device (Type I, II, III) of this invention providing quantitative measurements of EBMs, and, preferably in real time, comparing pharmacokinetic/pharmacodynamics parameters stored in memory with such EBM measurements. Such computations represent a machine implemented software component of the system which, when integrated with the given SMART® device and AEM utilized, provides a unitary system for providing definitive medication adherence monitoring over at least dose-to-dose (AMAM) but also over multiple dosages and over multiple days (IMAM and CMAM).

Accordingly, this aspect of the invention provides a method and system for using an Adherence Enabling Marker, $AEM_x$, (which may be an ordinary AEM or an i-AEM), or an Exhaled Drug Ingestion Marker X, $EDIM_x$ produced on ingestion or other form of administration or application (e.g. topical) of said $AEM_x$. The method involves characterizing the pharmacokinetics of the particular $EDIM_x$ in the exhaled breath of a subject, Y, or in a population of subjects, Z. The characterizing comprises measurement, to within defined confidence limits utilizing a SMART® detection device (or another device adequate to the task of appropriately defining such parameters for use in connection with the SMART® device or system as described herein) with sufficient accuracy to provide the parameters described herein below in Example 28.

According to this aspect of the invention, an apparatus for chronic medication adherence monitoring is provided as a SMART® device comprising:

A. a sensor selected for accurate detection in the exhaled breath of at least one subject of at least one Exhaled Drug Ingestion Marker X, $EDIM_x$ produced on ingestion of at least one Adherence Enabling Marker, $AEM_x$;

B. data storage (as in hard drive, flash drive, EEPROM, in a form now known or which is developed in the future) operatively coupled to the sensor, for retention of data generated by the sensor in the course of characterizing the pharmacokinetics of the $EDIM_x$ in the exhaled breath of a subject, Y, or in a population of subjects, Z; and C. computing means, either in the same unitary device or in a separate unit to which data obtained as in A and B above is transmitted or transferred (including, for example, a programmed central processing unit) which compares each such measurement for each subject or population of subjects with stored data, as described herein below, for said subject or population of subjects, preferably in real time or near real time. For each measurement of the concentration of $EDIM_x$, a measure of adherence A is generated by the computing means for each subject.

The characterizing data for storage preferably includes measurement data, to within defined confidence limits, of:

a. the Limit of Detection (LoD) of a sensor included in said device for said marker;

b. the background level of said marker or interferents in said subject or population of subjects;

c. the half life of appearance ($t_{1/2a}$) and elimination ($t_{1/2e}$) of said marker from the exhaled breath of said subject or population of subjects;

d. the steady state concentration of said marker in the exhaled breath at various time points during Adherence Enabling Marker (AEM) dosing, selected from the group consisting of trough ($C_{Trough,SS}$), maximum ($C_{MAX,SS}$), and other time point post dosing of the AEM concentrations of said subject or population of subjects; and e. the time required to attain the maximum concentration ($T_{MAX}$) of said marker from the exhaled breath of said subject or population of subjects.

Such a device according to this invention is preferably configured to integrate the pharmacokinetic parameters defined above to provide an adherence lookback window, $T_{AdhWindow}$, defined as the period of time required for the marker (EDIM) concentration in breath of the subject to decay from an initial value ($C_{EDIMo}$) to a lower concentration ($C_{EDIMLimit}$)

$$T_{AdhWindow} = \frac{t_{1/2e}}{0.693} * \ln\left(\frac{C_{EDIMo}}{C_{EDIMLimit}}\right)$$

wherein:

$C_{EDIMo}$=original or starting concentration of marker (EDIM) in breath at times equal to or greater than $T_{MAX}$ (i.e., $C_{EDIMo}$ $C_{MAX}$) of said patient;

$C_{EDIMLimit}$=the final concentration of EDIM in breath of said patient, provided that, if $C_{EDIMLimit}$ denotes the limit of EDIM detection due to the device LoD or background interference, it would define the maximum $T_{AdhWindow}$; and $t_{1/2e}$=the elimination half life for said EDIM.

Such a device preferably exhibits a $T_{AdhWindow}$ between about 1 hour and about 400 hours, and includes a sensor with a LoD for the marker of between 1 part per trillion and 5 parts per billion. In one preferred embodiment, the sensor is adapted to distinguish between ordinary and non-ordinary isotopes present in EDIMs and volatile compounds which otherwise would interfere with selective measurement of EDIMs in the exhaled breath. At any time during the $T_{AdhWindow}$, an exhaled breath sample of a subject is obtained and the adherence of the subject to the required regimen is definitively determined, based on measurement of the concentration of the EDIM at the time said breath sample or samples are obtained.

9.0 EXAMPLES

Having generally described this invention herein above, the following exemplary support is provided to further enable those skilled in the art to practice this invention to its full scope. This detailed written description and enabling disclosure is not, however, intended to be limiting on the invention. Rather, for an apprehension of the scope of the present invention, those skilled in the art are directed to the appended claims and their equivalents.

Example 1

Hardware Specifications and Performance—Type I Device

General Overview:

The SMART® mGC is capable of detecting aldehydes, ketones, esters, ethers, and miscellaneous volatile organic compounds with, e.g., boiling points between 20° C. (68° F.) and 98° C. (208° F.)

Figure 9:
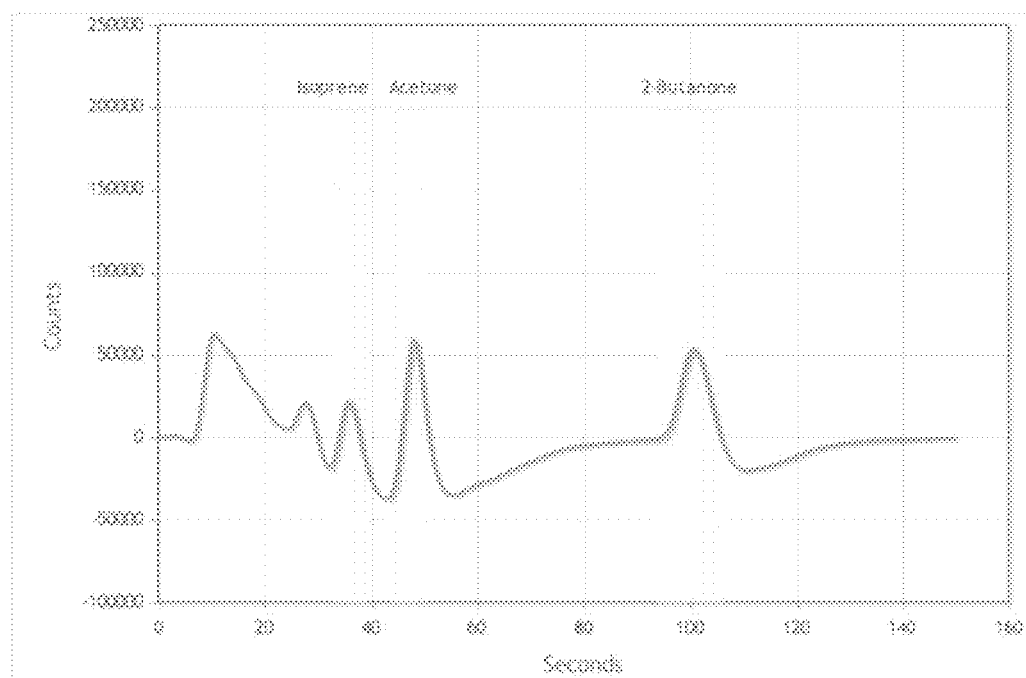

FIG. 9 shows a typical output chromatogram detecting key constituents in the breath, including acetone and isoprene, with clear separation of 2-butanone, derived from ingestion of 2-butanol.

In one specific embodiment of the present invention, the SMART® device has the following specifications. These specifications are provided to ensure a complete and enabling written description of this invention, but those skilled in the art will appreciate that these specifications should not be interpreted as limiting on the invention.

Operating Principle: Isothermal gas chromatography using ambient air carrier gas and solid-state detector Enclosure Size: 4.1"×8.9"×2.1" (3.6" max)

Weight: 2.5 lbs. (1.1 kg)

Operating Temperature: 10° C. to 34° C.

Operating Humidity: 10% to 90% (non-condensing)

Storage Temperature: −20° C. to 60° C.

Warm-up Time: <10 minutes oven warm-up for analysis

Sample: flow activated collection

User Interface:

Single button push to start

Backlit LCD text prompts

Audible tone/voice prompts

Data Storage: Non-user accessible USB flash drive

Color video frame image of user's face.

Maintenance: Scrubber replacement on a scheduled basis

Electronic Microcontroller

The SMART® electronic controller resides on a single, multi-layer printed circuit board and contains, in a preferred embodiment, the following:
- STM 32F107 series 32-bit microcomputer and support circuitry
- Battery backup for the STM 32F107 clock/calendar
- 16 gigabyte USB memory stick for data storage
- Voltage regulators and fusing for all circuitry and peripheral devices
- Interface circuitry for serial, SPI, and USB communication
- Pushbutton input
- Audible sound generation
- Driver circuitry and connectors for all pumps, valves, fans, and heaters
- Analog signal conditioning circuitry for the GC detector, temperature, pressure, and flow sensors The controller firmware is written in C or the equivalent and supports a scripting language that allows high-level operating instructions to control the core peripheral and communications drivers, as well as signal processing. The specific sequencing of the SMART GC pumps, valves, heaters, fan, and other peripherals is determined by encrypted, high-level script commands stored on the USB memory stick.

Performance Specifications

The primary performance specifications based upon 2-butanone for the SMART® mGC are:
- Detection Threshold: 5 ppb 2-butanone in breath, (nominal)
- Measurement Range: 5 ppb to 2.5 ppm of 2-butanone in breath.
- Carry-Over: <5 ppb 2-butanone equivalent
- Analyte Retention Time Stability: ±3 to about +5 seconds of (nominal) retention time (Specific to 2-butanone)
- Accessories
- Individually-Packaged Mouthpieces/straws 130.
- Power Cord
- Optionally, cellular router, mobile data (e.g., WiFi) hotspot Patient Population Patients include those for whom a clinician would like to analyze gaseous samples (e.g., human breath) for suitable organic molecules of clinical interest (e.g., ingestion of 2-butanol as an AEM).

Environments of Use

The SMART® mGC is intended to be used in a hospital, clinical laboratory, sub-acute care facility, physician's office, or in the home setting with or without supervision of a qualified individual.

Materials—Biocompatibility

The following discusses the level and type of patient contact with the device and the associated materials.

The SMART® mGC is not in contact, direct or indirect, with the patient, except for the disposable mouthpiece.

The patient only exhales into the mouthpiece of the device, (straw) 130. The straw/mouthpiece 130 in one embodiment is made of ProFax SR 549M, a polypropylene copolymer, or Marlex®, a high-density polyethylene (HDPE). The mouthpiece 130 is commercially available.

Example 2

SMART® mGC Chromatographic Separation of Acetone, Isoprene and Ethanol—Type I Device.

As shown in FIG. 9, a very clean separation of ethanol, acetone and isoprene is achieved when these compounds are simultaneously adsorbed to the sample concentrator followed by thermal desorption, separation via the mGC, and detection by the MOS sensor.

Example 3

Clinical (In Vivo, Human) and Potential Interferents (In Vitro, Benchtop and Clinical) Studies to Optimize and Validate the SMART® System and Composition According to this Invention To support development and facilitate regulatory filings, a number of complementary in vitro (benchtop: Interference Studies 1 through 4) and clinical (human: Clinical Studies 1 through 4) studies have been carried out to characterize the SMART® Adherence System. In terms of human exposure, the system has been safely used to date in 33 human studies (oral, sublingual, and microbicide administration routes), encompassing 1,318 experiments in 328 subjects and 8,524 breath analyses. Of particular note, three recent prospective, blinded, randomized, cross over clinical validation studies (127 subjects with 472 experiments and 2,464 breath analyses) using the SMART® Adherence System designed for oral medications were executed that focused on identifying an optimal adherence-enabling marker (AEM) formulation and carrying out receiver operating characteristic (ROC) curve analyses to make an optimal cutoff determination and assess diagnostic performance (Clinical Studies 1, 2 and 3). In addition, a clinical study (Clinical Study 4), examining the impact of different subject factors on usability, was executed to determine how patient-friendly the SMART system was in subjects having different disease states. (e.g., physical, mental, musculoskeletal).

Type I of the SMART® device according to this invention detects a wide variety of volatile organic compounds (VOCs), including but not limited to alcohols, aldehydes, ketones, esters, and ethers in a qualitative, semi-quantitative, and/or quantitative manner. The ketone, 2-butanone, was selected as a prototypical VOC for detailed device testing according to Clinical and Laboratory Standards Institute (CLSI) protocols. A desktop gas chromatograph (GC), the Hewlett Packard Gas Chromatograph Model 5890A, was used as the predicate device. The mGC is operated by a trained individual, and can be used in the health care, clinical laboratory, or home settings.

The SMART® mGC device is intended to be used by lay people (or, of course, clinicians), most frequently in their homes, and will definitively document and report, in real-time, adherence to medications in the clinical trial or disease management settings. The mGC used in the SMART® Adherence System was designed to reliably measure e.g. 2-butanone in human breath after ingestion of SMART® drugs which have 2-butanol, a 2° alcohol that is designated by the FDA as a food additive (generally recognized as safe [GRAS]), incorporated into the dosage form containing the active pharmaceutical ingredient (API). The ketone, 2-butanone, termed the exhaled drug ingestion marker (EDIM), rapidly appears in breath after ingestion of the SMART® drug containing 2-butanol, due to its efficient enzymatic oxidation by alcohol dehydrogenase (ADH), primarily via the ααADH isoform. The 2-butanol is incorporated into a SMART medication in a manner that has minimal-to-no impact on the chemistry, manufacturing and controls (CMC) of the API, has no impact on the bioavailability of the API, and does not introduce any extra steps in the clinical trial material (CTM) handling process. The formulation approaches used to incorporate the AEM, 2-butanol, into the API medication form (e.g., hard gel capsule, powder, or soft gel containing 2-butanol) are disclosed herein.

To demonstrate the efficacy and safety of the Type 1 device-based SMART® Adherence Monitoring System, two types of key investigations using hard gelatin study capsules containing 2-butanol were executed:
 1) clinical studies to define:
  a) optimal configuration of the SMART® System—AEM formulation in hard gel capsule (Clinical Study 1)
  b) SMART® System performance (sensitivity, specificity, accuracy)—AEM formulation in hard gel capsule (Clinical Study 2)
  c) optimal configuration of the SMART® System—AEM formulation in softgel capsule (Clinical Study 3)
  d) usability of the SMART® System in a simulated home setting (Clinical Study 4)
 2) studies to determine the impact of the following potential interferents:
  a) new home environment
  b) ethanol
  c) cigarette smoking
  d) various consumer products (e.g., fruit gum, hard candies, fruit, mouthwash)

These studies and their outcomes are reported here in support of the claims made with respect to the formulation, and the SMART® Adherence System utilizing the present formulation.

Clinical Studies using hard gelatin study capsules (Clinical Studies 1 and 2), and one clinical study using soft gelatin study capsules (Clinical Study 3) were conducted for the SMART® Adherence System. Except where noted in the protocol, all study subjects refrained from eating, drinking, or smoking for 15 minutes prior to beginning the study and throughout the duration of the study visit. The timing and type of recent food and drink ingestion and cigarette use was documented, along with standard subject demographics and past medical history (PMH), medications, and smoking history.

For Clinical Studies 1 and 2, study capsules in sealed opaque Licaps® capsules (AEM formulation placed in sealed size 4 Licaps, which in turn, was placed within size 0 Licaps®) were made the day of the study visit by a certified pharmacy (e.g., Westlab Pharmacy, Gainesville, Fla.) according to the randomization schedule. Licaps® capsules are two-piece (cap and body) gelatin capsules that can be specially sealed using a $50\%_2$:50% ethanol and water mixture to fuse the gelatin edges for secure containment of liquids. Study capsules were used within 24 hours of preparation. For the clinical study (Clinical Study 3) using soft gelatin study capsules, the soft gelatin 2-butanol formulation was placed in an opaque, (e.g., white) size 0 Licaps® capsule. The ethanol formulation was sealed inside an opaque size 4 Licaps® capsule and overencapsulated in a sealed, opaque size 0 Licaps® capsule (capsule in capsule configuration). The study capsules were used within 5 days of packaging by a certified pharmacy (e.g., Westlab Pharmacy, Gainesville, Fla.) according to the randomization schedule.

Each SMART® device had a complete 2-butanone calibration check (0, 10, 30, 100, 300, and 1000 ppb 2-butanone standards in breath) at the beginning and end of the study, whereas a two point 2-butanone calibration check (0, 10, and 300 ppb 2-butanone standards in breath) was done prior to first use on any given study day unless noted otherwise in a protocol. Calibration data was tracked and recorded throughout the study. 2-Butanone is detected by the SMART® Device at a retention time of 100 seconds in human breath and causes a concentration-dependent increase in device response. Data transmission occurred using a wireless router.

After each breath into the SMART® Device, a variety of key time/date-stamped data was stored locally on the device and automatically uploaded to HIPAA-compliant servers, including but not limited to: raw signal data, breath chromatogram, yes/no ingestion event assessment generated from the peak-detection algorithm, photograph of study participant's face for biometric authentication, and SMART® Device operating conditions.

Clinical Study 1 entitled, Clinical Study to Determine the Optimal Configuration of the SMART GC System, was a prospective, randomized, triple-blind, crossover study in 50 study participants (age 18 years and older; no known allergies to the study capsule formulations) conducted at the University of Florida. Four (4) hard gelatin formulations were studied:
 2-butanol (20 mg)
 2-butanol (20 mg), vanillin (5 mg), DL-menthol (0.7 mg), and PEG-400 (9.3 mg)
 2-butanol (40 mg)
 2-butanol (40 mg), vanillin (10 mg), DL-menthol (1.4 mg), and PEG-400 (18.6 mg)

The study design consisted of 50 study subjects, each of whom received all four formulations (designated as formulations 1, 2, 3, and 4) over four study visits, each visit consisting of breath sampling intervals at baseline (0 min: prior to swallowing the capsule) and 10, 20, 30, 45 and 60 minutes post-ingestion. Each study subject was randomized to a specific device for the duration of the study (10 devices; 5 study subjects per device) and randomized to receive all 4 formulations which were self-administered under the supervision of a nurse (directly observed ingestion of the study capsule) over 4 study visits with at least 1 day between visits. This design is consistent with a traditional pharmacokinetic (PK)-type four period crossover study that assumes no carryover (i.e., sequence) effect due to adequate separation of the dosing periods (in this case, one day separation).

From the breath chromatograms, measurements of breath concentrations of 2-butanone were obtained at baseline (prior to ingestion of the study capsule) and at 10, 20, 30, 45, and 60 minutes after ingestion of the study capsule.

The goal of Clinical Study 1 was to define the optimal operating configuration of the SMART® System using hard gelatin study capsules containing 2-butanol. In terms of configuring the SMART® System for optimal performance, the primary outcome of Study 1 was to determine the optimal study capsule formulation (dose of 2-butanol and addition of other ingredients such as flavorants) and the breath kinetics of 2-butanone. The outcome measure was 2-butanone concentration (in ppb) recorded repeatedly at each time point during the sampling interval. The dependent variable for analysis was the change in 2-butanone concentration from baseline (Time 0). The change in 2-butanone concentration from baseline ("delta over baseline") provided a statistical adjustment for the potential that some subjects may have a recorded non-zero 2-butanone concentration at Time 0.

Additional analyses (e.g., exploratory covariate analyses in main effects model) that considered the concomitant effects of demographic characteristics (e.g., age, body mass index [BMI], ethnicity, race, gender) and other factors such as the time since last meal were conducted. Collectively, all of these analyses were considered for the determination of the best candidate for study capsule formulation for Clinical Study 2.

All analyses and data summaries were performed using SAS Version 9.3. The SAS MIXED procedure was employed for analysis of the two principal outcome measures. Data was summarized with respect to the following:

Demographic and other descriptive study subject characteristics by formulation 2-butanone concentrations ("2BC") by formulation and time Delta over baseline (change from Time 0) 2BC by treatment and time b) and c) by demographic and other specified factors Extent of 2BC as calculated by the AUC-like "polygon" of values obtained from the discrete 10 to 60 minute post-ingestion time points Minimum, mean, and maximum 2BC across time Frequency distribution of time to maximum 2BC Frequency distribution of time to "threshold" 2BC, defined as a 5 ppb, 7.5 ppb, and 10 ppb delta over baseline value Study participant factors including but not limited to the following were analyzed for impact on results (references to Figure nos): 16*a* Age; 16*b* Gender; 16*c* Ethnicity; 16*d* Body Mass Index (BMI); 16*e* Time From Last Meal; 16*f* Alcohol Use; 16*g* Tobacco Use; none of these factors appeared to be confounding factors (see below).

Figure 17A:
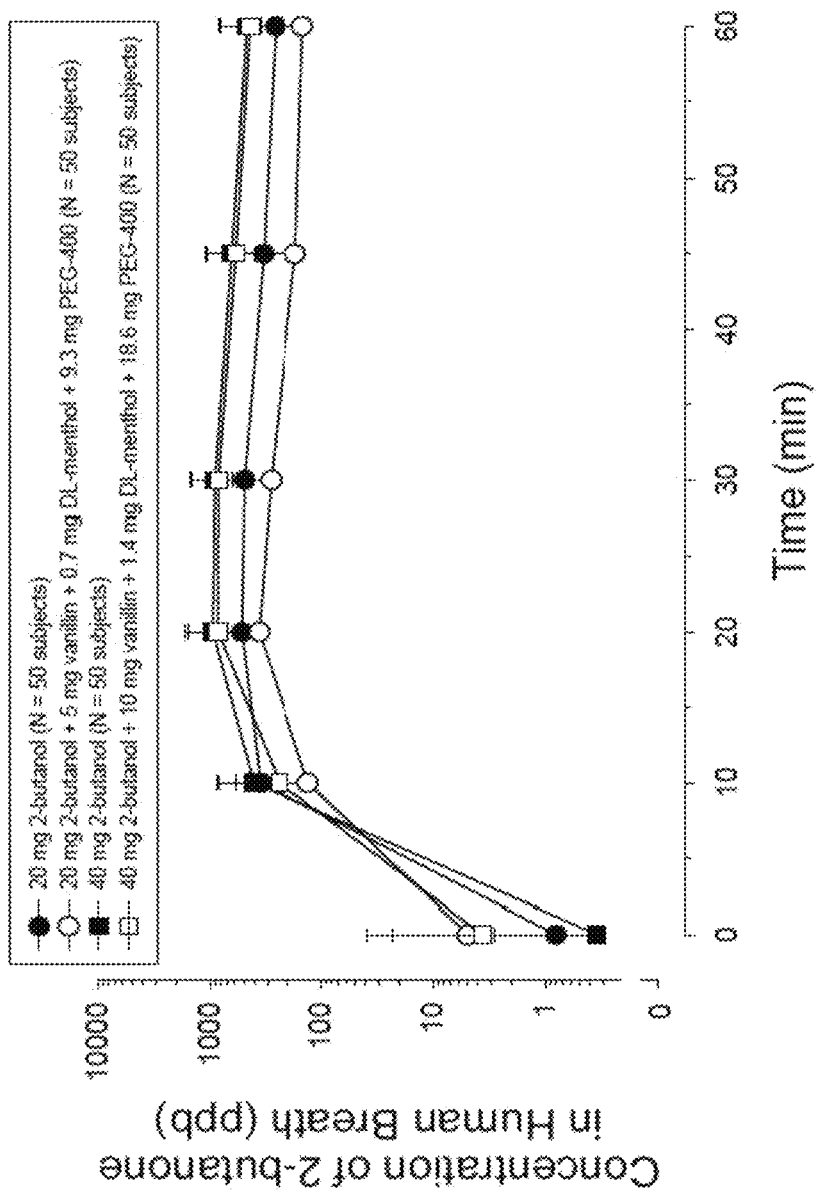

Results for Clinical Study 1:

2-Butanone Breath Concentration-Time Relationship—Effect of Adherence-Enabling Marker (AEM) Formulation, see FIG. 17*a*

Baseline 2-Butanone Concentrations in Human Breath (200 subject visits) Distribution Zero concentrations (<LOD): 190/200 (95%)

Non-zero concentrations (>LOD): 10/200 (5%) Central Tendency

Mean (SD): 2.4 (19.5) ppb

Median: 0 ppb

Min, Max: 0, 238.8 ppb Characteristics of Non-zero Baseline Concentrations

One Subject: 3 values (132.4, 238.8, 31.6 ppb)

Seven Subjects: 7 values (7.7, 5.1, 5.1, 6.4, 31.3, 17.3, 8.5 ppb)

Note: 9/10 and 8/10 of the non-zero values were found in subject participants with a history of active tobacco and ethanol use, respectively.

Figure 17B:
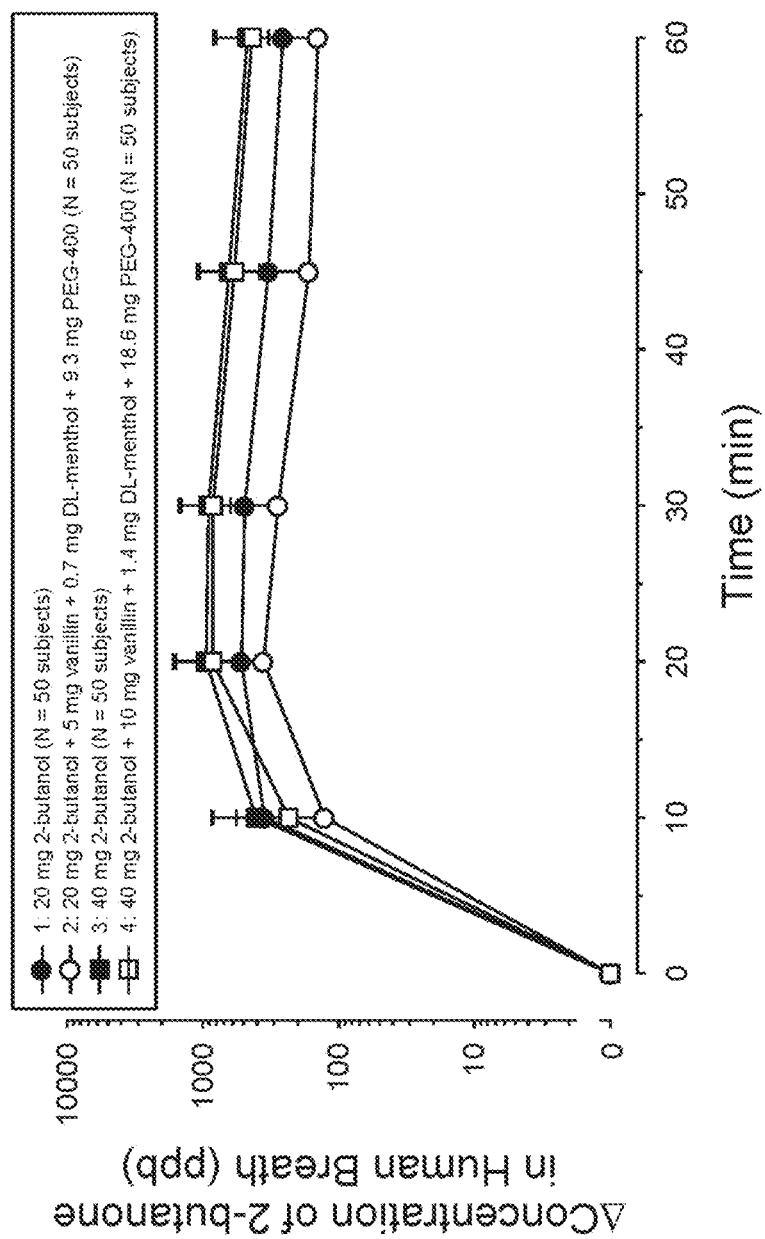

Δ2-Butanone (Change in Concentration from Baseline Values) Breath Concentration-Time Relationship, See FIG. 17*b*:

Repeated Measures ANOVA, Main Effect Model

Visit: P=0.12

Formulation: P<0.0001

Time: P<0.0001

AEM Formulation Rank Order: 3>4>1>2

Figure 17C:
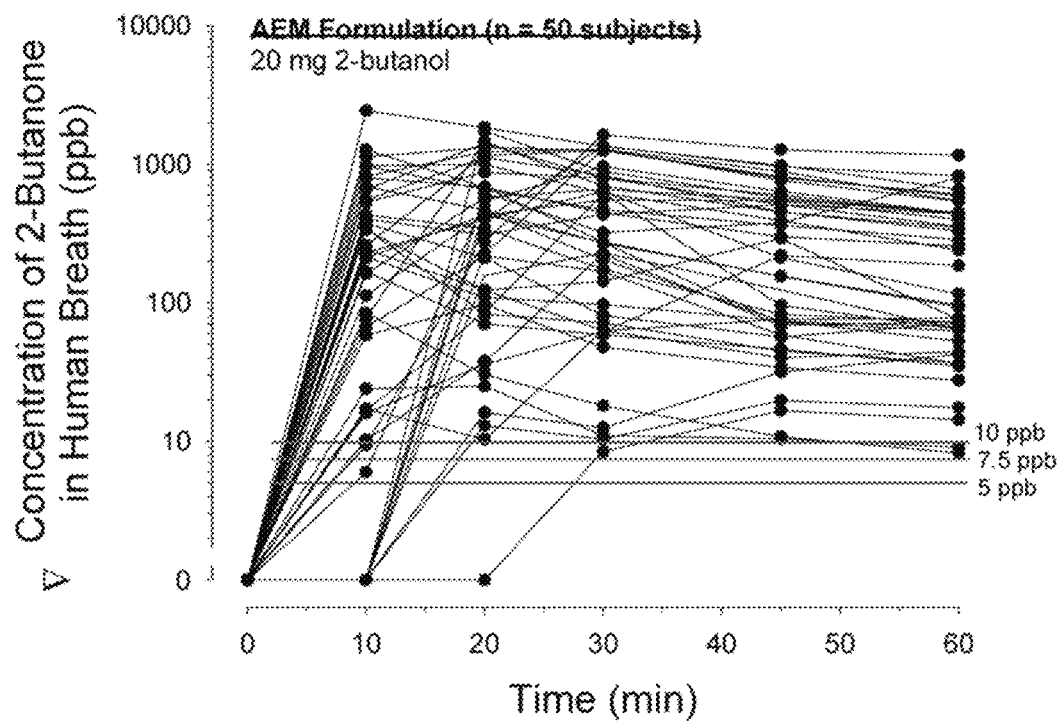

Effect of Adherence-Enabling Marker (AEM) Formulation on Δ2-Butanone Breath Concentration-Time Relationship: Effect of AEM Formulation; Individual Δ2-Butanone Concentration-Time Curves in 50 Subjects: 20 mg 2-Butanol—See FIG. 17*c*

Ingestion of 40 mg 2-butanol was effective in rapidly generating levels of 2-butanone in breath that exceeded threshold concentrations. A rise in breath 2-butanone levels was detected by the mGC in all 50 subjects. Although significant inter-individual variation in the 2-butanone breath concentration-time relations was present, 98% and 100% of subjects had 2-butanane concentrations ≥5 ppb threshold at 20 min and 30 min, respectively.

Figure 17D:
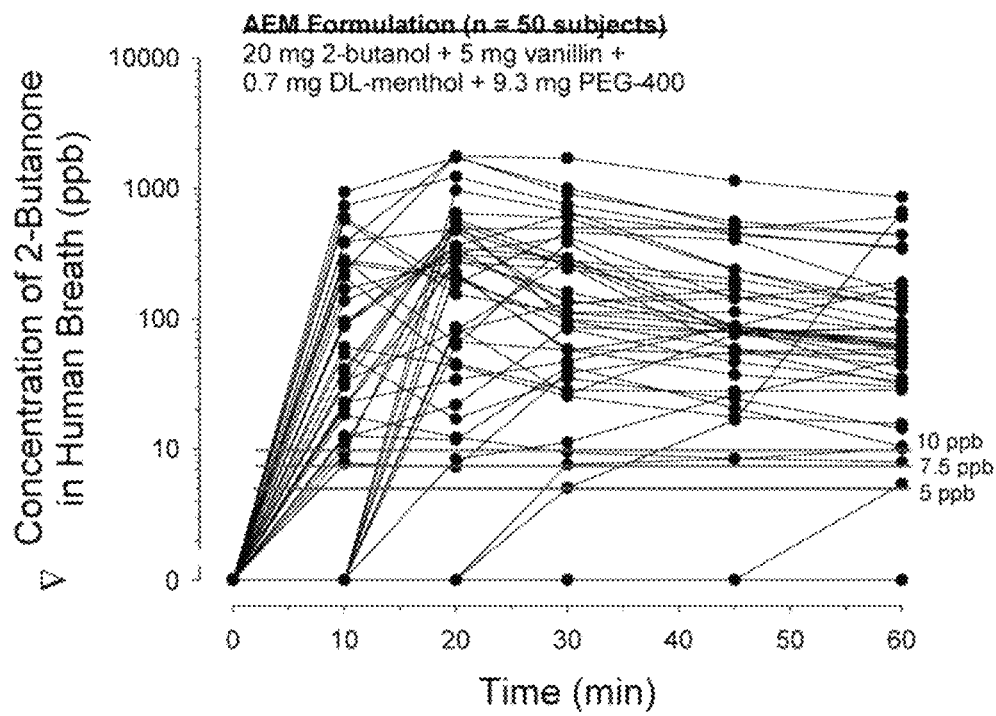

Individual Δ2-Butanone Concentration-Time Curves in 50 Subjects: 20 mg 2-Butanol Combo—see FIG. 17*d*

Compared to 20 mg 2-butanol, ingestion of the 20 mg 2-butanol combo produced less favorable 2-butanone concentration-time relations:

4% (2/50) of subjects (subjects 26 and 33) were non-responders—no rise in 2-butanone levels was detected in breath by the mGC over the 60 min study period Greater inter-individual variability was present, including several cases of 2-butanone exceeding threshold levels only at later times following ingestion of the formulation Conclusion: addition of vanillin/DL-menthol/PEG-400 reduced the prompt appearance of breath 2-butanone, a process likely attributable to slower 2-butanol release.

Figure 17E:
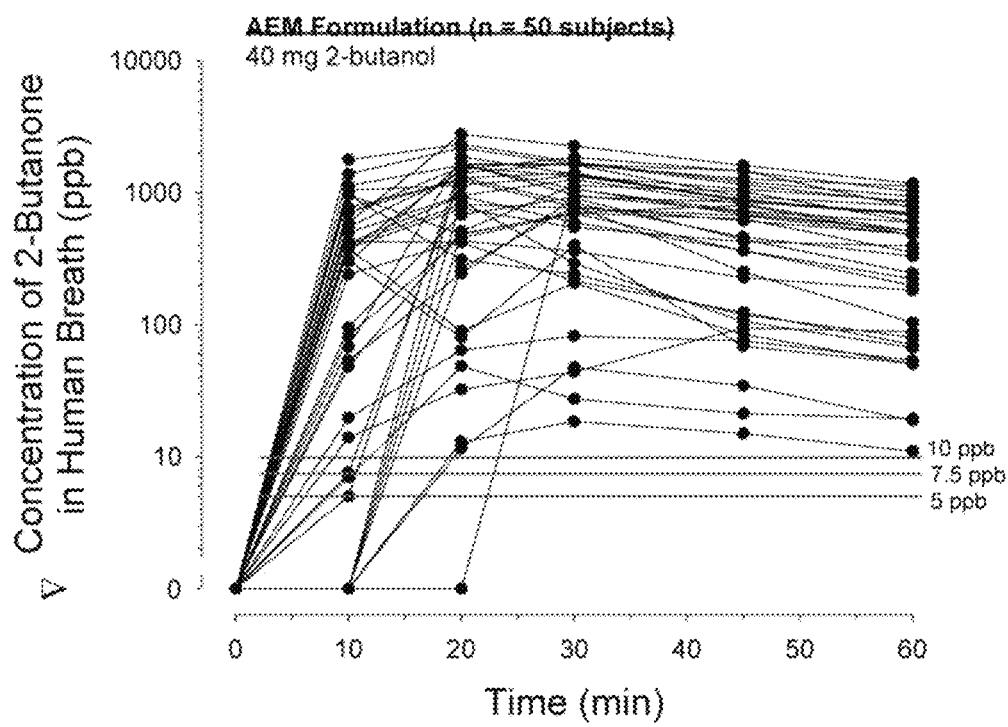

Individual Δ2-Butanone Concentration-Time Curves in 50 Subjects: 40 mg 2-Butanol—see FIG. 17*e*

Ingestion of 40 mg 2-butanol was very effective in rapidly generating levels of 2-butanone in breath that exceeded all threshold concentrations. A rise in breath 2-butanone levels was detected in 100% (50/50) of subjects. Although significant inter-individual variation in the 2-butanone breath concentration-time relations was present, 98% (49/50) and 100% (50/50) of subjects had 2-butanone concentrations greater than all 3 threshold concentrations at 20 min and 30 min, respectively. At 60 min post ingestion, 100% (50/50) of subjects had 2-butanone concentrations that persisted above all 3 threshold concentrations.

Figure 17F:
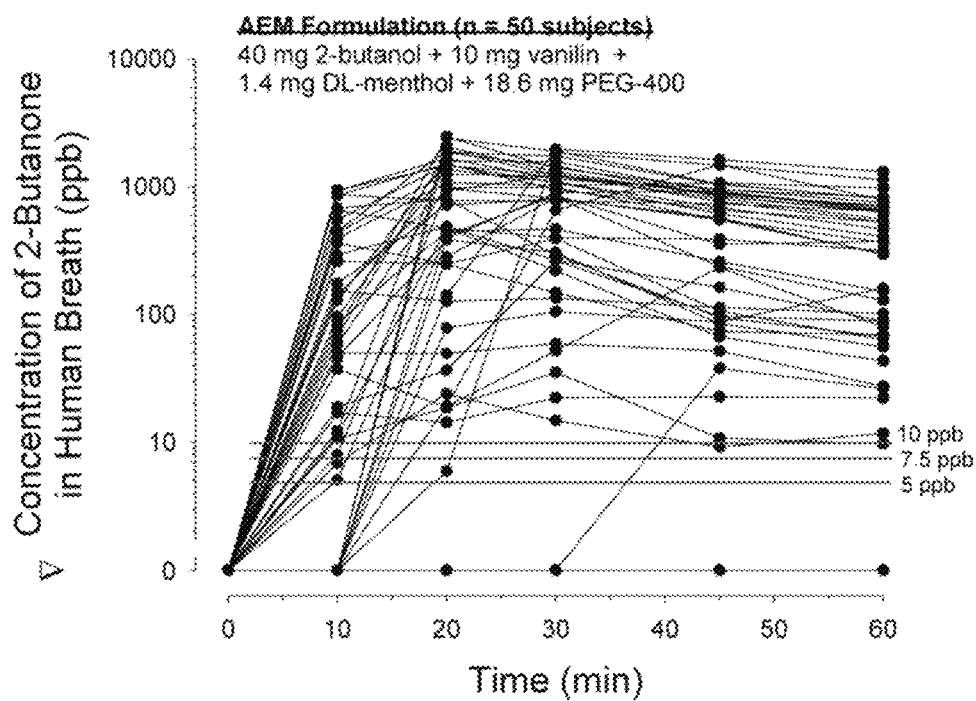

Individual Δ2-Butanone Concentration-Time Curves in 50 Subjects: 40 mg 2-Butanol Combo—see FIGS. 17*f* and 17*g*

Compared to 40 mg 2-butanol, ingestion of the 40 mg 2-butanol combo produced slightly less favorable 2-butanone concentration-time relations but was still robust in rapidly generating detectable levels of 2-butanone in breath:

2% (1/50) of subjects (subject 18) were non-responders—no rise in 2-butanone levels was detected in breath by the mGC over the 60 min study period Greater inter-individual variability with more cases of 2-butanone exceeding threshold levels at later times following ingestion of the formulation; however, 96%, 96%, and 98% of subjects exceeded the 5 ppb threshold at 20 min, 30 min, and 40 min, respectively, post-ingestion of 40 mg 2-butanol combo.

At 60 min post ingestion, 100% (50/50) and 98% (49/50) of subjects, who ingested formulation 3 (40 mg 2-butanol) and formulation 4 (40 mg 2-butanol combo), respectively, had 2-butanone concentrations that persisted above the 5 ppb threshold.

Conclusion: addition of vanillin/DL-menthol/PEG-400 slightly reduced the prompt appearance of breath 2-butanone, a process likely attributable to slower 2-butanol release, but overall performance was favorable.

Figure 17H:
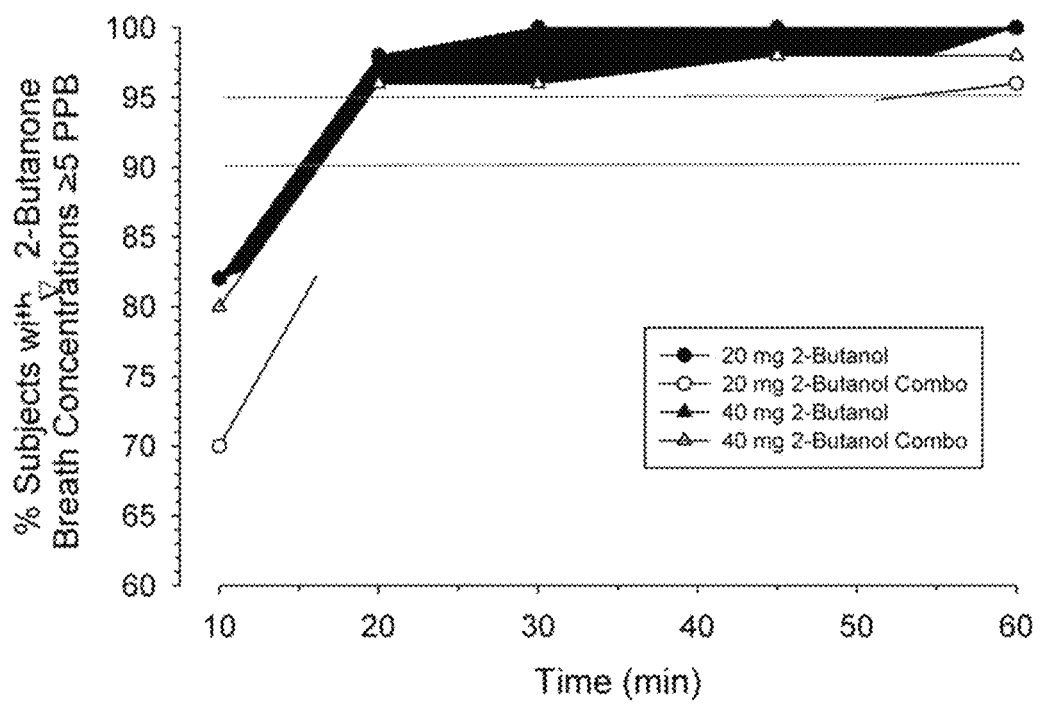

Distribution of 2-Butanone Concentrations by Time, AEM Formulation, and Concentration Threshold Levels; Percent of Subjects (N=50) with Δ2-Butanone Concentrations ≥5 PPB; see FIG. 17*h*

Conclusion: Using a 5 ppb rise in 2-butanone levels, 98%/100%/100% and 96%/96%/98% of subjects (N=50) exceeded this threshold level at 20, 30 and 45 min post-ingestion of 40 mg 2-Butanol and 40 mg 2-Butanol Combo, respectively. Differences among AEM formulations exist.

Figure 17I:
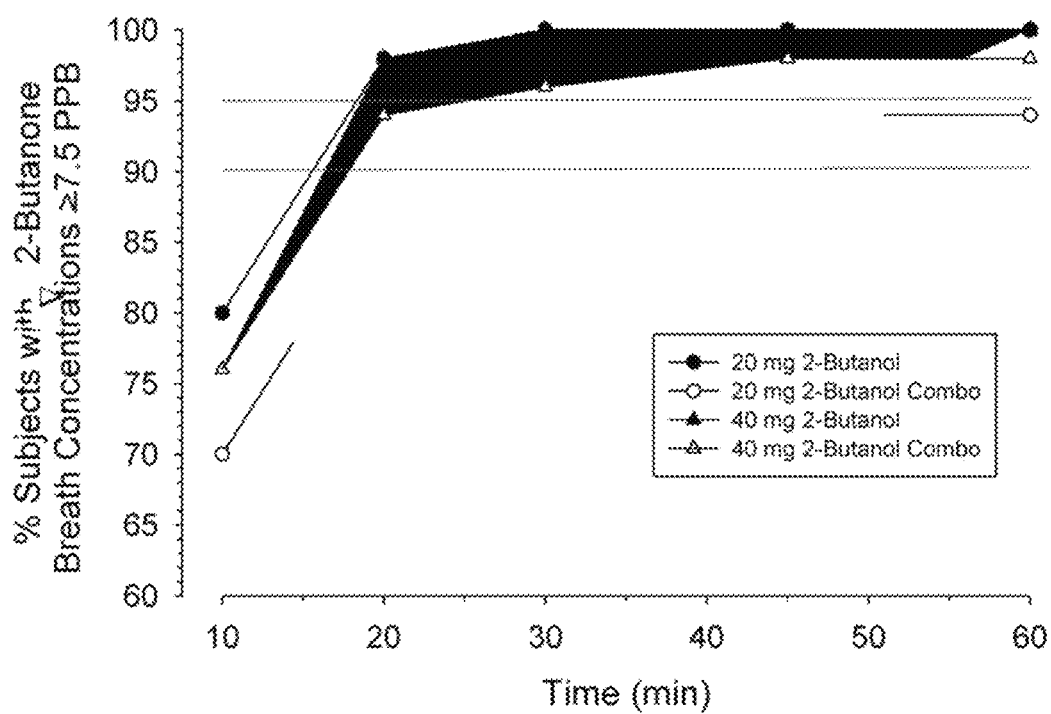

Percent of Subjects (N=50) with Δ2-Butanone Concentrations ≥7.5 PPB—see FIG. 17i Conclusion: Using a ≥7.5 ppb rise in 2-butanone levels, 98%/100%/100% and 94%/96%/98% of subjects (N=50) exceeded this threshold level at 20, 30 and 45 min post-ingestion of 40 mg 2-Butanol and 40 mg 2-Butanol Combo, respectively. Differences among AEM formulations exist.

Figure 17J:
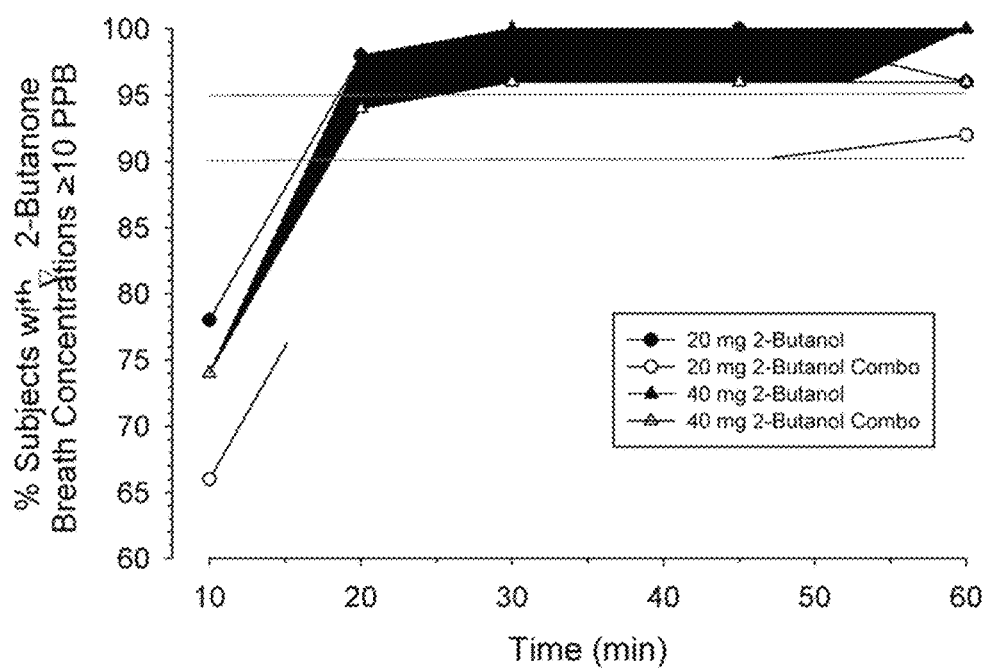

Percent of Subjects (N=50) with Δ2-Butanone Concentrations ≥10 PPB—see FIG. 17j

Conclusion: Using a ≥10 ppb rise in 2-butanone levels, 98%/100%/100% and 94%/96%/96% of subjects (N=50) exceeded this threshold level at 20, 30 and 45 min post-ingestion of 40 mg 2-Butanol and 40 mg 2-Butanol Combo, respectively. Differences among AEM formulations exist.

Δ2-Butanone Breath Concentration-Time Relationship: Exploratory Analysis of Covariates Repeated Measures ANOVA of 2-Butanone Concentration Change from Baseline (T=0 min): Covariates included in the main effects model.

Covariates: Demographics and Timing of Meal

Covariates: age, sex, race, body mass index (BMI), and time since last meal

| Factor | Δ2-Butanone Breath Concentration-Time Relationships: Main Effect Model with Covariates - P Values |
|---|---|
| Visit | 0.068 |
| Formulation | <0.0001 |
| Rank Order | 40 mg 2-butanol > 40 mg 2-butanol combo > 20 mg 2-butanol > 2 mg 2-butanol combo |
| Time | <0.0001 |
| Age | 0.87 |
| Gender | 0.45 |
| Ethnicity | 0.93 |
| BMI | 0.91 |
| Time - Last Meal | 0.0004 |

Conclusion: Unlike the time since last meal, demographics had no effect on the appearance of 2-butanone in human breath after the oral ingestion of 2-butanol.

Figure 18A:
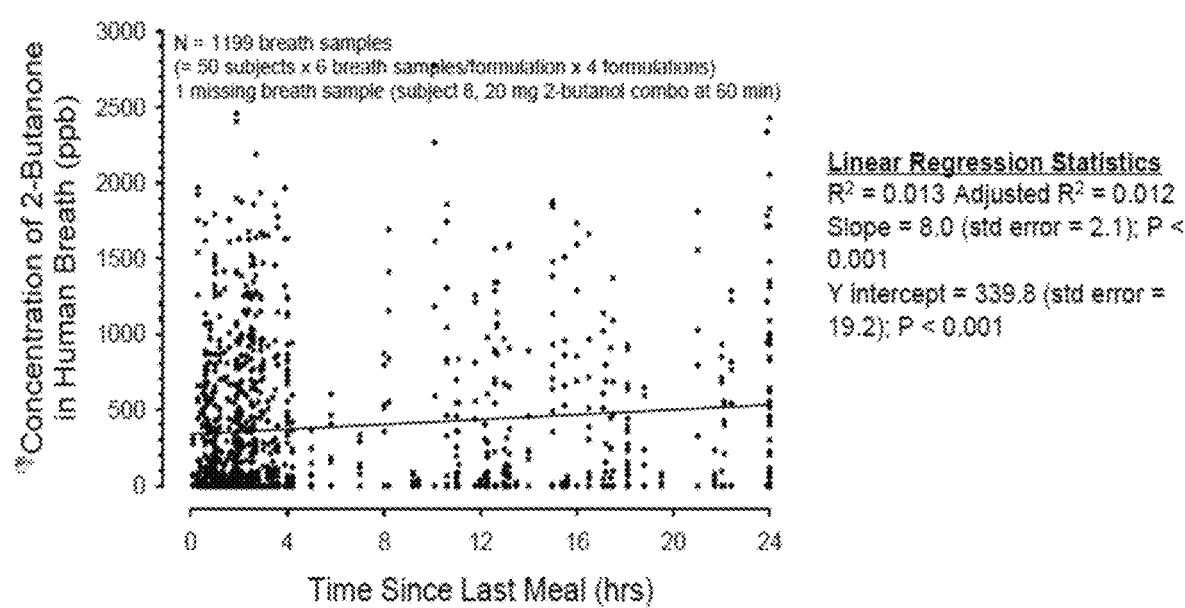

Effect of Meal Timing on D2-Butanone Concentrations Across All AEM Formulations—see FIG. 18a Conclusion: Eating a meal closer to the time of 2-butanol ingestion causes a relatively small but significant reduction in 2-butanone breath concentrations.

Figures 18B, 18C:
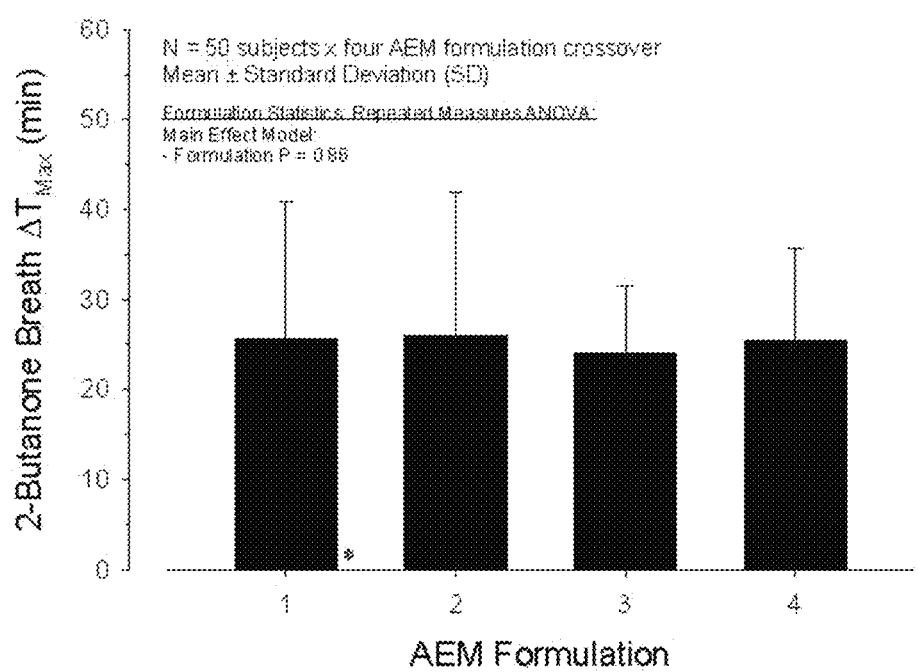

Covariates: Tobacco and Alcohol Use—see FIG. 18b

Conclusion: A history of tobacco (48% subjects) and alcohol (52% subjects) use by a significant fraction of the study population had no effect on the appearance of 2-butanone in human breath after the oral ingestion of 2-butanol.

$\Delta T_{max}$: Effect of AEM Formulation—see FIG. 18c

Formulation Key 1, 20 mg 2-butanol (N=50)
2, 20 mg 2-butanol combo (N=48)
3, 40 mg 2-butanol (N=50)
4, 40 mg 2-butanol combo (N=49)

See notations * and § in the figure:

*, 2 (subjects 26 and 33) out of 50 (4%) subjects were non-responders ($T_{Max}$>60 min)

§, 1 (subject 18) out of 50 (2%) subjects were non-responders ($T_{Max}$>60 min)

Figure 18D:
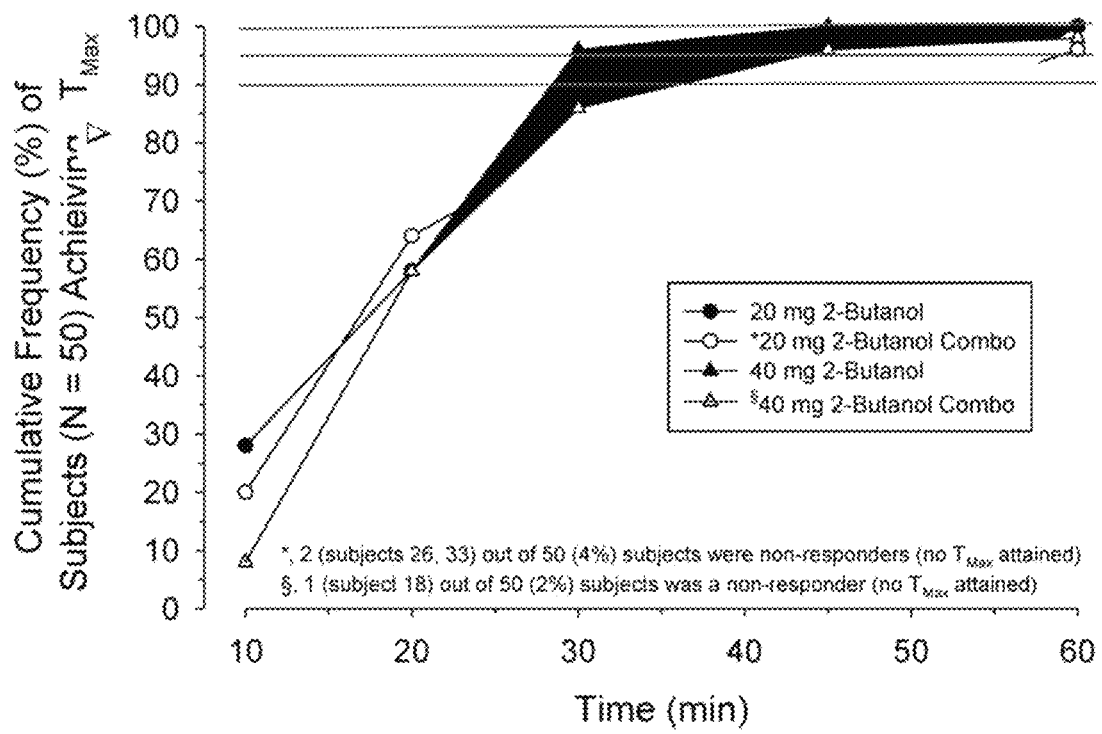

Cumulative Frequency (%) of Subjects Achieving $\Delta T_{Max}$ by Time and Formulation—see FIG. 18d.

Figure 18E:
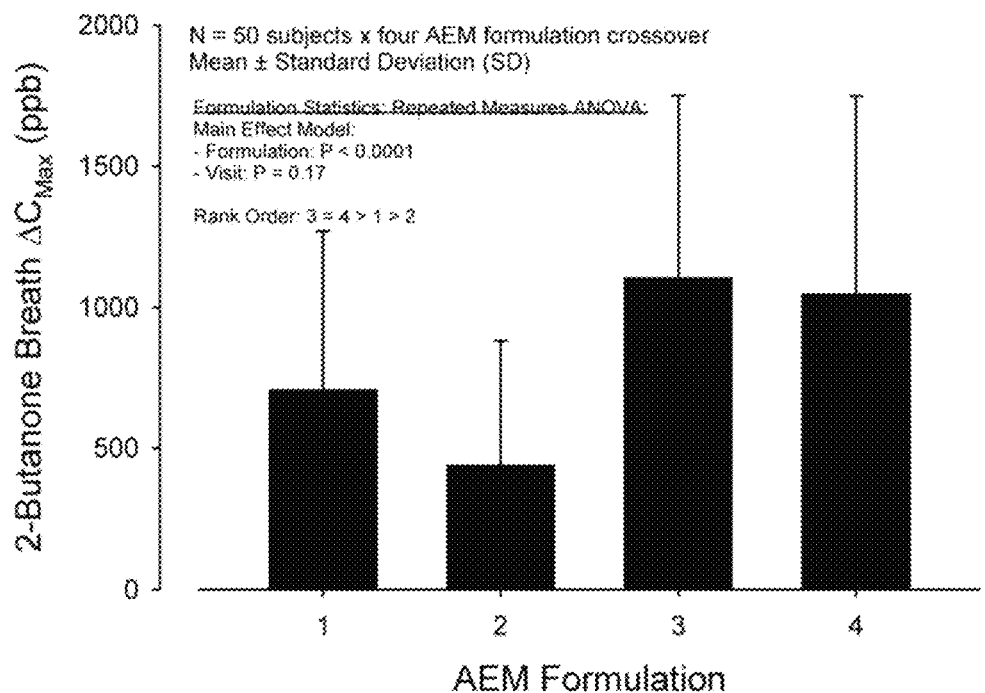

$\Delta C_{Max}$: Effect of AEM Formulation—see FIG. 18e

Formulation Key 1, 20 mg 2-butanol
2, 20 mg 2-butanol combo
3, 40 mg 2-butanol
4, 40 mg 2-butanol combo Conclusion: AEM formulation had a significant effect on $\Delta C_{Max}$.

Figure 18F:
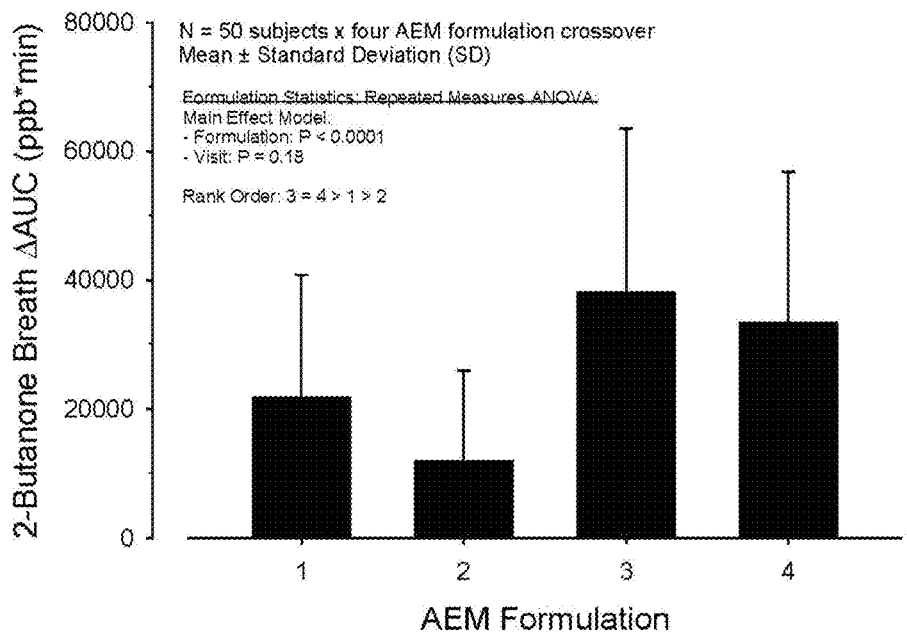

ΔAUC: Effect of AEM Formulation—see FIG. 18f

Formulation Key 1, 20 mg 2-butanol
2, 20 mg 2-butanol combo
3, 40 mg 2-butanol
4, 40 mg 2-butanol combo Conclusion: AEM formulation had a significant effect on ΔAUC.

SMART® Device Performance

Study Design: 10 SMART® Devices were assigned to 50 subjects, with 1200 total breath analyses=50 subjects×4 visits/subject×*6 breaths/visit.

*Note: 1 breath sample didn't upload (subject 8, visit 2 at 60 min)

5 subjects randomly assigned to use a single device SMART® Device performance

Overall performance: mGC measurements were stable over time and highly linear in regions (i.e., 2-butanone concentration ranges=0 to 100 and 300-3000 ppb) relevant to 2-butanol doses ingested in this study. 2 devices were replaced in study; subject 1 after visit 1 (device 212-03): wireless data upload was slow; subject 9 during visit 1: wireless data upload failed. Devices showed a 1.74× difference in sensitivity to 2-butanone in a concentration range=0 to 100 ppb; 7.25% (87 out of 1199 breath samples) had 2-Butanone retention times outside the window of detection (95 to 105 sec). 1 device (301-06) had camera issues (picture distortions). The mGC design was modified to address these relatively minor issues.

| SMART ® Device Use | | | | |
|---|---|---|---|---|
| Device # | Number Breath Samples | % Total | Number of Subjects Assigned to a Device | Time in Use (days) |
| 212-01 | 114 | 9.5% | 5 (subjects *10, 20, 40, 50) | 29 |
| 212-03 | 6 | .5% | 1 (subject *1) | 1 |
| 301-01 | 120 | 10.0% | 5 (subjects 2, 12, 22, 32, 42) | 29 |
| 301-03 | 120 | 10.0% | 5 (subjects 3, 13, 23, 33, 43) | 30 |
| 301-06 | 120 | 10.0% | 5 (subjects 4, 14, 24, 41, 44) | 29 |
| 301-07 | 120 | 10.0% | 5 (subjects 5, 15, 25, 35, 45) | 29 |
| 301-09 | 120 | 10.0% | 5 (subjects 9, 19, 29, 39, 49) | 29 |
| 301-10 | 126 | 10.5% | 6 (subjects 6, *10, 16, 26, 36, 46) | 29 |
| 301-14 | 96 | 8.0% | 4 (subjects 7, 27, 37, 47) | 29 |
| 301-16 | 119 | 9.9% | 5 (subjects 8, 18, 28, 38, 48) | 29 |
| 302-06 | 138 | 11.5% | 6 (subjects *1.11, 21, 31, 34, 51) | 35 |
| TOTAL | 1199 | 100.0% | | |

Figure 18G:
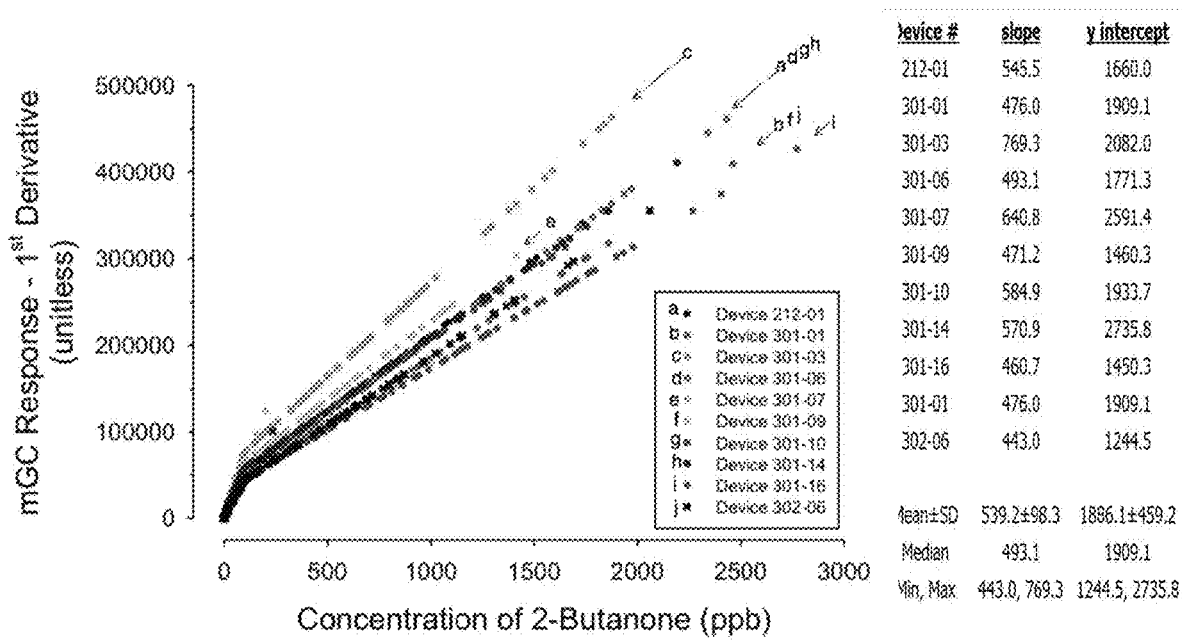

SMART® Device Performance: Full 2-Butanone Concentration Range—See FIG. 18g, which shows the 2-butanone breath concentration-mGC response relationships by device across the four AEM formulations; relationship between 2-butanone concentration and mGC response is curvilinear (i.e., square root function), but is highly linear in regions, including lower concentrations (0-100 ppb; see next slide) and higher (300-3000 ppb) concentrations relevant to the doses of 2-butanol ingested. Among the different devices, excellent stability over time (<5% variation) with calibration checks was noted.

Figure 18H:
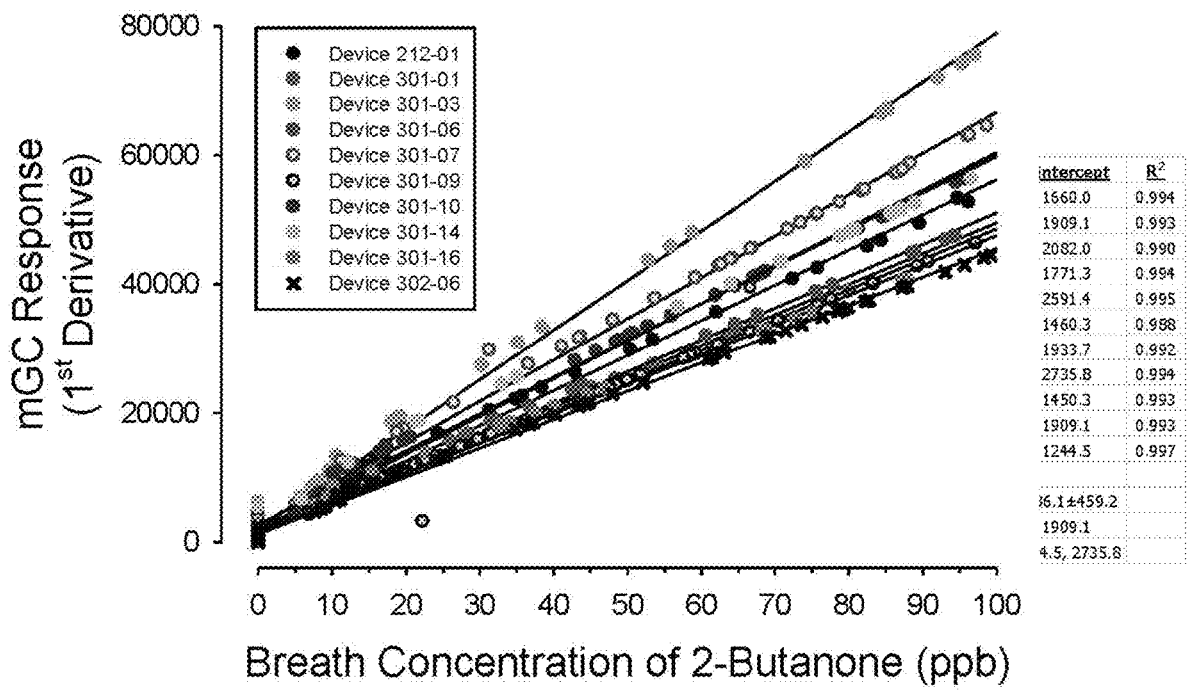
Figure 18I:
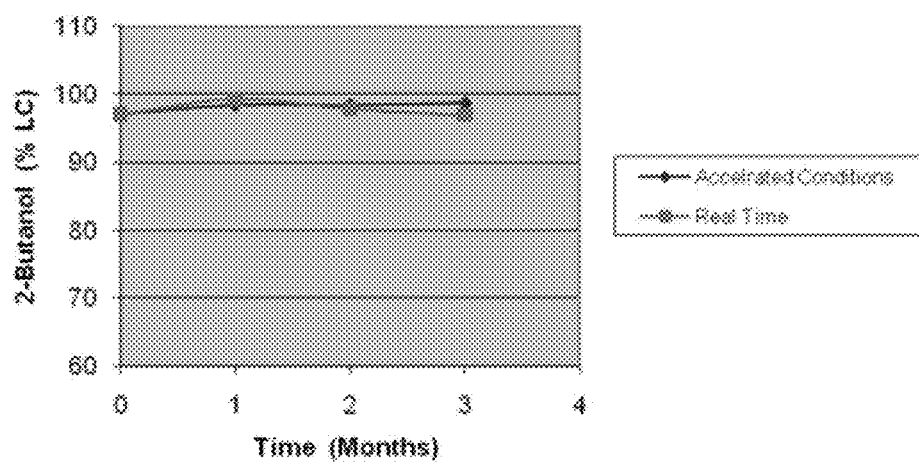
Figure 18J:
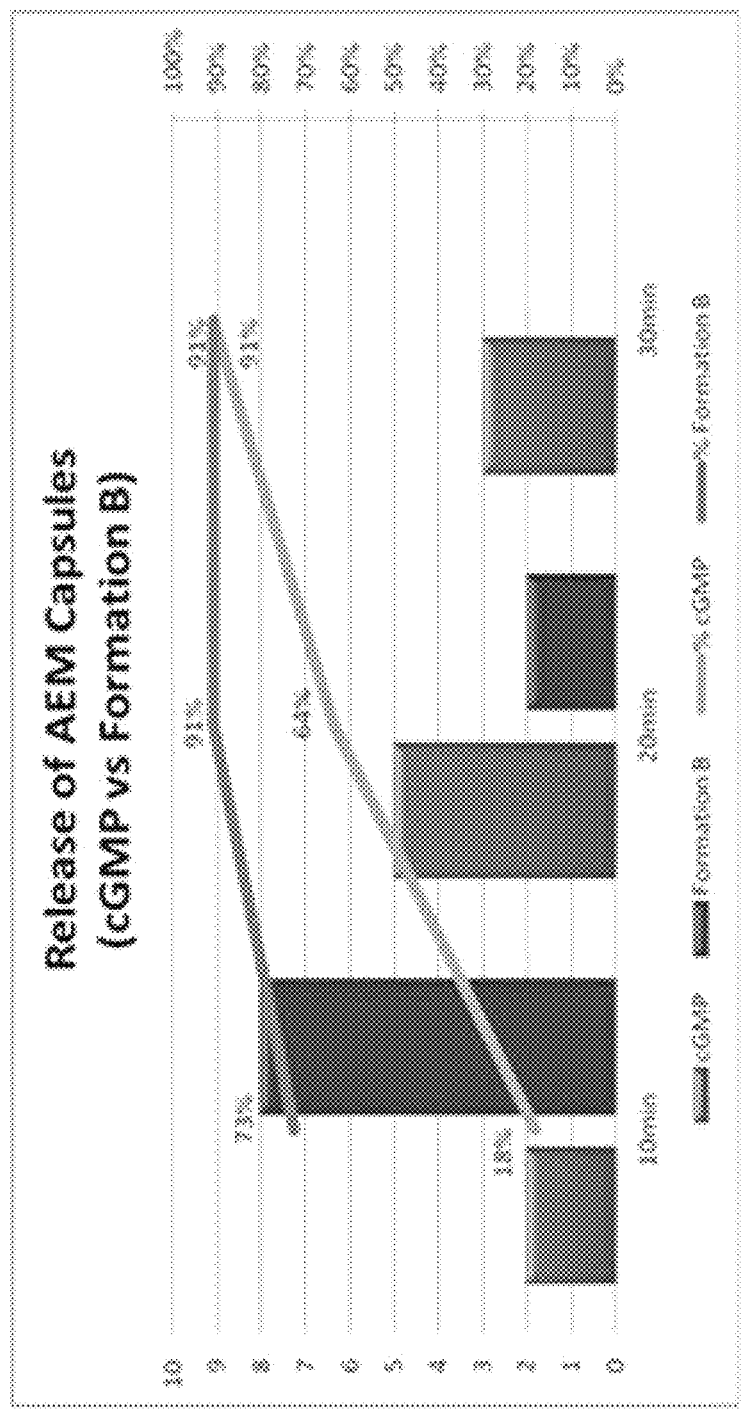

Sensitivity of mGC SMART® Devices: Low 2-Butanone Concentrations=0-100 ppb; see FIG. 18h
  Devices were highly linear at low 2-butanone concentrations (0-100 ppb), which are relevant to yes/no adherence decisions (rise in concentration=5-10 ppb)
  Variability in sensitivity present (max slope ratio=769/443=1.74)—preferably mGC slope is constant across devices SMART® Devices: Retention Time Shifts

| | | Retention Time (sec) | | | | |
|---|---|---|---|---|---|---|
| | | Out of Range Values | | | Within Range Values | |
| Device # | Number Breath Samples | <95 sec | >105 sec | Total | % Total × Device | 95-105 sec | % Total × Device |
| 212-01 | 114 | 0 | 0 | 0 | 0.0 | 114 | 100.0 |
| 212-03 | 6 | 2 | 0 | 2 | 33.3 | 4 | 66.7 |
| 301-01 | 120 | 0 | 0 | 0 | 0.0 | 120 | 100.0 |
| 301-03 | 120 | 60 | 0 | 60 | 50.0 | 60 | 50.0 |
| 301-06 | 120 | 4 | 0 | 4 | 3.3 | 116 | 96.7 |
| 301-07 | 120 | 0 | 0 | 0 | 0.0 | 120 | 100.0 |
| 301-09 | 120 | 23 | 0 | 23 | 19.2 | 97 | 80.8 |
| 301-10 | 126 | 0 | 0 | 0 | 0.0 | 126 | 100.0 |
| 301-14 | 96 | 0 | 0 | 0 | 0.0 | 96 | 100.0 |
| 301-16 | 119 | 0 | 0 | 0 | 0.0 | 119 | 100.0 |
| 302-06 | 138 | 0 | 0 | 0 | 0.0 | 138 | 100.0 |
| TOTAL | 1199 | 89 | 0 | 89 | 7.4 | 1110 | 92.6 |

Of the 1199 breath samples analyzed for 2-butanone content by the SMART® Device, 92.7% (1112 samples) were within the retention time (RT) detection window (95-105 sec). 4 devices accounted for 100% of the 89 out of range RT window breath samples, all of which were <95 sec: devices 301-03 (67.4%), 301-09 (25.8%), 301-06 (4.5%), and 212-03 (2.2%).

A new design version of mGC was created to address this issue.

Study Observations:
AEM Formulations
None of the subjects enrolled in the study reported any significant adverse events, including taste, smell, or gastrointestinal effects. across the four AEM formulations tested.
SMART® Device
No subject had difficulty providing a breath sample
No subject had problems with handling device
Conclusions for Clinical Study 1:
SMART® Adherence System performance was favorable
  Biology continues to prove reliable
  the EDIM (2-butanone) breath PK and its inter-individual variability across 50 subjects is sufficiently low to permit the EDIM (2-butanone) to be reliably detected in the breath of the test population
  baseline 2-butanone breath concentrations were generally low in the test population, and did not interfere with reliable and accurate adherence monitoring utilizing this AEM, particularly when the baseline breath correction is applied (i.e., use a rise of breath 2-butanone concentrations of 5 ppb above baseline values)
  Lead AEM formulation=40 mg 2-butanol combo: 96%, 96%, and 98% detection at a Δ2-Butanone concentration threshold of 5 ppb at 20, 30, and 45 min breath sampling times, respectively.
  SMART® devices performed well
  Appearance of 2-butanone in breath is highly dependent on AEM formulation:
    Dose-dependent effect of 2-butanol
    Combo-dependent effect
  The SMART system was easily used by subjects and the AEM formulations were well tolerated
  Covariate analysis indicates that age, gender, race, BMI, and chronic alcohol and tobacco use did not affect the generation of 2-butanone in breath after the ingestion of 2-butanol.
  Based on requirements for SMART® Adherence System performance, taste masking, long term softgel stability, and softgel manufacture, the 40 mg 2-butanol combo appears to the "optimal" candidate AEM formulation.

Clinical Study 2 entitled, Clinical Study to Determine the Sensitivity, Specificity, and Accuracy of the SMART Adherence System, was prospective, randomized, triple-blind, placebo-controlled, cross-over study in 30 volunteers (age 18 years and older; no known allergies to the study capsule formulations) conducted at the University of Florida.

The study was designed to determine the sensitivity, specificity, and accuracy of the SMART® System using hard gelatin study capsules containing 2-butanol. The primary study objective was to determine the diagnostic accuracy of the SMART® Breath Monitoring System in distinguishing between the ingestion of study capsules containing 2-butanol versus placebo capsules containing the same amount of ethanol instead of 2-butanol. The associated ingredients, (i.e., vanillin, DL-menthol, and PEG-400), were the same for both study capsule formulations.

A single formulation of the study capsule, namely Formulation 4 (i.e., 2-butanol [40 mg], vanillin [10 mg], DL-menthol [1.4 mg], and PEG-400 [18.6 mg]) was studied; each study subject was randomly assigned to ingest two types of capsules, namely a capsule containing 2-butanol [SMART capsule], and a capsule containing the same mass of ethanol and associated excipients as that used for the SMART capsule (placebo capsule).

Each study subject was randomized to receive a total of 3 SMART® capsules and 3 placebo capsules (50%:50% randomization with the capsule types) under the supervision of a nurse (directly observed ingestion) over 6 study visits with at least 1 day between visits. Thus, Clinical Study 2 contained a total of 180 study visits.

Each study subject was randomized to one 1 of 30 SMART® Devices for the duration of the study. Breath samples were obtained at baseline (pre-ingestion) and at 10, 20, and 30 minutes after ingesting the study capsule.

Device calibration data was tracked and recorded by Expert 1. Expert 2 manually read data outputs in a blinded manner and determined whether a SMART® or placebo capsule was ingested. At study completion, the assessments made by Expert 2 was compared against those automatically made by the SMART® Device using the optimized configuration derived from Study 1 (e.g., optimized formulation, time of breath sampling, proposed delta 2-butanone concentration cut-off levels).

The sample size, the optimal formulation, and timing of breath sampling used in Clinical Study 2 were determined based on the analysis of Clinical Study 1 results. Since the post-baseline 2-butanone breath concentration levels in study subjects who ingested the placebo capsule were observed to be close to zero (below the limit of detection) and the breath concentrations in study subjects who ingested the hard gelatin study capsule containing 2-butanol were well above 5 ppb, the difference in proportions of study subjects above this and even higher thresholds between the 2-butanol study capsule and placebo study capsule was quite large. This study enrolled 30 completed subjects to provide a sound framework for the estimation of normal distribution-based statistics.

Statistical analysis of the data from Clinical Study 2 was handled in a manner similar to that described in Clinical Study 1. The dependent variable was the change in 2-butanone breath concentration from baseline values. Performance metrics of the SMART® System were based on sensitivity/specificity analysis and accuracy determination endpoints. Analysis followed the guidance from the Clinical and Laboratory Standards Institute (CLSI) EP24-A2, entitled "*Assessment of the Diagnostic Accuracy of Laboratory Tests Using Receiver Operating Characteristic (ROC) Curves*". To assess the effectiveness of the SMART® System, ROC curves (plots of Se versus 1-Sp) were used to summarize the diagnostic performance of the SMART® System at 10, 20, and 30 minutes after study capsule ingestion using an automated detection algorithm (software) and an expert manual reader. Since the distributional nature of the 2-butanone breath concentration data is such that results are more dichotomous in nature (e.g., virtually close to zero or sufficiently greater than 10 ppb), sensitivity/specificity analysis used 2×2 tables where the relative sensitivity/specificity of the SMART® System was assessed at various concentration thresholds.

Data was summarized with respect to the following:
- Demographic and other descriptive study participant characteristics by formulation
- 2-butanone concentrations ("2BC") by formulation and time
- Delta over baseline (change from Time 0) 2BC by treatment and time
- b) and c) by demographic and other specified factors
- Extent of 2BC as calculated by the AUC-like "polygon" of values obtained from the discrete 10 to 30 minute post-ingestion time points
- Minimum, mean, and maximum 2BC across time
- Frequency distribution of time to maximum 2BC (over the 30 min time frame)
- Frequency distribution of time to "threshold" 2BC, defined as a 5 ppb, 7.5 ppb, and 10 ppb delta over baseline value Results for Clinical Study 2:

A total of 33 subjects (3 did not complete all visits for reasons unrelated to the study) participated in Clinical Study 2. Thirty three (33) subjects received placebo capsules, whereas 31 received SMART (2-butanol AEM formulation) capsules. A total of 184 visits (93 placebo, 91 SMART) were included in the analysis. Summary statistics for the demographics are shown in the Table below:

| Variable | | SMART (2-Butanol) | Placebo (Ethanol) |
|---|---|---|---|
| Gender [N(%)] | Male | 16 (51.6) | 18 (54.5) |
| | Female | 15 (48.4) | 15 (45.5) |
| Ethnicity [N(%)] | White | 22 (71.0) | 24 (72.7) |
| | Black (African American) | 7 (22.6) | 7 (21.2) |
| | Asian/Other | 2 (6.5) | 2 (6.1) |
| Age (yrs) | N | 31 | 33 |
| | Mean(SD) | 47.8 (13) | 48.4 (12.9) |
| | Median | 52 | 52 |
| | Min, Max | 25, 64 | 25, 64 |
| BMI (kg/m$^2$) | N | 31 | 33 |
| | Mean(SD) | 28.1 (6.2) | 28.4 (6.6) |
| | Median | 26.6 | 26.6 |
| | Min, Max | 19.8, 41.6 | 19.8, 42.6 |

Using a Δ2-butanone concentration cutoff value of 5 ppb, 181/184 (98.4%) intent to treat (ITT) cases were interpreted correctly by the SMART® Adherence System. Of the 3 cases not interpreted correctly, there was 1 false positive and 2 false negatives.

| | Breath Sampling Time | | | |
|---|---|---|---|---|
| | 10 min | 20 min | 30 min | Overall |
| Accuracy | 82.6% | 94.6% | 98.4% | 98.4% |
| Sensitivity | 64.8% | 90.1% | 96.7% | 97.8% |
| Specificity | 100% | 98.9% | 100% | 98.9% |

As shown in this table, the optimal breath sampling time after ingesting the capsule containing the AEM formulation (2-butanol) was 20 to 30 min where accuracies were approximately 95% and higher.

Conclusions for Clinical Study 2:

The SMART® Adherence System is highly accurate.

Clinical Study 3, designed on the basis of the results from Clinical Studies 1 and 2, is entitled, Clinical Study to Determine the Optimal Configuration of the SMART® Breath Monitoring System Using Soft Gelatin SMART® Capsules (see also Clinical Study 4 below), was conducted to determine the optimal configuration of the SMART® Breath Monitoring System using soft gelatin study capsules containing 2-butanol. The goals of this study were: 1) to establish the optimal cutoff 2-butanone breath concentration (e.g., increase of 5 ppb above baseline values) using Receiver Operating Characteristics (ROC) curves analysis, 2) to determine the SMART® Breath Monitoring System sensitivity, specificity, and accuracy at the optimal 2-butanone cutoff breath concentration, 3) to determine the range of optimal breath sampling time(s) (i.e., 20, 30, 40, 60, and 90 minutes) following 2-butanol study capsule ingestion, and 4) to establish the duration of 2-butanone persistence in breath.

A single formulation of the soft gelatin study capsule, (i.e., 2-butanol [40 mg], vanillin [10 mg], DL-menthol [1.4 mg], and PEG-400 [18.6 mg]) was studied. Each subject was randomly assigned to ingest two types of capsule formulations over 2 subject visits: 1) a capsule containing 2-butanol (SMART® Capsule); and 2) a placebo capsule containing ethanol. The placebo capsule contained the same mass of ethanol and associated excipients as used in the 2-butanol capsule. Ingestion of a capsule at each subject visit was verified through direct observation (i.e., directly observed therapy [DOT]) by the Clinical Research Coordinator(s).

44 subjects were enrolled and a total of 88 adherence assessments (44 capsules containing 2-butanol and 44 placebo capsules) were made using the SMART® Breath Monitoring System.

44 mGC units were employed in the study. A given subject was randomly assigned a specific mGC for use during both study visits. After a baseline breath sample was obtained (t=0 minutes), the subject ingested one study capsule (SMART or placebo), and then provided breath samples at 20, 30, 40, 60, and 90 minutes after ingestion of the capsule.

The sample size, the optimal formulation, and the timing of breath sampling were determined based on the analysis of Clinical Study 1 results of hard gelatin SMART Capsules.

The outcome measure was 2-butanone concentration (in ppb) recorded repeatedly at each time point during the sampling interval. The dependent variable was the change in 2-butanone breath concentration from baseline (Time 0) values. The change in 2-butanone concentration from baseline ("delta over baseline") provided a statistical adjustment for the potential that some subjects may have a recorded non-zero 2-butanone concentration at Time 0.

Performance metrics of the SMART® Breath Monitoring System were based on Receiver Operating Characteristic (ROC) curves analysis, including 2-butanone cutoff determination (e.g., 5 ppb rise above baseline values), sensitivity/specificity analysis, and accuracy determination endpoints. Analysis followed the guidance from the Clinical and Laboratory Standards Institute (CLSI) EP24-A2, entitled "*Assessment of the Diagnostic Accuracy of Laboratory Tests Using Receiver Operating Characteristic Curves*". To assess the effectiveness of the SMART® Breath Monitoring System, ROC curves (plots of Se versus 1-Sp; and plots of cutoff concentrations versus Se and Sp) were used to summarize the diagnostic performance of the SMART® System at 20, 30, 40, 60, and 90 minutes after capsule ingestion at a single cutoff 2-butanone breath concentration (e.g., 5 ppb rise above baseline values), using an automated detection algorithm (software) and the manual mGC reader.

Data was summarized with respect to the following:
Demographic and other descriptive study subject characteristics
2-butanone concentrations ("2BC") by formulation (placebo and SMART® Capsules)
Delta over baseline (change from Time 0) 2BC by formulation (placebo and SMART® Capsules)
b) and c) by demographic and other specified factors
Extent of 2BC as calculated by the AUC-like "polygon" of values obtained from the discrete 20 to 90 minute post-ingestion time points
Minimum, mean, and maximum 2BC across time
Frequency distribution of time to maximum 2BC
Frequency distribution of time to "threshold" 2BC, defined as the single BC cutoff concentration (e.g., 5 ppb delta over baseline values)
Results for Clinical Study 3:

A total of 44 subjects participated in Clinical Study 3. All subjects completed both visits, and therefore randomly received a placebo capsule and SMART (2-butanol AEM formulation) capsule over two visits. Thus, a total of 88 visits were included in the analysis. Summary statistics for the demographics are shown in the below table:

| Characteristic | Parameter | DR 0054 |
| --- | --- | --- |
| Age (Years) | n | 44 |
|  | Mean | 40.34 |
|  | Std. Dev. | 18.16 |
|  | Median | 39.00 |
|  | Minimum | 19.0 |
|  | Maximum | 78.0 |
| BMI (kg/m2) | n | 44 |
|  | Mean | 25.75 |
|  | Std. Dev. | 4.93 |
|  | Median | 24.95 |

-continued

| Characteristic | Parameter | DR 0054 |
| --- | --- | --- |
|  | Minimum | 17.4 |
|  | Maximum | 39.5 |
| Time - Meal (hrs) | n | 44 |
|  | Mean | 6.37 |
|  | Std. Dev. | 5.95 |
|  | Median | 3.00 |
|  | Minimum | 0.5 |
|  | Maximum | 19.5 |
| Gender n (%) | Male | 20 (45.45) |
|  | Female | 24 (54.55) |
| Tobacco Use n(%) | Yes | 16 (36.36) |
|  | No | 28 (63.64) |
| Alcohol Use n(%) | Yes | 33 (75.00) |
|  | No | 11 (25.00) |

With a Δ2-butanone concentration cutoff concentration of 5 ppb, the results of SMART performance using the soft gel-based capsule containing the AEM (2-butanol) formulation are depicted in the Table below. Although the SMART® Adherence System continues to be highly accurate, the soft gel capsule-based delivery of the AEM (2-butanol) appears to be slower in releasing the 2-butanol in the stomach relative to the hard gel capsule-based approaches used in Clinical Study 1 and 2. In the latter case (hard gel capsule), a breath sampling time of 20 to 30 min was associated with high accuracy, whereas in the former case (softgel capsule), breath sampling times of 40 min and longer are required.

| | Breath Sampling Time (N = 44 subjects) | | | | |
| --- | --- | --- | --- | --- | --- |
| | 20 min | 30 (min) | 40 (min) | 60 (min) | 90 (min) |
| Accuracy | 76.1 | 87.5 | 92.0 | 97.7 | 94.3 |
| Sensitivity | 52.3 | 75.0 | 84.0 | 95.5 | 97.7 |
| Specificity | 100 | 100 | 100 | 100 | 90.9 |

With regard to adverse events, across the 88 visits with 44 subjects, only 4 reports of taste and/or mild "stomach tingling or upset" were noted in four different subjects (subjects 0054-01, 0054,03, 0054-07, and 0054-30)—all of which received placebo (ethanol containing) capsules. In other words, no adverse events, including reports of mild tastes/smells and/or gastrointestinal issues, were reported in any subjects ingesting softgels containing the AEM (2-butanol) formulation.

Conclusions for Clinical Study 3:
The SMART Adherence System using softgels to deliver the AEM (2-butanol) is highly accurate, but requires longer breath sampling times to do so.

Clinical Study 4 entitled, Usability Validation Study of the SMART® Adherence Device, fulfilled the validation plan activity identified in Section 5.6 of the IEC 62366:2007 International Standard, Application of Usability Engineering to Medical Devices. Additional guidance was obtained from the draft document Guidance for Industry and Food and Drug Administration Staff: Applying Human Factors and Usability Engineering to Optimize Medical Device Design.

Twenty-five (25) study subjects who represent potential users of the SMART® Device were enrolled in this study, conducted at a typical market research facility (Jackson Associates Research Facility, Woburn, Mass.) which was mocked up to represent a typical home environment in which users would interact with the device.

The purpose of this study was to validate the usability of the SMART® Device and its accompanying user documentation. The study objectives were to: 1) demonstrate that the SMART Device can be set up and used by representative users under simulated use conditions without producing patterns of failures that could result in a negative impact or injury to themselves, 2) verify that the device documentation and training provided as part of this study are effective, 3). ensure that the potential use-related safety issues associated with using the device were adequately mitigated, and 4) verify whether the validation success criteria were met.

Study subjects received the expected training that users would receive prior to use. Test sessions occurred no sooner than one day after the training session for all individuals. Study subjects were presented a task scenario and asked to work through various subtasks with the device independently.

The test moderator recorded completion rates and noted positive and negative comments, usability issues, errors, and number of times subjects required assistance to use the device appropriately. Following the completion of all tasks, the moderator conducted a separate, in-depth interview to gather more detailed understanding of any observed use errors, usability problems, and near misses.

The study results reported the successes and the extent of failures for all listed tasks. Each instance of task failure was evaluated to determine its root cause. Every study subject who experienced a difficulty or a failure was interviewed about that difficulty or failure to determine the cause from the study subject's perspective. Direct performance data were used for support. Observation notes, video recordings, and procedure artifacts were used, if necessary. Data analysis also included subjective feedback regarding critical task experience, difficulties, "close calls," and any task failures by study subjects.

Both performance-based and subjective data were further analyzed to ensure that no new risks were identified. A determination was made if any of the investigated failures would have led to user harm. Following the test, the objective and subjective measures were analyzed and any usability or safety issues with the User Guide or Quick Reference Card were identified.

Xhale Smart analyzed any failures uncovered in this testing and updated the risk analysis. The follow-up risk analysis used the same approach that Xhale Smart took in the course of its prior risk management assessments, leading to the final disposition of use errors and usability issues as acceptable or not. The failures were described, as well as whether or not failures that occurred were associated with the design of the device, its labeling or documentation system and the extent of the association. The analysis of residual risk determined if design modifications were indicated or if not, the analysis demonstrated the impossibility or impracticality of reducing these risks further and that the residual risk was outweighed by the benefits offered by the device. If design modifications were indicated, and were significant, they were implemented and validated.

Results and Conclusions for Clinical Study 4:

In terms of usability, the SMART® Device was validated 1) Test tasks were successfully completed according to the success criteria, and all failures were investigated and shown to not have led to subsequent user or healthcare professional harm, and 2) No safety-related errors or usability issues were noted that could be further mitigated through design, training, or labeling, and none of the observed use errors, near misses, and usability issues (if any were observed) presented an unacceptable risk to the safety and effective use of the device.

Summary of Clinical Validation Work (Clinical Study 1, 2, 3, and 4)

In summary, the Type 1-based SMART system was found to be not only patient friendly in terms of usability across a wide range of disease states, but its performance was also favorable across a wide range of subject factors, including age, gender, race, body mass index (BMI), disease conditions, and time of food ingestion, and even in populations enriched with subjects who chronically consumed alcohol and/or used tobacco products. Specifically, after ingestion of the gelatin capsules containing an optimized AEM formulation, the following notable clinical findings were found: 1) greater than 98% of subjects gave an overall positive response (detection of breath marker by the Type 1 SMART® Device), and 2) adherence accuracies exceeding 95% can be achieved when a 20-90 min breath marker detection window is employed. Given the above results, we conclude that the SMART® Adherence System holds significant promise as a novel technology to definitively measure and monitor medication adherence in various clinical settings.

Example 4

Interference Studies to the SMART Adherence System Using 2-Butanol as the AEM and a Type 1 Device A series of four experiments were carried out to evaluate the effect of potential interferents on the function of the SMART® Adherence System utilizing a Type I Device and 2-butanol as the AEM. For the sake of brevity, summaries of results and conclusions are provided. As shown below and illustrated above in Clinical Study 1, 2, and 3 (excellent accuracy across diverse subject populations enriched with smokers, ethanol drinkers, and enrollees fed ad lib), the Type I device-based SMART® system can perform well, even in the presence of a wide variety of consumer products, ethanol, cigarette smoking.

These four interferents were selected for study, because they were deemed to have the highest likelihood of reducing the efficacy of a Type I device-based SMART® Adherence System using 2-butanol as the AEM. We previously reported that food (e.g., yogurt, cheddar cheese, black tea, tomatoes), which contains the greatest content of 2-butanol and/or 2-butanone, and the fed state did not affect the SMART® Adherence System (Morey et al, Oral Adherence Monitoring Using a Breath Test to Supplement Highly Active Antiretroviral Therapy, *AIDS Behav* 17(1):298-306. 2013).

Interference Study 1: New Home Environment

Summary

The purpose of this study was to evaluate indoor air samples from five recently built homes for the presence of volatile organic compounds (VOCs) that could potentially interfere with the function of the 2-butanone-based SMART® mini-gas chromatographs (mGC) System by providing an additional source of VOC with a retention time (100±5 sec) similar to that of 2-butanone on the mGC. Indoor air from each home was tested on-site using four separate SMART® mGCs. Paired air samples were collected from each home to confirm the identity of the VOCs present, using tandem gas chromatography mass spectrometry (GC/MS). All homes contained VOCs that are typically associated with the use of construction materials (e.g., acetone, isopropyl alcohol, butanal, and 2-butanone). The 2-butanone levels measured by the SMART® mGCs (identity verified by GC/MS) in the ambient indoor air from the new homes was low (range: 5.9 to 16.5 ppb) and could potentially contribute to the measured breath 2-butanone concentrations of home residents. However, at least three reasons exist that substantially mitigate the potential of the new construction environment to adversely impact the function of the SMART® mGC system: 1) the SMART® mGC system uses a baseline breath sample to measure background concentrations of 2-butanone concentrations in breath, 2) the equilibration between ambient concentrations of 2-butanone levels in the air and those in the blood of humans occur relatively slowly (e.g., hours),[4,5] and 3) much higher levels of 2-butanone are typically generated in breath, relative to those found in homes with new construction, following ingestion of AEM, 2-butanol.

Introduction

The SMART® miniature gas chromatograph (mGC) measures the concentration of 2-butanone in exhaled breath following the ingestion of the AEM, 2-butanol. Therefore, specific volatile organic compounds (VOCs), previously identified in a previous study (internal Xhale Document DR-0026), which have retention times on the SMART mGC similar to 2-butanone (i.e., 100±5 seconds) have the potential to interfere with the performance of the SMART® mGC Adherence System.

Materials used in home construction including paints, sealants, synthetic or laminated flooring, carpeting and other furnishings, may release VOCs in the home environment. The highest levels (i.e., worst case scenario) of VOCs in indoor home environments are found during the months immediately following the home construction.[1,2,3] Those materials that release 2-butanone or other VOCs with retention times similar to 2-butanone on the SMART® mGC (i.e., 100±5 seconds from that of 2-butanone), could introduce interfering VOCs into the breath of new home residents, and alter the real (2-butanone) or apparent (non-2-butanone VOC with a retention time between 95 to 105 sec) mGC-derived concentration of 2-butanone in breath. The purpose of this study was to sample indoor air from new homes (i.e., worst case scenario) on site using the SMART® mGC and GC/MS and to screen for the presence of VOCs that could potentially interfere with the 2-butanone-based mGC SMART® Adherence System.

Materials and Methods

Test Articles and Formulations

Four SMART® mGCs were used for this study to detect of 2-butanone indoor air of new homes. The SMART® mGCs with serial numbers 100113060024, 100113.060028, 100113060033, and 100113060047 were used in the study. These units are identified as 600-24, 600-28, 600-33, and 600-47, respectively, in this report.

1-L Tedlar gas sampling bags used for standard preparation were purchased from SKC Inc. (Eighty Four, Pa.). A single 10.0 mL Hamilton (Reno, Nev.) gas-tight syringe (Model Number 1010) was used for the dilution of the 2-butanone gas standard.

GC/MS samples were collected on stainless steel Tenax TA sample tubes (Model #C1-AXXX-5003) manufactured by Markes International Incorporated (Cincinnati, Ohio) using a 100 mL Hamilton (Reno, Nev.) gas-tight syringe (Model #1100).

Reference standards for the four SMART® mGCs and the Thermo ISQ GC/MS were completed at the University of Florida Innovation Hub on Sep. 24, 2013. A National Institute of Standards and Technology (NIST) certified 2-butanone gas standard was diluted into Tedlar gas sampling bags containing dry ultra-high purity (UHP) nitrogen to create standards containing 2-butanone concentrations of 0, 10, 30, 100, 300, and 1000 ppb. The 2-butanone calibration curves generated from these standards on each of the four SMART® mGCs and the GC/MS were created.

Study Design

Indoor air samples from five homes (identified in this report as Homes 1-5) were analyzed using the four SMART® mGCs. A single room air sample of ~30 mL was taken and automatically analyzed by the individual mGCs at each location. One paired sample was collected from each of the five homes (Homes 1 through 5) for tandem gas chromatography mass spectrometry (GC/MS), in order to qualitatively assess and identify the VOCs in the indoor environment. Air samples collected for the GC/MS analysis were prepared by drawing 50 cc of air through a clean Tenax gas sampling tube over 1 minute using a 100 mL gas tight syringe. Immediately after taking the sample, the tube was capped and the identification number of the tube recorded. The tubes were returned to the Innovation Hub for GC/MS analysis.

The homes used for this study were new-constructions (never occupied), and contained similar materials and fixtures (e.g., painted, flooring, cabinets) that had been installed within 30 days of sample collection. Homes 1 and 2 were located in the same housing development and were manufactured by the same builder. A different developer manufactured Homes 3, 4 and 5. Homes 3 and 4 were located in same neighborhood, and Home 5 was located in a separate development. No information was collected to identify the specific materials used in construction.

Data Storage and Processing

All SMART® mGC data was automatically collected on the device and subsequently transmitted to and stored on the Xhale Inc. secured servers. First derivative plots for the standards and breath samples collected by the SMART® mGCs were imported into Microsoft Excel® to determine 2-butanone peak height and retention times. GC/MS data was collected on the instrument's control computer and are stored on compact disk. GC/MS chromatograms were analyzed using Thermo Scientific Xcaliber® software. VOCs were identified by matching collected mass spectra to corresponding library spectra in the NIST database.

Statistical Analyses

For the interference screen, potential interferents were defined as those VOCs that generate a measured 2-butanone response of ≥5 ppb on the SMART® mGC. Data are expressed as mean±standard deviation. The effect of new home environments on the 2-butanone concentrations measured in air by the SMART® mGC were evaluated using a two-way analysis of variance (ANOVA) (factors: home and device) (SigmaPlot 11.2, Systat Software, Inc., San Jose, Calif.). P values <0.05 were considered statistically significant.

Results and Discussion

All SMART® mGCs used in this study responded similarly to the environmental VOCs in each home tested. The mean 2-butanone levels measured in the indoor air from the five homes ranged from 5.9-16.5 ppb. These levels are consistent with the indoor air 2-butanone concentrations measured in new site-built homes by Lindstrom et al (1-33 ppb)[3] and Hodgson et al (2.4-42.1 ppb with an average concentration of 8.8 ppb).[2] The 2-butanone measurement was similar among the four different devices (p=0.71) and the coefficient of variation (CV) in measured 2-butanone concentration across the four SMART® mGCs was <15% at each location.

A qualitative analysis of the environmental air by GC/MS, was used to identify VOCs present in the indoor air of each home. Representative chromatograms (e.g., from Home 2) were created, and the identities of the VOCs observed on the SMART® mGC and the GC/MS confirmed. 2-butanone was identified by GC/MS in all the homes tested (i.e., 5/5). The VOCs identified by the GC/MS in the homes sampled in this study, are consistent with the low levels of VOCs commonly found in construction materials: 1,3-dimethylcyclohexane, 1-butanol, 1-methoxy-2-propanol, 1-pentanol, 1-pentene, 2,2-dimethylhexane, 2-butanone, 2-methyl-1-propanol, 2-methylheptane, 2-methylhexane, 2-methylpentane, 2-propoxyethanol, 3-methylheptane, 3-methylhexane, acetone, acrylonitrile, benzene, butanal, butyric acid, chloroform, cyclohexane, cyclopentane, ethanol, ethyl acetate, hexanal, hexane, isobutyl alcohol, isobutyl ether, isoprene, isopropanol, methyl vinyl ketone, methylcyclohexane, methylcyclopentane, methyisopropylketone, n-butyl acetate, n-propyl acetate, pentanal, pentane, pentyl alcohol, propanoic acid, propylene glycol, tetrahydrofuran, and toluene.

There are two processes by which VOCs from ambient air could appear in exhaled breath. The first is by being exhaled from the lungs immediately after inhalation (i.e., the VOC does not partition out of the inhaled air and remains in the vapor phase during exhalation). The second is through absorption of the VOC from the lungs into blood and body tissues followed by a later partitioning from blood or tissues back into exhaled breath. Uptake kinetics of 2-butanone for inhalation exposure have been studied in human subjects exposed to high concentrations of 2-butanone (100,000-200,000 ppb)[4,5] and indicate that, at least for 2-butanone, both of these processes occur simultaneously to varying degrees and take hours to attain equilibrium. These studies reported pulmonary uptake of 2-butanone from air of ≤70%, and exhaled air 2-butanone concentrations ranged between 6%[5] and 50%[4] of the inhaled concentration.

It is important to note that regardless of the extent of uptake, ambient VOC levels represent the highest concentration that will appear in exhaled breath from inhalation exposure alone.

Conclusions

The 2-butanone levels measured by the SMART® mGCs in the indoor air of five new construction homes ranged between 5.9 and 16.5 ppb. Given the sensitivity of the SMART® mGC, the indoor air 2-butanone level determined in this study may contribute to the measured breath 2-butanone concentrations of home residents. However, the risk of the new home environment causing inaccurate (i.e., false positive or false negative) results readying by the SMART® Adherence System is minimal for at least 3 reasons. First, the SMART® mGC system is capable of using a baseline breath sample to measure background concentrations of 2-butanone concentrations in breath, Second, the equilibration between ambient concentrations of 2-butanone levels in the air and those in the blood of humans occur relatively slowly (e.g., hours),[4,5]. Interfering VOCs from ambient air in new homes should contribute equally to the baseline and sample breaths. Since the SMART® System monitors the change in exhaled 2-butanone by subtracting the baseline levels (prior to ingestion of the AEM from the sample breath, constant background levels of 2-butanone should be effectively eliminated from the determination. Third, much higher levels of 2-butanone are typically generated in breath, relative to those found in homes with new construction, following ingestion of the AEM, 2-butanol.

REFERENCES

[1] Retrieved from http://www.epa.gov/iaq/voc.html
[2] Hodgson, A. T., Rudd, A. F., Beal, D., Chandra, S., Volatile Organic Compound Concentrations and Emission Rates in New Manufactured and Site-Built Houses, Indoor Air, (2000) 10(3): 178-92.
[3] Lindstrom, A. B., Proffitt, Effects of modified residential construction on indoor air quality, Indoor Air, (1995) 5, 258-269
[4] Liira, J., Riihimaki, V., Engstrom, K, Pfaffli, P., Coexposure of man to m-xylene and methyl ethyl ketone—Kinetics and metabolism, Scand J Work Environ Health, (1988) 14(5):322-327.
[5] Dick, R B; Brown, W D; Setzer, J V, Effects of short duration exposures to acetone and methyl ethyl ketone, Toxicol Lett, (1988) 43:31-49.

Interference Study 2: Cigarette Smoke

Summary

Cigarette smoke is known to contain a large number of volatile organic compounds (VOCs), many present at high concentrations. Compounds introduced in human breath as a result of smoking events (e.g., 2-butanone, ethyl acetate) could potentially interfere with the function of the 2-butanone-based SMART® mini-gas chromatographs (mGC) System by providing an additional source of VOC with a retention time (100±5 sec) similar to that of 2-butanone on the mGC. The objectives of this study were twofold: 1) evaluate the presence of potential interferents in the home environments (n=5 homes) of smokers, and 2) screen breath samples from smokers (n=5 volunteers) for potential interferents from smoking two commonly used cigarette brands (i.e., Newport and Marlboro). The kinetics of potentially interfering breath VOCs from five (5) study subjects were evaluated following smoking events (T=0, 10 and 15 minutes), in support of a plan to understand and mitigate potential risks of smoking causing detrimental effects on SMART® mGC System performance.

Screening of VOCs from the home environments showed that only one of the five (1/5) homes had a mean indoor air 2-butanone concentration ≥5 ppb (mean concentration 6.9 ppb). Smoking did not result in a clinically significant change (i.e. ≥5 ppb) from the baseline breath 2-butanone concentration on the SMART® mGC, in any of the study participants. Any potential risk of inaccurate 2-butanone results in human breath from smoking can be adequately mitigated by 1) collecting a baseline breath sample prior to ingestion of the AEM, 2-butanol, and 2) having a 15 minute wait period from smoking, before a subject breath sample is given. This finding is consistent with the results of clinical studies (Example 3, Clinical Study 1, 2, and 3) investigating the performance of the SMART® mGC System, which demonstrated favorable performance, even in subject populations enriched with participants having a significant smoking history.

Introduction

The Centers for Disease Control and Prevention estimates that approximately 19% of the adult American population smoke cigarettes.[1] Cigarette smoke contains over 4400 compounds including 2-butanone.[2,3] Volatile organic compounds (VOCs) present in cigarette smoke (i.e., 2-butanone, ethyl acetate) may interfere with the SMART® mGC System by having similar retention times (i.e., 100±5 seconds) as the breath marker, 2-butanone, that is generated after ingestion of the AEM, 2-butanol. The purpose of this study was to screen VOCs associated with smoking two widely used cigarette brands (i.e., Newport and Marlboro) that could potentially interfere with SMART® mGC function. Specifically, these cigarettes may release 2-butanone or other VOCs with retention times similar to 2-butanone on the SMART® mGC, into the breath of smokers (and passive non-smokers), and alter the real (2-butanone) or apparent (non-2-butanone VOC with a retention time=95 to 105 sec) mGC-derived concentration of 2-butanone in breath.

The kinetics (time-dependent behavior) of these potential interferents in human breath were evaluated in support of a plan to understand and mitigate potential risks of smoking causing detrimental effects on SMART® mGC System performance.

Materials and Methods

Test Articles and Formulations

Five Xhale mGCs were used for this study. One mGC device was used per person, and the instruments were randomly assigned to each individual. The mGCs used had serial numbers 100112120003, 100113030039, 100113030041, 100113030043, and 100113030044. These units will be identified as 212-03, 303-39, 303-41, 303-43, and 303-44 in this report, respectively.

1-L Tedlar gas sampling bags were purchased from SKC Inc. (Eighty Four, Pa.). Each bag was used only once. A single 10.0 mL Hamilton gas-tight syringe (Model Number 1010, Fisher Scientific part number 14-815-183) was used for the dilution of the 2-butanone gas standard. 2-Butanone standards were created by diluting appropriate aliquots of a primary NIST certified dry nitrogen 10 ppm 2-butanone gas standard (Matheson Tri-Gas MICRO MAT 58 Item Number GMT2677977TH, Lot Number 109-26-07599, Expiration Date May 11, 2014) into 1-L Tedlar bags containing blank breath. The two cigarette brands used for this study (Marlboro and Newport) were purchased from a Publix Supermarket in Gainesville Fla. on May 3, 2013. These brands were chosen based on cigarette brand preferences reported for the general smoking population and represent the two most popular brands of cigarettes in the United States. 4

Butanone Standard Creation and Analysis

Dilution of a NIST-certified 2-butanone gas standard into Tedlar gas sampling bags containing a blank breath sample was performed to create a standard curve at four concentrations (0, 10, 100, and 1000 ppb). The standard curve for 2-butanone was analyzed on each of the four SMART® mGCs used in this study, at the Nanoscale Research Facility of the University of Florida.

Investigational Plan

All samples (i.e., indoor and breath) for this study were collected in the individual subjects' homes (n=5 in total) on two consecutive days for each subject. Each subject was fully informed on the experimental procedures, and the study was approved by the Western Institutional Review Board (WIRB), Protocol Number 20130515.

Exclusion criterion: Subjects with severe lung disease (e.g., advanced chronic obstructive pulmonary disease, COPD) or those physically unable to provide breath samples into the SMART® mGC.

Breath samples were collected from five (5) adult (over the age of 21) study participants who were current smokers, and smoked in their homes. The study subjects will be identified in this report as SA-1, SA-2, SA-3, SA-4, and SA-5. The smoking frequency (i.e., self-reported cigarette packs smoked per day) of these subjects, and the number of active smokers in the home for SA-1, SA-2, SA-3, SA-4, and SA-5 were 0.5/2.5/2/1/1.5 and 4/2/1/3/2, respectively.

Each subject participated in the study for two (2) days. The study volunteers were randomized to smoke a single cigarette from each of the two (2) mentioned brands (i.e., Marlboro and Newport). A minimum of one (1) day was allowed between smoking the different cigarette brands. No replicate of a given cigarette brand was carried out for a given subject. Participants were allowed food products and beverages ad libitum but were instructed not to take anything by mouth for 15 minutes prior to collection of the first breath sample and to refrain from smoking for a minimum of one (1) hour prior to providing the first breath sample.

A total of five (5) samples were collected using the SMART® mGCs during each home visit: one (1) room air sample and four (4) participant breath samples. Paired baseline breath 2-butanone levels were established from the study participants prior to each smoking event by collecting a "blank" breath sample (T=−10 min). The study volunteers smoked the randomly assigned cigarette brand (i.e., either Marlboro or Newport) to completion, in their normal manner. Immediately after finishing the cigarette, each subject breathed into their designated SMART® mGC to provide a time 0 (T=0 min) sample. Additional post-cigarette breath samples were collected after 10 (T=10 min) and 20 minutes (T=20 min), thereafter. The study subjects had a minimum of one (1) day wait period between smoking the different cigarette brands, after which the study protocol was repeated for each individual with the remaining cigarette brand used in this interference screen (i.e., either Marlboro or Newport). During the wait period between the two study dates, the subjects were not given any restrictions with regard to their regular smoking habits.

Data Storage and Processing

All data was automatically uploaded and stored on a secured and dedicated Xhale server. First derivative of mGC sensor response versus time plots for the standards and breath samples were used to determine 2-butanone peak heights and retention times.

Statistical Analyses

Exclusion of subject SA-5 from the statistical analysis: Breath samples collected from study volunteer SA-5 resulted in a total loss of signal in the early part of the SMART® mGC chromatogram. This loss of signal was considered a confounding variable for the purposes of evaluating smoking interferences and the data was therefore excluded from the analysis. Although we could not confirm the exact cause of the breath VOC(s) that resulted in signal loss, this finding is consistent with the interference observed at high concentrations of breath ethanol (e.g., 300,000 ppb ethanol). Participant SA-5 reported consuming approximately 50 beers/week, and reported consuming an unspecified amount of beer approximately two (2) hours prior to the beginning of the study. The data obtained from the indoor air of this study participant was included in the analysis.

For the interference screen, data are expressed as mean±standard deviation. Delta baseline was calculated as the mean change from baseline in 2-butanone concentration (2-butanone concentration after smoking—2-butanone at baseline). 2-butanone concentrations below the level of detection (LoD) of the mGC (i.e., 5 ppb) were considered zero for the delta baseline calculations. To determine the effect of cigarette smoking on breath 2-butanone concentrations measured by the SMART® mGC, and whether significant differences exist between cigarette brands (i.e., Marlboro vs. Newport) exist, the data were compared using repeated measures analysis of variance (ANOVA) (Sigma-Plot 11.2, Systat Software, Inc., San Jose, Calif.). P-values <0.05 were considered statistically significant. Clinically significant interference from smoking cigarettes was defined as breath VOCs that changed the mean baseline (prior to smoking) 2-butanone breath concentration by ≥5 ppb, the putative 2-butanone cutoff value supported by prior clinical mGC SMART® system performance studies (e.g., Example 3, Clinical Studies 1, 2, and 3).

Results and Discussion

The SMART® Adherence System is used to confirm ingestion of medication that is associated with the AEM, 2-butanol. This is accomplished by evaluating the change in breath 2-butanone concentrations from baseline after ingestion of 2-butanol. Cigarette smoking introduces a large number of VOCs in the breath of smokers. The presence of 2-butanone and other VOCs reported to be in cigarette smoke (e.g., ethyl acetate and 3-methyl-1-butanol) that have retention times similar (100±5 seconds) to that of 2-butanone on the SMART® mGC (Xhale Document No.: DR-0026), may interfere with the performance of the SMART® Adherence System and cause inaccurate 2-butanone results (i.e., false positives or false negatives). This study evaluated the effects of VOCs from cigarette smoke present in 1) indoor air of homes of people who smoke in the house, and 2) breath samples from smokers at various times following a smoking event, on the apparent 2-butanone concentration measured by the SMART® mGC, in the absence of ingesting the AEM, 2-butanol.

The indoor air concentrations of 2-butanone were measured using the SMART mGCs in each home, on two separate occasions (one air sample per home visit). The mean 2-butanone levels were measured to be below the LoD (<5 ppb) in four of the five homes tested (Homes 1, 2, 3 and 5). Indoor air from Home 4 had the highest mean concentration of 2-butanone measured by the SMART® mGC and was 6.9 ppb, which is slightly higher than the LoD.

The baseline breath levels (i.e., prior to smoking) of 2-butanone measured by the SMART® mGC in the breath of study participants (n=4) ranged between below LoD (5 ppb) and 254.7 ppb. Note: In another study (protocol: Example 3, Clinical Study 1), it should be noted that although high breath levels (132.4, 238.8, and 31.6 ppb) of background 2-butanone were noted in subject 49, who was a smoker and admitted to consuming a significant amount of alcoholic beverages in an ongoing basis, he/she still responded favorably to the ingestion of the AEM, 2-butanol, by generating large increases in breath 2-butanone concentrations above these higher than normal baseline levels. The baseline 2-butanone breath concentrations for participants SA-2 and SA-4 were below the LoD for both study visits. The remaining study subjects showed large interpersonal variability in their baseline breath (i.e. prior to smoking the study cigarette) 2-butanone concentrations measured during the two home visits. The baseline breath 2-butanone concentrations measured for SA-1 were 5 ppb during the first home visit and 254.7 ppb during the second. In contrast, SA-3 had a relatively high baseline breath 2-butanone concentration of 179.3 ppb during the first home visit, and 5 ppb during the second visit. Although both SA-2 and SA-3 had elevated 2-butanone levels in their baseline breath on the day that they were given the Marlboro study cigarette, these concentrations were measured prior to smoking, and therefor are independent of the cigarette brand used in this study.

During those visits with elevated baseline 2-butanone, subjects SA-1 and SA-3 showed decreases in their respective 2-butanone breath concentrations with time that are consistent with the blood elimination kinetics of 2-butanone ($t_{1/2}$=49-96 minutes).[4] These levels are approximately 50 times greater than the 3-4 ppb of breath 2-butanone that would be expected from the median blood 2-butanone concentration in the general population (5.4 ppb) determined by the third National Health and Nutrition Survey (NHANES III).[6] This suggests the transient high baseline levels of 2-butanone observed in these study subjects are incidental, and are not representative of the general population.

Breath samples were collected from each study subject at 10 minutes prior to smoking (Baseline breath; T=−10 minutes), immediately (T=0 minutes), at 10 minutes (T=10 minutes) and 20 minutes (T=20 minutes), following smoking each cigarette brand (i.e., Newport and Marlboro). The SMART® mGC $1^{st}$ derivative chromatograms show that cigarette smoke introduced breath VOCs with retention times on the SMART® mGC outside the interference window for 2-butanone (i.e., 100±5 seconds). The SMART® mGC can discriminate between 2-butanone and VOCs with retention times greater than ±5 seconds from 2-butanone. These VOCs are outside the interference window, and do not interfere with the measurement of 2-butanone by the SMART® mGC.

The change in baseline (pre-smoking) 2-butanone concentrations registered by the SMART® mGC for both cigarette brands at T=0, T=10 and T=20 minutes showed that no significant difference was observed in interfering breath VOCs between the two cigarette brands (i.e., Newport and Marlboro) screened. Smoking did not result in a change in the mean baseline (i.e., pre-smoking) 2-butanone level ≥5 ppb at any of the time points following the smoking event.

Conclusions

This study evaluated VOCs associated with smoking two commonly used cigarette brands (i.e., Newport and Marlboro), for potential interference with SMART® mGC System performance. The kinetics of these potential interferents in human breath were evaluated in support of a plan to mitigate the risk of inaccurate SMART® mGC System results that may be associated with smoking.

VOCs present in the home environments had minimal effects on the 2-butanone concentration measured by the SMART® mGC. Only one of the five (1/5) homes resulted in mean indoor air 2-butanone concentrations above ≥5 ppb (mean concentration 6.9 ppb). The presence of smoking-derived VOCs, and the kinetics of potential interferents in human breath associated with smoking events was evaluated in study subjects following use of Newport and Marlboro cigarettes. Smoking did not result in a clinically significant change (i.e., ≥5 ppb) from the baseline breath 2-butanone concentration on the SMART® mGC.

It appears that any potential risk of inaccurate 2-butanone results in human breath from smoking can be adequately mitigated by 1) collecting a baseline breath sample prior to ingestion of the AEM, 2-butanol, and 2) having a 15 minute wait period from smoking, before a subject breath sample is given. This finding is consistent with the results of clinical studies (Example 3: Clinical Study 1, 2, and 3) investigating the performance of the SMART® mGC System, which demonstrated favorable performance, even in subject populations enriched with participants having a significant smoking history.

REFERENCES

[1] Centers for Disease Control and Prevention. Current Cigarette Smoking Among Adults-United States, 2011. Morbidity and Mortality Weekly Report 2012; 61(44): 889-94

[2] Polzin, G. M., Kosa-Mains, R., Ashley, D. L., Watson, C. H. Analysis of Volatile Organic Compounds in Mainstream Cigarette Smoke, Environ. Sci. Technol. 2007, 41, 1297-1302.

[3] "Toxic Volatile Organic Compounds in Environmental Tobacco Smoke: Emission Factors for Modeling Exposures of California Populations" by Lawrence Berkeley Laboratory under the sponsorship of the California Air Resources Board. May 1994. http://www.arb.ca.gov/research/apr/past/a133-186.pdf

[4] Tobacco Brand Preferences. Center for Disease Control and Prevention http://www.cdc.gov/tobacco/data_statistics/fact_sheets/tobacco_industry/brand_preference/

[5] Lab data reference, SMART Logbook No. 8, pages 15-24—Document on file at Xhale, Inc., Gainesville, Fla.

[6] Churchill, J. E., Ashley, D. L., Kaye, W. E. Recent Chemical Exposures and Blood Volatile Organic Compound Levels in a Large Population Based Sample. Arch. Environ. Health. 2001, 56(2), 156-166.

Interference Study 3: Consumer Products

Summary

The current study screened specific consumer products, based on knowledge of their flavorant content, that could potentially interfere with the performance of the 2-butanone-based SMART® mini-gas chromatographs (mGC) System. This could occur by the consumer products providing an additional breath source of 2-butanone and/or of a non-2-butanone VOC with a SMART® mGC retention time similar to that of 2-butanone (100±5 sec). In the SMART® mGC System, the breath marker, 2-butanone, is generated and detected (as change from baseline concentration) in human breath by the mGC after ingesting the AEM, 2-butanol.

The effects of fifteen different consumer goods, including fruits (banana), drinks (fruit drinks, coffee), candies, and health products (toothpaste, cough drops) on apparent 2-butanone breath levels measured on the SMART® mGC were studied in four volunteer study participants using a cross over design. Each consumer product was kept in the mouth for 30 seconds, then expectorated. 2-butanone concentrations were measured in baseline breath (i.e., in the absence of consumer product) and at various time intervals after the products were expectorated. Breath samples collected immediately (0 min), 10 min and 15 min, after the consumer goods were eliminated from the mouth, showed that 10/15 (67%), 3/15 (20%), and 0/11 (0%) products caused an increase in baseline (pre-consumer product) 2-butanone levels ≥5 ppb, respectively. This finding is consistent with the results of clinical studies (Example 3: Clinical Studies 1, 2, and 3) investigating the performance of the SMART® mGC System, which demonstrated favorable performance, even in subject populations who ingested food and drank liquids ad libitum but were nothing per orum (NPO) 15 min or longer prior to study initiation (provision of baseline breath sample). Taken together, these results suggest two findings: 1) most foods will not interfere with the performance of the SMART® mGC system, and/or 2) any potential interfering VOC is adequately cleared from the mouth within the 15 min NPO window.

Introduction

Natural and synthetic flavorants present in consumer products may contain volatile organic compounds (VOCs) that can interfere with the performance of the 2-butanone-based SMART® mGC System. This could occur by the consumer products providing an additional breath source of 2-butanone and/or of a non-2-butanone VOC with a SMART® mGC retention time similar to that of 2-butanone (100±5 sec). In the SMART® mGC System, the breath marker, 2-butanone, is generated and detected (as change from baseline concentration) in human breath by the mGC after ingesting the AEM, 2-butanol. Based on our knowledge of what VOCs have a similar retention time to 2-butanone and the flavorant composition of food, the purpose of this study was to perform a screen of various foods, drinks, and other consumer goods, which would be the most likely to interference with the system by introducing interfering VOCs in the mouth, and subsequently alter the concentrations of 2-butanone measured in exhaled breath (i.e., in the absence of the AEM. The kinetics of these potential interferents in human breath were evaluated in support of a plan to mitigate the risk of inaccurate 2-butanone results on the SMART® System. We previously demonstrated that foods (e.g., yogurt, cheddar cheese, black tea, tomatoes), which are known to contain the highest endogenous content of the AEM, 2-butanol and the breath marker, 2-butanone, do not appear to interfere with the SMART® mGC System, even when rapidly ingested in large quantities.[1]

Materials and Methods

Test Articles and Formulations

Four SMART® mGCs from Xhale Inc. were used for this study. One mGC device was used per person, and the instruments were randomly assigned to each individual. The mGCs used had serial numbers 100112120001, 100112120003, 100113010007, and 100113010010. These units are identified as 212-01, 212-03, 301-07, and 301-10 in this report.

1-L Tedlar gas sampling bags were purchased from SKC Inc. (Eighty Four, Pa.). Each bag was used only once. A single 10.0 mL Hamilton gas-tight syringe (Model Number 1010, Fisher Scientific part number 14-815-183) was used for the dilution of the 2-butanone gas standard.

2-Butanone standards were created by diluting a primary NIST certified 10 ppm 2-butanone gas standard in dry nitrogen (Matheson Tri-Gas MICRO MAT 58 Item Number GMT2677977TH, Lot Number 109-26-07599, Expiration Date May 11, 2014) into 1-L Tedlar bags containing blank breath. The 15 consumer products selected for this study were all purchased from Publix Supermarket in Gainesville Fla. the day before the study began (except for the Arcor Strawberry Buds Candy, which was supplied by the study sponsor). The products tested, and the abbreviation used in this report were as follows: Fruit (banana), Health products (Cologne Total toothpaste; Fresh Burst mouthwash, triple soothing strawberry cough drop); Candies (various types of gum, flavored hard candies, jelly fruit slices, and cinnamon breath mints), and Beverages (Nestle coffee with creamer, Arizona fruit drink).

Butanone Standard Creation and Analysis

Dilution of a NIST-certified 2-butanone gas standard into Tedlar gas sampling bags containing a blank breath sample was performed to create a standard curve at four concentrations (0, 10, 100, and 1000 ppb). Standard curves for 2-butanone were created for each of the four SMART® mGCs used in this study.

Investigational Plan

Each subject was fully informed on the experimental procedures, and the study was approved by the Institutional Review Board (IRB), University of Florida. Exclusion Criteria: Subjects found physically unable to provide breath samples.

Breath samples were analyzed using the individual mGCs from four (4) adult study participants. The participants were instructed not to consume alcoholic beverages the day before the study, and not to eat, drink or smoke for 15 minutes prior to the beginning of the study.

The study was carried out in two phases. The first phase screened 15 consumer products, to evaluate interference of mouth VOCs with the SMART® mGC immediately after, and 10 minutes following each product. A baseline 2-butanone level was established for each subject by analyzing a "blank" breath sample 10 minutes before placing each consumer product in their mouth. To maximize the concentrations of mouth VOC, the subjects kept each consumer product in their mouth and mixed it around for 30 seconds, and then expectorated. Immediately after each product was eliminated from the mouth, the study subjects breathed into their designated SMART® mGC to provide a time 0 (T=0 min) sample. A second post-consumer product breath sample was collected 10 minutes later (T=10 min). To prevent carry-over of potential interferents between the products, the study participants rinsed their mouths thoroughly with water after each item tested, and waited a minimum of 15 minutes before repeating the procedure for the remaining products.

For the second phase of the study, nine products were chosen from the initial screen to evaluate the presence of interfering VOCs in the breath after 15 minutes (T=15 minutes) from the time the items were expectorated. The study protocol was the same as described for the initial screen, with the exception of the time intervals used to collect the post-consumer product breath samples. In this study, the participants waited for 15 minutes after eliminating each consumer product from their mouth before providing the post-consumer product breath sample. The consumer products chosen for the second phase of testing were identified in the initial screen as having the highest levels of potential interferents.

Clinical significant interference from consumer products was defined as breath VOCs that changed the mean baseline (pre-consumer product) 2-butanone breath concentration by ≥5 ppb.

Data Storage and Processing

All data was automatically stored to the Xhale secured servers. First derivative plots for the standards and breath samples were imported into Microsoft Excel (Redmond, Wash.), and the peaks and retention times were determined for each compound.

Statistical Analyses

For the interference screen, data are expressed as mean±standard deviation. Delta baseline was calculated as the mean change from baseline 2-butanone (mGC SMART® 2-butanone concentration after consumer product—mGC SMART® 2-butanone at baseline) in parts per billion (ppb). 2-butanone concentrations below the LoD (i.e., 5 ppb) were considered zero for the delta baseline calculations.

Descriptive statistics of the data were calculated using SigmaPlot 11.2, Systat Software, Inc. (San Jose, Calif.).

Results and Discussion

The SMART® Adherence System is used to confirm ingestion of a medication that is associated with the AEM, 2-butanol. This is accomplished by evaluating the change in breath 2-butanone concentrations from baseline levels, after ingestion of the AEM, 2-butanol. Eating/drinking foods, and/or using healthcare products that contain either 2-butanone, or a non-2-butanone VOC with a retention time similar to 2-butanone on the SMART® mGC (100±5 seconds) may result in inaccurate results (i.e., false positive or false negative results). Four VOCs (methyl acrylate, ethyl acetate, 3-butene-1-ol and cyclohexane) were previously identified as having similar retention times on the SMART® mGC as 2-butanone. One of these VOCs, ethyl acetate, elutes within 1 second of 2-butanone, and is a flavoring agent found in food or health products. This acetate is naturally occurring in fruits,[3] and it is a direct food additive (40 CFR 180.910) used as fruit essence in food items.[4] The interference screen of consumer goods was done using products known to contain natural or synthetic flavoring agents that would be likely to interfere with the SMART® mGC System.

The baseline levels of 2-butanone measured in the breath of study participants (n=4) before each consumer product were below the LoD (<5 ppb) for both the first and second part of the study. In the first phase of the study 15 consumer products were used to determine their potential to interfere with the SMART® mGC system. The mean concentrations of apparent 2-butanone measured by the SMART mGC in exhaled breath immediately was measured after each product was expelled from the mouth. The change in baseline (pre-consumer product) 2-butanone concentrations registered by the SMART® mGC for each consumer product at T=0 minutes was determined. At T=0 minutes, as illustrated, 10 of the 15 (67%) products tested resulted in a change in the mean baseline (pre-consumer product) 2-butanone level ≥5 ppb. These foods produce a clinically significant interference on the SMART® mGC at T=0 minutes. Of the 15 consumer goods, the banana caused the SMART® mGC to register the highest change in the mean breath concentration of 2-butanone (1481.3±296.0 ppb).

The breath samples taken 10 minutes after the consumer products were expectorated from the mouth show that the 2-butanone concentration measured by the SMART® mGC were below the LoD (5 ppb) of the SMART® mGC for 11 of the 15 (73%) products. The changes from baseline breath (pre-consumer product) 2-butanone concentrations registered for each consumer product at T=10 minutes was determined. Three of the 15 (3/15) products resulted in a change in the mean baseline (pre-consumer product) 2-butanone level ≥5 ppb at T=10 minutes. The SMART® mGC 1st derivative chromatograms show that the banana also introduced breath VOCs (e.g., ethanol) with early retention times on the SMART® mGC (retention times in the 20-60 second range), that do not interfere with the 2-butanone measurement. This was observed with other consumer products as well (data not shown). The presence of these additional breath VOCs do not have clinical significance for the SMART® mGC, but can be qualitatively assessed if interference from consumer products is suspected. At T=10 minutes, three of the 15 (20%) consumer goods produce a clinically significant interference on the SMART® mGC at 10 minutes.

The second phase of the study was done to determine if a 15 minute wait after consumer products are expelled from the mouth, is adequate for the measured 2-butanone levels to return to baseline. The concentrations of 2-butanone in the baseline breath, and 15 minutes post-consumer product were determined. At T=15 minutes, the 2-butanone concentrations in breath were below the LoD (5 ppb) of the SMART® mGC, for all the consumer products. This indicates that within 15 minutes of eliminating the products from the mouth, the breath 2-butanone response on the SMART® mGC returns to baseline levels. The consumer products do not produce a clinically significant interference on the SMART mGC 15 minutes after they are eliminated from the mouth.

The potential interference of Listerine mouthwash on the SMART® mGC at T=0 and T=10 minutes was not determined in this study. Listerine did not produce a measurable change in the mean baseline (pre-consumer product) 2-butanone levels at either sampling times. However, a qualitative assessment of the SMART® mGC 1st derivative chromatograms from the breaths samples obtained at T=0 and T=10 minutes, indicates that Listerine, which contains 20% v. ethanol, may cause a negative bias in 2-butanone measurements at these time points. Ethanol interference with the SMART® mGC was evaluated, and is presented in Example 3: Interference Study 4. A qualitative assessment of Listerine mouthwash interference with the 2-butanone measurement on the SMART® mGC was also done using the $1^{st}$ derivative chromatograms from T=15 minute. The breath 2-butanone response on the SMART® mGC returns to baseline (pre-consumer product) within 15 minutes after the time the mouthwash is eliminated from the mouth.

The persistence of the interfering breath VOCs (i.e., apparent 2-butanone concentrations >5 ppb above baseline) from consumer products was determined. The first phase of the study showed that at T=0 minutes, 10/15 (67%) and at T=10 minutes 3/15 (20%) of the products result in a change in the mean baseline (pre-consumer product) 2-butanone level ≥5 ppb. The second phase of the study indicates that 2-butanone response on the SMART® mGC returns to baseline within 15 minutes after expectorating the consumer products from the mouth.

Conclusions

Food, drink, or other consumer products may contain VOCs that have the potential to adversely impact the performance of the 2-butanone-based SMART® Type 1 (mGC) System. This could occur by introducing additional 2-butanone and/or non-2-butanone VOCs to human breath that have a similar SMART® mGC retention time to 2-butanone (100±5 sec). However, within 15 minutes from the time the products are eliminated from the mouth, the breath 2-butanone concentration response on the SMART® mGC returns to baseline (pre-consumer product). Therefore, the risk of inaccurate 2-butanone results in human breath associated with the studied consumer products can be adequately mitigated by 1) collecting a baseline breath sample prior to ingestion of the AEM, 2-butanol, and 2) having a 15 minute wait period from use of food or drink (note: this does not refer to the ingestion of standard liquids commonly used to ingest medications such as water, tea, coffee, etc.), before a subject breath sample is given.

This finding is consistent with the favorable SMART® mGC System performance results of clinical studies (Example 3: Clinical Studies 1-3), where subjects were allowed to be fed ad libitum prior to enrollment but kept nothing per orum (NPO) 15 min prior to providing the baseline breath sample.

REFERENCES

[1] Morey T E, Wasdo S, Wishin J, Quinn B, Booth M, Gonzalez D, Derendorf H, McGorray S P, Simoni J, Melker R J, Dennis D M: Oral Adherence Monitoring Using a Breath Test to Supplement Highly Active Antiretroviral Therapy, AIDS Behav, 17(1), 298-306, 2013.
[2] Lab data reference, Xhale Logbook BPQ 2012-1, pages 45-48 and page 53. Document on file at Xhale, Inc., Gainesville, Fla.
[3] http://www.epa.gov/opprd001/inerts/ethyl_amyl_acetate.pdf
[4] http://www.epa.gov/iris/subst/0157.htm Interference Study 4: Ethanol Summary Interference testing was performed to determine the effect of increasing concentrations of ethanol in the breath on the 2-butanone-based SMART® mGC System. Test samples were prepared using breath samples (n=5 study volunteers) spiked with 50 ppb 2-butanol, and ethanol concentrations of 0, 30,000, 100,000, and 300,000 ppb. The effects of ethanol were determined by comparing the 2-butanone retention time and SMART® mGC response (2-butanone 1st derivative peak height) in control samples (i.e., no ethanol) and test samples containing the various concentrations of ethanol.

High concentrations of ethanol in breath did not affect the retention time of 2-butanone on the SMART® mGC but did reduce the mGC response to 2-butanone. For example, using the upper limit of the 95% confidence interval (per CLSI EP7-A2 guidance), ethanol at 30,000, 100,000, and 300,000 ppb in breath reduced the SMART☐☐mGC response to 50 ppb 2-butanone alone by 50%, 64%, and 74%, respectively. However, it should be noted that this reduction in apparent 2-butanone breath concentration by ethanol should not be a significant issue with regard to SMART® mGC performance, because the majority of unique subjects in clinical studies, who ingest the AEM, 2-butanol, generate increases in breath 2-butanone concentration above baseline values much greater than 5 ppb (Example 3: Clinical Studies 1-3). This finding is consistent with the results of clinical studies (Example 3: Clinical Studies 1-3) investigating the performance of the SMART® mGC System, which demonstrated favorable performance, even in subject populations enriched with participants having a significant alcohol drinking history. Last, the potential negative impact of high concentrations of ethanol on the measurement of 2-butanone in breath can be rapidly recognized, assessed, and mitigated by examining the "front end" of the SMART® mGC chromatogram.

Introduction

Ethanol is a volatile organic compound (VOC) that is typically found in the exhaled breath in trace amounts (low parts per billion or ppb), as a result of endogenous processes (e.g., sugar metabolism in the colon). A previous study by Morey et al., (2012) [1] showed that endogenous ethanol present in the breath matrix did not interfere with the ability of the SMART® mGC to measure 2-butanone, the breath marker used in the SMART® System. Ingesting drink products containing ethanol (e.g., alcoholic beverages) may increase the concentrations of breath ethanol to levels that are several orders of magnitudes greater than endogenous levels. For example, the legal limit of intoxication in most jurisdictions of the United States is a blood alcohol content (BAC) of 0.08% (80 mg ethanol per dL blood), which corresponds to a breath alcohol concentration (BrAC) of approximately 200 ppm (200,000 ppb).

The objective of this study was to evaluate the potential of elevated ethanol concentrations to interfere with the ability of the SMART® mGC to measure 2-butanone in human breath. To determine the degree of interference from ethanol, the mGC response (i.e., 2-butanone peak height) and 2-butanone retention time, were measured in breath samples "spiked" with 50 ppb 2-butanone in the presence of progressively increasing concentrations of ethanol (0, 30,000, 100,000, and 300,000 ppb). The 50 ppb concentration of 2-butanone was selected for the interference test because 1) it reflects a typical lower end concentration of 2-butanone that appears in breath after ingestion of a typical dose of 2-butanol (i.e., 20 and 40 mg) (Example 3: Clinical Study 1-3), 2) it is close to the anticipated yes/no cutoff which will be used to determine medication adherence, and 3) based on prior device validation testing, it can be reliably used to measure a potential decrease in the mGC response.

Materials and Methods

Test Articles and Formulations

Interference testing was conducted using four (4) SMART® mGCs from Xhale Inc. The mGCs used had serial numbers 100113010009, 100113010010, 100113010011, and 100113010015, and are identified as 10009, 10010, 10011, and 10015, respectively, in this report.

1-L Tedlar gas sampling bags were purchased from SKC Inc. (Eighty Four, Pa.). Each bag was used only once. A single 10.0 mL Hamilton gas-tight syringe (Model Number 1010, Fisher Scientific part number 14-815-183) was used for the dilution of the 2-butanone gas standard.

The 200 proof anhydrous (>99.5%) ethanol used in this study was purchased from Sigma-Aldrich (part number 459835-100ML, Batch 54096BM). This neat standard was diluted in deionized water (DI) to make working solutions for injection into the Tedlar bags containing blank breath spiked with 2-butanone. 2-Butanone standards were created by diluting a primary NIST certified 10 ppm 2-butanone gas standard in dry nitrogen (Matheson Tri-Gas MICRO MAT 58 Item Number GMT2677977TH, Lot Number 109-26-07599, Expiration Date 5/11/14) into 1-L Tedlar bags containing blank breath.

2-Butanone Standard Creation and Analysis

The four SMART® mGCs used in this study were calibrated at the Nanoscale Research Facility of the University of Florida. Dilution of a NIST-certified 2-butanone gas standard into Tedlar gas sampling bags containing a blank breath sample was performed to create a calibration curve at four concentrations (0, 10, 25, and 50 ppb). Standard curves for 2-butanone were created on each of the four SMART® mGC.

Investigational Plan

The methodology in this study was developed using guidance from the Clinical and Laboratory Standards Institute (CLSI). Interference Testing in Clinical Chemistry; Approved Guideline, EP7-A2.

Ethanol interference with 2-butanone measurement was evaluated using paired-difference testing, by measuring the SMART® mGC response of 2-butanone (50 ppb) in the presence of increasing ethanol concentrations (30,000, 100,000, and 300,000 ppb), in spiked human breath samples.

The studies were performed in the Nanoscale Research Laboratory at the University of Florida. Each subject was fully informed on the experimental procedures, and the study was approved by the Western Institutional Review Board (WIRB) protocol 20130515.

Breath samples were collected from five (5) adult study participants. In order to provide baseline breath samples relatively free of VOCs including ethanol, participants were instructed not to consume alcoholic beverages for one day (24 h) and not to eat, drink or smoke for 15 minutes prior to their study visits. Each study volunteer provided six separate breath samples into individual 1-L Tedlar gas sampling bags over a period of 30 minutes (up to five minute break periods were allowed between breath samples).

Exclusion Criteria: Subjects found to have a high level of ethanol in their breath, or those physically unable to exhale 1-L breath samples into the Tedlar gas sampling bags.

After collection, the five breath samples from each participant were given a subject identifier (A, B C, D or E) and labeled individually as VOC 1 to 5. All samples were allowed to equilibrate overnight before the addition of 2-butanone or ethanol. After initial equilibration, bags VOC 2, VOC 3, VOC 4 and VOC 5 from each subject were spiked with 50 ppb of 2-butanone. Bags VOC 3, VOC 4 and VOC 5 from each subject were additionally spiked with 1 µL aliquots of aqueous ethanol standards to make breath samples containing 30,000, 100,000, and 300,000 ppb ethanol. Sample preparation of stock solutions, 2-butanone samples and test samples (i.e., containing three concentrations of ethanol) is listed below:

50 Ppb 2-Butanone

The 50 ppb 2-butanone concentration was obtained by diluting 5 cc of the 10 ppm of a NIST-certified 2-butanone gas standard, into Tedlar gas sampling bags containing 1-L blank breath sample. For the testing pool, neat ethanol was first diluted into DI water, then 1 µL aliquots were injected into 1-L of blank breath to make the ethanol standards used in this study as follows:

30,000 ppb Ethanol 70.5 µL of ethanol (55.7 µg) was diluted to 1.00 mL with water to produce a 55.7 µg/mL bag spiking solution. One µl of spiking solution was injected into an equilibrated 1-L Tedlar bag containing blank human breath to produce a 30,000 ppb (30 ppm) breath ethanol standard. 55.7 µg of ethanol/i L of breath=1308 µg/24.789 L of breath 100,000 ppb Ethanol 235 µL of ethanol (186 µg) was diluted to 1.00 mL with water to produce a 186 µg/mL bag spiking solution. One µl of spiking solution was injected into an equilibrated 1-L Tedlar bag containing blank human breath to produce a 100,000 ppb (100 ppm) breath ethanol standard.

186 µg of ethanol/i L of breath=4611 µg/24.789 L of breath 300,000 ppb Ethanol

705 µL of ethanol (557 µg) was diluted to 1.00 mL with water to produce a 557 µg/mL bag spiking solution. One µl of spiking solution was injected into an equilibrated 1-L Tedlar bag containing blank human breath to produce a 300,000 ppb (30 ppm) breath ethanol standard.

557 µg of Ethanol/1 L of Breath=13807 µg/24.789 L of Breath

Sample bags were allowed to equilibrate for two hours after addition of the final spiking component before analysis. The SMART® mGC 2-butanone response was evaluated in the spiked study bags (5 breath samples per test concentration), using each of the four (4) study SMART® mGC units.

Data Storage and Processing

All data was automatically stored to the Xhale secured servers. First derivative plots for the standards were imported into Microsoft Excel (Redmond, Wash.), and the peaks and retention times were determined for each compound.

Statistical Analyses

The degree of ethanol interference with the SMART® mGCs was calculated for each concentration of ethanol using Equation 1. For each device, results are expressed as mean percent interference at each concentration of ethanol (n=5 breath samples).

$$100 \times (mGC\ [response]_{((Interferent+Analyte))} - [mGC\ response]_{((Analyte))}) / [mGC\ response]_{((Analyte))} \quad (1)$$

where: the interferent is Ethanol the analyte is 2-butanol (50 ppb)

Statistical analysis of ethanol interference on mGC response to 50 ppb 2-butanone was carried out using one way analysis of variance (ANOVA) (SigmaPlot 11.2, Systat Software, Inc., San Jose, Calif.). P-values <0.05 were considered statistically significant. The upper limit of the 95% confidence interval (CI) for the interference effect was calculated across the four devices (n=4 devices). Clinical significant interference from ethanol was defined as a change in the SMART® mGC 2-butanol response of ≥20%.

Results and Discussion

The interfering effects from elevated concentrations of ethanol were determined on the ability of the SMART® mGC to detect 2-butanone at two levels using guidance from CLSI EP7: 1) response to 2-butanone as measured by the $1^{st}$ derivative, and 2) 2-butanone retention times. Summary of the 2-butanone retention times and mGC response (i.e., $1^{st}$ Derivative peak height) for control (i.e., 50 ppb 2-butanone without ethanol) and test samples (i.e., 50 ppb 2-butanol with ethanol at the specified concentrations) were created. Ethanol did not affect the retention time of 2-butanone on the SMART® mGC. In contrast, all concentrations of ethanol tested in this study caused a statistically significant decrease ($P<0.05$) in the SMART® mGC response to 50 ppb 2-butanone relative to control.

The percent interference observed for each of the four SMART® mGCs, that resulted from ethanol (30,000, 100,000, and 300,000 ppb) added to breath samples containing 50 ppb of 2-butanone was determined. At the lowest concentration of ethanol (30,000 ppb), the mean 2-butanone response on the mGCs ranged between −15.3% (mGC #10010) and −48.6% (mGC #10009) relative to control (i.e., 50 ppb 2-butanone without ethanol). At the highest concentration of ethanol (300,000 ppb) the mean mGC 2-butanone response showed a decrease of up to −70.3% (mGC #10010). Increasing ethanol concentrations resulted in a negative bias in the SMART® mGC response to 50 ppb 2-butanone on all the SMART® mGCs.

The overall interference caused by ethanol (30,000, 100,000, and 300,000 ppb) when added to breath samples containing 50 ppb 2-butanone was calculated as the upper limit of the 95% confidence interval (per CLSI EP7-A2 guidance) using the mean percent interference observed for each device (n=4 devices). Interference from ethanol with the 2-butanone response on the SMART® mGCs was calculated to be −50% (30,000 ppb), −64% (100,000 ppb), and −74% (300,000 ppb).

An ethanol concentration of 300,000 ppb can temporarily saturate the detector, and because of 1st derivative artifacts, appears as a loss of signal at the front-end of the chromatogram (this typically occurs between 25 and 40 s). However, since 2-butanone elutes much later than ethanol (approximately 70 seconds later), although the SMART® mGC response for 50 ppb 2-butanone is significantly decreased (by up to 50% at 30,000 ppb ethanol), a 2-butanone peak remains distinguishable even at the highest ethanol concentration (i.e., 300,000 ppb) studied. The presence of a distinguishable ethanol peak, or the apparent loss mGC response observed in the "front end" of the mGC chromatogram can be qualitatively assessed, and be used as an indicator of potential ethanol interference with the SMART® mGC System.

Conclusions

High concentrations of ethanol in breath can potentially interfere with the performance of the SMART® System by decreasing the 2-butanone response on the SMART® mGC. Using the upper limit of the 95% confidence interval (per CLSI EP7-A2 guidance), ethanol at 30,000, 100,000, and 300,000 ppb in breath reduced the SMART® mGC response to 50 ppb 2-butanone alone by 50%, 64%, and 74%, respectively. In contrast, the retention time of 2-butanone on the SMART® mGC was not affected by the presence of high concentrations of ethanol in breath.

The risk of inaccurate 2-butanone results in human breath (i.e., false negative results) that is associated with high breath concentrations of ethanol can be mitigated by at least two factors. First, this reduction in apparent 2-butanone breath concentration by ethanol will not be a significant issue with regard to SMART® mGC performance, because the majority of subjects (i.e., 98.4% positive response rate in 185 subjects) in clinical studies, who ingest the AEM, 2-butanol, generate increases in breath 2-butanone concentration above baseline values much greater than 5 ppb (Example 3: Clinical Studies 1-3). This finding is consistent with the results of clinical studies (Example 3: Clinical Studies 1-3) investigating the performance of the SMART® mGC System, which demonstrated favorable performance, even in subject populations enriched with participants having a significant alcohol drinking history.

Second, the potential negative impact of high concentrations of ethanol on the measurement of 2-butanone in breath can be rapidly recognized and mitigated by a qualitative assessment of the "front end" of the SMART® mGC chromatogram. Specifically, if a 2-butanone peak is not found on the SMART® mGC after ingesting the AEM, 2-butanol, and the mGC chromatogram indicates the presence of breath ethanol or signal loss, it would indicate that the presence of an interferent (i.e., alcohol) may have caused the breath concentration of 2-butanone to be falsely low.

REFERENCES

[1] Morey et al, Oral Adherence Monitoring Using a Breath Test to Supplement Highly Active Antiretroviral Therapy, *AIDS Behav* 17(1):298-306. 2013

[a] Lab data reference, SMART Logbook No. 8, pages 13-14—Document on file at Xhale, Inc., Gainesville, Fla.

[2] Wang, C., Yin, L., Xhang, L., Xiang, D., Gao, R. Metal Oxide Gas Sensors: Sensitivity and Influencing Factors. Sensors 2010, 10, 2088-2106.

[3] Barsan, N., Weimar, U., Understanding the Fundamental Principles of Metal oxide based gas sensors; the example of CO sensing with SnO2 sensors in the presence of humidity. J. Phys. Condens. Matter 15 (2003) R813-R839.

[4] Logen, B. K., Sistefano, S. Ethanol Content of Various Foods and Soft Drinks and their Potential for Interference with a Breath-Alcohol Test. Journal of Analytical Toxicology, Vol. 22, May/June 1998, 181-183.

[5] Phillips M, Greenberg J: Endogenous breath ethanol concentrations in abstinent alcohol abusers and normals Alcohol 5(3):263-265, 1988.

Overall Conclusions from Interference Studies

In conclusion the results of the four potential interferent studies indicate that the impact of potential interferents can be mitigated or even eliminated by using a baseline breath sample to detect any background EDIMs and correct for it and/or simply waiting a period of time for volatiles to clear from the mouth.

Furthermore, two alternate designs of the SMART® Adherence System can be used to markedly mitigate and even eliminate these potential interference to adherence system function: In a first embodiment to overcome interference, an adherence system is implemented that uses a Type I SMART® device to measure the simultaneous appearance in human breath of two or more EDIMs in human breath after ingestion of a medication labeled with two (or more) different AEMs. Example 4a illustrates and enables this approach. The appearance of multiple EDIMs after ingesting a medication labeled with more than one AEM will be so highly distinctive that it will not only eliminate most interferences, but it may well eliminate the need for a baseline breath sample in order to accurately detect adherence in the SMART® Adherence System.

Second, an adherence system that uses a Type II SMART® device (e.g., infrared based detector that measures e.g. deuterated EDIMs) will have no environmental or endogenous interferents. It is essentially free of interferents and should not require a baseline breath sample. Likewise, the latter approach using a Type 2 device (e.g., mid-IR) makes it technologically much easier to design and implement a SMART systems used for intermediate medication adherence monitoring (IMAM) and chronic medication adherence monitoring (CMAM), because an AEM like isopropyl alcohol will generate acetone, which has a breath half life of several hours to approximately a day. Because humans have significant amounts of endogenous acetone in breath, this limits the utility of this approach using a Type I device (mGC-MOS) since it would react to the endogenous acetone.

In contrast, a Type 2 device (e.g., mid-IR), would detect deuterated acetone which would be generated from deuterated isopropyl alcohol. Furthermore, mid=IR system can be extremely sensitive (ppt range) to measuring deuterated water.

Example 4a

Illustrations of how Multiple AEMs can be Employed in the SMART® Adherence System to Generate Different EDIMs in Human Breath that are Measured by a Type 1 SMART® Device.

The use of more than AEM in the SMART Adherence System to generate more than one EDIM can have a number of advantages: 1) the simultaneous appearance of multiple EDIMs in breath will essentially eliminate potential interferents (e.g., environmental, endogenous)

This example describes how two different AEMs (2-butanol and 2-pentanone) can be used to generate two different EDIMs with similar half lives in human breath that are measured by a Type 1 SMART® device.

Appearance of 2-butanone and 2-pentanone as the EDIMs in fasting humans after ingestion of a hard gel capsule containing an AEM formulation composed of 60 mg 2-butanol and 60 mg 2-pentanone. Note in the case of 2-butanol, the EDIM is a metabolite of the AEM, whereas in the case of 2-pentanone, it serves the role as the AEM and the EDIM (comes out in breath intact and not metabolized). The data shows that although inter-individual variability of EDIM appearance is greater than intra-individual variability, it does not affect the ability of the Type 1 device-based SMART® Adherence System to assess adherence. Likewise, it appears that early appearance of the EDIM in the breath following oral ingestion is primarily dependent on absorption of the AEM through the stomach mucosa and not enzymatic conversion of the secondary alcohol, 2-butanol, to 2-butanone.

Summary

A work- or residence-based, self-administered medication adherence monitoring system using exhaled breath is useful to identify and reduce clinical trial nonadherence. We studied the inter- and intra-individual variability for the exhalation of two adherence markers (2-butanone, 2-pentanone) in healthy subjects (n=5) with six replicates following oral consumption of encapsulated 2-butanol and 2-pentanone. Minimal-to-no intra-individual variability was observed for one-compartment pharmacokinetic parameters. Some inter-individual variability was noted for half-life, maximal concentrations, and area-under-the-curve estimates. Intra- or inter-individual variation in the time to achieve threshold concentrations of 2-butanone or 2-pentanone to signal adherence was not observed. ROC analysis revealed positive and negative predictive values near unity for breath sampling times >5 min and assumed adherence rates of 50-90%. The concurrent exhalation of 2-butanone and 2-pentanone indicates that enzymatic catalysis of 2-butanol to 2-butanone is not a rate limiting step of the system. We conclude that even with mild inter-individual variability, the system signals adherence from time points 10-60 min.

Introduction

Adherence to prescribed medication regimens is an important, uncontrolled source of variation in clinical trials spanning many therapeutic classes [1-5]. Peck attests to this fact by noting that unknown adherence behavior by subjects is the single largest determinant of variation in biological responses following theophylline administration [6]. This result is largely due to propagation of erroneous assumptions that subjects actually were adherent into calculations of pharmacokinetics (PK), pharmacodynamics (PD), and primary clinical endpoints. These ideas are borne into reality with such clinical trials as the Preexposure Prophylaxis Initiative (iPrEx) wherein subjects with >90% adherence had a 73% risk reduction for HIV acquisition with oral tenofovir disoproxil fumarate and emtricitabine therapy, but subjects with <90% adherence had only a 21% benefit [1, 7]. Similarly, Woldu and colleagues discovered that nonadherence was " . . . a common and significant source of treatment nonresponse . . . " for 190 therapy-resistant, depressed adolescents contemplating suicide and believed by investigators to be receiving selective serotonin reuptake inhibitors [8]. Additionally, whereas great attention is focused on drug formulation to exert rigid tolerances on chemistry manufacturing and control (CMC), minimal-to-no effort occurs to even measure adherence. Moreover, subject adherence is the last, potentially measurable and/or governable event prior to uncontrollable PK and PD properties that are unique to each subject. For these reasons, we assert that subject adherence is important to measure in clinical trials and previously suggested a new method to achieve this aim [9-11].α

This novel technique entails co-packaging an innocuous, chemical taggant with an oral medication. The taggant (or its metabolite) may appear in exhaled breath after absorption by the gastrointestinal mucosa. For example, we demonstrated in a feasibility study that 2-butanone is rapidly exhaled (5-15 min) after subjects swallowed encapsulated 2-butanol [9]. Furthermore, 2-butanone can be readily measured by a home- or work-based, portable, self-administered, HIPAA-compliant, miniature gas chromatographic (mGC) device that conveys this information to a central data repository for review by study coordinators or health care personnel [10]. Moreover, this technique can be used for non-oral routes of delivery, such as vaginal or rectal administration [10]. Herein, we sought to determine the intra- and inter-individual variability associated with this technique to monitor oral adherence with respect to exhalation of 2-butanone, a metabolite of 2-butanol (a taggant incorporated into a capsule) catalyzed by aa-alcohol dehydrogenase (ADH), an enzymatic isoform not subject to ethnic variations as are other variants of ADH [12-14]. Additionally, because 2-butanol essentially serves as an inactive "prodrug" for adherence verification, we also added 2-pentanone that we hypothesize is exhaled without the need for metabolism due to its physical characteristics.

Methods

Test Materials. 2-butanol (60 mg), 2-pentanone (60 mg), and inert L-carvone (30 mg) were inserted within a hard gel capsule (size 3, LiCaps®, Capsugel, Greenwood, S.C.).

2-butanol was purchased from Penta Manufacturing Company (Fairfield, N.J.). 2-pentanol and L-carvone were purchased from Sigma-Aldrich (St. Louis, Mo.). Each capsule constituent had a unique role. 2-butanol was used as a taggant that is metabolized to produce 2-butanone, a volatile marker that appears in breath. 2-pentanone was also used as a taggant, but we hypothesized that its inherent volatility would allow exhalation without need for metabolism. L-carvone tastes like spearmint and was used as a flavor mask. All capsules were filled on the day of the experiment.

Subject Enrollment and Protocol. This protocol (20100140) was approved by the Western Institutional Review Board (Olympia, Wash.). Healthy subjects (n=5) aged >18 years of age and of either sex were recruited. Informed, written consent was obtained from all enrolled subjects. The study consisted of a single experimental limb with six replicates per subject. Therefore, for five subjects with six replicated experiments, a total of 30 studies were performed. Subjects were free to eat ad lib prior to participation in the study. At commencement of the experiments, subjects provided a baseline breath sample (designated time 0 min) into the mGC for analysis as described subsequently. Then, subjects orally consumed the previously detailed capsule with 177 mL (6 ounces) of water. Following ingestion, we observed the breath concentration-time relationships of 2-butanone and 2-pentanone by collecting single-breath samples at times 5, 10, 15, 20, 30, 45, and 60 min. After 60 min, the experiment was concluded. After at least one day's respite, subjects returned for replicate experiments on five additional occasions.

2-Butanone and 2-Pentanone Measurement in Human Breath by mGC. Breath specimens were analyzed "real-time" to measure the concentrations of 2-butanone and 2-pentanone using the mGC (Xhale, Inc. Gainesville, Fla.) as previously described [9-11, 15]. In brief, a mouthpiece (FST®, Intoximeters, Inc., St. Louis, Mo.) was attached to the inlet of the mGC. A 15 mL side-stream sample was aspirated during a single exhalation over 5 s through this inlet port to a room temperature concentrator trap containing 4 mg of Tenax TA (Sigma-Aldrich). The trap temperature was then increased to 130° C. and the volatile components transferred to a 5 m by 0.53 mm internal diameter, metal clad, BAC-1 capillary column (Restek Corp, Bellefonte, Pa.) operated at 55° C. The effluent from the column then flowed to the metal oxide detectors. Separation of the markers from other volatile organic compounds present in the sample (i.e., acetone and isoprene) occurred in approximately 2 min. Data were tabulated and graphically presented over time to determine the concentrations of 2-butanone and 2-pentanone in a given breath specimen. Data are reported in parts-per-billion (ppb) based on molar fractions to account for differing ambient atmospheric pressures and temperature [10]. A sample mGC chromatogram of a human breath sample following ingestion of the hard gel capsule containing 60 mg 2-butanol and 60 mg 2-pentanol is shown in FIG. 70A.

Data Analysis

Pharmacokinetic Analysis. Analyte breath concentrations reported as ppb were converted to ng/mL by multiplying each concentration by the molecular weight of the respective molecule to allow proper functioning of conventional PK software for noncompartmental analysis (WinNonlin 5.2, Pharsight Corporation, St. Louis, Mo.). Estimates were generated for the following PK parameters (abbreviation, unit): first-order elimination rate constant (Lambda_Z, min-1), half-life of elimination (Half-life, min), maximal drug concentration ($C_{MAX}$, μg/mL), time at maximal drug concentration ($T_{MAX}$, min), area under concentration versus time curve from zero to the last time point ($AUC_{0-LAST}$, min*μg/mL), area under concentration versus time curve from zero to infinity ($AUC_{0-\infty}$, min*μg/mL), percentage of area under concentration versus time curve from zero to infinity, which is extrapolated from $AUC_{0-t}$ (% AUC Extrap) and the mean residence time (MRT, min). The area under concentration versus time curve (AUC) was calculated using the linear trapezoidal rule. All values are reported separately for each subject as mean±standard deviation following conversion from ng/mL to ppb. For parameters obtained from the non-compartmental analysis, the coefficient of variation across subjects was calculated for each replicate. Additionally, the threshold time ($T_{Thresh}$) was determined that represents the time for the breath concentration of 2-butanone or 2-pentanone to exceed the detection concentration for mGC.

Receiver Operator Curves. ROC analysis was conducted using SigmaPlot 12.3 (Systat Software, Inc., Chicago, Ill.). When modeling positive and negative predictive values based on measured concentrations of 2-butanone or 2-pentanone, we assumed pre-test probability rates of 50%, 70%, and 90% for actual adherence.

Results

Each of the five subjects successfully completed a total of six replicated studies. Demographically, subjects were aged 47±5 years with 3 men and 2 women, all of non-Hispanic, white race self-identification. Their mean body mass and mean height was 89±30 kg and 179±15 cm, respectively, for a calculated mean body mass index of 27±5 kg/m2. No adverse events were reported or observed. For all 30 visits, 2-butanone and 2-pentanone appeared in breath as measured by the mGC. The overall concentration-time plots for 2-butanone and 2-pentanone are shown in FIG. 70B and demonstrate the similarity of these relationships for both exhaled markers. The PK parameter estimates from the noncompartmental analysis for 2-butanone and 2-pentanone are noted in the following Table 4a-I:

TABLE 4a-I

Exhaled 2-butanone and 2-pentanone pharmacokinetic parameter estimates for noncompartmental analysis for human subjects (n = 5) with six replicates for each subject. $T_{Thresh}$ represents the time for the breath concentration of 2-butanone or 2-pentanone to exceed the detection concentration for the miniature gas chromatograph (mGC). Data expressed as mean (standard deviation) for 30 observations (5 subjects with 6 replicates per subject).

| Parameter | 2-butanone | 2-pentanone | P |
|---|---|---|---|
| $T_{Thresh}$ (min) | 6.2 (2.2) | 5.7 (1.7) | 0.08 |
| LAMBDA_Z (min$^{-1}$) | 0.036 (0.013) | 0.033 (0.012) | <0.01 |
| Half-life (min) | 21.6 (8.0) | 23.7 (9.1) | 0.03 |
| $C_{MAX}$ (ppb) | 1376 (820) | 1424 (741) | 0.25 |
| $T_{MAX}$ (min) | 17.8 (8.8) | 14.8 (8.0) | <0.01 |
| $AUC_{0-LAST}$ (min · ppb) | 41820 (27104) | 45614 (25196) | <0.01 |
| $AUC_{0-\infty}$ (min · ppb) | 51190 (32170) | 58214 (32308) | <0.01 |
| % AUC Extrap | 17.9 (8.4) | 19.7 (8.9) | 0.10 |
| $MRT_{0-LAST}$ (min) | 25.7 (4.8) | 25.4 (4.1) | 0.32 |

Both exhaled markers appeared quickly in breath with similar $T_{Thresh}$ values of approximately 5-6 min. Comparing 2-butanone and 2-pentanone, significant differences of modest magnitude were observed for LAMDA_Z, half-life, $T_{MAX}$, $AUC_{0-LAST}$, and $AUC_{0-\infty}$. In most cases, 2-butanone and 2-pentanone concentrations could be quantified in breath within 5 min post-ingestion and were still detectable at 60 min, the scheduled termination for each study.

Inter-subject Variability. To discover the possible presence of inter-subject variability, the mean concentrations for 2-butanone and 2-pentanone for each time point were plotted by subject (FIG. 70C). As expected, time markedly affected the concentration of both exhaled markers ($P<0.01$). Additionally, the particular subject significantly affected the concentration-time relationships ($P<0.01$). Calculated PK parameters for 2-butanone and 2-pentanone are shown in Tables 4a-II and 4a-III, respectively.

TABLE 4a-II

Inter-individual, exhaled 2-butanone pharmacokinetic parameter estimates for noncompartmental analysis for human subjects (n = 5) with six replicates for each subject. $T_{Thresh}$ represents the time for the breath concentration of 2-butanone to exceed the detection concentration for the miniature gas chromatograph (mGC). Data expressed as mean (standard deviation).

| Parameter | SUBJECT 1 | SUBJECT 2 | SUBJECT 3 | SUBJECT 4 | SUBJECT 5 | P |
|---|---|---|---|---|---|---|
| $T_{Thresh}$ (min) | 6.7 (2.6) | 5.0 (0.0) | 5.8 (2.0) | 5.8 (2.0) | 7.5 (2.7) | 0.38 |
| LAMBDA_Z ($min^{-1}$) | 0.033 (0.008) | 0.034 (0.005) | 0.024 (0.008) | 0.043 (0.010) | 0.046 (0.017) | <0.01 |
| Half-life (min) | 22.6 (6.1) | 20.6 (3.2) | 30.7 (9.0) | 16.4 (3.4) | 17.5 (8.9) | <0.01 |
| $C_{MAX}$ (ppb) | 1297 (451) | 1926 (240) | 1021 (710) | 2238 (709) | 398 (258) | <0.01 |
| $T_{MAX}$ (min) | 21.7 (10.3) | 20.8 (4.9) | 11.7 (10.8) | 18.3 (8.2) | 16.7 (7.5) | 0.37 |
| $AUC_{0-LAST}$ (min · ppb) | 45298 (16577) | 66466 (5169) | 19608 (11599) | 68147 (18758) | 9581 (7641) | <0.01 |
| $AUC_{0-\infty}$ (min · ppb) | 59106 (19881) | 82628 (10044) | 25623 (15159) | 77593 (19556) | 10999 (8576) | <0.01 |
| % AUC Extrap | 22.6 (11.0) | 19.2 (3.5) | 23.2 (4.7) | 12.6 (3.3) | 12.0 (10.5) | 0.02 |
| $MRT_{0-LAST}$ (min) | 29.3 (5.9) | 27.7 (1.6) | 22.7 (5.5) | 26.2 (3.2) | 22.9 (3.6) | 0.06 |

TABLE 4a-III

Inter-individual, exhaled 2-pentanone pharmacokinetic parameter estimates for noncompartmental analysis for human subjects (n = 5) with six replicates for each subject. $T_{Thresh}$ represents the time for the breath concentration of 2-pentanone to exceed the detection concentration for the miniature gas chromatograph (mGC). Data expressed as mean (standard deviation)

| Parameter | SUBJECT 1 | SUBJECT 2 | SUBJECT 3 | SUBJECT 4 | SUBJECT 5 | P |
|---|---|---|---|---|---|---|
| $T_{Thresh}$ (min) | 5.8 (2.0) | 5.0 (0.0) | 5.8 (2.0) | 5.0 (0.0) | 6.7 (2.6) | 0.43 |
| LAMBDA_Z ($min^{-1}$) | 0.029 (0.007) | 0.030 (0.004) | 0.023 (0.009) | 0.040 (0.08) | 0.042 (0.015) | <0.01 |
| Half-life (min) | 24.8 (5.6) | 23.2 (2.6) | 34.6 (13.3) | 17.9 (3.5) | 17.8 (5.2) | <0.01 |
| $C_{MAX}$ (ppb) | 1328 (396) | 1850 (180) | 1134 (859) | 2072 (697) | 536 (290) | <0.01 |
| $T_{MAX}$ (min) | 20.0 (9.5) | 15.8 (4.9) | 10.0 (10.0) | 15.0 (7.7) | 13.3 (6.1) | 0.34 |
| $AUC_{0-LAST}$ (min · ppb) | 49094 (17665) | 68008 (6249) | 31020 (18913) | 66164 (17202) | 13783 (9108) | <0.01 |
| $AUC_{0-\infty}$ (min · ppb) | 65626 (21989) | 87240 (9622) | 45947 (34360) | 76450 (19188) | 15806 (10707) | <0.01 |
| % AUC Extrap | 24.5 (9.7) | 21.9 (2.6) | 27.1 (9.1) | 13.6 (2.7) | 11.1 (5.5) | <0.01 |
| $MRT_{0-LAST}$ (min) | 28.4 (4.9) | 27.3 (1.4) | 23.7 (4.6) | 25.6 (2.6) | 22.2 (3.4) | 0.40 |

Although significant differences were observed for several PK parameters, we did not observe significant inter-subject variability with respect to $T_{Thresh}$ for either 2-butanone ($P=0.38$) or 2-pentanone ($P=0.43$).

Intra-subject Variability. To determine the degree of intra-subject variability in exhalation of the breath markers, we re-indexed the concentration-time relationships for 2-butanone and 2-pentanol by replicated group 1-6 (FIG. 70D). For all subjects, these relationships were significantly affected by time as expected, but the replicate groups had no overall effect for either 2-butanone ($P=0.32$) or 2-pentanone ($P=0.12$). PK parameter estimates were calculated for 2-butanone (Table 4a-IV) and 2-pentanone (Table 4a-V) by replicate groups.

TABLE 4a-IV

Intra-individual, exhaled 2-butanone pharmacokinetic parameter estimates for noncompartmental analysis for human subjects (n = 5) with six replicates for each subject. $T_{Thresh}$ represents the time for the breath concentration of 2-butanone to exceed the detection concentration for the miniature gas chromatograph (mGC). Data expressed as mean (standard deviation) for the same 5 subjects in each replicate.

| Parameter | REPLICATE1 | REPLICATE2 | REPLICATE3 | REPLICATE4 | REPLICATE5 | REPLICATE6 | P |
|---|---|---|---|---|---|---|---|
| $T_{Thresh}$ (min) | 5.0 (0.0) | 7.0 (2.7) | 6.0 (2.2) | 6.0 (2.2) | 7.0 (2.7) | 6.0 (2.2) | 0.72 |
| LAMBDA_Z ($min^{-1}$) | 0.036 (0.011) | 0.033 (0.013) | 0.048 (0.019) | 0.038 (0.013) | 0.026 (0.007) | 0.037 (0.004) | 0.04 |
| Half-life (min) | 21.1 (7.0) | 24.1 (9.8) | 16.4 (5.7) | 21.2 (11.8) | 27.7 (6.7) | 18.9 (1.9) | 0.09 |
| $C_{MAX}$ (ppb) | 1793 (585) | 1361 (502) | 1175 (1089) | 1449 (1259) | 1227 (630) | 1251 (887) | 0.47 |
| $T_{MAX}$ (min) | 15.0 (7.1) | 21.0 (10.2) | 17.0 (9.7) | 19.0 (10.8) | 15.0 (10.6) | 20.0 (6.1) | 0.85 |
| $AUC_{0-LAST}$ (min · ppb) | 53278 (26769) | 44693 (19393) | 36508 (33613) | 44467 (38862) | 37792 (26067) | 34184 (24534) | 0.19 |
| $AUC_{0-\infty}$ (min · ppb) | 64618 (33892) | 58070 (24341) | 42226 (38250) | 52141 (43170) | 491783 (32325) | 40905 (29441) | 0.10 |
| % AUC Extrap | 41.3 (13.8) | 47.3 (16.2) | 31.3 (16.2) | 37.3 (20.9) | 54.6 (11.3) | 39.2 (7.1) | 0.07 |
| $MRT_{0-LAST}$ (min) | 24.4 (4.0) | 28.3 (6.2) | 24.8 (4.2) | 23.9 (4.6) | 26.6 (6.4) | 26.5 (3.6) | 0.60 |

TABLE 4a-V

Intra-individual, exhaled 2-pentanone pharmacokinetic parameter estimates for noncompartmental analysis for human subjects (n = 5) with six replicates for each subject. $T_{Thresh}$ represents the time for the breath concentration of 2-pentanone to exceed the detection concentration for the miniature gas chromatograph (mGC). Data expressed as mean (standard deviation) for the same 5 subjects in each replicate.

| Parameter | REPLICATE1 | REPLICATE2 | REPLICATE3 | REPLICATE4 | REPLICATE5 | REPLICATE6 | P |
|---|---|---|---|---|---|---|---|
| $T_{Thresh}$ (min) | 5.0 (0.0) | 7.0 (2.7) | 5.0 (0.0) | 6.0 (2.2) | 5.0 (0.0) | 6.0 (2.2) | 0.37 |
| LAMBDA_Z ($min^{-1}$) | 0.030 (0.012) | 0.032 (0.015) | 0.042 (0.018) | 0.033 (0.008) | 0.027 (0.004) | 0.034 (0.004) | 0.17 |
| Half-life (min) | 27.5 (15.2) | 26.1 (12.6) | 18.7 (6.7) | 22.7 (8.3) | 26.1 (3.9) | 20.9 (2.6) | 0.32 |
| $C_{MAX}$ (ppb) | 1885 (558) | 1472 (493) | 1253 (9038) | 1519 (1152) | 1297 (595) | 1119 (694) | 0.31 |
| $T_{MAX}$ (min) | 15.0 (7.1) | 15.0 (10.0) | 12.0 (7.6) | 12 (7.6) | 15.0 (10.6) | 20 (6.3) | 0.67 |
| $AUC_{0-LAST}$ (min · ppb) | 61008 (22007) | 49788 (16350) | 40006 (31881) | 46918 (34952) | 41780 (24960) | 34184 (21188) | 0.05 |
| $AUC_{0-\infty}$ (min · ppb) | 81227 (31128) | 66524 (23396) | 48111 (37965) | 56515 (40544) | 54688 (32234) | 42218 (32234) | 0.03 |
| % AUC Extrap | 22.8 (12.6) | 23.0 (11.7) | 14.8 (8.7) | 16.6 (7.0) | 22.2 (7.7) | 18.5 (3.4) | 0.23 |
| $MRT_{0-LAST}$ (min) | 25.2 (2.5) | 27.3 (5.1) | 24.1 (5.1) | 24.2 (3.6) | 25.3 (5.4) | 26.5 (3.2) | 0.73 |

In contrast, to Table 4a-II and 4a-III, only LAMDA_Z attained statistical significance for 2-butanol and AUC0-∞ for 2-pentanone. Importantly, $T_{Thresh}$ for 2-butanone (P=0.72) or 2-pentanone (P=0.37) did not significantly differ between replicates and had a range of 5-7 min. 3 Additionally, we plotted the all concentration values of 2-butanone (n=240) against that for concurrently collected 2-pentanone (FIG. 70E). The regressed line demonstrated a very high coefficient of determination (r2=0.93) and a slope near identity (0.99±0.02).

ROC Analysis. We performed ROC determinations to understand the ability of this system to predict adherence. Values for ROC analysis are noted in Table 4a-VI for both 2-butanone and 2-pentanone.

TABLE 4a-VI

Receiver operator curve (ROC) data for exhaled 2-butanone and 2-pentanone from human subjects (n = 5 subjects with 6 replicates/subject) after orally consuming encapsulated 2-butanol and 2-pentanone. Data shown are ROC areas with parenthetical 95% confidence intervals. $P_{0.50}$ is the Type I error risk that a ROC area for a given time point is different from a ROC area of 0.50.

|  | 2-butanone | | 2-pentanone | |
|---|---|---|---|---|
| Time (min) | ROC Area | $P_{0.50}$ | ROC Area | $P_{0.50}$ |
| 5 | 0.88 (0.81-0.96) | <0.01 | 0.93 (0.87-0.99) | <0.01 |
| 10 | 1.00 (1.00-1.00) | <0.01 | 1.00 (1.00-1.00) | <0.01 |
| 15 | 1.00 (1.00-1.00) | <0.01 | 1.00 (1.00-1.00) | <0.01 |
| 20 | 1.00 (1.00-1.00) | <0.01 | 1.00 (1.00-1.00) | <0.01 |
| 30 | 1.00 (1.00-1.00) | <0.01 | 1.00 (1.00-1.00) | <0.01 |
| 45 | 1.00 (1.00-1.00) | <0.01 | 1.00 (1.00-1.00) | <0.01 |
| 60 | 1.00 (1.00-1.00) | <0.01 | 1.00 (1.00-1.00) | <0.01 |

The ROC areas for both taggants escalated rapidly to unity during the first 10 min after capsule ingestion and remained sustained up to 60 min, the conclusion of the study.

Additional sensitivity and specificity data at suggested cut-off concentrations are tabulated for 2-butanone and 2-pentanone in tables 4a-VII and 4a-VIII, respectively.

TABLE 4a-VII

Sensitivity and specificity analysis detailing accuracy over 5-60 min with suggested "cut off" concentrations for exhaled 2-butanone from human subjects (n = 5 subjects with 6 replicates/subject) after orally consuming encapsulated 2-butanol and 2-pentanone. Cut-off represents the concentration of 2-butanone above which a subject is identified as adherent. Parenthetical values are 95% confidence intervals. Abbreviations: PPV, positive predictive value; NPV, negative predictive value. Predictive values were based on sensitivity and specificity for an assumed rate of adherence as specified in the table.

| Time (min) | Cut-off (ppb) | Sensitivity | Specificity | Assumed Adherence Rate (%) PPV/NPV | | |
|---|---|---|---|---|---|---|
| | | | | 50 | 70 | 90 |
| 5 | 20.9 | 0.77 (0.58-0.90) | 1.00 (0.88-1.00) | 1.00/ 0.81 | 1.00/ 0.65 | 1.00/ 0.32 |
| 10 | 15.1 | 1.00 (0.88-1.00) | 1.00 (0.88-1.00) | 1.00/ 1.00 | 1.00/ 1.00 | 1.00/ 1.00 |
| 15 | 29.8 | 1.00 (0.88-1.00) | 1.00 (0.88-1.00) | 1.00/ 1.00 | 1.00/ 1.00 | 1.00/ 1.00 |
| 20 | 40.1 | 1.00 (0.88-1.00) | 1.00 (0.88-1.00) | 1.00/ 1.00 | 1.00/ 1.00 | 1.00/ 1.00 |
| 30 | 9.2 | 1.00 (0.88-1.00) | 1.00 (0.88-1.00) | 1.00/ 1.00 | 1.00/ 1.00 | 1.00/ 1.00 |
| 45 | 2.1 | 1.00 (0.88-1.00) | 1.00 (0.88-1.00) | 1.00/ 1.00 | 1.00/ 1.00 | 1.00/ 1.00 |
| 60 | 2.0 | 1.00 (0.88-1.00) | 1.00 (0.88-1.00) | 1.00/ 1.00 | 1.00/ 1.00 | 1.00/ 1.00 |

TABLE 4a-VIII

Sensitivity and specificity analysis detailing accuracy over 5-60 min with suggested "cut off" concentrations for exhaled 2-pentanone from human subjects (n = 5 subjects with 6 replicates/subject) after orally consuming encapsulated 2-butanol and 2-pentanone. Cut-off represents the concentration of 2-butanone above which a subject is identified as adherent. Parenthetical values are 95% confidence intervals. Abbreviations: PPV, positive predictive value; NPV, negative predictive value. Predictive values were based on sensitivity and specificity for an assumed rate of adherence as specified in the table.

| Time (min) | Cut-off (ppb) | Sensitivity | Specificity | Assumed Adherence Rate (%) PPV/NPV | | |
|---|---|---|---|---|---|---|
| | | | | 50 | 70 | 90 |
| 5 | 29.1 | 0.87 (0.69-0.96) | 1.00 (0.88-1.00) | 1.00/ 0.88 | 1.00/ 0.76 | 1.00/ 0.45 |
| 10 | 56.5 | 1.00 (0.88-1.00) | 1.00 (0.88-1.00) | 1.00/ 1.00 | 1.00/ 1.00 | 1.00/ 1.00 |
| 15 | 59.1 | 1.00 (0.88-1.00) | 1.00 (0.88-1.00) | 1.00/ 1.00 | 1.00/ 1.00 | 1.00/ 1.00 |
| 20 | 57.5 | 1.00 (0.88-1.00) | 1.00 (0.88-1.00) | 1.00/ 1.00 | 1.00/ 1.00 | 1.00/ 1.00 |
| 30 | 27.6 | 1.00 (0.88-1.00) | 1.00 (0.88-1.00) | 1.00/ 1.00 | 1.00/ 1.00 | 1.00/ 1.00 |
| 45 | 10.0 | 1.00 (0.88-1.00) | 1.00 (0.88-1.00) | 1.00/ 1.00 | 1.00/ 1.00 | 1.00/ 1.00 |
| 60 | 3.5 | 1.00 (0.88-1.00) | 1.00 (0.88-1.00) | 1.00/ 1.00 | 1.00/ 1.00 | 1.00/ 1.00 |

Also, calculated positive and negative predictive values are noted for both taggants in these tables for pre-test probability adherence rates of 50%, 70%, and 90%, the adherence rate from the iPrEx study [1, 7]. From times 10-60 min, positive and negative predictive values were 1.00 and 1.00, respectively, for adherence rates of 50%-90%.

Discussion

In this study, 2-butanone and 2-pentanone concentrations could be measured by mGC in every subject's and every replicate's breath following ingestion of encapsulated 2-butanol and 2-pentanone. In most cases, detectable concentrations were observed as early as 5 min and in all cases by 10 min after ingestion. As illustrated in FIGS. 70C and 70D and in the tabulated PK data, we observed more inter-individual variability compared to intra-individual variability. We suggest that the majority of inter-individual variability is may be due to bioavailability of 2-butanol and 2-pentanone. To our knowledge, minimal-to-no research has been reported describing the bioavailability of these compounds in humans, although some animal work has been published. Dietz and colleagues fed 2-butanol to rats to understand this compound's metabolism [16]. They reported that approximately 97% of ingested 2-butanol is metabolized to 2-butanone, that the major site of metabolism is the liver, and that transformation rate is dependent on liver blood perfusion. In the absence of detailed human data for 2-butanol or 2-pentanone, we hypothesize that consideration of another alcohol's (i.e., ethanol) PK may be instructive since the PK of ethanol has been well studied due to its legal implications. In a review, Norberg and colleagues noted that gastrointestinal absorption is an important parameter of ethanol PK and that the " . . . major factor governing the absorption rate of ethanol is whether the drink is taken on an empty stomach (overnight fast) or together with or after a meal" with minor factors including meal composition, liver blood flow, and others [17]. Notwithstanding, although we did not control for feeding state in the present study, in another investigation we demonstrated that fasting or consumption of a high fat meal did not affect production of 2-butanone in humans [9]. The total dose of ethanol in human studies is, however, orders of magnitude greater than that for 2-butanol. Assuming 10 g of ethanol in a standard drink and reiterating that the authors used 0.060 g of 2-butanol, a single ethanol beverage contains 166,667-fold more alcohol. The experimental model used herein unfortunately does not allow control for other factors affecting absorption across the gastrointestinal mucosa or differing blood perfusion from gastric veins to the portal venous circulation of the liver.

Irregular elimination of 2-butanone and 2-pentanone by exhalation between subjects may also lead to the inter-individual variability. Again looking to ethanol for guidance, Lindberg and Grubb concluded that the volume of respiratory dead space in a particular subject markedly affects the arterial blood-to-breath concentrations of another exhaled ethanol [18]. Likewise, variations in voluntary breath patterns may cause some PK differences even though careful instructions and practice exhalation were provided to each subject in the present report. That is, Boshier and colleagues observed that different subject respiratory maneuvers (e.g., hyperventilation, breath holding) significantly modified the exhaled concentrations of ethanol, methanol, and acetone [19]. For these additional reasons, PK may vary both between individuals although little variation was observed within an individual subject over 6 replicated studies.

In the broader context, however, the magnitude of these inter- and intra-individual variations must be placed in the clinical context of the required concentrations to measure adherence when deployed to study subjects. That is, the primary purpose of addition of the taggants 2-butanol and 2-pentanone was to facilitate monitoring of oral adherence using a portable, self-administered, HIPAA-compliant mGC. To that end, PK parameters must be considered in the context of the capabilities of the mGC and clinical trial design. Notwithstanding the observed PK inter-individual variability, 2-pentanone and 2-butanone concentrations could be readily quantified in all 30 visits by the mGC. Considering the lower concentration limits of quantification for the mGC of approximately 1.0 ppb for both 2-butanone and 2-pentanone, the observed $C_{MAX}$ ranges for 2-butanone (398-2,238 ppb) and 2-pentanone (536-2,072 ppb) were more than suitable to measure these analytes. In fact, such large concentrations emanating from the lungs with $T_{MAX}$ values of 10-22 min suggest that subjects may be able to provide breath specimens to the mGC in a much shorter time frame after consuming a capsule. Likewise, the rapid rate of rise for both exhaled compounds to $T_{Thresh}$ values of 5-6 min alludes to the possibility of measuring the compounds sooner after ingestion of the capsule. That is, the window to provide a breath sample is currently 5-60 min. This period may be broadened to include some values <5 min and perhaps longer than 60 min. Rapid detection of these molecules in breath following oral administration allows for flexibility and convenience for subjects actually providing breath specimens.

Additionally, we determined that the variability did not impact overall assessments of capsule consumption using ROC analysis. At every time point after consumption based on $P_{0.50}$ values, this system was markedly better than guessing. Similarly, the positive and negative predictive values for a variety of pre-test probabilities were unity for time points after 5 min for both 2-butanone and/or 2-pentanone. The negative predictive value data reported herein are improved compared to earlier studies of 2-butanone wherein these values were 0.31-0.89 for time points 30-60 min after ingestion [9]. We believe that the 50% increase in 2-butanol mass from 40 mg to 60 mg likely accounted for this improvement in the last half of study observations and suggests that study design will inform decision making about the dose of adherence marker for an particular clinical trial. The negative predictive value data from time points 0-20 min were very similar and appeared to not change with increased 2-butanol mass whereas the positive predictive value data were similar for all time points. Recently, van der Straten and colleagues observed that a breath test for use of vaginal placement of tenofovir placebo gel or lubricated condoms was " . . . 100% accurate . . . " although these investigators used esters of 2-butanol and 2-pentanol [11]. To date, there are no previous reports of exhaled 2-pentanone for review and comparison to the data presented herein. Therefore, the system provided adequate adherence signals even with intra- and inter-individual variability, differing doses between studies, and both oral and vaginal routes (rectal administration remains to be examined).

Three limitations warrant mention when considering this data that may be valuable to those skilled in the art when practicing the present invention and implementing the SMART® system. (A) Resolution and duration of sampling: Earlier and more frequent sampling at times <5 min enable fine discrimination of the minimum latency before a breath sample can be provided to measure adherence. Increasing the duration of sampling allows sufficient decrements in exhaled marker concentrations (which were approximately 100-1,000 ppb at 60 min) to improve error revolving around the AUC PK parameters. (B) Differences in ambient temperature and pressure require us to report exhaled gas parameters as ppb based on molar fractions [10]. In this study, we provided a constant mass (60 mg) of 2-butanol (molar mass: 74.13 g/mol) and 2-pentanol (molar mass: 86.13 g/mol) which leads to differing molar doses because these two compounds have different molecular weights. That is, we provided 13.8% more 2-butanol than 2-pentanol based on molar dosing which complicates data interpretation. Notwithstanding, the exhalation of both these markers was approximately the same based on the slope of identity noted in FIG. 70E, which indicates two findings: 1) the PK parameters of the AEMs and their EDIMs are similar (not surprising given their structural similarities and close molecular weights), and 2) the processes of absorption of the AEMs (2-butanol and 2-butanone) from the gastrointestinal tract (e.g., stomach) are very rapid and enzymatic conversion of 2-butanol to 2-butanone is not rate limiting. This finding of a slope of 1 for equal mass dosing (60 mg) of 2-butanol and 2-pentanone, imply that different drugs and/or dosage forms could be effective labeled by varying the ratio of 2-butanol to 2-pentanone. For example, because their structures and molecular characteristics are so similar, it is expected that their PK parameters should be very similar. This finding is consistent with the slope of 1 found in FIG. 70E. Thus, it would be expected based on this disclosure that an orally administered AEM formulation containing a 2-butanol: 2-pentanone dose ratio of 10:1, 3:1, 1:1, 1:3, 1:10 would yield an 2-butanone: 2-pentanone EDIM ratio of 10, 3, 1, 0.33, and 0.10, respectively. This would manifest as a graph as shown in FIG. 70E with 2-butanone (y axis): 2-pentanone (x axis) slopes of 10, 3, 1, 0.33, and 0.10, respectively. (C) The subjects reported in this pilot project were healthy and of a modest magnitude number.

Greater numbers of subjects and cohorts with HIV/AIDS and other diseases increases the data available for application of this system to these particular populations.

Conclusions

The results of this pilot study demonstrate that 2-butanone and 2-pentanone can be detected in breath following oral administration. For the purposes of measuring oral adherence within the context of mGC use and relatively large exhaled concentrations of 2-butanone and 2-pentanone, the variability in PK appears to have a negligible effect on adherence signals.

REFERENCES

1. Grant R M, Lama J R, Anderson P L, et al. Preexposure chemoprophylaxis for HIV prevention in men who have sex with men. N Engl J Med. 2010; 363:2587-99.
2. Hogg R S, Heath K, Bangsberg D, et al. Intermittent use of triple-combination therapy is predictive of mortality at baseline and after 1 year of follow-up. AIDS. 2002; 16:1051-8.
3. Lo R V, Teal V, Localio A R, et al. Relationship between adherence to hepatitis C virus therapy and virologic outcomes: a cohort study. Ann Intern Med. 2011; 155: 353-60.
4. Rolnick S, Pawloski P, Bruzek R, et al. PS2-32: Barriers and facilitators for medication adherence. Clin Med Res. 2011; 9:157.
5. Allen N E, Sherrington C, Suriyarachchi G D, et al. Exercise and motor training in people with Parkinson's disease: a systematic review of participant characteristics, intervention delivery, retention rates, adherence, and adverse events in clinical trials. Parkinsons Dis. 2012; 2012:854328.
6. Harter J G, Peck C C. Chronobiology. Suggestions for integrating it into drug development. Ann N Y Acad Sci. 1991; 618:563-71.
7. Interim Guidance: Preexposure Prophylaxis for the Prevention of HIV Infection in Men Who Have Sex with Men. MMWR Morb Mortal Wkly Rep. 2011; 60:65-8.
8. Woldu H, Porta G, Goldstein T, et al. Pharmacokinetically and clinician-determined adherence to an antidepressant regimen and clinical outcome in the TORDIA trial. J Am Acad Child Adolesc Psychiatry. 2011; 50:490-8.
9. Morey T E, Booth M, Wasdo S, et al. Oral Adherence Monitoring Using a Breath Test to Supplement Highly Active Antiretroviral Therapy. AIDS Behav. 2012; [Epub ahead of print].
10. Morey T E, Wasdo S, Wishin J, et al. Feasibility of a breath test for monitoring adherence to vaginal administration of anti-retroviral microbicide gels. J Clin Pharmacol. 2012; [Epub ahead of print].
11. van der Straten A, Cheng H, Wasdo S, et al. A novel breath test to directly measure use of vaginal gel and condoms. AIDS Behav. 2012; In Press.
12. Reddy B, Reddy A, Nagaraja T, et al. Single nucleotide polymorphisms of the alcohol dehydrogenase genes among the 28 caste and tribal populations of India. Int J Hum Genet. 2006; 6:309-16.
13. Bosron W F, Magnes L J, Li T K. Human liver alcohol dehydrogenase: ADH Indianapolis results from genetic polymorphism at the ADH2 gene locus. Biochem Genet. 1983; 21:735-44.
14. Edenberg H, Bosron W F. Alcohol Dehydrogenases, In: Guengerich F (editor). Biotransformation Vol. 3, Comprehensive Toxicology. New York, N.Y.: Pergamon Press; 1997. pp. 119-31.
15. Morey T, Booth M M, Prather R A, et al. Measurement of ethanol in gaseous breath using a miniature gas chromatograph. J Anal Toxicol. 2011; 35:134-42.
16. Dietz F K, Rodriguez-Giaxola M, Traiger G J, et al. Pharmacokinetics of 2-butanol and its metabolites in the rat. J Pharmacokinet Biopharm. 1981; 9:553-76.

17. Norberg A, Jones A W, Hahn R G, et al. Role of variability in explaining ethanol pharmacokinetics: research and forensic applications. Clin Pharmacokinet. 2003; 42:1-31.
18. Lindberg L, Grubb D. Simultaneously recorded single-exhalation profiles of ethanol, water vapour and CO(2) in humans: impact of pharmacokinetic phases on ethanol airway exchange. J Breath Res. 2012; 6:036001.
19. Boshier P R, Priest O H, Hanna G B, et al. Influence of respiratory variables on the on-line detection of exhaled trace gases by PTR-M S. Thorax. 2011; 66:919-20.
20. Lindbom L, Pihlgren P, Jonsson E N. PsN-Toolkit—a collection of computer intensive statistical methods for non-linear mixed effect modeling using NONMEM. Comput Methods Programs Biomed. 2005; 79:241-57.
21. Keizer R J, van B M, Beijnen J H, et al. Pirana and PCluster: a modeling environment and cluster infrastructure for NONMEM. Comput Methods Programs Biomed. 2011; 101:72-9.

Example 4b: Illustration of how Two Different AEMs (2-Butanol and 2-Isopropyl Alcohol) can be Used to Generate Two Different EDIMs with Different Half Lives in Human Breath that are Measured by a Type 1 SMART® Device A fasting subject ingested a soft gel containing an AEM formulation consisting of 2-butanol (40 mg) and isopropyl alcohol (30 mg). Shown in Panel A of FIG. 71 is the $1^{st}$ derivative mGC response (proportional to EDIM breath concentration) in a Type 1 SMART Device for acetone and 2-butanone as a function of breath sampling times post ingestion of the capsule.

Panel B depicts the change from baseline of the $1^{st}$ derivative mGC response. Time 0 is baseline (immediately before capsule is ingested containing the two AEMs). Within 10 minutes, rises in the breath concentration of both 2-butanone and acetone can be easily noted, peaking with a Tmax of 20 min. Note how the 2-butanone levels in breath begin to fall after 20 min, whereas those of acetone slowly continue to rise over the study period. These findings are consistent with a half life of 2-butanone of about 45 minutes and a half life of acetone ranging from 6.4 hrs (see Example 26 herein) to 17-27 hrs (previously reported with isopropanol poisoning (see, e.g., Jones, J. Anal Toxical (January-February 200) 24 (1): 8-10. hrs). Thus, not only will the use of combined EDIMs essentially eliminate potential interferents, it may eliminate the need for a baseline breath to be taken, and it enhances certainty when practicing this invention in the AMAM, IMAM, and, especially, CMAM modes.

The use of an AEM, like IPA, which generates a longer half life EDIM, like acetone, allows for much longer look back periods in terms of adherence behavior and makes chronic medication adherence monitoring (CMAM) viable (see Example 26 for further details).

The mean acetone concentration in human breath has been found to range from 293 to 870 ppb over a 30 day period (Diskin A M et al: *Physiol Meas* 24:107-119, 2003). Note that the background level of 2-butanone is very low whereas, as expected, the human breath contains a significant quantity of acetone as a result of lipid metabolism.

Example 5

Breath Kinetics of Exhaled d6-Acetone and d7-Isopropanol Following the Topical Application of d8-Isopropanol in a Carbomer Gel.

Transdermal:

240 mg of d8-isopropanol was mixed with 3 mL of a carbomer-based aloe gel. This gel was applied to an approximately 20 cm$^2$ area of the inner left forearm and covered with a Tagaderm occlusive dressing. To further reduce the permeability of the dressing, the transparent section was covered with a small section of teldar polymer prior to use.

Oral:

Either 100 mg d8-isopropanol or 20 mg d6 isopropanol was delivered orally. For oral dosing, 100 or 20 mg of neat d8-isopropanol were placed in a size 4 licap and the licap was swallowed along with 60-100 mL of water. Following administration of d8-isopropanol, exhaled breath was monitored in real time for the presence of d6-acetone and d7-isopropanol using the Orbitrap LCMS.

Figure 64:
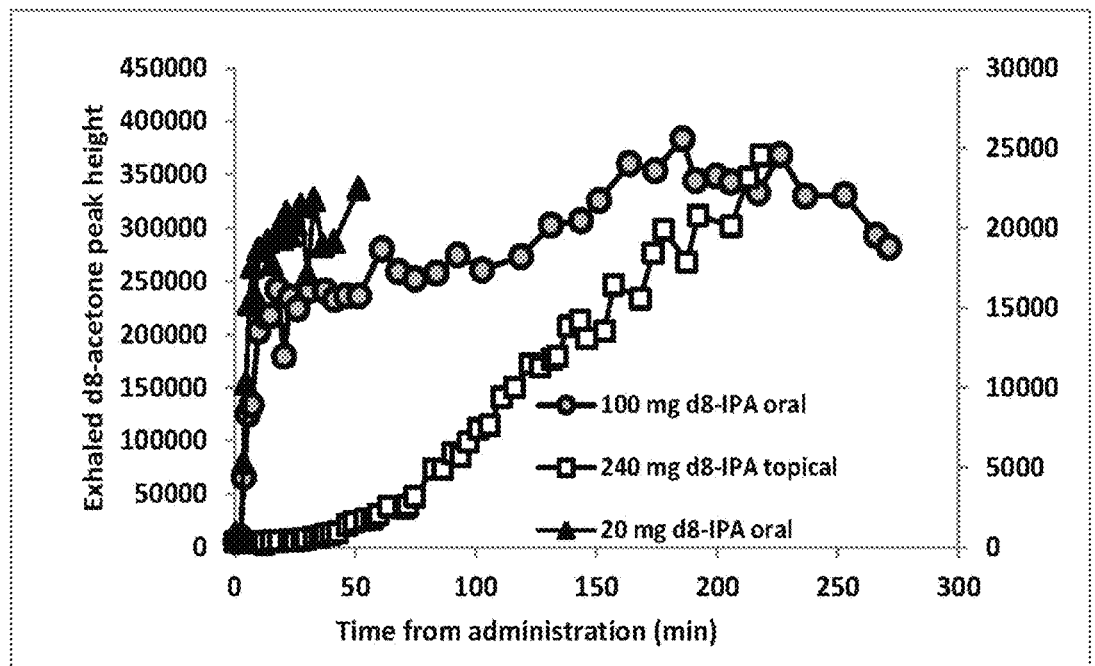

Results:

Following application or ingestion, d6-acetone and d7-isopropanol levels were monitored in exhaled breath samples using the LTQ-LCMS. Single full breath samples were administered directly into the modified ESI source at 5 min intervals for ~4 hours. The ESI source was operated in positive ion mode. A 0.2% NH$_4$OH:water mobile phase was introduced into the source at a flow rate of 0.1 mL/min during sampling to produce ammonium adducts of the analytes of interest. As can be seen in FIG. 64, by 15 minutes post-ingestion of either 100 mg d8-IPA (left hand axis) or 20 mg d8-IPA (right hand axis), D6-acetone levels in the exhaled breath began to level out and remain at maximum levels for several hours. By contrast, d-8 isopropanol delivered transdermally (right hand axis) resulted in much slower kinetics of appearance of d-6 acetone in the exhaled breath, with a maximum concentration still not achieved by 200 minutes post application.

These data demonstrate that deuterated secondary alcohol, when administered either topically or orally, results in readily detectable deuterated VOCs (d6-acetone) in the exhaled breath for definitive confirmation of medication adherence, albeit with different kinetics of appearance depending on the mode of delivery (oral or transdermal).

Example 6

(Ester Example 1)—GRAS Agent Listed as Food Additive—Aspartame: An Ester Food Additive Metabolized by Human Gut Esterases and Gut Peptidases (See FIG. 43)

Drug Class: Food additive, considered GRAS by FDA; artificial sweetener

Mechanism: mimics the taste of sugar in humans

Enzyme(s) for Metabolism: rapidly metabolized by human gut esterases and gut peptidases in humans Metabolites: L-aspartic acid+L-Phenylalanine+Methanol NICE Embodiment—Chemical Group Site(s) of Isotopic Label(s) on Parent Molecular Structure: Preferred site is the methyl group on Aspartame (indicated by red circle) but may include other locations on the parent molecule.

NICE Embodiment—Type of Isotopic Labeling on Preferred Site(s): Insert isotopic label(s) on the preferred site, including but not limited to a) a single label of a given isotope type (e.g., one Deuterium label=CDH2) on the preferred site(s), b) multiple labels of a given isotope (e.g., greater than one deuterium=CD2H or CD3) on the preferred site(s), or c) combinations of different types and numbers of isotopes (e.g., deuterium, carbon and/or oxygen=13CDH2, 13CHD2, or 13CD3) on one or more locations of the preferred site(s).

NICE Embodiment—Preferred Labeled Entity for Detection: isotopic (e.g., deuterium) labeled methanol in the breath; a less preferred embodiment would be labeled metabolic products of methanol (formaldehyde, formic acid and/or CO2—see FIG. 7 for details of metabolism of methanol). Isotopic labeling of larger metabolic fragments derived from the parent, which could be semi-volatile or non-volatile, could also serve as i-EDIMs.

Example 7

Esterase Example 2

FDA Approved Drug—Aspirin (Acetylsalicylic Acid): An ester drug metabolized by aspirin esterases in humans
(See FIG. 44)
Drug Class: Over the counter (OTC) drug
Mechanism: Nonsteroidal anti inflammatory drug (NSAID)—irreversibly inhibits cyclooxygenase (COX) via acetylation of the serine residue at the active site of COX, which suppresses production of prostaglandins and thromboxanes
Enzyme(s) for Metabolism: Acetylsalicylic Acid (ASA) esterases
Metabolites: 2 acids (salicylic acid and acetic acid) NICE Embodiment—Chemical Group Site(s) of Isotopic Label(s) on Parent Molecular Structure: Preferred site is the methyl group on ASA (indicated by red circle) but may include other locations on the parent molecule.

NICE Embodiment—Type of Isotopic Labeling on Preferred Site(s): NICE Embodiment—Type of Isotopic Labeling on Preferred Site(s): Insert isotopic label(s) on the preferred site, including but not limited to a) a single label of a given isotope type (e.g., one Deuterium label=CDH2) on the preferred site(s), b) multiple labels of a given isotope (e.g., greater than one deuterium=CD2H or CD3) on the preferred site(s), or c) combinations of different types and numbers of isotopes (e.g., deuterium, carbon and/or oxygen=13CDH2, 13CHD2, or 13CD3) on one or more locations of the preferred site (s).

NICE Embodiment—Preferred Labeled Entity for Detection: isotopic (e.g., deuterium) labeled acetic acid in the breath; a less preferred embodiment would be labeled metabolic products of acetic acid, CO2. Isotopic labeling of larger metabolic fragments derived from the parent, which could be semi-volatile or non-volatile, could also serve as i-EDIMs, particularly if the liquid phase of breath is being analyzed.

Example 8

(Ester Example 3)—GRAS Agents Listed as Food Additives—Methyl, Ethyl, Propyl and Butyl Parabens: Ester Food Additives Metabolized by Human Carboxylesterases and Tissue Esterases (See table 4)
Drug Class: Paraben' is an abbreviation for para-hydroxybenzoic acid. Parabens are a family of alkyl esters of para-hydroxybenzoic acid that differ at the para position of the benzene ring. There are four widely marketed para-hydroxybenzoic acid (POHBA) esters: methylparaben, ethylparaben, propylparaben, and butylparaben. Used as food additives/preservatives; considered GRAS by FDA; Europe uses as ADI (acceptable daily intake) up to 10 mg/kg per day for methyl and ethyl paraben
Mechanism: inhibits bacterial growth; food additive Enzyme(s) for Metabolism: rapidly metabolized by carboxylesterases and tissue esterases in humans Metabolites: para-hydroxybenzoic acid (POHBA)+corresponding alcohol (see below for details)
NICE Embodiment—Chemical Group Site (s) of Isotopic Label(s) on Parent Molecular Structure: Preferred site is the methyl group on Aspartame (indicated by red circle) but may include other locations on the parent molecule.

NICE Embodiment—Type of Isotopic Labeling on Preferred Site(s): Insert isotopic label(s) on the preferred site, including but not limited to a) a single label of a given isotope type (e.g., one Deuterium label=CDH2) on the preferred site(s), b) multiple labels of a given isotope (e.g., greater than one deuterium=CD2H or CD3) on the preferred site(s), or c) combinations of different types and numbers of isotopes (e.g., deuterium, carbon and/or oxygen=13CDH2, 13CHD2, or 13CD3) on one or more locations of the preferred site(s).

NICE Embodiment—Preferred Labeled Entity for Detection: isotopic (e.g., deuterium) labeled alcohols in the breath; a less preferable embodiment is labeled distal metabolic products of the alcohols and acids generated from the different parabens. Isotopic labeling of larger metabolic fragments derived from the parent, which could be semi-volatile or non-volatile, could also serve as i-EDIMs, particularly if the liquid phase of breath is being analyzed.

TABLE 4

GRAS Agents Listed As Food Additives - Methyl, Ethyl, Propyl and Butyl Parabens:
Ester food additives metabolized by human carboxylesterases and tissue esterases

| Paraben | Molecular Structure | Chemical Properties | Breath Metabolites |
|---|---|---|---|
| Methyl paraben (Methyl-4-Hydroxybenzoate) | (structure: methyl 4-hydroxybenzoate) | CAS: 99-76-3 MF: C8H8O3 MW: 152.15 MP: 126° C. SOLID | Methanol + para-hydroxybenzoic acid (POHBA) |

TABLE 4-continued

GRAS Agents Listed As Food Additives - Methyl, Ethyl, Propyl and Butyl Parabens:
Ester food additives metabolized by human carboxylesterases and tissue esterases

| Paraben | Molecular Structure | Chemical Properties | Breath Metabolites |
|---|---|---|---|
| Ethyl paraben<br>Ethyl-4-<br>Hydroxybenzoate | 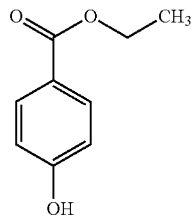 | CAS: 120-47-8<br>MF: $C_9H_{10}O_3$<br>MW: 166.1766<br>BP: 297° C.<br>MP: 117° C.<br>SOLID | Ethanol +<br>POHBA |
| Propyl paraben<br>Propyl-4-<br>Hydroxybenzoate | 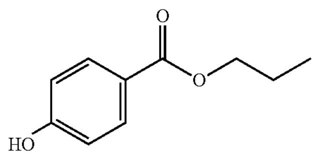 | CAS: 94-13-3<br>MF: $C_{10}H_{12}O_3$<br>MW: 180.20348<br>MP: 97° C.<br>SOLID | Propanol +<br>POHBA |
| Butyl paraben<br>Butyl-4-<br>Hydroxybenzoate | 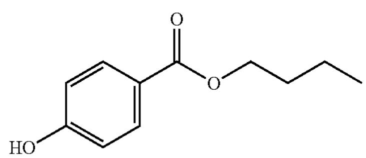 | CAS: 94-26-8<br>MF: $C_{11}H_{14}O_3$<br>MW: 194.23036<br>MP: 70° C.<br>SOLID | Butanol +<br>POHBA |

Example 9

(Esterase Example 4)—FDA Approved Drug—Clofibrate: An Ester Drug Metabolized by Esterases in Humans (See FIG. 45)
Drug Class: Prescription
Mechanism: Hypolipidemic drug, known to induce peroxisome proliferation; a member of a large class of diverse exogenous and endogenous chemicals known as peroxisome proliferators; Activation of the peroxisome proliferator activated receptor-(PPAR-α) key aspect of efficacy Enzyme(s) for Metabolism: Human Esterases
Metabolites: Carboxylic acid derivative of Clofibrate+ Ethanol
NICE Embodiment—Chemical Group Site(s) of Isotopic Label(s) on Parent Molecular Structure: Preferred site is the ethyl group on clofibrate, particularly on the methyl group (indicated by red circle) but may include other locations on the parent molecule.
NICE Embodiment—Type of Isotopic Labeling on Preferred Site(s): Insert isotopic label(s) on the preferred site, including but not limited to a) a single label of a given isotope type (e.g., one Deuterium label=CH2CH2D) on the preferred site(s), b) multiple labels of a given isotope (e.g., greater than one deuterium=CH2CHD2, CH2D3, CHDCD3, CD2CD3) on the preferred site(s), or c) combinations of different types and numbers of isotopes (e.g., deuterium, carbon and/or oxygen on one or more locations of the preferred site(s).
NICE Embodiment—Preferred Labeled Entity for Detection: isotopic (e.g., deuterium-based) labeled ethanol in the breath; a less preferred embodiment would be labeled metabolic products of ethanol. Isotopic labeling of larger metabolic fragments derived from the parent, which could be semi-volatile or non-volatile, could also serve as i-EDIMs, particularly if the liquid phase of breath is being analyzed.

Example 10

(Esterase Example 5)—FDA Approved Drug—Esmolol: A Drug Metabolized by Arylesterase Located within the Cytosol of Human Red Blood Cells (See FIG. 46)
Drug Class: Controlled/prescription drug
Mechanism: Ester-based ultra short acting beta blocker that is beta1 receptor selective
Enzyme(s) for Metabolism: In contrast to most ester-containing drugs, the hydrolysis of esmolol is mediated by an esterase in the cytosol of red blood cells (RBC) called arylesterase.
Metabolites: carboxylic acid derivative of Esmolol+ Methanol
NICE Embodiment—Chemical Group Site(s) of Isotopic Label(s) on Parent Molecular Structure: Preferred site is the methyl group on esmolol (indicated by red circle) but may include other locations on the parent molecule.
NICE Embodiment—Type of Isotopic Labeling on Preferred Site(s): NICE Embodiment—Type of Isotopic Labeling on Preferred Site(s): Insert isotopic label(s) on the preferred site, including but not limited to a) a single label of a given isotope type (e.g., one Deuterium label=CDH2) on the preferred site(s), b) multiple labels of a given isotope (e.g., greater than one deuterium=CD2H or CD3) on the preferred site(s), or c) combinations of different types and numbers of isotopes (e.g., deuterium, carbon and/or oxygen=13CDH2, 13CHD2, or 13CD3) on one or more locations of the preferred site(s).
NICE Embodiment—Preferred Labeled Entity for Detection: isotopic (e.g., deuterium) labeled methanol in the breath; a less preferred embodiment would be labeled metabolic products of methanol. Isotopic labeling of larger metabolic fragments derived from the parent, which could be semi-volatile or non-volatile, could also serve as i-EDIMs, particularly if the liquid phase of breath is being analyzed.

Example 11

(CYP450 Example 1)—CYP-3A4-Mediated Metabolism FDA Approved Drug: Verapamil—an L-Type Calcium Channel Blocker (see FIG. 47)

Verapamil (2,8-bis-(3,4-dimethoxyphenyl)-6-methyl-2-isopropyl-6-azaoctanitrile) is a L-type calcium channel blocker that liberates formaldehyde upon oxidative dealkylation (N-demethylation) by CYP-3A4. Orally administered verapamil undergoes extensive metabolism in the liver. One major metabolic pathway is the formation of norverapamil (N-methylated metabolite of verapamil) and formaldehyde by CYP-3A4. Although dependent upon the number of alternate metabolic pathways, the rate of formation of a specific metabolite(s) (i.e., verapamil→norverapamil and formaldehyde via CYP-3A4) generally appears to be predictive of in vivo functional enzyme competence. In fact verapamil is metabolized by 0-demethylation (25%) and Ndealkylation (40%). The CYP-3A4 is most the important enzyme in humans for metabolizing drugs. It has been estimated that the CYP-3A4 isoform of the P450 system is responsible for metabolizing 55-60% of all pharmaceutical agents. The CYP3A4 plays a critical role in metabolizing many drugs, including several cytotoxic drugs such as paclitaxel, docetaxel, vinorelbine, vincristine, irinotecan, topotecan, ifosfamide, cyclophosphamide, and tamoxifen. Thus, alterations in CYP-3A4 function frequently lead to drug-induced increases in morbidity and mortality. The isotopic labels shown in Table 2 (preferably deuterium), where appropriate, can be used to label various atoms (red circle) of verapamil, which in turn, will generate isotopic-labeled formaldehyde that will serve as the preferred embodiment of the i-EDIM in this example. In addition, isotopic labeling of larger metabolic fragments (e.g., norverapamil, etc.) derived from the parent, which could be semi-volatile or nonvolatile, could also serve as i-EDIMs, particularly if the liquid phase of breath is being analyzed.

Example 12

CYP450 Example 2—CYP-3A4-Mediated Metabolism FDA Approved Drug: Amiodarone—An Antiarrhythmic Drug (see FIG. 48)

Amiodarone is one the most effective antiarrhythmic drugs in clinical medicine. It is highly effective in treating atrial fibrillation, particularly in preventing its re-occurrence. Although this drug has a complex mechanistic profile (blocks sodium channels, beta receptors, calcium channels, and potassium channels) its major electrophysiological action is to prolong repolarization in cardiac tissue, predominantly by blocking potassium channels. Therefore, it is classified as a Class III antiarrhythmic drug according to the Vaughn-William Classification. The isotopic labels shown in Table 2 (preferably deuterium), where appropriate, can be used to label various atoms (red circle) of amiodarone, which in turn, will generate isotopic-labeled acetaldehyde that will serve as the preferred embodiment of the i-EDIM in this example. In addition, isotopic labeling of larger metabolic fragments derived from the parent, which could be semi-volatile or nonvolatile, could also serve as i-EDIMs, particularly if the liquid phase of breath is being analyzed.

Example 13

CYP450 Example 3—CYP-3A4-Mediated Metabolism FDA Approved Drug: Propafenone—An Antiarrhythmic Drug (see FIG. 49)

Propafenone is an antiarrhythmic drug that acts by primarily blocking sodium channels, and is classified as a Class IC antiarrythmic drug according to the Vaughn-William Classification. The isotopic labels shown in Table 2 (preferably deuterium), where appropriate, can be used to label various atoms (red circle) of propafenone, which in turn, will generate isotopic-labeled propionaldehyde that will serve as the preferred embodiment of the i-EDIM in this example. In addition, isotopic labeling of larger metabolic fragments derived from the parent, which could be semivolatile or non-volatile, could also serve as i-EDIMs, particularly if the liquid phase of breath is being analyzed.

Example 14

CYP450 Example 4—CYP-3A4-Mediated Metabolism FDA Approved Drug: Diltiazem—An Antiarrhythmic Drug (see FIG. 50)

Diltiazem is a L-type calcium channel blocker, which undergoes complex biotransformation, including deacetylation, N-demethylation, and Odemethylation. Of these pathways, CYP-3A4 probably plays a more prominent role than CYP2D6 in the metabolism of diltiazem. The isotopic labels shown in Table 2 (preferably deuterium), where appropriate, can be used to label various atoms (red circle) of diltiazem, which in turn, will generate isotopic-labeled formaldehyde and/or acetic acid that will serve as the preferred embodiments of the i-EDIMs in this example. In addition, isotopic labeling of larger metabolic fragments derived from the parent, which could be semi-volatile or non-volatile, could also serve as i-EDIMs, particularly if the liquid phase of breath is being analyzed.

Example 15

CYP450 Example 5—CYP-2D6-Mediated Metabolism FDA Approved Drug: Codeine—A Prodrug Narcotic for Analgesia (see FIG. 51)

Shown is an example where the CYP substrate is a prodrug (codeine) that is converted by the P450 system (CYP 2D6) into the active drug (morphine). Morphine has a significantly higher affinity for the μ opioid receptor than codeine, and thus is thought to mediate the analgesic properties of codeine. Only about 10% of codeine is normally converted to morphine in vivo. In this embodiment, the NICE system could be used to not only ensure that codeine is efficacious (i.e., ensures adequate conversion to morphine) but also to ensure that an inordinate amount of codeine isn't converted to morphine if a subject has a super functional of CYP-2D6. The latter scenario would cause an adverse drug reaction (ADR) because an excessive amount of morphine would be present in the body. Likewise, in the former scenario, the NICE system would identify those subjects that wouldn't get adequate pain relief from this drug, because not enough morphine is produced from codeine. The function of CYP 2D6 is altered by a great many factors including but not limited to genetics or drug-drug interactions. For example, because 6-10% of Caucasians have poorly functional CYP2D6, they do not get adequate pain relief from codeine. Furthermore, a number of medications are potent CYP2D6 inhibitors and reduce or even completely eliminate the efficacy of codeine. The most notorious of these are the SSRIs including fluoxetine (Prozac) and citalopram (Celexa). The high end PO dose of codeine is typically 240 mg given over 24 hours. The small arrow indicates the site of catalytic action by the CYP enzyme to liberate the formaldehyde. The isotopic labels shown in Table 2 (preferably deuterium), where appropriate, can be used to label various atoms (red circle) of codeine, which in turn, will generate isotopic-labeled formaldehyde that will serve as the preferred embodiment of the i-EDIM in this example. In addition, isotopic labeling of larger metabolic fragments derived from the parent, which could be semi-volatile or non-volatile, could also serve as i-EDIMs, particularly if the liquid phase of breath is being analyzed.

Example 16

CYP450 Example 6—CYP-1A2-Mediated Metabolism FDA Approved Drug: Olanzapine—An Antipsychotic Agent (see FIG. 52)

Olanzapine is one of the most widely used antipsychotic drugs in the world. It is used to treat schizophrenia. The major metabolic pathway for olanzapine is mediated by CYP-1A2. Its metabolism is well predicted by using the caffeine breath test as a probe to examine the ability of the CYP450 system to metabolism olanzapine. The small arrow indicates the site of catalytic action by the CYP enzyme to liberate the formaldehyde. The isotopic labels shown in Table 2 (preferably deuterium), where appropriate, can be used to label various atoms (red circle) of olanzapine, which in turn, will generate isotopic-labeled formaldehyde that will serve as the preferred embodiment of the i-EDIM in this example. In addition, isotopic labeling of larger metabolic fragments derived from the parent, which could be semivolatile or non-volatile, could also serve as i-EDIMs, particularly if the liquid phase of breath is being analyzed.

Example 17

Figure 53:
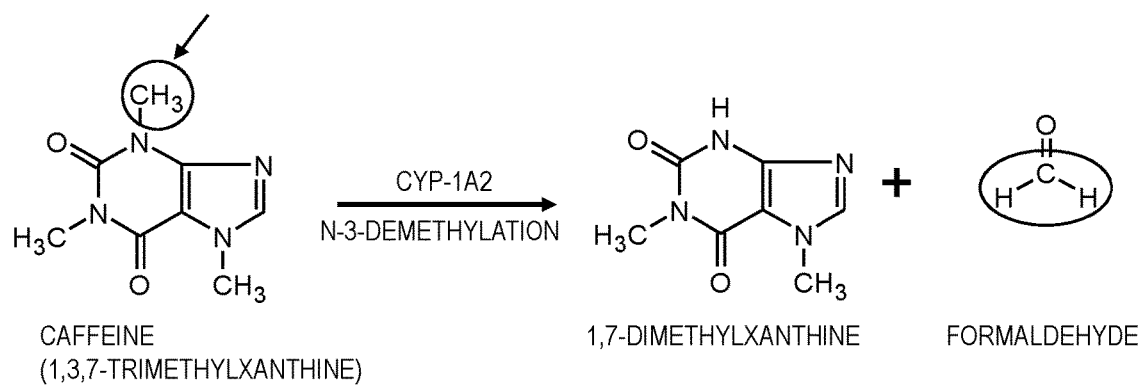
Figure 54:
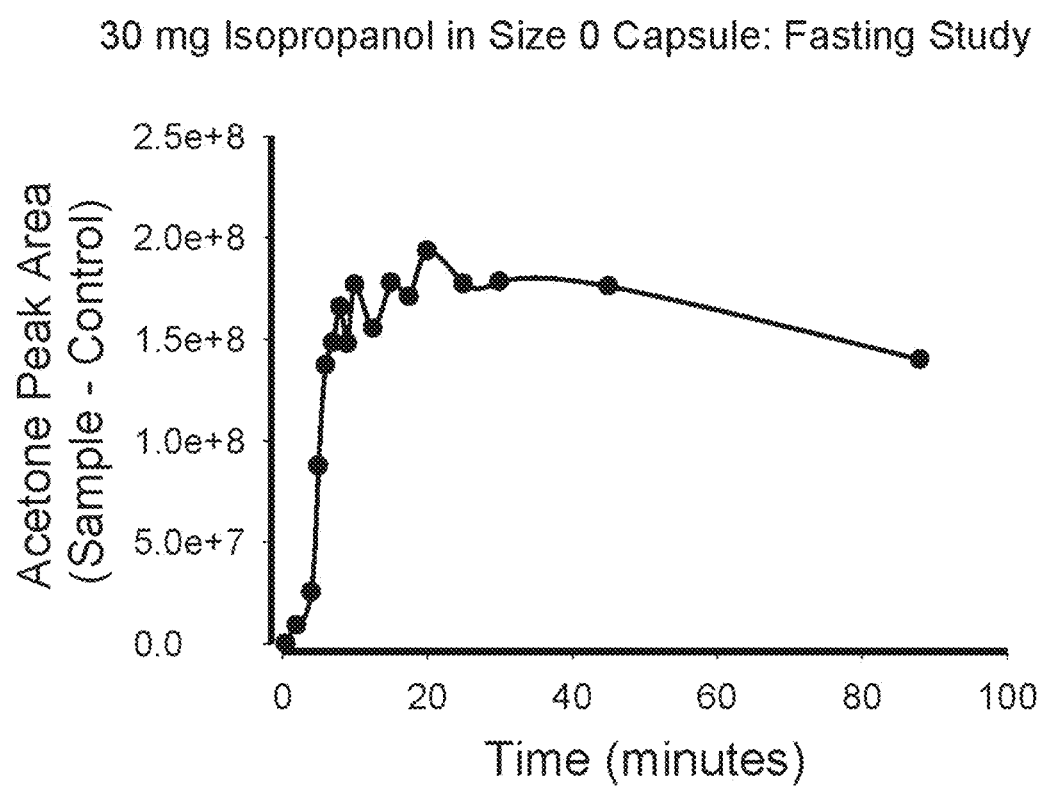

CYP450 Example 7—CYP-1A2-Mediated Metabolism Class 1 Drug: Caffeine—A Food Additive (FIG. 53)

Caffeine is a xanthine-type drug that is widely found in many foods, including beverages. Caffeine is a central nervous stimulant. It has been generally accepted as a specific in vivo probe for CYP1A2 activity. Approximately 80% of caffeine given orally to humans is converted to theophylline. Caffeine has been shown to provide an accurate phenotypic probe for measuring CYP1A2 activity, particularly when predicting the ability of olanzapine to be metabolized in vivo. The small arrow indicates the site of catalytic action by the CYP enzyme to liberate the formaldehyde. The isotopic labels shown in Table 2 (preferably deuterium), where appropriate, can be used to label various atoms (red circle) of caffeine, which in turn, will generate isotopic-labeled formaldehyde that will serve as the preferred embodiment of the i-EDIM in this example. In addition, isotopic labeling of larger metabolic fragments derived from the parent, which could be semi-volatile or non-volatile, could also serve as i-EDIMs, particularly if the liquid phase of breath is being analyzed.

Example 18

Approaches to Assessing Medication Adherence Using "Cold" Isotopic (Deuterium)-Based Chemistry and C—H (C-D) Stretching Vibrational Modes in the Mid-IR Region Using a ThermoFisher Nicolet 6700 FT-IR Spectrometer with 16-L Gemini Long Path Gas Cell, FTIR Conditions: Auxiliary Experiment Module: High Resolution Gas Sampling with MCT/A Detector (cooled with liquid nitrogen), KBr Beam Splitter. Range: 4000-650 $cm^{-1}$, Gain: 8, Aperture: 4.

Fill two 5-L Tedlar gas sampling bag with blank breath. Allow each bag to sit for at least 1 hour. Add 1 µL of neat volatile organic compound (e.g., acetone, d6-acetone, isopropanol) to one of the 5-L Tedlar gas sampling bags filled with blank breath. Allow this bag to sit for at least 1 hour. Evacuate the gas cell then fill the gas cell with the contents of the 5-L Tedlar gas sampling bag filled with blank breath. Collect a background spectrum. Evacuate the gas cell then fill the gas cell with the contents of the 5-L Tedlar gas sampling bag containing the volatile organic compound in blank breath. Collect a sample spectrum. See FIGS. 23-39 for results.

Example 19

Detection of Breath Acetone Using Mass Spectroscopy and mGC-MOS: Isopropanol and Perdeuterated Isopropanol as Adherence Enabling Markers (i-AEMs) in the SMART™ Adherence System Isopropanol (IPA) and acetone are listed by the FDA as direct food additives (GRAS). Isopropanol and acetone are listed as excipients in the FDA's IIG list. Isopropanol and acetone are listed in the FDA's Q3C guidance. Class III Solvent: 50 mg or less, no concern. Permissible Daily Exposure (PDE): IPA 138 mg/day orally; and acetone 210 mg/day orally; Deuterations deemed safe by FDA.

Note: In humans acetone has a metabolic t=17-27 hrs, see, for example, Jones-A W, J Analytical Toxicology, 24:8-10, 2000.

Figure 55A:
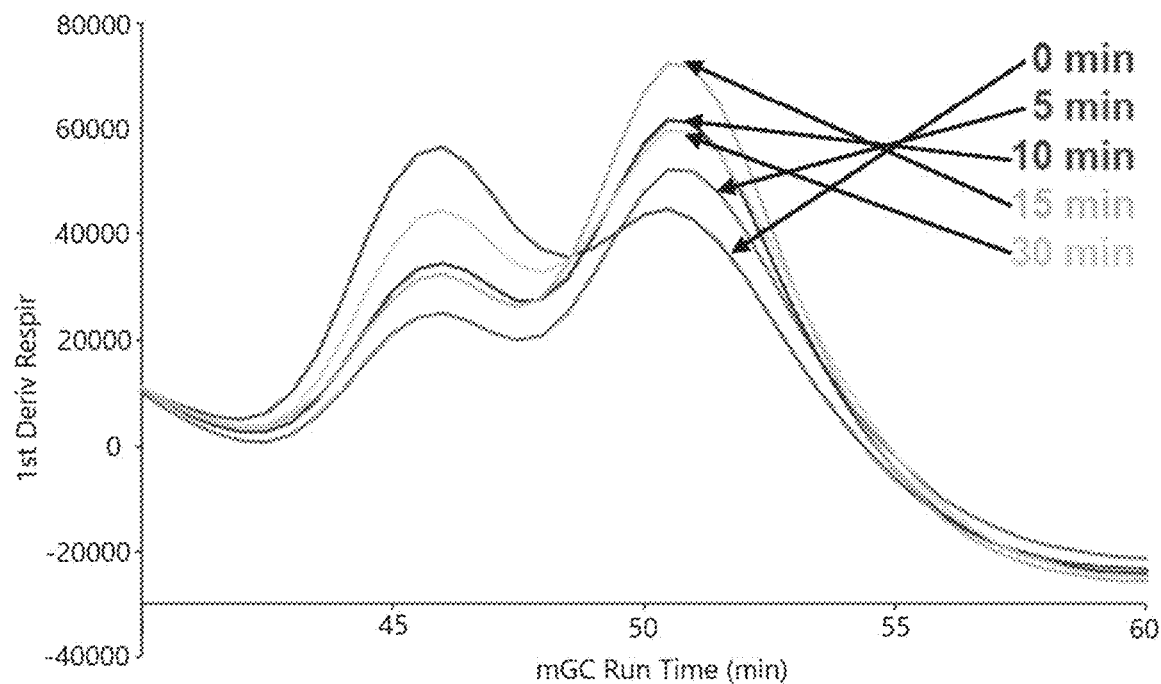
Figure 55B:
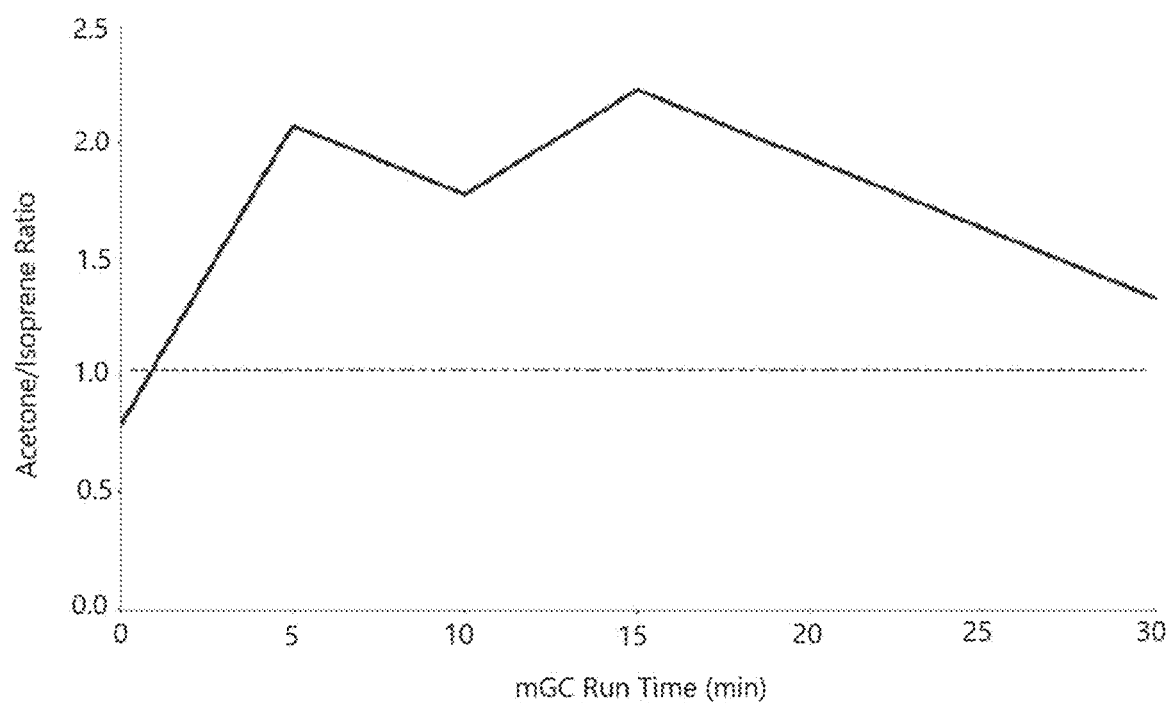

See FIGS. 55A and B, which provide a breath profile (exhalation provided to OrbiTrap, LC/MS/MS) from a 30 mg bolus of IPA delivered in a size O capsule to a fasting subject, showing IPA induced increase above baseline for acetone in the exhaled breath of the subject. See FIGS. 55A and B for mGC analysis after ingestion of 10 mg IPA. FIG. 55A shows the first derivative of the mGC profile for 0, 5, 10, 15, and 30 minutes post ingestion of 10 mg IPA. These results were obtained even without optimization of the mGC for "early eluters" (system peak, isoprene and acetone). FIG. 55B shows the ratio of first derivatives for the acetone/isoprene mGC profiles.

From these studies, we conclude that low quantities of isopropanol are effective to serve as an AEM but even more so as an i-AEM using the mGC, (i.e. with or without the need for deuterations to document adherence. Isopropanol could generate either a primary (acetone alone) or secondary breath marker (e.g., acetone+2-butanone) to document adherence. Given the long half-life of acetone in humans (17-27 hrs), use of this breath marker could serve as a marker of chronic adherence, and could complement the "acute" adherence measurement made using the breath marker, 2-butanone.

Note: In humans acetone has been reported to have a metabolic $t_{\frac{1}{2}}$=17-27 hrs, see, for example, Jones-A W, J Analytical Toxicology, 24:8-10, 2000.

Example 20

GC/MS and OrbiTrap (LC/MS/MS) Analysis

Protocol: Participant ingested 100 mg of d8-2 propanol in a size 3 LiCap 2 h after lunch. Breath samples were analyzed by LC/MS and GC/MS for the presence of d8-Acetone. GC/MS samples were collected at 0, 5, and 15 min after ingestion. Direct breath samples (4 s per breath) were analyzed by LC/MS for 270 minutes after ingestion of the pill using the ESI source with ammonia modified water (0.1%) as an ionizing solution.

Note: Acetone (m/z 58, [(CH3)2C=O)]+); d8-Acetone (m/z 64, [(CD3)2C=O)]+).

Example 21

Real Time Analysis of Acetone Breath Kinetics Following Ingestion of 3 mg d8-Isopropanol Using the OrbiTrap LC/MS/MS See FIGS. 56A, 56B, 57A, 57B, and 57C.

ESI Direct exhaled breath analysis after ingestion of 3 mg d8-isopropanol in a size 3 LiCap. Selected ion chromatograms characteristic for NH4 Adducts of Acetone and d6-Acetone.

Figure 57A:
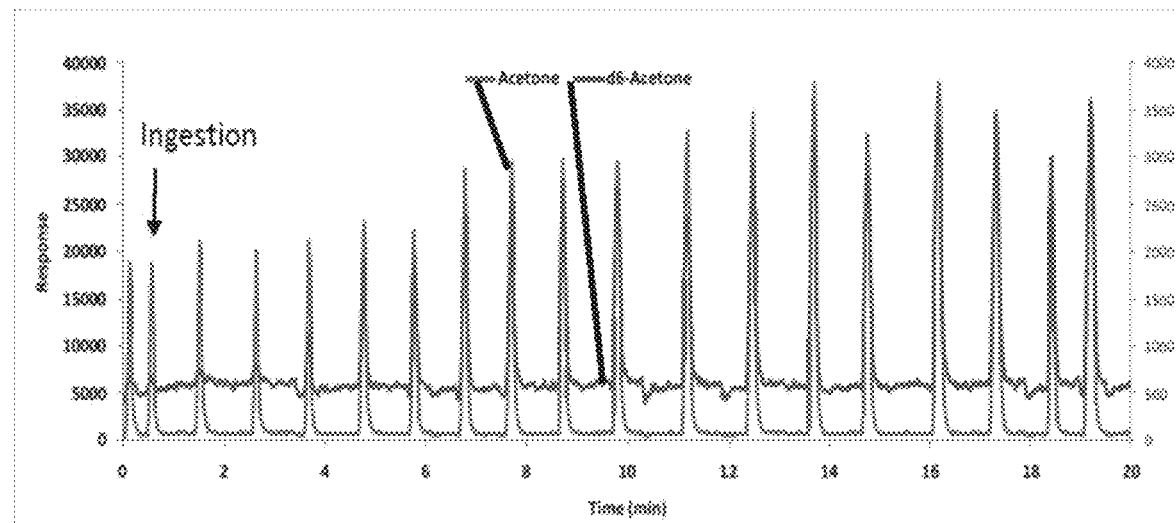
Figure 57B:
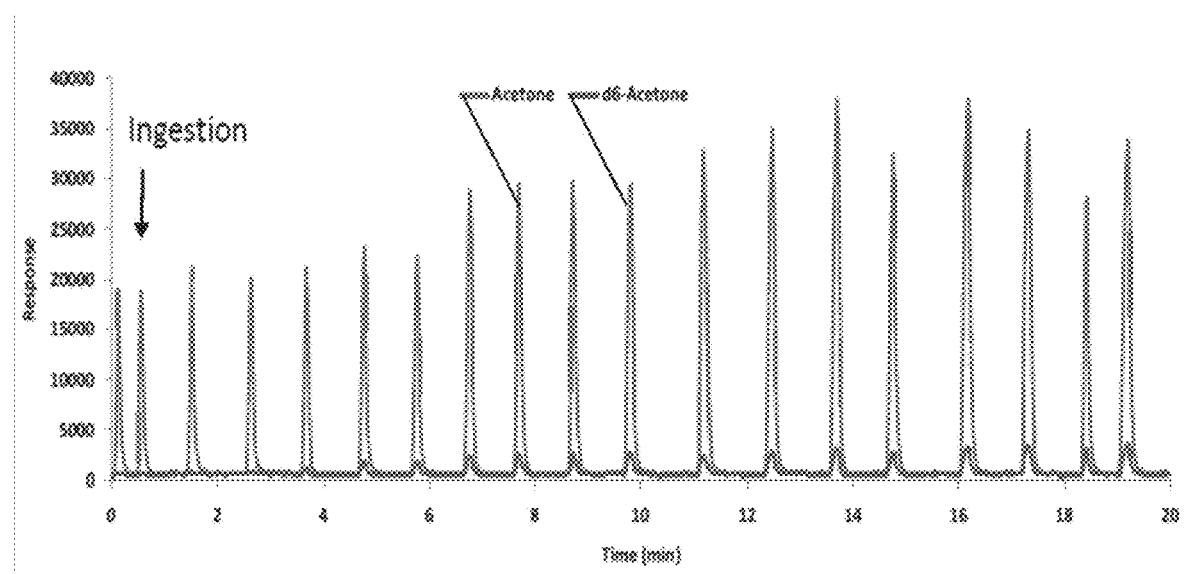
Figure 57C:
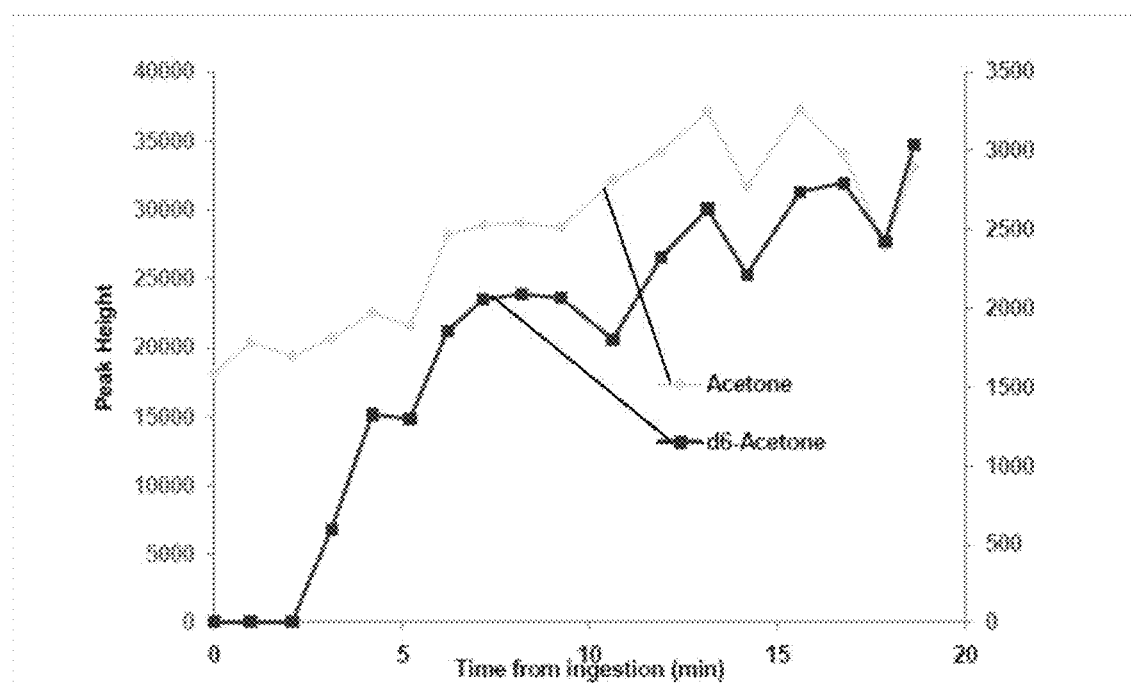

Ingestion Capsule was ingested immediately after subject consumed a carbohydrate meal. In FIG. 57C, two y axis scales are included to show differences, with the left axis=endogenous acetone, and the right axis=d6-Acetone.

Example 22

Figure 58:
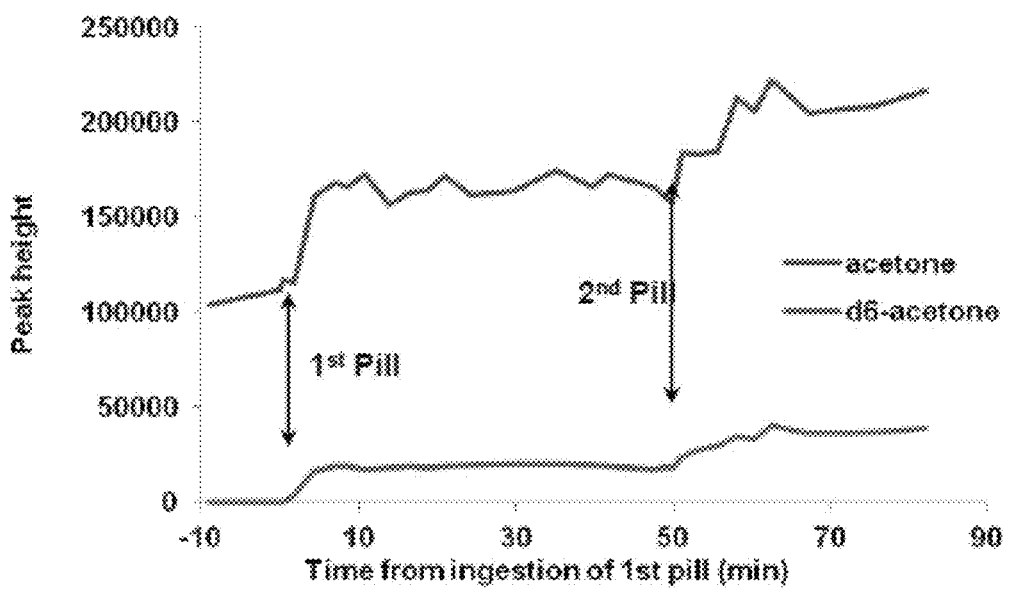

Real Time Analysis of Acetone Breath Kinetics Following Ingestion of 10 mg d8-Isopropanol and 10 mg Isopropanol Using the OrbiTrap LC/MS/MS See FIG. 58. Breath kinetics of acetone and d6-acetone following the simultaneous ingestion of 10 mg 2-propanol and 10 mg d8-2-propanol in a size 3 LiCap. The subject ingested one capsule containing the 20 mg mixture at t=0 and a second capsule 50 min later. A rise in both acetone and the deuterated analog is apparent within 2 min following administration of either dose. Proportional rise in peak height indicate deuterations do not have a significant effect on the metabolic conversion to acetone from IPA by secondary alcohol dehydrogenase (2° ADH).

Example 23

Breath Kinetics of Exhaled 2-Butanol and 2-Butanone Following the Concurrent Ingestion of 2-Butanol and Ethanol
Instrumentation and Methods:
20 mg of 2-butanol in a size 3 LiCap was ingested along with one shot (44 mL) of 100 proof ethanol (50% v/v). Following ingestion, ethanol, acetone, 2-butanol and 2-butanone levels were monitored in exhaled breath samples using the LTQ-LCMS. Single 5 s breath samples were administered directly into the modified ESI source at 5 min intervals for 45 min.

The ESI source was operated in positive ion mode. A 0.2% NH$_4$OH:water mobile phase was introduced into the source at a flow rate of 0.1 mL/min during sampling to produce ammonium adducts of the analytes of interest.

A mass spectrum of a single breath sample was taken before the ingestion of 2-butanol with ethanol. Of the four analytes highlighted, only acetone was positively identified. A small peak at 90 was likely due to isotopic interference from the unknown background component appearing at m/z=88 and not 2-butanone. For a mass spectrum of a single breath sample taken 5 min after the ingestion of 2-butanol and ethanol, Ethanol, 2-butanone and acetone were present as prominent peaks, but 2-butanol was barely detectable above baseline.

Even with a reasonable dose of ethanol present in the stomach, the kinetics of 2-butanone appears unaffected (or at least very similar to a typical response following the ingestion of just 2-butanol) and no significant 2-butanol was detected. The orbitrap was configured to capture sequential spectra (~5 spectra per second) and these spectra were recorded for the duration of the experiment (60-90 min usually) to produce a real time continuous trace. The electrospray interface on the orbitrap was modified to allow a subject to blow exhaled breath samples directly into the source while the mass spectra were being collected. The rapid clearance of the breath samples from the source allowed us to capture and characterize mass spectra from exhaled breath samples in real time. In theory we could use the orbitrap to capture and distinguish every exhaled breath that a subject makes during an experiment but in practice we typically don't need to collect more than one breath sample per minute.

Figure 59A:
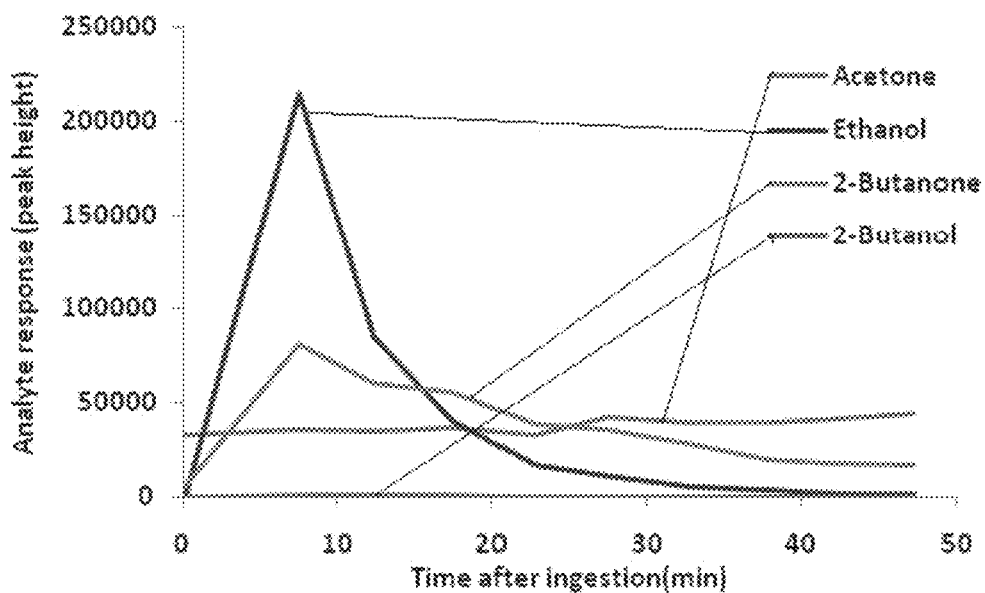
Figure 59B:
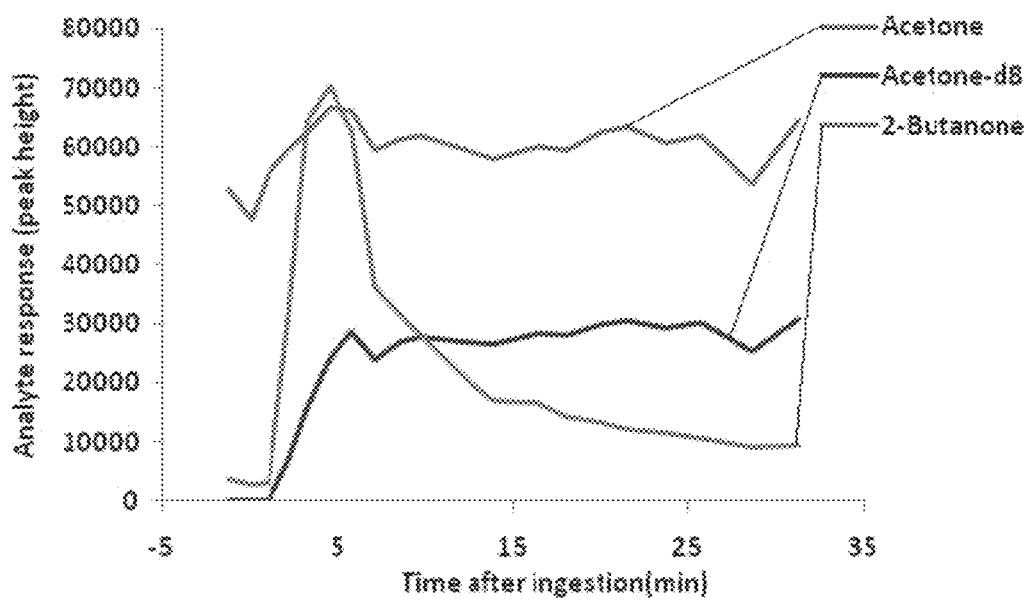

FIG. 59A plots the peak height of each ion of interest as a function of time yields the breath kinetics for each potential breath marker. Even with a reasonable dose of ethanol present in the stomach, the kinetics of 2-butanone appears unaffected (or at least very similar to a typical response following the ingestion of just 2-butanol) and no significant 2-butanol was detected. FIG. 59B shows the breath kinetics of 2-butanone and d6-acetone following ingestion of neat 2-butanol (40 mg) and d8-isopropanol after lunch.

Example 24

Figure 60A:
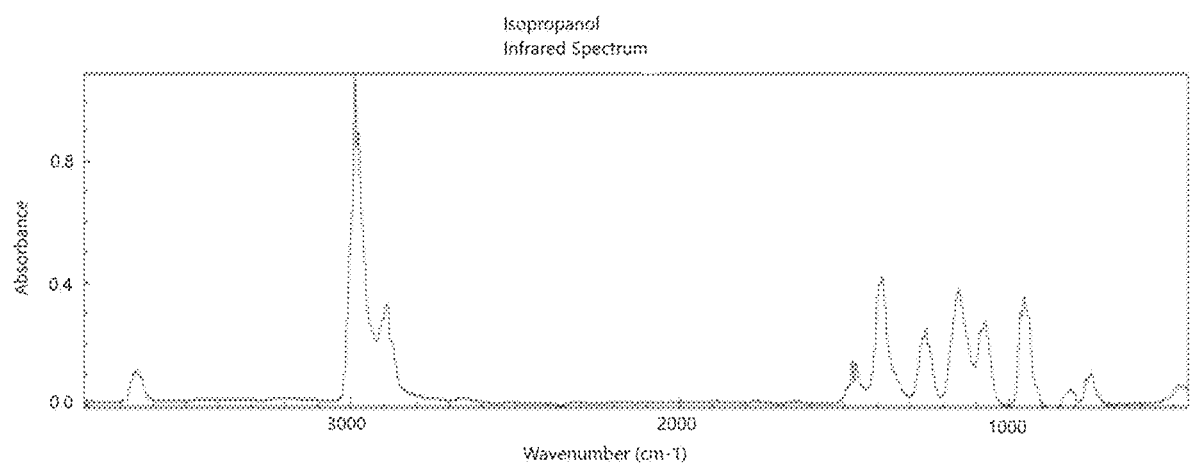
Figure 60B:
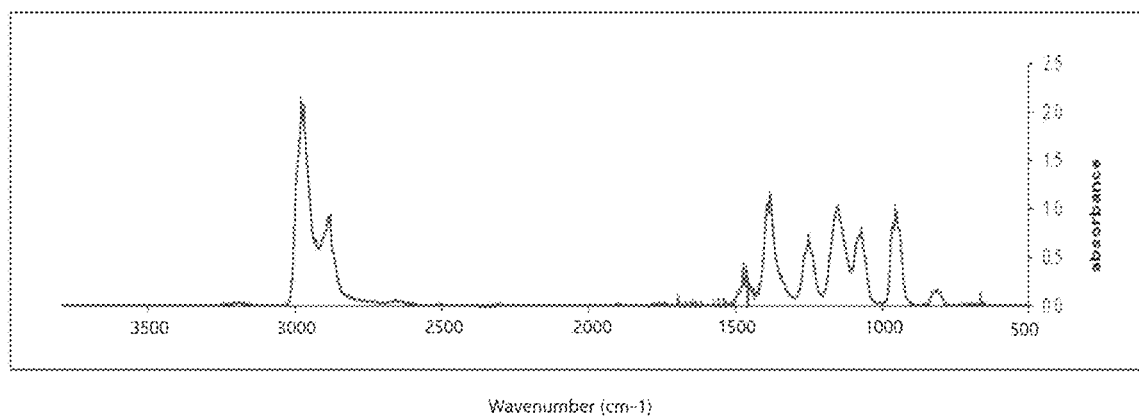

FTIR Analysis of Acetone and Isopropyl Alcohol Along with their Perdeuterated Isotopologues Comparison of NIST Webbook Gas Phase IR Spectra for Isopropyl Alcohol versus one obtained using the UF Nanomedicine Thermo Nicolet 6700 FTIR is shown in FIGS. 60A and B. In FIG. 60A, there is provided a tracing showing the infrared spectrum from a NIST Webbook Gas Phase IR Spectrum of 2-Propanol (see http://webbook.nist.gov/cgi/cbook.cgi?ID=C67630&Units=SI&Type=IR-SPEC&Index=2#IR-SPEC)

whereas in FIG. 60B, there is provided a spectrum obtained by the inventors using a Thermo Nicolet 6700 FTIR Gas Phase IR Spectrum of 2-Propanol. The reproducibility of the spectra is clear.

In FIG. 61 (panel a) there is provided a tracing of the FTIR analysis of acetone and d6-acetone showing clear areas where these spectra are distinguishable from each other. Panel A' shows a detail of the region between 3300 cm-1 to 2000 cm-1.

In FIG. 61, panel B, there is provided a tracing of the FTIR analysis of IPA and d8-IPA, again showing clear areas where these spectra are distinguishable from each other.

Figure 62:
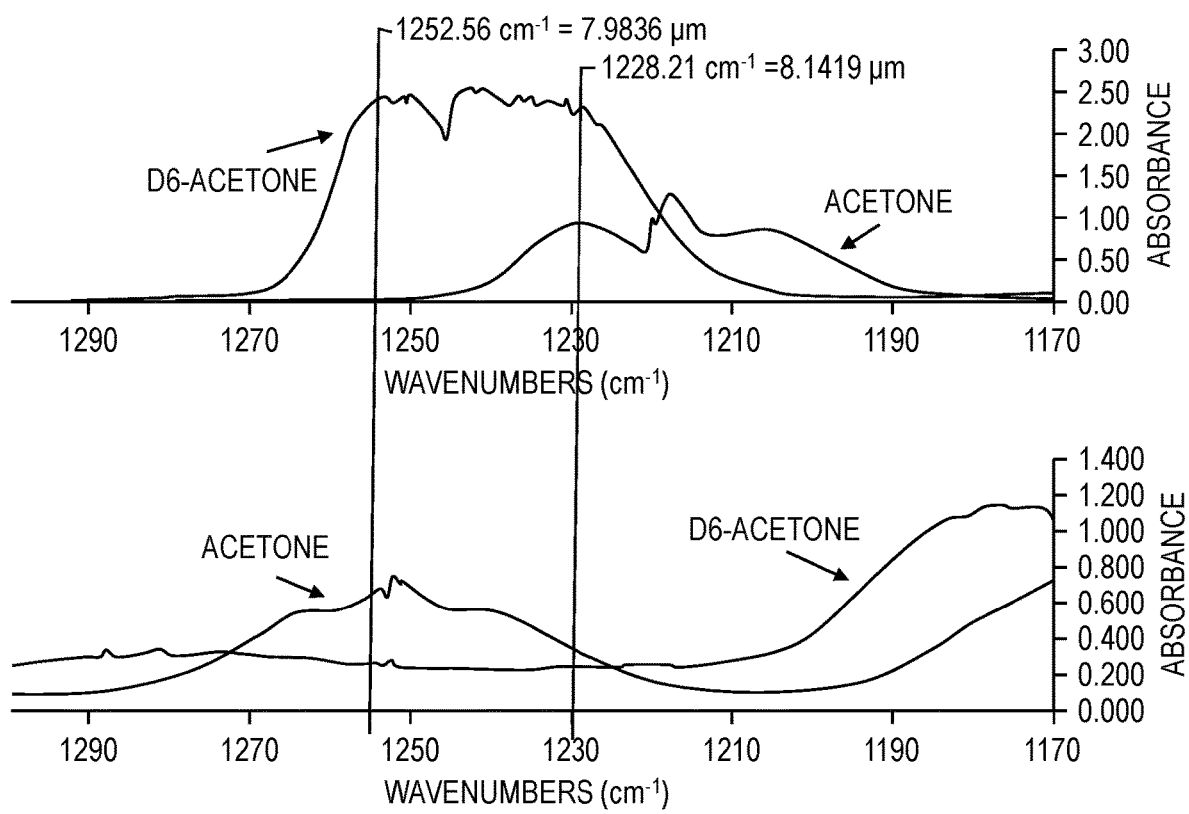

In FIG. 62, there is provided FTIR Spectra of Acetone and Isopropyl Alcohol with their perdeuterated isotopologues, with a detail of each tracing in the Fingerprint Region (1170 $cm^{-1}$ to 1300 $cm^{-1}$, 8.5470 mm to 7.6923 mm). The ability of this technique to distinguish between the perdeuterated and non-deuterated molecules is clear. The lines drawn at 1252.56 $cm^{-1}$=7.9836 μm and 1228.21 $cm^{-1}$=8.1419 μm indicate optimal wavenumbers to monitor acetone and deuterated acetone in a small wavenumber window (24 $cm^{-1}$).

Figure 63:
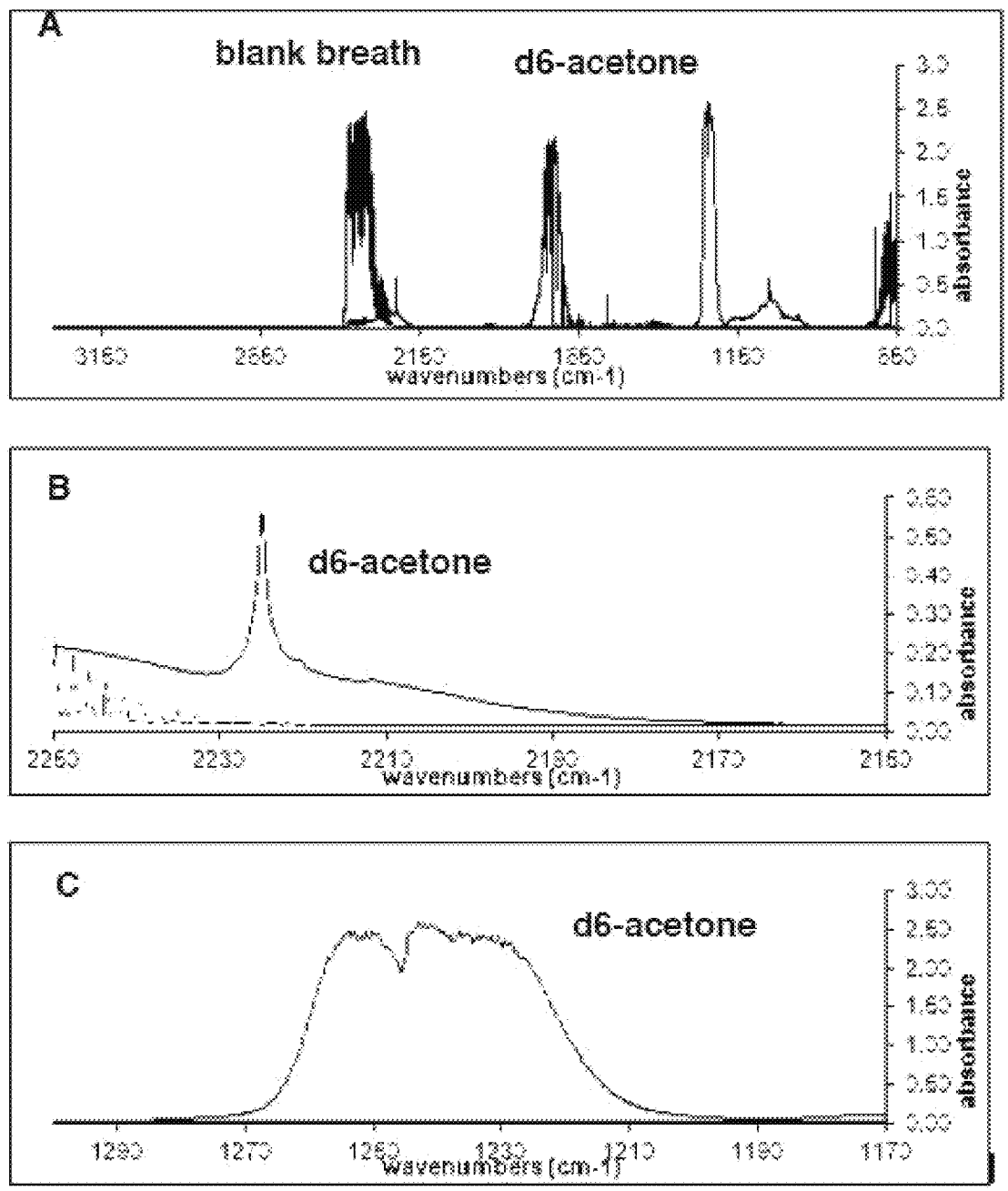

In FIG. 63, there is provided (panel A), FTIR Spectra of d6-acetone versus Blank Breath, with details of portions of these spectra being shown in panels B and C. As can be seen, there are clear portions of these spectra which are not interfered with by compounds in the endogenous breath, making it clear that the d6-acetone is an excellent i-EBM.

Example 25

Use of an i-API as its Own i-AEM to Produce a Specific and Cognate i-EBM

Those skilled in the art will appreciate from the present disclosure that in one preferred mode of practicing this invention, the i-AEM is a marker that is included in a dosage form for delivery to a subject at the same time that an API is delivered to a subject, to enable confirmation (by detection of the i-EBM in the breath produced from the i-AEM) of delivery of the API to the subject. In another preferred mode of carrying out the present invention, however, the API itself may include a non-ordinary but stable isotope and thereby can act as its own i-AEM, to produce in the exhaled breath, an i-EBM specific to that API. One example of such a system involves the use of a deuterated form of propofol. Propofol is detected in the exhaled breath after intravenous administration of propofol to the subject (see U.S. Pat. Nos. 6,981, 947, and 7,104,963 and their related foreign counterparts). In a particular application, where it is advantageous to measure an i-EBM in the exhaled breath, inclusion of a fraction of deuterated propofol (i-propofol) in the propofol that is administered intravenously, permits detection of the i-propofol or metabolites thereof in the exhaled breath can provide data that might not otherwise be available. Of course, many other i-APIs may be contemplated for use according to this invention with an appropriate SMART® device. In fact, Concert Pharmaceuticals, Inc., (Lexington, Mass.), has announced that it "uses deuterium-based chemistry to create and develop highly differentiated new medicines by leveraging decades of pharmaceutical and clinical experience to reduce time, risk and expense." Such compounds would serve as i-AEMs for themselves, either as the cognate parent compounds or as metabolites thereof, which appear as i-EBMs in the exhaled breath. Of course, in combination with the i-API, additional i-AEMs may be included to assist refinement of the i-EBM analysis—such that different half lives of different species may be determined. As a result, quite specific adherence data is made possible at a much more refined degree of granularity than has ever before been available. Thus, for example, i-EBMs generated from the i-API may have a half life of several minutes, while i-EBMs generated from exogenous i-AEMs (i.e. i-AEMs that are not the i-API itself or any part of the i-API, but included with the i-API in a dosage form), may exhibit half lives of several hours to days. By measuring both types of i-EBMs in the exhaled breath utilizing the SMART® technology, it is possible to determine total dosage adherence information, including when a given dose was taken, which dose/doses were missed and when, and the like. Thus, for example, i-IPA (e.g., deuterated isopropyl alcohol) produces i-acetone (e.g., deuterated acetone) which can be detected in the exhaled breath for several days, while i-2-butanol (e.g., deuterated 2-butanol) gives rise to i-butanone (e.g., deuterated butanone) which exhibits a very short half life of several minutes to one or two hours in the exhaled breath.

Example 26

Breath Kinetics of Exhaled d6-Acetone Following the Ingestion of 100 mg of d8-Isopropanol Per Diem for 5 Days.

100 mg aliquots (125 μL) of neat d8-isopropanol were ingested at 24 h intervals for a period of 5 days. Each aliquot was administered in a size 0 LiCap along with ~200 mL of water.

Throughout the study, acetone and d6-acetone levels were monitored in exhaled breath using the LTQ-LCMS. Each breath sample consisted of a single full breath exhaled directly into the modified ESI source. The ESI source was operated in positive ion mode using a 0.1% $NH_4OH$:water mobile phase (at 0.1 mL/min) as an ionizing medium. Both acetone and d6-acetone were present as protonated ammonium adducts and monitored using m/z=76 and m/z=82, respectively.

Following the ingestion of each aliquot, breath samples were taken every 2 min for the first 30 min following ingestion, every 5 min from 30-60 min after ingestion and every 10 min from 60-120 min. Additional breath samples were collected at 9 h and 20 h after ingestion. After the final dose, breath samples were taken once every 24 h for the next 3 days (total study time=8 days).

Figure 65:
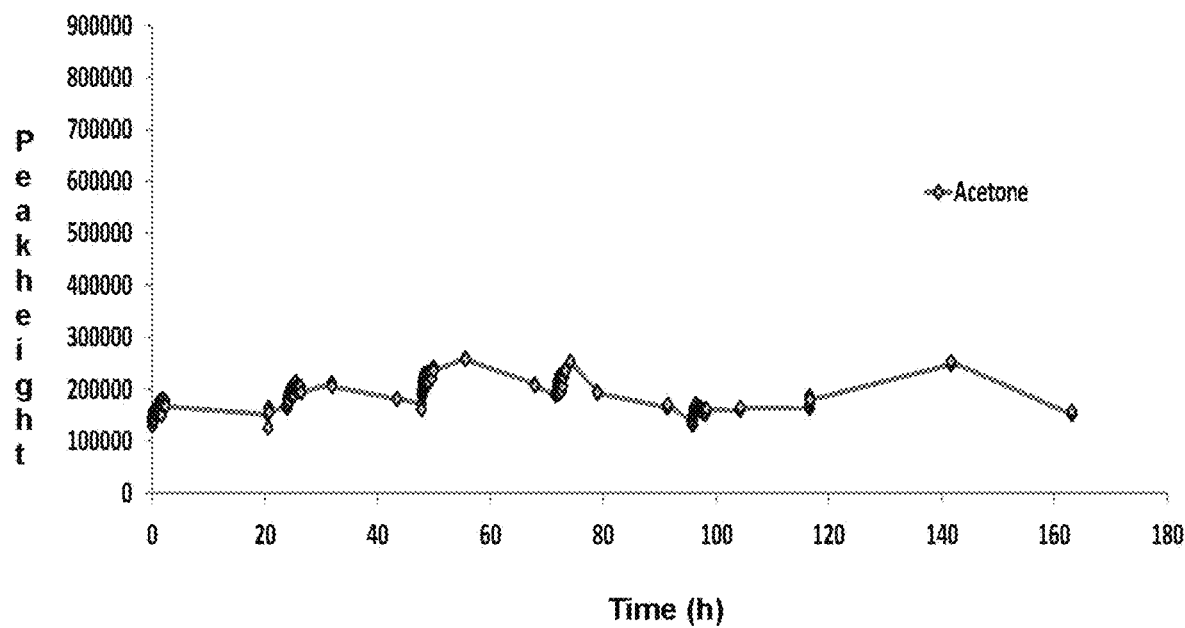

FIG. 65 shows that native acetone peak heights remained reasonably constant throughout the study.

Figure 66:
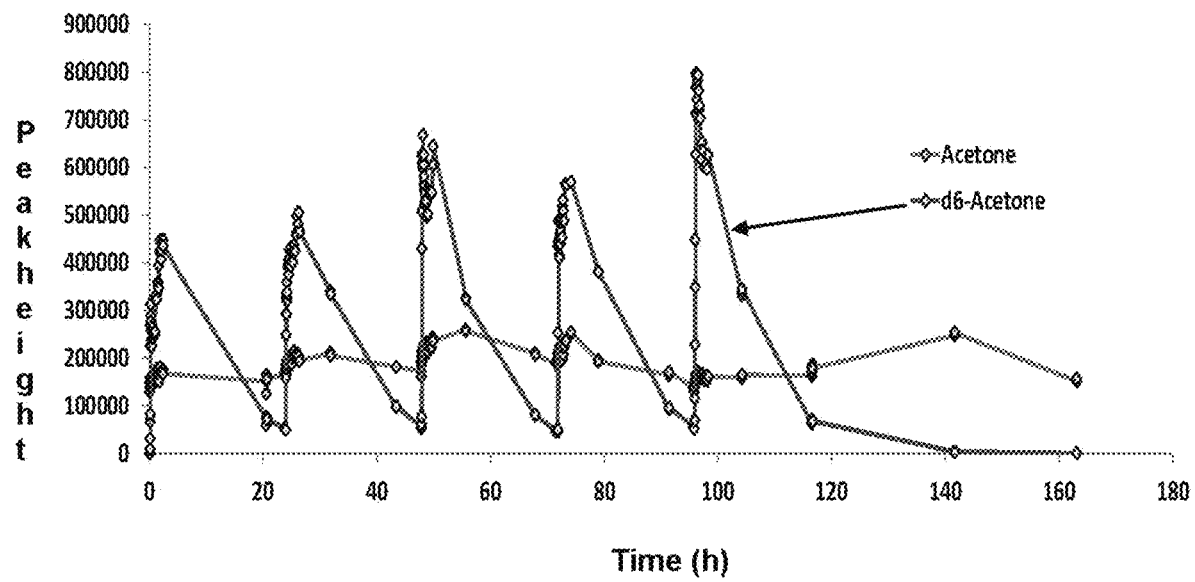

FIG. 66 shows that baseline levels for ion 82 (the ion used to monitor d6-acetone) were low and less than 1000 (<1% of typical acetone levels). An increase of exhaled d6-acetone was apparent within 2-4 minutes of ingesting each dose of d8-IPA. Maximum breath levels were achieved after 1-2 h and ranged from 450,000 to 800,000 peak height. (~2-5× native acetone).

FIG. 67 shows that 24-hour trough levels were relatively unchanged over the course of the study and were ~10% of peak maximum:

| Day | Trough Peak Height |
|---|---|
| 1 | 51988 |
| 2 | 54470 |
| 3 | 47369 |
| 4 | 54955 |
| 5 | 62324 |

Figure 68:
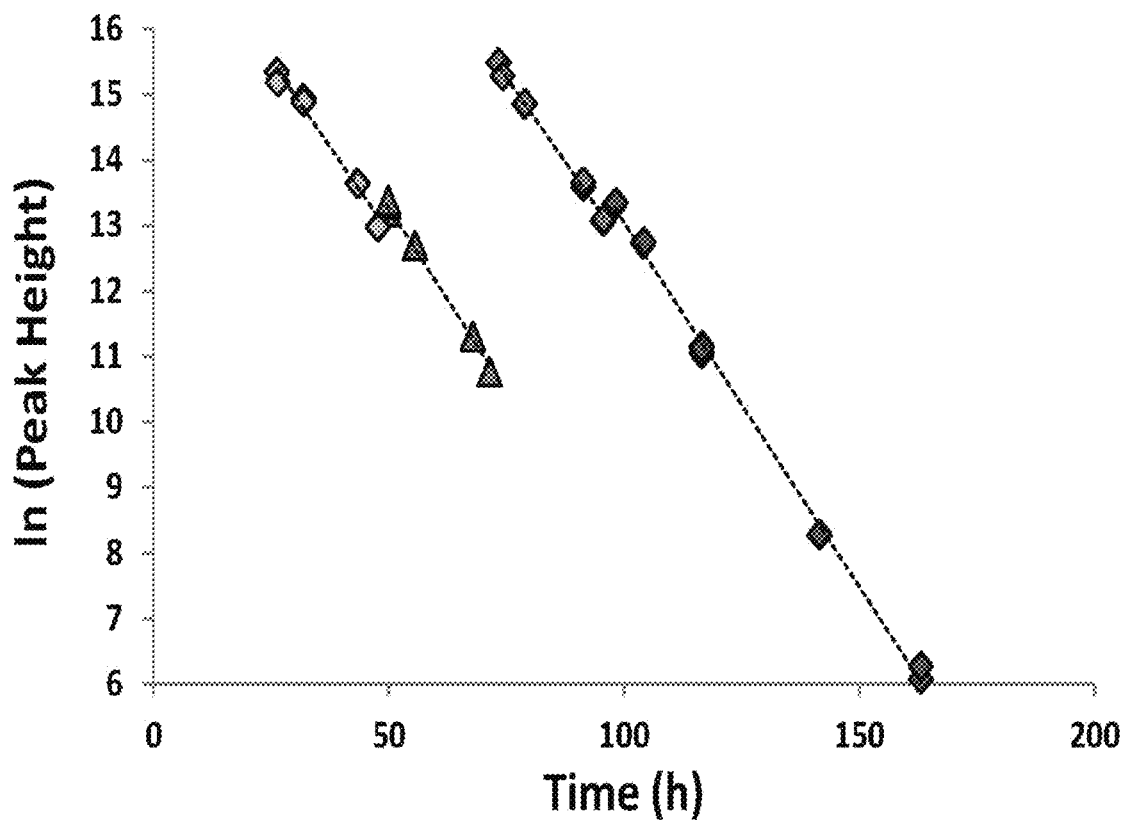
FIG. 68 shows that the decline of d6-acetone in exhaled breath followed a first order decay (2-24 h post ingestion). The rate constant (k) for this decay was consistent throughout the study.

FIG. 68 shows that the decline of d6-acetone in exhaled breath followed a first order decay (2-24 h post ingestion). The rate constant (k) for this decay was consistent throughout the study:

| Day | k (h$^{-1}$) |
|---|---|
| 2 | −0.1045 |
| 3 | −0.1123 |
| 4 | −0.1034 |
| 5 | −0.1113 |

Average k = −0.1079
t½ ~6.4 h

FIG. 69 shows that at this rate of elimination, approximately 6-10% of maximum peak response remains after 24 h. Such kinetics should produce steady-state trough levels that are also 10% of the maximum peak. This matches the observed trough levels during the study. 21 h after the final dose, exhaled d6-acetone produced a peak height of ~62000, which is 34% of the average acetone level measured during the study. By 45 h, the d6-acetone level had fallen to 3886. d6-Acetone returns to baseline (more specifically, ion 82 levels return to baseline) after 65 hours.

Example 27

Isopropyl Alcohol (IPA) as an AEM Using a SMART® Type I Device

An mGC-MOS device was used to analyze breath samples before and after ingestion of 100 mg of Isopropyl Alcohol (IPA). Standards at four different concentrations (333, 666, 1662, and 3323 ppb-moles) were created by adding neat quantities of IPA to UHP nitrogen in 1-L Tedlar gas sampling bags (SKC Inc, Eighty Four, Pa.). The mGC-MOS chromatograms are shown in FIG. 72A, and the calibration curve for these standards is shown in FIG. 72B. For the first 5 days of this study, a placebo capsule containing 100 mg of water was ingested each morning and breath samples were analyzed using a mGC-MOS device at 0, 15, and 30 minutes. For the last 5 days of this study, a capsule containing 100 mg of isopropyl alcohol was ingested each morning and breath samples were analyzed at the same time points as in the placebo part of this study (0, 15, and 30 minutes). The results from this study are shown in FIG. 72C. Note how the ingestion of IPA (100 mg) rapidly (15 and 30 min after oral ingestion of IPA) increased the breath acetone levels by greater than 6× those of baseline acetone concentrations. This rise in breath acetone concentration is very distinctive in terms of documenting medication adherence, because the human body when resting in the home setting carrying out adherence measurements could not generate this type of rise in endogenous acetone levels over this short (15 and 30 min) a time frame. Consistent with a half life of less than 10 hours in breath in this subject, the trough concentrations of acetone rapidly reached steady state within 1-2 days, and are consistent with those obtained in another subject, who ingested 100 mg d8-IPA and used breath analysis by the OrbiTrap (FIG. 66).

Example 28

AMAM, IMAM and CMAM Using the SMART System According to this Invention

In implementing a SMART® system according to this invention for use as a "gold standard" for acute medication adherence monitoring (AMAM; adherence assessment "look back window" up to 2-3 hours), intermediate medication adherence monitoring (IMAM; adherence assessment "look back window" up to 24 hours), and/or chronic medication adherence monitoring (CMAM; adherence assessment "look back window" that is three days to even weeks), five key inter-related factors are involved:

Factor 1: the half life of the EDIM in humans;
Factor 2: the concentration of EDIM in breath;
Factor 3: the limit of detection (LoD) of the sensor to detect the EDIM in breath;
Factor 4: the level of any background EDIM or interferents that can mimic the EDIM on the sensor, which may be present in breath; and
Factor 5: significant absorption of the AEM from the stomach (e.g., adequate AEM permeability through the thick gastric epithelium), which is a requirement for AMAM capabilities but not for CMAM or IMAM capabilities.

By orchestrating the quartet of factors (1-4 above, i.e. by administering a dose of AEM to generate the highest concentration of EDIM having the longest half life in breath, which in turn is detected with the most sensitive sensor that has no background interference in breath, including no EBM already present in breath (e.g., no endogenous acetone) or no other breath markers that could mimic the presence of the EBM to the sensor), a SMART® architecture for a CMAM system with the longest (days to weeks) "look back" time window in terms of assessing adherence is enabled. As shown in multiple examples herein, this framework is preferably (but not exclusively) achieved by using cold isotopologues of AEMs that generate highly distinctive cold isotopologue-based EDIMs, which are detected by Type 1 or, preferably, Type 2 (e.g. infrared-based) SMART® devices according to this invention. This approach also makes it feasible to use very low quantities of AEM, including the formulation strategy of simply spraying a few mg of cold isotopologue-based AEM(s) on the surface of a solid oral dosage form (SODF) (and, depending on volatility, overcoating to entrap and prevent loss of the AEM). In contrast, the quartet of factors consisting of a dose of AEM that generates the lowest concentration of an EDIM having the shortest half life in breath, which in turn is detected with the least sensitive sensor that has the most significant background interference (EBM already present in breath and/or the presence of other breath markers that can mimic the EBM to the sensor) provides for the shortest medication adherence assessment "look back" window period. Ideally, the optimal SMART® architecture for an AMAM system that provides a shorter (up to 1-2 hrs) adherence "look back" window period entails production of an EDIM having a short half life in breath that is detected with a sensor that is sensitive to the EDIM and has no background interference to contend with. Unlike a system designed only for CMAM, one that encompasses AMAM with or without IMAM and/or CMAM capabilities requires the AEM to have significant absorption in the stomach, so the EDIM is able to promptly appear in the breath via metabolism of the AEM, where a prompt rise above baseline breath EDIM levels indicates acute adherence. If the AEM is absorbed in only the small intestine (e.g., duodenum), the appearance of the EDIM in breath is totally dependent on the highly variable periods of time it takes for the stomach to empty its contents (e.g., AEM) into the upper small intestine for absorption. In contrast, it is not a prerequisite with IMAM (up to 1 day adherence "look back" window) and CMAM (days to weeks adherence "look back" window) that the AEM have significant absorption in the stomach to function properly, because duodenal absorption is adequate, given the longer half life of the EDIM used in CMAM. However, it is important to note that even an EDIM highly suitable for CMAM (longer half life in breath) can be effectively used for AMAM (pill by pill adherence assessments), if it is significantly absorbed from the stomach, and a baseline breath sample is obtained in addition to one at a slightly later time (e.g., 20-30 min) after ingestion of the AEM, because even compounds at steady state levels in the blood with longer half lives show a significant EDIM concentration rise with each dose. This rise above baseline (trough) levels of the EDIM is easily detected with a two breath script.

When humans orally ingest 2° alcohols as the AEM, the following findings have been noted: 1) absorption of the 2° alcohols (AEMs) in the gastrointestinal tract is complete (fractional absorption is unity) and very rapid, relative to the rate of metabolism of the AEM (2° alcohol) to the EDIM (ketone), 2) metabolism of the 2° alcohols to their corresponding ketones is complete, given the high degree of $1^{st}$ pass metabolism, and 3) the concentrations of EDIM in breath rapidly equilibrate with those in blood, and reflect the free concentration of EDIM in blood (and plasma).

Considering these five factors as each relates to SMART® Adherence System function:

Factor 1: EDIM Half Life in Breath

After ingesting various doses of AEMs (e.g., 2-butanol, isopropyl alcohol), we have determined the EDIM breath concentration-time relationships, including the half life in breath of various EDIMs, including 2-butanone (Example 3 and Morey et al, AIDS Behav 17(1):298-306. 2013), 2-pentanone (Example 3), and acetone (Example 5; FIG. 69). As it relates to the SMART® Adherence System, the concentration rise (rapid absorption of AEM and conversion to EDIM) and decay of the EDIM with time in breath following oral administration of the AEM is well described by a 1 compartmental (monoexponential) pharmacokinetic (PK) model, reflecting absorption and elimination, which can be described by the following equation (derived from Miller's Anesthesia, 6th Edition, p 81, 2005, Ed: Ronald D. Miller, Elsevier Churchill Livingstone, Philadelphia, Pa.):

$$C_{EDIM}(t) = C_{EDIMo} * F * \frac{k_a}{k_a - k_e} * (e^{-k_e t} - e^{-k_a t}) \qquad \text{Equation 1}$$

where:

$C_{EDIM}(t)$=concentration of EDIM in breath as a function of time (t);

$C_{EDIMo}$=maximum concentration of EDIM in breath derived from dividing the dose of EDIM (complete conversion of AEM dose to EDIM) by the volume of distribution ($V_d$) for the EDIM;

F=fraction bioavailable of AEM (complete conversion to EDIM, so F=1);

$k_a$=$1^{st}$ order rate constant for absorption of AEM into the compartment (absorption is very rapid for 2° alcohol AEM with complete conversion to corresponding ketone);

$k_e$=$1^{st}$ order rate constant for elimination of the EDIM from the compartment;

e=Euler's number, (2.71828 . . . ; i.e. the base for the natural logarithm, whereby ln $e^x$=x).

The time to attain the maximum concentration of EDIM in breath ($T_{MAX}$) is given by the following equation:

$$T_{MAX} = \frac{1}{(ka - ke)} * \ln\left(\frac{ka}{ke}\right) \qquad \text{Equation 2}$$

Following the oral ingestion of 2° alcohols (and most suitable AEMs), gastrointestinal absorption is complete and metabolic conversion to its corresponding ketone is very rapid. Therefore, because $k_a \gg k_e$ and F is 1, Equation 1 simplifies to Equation 3:

$$C_{EDIM}(t) = C_{EDIMo} * e^{-k_e t} \qquad \text{Equation 3}$$

The $1^{st}$ order rate elimination constant ($k_e$) of the EDIM is related to the elimination half life ($t_{1/2e}$) of the EDIM (time required for the EDIM concentration to fall by half in breath) by the following equation:

$$t_{1/2e} = \frac{0.693}{ke} \qquad \text{Equation 4}$$

Because the conversion of the AEM to the EDIM is complete and relatively rapid, the $t_{1/2e}$ provides an excellent measure of the time it takes to achieve steady state EDIM levels in breath, both trough ($C_{Trough}$) and maximal ($C_{MAX}$), as it reflects blood levels of EDIM, after a constant oral dosing regimen of the AEM is initiated (see FIG. 66 & FIGS. 72A and B). Moreover, during dosing with AEMs, a time of four half lives is required to reach approximately 94% of steady state EDIM concentrations in breath (see FIG. 73). The time to steady state is independent of the dose, but the fluctuations (concentration swing between each dosing) is proportional to the AEM dosage interval (T) divided by the EDIM elimination half life ($t_{1/2e}$) in breath. In addition, the steady state concentration achieved with chronic oral AEM dosing is proportional to the AEM dose divided by dosage interval (T).

FIG. 73 provides a graphic representation of the fundamental pharmacokinetic relationships for six successive administrations of an oral drug. The light line is the pattern of drug accumulation during repeated administration of a drug at an interval equal to its elimination half life, when drug absorption is very rapid relative to elimination. The concentration maxima approach 2 and the minima approach 1 during the steady state. The heavy line depicts the pattern during administrating of equivalent dosage by continuous intravenous infusion. Curves are based upon a one compartment model. The x axis represents time, as indicated by multiples of elimination half life ($t_{1/2e}$). (Reference: modification of FIGS. 1-6, page 27, Goodman and Gilman, The Pharmacological Basis of Therapeutics, $8^{th}$ Edition, 1993, Pergamon Press, New York, N.Y. Abbreviation Key: $C_{Trough}$, trough concentration of EDIM (circle symbols); $C_{MAX}$, maximum concentration of EDIM in breath (horizontal dotted lines).

As shown in FIG. 73, repeated oral administrations of the AEM produces accumulation of the EDIM, the magnitude of which depends upon its elimination half life ($t_{1/2}$) and dosage interval (T).

The ability to use this technology to produce a "look back window" on overall medication adherence (chronic adherence), without the need to use the system on a daily basis, and still have an accurate picture of adherence behavior over a defined preceding period of time (hours to weeks) is clinically important and inventive. It reduces subject burden by eliminating the requirement to use the adherence system on a pill by pill basis as in acute medication adherence monitoring (AMAM). On the other hand, to carry out ideal pharmacometric modeling, most PK experts find dose by dose documentation of adherence (yes/no determinations) and the timing between successive doses (interdose intervals) most desirable. An AEM that shows significant absorption in the stomach that generates an EDIM with a longer half life in breath can be easily used in AMAM, IMAM and/or CMAM modes (see Example 5).

The accumulation factor (Katzung B G, Basic and Clinical Pharmacology, page 39, 6th Edition, 1995, Appleton & Lange, Norwalk, Conn.) predicts the ratio of the steady state concentration of the EDIM in breath to that following the first dose of AEM.

$$AF = \frac{1}{F_{Lost}} \quad \text{Equation 5}$$

where:

AF=accumulation factor; and $F_{Lost}$=fraction lost in one dosage interval (T), prior to the next dose.

The fraction of the EDIM lost in one dosage interval (T) just before the administration of the next dose of AEM can be determined from re-arranging Equations 1 and 3 into the following equation:

$$F_{Lost} = 1 - e^{-0.693\left(\frac{T}{t_{1/2e}}\right)} \quad \text{Equation 6}$$

Thus, the only PK parameter that determines $F_{Lost}$ is the ratio of the dosage interval (T) to the elimination half life $(t_{1/2e})$. The peak $(C_{MAX,ss})$ and trough $(C_{Trough,SS})$ EDIM concentrations at steady state (4 EDIM half lives to achieve 94% of steady state EDIM concentration) is equal to peak and trough levels obtained after the 1$^{st}$ AEM dose multiplied by the AF. This is shown below:

$$C_{MAX,SS} = AF \cdot C_{MAX,1st\ Dose} \quad \text{Equation 7}$$

$$C_{Trough,SS} = AF \cdot C_{Trough,1st\ Dose} \quad \text{Equation 8}$$

The fraction remaining ($F_{Remaining}$), is simply equal to 1 minus $F_{Lost}$. As illustrated in the below Table A, there is an inverse relationship between the accumulation factor (AF) and the $T/t_{1/2e}$ ratio:

TABLE A

Effect of AEM Dosage Interval (T) and EDIM half life $(t_{1/2})$ in Breath on the Accumulation Factor (AF).

| T (Dosage Interval) (hrs) | $t_{1/2e}$ (hrs) | $T/t_{1/2e}$ | $F_{Remaining}$ | $F_{Last}$ | Accumulation Factor (AF) |
|---|---|---|---|---|---|
| 0.24 | 24 | 0.01 | 0.933 | 0.007 | 144.801 |
| 1.2 | 24 | 0.05 | 0.966 | 0.034 | 29.363 |
| 2.4 | 24 | 0.1 | 0.933 | 0.067 | 14.936 |
| 4.8 | 24 | 0.2 | 0.871 | 0.129 | 7.727 |
| 7.2 | 24 | 0.3 | 0.812 | 0.188 | 5.327 |
| 9.5 | 24 | 0.4 | 0.758 | 0.242 | 4.131 |
| 12 | 24 | 0.5 | 0.707 | 0.293 | 3.415 |
| 14.4 | 24 | 0.6 | 0.660 | 0.340 | 2.940 |
| 16.8 | 24 | 0.7 | 0.616 | 0.384 | 2.602 |
| 19.2 | 24 | 0.8 | 0.574 | 0.426 | 2.350 |
| 21.6 | 24 | 0.9 | 0.536 | 0.464 | 2.155 |
| 24 | 24 | 1 | 0.500 | 0.500 | 2.000 |
| 48 | 24 | 2 | 0.250 | 0.750 | 1.333 |
| 72 | 24 | 3 | 0.125 | 0.875 | 1.143 |
| 96 | 24 | 4 | 0.063 | 0.937 | 1.067 |
| 120 | 24 | 5 | 0.031 | 0.969 | 1.032 |
| 144 | 24 | 6 | 0.016 | 0.984 | 1.016 |
| 168 | 24 | 7 | 0.008 | 0.992 | 1.008 |
| 192 | 24 | 8 | 0.004 | 0.935 | 1.004 |
| 216 | 24 | 9 | 0.002 | 0.998 | 1.002 |
| 240 | 24 | 10 | 0.001 | 0.999 | 1.001 |

In other words, the oral administration of AEMs at frequent intervals that generate long half life EDIMs is associated with the greatest degree of accumulation. For example, if an AEM is orally administered that generates an EDIM with an elimination half life of 24 hours ($t_{1/2e}$=24 hours) on a BID (Q 12 hour basis: T=12 hours), the $T/t_{1/2e}$ ratio is 0.5, and the accumulation factor is 3.415. Thus, the steady state values of trough ($C_{Trough}$) and maximum ($C_{MAX}$) EDIM concentrations are 3.415× greater than those following the 1$^{st}$ oral dose for an EDIM with a value of T/t, equal to 0.5.

The time that must elapse in order for the EDIM to decrease from its steady state values of $C_{Trough}$ and $C_{MAX}$ to a lower level is readily calculated using Equation 3, and is used to determine for how long a subject has not taken their medication.

After the oral administration of the AEM 2-butanol (40 and 60 mg) to humans, the half life of the EDIM 2-butanone was found to be 11-22 min (Morey T E, et al *AIDS Behav,* 17(1), 298-306, 2013; Example 4a). As demonstrated in this patent disclosure, isopropyl alcohol (IPA) has been found to be a promising AEM. The above analysis can be applied to IPA as the AEM, which rapidly generates the EDIM, acetone, with a longer half life in breath. For example, Jones-J et al (Anal Toxicol 2000, 24(1):8-10) found the mean elimination half life of acetone in humans ranged from 17 to 27 hours with an average of 22 hours. We have found, however, that the elimination half life of acetone (d6-acetone) in human breath following ingestion of deuterated isopropyl alcohol (d8-IPA) was between 6.4 hours (FIG. 69) and 8.5 hrs (Example 5). Using these 5 half lives of acetone (6.4, 8.5, 17, 22, and 27 hrs) after the ingestion of IPA at various dosage intervals (T), the following table (Table B) illustrates the following accumulation factors (AF) for acetone in breath. Similar to what was described above for Table A, the accumulation factors shown in Table B can be used to determine the length of time a subject was not adherent to a medication containing IPA, which equals the length of time that elapsed from the expected original EDIM concentration in breath (e.g., assume $C_{Trough,ss}$ are being made) to the concentration measured at a randomly called trough time, as determined by the EDIM $t_{1/2e}$ Equation 3 by using the EDIM $t_{1/2e}$ and solving for the time (t) to decay from the higher to the lower EDIM breath concentration:

TABLE B

Accumulation Factor (AF) of acetone as a function of various elimination half lives ($t_{1/2e}$) and AEM (i.e., isopropyl alcohol, IPA) dosing intervals (T). More frequent dosing with IPA and a longer $t_{1/2e}$ lead to greater accumulation.

| AEM Dosing Interval | T (Dosage Interval) (hrs) | $t_{1/2e}$ (hrs) | T/$t_{1/2e}$ | $F_{Remaining}$ | $F_{Lost}$ | Accumulation Factor (AF) |
|---|---|---|---|---|---|---|
| QD  | 24 | 6.4  | 3.750 | 0.074 | 0.926 | 1.080 |
| QD  | 24 | 8.5  | 2.824 | 0.141 | 0.859 | 1.165 |
| QD  | 24 | 17   | 1.412 | 0.376 | 0.624 | 1.602 |
| QD  | 24 | 22   | 1.091 | 0.470 | 0.530 | 1.885 |
| QD  | 24 | 27   | 0.889 | 0.540 | 0.460 | 2.174 |
| BID | 12 | 6.4  | 1.875 | 0.273 | 0.727 | 1.375 |
| BID | 12 | 8.5  | 1.412 | 0.376 | 0.624 | 1.602 |
| BID | 12 | 17   | 0.706 | 0.613 | 0.387 | 2.585 |
| BID | 12 | 22   | 0.545 | 0.685 | 0.315 | 3.177 |
| BID | 12 | 27   | 0.444 | 0.735 | 0.265 | 3.772 |
| TID | 8  | 6.4  | 1.250 | 0.421 | 0.579 | 1.726 |
| TID | 8  | 8.5  | 0.941 | 0.521 | 0.479 | 2.087 |
| TID | 8  | 17   | 0.471 | 0.722 | 0.278 | 3.594 |
| TID | 8  | 22   | 0.364 | 0.777 | 0.223 | 4.489 |
| TID | 8  | 27   | 0.296 | 0.814 | 0.186 | 5.387 |

Note:
QD (Q 24 hrs), BID (Q 12 hrs), and TID (Q 8 hrs) indicates once, twice, and three times per day oral dosing.

Factor 2: Concentration of EDIM in Breath

The concentration of EDIM in breath generated from the administration of a dose of AEM is an important factor in the overall function of the SMART® Adherence System. The dose of the AEM, because it is quickly converted to the EDIM (e.g., 2-butanol and isopropyl alcohol conversion to 2-butanone and acetone, respectively) in the blood plays a pivotal role in establishing the EDIM concentration in human breath. The ultimate concentration of EDIM in breath will depend on its volume of distribution ($V_d$) and the quantity of EDIM liberated from the orally administered dose of AEM. Since the $V_d$ is fixed in a given person for a given molecular entity, only the AEM dose can be readily altered to increase or decrease the initial EDIM concentrations attained in breath.

Figure 56A:
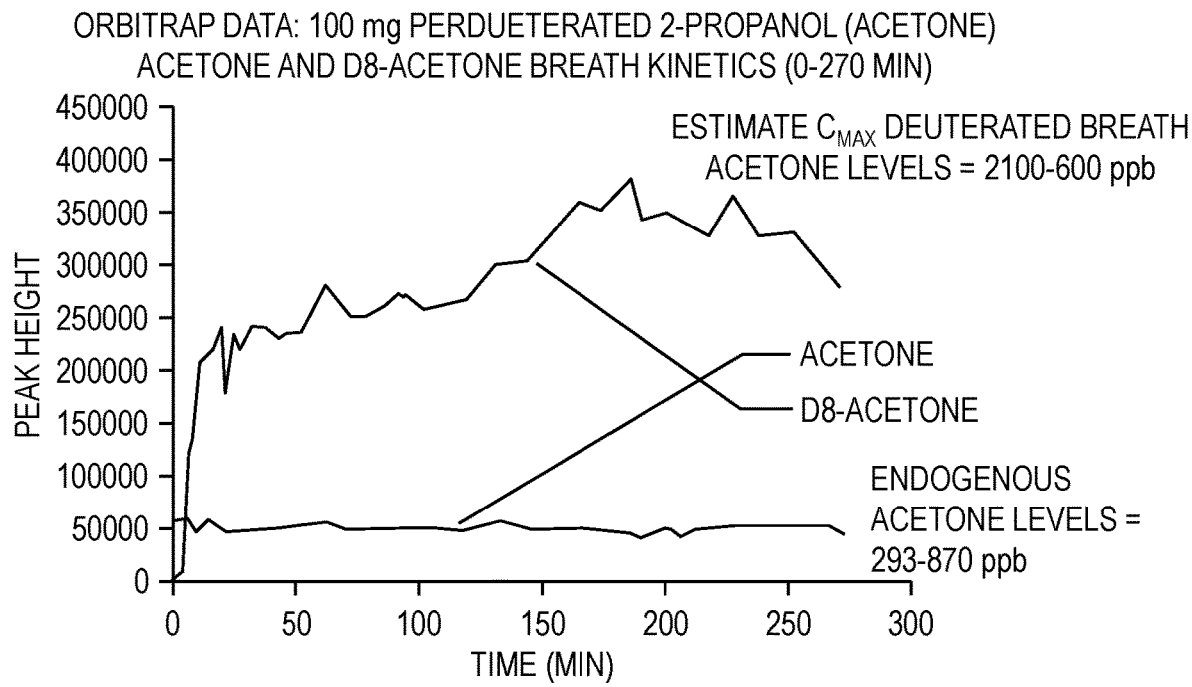
Figure 56B:
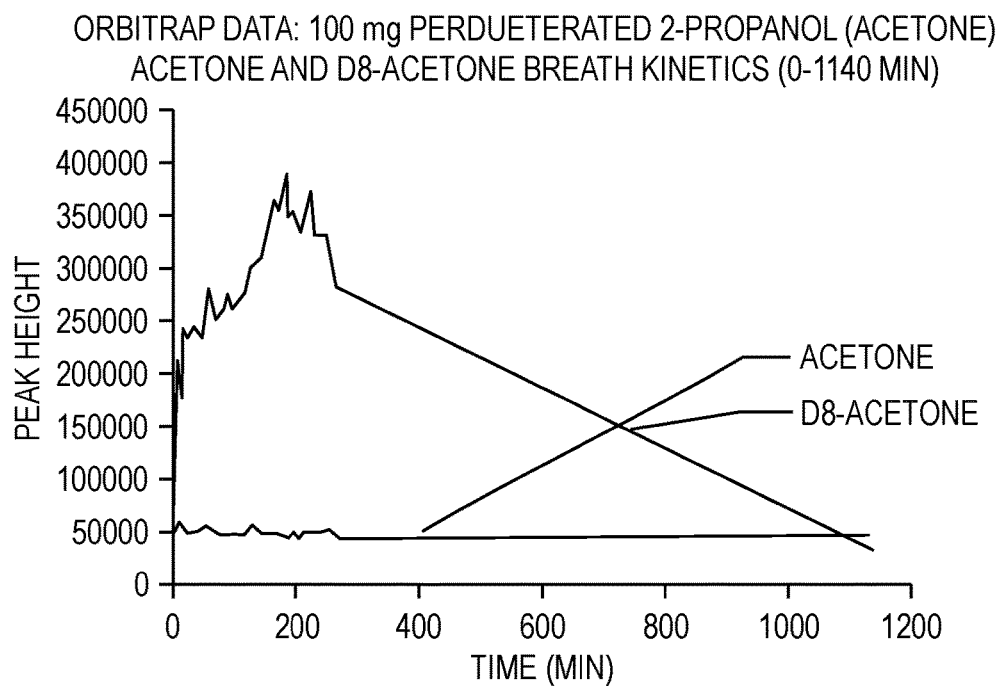

Using the OrbiTrap LC/MS/MS system to measure acetone levels in real time following ingestion of IPA, the relationship between IPA (AEM) dose and the yield of acetone (EDIM) in the breath can be readily ascertained. For example, as illustrated in FIGS. 56A and B, a single 100 mg dose of d8-IPA caused an OrbiTrap response that was approximately 5.14× greater (peak height: 360,000 versus 70,000) than that caused by the constant level of background endogenous breath acetone over the course of the study. Furthermore, if one assumes that this healthy subject had a typical normal breath acetone concentration of 582 ppb (Diskin A M et al: Physiol Meas 24:107-119, 2003), this would translate to a maximum d6-acetone concentration ($C_{MAX}$) of 2,993 ppb (=582 ppb×5.14) in breath at 3 hours ($T_{MAX}$) caused by ingesting 100 mg of d8-IPA. Thus, the background acetone served as an "internal control" for understanding the concentration-time relationship of d6-acetone. Assuming dose proportionality (linear PK), if we dosed with the FDA established permissible daily exposure (PDE) of IPA (138 mg orally per day), this would have caused an acetone $C_{MAX}$ of 4131 ppb. Note: because the peak response (sensitivity) of the OrbiTrap is the same for acetone and d6-acetone, this approach is technically viable.

Also note, as expected, there is an absence of any significant d6-acetone in human breath prior to ingestion of the d8-IPA. This is a major advantage of using non-ordinary cold isotopologues in this invention. Specifically, it provides the foundation for a SMART® Adherence System with no interferents, the longest adherence "look back" time window in terms of assessing chronic adherence (CMAM), and the use of IR sensors with tremendous sensitivity (parts per trillion). Consistent with the yield of d6-acetone in breath following ingestion of d8-IPA using the OrbiTrap system, when a Type 1 (mGC) SMART® device was employed (FIGS. 72A-C), similar high concentrations of acetone (2700 to 3000 ppb) in breath were found after ingesting 100 mg IPA for 5 successive days.

The maximum safe doses of AEM are well defined by US regulatory authorities. For example, the AEMs 2-butanol and IPA, appear to be safe as noted by a number of regulatory agency listings. They are included as direct food additives in the FDA EAFUS (Everything Added to Food in the United States) listing. Likewise, according to the FDA's Q3C Guidance for Industry, the permissible daily exposure (PDE) for 2-butanol and IPA is 300 and 138 mg/day, respectively. The PDE defines the dose of compound that a human can chronically ingest for the rest of their lives with no regulatory concern. Therefore, from a toxicological perspective, these types of AEMs (e.g., 2-butanol and IPA) are excellent candidates for use to document adherence. It should be noted that other classes of compounds, including but not limited to sulfur containing molecules, (e.g. allicin (garlic) and dimethyl sulfoxide (DMSO)) are listed in the FDA food database and generate short and long acting metabolites in breath, which would be suitable for the SMART Adherence System. For example, the FDA in its Q3C guidance lists the PDE for DMSO as 50 mg per day. DMSO has an elimination half life of 12-15 hours in humans and gives rise to highly volatile markers such as dimethyl sulfide (DMS). Because these molecules are present in various foods and specific pathological conditions, the use of cold non-ordinary isotopes on the hydrogen, carbon, sulfur, and/or oxygen atoms of these types of AEM is very promising and would easily distinguish these EDIMs from background interferents, particularly when a Type 2 (IR) device can measure these at very low concentration (low ppt), which would not be associated with malodorous smells.

Factor 3: Limit of Detection (LoD) of the SMART® Device (Type 1 vs 2) to the EDIM Another key factor in determining how long the EDIM can be accurately measured in the breath of humans is the limit of detection (LoD) of the SMART® device. For example, in the current configuration, a Type 1 SMART® device has a minimum LoD in the low part per billion (1-5 ppb), whereas a Type 2 SMART® device using infrared (IR), including near or mid IR type systems (e.g., cavity ring detection by Picarro, Sunnyvale, Calif.; or tunable lasers by Daylight Solutions, San Diego, Calif.) measurements of isotopologues of volatile compounds in the gas phase (e.g., deuterated water such as DHO) are detectable down to a LoD in the parts per trillion (1-1000 ppt). Naturally, it is not required for the system to operate at the LoD, and workable results are achievable in the tens of parts be billion range or higher.

Factor 4: Level of Background Interference to Measurement of the EDIM

The level of any background EDIM in breath or interferents that can mimic the EDIM in breath on the sensor can significantly reduce the length of the adherence "look back" window period, even if the sensor has a very low LoD to the EDIM. For example, humans naturally have mean endogenous levels of acetone ranging from 293 to 870 (average of the means=582) ppb (Diskin A M et al: *Physiol Meas* 24:107-119, 2003), but can undergo significant variation between humans and even with an individual during the day. Because endogenous acetone levels reflect a complex array of many physiological processes (e.g., lipolysis, circadian rhythms, etc.), the content of this ketone in blood and hence breath can vary significantly over time within an individual and between individuals.

This finding has two consequences with regard to using IPA as an AEM in the SMART® Adherence System using a Type 1 SMART® device. First, a significant fraction of orally ingested IPA (deuterated or non-deuterated) can be absorbed through the stomach and cause a rapid rise above baseline levels in acetone, the levels of which are several multiples of background endogenous acetone when IPA is ingested at doses that are deemed safe. If a baseline acetone level is obtained, IPA can be used for effective AMAM. In the time period to obtain the 2 breaths (e.g., 20 or 30 min), no ordinary physiological process can increase acetone to those levels. This point is not relevant for d6-IPA because there is no background d6-acetone to contend with in the SMART® Adherence System. Second, in contrast, with CMAM, unless the amount of IPA (not non-ordinary isotopically labeled IPA) that is given orally produces such a high amount of acetone in the breath, which can be clearly distinguished from normal variations in endogenous breath acetone concentrations during activities of daily living (ADL), it is quite susceptible to false positive and false negatives that limits its utility when used for IMAM (adherence window up to 1 day), because in this case the limiting factor for the adherence window ($C_{EDIM,Limit}$) is not sensor sensitivity (Type 1 mGC device has an LoD of 1-5 ppb) but rather the level of background endogenous acetone. This high level of endogenous acetone and the variability of these levels within and between individuals over sustained periods of time during ADL limits the adherence window "look back" period to AMAM and/or IMAM; it is not suitable for CMAM.

In contrast, the use of deuterated isopropyl alcohol (d8-IPA) as the AEM produces deuterated acetone (d6-acetone) that does not suffer from this limitation (no background levels present), provides a long adherence "look back" window (see below, $T_{AdhWindow}$ and values shown in Table D), and is highly suitable for CMAM, even for longer periods of the adherence window look back time (see Equation 9 below: $T_{AdhWindow}$ and Table D).

With regard to background interference affecting another AEM, 2-butanol (ordinary isotopic form=no cold isotopes used), the concentration of 2-butanone in breath is typically very low but occasionally subjects will have higher levels. In order to maximize the sensitivity, specificity, and accuracy of a 2-butanone-based AMAM SMART® system, it is necessary to include a baseline breath sample to mitigate its effect. A rise in 2-butanone levels, typically 5 ppb or greater in breath, are highly indicative of adherence (see Example 3, Clinical Studies for details). Recall that 2-butanol is suitable for AMAM because 2-butanone has an elimination half life in breath of 11-22 min. Similar to non-ordinary cold isotopologues of acetone that are generated when d8-IPA is used as the AEM, the use of d10-2-butanol that generate d8-2-butanone eliminates any potential for background interference to 2-butanone already present in breath at the start of the adherence assessment. However, it still does not make it suitable for IMAM or CMAM because the elimination half life of 2-butanone is the same for both cold non-ordinary (e.g., deuterated) or ordinary 2-butanone in human breath. For simple molecules like 2-butanol, 2-butanone, IPA, and acetone, isotopic substitutions on their structures with cold non-ordinary isotopes does not cause significant changes in their PK properties. Consistent with this statement, FIG. 58 shows the parallel rise (concentration-time relations) of deuterated acetone and ordinary acetone following the ingestion of a capsule containing both d8-IPA and ordinary IPA. In contrast, substitutions on much more complex molecular entities such as the deuterated form of the antidepressant, paroxetine, can cause changes, albeit somewhat subtle, in its PK properties, including but not limited to its susceptibility to CYP-450 metabolism (Concert Pharmaceuticals, Lexington, Mass.; website: http://www.concertpharma.com/index.html).

Given the four factors just discussed, for a specific EDIM with a given half life in breath, how would one establish the adherence window ($T_{AdhWindow}$, Equation 9), where adherence can be assessed? The time required for the EDIM to fall from a specific concentration, termed $C_{EDIM,o}$, such as from its trough ($C_{EDIM,Trough}$) or peak ($C_{EDIM,MAX}$) levels, to some limiting concentration, termed $C_{EDIM,Limit}$ will define the maximum "look back" detection window. The $C_{EDIM,Limit}$ is defined by the greater of two factors: 1) SMART® device sensitivity, or 2) EDIM background interference (e.g., variation in the endogenous levels of acetone if the EDIM is IPA generated acetone). Major advantages of using cold non-ordinary isotopologues as the AEMs in the SMART® Adherence System include: 1) they generate EDIMs, which have no background interference, and 2) they can be detected with Type 2 SMART® Devices that have outstanding LoDs (part per trillion level detection levels). Therefore, the adherence "look back" window will be greater when cold non-ordinary isotopologues are used as the AEMs. Equation 9 (from a re-arranged Equation 3) provides the maximum length of time (adherence "look back" window), defined as $T_{AdhWindow}$, that it will take for an EDIM to decay from an initial level, termed $C_{EDIM,o}$ (e.g., EDIM trough [$CO_{Trough}$] or max [$C_{MAX}$]) to a limiting EDIM concentration, termed $C_{EDIM,Limit}$, either due to a device LoD limitation or a background interferent level.

$$T_{AdhWindow} = \frac{t_{1/2e}}{0.693} * \ln\left(\frac{C_{EDIM,o}}{C_{EDIM,Limit}}\right) \quad \text{Equation 9}$$

Table C provides various values of $T_{AdhWindow}$ depending upon the $t_{1/2e}$, $C_{EDIM,o}$, and $C_{EDIM,Limit}$ of the EDIM. Table D specifically provides this information using the four elimination half lives (6.4, 8.5, 17, 22, and 27 hrs) reported in the text for the EDIM, acetone:

TABLE C

Adherence "Look Back" Window Period, termed $T_{AdhWindow}$, as measured in hours for an EDIM. Values were calculated from Equation 9. The relationship between the length of time (hours) that will elapse for the initial EDIM concentration ($C_{EDIM, o}$) to decay to the EDIM limit concentration ($C_{EDIM, Limit}$) (whatever is greater, either the LoD of the sensor or background EDIM levels is applicable), given the EDIM half life in breath ($t_{1/2e}$). The $C_{EDIM, o}$ could represent various concentrations, but preferably trough EDIM ($C_{Trough}$), maximum EDIM concentration ($C_{MAX}$), and/or some EDIM concentration at a fixed time post dosing (e.g., 20 or 30 min) during a dosing interval.

| Iniial EDIM Breath Conc | EDIM Limit Conc | Decay Time (hrs): EDIM Initial Concentration to EDIM Limit Concentration Half Life of EDIM in Human Breath (hrs) | | | | | | | | | |
|---|---|---|---|---|---|---|---|---|---|---|---|
| | | 0.5 | 0.75 | 1 | 2 | 4 | 6 | 8 | 12 | 18 | 24 |
| 100 ppb | 10 ppt | 6.7 | 10.0 | 13.3 | 26.6 | 53.2 | 79.8 | 106.4 | 159.6 | 239.4 | 319.2 |
| | 100 ppt | 5.0 | 7.5 | 10.0 | 19.9 | 39.8 | 59.8 | 79.7 | 119.5 | 179.3 | 239.0 |
| | 1 ppb | 3.3 | 5.0 | 6.6 | 13.3 | 26.6 | 39.8 | 53.1 | 79.7 | 119.5 | 159.4 |
| | 5 ppb | 2.2 | 3.2 | 4.3 | 8.6 | 17.3 | 25.9 | 34.6 | 51.8 | 77.8 | 103.7 |
| 250 ppb | 10 ppt | 7.3 | 11.0 | 14.6 | 29.2 | 58.5 | 87.7 | 117.0 | 175.4 | 263.2 | 350.9 |
| | 100 ppt | 5.7 | 8.5 | 11.3 | 22.6 | 45.2 | 67.8 | 90.4 | 135.6 | 203.4 | 271.2 |
| | 1 ppb | 5.0 | 7.5 | 10.0 | 19.9 | 39.8 | 59.8 | 79.7 | 119.5 | 179.3 | 239.0 |
| | 5 ppb | 2.8 | 4.2 | 5.6 | 11.3 | 22.6 | 33.8 | 45.1 | 67.7 | 101.5 | 135.4 |
| 500 ppb | 10 ppt | 7.8 | 11.7 | 15.6 | 31.2 | 62.5 | 93.7 | 125.0 | 187.4 | 281.2 | 374.9 |
| | 100 ppt | 6.2 | 9.2 | 12.3 | 24.6 | 49.2 | 73.8 | 98.4 | 147.6 | 221.4 | 295.2 |
| | 1 ppb | 4.5 | 6.7 | 9.0 | 17.9 | 35.8 | 53.8 | 71.7 | 107.5 | 161.3 | 215.0 |
| | 5 ppb | 3.3 | 5.0 | 6.6 | 13.3 | 26.6 | 39.8 | 53.1 | 79.7 | 119.5 | 159.4 |
| 750 ppb | 10 ppt | 8.1 | 12.2 | 16.2 | 32.4 | 64.8 | 97.2 | 129.6 | 194.4 | 291.6 | 388.8 |
| | 100 ppt | 6.4 | 9.7 | 12.9 | 25.8 | 51.5 | 77.3 | 103.0 | 154.6 | 231.8 | 309.1 |
| | 1 ppb | 4.8 | 7.2 | 9.6 | 19.1 | 38.2 | 57.4 | 76.5 | 114.7 | 172.1 | 229.4 |
| | 5 ppb | 3.6 | 5.4 | 7.2 | 14.5 | 29.0 | 43.4 | 57.9 | 86.9 | 130.3 | 173.8 |
| 1000 ppb | 10 ppt | 8.3 | 12.5 | 16.6 | 33.2 | 66.5 | 99.7 | 133.0 | 199.4 | 299.2 | 398.9 |
| | 100 ppt | 6.7 | 10.0 | 13.3 | 26.6 | 53.2 | 79.8 | 106.4 | 159.6 | 239.4 | 319.2 |
| | 1 ppb | 5.0 | 7.5 | 10.0 | 19.9 | 39.8 | 59.8 | 79.7 | 119.5 | 179.3 | 239.0 |
| | 5 ppb | 3.8 | 5.7 | 7.6 | 15.3 | 30.6 | 45.8 | 61.1 | 91.7 | 137.5 | 183.4 |
| 1500 ppb | 10 ppt | 8.6 | 12.9 | 17.2 | 34.4 | 68.8 | 103.2 | 137.6 | 206.4 | 309.6 | 412.8 |
| | 100 ppt | 6.9 | 10.4 | 13.9 | 27.8 | 55.5 | 83.3 | 111.0 | 166.6 | 249.8 | 333.1 |
| | 1 ppb | 5.3 | 7.9 | 10.6 | 21.1 | 42.2 | 63.4 | 84.5 | 126.7 | 190.1 | 253.4 |
| | 5 ppb | 4.1 | 6.2 | 8.2 | 16.5 | 33.0 | 49.4 | 65.9 | 98.9 | 148.3 | 197.8 |
| 2000 ppb | 10 ppt | 8.8 | 13.2 | 17.6 | 35.2 | 13.2 | 105.7 | 140.9 | 211.4 | 317.1 | 422.8 |
| | 100 ppt | 7.2 | 10.7 | 14.3 | 28.6 | 10.7 | 85.8 | 114.4 | 171.5 | 257.3 | 343.0 |
| | 1 ppb | 5.5 | 8.2 | 11.0 | 21.9 | 8.2 | 65.8 | 87.8 | 131.6 | 197.5 | 263.3 |
| | 5 ppb | 4.3 | 6.5 | 8.6 | 17.2 | 6.5 | 51.9 | 68.8 | 103.8 | 155.7 | 207.5 |

TABLE D

Adherence "Look Back" Window Period, termed $T_{AdhWindow}$, as measured in hours and days using acetone as the EDIM. Values were calculated from Equation 9. The relationship between the length of time (hours) that will elapse for the initial acetone (EDIM) concentration ($C_{EDIM, o}$) to decay to the acetone (EDIM) limit concentration ($C_{EDIM, Limit}$) (whatever is greater, either the LoD of the sensor or background acetone levels is applicable), given the acetone half life in breath ($t_{1/2e}$). The $C_{EDIM, o}$ could represent various concentrations, but preferably trough EDIM ($C_{Trough}$), maximum EDIM concentration ($C_{MAX}$), and/or some acetone concentration at a fixed time post dosing (e.g., 20 or 30 min) during a dosing interval.

| Iniial Acetone Breath Conc | Acetone Limit Conc | Decay Time (hrs): Acetone (EDIM) Initial Concentration to Acetone Limit Level Half Life of Acetone in Human Breath (hrs) | | | | | Decay Time (days): Acetone (EDIM) Initial Concentration to Acetone Limit Level Half Life of Acetone in Human Breath (hrs) | | | | |
|---|---|---|---|---|---|---|---|---|---|---|---|
| | | 6.4 | 8.5 | 17 | 22 | 27 | 6.4 | 8.5 | 17 | 22 | 27 |
| 100 ppb | 10 ppt | 85.1 | 113.1 | 226.1 | 292.6 | 359.1 | 3.5 | 4.7 | 9.4 | 12.2 | 15.0 |
| | 100 ppt | 63.7 | 84.7 | 169.3 | 219.1 | 268.9 | 2.7 | 3.5 | 7.1 | 9.1 | 11.2 |
| | 1 ppb | 42.5 | 56.4 | 112.9 | 146.1 | 179.3 | 1.8 | 2.4 | 4.7 | 6.1 | 7.5 |
| | 5 ppb | 27.6 | 36.7 | 73.4 | 95.0 | 116.6 | 1.2 | 1.5 | 3.1 | 4.0 | 4.9 |
| 250 ppb | 10 ppt | 93.6 | 124.3 | 248.5 | 321.6 | 394.7 | 3.9 | 5.2 | 10.4 | 13.4 | 16.4 |
| | 100 ppt | 72.3 | 96.1 | 192.1 | 248.6 | 305.1 | 3.0 | 4.0 | 8.0 | 10.4 | 12.7 |
| | 1 ppb | 63.7 | 84.7 | 169.3 | 219.1 | 268.9 | 2.7 | 3.5 | 7.1 | 9.1 | 11.2 |
| | 5 ppb | 36.1 | 47.9 | 95.9 | 124.1 | 152.3 | 1.5 | 2.0 | 4.0 | 5.2 | 6.3 |
| 500 ppb | 10 ppt | 100.0 | 132.8 | 265.5 | 343.6 | 421.7 | 4.2 | 5.5 | 11.1 | 14.3 | 17.6 |
| | 100 ppt | 78.7 | 104.6 | 209.1 | 270.6 | 332.1 | 3.3 | 4.4 | 8.7 | 11.3 | 13.8 |
| | 1 ppb | 57.3 | 76.2 | 152.3 | 197.1 | 241.9 | 2.4 | 3.2 | 6.3 | 8.2 | 10.1 |
| | 5 ppb | 42.5 | 56.4 | 112.9 | 146.1 | 179.3 | 1.8 | 2.4 | 4.7 | 6.1 | 7.5 |
| 750 ppb | 10 ppt | 103.7 | 137.7 | 275.4 | 356.4 | 437.4 | 4.3 | 5.7 | 11.5 | 14.9 | 18.2 |
| | 100 ppt | 82.4 | 109.5 | 219.0 | 283.4 | 347.8 | 3.4 | 4.6 | 9.1 | 11.8 | 14.5 |
| | 1 ppb | 61.2 | 81.3 | 162.5 | 210.3 | 258.1 | 2.5 | 3.4 | 6.8 | 8.8 | 10.8 |
| | 5 ppb | 46.3 | 61.5 | 123.1 | 159.3 | 195.5 | 1.9 | 2.6 | 5.1 | 6.6 | 8.1 |

TABLE D-continued

Adherence "Look Back" Window Period, termed $T_{AdhWindow}$, as measured in hours and days using acetone as the EDIM. Values were calculated from Equation 9. The relationship between the length of time (hours) that will elapse for the initial acetone (EDIM) concentration ($C_{EDIM, o}$) to decay to the acetone (EDIM) limit concentration ($C_{EDIM, Limit}$) (whatever is greater, either the LoD of the sensor or background acetone levels is applicable), given the acetone half life in breath ($t_{1/2e}$). The $C_{EDIM, o}$ could represent various concentrations, but preferably trough EDIM ($C_{Trough}$), maximum EDIM concentration ($C_{MAX}$), and/or some acetone concentration at a fixed time post dosing (e.g., 20 or 30 min) during a dosing interval.

| Inital Acetone Breath Conc | Acetone Limit Conc | Decay Time (hrs): Acetone (EDIM) Initial Concentration to Acetone Limit Level Half Life of Acetone in Human Breath (hrs) | | | | | Decay Time (days): Acetone (EDIM) Initial Concentration to Acetone Limit Level Half Life of Acetone in Human Breath (hrs) | | | | |
|---|---|---|---|---|---|---|---|---|---|---|---|
| | | 6.4 | 8.5 | 17 | 22 | 27 | 6.4 | 8.5 | 17 | 22 | 27 |
| 1000 ppb | 10 ppt | 106.4 | 141.3 | 282.5 | 365.6 | 448.7 | 4.4 | 5.9 | 11.8 | 15.2 | 18.7 |
| | 100 ppt | 85.1 | 113.1 | 226.1 | 292.6 | 359.1 | 3.5 | 4.7 | 9.4 | 12.2 | 15.0 |
| | 1 ppb | 63.7 | 84.7 | 169.3 | 219.1 | 268.9 | 2.7 | 3.5 | 7.1 | 9.1 | 11.2 |
| | 5 ppb | 48.9 | 64.9 | 129.9 | 168.1 | 206.3 | 2.0 | 2.7 | 5.4 | 7.0 | 8.6 |
| 1500 ppb | 10 ppt | 110.1 | 146.2 | 292.4 | 378.4 | 464.4 | 4.6 | 6.1 | 12.2 | 15.8 | 19.4 |
| | 100 ppt | 88.8 | 118.0 | 236.0 | 305.4 | 374.8 | 3.7 | 4.9 | 9.8 | 12.7 | 15.6 |
| | 1 ppb | 67.6 | 89.8 | 179.5 | 232.3 | 285.1 | 2.8 | 3.7 | 7.5 | 9.7 | 11.9 |
| | 5 ppb | 52.7 | 70.0 | 140.1 | 181.3 | 222.5 | 2.2 | 2.9 | 5.8 | 7.6 | 9.3 |
| 2000 ppb | 10 ppt | 105.7 | 140.9 | 211.4 | 317.1 | 422.8 | 4.4 | 5.9 | 8.8 | 13.2 | 17.6 |
| | 100 ppt | 85.8 | 114.4 | 171.5 | 257.3 | 343.0 | 3.6 | 4.8 | 7.1 | 10.7 | 14.3 |
| | 1 ppb | 65.8 | 87.8 | 131.6 | 197.5 | 263.3 | 2.7 | 3.7 | 5.5 | 8.2 | 11.0 |
| | 5 ppb | 51.9 | 68.8 | 103.8 | 155.7 | 207.5 | 2.2 | 2.9 | 4.3 | 6.5 | 8.6 |

Note:
The values of the acetone breath elimination half lives (6.4, 8.5, 17, 22, and 27 hrs) included in the analysis were those discussed in Example 5.

Factor 5: Permeability of the AEM for stomach absorption
Because the gastric surface is lined by a thick epithelium, most compounds do not have significant absorption through the stomach into the portal vein and hence the liver. Most therapeutic drugs enter the blood (portal vein) via absorption through the small intestine (e.g., duodenum). However, following oral ingestion, it is well known that simple lower molecular weight compounds, including but not limited to alcohols (e.g., ethanol, 2-butanol, IPA) have a significant fraction (e.g., 25-30%) of their systemic absorption into the body from the stomach (Jones A W. Forensic Sci Rev. 2011; 23:91-136). This finding is consistent with all the data submitted in this patent disclosure, and is a prerequisite to carry out effective AMAM, where the system is measuring definitive adherence on a pill by pill (dose by dose) basis. It is a prerequisite for effective AMAM that the AEM be absorbed directly through the gastric wall. This is highly desirable, because the breath marker (EDIM) appearance is not dependent on duodenal absorption, which in turn is highly dependent on the extremely variable process of gastric emptying. A number of factors can have a major impact on the time for gastric emptying, including but not limited to food type, stress, and drugs. In contrast, significant gastric absorption is not a requirement for a molecule to serve as an effective AEM in the setting of IMAM or CMAM.

Examples of Different SMART® Adherence System Embodiments

Since most oral drugs being administered in the current health care environment are administered once per day (i.e., QD, or every 24 hours), the examples hereafter mentioned will assume that the therapeutic agent, which is linked to the AEM, is given once per day each morning at 8 am. However, the analysis (equations and tables) listed above also readily enable methods to provide adherence solutions according to alternate regimens, depending upon specific needs and the clinical environment. These factors include: 1) AMAM, IMAM, and CMAM using those drugs that are also given orally multiple times per day, including but not limited to twice (BID), three (TID), or four (QID) times per day; 2) multiple variations on how the SMART® Adherence System can be designed that use a) combinations of ordinary and/or non-ordinary isotopes in AEM(s) that generate EDIMs with different elimination half lives in breath, and b) two (pre-ingestion of medication containing the AEM [baseline breath] and post-ingestion of medication linked to AEM(s)) or one (post-ingestion of medication linked to AEM(s)) breath samples during an adherence assessment; 3) either one or multiple AEMs that generate one or multiple EDIMs, respectively, 4) different timing of the breath sampling, relative to $T_{MAX}$, during the dosage interval (T) to ensure the greatest reliability of the adherence assessment (e.g., ensure that deceit is not occurring and to minimize or eliminate any potential interferents to SMART® Adherence System function).

The illustrative examples provided herein teach how SMART® Adherence Systems according to this invention can be readily designed and assembled to provide individual AMAM, IMAM, CMAM capabilities along with combinations of their capabilities (e.g., AMAM plus CMAM capabilities) employing features that provide different levels of certainty that the system is providing accurate adherence assessments (safeguards to ensure that subjects/patients are not deceiving the system). In addition, when using the SMART® Adherence System technology, while it will generally be preferable to configure the system at the level of the individual subject or patient, as opposed to using global pharmacokinetic (PK) parameters, those skilled in the art will appreciate that the latter is included in this invention. The significant variability known to exist in PK parameters (e.g., $t_{1/2e}$, $C_{Trough}$, $C_{MAX}$, $T_{MAX}$ etc.) between individuals can be eliminated by determining key PK parameters at the level of the individual subject/patient. In addition, this approach also provides a period for the subject/patient to become acclimated with the SMART® Adherence System, which may facilitate proper use of the system later in trials or disease management. However, strategies to employ the SMART® Adherence System in the clinical setting based on population PK is also described. In addition, as a rule of thumb, it is preferred to use AEMs containing non-ordinary cold isotopes as part of their molecular structure to generate EDIMs labeled with cold non-ordinary isotopes, which confer two major advantages: 1) no background interference, which provides a longer adherence look back window and may obviate the need for a $2^{nd}$ breath when using the SMART® Adherence System, and 2) a Type 2 (IR-based) SMART® device as disclosed herein may be implemented that has a lower LoD than the Type 1 (GC) SMART® device.

Example 28a

In this example, an initial $1^{st}$ AEM dose pharmacokinetic (PK) analysis over a period of 0 to a maximum of 24 hours is carried out. From the EDIM breath concentration-response data thus generated, the EDIM elimination half life ($t_{1/2e}$), time to maximum EDIM concentration ($T_{max}$), $1^{st}$ Dose EDIM $C_{Trough}$, $1^{st}$ dose EDIM $C_{MAX}$, accumulation factor (AF), EDIM concentration at key times such as 20 and 30 min post ingestion of the AEM contained in the medication (e.g., $C_{20\ min}$ or $C_{30\ min}$), steady state trough EDIM concentration ($C_{Trough,\ SS}$), steady state maximum EDIM concentration ($C_{MAX,\ SS}$), and the adherence "look back" window time ($T_{AdhWindow}$) are all generated. Note: To ensure an accurate EDIM $t_{1/2e}$ ideally the last time point measured in this $1^{st}$ dose PK analysis includes the EDIM trough concentration (i.e., the concentration at the time point just prior to the $2^{nd}$ dose). The AEM could either consist of ordinary or non-ordinary cold isotopes, which generate ordinary and non-ordinary cold isotopic labeled EDIMs. The EDIM levels in breath are measured using the appropriate SMART® device type as disclosed herein.

In this example shown below, the experimental d6-acetone (EDIM) concentration-time data from FIG. 67 following ingestion of the $1^{st}$ dose of 100 mg d8-IPA is shown in FIG. 74. The black circles indicate the actual data points obtained in the subject. This data was curve fit to Equation 1, and PK parameters were determined as described in connection with FIG. 74. FIG. 75 shows the EDIM breath PK after ingestion of 5 sequential doses of 100 mg d8-IPA that attained steady state levels after 4-5 doses. In the case of using cold non-ordinary isotope labeled EDIMs (d6-acetone), the $T_{AdhWindow}$ is totally dependent on the EDIM concentration, elimination half life of the d6-acetone, and the LoD of the SMART® Type 1 (IR) device to d6-acetone.

As shown in FIG. 75, the strategy outlined easily provides an adherence window of 4-5 days and is highly suitable for CMAM. In addition, it is also highly suitable for AMAM, because when a two breath script is used during an adherence assessment, the rise in d6-acetone over baseline levels, even with accumulation (see FIG. 74), would be easily detected if the measurements were made at values less than $T_{MAX}$ (e.g., 20-30 min). The latter strategy of asking subjects to provide a baseline (trough) breath sample and one immediately thereafter at a time prior to $T_{MAX}$, such as 20 or 30 min post-ingestion of the medication containing the AEM (determined by $1^{st}$ single dose PK), not only enables AMAM and IMAM in addition to CMAM, but also has other benefits. Specifically, if the system is used in CMAM mode and the subjects are randomly called to provide a trough breath sample on random days (e.g., sample provided immediately before their 8 AM dosing), it would be rapidly apparent in a subject who was not adherent, because their trough EDIM levels would be markedly lower than steady state trough EDIM levels (degree of non-adherence provided by $T_{AdhWindow}$), if the subject did not try to deceive the system by attempting to ingest the medication prior to providing the trough breath sample. If the subject did try to deceive the system, such behavior would be detected if the measured EDIM trough concentration or that at 20 or 30 min post ingestion were significantly higher than expected. Likewise, other approaches involving the random calling of subjects could be used in CMAM to effectively detect non-adherent and/or deceitful behavior in a drug being taken at 8 am each day by: 1) having a subject provide two breath samples using a fixed time interval (30 min) at times before $T_{MAX}$ but after 8 AM (trough time); the EDIM breath concentration with the $2^{nd}$ breath must be rising relative to the concentration with the $1^{st}$ breath; 2) having the subject provide two breath samples spaced 20 or 30 min apart beginning at a time after $T_{MAX}$, say at 8 PM, approximately 12 hours after the medicine was taken (or should have been taken) containing the AEM (pill taken at trough, approximately 8 AM). Under these circumstances, the $2^{nd}$ breath sample must have an EDIM concentration that is less than (or roughly constant) that observed with the $1^{st}$ breath concentration; if the $2^{nd}$ breath EDIM concentration is greater than the $1^{st}$ breath concentration, it would clearly indicate the subject just ingested the medication to make it appear he/she was adherent to the drug regimen; and 3) as shown in FIG. 76, a second AEM, (such as 2-butanol), which generates an EDIM, (2-butanone), which has a short elimination half life of 11-22 min (presence in breath at typical doses is 2-3 hours) could be added, which would clearly identify situations where the subject is trying to abruptly take the medication when randomly called, when they had not been taking it consistently over the longer term. For example, randomly calling a subject at 8 PM at night, who was instructed to ingest a medication given daily at 8 AM that contains the AEMs d8-IPA and d10-2-butanol, if he/she provided a single breath sample at 8 PM and it contained both d8-2-butanone and d6-acetone, it would immediately indicate deceptive behavior (since the 2-butanone would never be detectable in breath 12 hours after the once per day morning dose). The conclusion is drawn that the subject attempted to deceive the system by acutely taking the medication at around 8 PM that night, as opposed to 8 AM daily. In this disclosure, we have taught how more than one AEM can be used to generate multiple EDIMs, which are readily detected by sensors. This exemplary disclosure teaches those skilled in the art how the SMART® Adherence System can be slightly modified to provide highly accurate assessments of medication adherence, particularly when these measurements are coupled to a concurrent biometric measurement (e.g., subject photograph at the time of provision of a breath sample).

How would the SMART® Adherence System perform if the subject ingested ordinary IPA, as opposed to d8-IPA, at the same doses? In this case, the acetone concentrations generated as the EDIM from IPA would be additive to the preexisting concentration of endogenous acetone in breath. Here, the limiting EDIM breath concentration would not be dependent on the LoD of the Type 1 Sensor (GC-based with an LoD=5 ppb) but rather the high and variable concentration of endogenous acetone. For illustration purposes, it is assumed that the endogenous concentration of acetone is at the mean range of acetone breath levels (i.e., 582 ppb) found in humans over a 30 day period (Diskin A M et al, *Physiol Meas* 24:107-119, 2003). Thus, after ingestion of IPA, the acetone levels are approximately additive (endogenous+IPA-derived) and the acetone $C_{MAX}$ and $C_{Trough}$ levels are 2401 ppb (=582+1819 ppb) and 849 ppb (=582+267 ppb), respectively. Thus, using a limiting acetone (EDIM) concentration of 582 ppt, the $T_{AdhWindow}$ for $C_{Trough}$ and $C_{MAX}$ levels of acetone according to Equation 9 is 17.4 hrs and 4.6 hrs, respectively. It is immediately apparent that the significant background endogenous acetone levels markedly reduces the effective $T_{AdhWindow}$ using ordinary IPA.

With ordinary IPA using Cm, the system could be used in IMAM but not CMAM mode. Furthermore, because IMAM relies on measurements up to a day after ingestion of the medication containing the AEM, all the factors that can cause acetone breath levels to vary over that 1 day period can negatively impact SMART®. With regard to SMART® system performance, the advantages of using d8-IPA are apparent based on this disclosure. Accordingly, if a Type 1 (GC-based) SMART device is used for IMAM, it would be ideal to use an ordinary isotope-based AEM that generates a distinctive EDIM (minimal to no background interference; no endogenous levels) that is sensitively detected with the sensor.

With CMAM, if a subject is regularly or randomly asked to provide a breath sample to the SMART® device at a particular time in a day (e.g., time at trough, peak concentration, or 20 to 30 min post ingestion of the medication containing the AEM), if his/her EDIM concentration falls within their personal EDIM concentration band (preferential approach), they will have been adherent over a period of time determined by PK. If the opposite is true, they are deemed non-adherent, and the length of non-adherence is determined by the equations/tables provided herein (based on PK principles). The ingestion of IPA as the AEM, either ordinary and/or non-ordinary isotopic labeled IPA, can be used for AMAM, IMAM, and/or CMAM.

The discussion above centers around the use of single AEM dose PK, tailored at the level of the individual subject, as being the ideal approach to determine the key PK parameters that enable the use of the SMART® Adherence System. As mentioned previously, this is the preferred approach. The single dose PK strategy in a given individual allows PK parameters along with their standard errors (and confidence intervals) to be extended to determinations carried out over a number of days in a given individual to provide even better PK parameters in a particular individual, which could take into account day to day variability such as food, etc. However, the premonitory "lead in" period can be abolished if the same PK parameters are derived from the 1$^{st}$ dose AEM technique, but it is carried out in a large number of subjects to determine global population-based PK estimates (see Example 3 for different examples of this analysis). These same parameters, as described above, are determined using standard statistical approaches and the 90%, 95%, and 99% confidence intervals are determined. Depending upon the clinical circumstances, the 90%, 95%, or 99% confidence interval global PK parameter ranges are employed to guide use and interpretation of the SMART® Adherence System data generated for individual subjects.

Example 28b

In this example, the trough concentration of EDIM ($CO_{Trough}$) and the concentration of EDIM at a time post ingestion (e.g., 30 min), termed $C_{30\,min}$, is determined at each AEM dose over a period of 4-7 days. Using experimentally derived PK parameters and applying them to Equation 1, allows the d6-acetone (EDIM) concentration-time relationship to be created (FIG. 77, top panel). Specifically, FIG. 77 illustrates the EDIM (d6-acetone) concentration-time relationships for the 1$^{st}$ seven doses of medication containing the AEM (100 mg d8-IPA). The bottom panel of FIG. 77 illustrates the relationship between d6-acetone $C_{Trough}$ levels against time (AEM doses 1 through 7). This experimental data (bottom panel) was curve fit to the equation shown in the bottom panel, providing an estimate along with their standard errors of the fit of the 1$^{st}$ order elimination rate constant ($k_e$) (and hence the EDIM elimination half life ($t_{1/2e}$)) and the steady state EDIM trough concentration ($C_{Trough,SS}$). Using Equation 9, as described in the legend of FIG. 77, by substituting the d6-acetone $C_{Trough,SS}$ value as $C_{EDIMo}$, the d6-acetone elimination half life as the EDIM elimination half life ($t_{1/2e}$), and the Type 2 sensor cutoff concentration (10 or 100 ppt) as the $C_{EDIM,Limit}$ value, the adherence "look back" window time ($T_{AdhWindow}$) is readily calculated, which in this case is the time it would take for the d6-acetone concentration to decay from $C_{Trough,SS}$ to the Type 2 sensor LoD level for d6-acetone. Note: $C_{30\,min}$ can also be measured and used as $C_{EDIMo}$ value, because of the numerous benefits it can promulgate in terms of system accuracy and preventing subjects from successfully deceiving the system (see discussion in Example 28a above).

The discussion in Example 28b above centers around the use of serial EDIM $C_{Trough}$ (with or without $C_{30\,min}$) measurements to estimate the EDIM elimination half life ($t_{1/2e}$) at the level of the individual subject, as being the ideal approach to determine the key PK parameters that enable the use of the SMART® Adherence System. As mentioned previously, this is the preferred approach. The serial EDIM $C_{Trough}$ PK strategy in a given individual allows determination of PK parameters, including EDIM $t_{1/2e}$ and steady state levels of trough EDIM concentration ($C_{Trough,ss}$).

This in turn allows the $T_{AdhWindow}$ to be determined as described previously, along with their standard errors (and confidence intervals). However, the premonitory "lead in" period can be abolished if the same PK parameters derived from the EDIM CTrough studies at the individual level are now carried out in a large number of subjects to determine global population-based PK estimates. These same parameters, as described above, are determined using standard statistical approaches to derive the 90%, 95%, and 99% confidence intervals. Depending upon the clinical circumstances, the 90%, 95%, or 99% confidence interval global PK parameter ranges are used to guide use and interpretation of the SMART® Adherence System data generated for individual subjects.

Example 29

Breath-Based Naltrexone Adherence Tool to Manage Narcotic-Addicted HIV Patients and SMART® Naltrexone Formulation We found that 1) naltrexone can be formulated with acceptable stability in a hard gel capsule in an isotropic solution consisting of 2-butanol and oleic acid, and 2) after oral ingestion in humans, this type of naltrexone formulation rapidly and reliably causes a robust increase in the concentration of breath markers (e.g., 2-butanone) that can be effectively used to definitively document ingestion of the naltrexone dose form using the SMART Adherence System. Based on these results, we conclude that the pharmaceutical development of a viable thermodynamically stable SMART formulation of naltrexone is highly feasible, and the SMART Adherence System can be effectively employed to definitively document ingestion of the SMART naltrexone formulations. The use of SMART naltrexone formulations in the SMART Adherence System holds significant promise to ensure that high risk subjects such as opioid-addicted HIV patients ingest this narcotic receptor antagonist as directed by their health care provider. This work further confirms the utility of this invention for making a wide variety of SMART medication formulations for which adherence monitoring is enabled by utilizing the SMART device disclosed herein.

In this study, eight subjects were given four different formulations in a double blind, randomized, crossover manner. These formulations were:

| Formulation | Naltrexone Base (powder) | 2-Butanol | Isopropanol | Oleic Acid | L-Carvone | |
|---|---|---|---|---|---|---|
| 1 | 45.2 mg | 80 mg (98 uL) | — | 160 mg (179 uL) | — | Formulation Inside White Size 0 LiCaps Capsule |
| 2 | 45.2 mg | 40 mg (49 uL) | 30 mg (38 uL) | 160 mg (179 uL) | — | Formulation Inside White Size 0 LiCaps Capsule |
| 3 | 45.2 mg | 40 mg (49 uL) | — | 160 mg (179 uL) | 30 mg (32 uL) | Formulation Inside White Size 0 LiCaps Capsule |
| 4 | 45.2 mg | 40 mg (49 uL) | — | — | — | Naltrexone base powder placed inside Size 0 LiCap Capsule that also contains a Size 2 LiCap Capsule containing 2-buitanol |

All of these formulations contained 45.2 mg of naltrexone base powder and either 40 mg or 80 mg of 2-butanol. Three of these formulations (F1, F2, F3) had the naltrexone and 2-butanol mixed with the excipient (160 mg of oleic acid) with either 30 mg of isopropanol or L-carvone, then placed inside of a white size 0 LiCaps capsule. One of the formulations (F4) served as a check on the effect that the excipient had on the naltrexone and 2-butanol by having no excipient present but rather having 40 mg of 2-butanol placed inside of a size 2 LiCap capsule, then having this capsule placed inside of a while size 0 LiCap capsule that contained the naltrexone base powder. All formulations were prepared by a certified compounding pharmacy (Westlab Pharmacy, Gainesville, Fla.) on the same day that they were used in the study.

Breath samples taken at time points of −5 minutes (used as a blank breath sample taken prior to pill ingestion), 0 minutes (taken immediately after pill ingestion), 10, 20, 40, 60, and 90 minutes post pill ingestion were collected by having the subject breath directly into a mouthpiece attached to a Xhale SMART mGC. Each subject used one of eight mGCs for the length of the study (the same mGC for each of the four visit dates), with the mGC initially calibrated for 2-butanone one day before the study started and again after the last subject was finished with the study. The mGC initial and final 2-butanone calibration results were collected. Calibration standards for acetone were analyzed after the final calibration standards for 2-butanone were analyzed. Breath samples (100 cc) were collected at the 30 minute time point post-ingestion onto Markes 3½"×¼" stainless steel thermal desorption tube packed with Tenax TA for GC/MS analysis. The GC/MS was calibrated using the same standards used for the mGC initial calibrations by collecting 100 cc from the gas standards in the Tedlar bags onto the Markes thermal desorption tubes. All of the Markes Tenax TA tubes for both the standards and samples were stored in a refrigerator located in the laboratory at Xhale Inc. until their analysis to provide 2-butanone breath concentration data resulting from ingestion of the four formulations for each subject at each time point. This data shows the average of the results for each formulation, and shows the dose-dependence relationship between the amount of 2-butanol ingested and the corresponding concentration of 2-butanone in the breath samples in this study. There is no statistically significant difference in using an excipient versus having the taggant separated from the naltrexone base (by using a pill-in-pill design).

One of the formulations (F2) used in this study contained 30 mg of isopropyl alcohol in addition to the naltrexone base and 2-butanol. Isopropyl alcohol is metabolized to acetone in the same manner that 2-butanol is metabolized to 2-butanone. Since only this formulation contained isopropyl alcohol, breath samples in the subjects who ingested this formulation should show a statistical increase in breath acetone concentrations over baseline levels. Since the acetone standards for the calibration curve were created in blank breath, which contains a significant amount of acetone, acetone concentrations were calculated using the calibration curve and then normalized to the t=0 time point. The average of the results for each formulation unambiguously shows the increase in acetone breath concentrations caused by the ingestion of 30 mg of isopropyl alcohol. The breath 2-butanone concentrations determined by collecting a breath sample at the 30 minute time point followed by GC/MS analysis was compared to an average of the 2-butanone breath concentrations using the Xhale SMART mGCs between the 20 minute and 40 minute time points. The 2-butanone breath concentrations obtained using both techniques. While the GC/MS retains linearity past 1000 ppb of 2-butanone, the mGC has a much smaller linearity range (up to 50 ppb of 2-butanone). The higher the breath concentration of 2-butanone, the lower the sensitivity (defined as the slope of the calibration curve) the mGC has for this compound. This loss in sensitivity results in a much greater precision at high concentrations, which can result in a deviation between values obtained using this instrument versus a research-grade GC/MS instrument. The technique used to collect breath samples analyzed by both instruments (side-stream collection onto a trap containing a very small amount of adsorbent for the mGC versus in-line collection onto a trap containing 300 mg of adsorbent for the GC/MS) can also lead to a poor correlation between these two analytical techniques, particularly at high concentrations.

The results obtained indicate that the ingestion of isotropic thermodynamically stable formulations of naltrexone containing alcohols such as 2-butanol and isopropanol (IPA) reliability and rapidly generate significant levels of 2-butanone and acetone above baseline levels, respectively. The formulations contained the appropriate amount of 2-butanol and naltrexone, were stable, and showed no evidence of naltrexone degradation during storage. Finally, the results indicate that the SMART system can be effectively employed to definitively detect ingestion of the SMART naltrexone formulations, using a pre-established 2-butanone cutoff concentration of 5 ppb or greater at early breath sampling times post ingestion. Specifically, every subject, who ingested F1, F2, F3, and F4 would be have been detected by the SMART system (100% sensitivity).

Example 30

Production and Use of Carbonates for Use as Surface Coatings or Markings for API Adherence Monitoring Those skilled in the art will appreciate, based on the following specifics, that a wide range of solid forms of the markers (primary or secondary alcohols or other markers) disclosed herein may be manufactured for surface coating.

Two different carbonates were synthesized for this work according to the following schemes:

General Scheme:

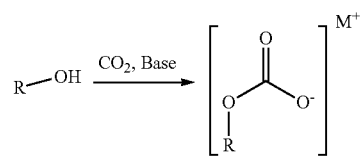

M = Ca, Na or K
R = 2-Butanol, Isopropanol

Preparation of Sodium Isopropyl Carbonate:

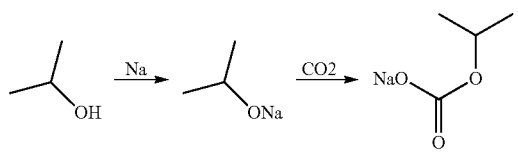

Isopropanol (1000 mL) was taken lab reactor and added Na metal (6 g). The reaction mixture was heated to 80° C. for 3 h (sodium metal dissolved, clear solution was observed). The reaction mixture was cooled to 0 to 5° C. and purged CO2 (thick suspension was observed after 30 min). Aliquot were drawn after 30 min, concentrated and the solid obtained was analyzed by 1H NMR. The reaction mixture was allowed to stir for additional 30 min. The complete reaction mixture was rinsed with isopropanol (100 mL) and transferred to an R.B flask, concentrated under vacuum to get white solid. The solid obtained after concentration was dried under vacuum at 40° C. at 1 h to get 26 g of white solid.

Sodium isopropoxy carbonate is formed according to this method. The MAC from isopropanol seems to decompose at 60° C. MAC on treatment with water decomposes and white solid was isolated. The 13C NMR shows only one peak at 161.9 ppm.

Synthesis of Sodium Butan-2-Yl Carbonate:

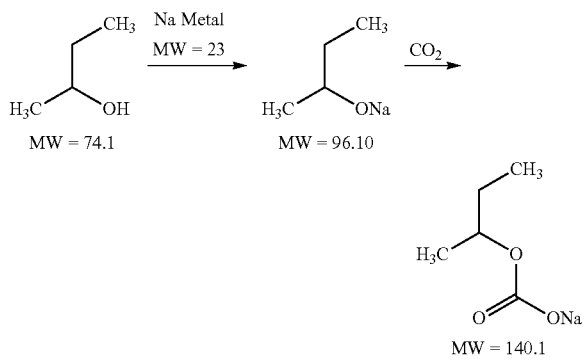

Synthesis 1: Three grams of Na metal was dissolved in 1000 mL of anhydrous 2-butanol at 90° C. The solution was cooled to between 0 and 5° C. and purged with $CO_2$ for 45 minutes. The resulting suspension was concentrated under high vacuum at 40-50° C. to obtain 15 g of white solid.

$^1$H-NMR: δ ppm (in D2O)=0.89 (triplet, 3H), 1.17 (doublet, 3H), 1.50 (multiplet, 2H), 4.38 (multiplet, 1H)

$^{13}$C-NMR: δ ppm (in D2O)=9.48, 19.59, 28.97, 73.96 and 159.61. IR: ν (cm$^{-1}$)=1651, 1458, 1369 and 1289 (indicative of an alkyl carboxylate).

Synthesis 2: Six grams of Na metal was dissolved in 100 mL of anhydrous isopropanol at 80° C. The solution was cooled to between 0 and 5° C. and purged with $CO_2$ for 60 minutes. The resulting suspension was concentrated under high vacuum at 45° C. to obtain 26 g of white solid.

$^1$H-NMR: δ ppm (in D2O)=1.17 (doublet, 6H), 4.53 (multiplet, 1H)$^{13}$C-NMR: δ ppm (in D2O)=21.89, 69.13 and 159.26. IR: ν (cm$^{-1}$)=1650, 1458, 1369 and 1292 (indicative of an alkyl carboxylate).

The butan-2-yl carbonate and Sodium isopropyl carbonate were each separately included in medication capsules, and ingested. The carbonate quickly is converted in vivo into the cognate alcohol and that is quickly metabolized, in the case of the sodium isopropyl carbonate, into acetone and, in the case of the butan-2-yl carbonate, into the butanone. These ketones were quickly detected in the exhaled breath.

API Surface Coating and Release of EBM on Ingestion:

Having demonstrated that the carbonate form of an alcohol, which is a solid at room temperature, is quickly and efficiently liberated in the exhaled breath as the desired EBM, those skilled in the art know how to formulate powders for surface coating or marking of API's. In particular, about 10 to 100 mg of the carbonate is formulated with a desiccant and flow promoter for dispensation onto the surface of a dosage form. The surface coating or marking is preferably deposited onto the surface of the API at a position where a barrier film separates the surface coating from the API and this surface coating is preferably over-coated by a barrier to prevent moisture from seeping into the surface coating, and/or to prevent any loss of the surface coating to the atmosphere or from being abraded during packaging, shipping or handling. In a highly preferred embodiment, a user of the surface coated API would have no way of knowing that the surface coating includes a marker which, when the API is ingested, is quickly released and evolves the EBM. Where one or more non-ordinary isotope(s) is/are included in the surface coating, e.g. in the isopropyl or butyl carbonate, even smaller quantities of the marker may be included—e.g. 0.001 to 50 mg, alternatively 0.01 to 25 mg, alternatively 0.1 to 15 mg, and most preferably, anywhere from about 1 to 20 mg is sufficient to produce a readily detectable evolution of non-ordinary isotope containing EBM. In another embodiment according to this aspect of the invention, the marker powder is encapsulated and included in an encapsulated state in a fill formulation in a capsule with an API.

Those skilled in the art, based on these examples, would appreciate that similar syntheses carried out with more complex secondary alcohols or primary alcohols produce carbonates with varying properties and abilities to act as EDIMs to produce EBMs. Likewise, other metal salts of these carbonates find utility according to the present disclosure in various contexts as needed.

What is claimed is:

1. A method for monitoring a subject with a medication adherence device to determine whether the subject has ingested a medication comprising an isotopically-labelled exhaled drug ingestion marker (EDIM) or a taggant that generates the isotopically-labelled EDIM, wherein the medication adherence device comprises a mouthpiece, a gas capture device, a catalytic incinerator, a sensor for detecting isotopically-labelled compounds, and a computer, said method comprising
- (a) receiving exhaled breath from the subject into the mouthpiece, wherein the mouthpiece transfers volatile compounds in the exhaled breath to the gas capture device, the gas capture device being connected to and adapted to receive the volatile compounds from the mouthpiece;
- (b) capturing the volatile compounds with the gas capture device and releasing at least a portion of the volatile compounds to the catalytic incinerator, the catalytic incinerator being connected to and adapted to receive the at least a portion of the volatile compounds from the gas capture device;
- (c) combusting the at least a portion of the volatile compounds to form carbon dioxide, water, or both, and transferring the carbon dioxide, the water, or both, to the sensor for detecting isotopically-labelled compounds, the sensor being connected to and adapted to receive the carbon dioxide, the water, or both, from the catalytic incinerator;
- (d) detecting with the sensor whether isotopically-labelled carbon dioxide, isotopically-labelled water, or both, is present or absent in the carbon dioxide, the water, or both, that was transferred from the catalytic incinerator; and
- (e) if the isotopically-labelled carbon dioxide, the isotopically-labelled water, or both, is detected as being present, determining with the computer that the subject ingested the medication, or if the isotopically-labelled carbon dioxide, the isotopically-labelled water, or both, is not detected as being present; determining with the computer that the subject did not ingest the medication.

2. The method of claim 1, wherein the medication adherence device further comprises at least one volatile compound separator between the gas capture device and the catalytic incinerator, wherein in step (b), the method further comprises receiving the at least a portion of the volatile compounds from the gas capture device, separating the at least a portion of the volatile compounds, transferring the separated at least a portion of the volatile compounds to the catalytic incinerator.

3. The method of claim 1, wherein the sensor for detecting isotopically-labelled compounds is an infrared sensor.

4. The method of claim 3, wherein in step (d), the method comprises using the infrared sensor to detect whether deuterated water is present or absent in the water transferred from the catalytic incinerator.

5. The method of claim 1, wherein the medication adherence device further comprises at least one biometric capture device, wherein in step (a), the method further comprises concurrently capturing with the biometric capture device a biometric specific to the subject while the subject's exhaled breath is received into the mouthpiece.

6. The method of claim 5, wherein the biometric capture device is a camera, and wherein the camera concurrently captures a still image of the subject while the subject's exhaled breath is received into the mouthpiece.

7. The method of claim 1, wherein the medication adherence device further comprises a wireless data transceiver, and wherein in step (e), the method further comprises transmitting the determination by the computer that the subject ingested the medication or did not ingest the medication to a remote location using the wireless data transceiver.

8. The method of claim 1, wherein the EDIM or the taggant that generates the EDIM is a Generally Recognized as Safe (GRAS) compound.

9. The method of claim 1, wherein the EDIM or the taggant is isotopically-labelled with deuterium.

10. The method of claim 1, wherein the EDIM or taggant is isotopically-labelled with $^{13}C$.

11. The method of claim 1, wherein the gas capture device is configured to selectively exclude water.

12. The method of claim 1, wherein the gas capture device is configured to selectively exclude one or more of hydrogen, nitrogen, and carbon dioxide.

13. The method of claim 1, further comprising providing the medication to the subject, prior to step (a).

14. The method of claim 1, wherein in step (e), the computer measures a concentration of the isotopically-labelled carbon dioxide, the isotopically-labelled water, or both, if present, and determines that the subject ingested the medication or that the subject did not ingest the medication based on the concentration of the isotopically-labelled carbon dioxide, the isotopically-labelled water, or both.

15. The method of claim 14, wherein in step (e), the computer further calculates a concentration of the EDIM or the taggant in the exhaled breath based on the concentration of the isotopically-labelled carbon dioxide, the isotopically-labelled water, or both.

16. The method of claim 1, wherein the medication further comprises a therapeutic agent.

17. The method of claim 14, wherein the medication further comprises a therapeutic agent.

* * * * *